US012467064B2

(12) United States Patent
Ting et al.

(10) Patent No.: US 12,467,064 B2
(45) Date of Patent: Nov. 11, 2025

(54) ARTIFICIAL EXPRESSION CONSTRUCTS FOR SELECTIVELY MODULATING GENE EXPRESSION IN INTERNEURONS

(71) Applicants: Allen Institute, Seattle, WA (US); Seattle Children's Hospital, Seattle, WA (US)

(72) Inventors: Jonathan Ting, Lake Forest Park, WA (US); Boaz P. Levi, Seattle, WA (US); John K. Mich, Seattle, WA (US); Edward Sebastian Lein, Mercer Island, WA (US); Franck Kalume, Bothell, WA (US)

(73) Assignees: Allen Institute, Seattle, WA (US); Seattle Children's Hospital, Seattle, WA (US)

( * ) Notice: Subject to any disclaimer, the term of this patent is extended or adjusted under 35 U.S.C. 154(b) by 1014 days.

(21) Appl. No.: 17/283,232

(22) PCT Filed: Oct. 3, 2019

(86) PCT No.: PCT/US2019/054539
§ 371 (c)(1),
(2) Date: Apr. 6, 2021

(87) PCT Pub. No.: WO2020/076614
PCT Pub. Date: Apr. 16, 2020

(65) Prior Publication Data

US 2021/0348195 A1 Nov. 11, 2021

Related U.S. Application Data

(60) Provisional application No. 62/810,281, filed on Feb. 25, 2019, provisional application No. 62/749,012, filed on Oct. 22, 2018, provisional application No. 62/742,835, filed on Oct. 8, 2018.

(51) Int. Cl.
*C12N 15/86* (2006.01)
*A01K 67/0278* (2024.01)
*A61K 35/30* (2015.01)
*C12N 5/0793* (2010.01)

(52) U.S. Cl.
CPC .......... *C12N 15/86* (2013.01); *A01K 67/0278* (2013.01); *A61K 35/30* (2013.01); *C12N 5/0619* (2013.01); *A01K 2217/052* (2013.01); *A01K 2227/105* (2013.01); *A01K 2227/106* (2013.01); *C12N 2510/00* (2013.01); *C12N 2750/14043* (2013.01)

(58) Field of Classification Search
CPC ........ C12N 5/0619; C12N 2750/14043; C12N 15/86; A61K 48/00
See application file for complete search history.

(56) References Cited

U.S. PATENT DOCUMENTS

| | | | | |
|---|---|---|---|---|
| 7,125,676 | B2 | 10/2006 | George, Jr. et al. | |
| 7,129,343 | B2 | 10/2006 | Li et al. | |
| 9,579,399 | B2 | 2/2017 | Roska et al. | |
| 10,287,607 | B2 | 5/2019 | Tagliatela | |
| 2004/0087028 | A1 * | 5/2004 | Cunningham ......... | C12N 15/86 435/235.1 |
| 2005/0260576 | A1 | 11/2005 | George et al. | |
| 2009/0162332 | A1 | 6/2009 | Davidson et al. | |
| 2015/0044667 | A1 | 2/2015 | Crino | |
| 2017/0029464 | A1 | 2/2017 | Korbelin et al. | |
| 2017/0166926 | A1 | 6/2017 | Deverman et al. | |
| 2018/0078658 | A1 | 3/2018 | Fishell et al. | |
| 2019/0024118 | A1 * | 1/2019 | Tagliatela .............. | C12N 15/86 |
| 2019/0030186 | A1 | 1/2019 | Bursac | |
| 2021/0015898 | A1 | 1/2021 | Mich et al. | |

FOREIGN PATENT DOCUMENTS

| | | | | |
|---|---|---|---|---|
| WO | WO2016059162 | A1 | 4/2016 | |
| WO | WO-2016161124 | A1 * | 10/2016 | ......... A61K 38/1796 |
| WO | WO2016186772 | A2 | 11/2016 | |
| WO | WO2017100671 | A1 | 6/2017 | |

OTHER PUBLICATIONS

Dayton, R. D., Grames, M. S., & Klein, R. L. (2018). More expansive gene transfer to the rat CNS: AAV PHP. EB vector dose-response and comparison to AAV PHP. B. Gene therapy, 25(5), 392-400. (Year: 2018).*
Zhou, Qing-Ping, et al. "Identification of a direct Dlx homeodomain target in the developing mouse forebrain and retina by optimization of chromatin immunoprecipitation." Nucleic acids research 32.3 (2004): 884-892 (Year: 2004).*
Esau, Crystal. Characterization of the Dlx Enhancers in the Developing Mouse. Diss. Université d'Ottawa/University of Ottawa, 2013. (Year: 2013).*
Zerucha T, et al., 2000. A highly conserved enhancer in the Dlx5/Dlx6 Intergenic region is the site of cross-regulatory interactions between DLX genes in the embryonic forebrain. The Journal of Neuroscience 20:709-721 (Year: 2000).*
Park, Byung K., et al. "Intergenic enhancers with distinct activities regulate Dlx gene expression in the mesenchyme of the branchial arches." Developmental biology 268.2 (2004): 532-545. (Year: 2004).*

(Continued)

*Primary Examiner* — Kevin K Hill
*Assistant Examiner* — Allison Marie Johnson
(74) *Attorney, Agent, or Firm* — C. Rachal Winger; Chrystal Quisenberry; Lee & Hayes PC

(57) ABSTRACT

Artificial expression constructs for selectively modulating gene expression in selected central nervous system cell types are described. The artificial expression constructs can be used to selectively express synthetic genes or modify gene expression in GABAergic interneurons.

18 Claims, 104 Drawing Sheets

Specification includes a Sequence Listing.

(56) References Cited

OTHER PUBLICATIONS

Japanese Office Action mailed Sep. 12, 2023 for Japanese Patent Application No. 2020-555346, a foreign counterpart to U.S. Appl. No. 17/044,232, 5 pages.
Albright, et al., "Mapping the Structural Determinants Required for AAVrh.10 Transport across the Blood-Brain Barrier," Molecular Therapy, vol. 26, No. 2, 2018, pp. 510-523.
Catterall, et al., "NaV1.1 channels and epilepsy," Journal of Physiology, vol. 588, No. 11, 2010, pp. 1849-1859.
Chan, et al., "Engineered AAVs for efficient noninvasive gene delivery to the central and peripheral nervous systems," Nature Neuroscience, vol. 20, No. 8, 2017, pp. 1172-1179.
Cheah, et al., "Specific deletion of NaV1.1 sodium channels in inhibitory interneurons causes seizures and premature death in a mouse model of Dravet syndrome," PNAS USA, vol. 109, No. 36, 2012, pp. 14646-14651.
Chen, et al., "Molecular signatures of disease brain endothelia provide new sites for CNS-directed enzyme therapy," Nature Medicine, vol. 15, 2009, pp. 1215-1218.
Claes, et al., "De novo SCN1A mutations are a major cause of severe myoclonic epilepsy of infancy," Human Mutation, vol. 21, No. 6, 2003, pp. 615-621.
Deverman, et al., "Cre-dependent selection yields AAV variants for widespread gene transfer to the adult brain," Nature Biotechnology, vol. 34, No. 2, 2016, pp. 204-209.
Dimidschstein, et al., "A viral strategy for targeting and manipulating interneurons across vertebrate species," Nature Neuroscience, vol. 19, No. 12, 2016, pp. 1743-1749.
Dutton, et al., "Preferential inactivation of Scn1a in parvalbumin interneurons increases seizure susceptibility," Neurobiology of Disease, vol. 49, 2013, pp. 211-220.
Fujiwara, "Clinical spectrum of mutations in SCN1A gene: severe myoclonic epilepsy in infancy and related epilepsies," Epilepsy Res., vol. 70, No. 1, 2006, pp. 223-230.
Gambardella & Marini, "Clinical spectrum of SCN1A mutations," Epilepsia, vol. 50, No. 5, 2009, pp. 20-23.
Gersbach, et al., "Synthetic zinc finger proteins: the advent of targeted gene regulation and genome modification technologies," Acc. Chem. Res., vol. 47, No. 8, 2014, pp. 2309-2318.
Goldin, "Resurgence of sodium channel research," Annu. Rev. Physiol., vol. 63, 2001, pp. 871-894.
Gombash, et al., "Intravenous AAV9 efficiently transduces myenteric neurons in neonate and juvenile mice," Frontiers In Molecular Neuroscience, vol. 7, No. 81, 2014, 11 pages.
Han, et al., "Autistic-like behaviour in Scn1a+/− mice and rescue by enhanced GABA-mediated neurotransmission," Nature, vol. 489, 2012, pp. 385-390.
Han, et al., "NaV1.1 channels are critical for intercellular communication in the suprachiasmatic nucleus and for normal circadian rhythms," PNAS USA, vol. 109, No. 6, 2012, pp. 368-377.
Harkin, et al., "The spectrum of SCN1A-related infantile epileptic encephalopathies," Brain, vol. 130, No. 3, 2007, pp. 843-852.
Hawkins, et al., "Fine Mapping of a Dravet Syndrome Modifier Locus on Mouse Chromosome 5 and Candidate Gene Analysis by RNA-Seq," PLoS Genetics, vol. 12, No. 10, 2016, pp. 1-15.
Asiao, et al., "Upregulation of Haploinsufficient Gene Expression in the Brain by Targeting a Long Non-coding RNA Improves Seizure Phenotype in a Model of Dravet Syndrome," EBioMedicine, vol. 9, 2016, pp. 257-277.
Huang, et al., "Role of the Hepatitis B Virus Posttranscriptional Regulatory Element in Export of Intronless Transcripts," Molecular and Cellular Biology, vol. 15, No. 7, 1995, pp. 3864-3869.
Invitation to Pay Fees Dated Dec. 23, 2019 in International Application No. PCT/US19/54539, 2 pages.
Kalume, "Sudden unexpected death in Dravet syndrome: Respiratory and other physiological dysfunctions," Respiratory Physiology & Neurobiology, vol. 189, No. 2, 2013, pp. 324-328.
Kalume, et al., "Reduced Sodium Current in Purkinje Neurons from NaV1.1 Mutant Mice: Implications for Ataxia in Severe Myoclonic Epilepsy in Infancy," Journal of Neuroscience, vol. 27, No. 41, 2007, pp. 11065-11074.
Kalume, et al., "Sleep Impairment and Reduced Interneuron Excitability in a Mouse Model of Dravet Syndrome," Neurobiology of Disease, vol. 77, 2015, pp. 141-154.
Kalume, et al., "Sudden unexpected death in a mouse model of Dravet syndrome," Journal of Clinical Investigation, vol. 123, No. 4, 2013, pp. 1798-1808.
Kepecs & Fishell, "Interneuron cell types are fit to function," Nature, vol. 505, 2014, pp. 318-326.
Korbelin, et al., "A brain microvasculature endothelial cell-specific viral vector with the potential to treat neurovascular and neurological diseases," EMBO Molecular Medicine, vol. 8, No. 6, 2016, pp. 609-625.
Liu & Mertz, "HnRNP L binds a cis-acting RNA sequence element that enables intron-dependent gene expression," Genes & Development, vol. 9, 1995, pp. 1766-1780.
Livingston, et al., "A novel inherited mutation in the voltage sensor region of SCN1A is associated with Panayiotopoulos syndrome in siblings and generalized epilepsy with febrile seizures plus," Journal of Child Neurology, vol. 24, No. 4, 2009, pp. 503-508.
Marchio, et al., "Brain endothelial cell-targeted gene therapy of neurovascular disorders," EMBO Molecular Medicine, vol. 8, No. 6, 2016, pp. 592-594.
Matharu, et al., "CRISPR-mediated activation of a promoter or enhancer rescues obesity caused by haploinsufficiency," Science, vol. 363, No. 6424, 2019, pp. 186-194.
McClements & MacLaren, "Adeno-associated Virus (AAV) Dual Vector Strategies for Gene Therapy Encoding Large Transgenes," Yale Journal of Biology and Medicine, vol. 90, No. 4, 2017, pp. 611-623.
Mistry, et al., "Strain- and age-dependent hippocampal neuron sodium currents correlate with epilepsy severity in Dravet syndrome mice," Neurobiology of Disease, vol. 65, 2014, pp. 1-11.
Miyoshi, et al., "Genetic fate mapping reveals that the caudal ganglionic eminence produces a large and diverse population of superficial cortical interneurons," Journal of Neuroscience, vol. 30, No. 5, 2010, pp. 1582-1592.
Monory, et al., "The endocannabinoid system controls key epileptogenic circuits in the hippocampus," Neuron., vol. 51, No. 4, 2006, pp. 455-466.
Morbitzer, et al., "Regulation of selected genome loci using de novo-engineered transcription activator-like effector (TALE)-type transcription factors," PNAS USA, vol. 107, No. 50, 2010, pp. 21617-21622.
Naso, et al., "Adeno-Associated Virus (AAV) as a Vector for Gene Therapy," BioDrugs, vol. 31, No. 4, 2017, pp. 317-334.
ClinicalTrials.gov [Internet]. Bethesda (MD): National Library of Medicine (US). Apr. 23, 2018—Identifier NCT03505099, Pre-Symptomatic Study of Intravenous Onasemnogene Abeparvovec-xioi in Spinal Muscular Atrophy (SMA) for Patients With Multiple Copies of SMN2 (SPR1NT); Apr. 13, 2018; [8 screens]. Available from: https://clinicaltrials.gov/ct2/show/NCT03505099.
ClinicalTrials.gov [Internet]. Bethesda (MD): National Library of Medicine (US). Aug. 2, 2018—Identifier NCT03612869, Study of AAVrh10-h.SGSH Gene Therapy in Patients With Mucopolysaccharidosis Type IIIA (MPS IIIA) (AAVance); Jul. 4, 2018; [8 screens]. Available from: https://clinicaltrials.gov/ct2/show/NCT03612869.
ClinicalTrials.gov [Internet]. Bethesda (MD): National Library of Medicine (US). Dec. 10, 2018—Identifier NCT03770572, Gene Therapy for Children With CLN3 Batten Disease; Dec. 7, 2018; [9 screens]. Available from: https://clinicaltrials.gov/ct2/show/NCT03770572.
Nguyen, et al., "Engineering prokaryotic channels for control of mammalian tissue excitability," Nature Communications, vol. 7, 2016, 11 pages.
O'Roak, et al., "Exome sequencing in sporadic autism spectrum disorders identifies severe de novo mutations," Nature Genetics, vol. 43, No. 6, 2011, pp. 585-589.

(56) References Cited

OTHER PUBLICATIONS

Oakley, et al., "Temperature- and age-dependent seizures in a mouse model of severe myoclonic epilepsy in infancy" PNAS, vol. 106, No. 10, 2009, pp. 3994-3999.
Ogiwara, et al., "Nav1.1 Localizes to Axons of Parvalbumin-Positive Inhibitory Interneurons: A Circuit Basis for Epileptic Seizures in Mice Carrying an Scn1a Gene Mutation," Journal of Neuroscience, vol. 27, No. 22, 2007, pp. 5903-5914.
Ohmori, et al., "Rasmussen encephalitis associated with SCN1A mutation," Epilepsia, vol. 49, No. 3, 2007, pp. 521-526.
Search Report and Written Opinion Dated Jul. 19, 2019, for International Application No. PCT/US2019/026638, 12 pages.
Search Report and Written Opinion Dated Feb. 14, 2020 for International Application No. PCT/US19/54539, 13 pages.
Peron, et al., "A Cellular Resolution Map of Barrel Cortex Activity during Tactile Behavior," Neuron, vol. 86, No. 3, 2015, pp. 783-799.
"Predicted: Panthera pardus uncharacterized LOC109263725 (LOC109263725), transcript variant X2, ncRNA, Accession XR_002078354", retrieved on Jan. 27, 2020 from <<https://www.ncbi.nlm.nih.gov/nucleotide/XR_002078354.1?report=genbank &log$=nucltop&blast_rank=17 &RI D=30VXJA38016>>, Dec. 5, 2016, 2 pages.
Rubinstein, et al., "Dissecting the phenotypes of Dravet syndrome by gene deletion," Brain, vol. 138, Part 8, 2015, pp. 2219-2233.
Office Action Dated Apr. 18, 2023 in Japanese Application No. 2020-555346, 7 pages.
Lipinski, et al., "Clinical applications of retinal gene therapy," Prog. Retin. Eye Res., 2013, vol. 32, pp. 22-47.
Office Action for European Application No. 19785199.1, Dated May 6, 2024, 4 pages.
Choi, et al., "Optimization of AAV expression cassettes to improve packaging capacity and transgene expression on neurons", Molecular brain, vol. 7, No. 17, 2014, 10 pages.
Bagneris, et al., "Prokaryotic NavMs channel as a structural and functional model for eukaryotic sodium channel antagonism", PNAS, vol. 11, No. 23, 2014, 8428-8433.
Bazylinski et al. "*Magnetococcus marinus* gen. nov., sp. nov., a marine, magnetotactic bacterium that represents a novel lineage (u Magnetococcaceae fam. nov., Magnetococcales ord. nov.) at the base of the Alphaproteobacteria". International J of Systematic and Evolutionary Microbiology 2013, 63;3:801-808.
Korbel in et al. "A brain microvasculature endothelial cell-specific viral vector with the potential to treat neurovascular and neurological diseases". EMBO Molecular Medicine 2016, 8:609-625.
Office Action for U.S. Appl. No. 17/044,232, mailed on Jan. 31, 2024, Mich, "Rescuing Voltage-Gated Sodium Channel Function in Inhibitory Neurons", 10pgs.
Rudy, et al., "Three groups of interneurons account for nearly 100% of neocortical GABAergic neurons," Development Neurobiology, vol. 71, No. 1, 2011, pp. 45-61.
Scharfman, "Untangling Alzheimer's Disease and Epilepsy: "Untangling" Alzheimer's Disease and Epilepsy," Epilepsy Currents, vol. 12, No. 5, 2012, pp. 178-183.
Selot, et al., "Optimized AAV rh.10 Vectors That Partially Evade Neutralizing Antibodies during Hepatic Gene Transfer" Frontiers in Pharmacology, vol. 8, No. 441, 2017, 10 pages.
Shen, et al., "Structures of human Nav1.7 channel in complex with auxiliary subunits and animal toxins," Science, vol. 363, No. 6433, 2019, pp. 1303-1308.
Stenman, et al., "Identification of Two Distinct Progenitor Populations in the Lateral Ganglionic Eminence: Implications for Striatal and Olfactory Bulb Neurogenesis," Journal of Neuroscience, vol. 23, No. 1, 2003, pp. 167-174.
Stern, et al., "Impaired intracortical inhibition demonstrated in vivo in people with Dravet syndrome," Neurology, vol. 88, 2017, pp. 1659-1665.
Stuhmer, et al., "Expression from a Dlx gene enhancer marks adult mouse cortical GABAergic neurons," Cereb Cortex, vol. 12, No. 1, 2002, pp. 75-85.
Sula & Wallace, "Interpreting the functional role of a novel interaction motif in prokaryotic sodium channels," Journal of General Physiology, vol. 149, No. 6, 2017, pp. 613-622.
Tai, et al., "Impaired excitability of somatostatin- and parvalbumin-expressing cortical interneurons in a mouse model of Dravet syndrome," PNAS, vol. 111, No. 30, 2014, pp. E3139-E3148.
Ting, et al., "A robust ex vivo experimental platform for molecular-genetic dissection of adult human neocortical cell types and circuits," Scientific Reports, vol. 8, No. 1, 2018, 13 pages.
Verbeek, et al., "Seizure precipitants in Dravet syndrome: What events and activities are specifically provocative compared with other epilepsies?," Epilepsy & Behavior, vol. 47, 2015, pp. 39-44.
Weiss, et al., "Sodium channels SCN1A, SCN2A and SCN3A in familial autism" Molecular Psychiatry, vol. 8, No. 2, 2003, pp. 186-194.
Wu, et al., "Incidence of Dravet Syndrome in a US Population," Pediatrics, vol. 136, No. 5, 2015, pp. e1310-e1315.
Yang, et al., "Global CNS Transduction of Adult Mice by Intravenously Delivered rAAVrh.8 and rAAVrh.10 and Nonhuman Primates by rAAVrh.10," Molecular Therapy, vol. 22, No. 7, 2014, pp. 1299-1309.
Yao, et al., "Differential pattern of expression of voltage-gated sodium channel genes following ischemic brain injury in rats," Neurotoxicity Research, vol. 4, No. 1, 2002, pp. 67-75.
Yu, et al., "Reduced sodium current in GABAergic interneurons in a mouse model of severe myoclonic epilepsy in infancy," Nature Neuroscience, vol. 9, No. 9, 2006, pp. 1142-1149.
Yu, et al., "Sodium channel beta4, a new disulfide-linked auxiliary subunit with similarity to beta2" Journal of Neuroscience, vol. 23, No. 20, 2003, pp. 7577-7585.
Zerucha, et al., "A Highly Conserved Enhancer in the Dlx5/Dlx6Intergenic Region is the Site of Cross-Regulatory Interactions betweenDlx Genes in the Embryonic Forebrain," Journal of Neuroscience, vol. 20, No. 2, 2000, pp. 709-721.
Zufferey, et al., "Woodchuck Hepatitis Virus Posttranscriptional Regulatory Element Enhances Expression of Transgenes Delivered by Retroviral Vectors," Journal of Virology, vol. 73, No. 4, 1999, pp. 2886-2892.
Chan, et al, "Engineered AAVs for efficient non invasive gene delivery to the central and peripheral nervous systems", Nature Neuroscience Techinal Reports, vol. 20, No. 8, Jun. 26, 2017, pp. 1172-1179.
Cheah, et al "Specification deletion of NaV1.1 sodium channels in inhibitory interneurons causes seizures and premature death in a mouse model of Dravet Syndrome", Proceedings of the National Academy of sciences, vol. 109, No. 36, Sep. 4, 2012, pp. 14646-14651.
Dimidschstein, et al., "A viral strategy for targeting and manipulating interneurons across vertebrate species", Nature Neuroscience Technical Reports, vol. 19, No. 12, Dec. 1, 2016, pp. 1743-1749.
Extended European Search Report Dated Jan. 4, 2022 for European Patent Application No. 19785199.1, 8 pages.
Nathanson, "Short promoters in viral vectors drive selective expression in mammalian inhibitory neurons, but do not restrict activity to specific inhibitory cell-types", Frontiers in Neural Circuits, vol. 3, Nov. 9, 2009, pp. 1-24.
Canadian Office Action mailed on Oct. 10, 2023 for Canadian Patent Application No. 3,115,652, a foreign counterpart to U.S. Appl. No. 17/283,232, 3 pages.
Canadian Office Action mailed on Oct. 18, 2023, for Canadian Patent Application No. 3,096,407, a foreign counterpart to U.S. Appl. No. 17/044,232, 8 pages.
Japanese Office Action mailed Oct. 3, 2023 for Japanese Application No. 2021-543981, a foreign counterpart to U.S. Appl. No. 17/283,232, 7 pages.
Mendell, et al., "Single-Dose Gene-Replacement Therapy for Spinal Muscular Atrophy," N. Engl. J. Med., vol. 377, No. 18, 2017, pp. 1713-1722.
Office Action for Japanese Application No. 2021-543981, Dated Jun. 25, 2024, 8 pages.

(56) References Cited

OTHER PUBLICATIONS

Zerucha, et al., "A highly conserved enhancer in the Dlx5/Dlx6 intergenic region is the site of cross-regulatory interactions between Dlx genes in the embryonic forebrain", The Journal of Neuroscience, Jan. 2000, pp. 709-721.

* cited by examiner

1DIV/DPI 3DIV/DPI 6DIV/DPI

CN1389 pAAV-hI56i(core)-minBG-SYFP2-WPRE3-BGHpA (JT)

FIG. 12 (cont'd)

CN1389 pAAV-A1561(core)-minBG-SYFP2-WPRE3-BGHpA (JT)

```
                                                  SYFP2
 901  CAAGGCCAAC TTCAAGATCC GCCACAACAT CGAGGACGGC GGCGTGCAGC TCGCCGACCA CTACCAGCAG AACACCCCCA TCGGCGACGG
      GTTCCGGTTG AAGTTCTAGG CGGTGTTGTA GCTCCTGCCG CCGCACGTCG AGCGGCTGGT GATGGTCGTC TTGTGGGGGT AGCCGCTGCC

                                                  SYFP2
                                                  BlpI
 991  CCCCGTGCTG CTGCCCGACA ACCACTACCT GAGCTACCAG TCCAAGCTGA GCAAAGACCC CAACGAGAAG CGCGATCACA TGGTCCTGCT
      GGGGCACGAC GACGGGCTGT TGGTGATGGA CTCGATGGTC AGGTTCGACT CGTTTCTGGG GTTGCTCTTC GCGCTAGTGT ACCAGGACGA

                                                  BsrGI      AccI                          gamma
                             SYFP2                                      AscI       EcoRI   WPRE3
                                                             SalI       SacII              EcoRV
1081  GGAGTTCGTG ACCGCCGCCG GGATCACTCT CGGCATGGAC GAGCTGTACA AGTAAGTCGA CGGCGCGCCG CGGCCGCGAA TTCGATATCA
      CCTCAAGCAC TGGCGGCGGC CCTAGTGAGA GCCGTACCTG CTCGACATGT TCATTCAGCT GCCGCGCGGC GCCGGCGCTT AAGCTATAGT

                                                  gamma
                                                  WPRE3
1171  TAATCAACCT CTGGATTACA AAATTTGTGA AAGATTGACT GGTATTCTTA ACTATGTTGC TCCTTTTACG CTATGTGGAT ACGCTGCTTT
      ATTAGTTGGA GACCTAATGT TTTAAACACT TTCTAACTGA CCATAAGAAT TGATACAACG AGGAAAATGC GATACACCTA TGCGACGAAA

                             gamma                                                         alpha
                                                  WPRE3
1261  AATGCCTTTG TATCATGCTA TTGCTTCCCG TATGGCTTTC ATTTTCTCCT CCTTGTATAA ATCCTGGTTA GTTCTTGCCA CGGCGGAACT
      TTACGGAAAC ATAGTACGAT AACGAAGGGC ATACCGAAAG TAAAAGAGGA GGAACATATT TAGGACCAAT CAAGAACGGT GCCGCCTTGA
                             WPRE3-R (JT)

                             alpha
                             WPRE3                                                         BGH-pA
                                                                        XhoI
                                                                        SciI
1351  CATCGCCGCC TGCCTTGCCC GCTGCTGGAC AGGGGCTCGG CTGTTGGGCA CTGACAATTC CGTGGCTCGA GAGATCTTCG ACTGTGCCTT
      GTAGCGGCGG ACGGAACGGG CGACGACCTG TCCCCGAGCC GACAACCCGT GACTGTTAAG GCACCGAGCT CTCTAGAAGC TGACACGGAA

                                                  BGH-pA
1441  CTAGTTGCCA GCCATCTGTT GTTTGCCCCT CCCCCGTGCC TTCCTTGACC CTGGAAGGTG CCACTCCCAC TGTCCTTTCC TAATAAAATG
      GATCAACGGT CGGTAGACAA CAAACGGGGA GGGGGCACGG AAGGAACTGG GACCTTCCAC GGTGAGGGTG ACAGGAAAGG ATTATTTTAC

                                                  BGH-pA
                                                                                           BbsI
                                                                                           BbvII
1531  AGGAAATTGC ATCGCATTGT CTGAGTAGGT GTCATTCTAT TCTGGGGGGT GGGGTGGGGC AGGACAGCAA GGGGGAGGAT TGGGAAGACA
      TCCTTTAACG TAGCGTAACA GACTCATCCA CAGTAAGATA AGACCCCCCA CCCCACCCCG TCCTGTCGTT CCCCCTCCTA ACCCTTCTGT
                       BGH-R
```

FIG. 12 (cont'd)

CN1389 pAAV-hI56i(core)-minBG-SYFP2-WPRE3-BGHpA (JT)

```
           BGH-pA                 PmlI                                                R-ITR
1621   ATAGCAGGCA TGAGATCTCA CGTGCGGACC GAGCGGCCGC AGGAACCCCT AGTGATGGAG TTGGCCACTC CCTCTCTGCG CGCTCGCTCG
       TATCGTCCGT ACTCTAGAGT GCACGCCTGG CTCGCCGGCG TCCTTGGGGA TCACTACCTC AACCGGTGAG GGAGAGACGC GCGAGCGAGC

                                                    R-ITR
1711   CTCACTGAGG CCGGGCGACC AAAGGTCGCC CGACGCCCGG GCTTTGCCCG GGCGGCCTCA GTGAGCGAGC GAGCGCGCAG CTGCCTGCAG
       GAGTGACTCC GGCCCGCTGG TTTCCAGCGG GCTGCGGGCC CGAAACGGGC CCGCCGGAGT CACTCGCTCG CTCGCGCGTC GACGGACGTC

       R-ITR
        KasI
        NarI
        SfoI
        BbeI
1801   GGCGCCCTGA TGCGGTATTT TCTCCTTACG CATCTGTGCG GTATTTCACA CCGCATACGT CAAAGCAACC ATAGTACGCG CCCTGTAGCG
       CCGCGGGACT ACGCCATAAA AGAGGAATGC GTAGACACGC CATAAAGTGT GGCGTATGCA GTTTCGTTGG TATCATGCGC GGGACATCGC

                                                    f1 Origin
1891   GCGCATTAAG CGCGGCGGGT GTGGTGGTTA CGCGCAGCGT GACCGCTACA CTTGCCAGCG CCCTAGCGCC CGCTCCTTTC GCTTTCTTCC
       CGCGTAATTC GCGCCGCCCA CACCACCAAT GCGCGTCGCA CTGGCGATGT GAACGGTCGC GGGATCGCGG GCGAGGAAAG CGAAAGAAGG

                                                    f1 Origin
                              NgoMIV
                               NaeI
1981   CTTCCTTTCT CGCCACGTTC GCCGGCTTTC CCCGTCAAGC TCTAAATCGG GGGCTCCCTT TAGGGTTCCG ATTTAGTGCT TTACGGCACC
       GAAGGAAAGA GCGGTGCAAG CGGCCGAAAG GGGCAGTTCG AGATTTAGCC CCCGAGGGAA ATCCCAAGGC TAAATCACGA AATGCCGTGG

                                                    f1 Origin
2071   TCGACCCCAA AAAACTTGAT TTGGGTGATG GTTCACGTAG TGGGCCATCG CCCTGATAGA CGGTTTTTCG CCCTTTGACG TTGGAGTCCA
       AGCTGGGGTT TTTTGAACTA AACCCACTAC CAAGTGCATC ACCCGGTAGC GGGACTATCT GCCAAAAAGC GGGAAACTGC AACCTCAGGT

                       f1 Origin                                                           PsiI
2161   CGTTCTTTAA TAGTGGACTC TTGTTCCAAA CTGGAACAAC ACTCAACCCT ATCTCGGGCT ATTCTTTTGA TTTATAAGGG ATTTTGCCGA
       GCAAGAAATT ATCACCTGAG AACAAGGTTT GACCTTGTTG TGAGTTGGGA TAGAGCCCGA TAAGAAAACT AAATATTCCC TAAAACGGCT

2251   TTTCGGCCTA TTGGTTAAAA AATGAGCTGA TTTAACAAAA ATTTAACGCG AATTTTAACA AAATATTAAC GTTTACAATT TTATGGTGCA
       AAAGCCGGAT AACCAATTTT TTACTCGACT AAATTGTTTT TAAATTGCGC TTAAAATTGT TTTATAATTG CAAATGTTAA AATACCACGT

2341   CTCTCAGTAC AATCTGCTCT GATGCCGCAT AGTTAAGCCA GCCCCGACAC CCGCCAACAC CCGCTGACGC GCCCTGACGG GCTTGTCTGC
       GAGAGTCATG TTAGACGAGA CTACGGCGTA TCAATTCGGT CGGGGCTGTG GGCGGTTGTG GGCGACTGCG CGGGACTGCC CGAACAGACG

2431   TCCCGGCATC CGCTTACAGA CAAGCTGTGA CCGTCTCCGG GAGCTGCATG TGTCAGAGGT TTTCACCGTC ATCACCGAAA CGCGCGAGAC
       AGGGCCGTAG GCGAATGTCT GTTCGACACT GGCAGAGGCC CTCGACGTAC ACAGTCTCCA AAAGTGGCAG TAGTGGCTTT GCGCGCTCTG
```

FIG. 12 (cont'd)

CN1389 pAAV-hI56i(core)-minBG-SYFP2-WPRE3-BGHpA (JT)

```
                                                                   ZraI
     EcoO109I                                                      AatII
2521 GAAAGGGCCT CGTGATACGC CTATTTTTAT AGGTTAATGT CATGATAATA ATGGTTTCTT AGACGTCAGG TGGCACTTTT CGGGGAAATG
     CTTTCCCGGA GCACTATGCG GATAAAAATA TCCAATTACA GTACTATTAT TACCAAAGAA TCTGCAGTCC ACCGTGAAAA GCCCCTTTAC

2611 TGCGCGGAAC CCCTATTTGT TTATTTTTCT AAATACATTC AAATATGTAT CCGCTCATGA GACAATAACC CTGATAAATG CTTCAATAAT
     ACGCGCCTTG GGGATAAACA AATAAAAAGA TTTATGTAAG TTTATACATA GGCGAGTACT CTGTTATTGG GACTATTTAC GAAGTTATTA

                                                  AmpR
2701 ATTGAAAAAG GAAGAGTATG AGTATTCAAC ATTTCCGTGT CGCCCTTATT CCCTTTTTTG CGGCATTTTG CCTTCCTGTT TTTGCTCACC
     TAACTTTTTC CTTCTCATAC TCATAAGTTG TAAAGGCACA GCGGGAATAA GGGAAAAAAC GCCGTAAAAC GGAAGGACAA AAACGAGTGG
                EaeI

                                           AmpR
2791 CAGAAACGCT GGTGAAAGTA AAAGATGCTG AAGATCAGTT GGGTGCACGA GTGGGTTACA TCGAACTGGA TCTCAACAGC GGTAAGATCC
     GTCTTTGCGA CCACTTTCAT TTTCTACGAC TTCTAGTCAA CCCACGTGCT CACCCAATGT AGCTTGACCT AGAGTTGTCG CCATTCTAGG

                                           AmpR
2881 TTGAGAGTTT TCGCCCCGAA GAACGTTTTC CAATGATGAG CACTTTTAAA GTTCTGCTAT GTGGCGCGGT ATTATCCCGT ATTGACGCCG
     AACTCTCAAA AGCGGGGCTT CTTGCAAAAG GTTACTACTC GTGAAAATTT CAAGACGATA CACCGCGCCA TAATAGGGCA TAACTGCGGC

                                           AmpR
                                                       ScaI
2971 GGCAAGAGCA ACTCGGTCGC CGCATACACT ATTCTCAGAA TGACTTGGTT GAGTACTCAC CAGTCACAGA AAAGCATCTT ACGGATGGCA
     CCGTTCTCGT TGAGCCAGCG GCGTATGTGA TAAGAGTCTT ACTGAACCAA CTCATGAGTG GTCAGTGTCT TTTCGTAGAA TGCCTACCGT

                                           AmpR
                                                                          PvuI
3061 TGACAGTAAG AGAATTATGC AGTGCTGCCA TAACCATGAG TGATAACACT GCGGCCAACT TACTTCTGAC AACGATCGGA GGACCGAAGG
     ACTGTCATTC TCTTAATACG TCACGACGGT ATTGGTACTC ACTATTGTGA CGCCGGTTGA ATGAAGACTG TTGCTAGCCT CCTGGCTTCC

                                           AmpR
3151 AGCTAACCGC TTTTTTGCAC AACATGGGGG ATCATGTAAC TCGCCTTGAT CGTTGGGAAC CGGAGCTGAA TGAAGCCATA CCAAACGACG
     TCGATTGGCG AAAAAACGTG TTGTACCCCC TAGTACATTG AGCGGAACTA GCAACCCTTG GCCTCGACTT ACTTCGGTAT GGTTTGCTGC

                                           AmpR
                                       FspI                                                     AseI
3241 AGCGTGACAC CACGATGCCT GTAGCAATGG CAACAACGTT GCGCAAACTA TTAACTGGCG AACTACTTAC TCTAGCTTCC CGGCAACAAT
     TCGCACTGTG GTGCTACGGA CATCGTTACC GTTGTTGCAA CGCGTTTGAT AATTGACCGC TTGATGAATG AGATCGAAGG GCCGTTGTTA

                                           AmpR
     AseI
3331 TAATAGACTG GATGGAGGCG GATAAAGTTG CAGGACCACT TCTGCGCTCG GCCCTTCCGG CTGGCTGGTT TATTGCTGAT AAATCTGGAG
     ATTATCTGAC CTACCTCCGC CTATTTCAAC GTCCTGGTGA AGACGCGAGC CGGGAAGGCC GACCGACCAA ATAACGACTA TTTAGACCTC
```

FIG. 12 (cont'd)

CN1389 pAAV-hI56i(core)-minBG-SYFP2-WPRE3-BGHpA (JT)

```
                                     AmpR
             BsaI                  BmrI
3421  CCGGTGAGCG TGGGTCTCGC GGTATCATTG CAGCACTGGG GCCAGATGGT AAGCCCTCCC GTATCGTAGT TATCTACACG ACGGGGAGTC
      GGCCACTCGC ACCCAGAGCG CCATAGTAAC GTCGTGACCC CGGTCTACCA TTCGGGAGGG CATAGCATCA ATAGATGTGC TGCCCCTCAG
                                     AmpR
3511  AGGCAACTAT GGATGAACGA AATAGACAGA TCGCTGAGAT AGGTGCCTCA CTGATTAAGC ATTGGTAACT GTCAGACCAA GTTTACTCAT
      TCCGTTGATA CCTACTTGCT TTATCTGTCT AGCGACTCTA TCCACGGAGT GACTAATTCG TAACCATTGA CAGTCTGGTT CAAATGAGTA
3601  ATATACTTTA GATTGATTTA AAACTTCATT TTTAATTTAA AAGGATCTAG GTGAAGATCC TTTTTGATAA TCTCATGACC AAAATCCCTT
      TATATGAAAT CTAACTAAAT TTTGAAGTAA AAATTAAATT TTCCTAGATC CACTTCTAGG AAAAACTATT AGAGTACTGG TTTTAGGGAA
                                                              pUC ori
3691  AACGTGAGTT TTCGTTCCAC TGAGCGTCAG ACCCCGTAGA AAAGATCAAA GGATCTTCTT GAGATCCTTT TTTTCTGCGC GTAATCTGCT
      TTGCACTCAA AAGCAAGGTG ACTCGCAGTC TGGGGCATCT TTTCTAGTTT CCTAGAAGAA CTCTAGGAAA AAAAGACGCG CATTAGACGA
                                     pUC ori
3781  GCTTGCAAAC AAAAAAACCA CCGCTACCAG CGGTGGTTTG TTTGCCGGAT CAAGAGCTAC CAACTCTTTT TCCGAAGGTA ACTGGCTTCA
      CGAACGTTTG TTTTTTTGGT GGCGATGGTC GCCACCAAAC AAACGGCCTA GTTCTCGATG GTTGAGAAAA AGGCTTCCAT TGACCGAAGT
                                     pUC ori
3871  GCAGAGCGCA GATACCAAAT ACTGTCCTTC TAGTGTAGCC GTAGTTAGGC CACCACTTCA AGAACTCTGT AGCACCGCCT ACATACCTCG
      CGTCTCGCGT CTATGGTTTA TGACAGGAAG ATCACATCGG CATCAATCCG GTGGTGAAGT TCTTGAGACA TCGTGGCGGA TGTATGGAGC
                                     pUC ori
3961  CTCTGCTAAT CCTGTTACCA GTGGCTGCTG CCAGTGGCGA TAAGTCGTGT CTTACCGGGT TGGACTCAAG ACGATAGTTA CCGGATAAGG
      GAGACGATTA GGACAATGGT CACCGACGAC GGTCACCGCT ATTCAGCACA GAATGGCCCA ACCTGAGTTC TGCTATCAAT GGCCTATTCC
                                     pUC ori
4051  CGCAGCGGTC GGGCTGAACG GGGGGTTCGT GCACACAGCC CAGCTTGGAG CGAACGACCT ACACCGAACT GAGATACCTA CAGCGTGAGC
      GCGTCGCCAG CCCGACTTGC CCCCCAAGCA CGTGTGTCGG GTCGAACCTC GCTTGCTGGA TGTGGCTTGA CTCTATGGAT GTCGCACTCG
                                     pUC ori
4141  TATGAGAAAG CGCCACGCTT CCCGAAGGGA GAAAGGCGGA CAGGTATCCG GTAAGCGGCA GGGTCGGAAC AGGAGAGCGC ACGAGGGAGC
      ATACTCTTTC GCGGTGCGAA GGGCTTCCCT CTTTCCGCCT GTCCATAGGC CATTCGCCGT CCCAGCCTTG TCCTCTCGCG TGCTCCCTCG
                                     pUC ori
4231  TTCCAGGGGG AAACGCCTGG TATCTTTATA GTCCTGTCGG GTTTCGCCAC CTCTGACTTG AGCGTCGATT TTTGTGATGC TCGTCAGGGG
      AAGGTCCCCC TTTGCGGACC ATAGAAATAT CAGGACAGCC CAAAGCGGTG GAGACTGAAC TCGCAGCTAA AAACACTACG AGCAGTCCCC
                               pUC ori
                                                                                      PciI
4321  GGCGGAGCCT ATGGAAAAAC GCCAGCAACG CGGCCTTTTT ACGGTTCCTG GCCTTTTGCT GGCCTTTTGC TCACATGT (SEQ ID NO: 41)
      CCGCCTCGGA TACCTTTTTG CGGTCGTTGC GCCGGAAAAA TGCCAAGGAC CGGAAAACGA CCGGAAAACG AGTGTACA (SEQ ID NO: 95)
```

FIG. 13 (cont'd)

CN1390 pAAV-3xhI56i(core)-minBG-SYFP2-WPRE3-BGHpA (JT)

```
                                                   SYFP2
901   CTTCTTCAAG TCCGCCATGC CCGAAGGCTA CGTCCAGGAG CGCACCATCT TCTTCAAGGA CGACGGCAAC TACAAGACCC GCGCCGAGGT
      GAAGAAGTTC AGGCGGTACG GGCTTCCGAT GCAGGTCCTC GCGTGGTAGA AGAAGTTCCT GCTGCCGTTG ATGTTCTGGG CGCGGCTCCA

                                                   SYFP2
991   GAAGTTCGAG GGCGACACCC TGGTGAACCG CATCGAGCTG AAGGGCATCG ACTTCAAGGA GGACGGCAAC ATCCTGGGGC ACAAGCTGGA
      CTTCAAGCTC CCGCTGTGGG ACCACTTGGC GTAGCTCGAC TTCCCGTAGC TGAAGTTCCT CCTGCCGTTG TAGGACCCCG TGTTCGACCT

                                                   SYFP2
1081  GTACAACTAC AACAGCCACA ACGTCTATAT CACCGCCGAC AAGCAGAAGA ACGGCATCAA GGCCAACTTC AAGATCCGCC ACAACATCGA
      CATGTTGATG TTGTCGGTGT TGCAGATATA GTGGCGGCTG TTCGTCTTCT TGCCGTAGTT CCGGTTGAAG TTCTAGGCGG TGTTGTAGCT

                                                   SYFP2
1171  GGACGGCGGC GTGCAGCTCG CCGACCACTA CCAGCAGAAC ACCCCCATCG GCGACGGCCC CGTGCTGCTG CCCGACAACC ACTACCTGAG
      CCTGCCGCCG CACGTCGAGC GGCTGGTGAT GGTCGTCTTG TGGGGGTAGC CGCTGCCGGG GCACGACGAC GGGCTGTTGG TGATGGACTC

                                                   SYFP2
                  BlpI
1261  CTACCAGTCC AAGCTGAGCA AAGACCCCAA CGAGAAGCGC GATCACATGG TCCTGCTGGA GTTCGTGACC GCCGCCGGGA TCACTCTCGG
      GATGGTCAGG TTCGACTCGT TTCTGGGGTT GCTCTTCGCG CTAGTGTACC AGGACGACCT CAAGCACTGG CGGCGGCCCT AGTGAGAGCC

                 BsrGI        AccI                                                    gamma
             SYFP2                   AscI                    EcoRI                    WPRE3
                              SalI           SacII                 EcoRV
1351  CATGGACGAG CTGTACAAGT AAGTCGACGG CGCGCCGCGG CCGCGAATTC GATATCATAA TCAACCTCTG GATTACAAAA TTTGTGAAAG
      GTACCTGCTC GACATGTTCA TTCAGCTGCC GCGCGGCGCC GGCGCTTAAG CTATAGTATT AGTTGGAGAC CTAATGTTTT AAACACTTTC

                                                   gamma
                                                   WPRE3
1441  ATTGACTGGT ATTCTTAACT ATGTTGCTCC TTTTACGCTA TGTGGATACG CTGCTTTAAT GCCTTTGTAT CATGCTATTG CTTCCCGTAT
      TAACTGACCA TAAGAATTGA TACAACGAGG AAAATGCGAT ACACCTATGC GACGAAATTA CGGAAACATA GTACGATAAC GAAGGGCATA
                                                                                              WPRE3-R (JT)

                     gamma                                                  alpha
                                                   WPRE3
1531  GGCTTTCATT TTCTCCTCCT TGTATAAATC CTGGTTAGTT CTTGCCACGG CGGAACTCAT CGCCGCCTGC CTTGCCCGCT GCTGGACAGG
      CCGAAAGTAA AAGAGGAGGA ACATATTTAG GACCAATCAA GAACGGTGCC GCCTTGAGTA GCGGCGGACG GAACGGGCGA CGACCTGTCC
      WPRE3-R (JT)
```

FIG. 13 (cont'd)

CN1390 pAAV-3xAI561(core)-minBG-SYFP2-WPRE3-BGHpA (JT)

```
        sbha, WPRE3                                          BGH-pA
                                         XhoI, SalI
1621  GGCTCGGCTG TTGGGCACTG ACAATTCCGT GGCTCGAGAG ATCTTCGACT GTGCCTTCTA GTTGCCAGCC ATCTGTTGTT TGCCCCTCCC
      CCGAGCCGAC AACCCGTGAC TGTTAAGGCA CCGAGCTCTC TAGAAGCTGA CACGGAAGAT CAACGGTCGG TAGACAACAA ACGGGGAGGG

                                              BGH-pA
1711  CCGTGCCTTC CTTGACCCTG GAAGGTGCCA CTCCCACTGT CCTTTCCTAA TAAAATGAGG AAATTGCATC GCATTGTCTG AGTAGGTGTC
      GGCACGGAAG GAACTGGGAC CTTCCACGGT GAGGGTGACA GGAAAGGATT ATTTTACTCC TTTAACGTAG CGTAACAGAC TCATCCACAG
                                                                                      BGH-R

                                     BGH-pA
                                                         BbsI, BbvII                    PmlI
1801  ATTCTATTCT GGGGGGTGGG GTGGGGCAGG ACAGCAAGGG GGAGGATTGG GAAGACAATA GCAGGCATGA GATCTCACGT GCGGACCGAG
      TAAGATAAGA CCCCCCACCC CACCCCGTCC TGTCGTTCCC CCTCCTAACC CTTCTGTTAT CGTCCGTACT CTAGAGTGCA CGCCTGGCTC

                                                 R-ITR
1891  CGGCCGCAGG AACCCCTAGT GATGGAGTTG GCCACTCCCT CTCTGCGCGC TCGCTCGCTC ACTGAGGCCG GGCGACCAAA GGTCGCCCGA
      GCCGGCGTCC TTGGGGATCA CTACCTCAAC CGGTGAGGGA GAGACGCGCG AGCGAGCGAG TGACTCCGGC CCGCTGGTTT CCAGCGGGCT

                              R-ITR
                                                                KasI, NarI, SfoI, BbeI
1981  CGCCCGGGCT TTGCCCGGGC GGCCTCAGTG AGCGAGCGAG CGCGCAGCTG CCTGCAGGGG CGCCTGATGC GGTATTTTCT CCTTACGCAT
      GCGGGCCCGA AACGGGCCCG CCGGAGTCAC TCGCTCGCTC GCGCGTCGAC GGACGTCCCC GCGGACTACG CCATAAAAGA GGAATGCGTA

                                                                                 f1 Origin
2071  CTGTGCGGTA TTTCACACCG CATACGTCAA AGCAACCATA GTACGCGCCC TGTAGCGGCG CATTAAGCGC GGCGGGTGTG GTGGTTACGC
      GACACGCCAT AAAGTGTGGC GTATGCAGTT TCGTTGGTAT CATGCGCGGG ACATCGCCGC GTAATTCGCG CCGCCCACAC CACCAATGCG

                                            f1 Origin
                                                                                  NgoMIV, NaeI
2161  GCAGCGTGAC CGCTACACTT GCCAGCGCCC TAGCGCCCGC TCCTTTCGCT TTCTTCCCTT CCTTTCTCGC CACGTTCGCC GGCTTTCCCC
      CGTCGCACTG GCGATGTGAA CGGTCGCGGG ATCGCGGGCG AGGAAAGCGA AAGAAGGGAA GGAAAGAGCG GTGCAAGCGG CCGAAAGGGG

                                            f1 Origin
2251  GTCAAGCTCT AAATCGGGGG CTCCCTTTAG GGTTCCGATT TAGTGCTTTA CGGCACCTCG ACCCCAAAAA ACTTGATTTG GGTGATGGTT
      CAGTTCGAGA TTTAGCCCCC GAGGGAAATC CCAAGGCTAA ATCACGAAAT GCCGTGGAGC TGGGGTTTTT TGAACTAAAC CCACTACCAA
```

FIG. 13 (cont'd)

CN1390 pAAV-3xhI56i(core)-minBG-SYFP2-WPRE3-BGHpA (JT)

```
                                                        f1 Origin
2341  CACGTAGTGG GCCATCGCCC TGATAGACGG TTTTTCGCCC TTTGACGTTG GAGTCCACGT TCTTTAATAG TGGACTCTTG TTCCAAACTG
      GTGCATCACC CGGTAGCGGG ACTATCTGCC AAAAAGCGGG AAACTGCAAC CTCAGGTGCA AGAAATTATC ACCTGAGAAC AAGGTTTGAC

       f1 Origin                                 PsiI
2431  GAACAACACT CAACCCTATC TCGGGCTATT CTTTTGATTT ATAAGGGATT TTGCCGATTT CGGCCTATTG GTTAAAAAAT GAGCTGATTT
      CTTGTTGTGA GTTGGGATAG AGCCCGATAA GAAAACTAAA TATTCCCTAA AACGGCTAAA GCCGGATAAC CAATTTTTTA CTCGACTAAA

2521  AACAAAAATT TAACGCGAAT TTTAACAAAA TATTAACGTT TACAATTTTA TGGTGCACTC TCAGTACAAT CTGCTCTGAT GCCGCATAGT
      TTGTTTTTAA ATTGCGCTTA AAATTGTTTT ATAATTGCAA ATGTTAAAAT ACCACGTGAG AGTCATGTTA GACGAGACTA CGGCGTATCA

2611  TAAGCCAGCC CCGACACCCG CCAACACCCG CTGACGCGCC CTGACGGGCT TGTCTGCTCC CGGCATCCGC TTACAGACAA GCTGTGACCG
      ATTCGGTCGG GGCTGTGGGC GGTTGTGGGC GACTGCGCGG GACTGCCCGA ACAGACGAGG GCCGTAGGCG AATGTCTGTT CGACACTGGC

                                                                        EcoO109I
2701  TCTCCGGGAG CTGCATGTGT CAGAGGTTTT CACCGTCATC ACCGAAACGC GCGAGACGAA AGGGCCTCGT GATACGCCTA TTTTTATAGG
      AGAGGCCCTC GACGTACACA GTCTCCAAAA GTGGCAGTAG TGGCTTTGCG CGCTCTGCTT TCCCGGAGCA CTATGCGGAT AAAAATATCC

                                 ZraI
                                 AatII
2791  TTAATGTCAT GATAATAATG GTTTCTTAGA CGTCAGGTGG CACTTTTCGG GGAAATGTGC GCGGAACCCC TATTTGTTTA TTTTTCTAAA
      AATTACAGTA CTATTATTAC CAAAGAATCT GCAGTCCACC GTGAAAAGCC CCTTTACACG CGCCTTGGGG ATAAACAAAT AAAAAGATTT

                                                                                          AmpR
2881  TACATTCAAA TATGTATCCG CTCATGAGAC AATAACCCTG ATAAATGCTT CAATAATATT GAAAAAGGAA GAGTATGAGT ATTCAACATT
      ATGTAAGTTT ATACATAGGC GAGTACTCTG TTATTGGGAC TATTTACGAA GTTATTATAA CTTTTTCCTT CTCATACTCA TAAGTTGTAA
                                                                                EarI

                                                        AmpR
2971  TCCGTGTCGC CCTTATTCCC TTTTTTGCGG CATTTTGCCT TCCTGTTTTT GCTCACCCAG AAACGCTGGT GAAAGTAAAA GATGCTGAAG
      AGGCACAGCG GGAATAAGGG AAAAAACGCC GTAAAACGGA AGGACAAAAA CGAGTGGGTC TTTGCGACCA CTTTCATTTT CTACGACTTC

                                                        AmpR
3061  ATCAGTTGGG TGCACGAGTG GGTTACATCG AACTGGATCT CAACAGCGGT AAGATCCTTG AGAGTTTTCG CCCCGAAGAA CGTTTTCCAA
      TAGTCAACCC ACGTGCTCAC CCAATGTAGC TTGACCTAGA GTTGTCGCCA TTCTAGGAAC TCTCAAAAGC GGGGCTTCTT GCAAAAGGTT

                                                        AmpR
3151  TGATGAGCAC TTTTAAAGTT CTGCTATGTG GCGCGGTATT ATCCCGTATT GACGCCGGGC AAGAGCAACT CGGTCGCCGC ATACACTATT
      ACTACTCGTG AAAATTTCAA GACGATACAC CGCGCCATAA TAGGGCATAA CTGCGGCCCG TTCTCGTTGA GCCAGCGGCG TATGTGATAA

                                                        AmpR
                            ScaI
3241  CTCAGAATGA CTTGGTTGAG TACTCACCAG TCACAGAAAA GCATCTTACG GATGGCATGA CAGTAAGAGA ATTATGCAGT GCTGCCATAA
      GAGTCTTACT GAACCAACTC ATGAGTGGTC AGTGTCTTTT CGTAGAATGC CTACCGTACT GTCATTCTCT TAATACGTCA CGACGGTATT
```

FIG. 13 (cont'd)

CN1390 pAAV-3xhI56i(core)-minBG-SYFP2-WPRE3-BGHpA (JT)

```
                AmpR
                PvuI
3331  CCATGAGTGA TAACACTGCG GCCAACTTAC TTCTGACAAC GATCGGAGGA CCGAAGGAGC TAACCGCTTT TTTGCACAAC ATGGGGGATC
      GGTACTCACT ATTGTGACGC CGGTTGAATG AAGACTGTTG CTAGCCTCCT GGCTTCCTCG ATTGGCGAAA AAACGTGTTG TACCCCCTAG

                AmpR
3421  ATGTAACTCG CCTTGATCGT TGGGAACCGG AGCTGAATGA AGCCATACCA AACGACGAGC GTGACACCAC GATGCCTGTA GCAATGGCAA
      TACATTGAGC GGAACTAGCA ACCCTTGGCC TCGACTTACT TCGGTATGGT TTGCTGCTCG CACTGTGGTG CTACGGACAT CGTTACCGTT

                AmpR
                FspI  AseI
3511  CAACGTTGCG CAAACTATTA ACTGGCGAAC TACTTACTCT AGCTTCCCGG CAACAATTAA TAGACTGGAT GGAGGCGGAT AAAGTTGCAG
      GTTGCAACGC GTTTGATAAT TGACCGCTTG ATGAATGAGA TCGAAGGGCC GTTGTTAATT ATCTGACCTA CCTCCGCCTA TTTCAACGTC

                AmpR
                BsaI
3601  GACCACTTCT GCGCTCGGCC CTTCCGGCTG GCTGGTTTAT TGCTGATAAA TCTGGAGCCG GTGAGCGTGG GTCTCGCGGT ATCATTGCAG
      CTGGTGAAGA CGCGAGCCGG GAAGGCCGAC CGACCAAATA ACGACTATTT AGACCTCGGC CACTCGCACC CAGAGCGCCA TAGTAACGTC

                AmpR
                BmrI
3691  CACTGGGGCC AGATGGTAAG CCCTCCCGTA TCGTAGTTAT CTACACGACG GGGAGTCAGG CAACTATGGA TGAACGAAAT AGACAGATCG
      GTGACCCCGG TCTACCATTC GGGAGGGCAT AGCATCAATA GATGTGCTGC CCCTCAGTCC GTTGATACCT ACTTGCTTTA TCTGTCTAGC

                AmpR
3781  CTGAGATAGG TGCCTCACTG ATTAAGCATT GGTAACTGTC AGACCAAGTT TACTCATATA TACTTTAGAT TGATTTAAAA CTTCATTTTT
      GACTCTATCC ACGGAGTGAC TAATTCGTAA CCATTGACAG TCTGGTTCAA ATGAGTATAT ATGAAATCTA ACTAAATTTT GAAGTAAAAA

3871  AATTTAAAAG GATCTAGGTG AAGATCCTTT TTGATAATCT CATGACCAAA ATCCCTTAAC GTGAGTTTTC GTTCCACTGA GCGTCAGACC
      TTAAATTTTC CTAGATCCAC TTCTAGGAAA AACTATTAGA GTACTGGTTT TAGGGAATTG CACTCAAAAG CAAGGTGACT CGCAGTCTGG

                pUC ori
3961  CCGTAGAAAA GATCAAAGGA TCTTCTTGAG ATCCTTTTTT TCTGCGCGTA ATCTGCTGCT TGCAAACAAA AAAACCACCG CTACCAGCGG
      GGCATCTTTT CTAGTTTCCT AGAAGAACTC TAGGAAAAAA AGACGCGCAT TAGACGACGA ACGTTTGTTT TTTTGGTGGC GATGGTCGCC

                pUC ori
4051  TGGTTTGTTT GCCGGATCAA GAGCTACCAA CTCTTTTTCC GAAGGTAACT GGCTTCAGCA GAGCGCAGAT ACCAAATACT GTCCTTCTAG
      ACCAAACAAA CGGCCTAGTT CTCGATGGTT GAGAAAAAGG CTTCCATTGA CCGAAGTCGT CTCGCGTCTA TGGTTTATGA CAGGAAGATC

                pUC ori
4141  TGTAGCCGTA GTTAGGCCAC CACTTCAAGA ACTCTGTAGC ACCGCCTACA TACCTCGCTC TGCTAATCCT GTTACCAGTG GCTGCTGCCA
      ACATCGGCAT CAATCCGGTG GTGAAGTTCT TGAGACATCG TGGCGGATGT ATGGAGCGAG ACGATTAGGA CAATGGTCAC CGACGACGGT

                pUC ori
4231  GTGGCGATAA GTCGTGTCTT ACCGGGTTGG ACTCAAGACG ATAGTTACCG GATAAGGCGC AGCGGTCGGG CTGAACGGGG GGTTCGTGCA
      CACCGCTATT CAGCACAGAA TGGCCCAACC TGAGTTCTGC TATCAATGGC CTATTCCGCG TCGCCAGCCC GACTTGCCCC CCAAGCACGT
```

FIG. 13 (cont'd)

CN1390 pAAV-3xhI56i(core)-minBG-SYFP2-WPRE3-BGHpA (JT)

```
                                                  pUC ori
4321  CACAGCCCAG CTTGGAGCGA ACGACCTACA CCGAACTGAG ATACCTACAG CGTGAGCTAT GAGAAAGCGC CACGCTTCCC GAAGGGAGAA
      GTGTCGGGTC GAACCTCGCT TGCTGGATGT GGCTTGACTC TATGGATGTC GCACTCGATA CTCTTTCGCG GTGCGAAGGG CTTCCCTCTT
                                                  pUC ori
4411  AGGCGGACAG GTATCCGGTA AGCGGCAGGG TCGGAACAGG AGAGCGCACG AGGGAGCTTC CAGGGGGAAA CGCCTGGTAT CTTTATAGTC
      TCCGCCTGTC CATAGGCCAT TCGCCGTCCC AGCCTTGTCC TCTCGCGTGC TCCCTCGAAG GTCCCCCTTT GCGGACCATA GAAATATCAG
                                                  pUC ori
4501  CTGTCGGGTT TCGCCACCTC TGACTTGAGC GTCGATTTTT GTGATGCTCG TCAGGGGGGC GGAGCCTATG GAAAAACGCC AGCAACGCGG
      GACAGCCCAA AGCGGTGGAG ACTGAACTCG CAGCTAAAAA CACTACGAGC AGTCCCCCCG CCTCGGATAC CTTTTTGCGG TCGTTGCGCC
                    pUC ori
                                                  PciI
4591  CCTTTTTACG GTTCCTGGCC TTTTGCTGGC CTTTTGCTCA CATGT   (SEQ ID NO: 42)
      GGAAAAATGC CAAGGACCGG AAAACGACCG GAAAACGAGT GTACA   (SEQ ID NO: 96)
```

FIG. 14 (cont'd)

CR1203 scAAV-h156i-minBglobin-SYFP2-WPRE3-BGHpA (JT)

```
                                           hOlx I56i
631   AACCTTAAAT TGTCCCCAAT GTCTGCTTCA AATTGGATGG CACTGCAGCT GGAGGCTTTG TTCAGAATTG ATCCTGGGGA GCTACGAACC
      TTGGAATTTA ACAGGGGTTA CAGACGAAGT TTAACCTACC GTGACGTCGA CCTCCGAAAC AAGTCTTAAC TAGGACCCCT CGATGCTTGG
      I56i from Zerucha et al., 2000 in reverse from 14(                                        m/hDlx I56i-R (JT

                              TATA box                          transcriptional star   BamHI
        hDlx I56i                          Beta Globin minimal promoter                                BstBI
721   CAAAGTTTCA CAGTAGGGAG CTCGGGCTGG GCATAAAAGT CAGGGCAGAG CCATCTATTG CTTACATTTG CTTCTGGGAT CCAGATCTTT
      GTTTCAAAGT GTCATCCCTC GAGCCCGACC CGTATTTTCA GTCCCGTCTC GGTAGATAAC GAATGTAAAC GAAGACCCTA GGTCTAGAAA
        m/hDlx I56i-R (JT)

      BstBI   AfeI                                   SYFP2
         NheI
         BmtI     AgeI      NcoI
811   CGAAGCTAGC GCTACCGGTC GCCACCATGG TGAGCAAGGG CGAGGAGCTG TTCACCGGGG TGGTGCCCAT CCTGGTCGAG CTGGACGGCG
      GCTTCGATCG CGATGGCCAG CGGTGGTACC ACTCGTTCCC GCTCCTCGAC AAGTGGCCCC ACCACGGGTA GGACCAGCTC GACCTGCCGC

                                           SYFP2
901   ACGTAAACGG CCACAAGTTC AGCGTGTCCG GCGAGGGCGA GGGCGATGCC ACCTACGGCA AGCTGACCCT GAAGCTGATC TGCACCACCG
      TGCATTTGCC GGTGTTCAAG TCGCACAGGC CGCTCCCGCT CCCGCTACGG TGGATGCCGT TCGACTGGGA CTTCGACTAG ACGTGGTGGC

                                           SYFP2
991   GCAAGCTGCC CGTGCCCTGG CCCACCCTCG TGACCACCCT GGGCTACGGC GTGCAGTGCT TCGCCCGCTA CCCCGACCAC ATGAAGCAGC
      CGTTCGACGG GCACGGGACC GGGTGGGAGC ACTGGTGGGA CCCGATGCCG CACGTCACGA AGCGGGCGAT GGGGCTGGTG TACTTCGTCG

                                           SYFP2
1081  ACGACTTCTT CAAGTCCGCC ATGCCCGAAG GCTACGTCCA GGAGCGCACC ATCTTCTTCA AGGACGACGG CAACTACAAG ACCCGCGCCG
      TGCTGAAGAA GTTCAGGCGG TACGGGCTTC CGATGCAGGT CCTCGCGTGG TAGAAGAAGT TCCTGCTGCC GTTGATGTTC TGGGCGCGGC

                                           SYFP2
1171  AGGTGAAGTT CGAGGGCGAC ACCCTGGTGA ACCGCATCGA GCTGAAGGGC ATCGACTTCA AGGAGGACGG CAACATCCTG GGGCACAAGC
      TCCACTTCAA GCTCCCGCTG TGGGACCACT TGGCGTAGCT CGACTTCCCG TAGCTGAAGT TCCTCCTGCC GTTGTAGGAC CCCGTGTTCG

                                           SYFP2
1261  TGGAGTACAA CTACAACAGC CACAACGTCT ATATCACCGC CGACAAGCAG AAGAACGGCA TCAAGGCCAA CTTCAAGATC CGCCACAACA
      ACCTCATGTT GATGTTGTCG GTGTTGCAGA TATAGTGGCG GCTGTTCGTC TTCTTGCCGT AGTTCCGGTT GAAGTTCTAG GCGGTGTTGT

                                           SYFP2
1351  TCGAGGACGG CGGCGTGCAG CTCGCCGACC ACTACCAGCA GAACACCCCC ATCGGCGACG GCCCCGTGCT GCTGCCCGAC AACCACTACC
      AGCTCCTGCC GCCGCACGTC GAGCGGCTGG TGATGGTCGT CTTGTGGGGG TAGCCGCTGC CGGGGCACGA CGACGGGCTG TTGGTGATGG

                                           SYFP2
                 BlpI
1441  TGAGCTACCA GTCCAAGCTG AGCAAAGACC CCAACGAGAA GCGCGATCAC ATGGTCCTGC TGGAGTTCGT GACCGCCGCC GGGATCACTC
      ACTCGATGGT CAGGTTCGAC TCGTTTCTGG GGTTGCTCTT CGCGCTAGTG TACCAGGACG ACCTCAAGCA CTGGCGGCGG CCCTAGTGAG
```

FIG. 14 (cont'd)

CN1203 scAAV-hI56i-minBglobin-SYFP2-WPRE3-BGHpA (JT)

SYFP2 AscI WPRE3
NotI EcoRV
SacII
BsrGI EagI EcoRI

```
1531 TCGGCATGGA CGAGCTGTAC AAGTAAGTCG ACGGCGCGCC GCGGCCGCGA ATTCGATATC ATAATCAACC TCTGGATTAC AAAATTTGTG
     AGCCGTACCT GCTCGACATG TTCATTCAGC TGCCGCGCGG CGCCGGCGCT TAAGCTATAG TATTAGTTGG AGACCTAATG TTTTAAACAC
```

WPRE3

```
1621 AAAGATTGAC TGGTATTCTT AACTATGTTG CTCCTTTTAC GCTATGTGGA TACGCTGCTT TAATGCCTTT GTATCATGCT ATTGCTTCCC
     TTTCTAACTG ACCATAAGAA TTGATACAAC GAGGAAAATG CGATACACCT ATGCGACGAA ATTACGGAAA CATAGTACGA TAACGAAGGG
```

WPRE3

```
1711 GTATGGCTTT CATTTTCTCC TCCTTGTATA AATCCTGGTT AGTTCTTGCC ACGGCGGAAC TCATCGCCGC CTGCCTTGCC CGCTGCTGGA
     CATACCGAAA GTAAAAGAGG AGGAACATAT TTAGGACCAA TCAAGAACGG TGCCGCCTTG AGTAGCGGCG GACGGAACGG GCGACGACCT
```

WPRE3 BGH pA

```
1801 CAGGGGCTCG GCTGTTGGGC ACTGACAATT CCGTGGCTCG AGCGACTGTG CCTTCTAGTT GCCAGCCATC TGTTGTTTGC CCCTCCCCCG
     GTCCCCGAGC CGACAACCCG TGACTGTTAA GGCACCGAGC TCGCTGACAC GGAAGATCAA CGGTCGGTAG ACAACAAACG GGGAGGGGGC
```

BGH pA

```
1891 TGCCTTCCTT GACCCTGGAA GGTGCCACTC CCACTGTCCT TTCCTAATAA AATGAGGAAA TTGCATCGCA TTGTCTGAGT AGGTGTCATT
     ACGGAAGGAA CTGGGACCTT CCACGGTGAG GGTGACAGGA AAGGATTATT TTACTCCTTT AACGTAGCGT AACAGACTCA TCCACAGTAA
```

BGHpA-R (JT)

BGH pA R-ITRtrs
BbsI
Bbr7I SpeI

```
1981 CTATTCTGGG GGGTGGGGTG GGGCAGGACA GCAAGGGGGA GGATTGGGAA GACAATAGCA GGCATGACTA GTCCACTCCC TCTCTGCGCG
     GATAAGACCC CCCACCCCAC CCCGTCCTGT CGTTCCCCCT CCTAACCCTT CTGTTATCGT CCGTACTGAT CAGGTGAGGG AGAGACGCGC
```

R-ITRtrs

```
2071 CTCGCTCGCT CACTGAGGCC GGGCGACCAA AGGTCGCCCG ACGCCCGGGC TTTGCCCGGG CGGCCTCAGT GAGCGAGCGA GCGCGCAGAG
     GAGCGAGCGA GTGACTCCGG CCCGCTGGTT TCCAGCGGGC TGCGGGCCCG AAACGGGCCC GCCGGAGTCA CTCGCTCGCT CGCGCGTCTC
```

R-ITRtrs ApaI
PspOMI

```
2161 AGGGACAGAT CCGGGCCCGC ATGCGTCGAC AATTCACTGG CCGTCGTTTT ACAACGTCGT GACTGGGAAA ACCCTGGCGT TACCCAACTT
     TCCCTGTCTA GGCCCGGGCG TACGCAGCTG TTAAGTGACC GGCAGCAAAA TGTTGCAGCA CTGACCCTTT TGGGACCGCA ATGGGTTGAA
2251 AATCGCCTTG CAGCACATCC CCCTTTCGCC AGCTGGCGTA ATAGCGAAGA GGCCCGCACC GATCGCCCTT CCCAACAGTT GCGCAGCCTG
     TTAGCGGAAC GTCGTGTAGG GGGAAAGCGG TCGACCGCAT TATCGCTTCT CCGGGCGTGG CTAGCGGGAA GGGTTGTCAA CGCGTCGGAC
```

FIG. 14 (cont'd)

CN1203 scAAV~hI56i~minBglobin~SYFP2~WPRE3~BGHpA (JT)

KasI NarI SfoI BbeI (over GGCGCCTGAT); NdeI (over CGCATATGGT)

2341 AATGGCGAAT GGCGCCTGAT GCGGTATTTT CTCCTTACGC ATCTGTGCGG TATTTCACAC CGCATATGGT GCACTCTCAG TACAATCTGC
TTACCGCTTA CCGCGGACTA CGCCATAAAA GAGGAATGCG TAGACACGCC ATAAAGTGTG GCGTATACCA CGTGAGAGTC ATGTTAGACG

2431 TCTGATGCCG CATAGTTAAG CCAGCCCCGA CACCCGCCAA CACCCGCTGA CGCGCCCTGA CGGGCTTGTC TGCTCCCGGC ATCCGCTTAC
AGACTACGGC GTATCAATTC GGTCGGGGCT GTGGGCGGTT GTGGGCGACT GCGCGGGACT GCCCGAACAG ACGAGGGCCG TAGGCGAATG

2521 AGACAAGCTG TGACCGTCTC CGGGAGCTGC ATGTGTCAGA GGTTTTCACC GTCATCACCG AAACGCGCGA GACGAAAGGG CCTCGTGATA
TCTGTTCGAC ACTGGCAGAG GCCCTCGACG TACACAGTCT CCAAAAGTGG CAGTAGTGGC TTTGCGCGCT CTGCTTTCCC GGAGCACTAT

ZraI AatII (over CTTAGACGTC)

2611 CGCCTATTTT TATAGGTTAA TGTCATGATA ATAATGGTTT CTTAGACGTC AGGTGGCACT TTTCGGGGAA ATGTGCGCGG AACCCCTATT
GCGGATAAAA ATATCCAATT ACAGTACTAT TATTACCAAA GAATCTGCAG TCCACCGTGA AAAGCCCCTT TACACGCGCC TTGGGGATAA

SspI (over AATATTGAAA)

2701 TGTTTATTTT TCTAAATACA TTCAAATATG TATCCGCTCA TGAGACAATA ACCCTGATAA ATGCTTCAAT AATATTGAAA AAGGAAGAGT
ACAAATAAAA AGATTTATGT AAGTTTATAC ATAGGCGAGT ACTCTGTTAT TGGGACTATT TACGAAGTTA TTATAACTTT TTCCTTCTCA bla 2791 ATGAGTATTC AACATTTCCG TGTCGCCCTT ATTCCCTTTT TTGCGGCATT TTGCCTTCCT GTTTTTGCTC ACCCAGAAAC GCTGGTGAAA
TACTCATAAG TTGTAAAGGC ACAGCGGGAA TAAGGGAAAA AACGCCGTAA AACGGAAGGA CAAAAACGAG TGGGTCTTTG CGACCACTTT bla 2881 GTAAAAGATG CTGAAGATCA GTTGGGTGCA CGAGTGGGTT ACATCGAACT GGATCTCAAC AGCGGTAAGA TCCTTGAGAG TTTTCGCCCC
CATTTTCTAC GACTTCTAGT CAACCCACGT GCTCACCCAA TGTAGCTTGA CCTAGAGTTG TCGCCATTCT AGGAACTCTC AAAAGCGGGG bla 2971 GAAGAACGTT TTCCAATGAT GAGCACTTTT AAAGTTCTGC TATGTGGCGC GGTATTATCC CGTATTGACG CCGGGCAAGA GCAACTCGGT
CTTCTTGCAA AAGGTTACTA CTCGTGAAAA TTTCAAGACG ATACACCGCG CCATAATAGG GCATAACTGC GGCCCGTTCT CGTTGAGCCA bla ScaI (over GTTGAGTACT)

3061 CGCCGCATAC ACTATTCTCA GAATGACTTG GTTGAGTACT CACCAGTCAC AGAAAAGCAT CTTACGGATG GCATGACAGT AAGAGAATTA
GCGGCGTATG TGATAAGAGT CTTACTGAAC CAACTCATGA GTGGTCAGTG TCTTTTCGTA GAATGCCTAC CGTACTGTCA TTCTCTTAAT bla 3151 TGCAGTGCTG CCATAACCAT GAGTGATAAC ACTGCGGCCA ACTTACTTCT GACAACGATC GGAGGACCGA AGGAGCTAAC CGCTTTTTTG
ACGTCACGAC GGTATTGGTA CTCACTATTG TGACGCCGGT TGAATGAAGA CTGTTGCTAG CCTCCTGGCT TCCTCGATTG GCGAAAAAAC bla 3241 CACAACATGG GGGATCATGT AACTCGCCTT GATCGTTGGG AACCGGAGCT GAATGAAGCC ATACCAAACG ACGAGCGTGA CACCACGATG
GTGTTGTACC CCCTAGTACA TTGAGCGGAA CTAGCAACCC TTGGCCTCGA CTTACTTCGG TATGGTTTGC TGCTCGCACT GTGGTGCTAC

FIG. 14 (cont'd)

CR1203 scAAV-hI56i-minBglobin-SYFP2-WPRE3-BGHpA (JT)

```
                                     bla
3331  CCTGTAGCAA TGGCAACAAC GTTGCGCAAA CTATTAACTG GCGAACTACT TACTCTAGCT TCCCGGCAAC AATTAATAGA CTGGATGGAG
      GGACATCGTT ACCGTTGTTG CAACGCGTTT GATAATTGAC CGCTTGATGA ATGAGATCGA AGGGCCGTTG TTAATTATCT GACCTACCTC

                                     bla
                                                                                                BsaI
3421  GCGGATAAAG TTGCAGGACC ACTTCTGCGC TCGGCCCTTC CGGCTGGCTG GTTTATTGCT GATAAATCTG GAGCCGGTGA GCGTGGGTCT
      CGCCTATTTC AACGTCCTGG TGAAGACGCG AGCCGGGAAG GCCGACCGAC CAAATAACGA CTATTTAGAC CTCGGCCACT CGCACCCAGA

                                     bla
      BsaI
3511  CGCGGTATCA TTGCAGCACT GGGGCCAGAT GGTAAGCCCT CCCGTATCGT AGTTATCTAC ACGACGGGGA GTCAGGCAAC TATGGATGAA
      GCGCCATAGT AACGTCGTGA CCCCGGTCTA CCATTCGGGA GGGCATAGCA TCAATAGATG TGCTGCCCCT CAGTCCGTTG ATACCTACTT

                   bla
3601  CGAAATAGAC AGATCGCTGA GATAGGTGCC TCACTGATTA AGCATTGGTA ACTGTCAGAC CAAGTTTACT CATATATACT TTAGATTGAT
      GCTTTATCTG TCTAGCGACT CTATCCACGG AGTGACTAAT TCGTAACCAT TGACAGTCTG GTTCAAATGA GTATATATGA AATCTAACTA

3691  TTAAAACTTC ATTTTTAATT TAAAAGGATC TAGGTGAAGA TCCTTTTTGA TAATCTCATG ACCAAAATCC CTTAACGTGA GTTTTCGTTC
      AATTTTGAAG TAAAAATTAA ATTTTCCTAG ATCCACTTCT AGGAAAAACT ATTAGAGTAC TGGTTTTAGG GAATTGCACT CAAAAGCAAG

3781  CACTGAGCGT CAGACCCCGT AGAAAAGATC AAAGGATCTT CTTGAGATCC TTTTTTTCTG CGCGTAATCT GCTGCTTGCA AACAAAAAAA
      GTGACTCGCA GTCTGGGGCA TCTTTTCTAG TTTCCTAGAA GAACTCTAGG AAAAAAAGAC GCGCATTAGA CGACGAACGT TTGTTTTTTT

3871  CCACCGCTAC CAGCGGTGGT TTGTTTGCCG GATCAAGAGC TACCAACTCT TTTTCCGAAG GTAACTGGCT TCAGCAGAGC GCAGATACCA
      GGTGGCGATG GTCGCCACCA AACAAACGGC CTAGTTCTCG ATGGTTGAGA AAAAGGCTTC CATTGACCGA AGTCGTCTCG CGTCTATGGT

3961  AATACTGTTC TTCTAGTGTA GCCGTAGTTA GGCCACCACT TCAAGAACTC TGTAGCACCG CCTACATACC TCGCTCTGCT AATCCTGTTA
      TTATGACAAG AAGATCACAT CGGCATCAAT CCGGTGGTGA AGTTCTTGAG ACATCGTGGC GGATGTATGG AGCGAGACGA TTAGGACAAT

4051  CCAGTGGCTG CTGCCAGTGG CGATAAGTCG TGTCTTACCG GGTTGGACTC AAGACGATAG TTACCGGATA AGGCGCAGCG GTCGGGCTGA
      GGTCACCGAC GACGGTCACC GCTATTCAGC ACAGAATGGC CCAACCTGAG TTCTGCTATC AATGGCCTAT TCCGCGTCGC CAGCCCGACT

4141  ACGGGGGGTT CGTGCACACA GCCCAGCTTG GAGCGAACGA CCTACACCGA ACTGAGATAC CTACAGCGTG AGCTATGAGA AAGCGCCACG
      TGCCCCCCAA GCACGTGTGT CGGGTCGAAC CTCGCTTGCT GGATGTGGCT TGACTCTATG GATGTCGCAC TCGATACTCT TTCGCGGTGC

4231  CTTCCCGAAG GGAGAAAGGC GGACAGGTAT CCGGTAAGCG GCAGGGTCGG AACAGGAGAG CGCACGAGGG AGCTTCCAGG GGGAAACGCC
      GAAGGGCTTC CCTCTTTCCG CCTGTCCATA GGCCATTCGC CGTCCCAGCC TTGTCCTCTC GCGTGCTCCC TCGAAGGTCC CCCTTTGCGG

4321  TGGTATCTTT ATAGTCCTGT CGGGTTTCGC CACCTCTGAC TTGAGCGTCG ATTTTTGTGA TGCTCGTCAG GGGGGCGGAG CCTATGGAAA
      ACCATAGAAA TATCAGGACA GCCCAAAGCG GTGGAGACTG AACTCGCAGC TAAAAACACT ACGAGCAGTC CCCCCGCCTC GGATACCTTT

                                                          PciI
4411  AACGCCAGCA ACGCGGCCTT TTTACGGTTC CTGGCCTTTT GCTGGCCTTT TGCTCACATG TTCTTTCCTG CGTTATCCCC TGATTCTGTG
      TTGCGGTCGT TGCGCCGGAA AAATGCCAAG GACCGGAAAA CGACCGGAAA ACGAGTGTAC AAGAAAGGAC GCAATAGGGG ACTAAGACAC
```

FIG. 14 (cont'd)

CN1203 scAAV~h1561~minBglobin~SYFP2~WPRE3~BGHpA (JT)

```
4501  GATAACCGTA TTACCGCCTT TGAGTGAGCT GATACCGCTC GCCGCAGCCG AACGACCGAG CGCAGCGAGT CAGTGAGCGA GGAAGCGGAA
      CTATTGGCAT AATGGCGGAA ACTCACTCGA CTATGGCGAG CGGCGTCGGC TTGCTGGCTC GCGTCGCTCA GTCACTCGCT CCTTCGCCTT
                                                                                                 SapI
4591  GAGCGCCCAA TACGCAAACC GCCTCTCCCC GCGCGTTGGC CGATTCATTA ATGCAGCTGG CACGACAGGT TTCCCGACTG GAAAGCGGGC
      CTCGCGGGTT ATGCGTTTGG CGGAGAGGGG CGCGCAACCG GCTAAGTAAT TACGTCGACC GTGCTGTCCA AAGGGCTGAC CTTTCGCCCG
      SapI
4681  AGTGAGCGCA ACGCAATTAA TGTGAGTTAG CTCACTCATT AGGCACCCCA GGCTTTACAC TTTATGCTTC CGGCTCGTAT GTTGTGTGGA
      TCACTCGCGT TGCGTTAATT ACACTCAATC GAGTGAGTAA TCCGTGGGGT CCGAAATGTG AAATACGAAG GCCGAGCATA CAACACACCT
                                                                          XbaI
4771  ATTGTGAGCG GATAACAATT TCACACAGGA AACAGCTATG ACCATGATTA CGCCAAGCTC TCGAGATCTA G   (SEQ ID NO: 43)
      TAACACTCGC CTATTGTTAA AGTGTGTCCT TTGTCGATAC TGGTACTAAT GCGGTTCGAG AGCTCTAGAT C   (SEQ ID NO: 97)
```

FIG. 15

| Sequence Name | Enhancer & Promoter | Primary product(s) | Other components |
|---|---|---|---|
| CN1203 | hI56i<br>minBglobin | SYFP2 | WPRE3<br>BGHpA |
| CN1244 | hI56i<br>minBglobin | SYFP2 | WPRE3<br>BGHpA |
| CN1367 | hI56i<br>minBglobin | SYFP2<br>HisNavMs | P2A<br>WPRE3<br>BGHpA |
| CN1389 | hI56iCore<br>minBglobin | SYFP2 | WPRE3<br>BGHpA |
| CN1390 | 3XhI56iCore<br>minBglobin | SYFP2 | WPRE3<br>BGHpA |
| CN1498 | 3xhI56iCore<br>minCMV | SYFP2<br>NavBp | P2A<br>3xHA<br>WPRE3<br>BGHpA |
| CN1499 | 3xhI56iCore<br>minCMV | SYFP2<br>NavMs | P2A<br>3xHA<br>WPRE3<br>BGHpA |
| CN1500 | 3xhI56iCore<br>minCMV | SYFP2<br>NavSheP<br>D60N | P2A<br>3xHA<br>WPRE3<br>BGHpA |
| CN1838 | 3XzI46i<br>minBG | SYFP2 | WPRE3<br>SPA |

FIG. 16

| | | | |
|---|---|---|---|
| *-minB-BFP-W | *-H68-FP-T2A-enz-W | *-CMV-FP-I2-enz-W | *-mut-luc-E2A-enz-W |
| *-minB-CFP-W | *-H68-FP-T2A-TF-W | *-CMV-FP-I2-TF-W | *-mut-luc-E2A-TF-W |
| *-minB-GFP-W | *-H68-FP-T2A-rec-W | *-CMV-FP-I2-rec-W | *-mut-luc-E2A-rec-W |
| *-minB-OFP-W | *-H68-FP-T2A-CTP-W | *-CMV-FP-I2-CTP-W | *-mut-luc-E2A-CTP-W |
| *-minB-RFP-W | *-H68-FP-T2A-SM-W | *-CMV-FP-I2-SM-W | *-mut-luc-E2A-SM-W |
| *-minB-fRFP-W | *-H68-FP-T2A-NT-W | *-CMV-FP-I2-NT-W | *-mut-luc-E2A-NT-W |
| *-minB-YFP-W | *-H68-FP-T2A-CR-W | *-CMV-FP-I2-CR-W | *-mut-luc-E2A-CR-W |
| *-minB-Luc-W | *-H68-FP-T2A-chR-W | *-CMV-FP-I2-chR-W | *-mut-luc-E2A-chR-W |
| *-minC-BFP-W | *-H68-FP-T2A-gRNA-W | *-CMV-FP-I2-gRNA-W | *-mut-luc-E2A-gRNA-W |
| *-minC-CFP-W | *-H68-FP-T2A-Nuc-W | *-CMV-FP-I2-Nuc-W | *-mut-luc-E2A-Nuc-W |
| *-minC-GFP-W | *-RSV-FP-T2A-enz-W | *-SV40-FP-I2-enz-W | *-minR-luc-E2A-enz-W |
| *-minC-OFP-W | *-RSV-FP-T2A-TF-W | *-SV40-FP-I2-TF-W | *-minR-luc-E2A-TF-W |
| *-minC-RFP-W | *-RSV-FP-T2A-rec-W | *-SV40-FP-I2-rec-W | *-minR-luc-E2A-rec-W |
| *-minC-fRFP-W | *-RSV-FP-T2A-CTP-W | *-SV40-FP-I2-CTP-W | *-minR-luc-E2A-CTP-W |
| *-minC-YFP-W | *-RSV-FP-T2A-SM-W | *-SV40-FP-I2-SM-W | *-minR-luc-E2A-SM-W |
| *-minC-Luc-W | *-RSV-FP-T2A-NT-W | *-SV40-FP-I2-NT-W | *-minR-luc-E2A-NT-W |
| *-mut-BFP-W | *-RSV-FP-T2A-CR-W | *-SV40-FP-I2-CR-W | *-minR-luc-E2A-CR-W |
| *-mut-CFP-W | *-RSV-FP-T2A-chR-W | *-SV40-FP-I2-chR-W | *-minR-luc-E2A-chR-W |
| *-mut-GFP-W | *-RSV-FP-T2A-gRNA-W | *-SV40-FP-I2-gRNA-W | *-minR-luc-E2A-gRNA-W |
| *-mut-OFP-W | *-RSV-FP-T2A-Nuc-W | *-SV40-FP-I2-Nuc-W | *-minR-luc-E2A-Nuc-W |
| *-mut-RFP-W | *-minB-FP-T2A-enz-bG | *-H68-FP-I2-enz-W | *-CMV-luc-E2A-enz-W |
| *-mut-fRFP-W | *-minB-FP-T2A-TF-bG | *-H68-FP-I2-TF-W | *-CMV-luc-E2A-TF-W |
| *-mut-YFP-W | *-minB-FP-T2A-rec-bG | *-H68-FP-I2-rec-W | *-CMV-luc-E2A-rec-W |
| *-mut-Luc-W | *-minB-FP-T2A-CTP-bG | *-H68-FP-I2-CTP-W | *-CMV-luc-E2A-CTP-W |
| *-minR-BFP-W | *-minB-FP-T2A-SM-bG | *-H68-FP-I2-SM-W | *-CMV-luc-E2A-SM-W |
| *-minR-CFP-W | *-minB-FP-T2A-NT-bG | *-H68-FP-I2-NT-W | *-CMV-luc-E2A-NT-W |
| *-minR-GFP-W | *-minB-FP-T2A-CR-bG | *-H68-FP-I2-CR-W | *-CMV-luc-E2A-CR-W |
| *-minR-OFP-W | *-minB-FP-T2A-chR-bG | *-H68-FP-I2-chR-W | *-CMV-luc-E2A-chR-W |
| *-minR-RFP-W | *-minB-FP-T2A-gRNA-bG | *-H68-FP-I2-gRNA-W | *-CMV-luc-E2A-gRNA-W |
| *-minR-fRFP-W | *-minB-FP-T2A-Nuc-bG | *-H68-FP-I2-Nuc-W | *-CMV-luc-E2A-Nuc-W |
| *-minR-YFP-W | *-minC-FP-T2A-enz-bG | *-RSV-FP-I2-enz-W | *-SV40-luc-E2A-enz-W |
| *-minR-Luc-W | *-minC-FP-T2A-TF-bG | *-RSV-FP-I2-TF-W | *-SV40-luc-E2A-TF-W |
| *-CMV-BFP-W | *-minC-FP-T2A-rec-bG | *-RSV-FP-I2-rec-W | *-SV40-luc-E2A-rec-W |

FIG. 16 cont'd

| | | | |
|---|---|---|---|
| *-CMV-CFP-W | *-minC-FP-T2A-CTP-bG | *-RSV-FP-I2-CTP-W | *-SV40-luc-E2A-CTP-W |
| *-CMV-GFP-W | *-minC-FP-T2A-SM-bG | *-RSV-FP-I2-SM-W | *-SV40-luc-E2A-SM-W |
| *-CMV-OFP-W | *-minC-FP-T2A-NT-bG | *-RSV-FP-I2-NT-W | *-SV40-luc-E2A-NT-W |
| *-CMV-RFP-W | *-minC-FP-T2A-CR-bG | *-RSV-FP-I2-CR-W | *-SV40-luc-E2A-CR-W |
| *-CMV-fRFP-W | *-minC-FP-T2A-chR-bG | *-RSV-FP-I2-chR-W | *-SV40-luc-E2A-chR-W |
| *-CMV-YFP-W | *-minC-FP-T2A-gRNA-bG | *-RSV-FP-I2-gRNA-W | *-SV40-luc-E2A-gRNA-W |
| *-CMV-Luc-W | *-minC-FP-T2A-Nuc-bG | *-RSV-FP-I2-Nuc-W | *-SV40-luc-E2A-Nuc-W |
| *-SV40-BFP-W | *-mut-FP-T2A-enz-bG | *-minB-FP-I2-enz-bG | *-H68-luc-E2A-enz-W |
| *-SV40-CFP-W | *-mut-FP-T2A-TF-bG | *-minB-FP-I2-TF-bG | *-H68-luc-E2A-TF-W |
| *-SV40-GFP-W | *-mut-FP-T2A-rec-bG | *-minB-FP-I2-rec-bG | *-H68-luc-E2A-rec-W |
| *-SV40-OFP-W | *-mut-FP-T2A-CTP-bG | *-minB-FP-I2-CTP-bG | *-H68-luc-E2A-CTP-W |
| *-SV40-RFP-W | *-mut-FP-T2A-SM-bG | *-minB-FP-I2-SM-bG | *-H68-luc-E2A-SM-W |
| *-SV40-fRFP-W | *-mut-FP-T2A-NT-bG | *-minB-FP-I2-NT-bG | *-H68-luc-E2A-NT-W |
| *-SV40-YFP-W | *-mut-FP-T2A-CR-bG | *-minB-FP-I2-CR-bG | *-H68-luc-E2A-CR-W |
| *-SV40-Luc-W | *-mut-FP-T2A-chR-bG | *-minB-FP-I2-chR-bG | *-H68-luc-E2A-chR-W |
| *-H68-BFP-W | *-mut-FP-T2A-gRNA-bG | *-minB-FP-I2-gRNA-bG | *-H68-luc-E2A-gRNA-W |
| *-H68-CFP-W | *-mut-FP-T2A-Nuc-bG | *-minB-FP-I2-Nuc-bG | *-H68-luc-E2A-Nuc-W |
| *-H68-GFP-W | *-minR-FP-T2A-enz-bG | *-minC-FP-I2-enz-bG | *-RSV-luc-E2A-enz-W |
| *-H68-OFP-W | *-minR-FP-T2A-TF-bG | *-minC-FP-I2-TF-bG | *-RSV-luc-E2A-TF-W |
| *-H68-RFP-W | *-minR-FP-T2A-rec-bG | *-minC-FP-I2-rec-bG | *-RSV-luc-E2A-rec-W |
| *-H68-fRFP-W | *-minR-FP-T2A-CTP-bG | *-minC-FP-I2-CTP-bG | *-RSV-luc-E2A-CTP-W |
| *-H68-YFP-W | *-minR-FP-T2A-SM-bG | *-minC-FP-I2-SM-bG | *-RSV-luc-E2A-SM-W |
| *-H68-Luc-W | *-minR-FP-T2A-NT-bG | *-minC-FP-I2-NT-bG | *-RSV-luc-E2A-NT-W |
| *-RSV-BFP-W | *-minR-FP-T2A-CR-bG | *-minC-FP-I2-CR-bG | *-RSV-luc-E2A-CR-W |
| *-RSV-CFP-W | *-minR-FP-T2A-chR-bG | *-minC-FP-I2-chR-bG | *-RSV-luc-E2A-chR-W |
| *-RSV-GFP-W | *-minR-FP-T2A-gRNA-bG | *-minC-FP-I2-gRNA-bG | *-RSV-luc-E2A-gRNA-W |
| *-RSV-OFP-W | *-minR-FP-T2A-Nuc-bG | *-minC-FP-I2-Nuc-bG | *-RSV-luc-E2A-Nuc-W |
| *-RSV-RFP-W | *-CMV-FP-T2A-enz-bG | *-mut-FP-I2-enz-bG | *-minB-luc-E2A-enz-bG |
| *-RSV-fRFP-W | *-CMV-FP-T2A-TF-bG | *-mut-FP-I2-TF-bG | *-minB-luc-E2A-TF-bG |
| *-RSV-YFP-W | *-CMV-FP-T2A-rec-bG | *-mut-FP-I2-rec-bG | *-minB-luc-E2A-rec-bG |
| *-RSV-Luc-W | *-CMV-FP-T2A-CTP-bG | *-mut-FP-I2-CTP-bG | *-minB-luc-E2A-CTP-bG |
| *-minB-BFP-S | *-CMV-FP-T2A-SM-bG | *-mut-FP-I2-SM-bG | *-minB-luc-E2A-SM-bG |
| *-minB-CFP-S | *-CMV-FP-T2A-NT-bG | *-mut-FP-I2-NT-bG | *-minB-luc-E2A-NT-bG |
| *-minB-GFP-S | *-CMV-FP-T2A-CR-bG | *-mut-FP-I2-CR-bG | *-minB-luc-E2A-CR-bG |

FIG. 16 cont'd

| | | | |
|---|---|---|---|
| *-minB-OFP-S | *-CMV-FP-T2A-chR-bG | *-mut-FP-I2-chR-bG | *-minB-luc-E2A-chR-bG |
| *-minB-RFP-S | *-CMV-FP-T2A-gRNA-bG | *-mut-FP-I2-gRNA-bG | *-minB-luc-E2A-gRNA-bG |
| *-minB-fRFP-S | *-CMV-FP-T2A-Nuc-bG | *-mut-FP-I2-Nuc-bG | *-minB-luc-E2A-Nuc-bG |
| *-minB-YFP-S | *-SV40-FP-T2A-enz-bG | *-minR-FP-I2-enz-bG | *-minC-luc-E2A-enz-bG |
| *-minB-Luc-S | *-SV40-FP-T2A-TF-bG | *-minR-FP-I2-TF-bG | *-minC-luc-E2A-TF-bG |
| *-minC-BFP-S | *-SV40-FP-T2A-rec-bG | *-minR-FP-I2-rec-bG | *-minC-luc-E2A-rec-bG |
| *-minC-CFP-S | *-SV40-FP-T2A-CTP-bG | *-minR-FP-I2-CTP-bG | *-minC-luc-E2A-CTP-bG |
| *-minC-GFP-S | *-SV40-FP-T2A-SM-bG | *-minR-FP-I2-SM-bG | *-minC-luc-E2A-SM-bG |
| *-minC-OFP-S | *-SV40-FP-T2A-NT-bG | *-minR-FP-I2-NT-bG | *-minC-luc-E2A-NT-bG |
| *-minC-RFP-S | *-SV40-FP-T2A-CR-bG | *-minR-FP-I2-CR-bG | *-minC-luc-E2A-CR-bG |
| *-minC-fRFP-S | *-SV40-FP-T2A-chR-bG | *-minR-FP-I2-chR-bG | *-minC-luc-E2A-chR-bG |
| *-minC-YFP-S | *-SV40-FP-T2A-gRNA-bG | *-minR-FP-I2-gRNA-bG | *-minC-luc-E2A-gRNA-bG |
| *-minC-Luc-S | *-SV40-FP-T2A-Nuc-bG | *-minR-FP-I2-Nuc-bG | *-minC-luc-E2A-Nuc-bG |
| *-mut-BFP-S | *-H68-FP-T2A-enz-bG | *-CMV-FP-I2-enz-bG | *-mut-luc-E2A-enz-bG |
| *-mut-CFP-S | *-H68-FP-T2A-TF-bG | *-CMV-FP-I2-TF-bG | *-mut-luc-E2A-TF-bG |
| *-mut-GFP-S | *-H68-FP-T2A-rec-bG | *-CMV-FP-I2-rec-bG | *-mut-luc-E2A-rec-bG |
| *-mut-OFP-S | *-H68-FP-T2A-CTP-bG | *-CMV-FP-I2-CTP-bG | *-mut-luc-E2A-CTP-bG |
| *-mut-RFP-S | *-H68-FP-T2A-SM-bG | *-CMV-FP-I2-SM-bG | *-mut-luc-E2A-SM-bG |
| *-mut-fRFP-S | *-H68-FP-T2A-NT-bG | *-CMV-FP-I2-NT-bG | *-mut-luc-E2A-NT-bG |
| *-mut-YFP-S | *-H68-FP-T2A-CR-bG | *-CMV-FP-I2-CR-bG | *-mut-luc-E2A-CR-bG |
| *-mut-Luc-S | *-H68-FP-T2A-chR-bG | *-CMV-FP-I2-chR-bG | *-mut-luc-E2A-chR-bG |
| *-minR-BFP-S | *-H68-FP-T2A-gRNA-bG | *-CMV-FP-I2-gRNA-bG | *-mut-luc-E2A-gRNA-bG |
| *-minR-CFP-S | *-H68-FP-T2A-Nuc-bG | *-CMV-FP-I2-Nuc-bG | *-mut-luc-E2A-Nuc-bG |
| *-minR-GFP-S | *-RSV-FP-T2A-enz-bG | *-SV40-FP-I2-enz-bG | *-minR-luc-E2A-enz-bG |
| *-minR-OFP-S | *-RSV-FP-T2A-TF-bG | *-SV40-FP-I2-TF-bG | *-minR-luc-E2A-TF-bG |
| *-minR-RFP-S | *-RSV-FP-T2A-rec-bG | *-SV40-FP-I2-rec-bG | *-minR-luc-E2A-rec-bG |
| *-minR-fRFP-S | *-RSV-FP-T2A-CTP-bG | *-SV40-FP-I2-CTP-bG | *-minR-luc-E2A-CTP-bG |
| *-minR-YFP-S | *-RSV-FP-T2A-SM-bG | *-SV40-FP-I2-SM-bG | *-minR-luc-E2A-SM-bG |
| *-minR-Luc-S | *-RSV-FP-T2A-NT-bG | *-SV40-FP-I2-NT-bG | *-minR-luc-E2A-NT-bG |
| *-CMV-BFP-S | *-RSV-FP-T2A-CR-bG | *-SV40-FP-I2-CR-bG | *-minR-luc-E2A-CR-bG |
| *-CMV-CFP-S | *-RSV-FP-T2A-chR-bG | *-SV40-FP-I2-chR-bG | *-minR-luc-E2A-chR-bG |
| *-CMV-GFP-S | *-RSV-FP-T2A-gRNA-bG | *-SV40-FP-I2-gRNA-bG | *-minR-luc-E2A-gRNA-bG |
| *-CMV-OFP-S | *-RSV-FP-T2A-Nuc-bG | *-SV40-FP-I2-Nuc-bG | *-minR-luc-E2A-Nuc-bG |
| *-CMV-RFP-S | *-minB-FP-T2A-enz-S | *-H68-FP-I2-enz-bG | *-CMV-luc-E2A-enz-bG |

FIG. 16 cont'd

| | | | |
|---|---|---|---|
| *-CMV-fRFP-S | *-minB-FP-T2A-TF-S | *-H68-FP-I2-TF-bG | *-CMV-luc-E2A-TF-bG |
| *-CMV-YFP-S | *-minB-FP-T2A-rec-S | *-H68-FP-I2-rec-bG | *-CMV-luc-E2A-rec-bG |
| *-CMV-Luc-S | *-minB-FP-T2A-CTP-S | *-H68-FP-I2-CTP-bG | *-CMV-luc-E2A-CTP-bG |
| *-SV40-BFP-S | *-minB-FP-T2A-SM-S | *-H68-FP-I2-SM-bG | *-CMV-luc-E2A-SM-bG |
| *-SV40-CFP-S | *-minB-FP-T2A-NT-S | *-H68-FP-I2-NT-bG | *-CMV-luc-E2A-NT-bG |
| *-SV40-GFP-S | *-minB-FP-T2A-CR-S | *-H68-FP-I2-CR-bG | *-CMV-luc-E2A-CR-bG |
| *-SV40-OFP-S | *-minB-FP-T2A-chR-S | *-H68-FP-I2-chR-bG | *-CMV-luc-E2A-chR-bG |
| *-SV40-RFP-S | *-minB-FP-T2A-gRNA-S | *-H68-FP-I2-gRNA-bG | *-CMV-luc-E2A-gRNA-bG |
| *-SV40-fRFP-S | *-minB-FP-T2A-Nuc-S | *-H68-FP-I2-Nuc-bG | *-CMV-luc-E2A-Nuc-bG |
| *-SV40-YFP-S | *-minC-FP-T2A-enz-S | *-RSV-FP-I2-enz-bG | *-SV40-luc-E2A-enz-bG |
| *-SV40-Luc-S | *-minC-FP-T2A-TF-S | *-RSV-FP-I2-TF-bG | *-SV40-luc-E2A-TF-bG |
| *-H68-BFP-S | *-minC-FP-T2A-rec-S | *-RSV-FP-I2-rec-bG | *-SV40-luc-E2A-rec-bG |
| *-H68-CFP-S | *-minC-FP-T2A-CTP-S | *-RSV-FP-I2-CTP-bG | *-SV40-luc-E2A-CTP-bG |
| *-H68-GFP-S | *-minC-FP-T2A-SM-S | *-RSV-FP-I2-SM-bG | *-SV40-luc-E2A-SM-bG |
| *-H68-OFP-S | *-minC-FP-T2A-NT-S | *-RSV-FP-I2-NT-bG | *-SV40-luc-E2A-NT-bG |
| *-H68-RFP-S | *-minC-FP-T2A-CR-S | *-RSV-FP-I2-CR-bG | *-SV40-luc-E2A-CR-bG |
| *-H68-fRFP-S | *-minC-FP-T2A-chR-S | *-RSV-FP-I2-chR-bG | *-SV40-luc-E2A-chR-bG |
| *-H68-YFP-S | *-minC-FP-T2A-gRNA-S | *-RSV-FP-I2-gRNA-bG | *-SV40-luc-E2A-gRNA-bG |
| *-H68-Luc-S | *-minC-FP-T2A-Nuc-S | *-RSV-FP-I2-Nuc-bG | *-SV40-luc-E2A-Nuc-bG |
| *-RSV-BFP-S | *-mut-FP-T2A-enz-S | *-minB-FP-I2-enz-S | *-H68-luc-E2A-enz-bG |
| *-RSV-CFP-S | *-mut-FP-T2A-TF-S | *-minB-FP-I2-TF-S | *-H68-luc-E2A-TF-bG |
| *-RSV-GFP-S | *-mut-FP-T2A-rec-S | *-minB-FP-I2-rec-S | *-H68-luc-E2A-rec-bG |
| *-RSV-OFP-S | *-mut-FP-T2A-CTP-S | *-minB-FP-I2-CTP-S | *-H68-luc-E2A-CTP-bG |
| *-RSV-RFP-S | *-mut-FP-T2A-SM-S | *-minB-FP-I2-SM-S | *-H68-luc-E2A-SM-bG |
| *-RSV-fRFP-S | *-mut-FP-T2A-NT-S | *-minB-FP-I2-NT-S | *-H68-luc-E2A-NT-bG |
| *-RSV-YFP-S | *-mut-FP-T2A-CR-S | *-minB-FP-I2-CR-S | *-H68-luc-E2A-CR-bG |
| *-RSV-Luc-S | *-mut-FP-T2A-chR-S | *-minB-FP-I2-chR-S | *-H68-luc-E2A-chR-bG |
| *-minB-BFP-W-S | *-mut-FP-T2A-gRNA-S | *-minB-FP-I2-gRNA-S | *-H68-luc-E2A-gRNA-bG |
| *-minB-CFP-W-S | *-mut-FP-T2A-Nuc-S | *-minB-FP-I2-Nuc-S | *-H68-luc-E2A-Nuc-bG |
| *-minB-GFP-W-S | *-minR-FP-T2A-enz-S | *-minC-FP-I2-enz-S | *-RSV-luc-E2A-enz-bG |
| *-minB-OFP-W-S | *-minR-FP-T2A-TF-S | *-minC-FP-I2-TF-S | *-RSV-luc-E2A-TF-bG |
| *-minB-RFP-W-S | *-minR-FP-T2A-rec-S | *-minC-FP-I2-rec-S | *-RSV-luc-E2A-rec-bG |
| *-minB-fRFP-W-S | *-minR-FP-T2A-CTP-S | *-minC-FP-I2-CTP-S | *-RSV-luc-E2A-CTP-bG |
| *-minB-YFP-W-S | *-minR-FP-T2A-SM-S | *-minC-FP-I2-SM-S | *-RSV-luc-E2A-SM-bG |

FIG. 16 cont'd

| | | | |
|---|---|---|---|
| *-minB-Luc-W-S | *-minR-FP-T2A-NT-S | *-minC-FP-I2-NT-S | *-RSV-luc-E2A-NT-bG |
| *-minC-BFP-W-S | *-minR-FP-T2A-CR-S | *-minC-FP-I2-CR-S | *-RSV-luc-E2A-CR-bG |
| *-minC-CFP-W-S | *-minR-FP-T2A-chR-S | *-minC-FP-I2-chR-S | *-RSV-luc-E2A-chR-bG |
| *-minC-GFP-W-S | *-minR-FP-T2A-gRNA-S | *-minC-FP-I2-gRNA-S | *-RSV-luc-E2A-gRNA-bG |
| *-minC-OFP-W-S | *-minR-FP-T2A-Nuc-S | *-minC-FP-I2-Nuc-S | *-RSV-luc-E2A-Nuc-bG |
| *-minC-RFP-W-S | *-CMV-FP-T2A-enz-S | *-mut-FP-I2-enz-S | *-minB-luc-E2A-enz-S |
| *-minC-fRFP-W-S | *-CMV-FP-T2A-TF-S | *-mut-FP-I2-TF-S | *-minB-luc-E2A-TF-S |
| *-minC-YFP-W-S | *-CMV-FP-T2A-rec-S | *-mut-FP-I2-rec-S | *-minB-luc-E2A-rec-S |
| *-minC-Luc-W-S | *-CMV-FP-T2A-CTP-S | *-mut-FP-I2-CTP-S | *-minB-luc-E2A-CTP-S |
| *-mut-BFP-W-S | *-CMV-FP-T2A-SM-S | *-mut-FP-I2-SM-S | *-minB-luc-E2A-SM-S |
| *-mut-CFP-W-S | *-CMV-FP-T2A-NT-S | *-mut-FP-I2-NT-S | *-minB-luc-E2A-NT-S |
| *-mut-GFP-W-S | *-CMV-FP-T2A-CR-S | *-mut-FP-I2-CR-S | *-minB-luc-E2A-CR-S |
| *-mut-OFP-W-S | *-CMV-FP-T2A-chR-S | *-mut-FP-I2-chR-S | *-minB-luc-E2A-chR-S |
| *-mut-RFP-W-S | *-CMV-FP-T2A-gRNA-S | *-mut-FP-I2-gRNA-S | *-minB-luc-E2A-gRNA-S |
| *-mut-fRFP-W-S | *-CMV-FP-T2A-Nuc-S | *-mut-FP-I2-Nuc-S | *-minB-luc-E2A-Nuc-S |
| *-mut-YFP-W-S | *-SV40-FP-T2A-enz-S | *-minR-FP-I2-enz-S | *-minC-luc-E2A-enz-S |
| *-mut-Luc-W-S | *-SV40-FP-T2A-TF-S | *-minR-FP-I2-TF-S | *-minC-luc-E2A-TF-S |
| *-minR-BFP-W-S | *-SV40-FP-T2A-rec-S | *-minR-FP-I2-rec-S | *-minC-luc-E2A-rec-S |
| *-minR-CFP-W-S | *-SV40-FP-T2A-CTP-S | *-minR-FP-I2-CTP-S | *-minC-luc-E2A-CTP-S |
| *-minR-GFP-W-S | *-SV40-FP-T2A-SM-S | *-minR-FP-I2-SM-S | *-minC-luc-E2A-SM-S |
| *-minR-OFP-W-S | *-SV40-FP-T2A-NT-S | *-minR-FP-I2-NT-S | *-minC-luc-E2A-NT-S |
| *-minR-RFP-W-S | *-SV40-FP-T2A-CR-S | *-minR-FP-I2-CR-S | *-minC-luc-E2A-CR-S |
| *-minR-fRFP-W-S | *-SV40-FP-T2A-chR-S | *-minR-FP-I2-chR-S | *-minC-luc-E2A-chR-S |
| *-minR-YFP-W-S | *-SV40-FP-T2A-gRNA-S | *-minR-FP-I2-gRNA-S | *-minC-luc-E2A-gRNA-S |
| *-minR-Luc-W-S | *-SV40-FP-T2A-Nuc-S | *-minR-FP-I2-Nuc-S | *-minC-luc-E2A-Nuc-S |
| *-minB-BFP-bG | *-H68-FP-T2A-enz-S | *-CMV-FP-I2-enz-S | *-mut-luc-E2A-enz-S |
| *-minB-CFP-bG | *-H68-FP-T2A-TF-S | *-CMV-FP-I2-TF-S | *-mut-luc-E2A-TF-S |
| *-minB-GFP-bG | *-H68-FP-T2A-rec-S | *-CMV-FP-I2-rec-S | *-mut-luc-E2A-rec-S |
| *-minB-OFP-bG | *-H68-FP-T2A-CTP-S | *-CMV-FP-I2-CTP-S | *-mut-luc-E2A-CTP-S |
| *-minB-RFP-bG | *-H68-FP-T2A-SM-S | *-CMV-FP-I2-SM-S | *-mut-luc-E2A-SM-S |
| *-minB-fRFP-bG | *-H68-FP-T2A-NT-S | *-CMV-FP-I2-NT-S | *-mut-luc-E2A-NT-S |
| *-minB-YFP-bG | *-H68-FP-T2A-CR-S | *-CMV-FP-I2-CR-S | *-mut-luc-E2A-CR-S |
| *-minB-Luc-bG | *-H68-FP-T2A-chR-S | *-CMV-FP-I2-chR-S | *-mut-luc-E2A-chR-S |
| *-minC-BFP-bG | *-H68-FP-T2A-gRNA-S | *-CMV-FP-I2-gRNA-S | *-mut-luc-E2A-gRNA-S |

FIG. 16 cont'd

| | | | |
|---|---|---|---|
| *-minC-CFP-bG | *-H68-FP-T2A-Nuc-S | *-CMV-FP-I2-Nuc-S | *-mut-luc-E2A-Nuc-S |
| *-minC-GFP-bG | *-RSV-FP-T2A-enz-S | *-SV40-FP-I2-enz-S | *-minR-luc-E2A-enz-S |
| *-minC-OFP-bG | *-RSV-FP-T2A-TF-S | *-SV40-FP-I2-TF-S | *-minR-luc-E2A-TF-S |
| *-minC-RFP-bG | *-RSV-FP-T2A-rec-S | *-SV40-FP-I2-rec-S | *-minR-luc-E2A-rec-S |
| *-minC-fRFP-bG | *-RSV-FP-T2A-CTP-S | *-SV40-FP-I2-CTP-S | *-minR-luc-E2A-CTP-S |
| *-minC-YFP-bG | *-RSV-FP-T2A-SM-S | *-SV40-FP-I2-SM-S | *-minR-luc-E2A-SM-S |
| *-minC-Luc-bG | *-RSV-FP-T2A-NT-S | *-SV40-FP-I2-NT-S | *-minR-luc-E2A-NT-S |
| *-mut-BFP-bG | *-RSV-FP-T2A-CR-S | *-SV40-FP-I2-CR-S | *-minR-luc-E2A-CR-S |
| *-mut-CFP-bG | *-RSV-FP-T2A-chR-S | *-SV40-FP-I2-chR-S | *-minR-luc-E2A-chR-S |
| *-mut-GFP-bG | *-RSV-FP-T2A-gRNA-S | *-SV40-FP-I2-gRNA-S | *-minR-luc-E2A-gRNA-S |
| *-mut-OFP-bG | *-RSV-FP-T2A-Nuc-S | *-SV40-FP-I2-Nuc-S | *-minR-luc-E2A-Nuc-S |
| *-mut-RFP-bG | *-minB-FP-T2A-enz-W-bG | *-H68-FP-I2-enz-S | *-CMV-luc-E2A-enz-S |
| *-mut-fRFP-bG | *-minB-FP-T2A-TF-W-bG | *-H68-FP-I2-TF-S | *-CMV-luc-E2A-TF-S |
| *-mut-YFP-bG | *-minB-FP-T2A-rec-W-bG | *-H68-FP-I2-rec-S | *-CMV-luc-E2A-rec-S |
| *-mut-Luc-bG | *-minB-FP-T2A-CTP-W-bG | *-H68-FP-I2-CTP-S | *-CMV-luc-E2A-CTP-S |
| *-minR-BFP-bG | *-minB-FP-T2A-SM-W-bG | *-H68-FP-I2-SM-S | *-CMV-luc-E2A-SM-S |
| *-minR-CFP-bG | *-minB-FP-T2A-NT-W-bG | *-H68-FP-I2-NT-S | *-CMV-luc-E2A-NT-S |
| *-minR-GFP-bG | *-minB-FP-T2A-CR-W-bG | *-H68-FP-I2-CR-S | *-CMV-luc-E2A-CR-S |
| *-minR-OFP-bG | *-minB-FP-T2A-chR-W-bG | *-H68-FP-I2-chR-S | *-CMV-luc-E2A-chR-S |
| *-minR-RFP-bG | *-minB-FP-T2A-gRNA-W-bG | *-H68-FP-I2-gRNA-S | *-CMV-luc-E2A-gRNA-S |
| *-minR-fRFP-bG | *-minB-FP-T2A-Nuc-W-bG | *-H68-FP-I2-Nuc-S | *-CMV-luc-E2A-Nuc-S |
| *-minR-YFP-bG | *-minC-FP-T2A-enz-W-bG | *-RSV-FP-I2-enz-S | *-SV40-luc-E2A-enz-S |
| *-minR-Luc-bG | *-minC-FP-T2A-TF-W-bG | *-RSV-FP-I2-TF-S | *-SV40-luc-E2A-TF-S |
| *-CMV-BFP-bG | *-minC-FP-T2A-rec-W-bG | *-RSV-FP-I2-rec-S | *-SV40-luc-E2A-rec-S |
| *-CMV-CFP-bG | *-minC-FP-T2A-CTP-W-bG | *-RSV-FP-I2-CTP-S | *-SV40-luc-E2A-CTP-S |
| *-CMV-GFP-bG | *-minC-FP-T2A-SM-W-bG | *-RSV-FP-I2-SM-S | *-SV40-luc-E2A-SM-S |
| *-CMV-OFP-bG | *-minC-FP-T2A-NT-W-bG | *-RSV-FP-I2-NT-S | *-SV40-luc-E2A-NT-S |
| *-CMV-RFP-bG | *-minC-FP-T2A-CR-W-bG | *-RSV-FP-I2-CR-S | *-SV40-luc-E2A-CR-S |
| *-CMV-fRFP-bG | *-minC-FP-T2A-chR-W-bG | *-RSV-FP-I2-chR-S | *-SV40-luc-E2A-chR-S |
| *-CMV-YFP-bG | *-minC-FP-T2A-gRNA-W-bG | *-RSV-FP-I2-gRNA-S | *-SV40-luc-E2A-gRNA-S |
| *-CMV-Luc-bG | *-minC-FP-T2A-Nuc-W-bG | *-RSV-FP-I2-Nuc-S | *-SV40-luc-E2A-Nuc-S |
| *-SV40-BFP-bG | *-mut-FP-T2A-enz-W-bG | *-minB-FP-I2-enz-W-bG | *-H68-luc-E2A-enz-S |
| *-SV40-CFP-bG | *-mut-FP-T2A-TF-W-bG | *-minB-FP-I2-TF-W-bG | *-H68-luc-E2A-TF-S |
| *-SV40-GFP-bG | *-mut-FP-T2A-rec-W-bG | *-minB-FP-I2-rec-W-bG | *-H68-luc-E2A-rec-S |

FIG. 16 cont'd

| | | | |
|---|---|---|---|
| *-SV40-OFP-bG | *-mut-FP-T2A-CTP-W-bG | *-minB-FP-I2-CTP-W-bG | *-H68-luc-E2A-CTP-S |
| *-SV40-RFP-bG | *-mut-FP-T2A-SM-W-bG | *-minB-FP-I2-SM-W-bG | *-H68-luc-E2A-SM-S |
| *-SV40-fRFP-bG | *-mut-FP-T2A-NT-W-bG | *-minB-FP-I2-NT-W-bG | *-H68-luc-E2A-NT-S |
| *-SV40-YFP-bG | *-mut-FP-T2A-CR-W-bG | *-minB-FP-I2-CR-W-bG | *-H68-luc-E2A-CR-S |
| *-SV40-Luc-bG | *-mut-FP-T2A-chR-W-bG | *-minB-FP-I2-chR-W-bG | *-H68-luc-E2A-chR-S |
| *-H68-BFP-bG | *-mut-FP-T2A-gRNA-W-bG | *-minB-FP-I2-gRNA-W-bG | *-H68-luc-E2A-gRNA-S |
| *-H68-CFP-bG | *-mut-FP-T2A-Nuc-W-bG | *-minB-FP-I2-Nuc-W-bG | *-H68-luc-E2A-Nuc-S |
| *-H68-GFP-bG | *-minR-FP-T2A-enz-W-bG | *-minC-FP-I2-enz-W-bG | *-RSV-luc-E2A-enz-S |
| *-H68-OFP-bG | *-minR-FP-T2A-TF-W-bG | *-minC-FP-I2-TF-W-bG | *-RSV-luc-E2A-TF-S |
| *-H68-RFP-bG | *-minR-FP-T2A-rec-W-bG | *-minC-FP-I2-rec-W-bG | *-RSV-luc-E2A-rec-S |
| *-H68-fRFP-bG | *-minR-FP-T2A-CTP-W-bG | *-minC-FP-I2-CTP-W-bG | *-RSV-luc-E2A-CTP-S |
| *-H68-YFP-bG | *-minR-FP-T2A-SM-W-bG | *-minC-FP-I2-SM-W-bG | *-RSV-luc-E2A-SM-S |
| *-H68-Luc-bG | *-minR-FP-T2A-NT-W-bG | *-minC-FP-I2-NT-W-bG | *-RSV-luc-E2A-NT-S |
| *-RSV-BFP-bG | *-minR-FP-T2A-CR-W-bG | *-minC-FP-I2-CR-W-bG | *-RSV-luc-E2A-CR-S |
| *-RSV-CFP-bG | *-minR-FP-T2A-chR-W-bG | *-minC-FP-I2-chR-W-bG | *-RSV-luc-E2A-chR-S |
| *-RSV-GFP-bG | *-minR-FP-T2A-gRNA-W-bG | *-minC-FP-I2-gRNA-W-bG | *-RSV-luc-E2A-gRNA-S |
| *-RSV-OFP-bG | *-minR-FP-T2A-Nuc-W-bG | *-minC-FP-I2-Nuc-W-bG | *-RSV-luc-E2A-Nuc-S |
| *-RSV-RFP-bG | *-CMV-FP-T2A-enz-W-bG | *-mut-FP-I2-enz-W-bG | *-minB-luc-E2A-enz-W-bG |
| *-RSV-fRFP-bG | *-CMV-FP-T2A-TF-W-bG | *-mut-FP-I2-TF-W-bG | *-minB-luc-E2A-TF-W-bG |
| *-RSV-YFP-bG | *-CMV-FP-T2A-rec-W-bG | *-mut-FP-I2-rec-W-bG | *-minB-luc-E2A-rec-W-bG |
| *-RSV-Luc-bG | *-CMV-FP-T2A-CTP-W-bG | *-mut-FP-I2-CTP-W-bG | *-minB-luc-E2A-CTP-W-bG |
| *-minB-BFP-W-bG | *-CMV-FP-T2A-SM-W-bG | *-mut-FP-I2-SM-W-bG | *-minB-luc-E2A-SM-W-bG |
| *-minB-CFP-W-bG | *-CMV-FP-T2A-NT-W-bG | *-mut-FP-I2-NT-W-bG | *-minB-luc-E2A-NT-W-bG |
| *-minB-GFP-W-bG | *-CMV-FP-T2A-CR-W-bG | *-mut-FP-I2-CR-W-bG | *-minB-luc-E2A-CR-W-bG |
| *-minB-OFP-W-bG | *-CMV-FP-T2A-chR-W-bG | *-mut-FP-I2-chR-W-bG | *-minB-luc-E2A-chR-W-bG |
| *-minB-RFP-W-bG | *-CMV-FP-T2A-gRNA-W-bG | *-mut-FP-I2-gRNA-W-bG | *-minB-luc-E2A-gRNA-W-bG |
| *-minB-fRFP-W-bG | *-CMV-FP-T2A-Nuc-W-bG | *-mut-FP-I2-Nuc-W-bG | *-minB-luc-E2A-Nuc-W-bG |
| *-minB-YFP-W-bG | *-SV40-FP-T2A-enz-W-bG | *-minR-FP-I2-enz-W-bG | *-minC-luc-E2A-enz-W-bG |
| *-minB-Luc-W-bG | *-SV40-FP-T2A-TF-W-bG | *-minR-FP-I2-TF-W-bG | *-minC-luc-E2A-TF-W-bG |
| *-minC-BFP-W-bG | *-SV40-FP-T2A-rec-W-bG | *-minR-FP-I2-rec-W-bG | *-minC-luc-E2A-rec-W-bG |
| *-minC-CFP-W-bG | *-SV40-FP-T2A-CTP-W-bG | *-minR-FP-I2-CTP-W-bG | *-minC-luc-E2A-CTP-W-bG |
| *-minC-GFP-W-bG | *-SV40-FP-T2A-SM-W-bG | *-minR-FP-I2-SM-W-bG | *-minC-luc-E2A-SM-W-bG |
| *-minC-OFP-W-bG | *-SV40-FP-T2A-NT-W-bG | *-minR-FP-I2-NT-W-bG | *-minC-luc-E2A-NT-W-bG |
| *-minC-RFP-W-bG | *-SV40-FP-T2A-CR-W-bG | *-minR-FP-I2-CR-W-bG | *-minC-luc-E2A-CR-W-bG |

FIG. 16 cont'd

| | | | |
|---|---|---|---|
| *-minC-fRFP-W-bG | *-SV40-FP-T2A-chR-W-bG | *-minR-FP-I2-chR-W-bG | *-minC-luc-E2A-chR-W-bG |
| *-minC-YFP-W-bG | *-SV40-FP-T2A-gRNA-W-bG | *-minR-FP-I2-gRNA-W-bG | *-minC-luc-E2A-gRNA-W-bG |
| *-minC-Luc-W-bG | *-SV40-FP-T2A-Nuc-W-bG | *-minR-FP-I2-Nuc-W-bG | *-minC-luc-E2A-Nuc-W-bG |
| *-mut-BFP-W-bG | *-H68-FP-T2A-enz-W-bG | *-CMV-FP-I2-enz-W-bG | *-mut-luc-E2A-enz-W-bG |
| *-mut-CFP-W-bG | *-H68-FP-T2A-TF-W-bG | *-CMV-FP-I2-TF-W-bG | *-mut-luc-E2A-TF-W-bG |
| *-mut-GFP-W-bG | *-H68-FP-T2A-rec-W-bG | *-CMV-FP-I2-rec-W-bG | *-mut-luc-E2A-rec-W-bG |
| *-mut-OFP-W-bG | *-H68-FP-T2A-CTP-W-bG | *-CMV-FP-I2-CTP-W-bG | *-mut-luc-E2A-CTP-W-bG |
| *-mut-RFP-W-bG | *-H68-FP-T2A-SM-W-bG | *-CMV-FP-I2-SM-W-bG | *-mut-luc-E2A-SM-W-bG |
| *-mut-fRFP-W-bG | *-H68-FP-T2A-NT-W-bG | *-CMV-FP-I2-NT-W-bG | *-mut-luc-E2A-NT-W-bG |
| *-mut-YFP-W-bG | *-H68-FP-T2A-CR-W-bG | *-CMV-FP-I2-CR-W-bG | *-mut-luc-E2A-CR-W-bG |
| *-mut-Luc-W-bG | *-H68-FP-T2A-chR-W-bG | *-CMV-FP-I2-chR-W-bG | *-mut-luc-E2A-chR-W-bG |
| *-minR-BFP-W-bG | *-H68-FP-T2A-gRNA-W-bG | *-CMV-FP-I2-gRNA-W-bG | *-mut-luc-E2A-gRNA-W-bG |
| *-minR-CFP-W-bG | *-H68-FP-T2A-Nuc-W-bG | *-CMV-FP-I2-Nuc-W-bG | *-mut-luc-E2A-Nuc-W-bG |
| *-minR-GFP-W-bG | *-RSV-FP-T2A-enz-W-bG | *-SV40-FP-I2-enz-W-bG | *-minR-luc-E2A-enz-W-bG |
| *-minR-OFP-W-bG | *-RSV-FP-T2A-TF-W-bG | *-SV40-FP-I2-TF-W-bG | *-minR-luc-E2A-TF-W-bG |
| *-minR-RFP-W-bG | *-RSV-FP-T2A-rec-W-bG | *-SV40-FP-I2-rec-W-bG | *-minR-luc-E2A-rec-W-bG |
| *-minR-fRFP-W-bG | *-RSV-FP-T2A-CTP-W-bG | *-SV40-FP-I2-CTP-W-bG | *-minR-luc-E2A-CTP-W-bG |
| *-minR-YFP-W-bG | *-RSV-FP-T2A-SM-W-bG | *-SV40-FP-I2-SM-W-bG | *-minR-luc-E2A-SM-W-bG |
| *-minR-Luc-W-bG | *-RSV-FP-T2A-NT-W-bG | *-SV40-FP-I2-NT-W-bG | *-minR-luc-E2A-NT-W-bG |
| *-CMV-BFP-W-bG | *-RSV-FP-T2A-CR-W-bG | *-SV40-FP-I2-CR-W-bG | *-minR-luc-E2A-CR-W-bG |
| *-CMV-CFP-W-bG | *-RSV-FP-T2A-chR-W-bG | *-SV40-FP-I2-chR-W-bG | *-minR-luc-E2A-chR-W-bG |
| *-CMV-GFP-W-bG | *-RSV-FP-T2A-gRNA-W-bG | *-SV40-FP-I2-gRNA-W-bG | *-minR-luc-E2A-gRNA-W-bG |
| *-CMV-OFP-W-bG | *-RSV-FP-T2A-Nuc-W-bG | *-SV40-FP-I2-Nuc-W-bG | *-minR-luc-E2A-Nuc-W-bG |
| *-CMV-RFP-W-bG | *-minB-FP-T2A-enz-W-S | *-H68-FP-I2-enz-W-bG | *-CMV-luc-E2A-enz-W-bG |
| *-CMV-fRFP-W-bG | *-minB-FP-T2A-TF-W-S | *-H68-FP-I2-TF-W-bG | *-CMV-luc-E2A-TF-W-bG |
| *-CMV-YFP-W-bG | *-minB-FP-T2A-rec-W-S | *-H68-FP-I2-rec-W-bG | *-CMV-luc-E2A-rec-W-bG |
| *-CMV-Luc-W-bG | *-minB-FP-T2A-CTP-W-S | *-H68-FP-I2-CTP-W-bG | *-CMV-luc-E2A-CTP-W-bG |
| *-SV40-BFP-W-bG | *-minB-FP-T2A-SM-W-S | *-H68-FP-I2-SM-W-bG | *-CMV-luc-E2A-SM-W-bG |
| *-SV40-CFP-W-bG | *-minB-FP-T2A-NT-W-S | *-H68-FP-I2-NT-W-bG | *-CMV-luc-E2A-NT-W-bG |
| *-SV40-GFP-W-bG | *-minB-FP-T2A-CR-W-S | *-H68-FP-I2-CR-W-bG | *-CMV-luc-E2A-CR-W-bG |
| *-SV40-OFP-W-bG | *-minB-FP-T2A-chR-W-S | *-H68-FP-I2-chR-W-bG | *-CMV-luc-E2A-chR-W-bG |
| *-SV40-RFP-W-bG | *-minB-FP-T2A-gRNA-W-S | *-H68-FP-I2-gRNA-W-bG | *-CMV-luc-E2A-gRNA-W-bG |
| *-SV40-fRFP-W-bG | *-minB-FP-T2A-Nuc-W-S | *-H68-FP-I2-Nuc-W-bG | *-CMV-luc-E2A-Nuc-W-bG |
| *-SV40-YFP-W-bG | *-minC-FP-T2A-enz-W-S | *-RSV-FP-I2-enz-W-bG | *-SV40-luc-E2A-enz-W-bG |

FIG. 16 cont'd

| | | | |
|---|---|---|---|
| *-SV40-Luc-W-bG | *-minC-FP-T2A-TF-W-S | *-RSV-FP-I2-TF-W-bG | *-SV40-luc-E2A-TF-W-bG |
| *-H68-BFP-W-bG | *-minC-FP-T2A-rec-W-S | *-RSV-FP-I2-rec-W-bG | *-SV40-luc-E2A-rec-W-bG |
| *-H68-CFP-W-bG | *-minC-FP-T2A-CTP-W-S | *-RSV-FP-I2-CTP-W-bG | *-SV40-luc-E2A-CTP-W-bG |
| *-H68-GFP-W-bG | *-minC-FP-T2A-SM-W-S | *-RSV-FP-I2-SM-W-bG | *-SV40-luc-E2A-SM-W-bG |
| *-H68-OFP-W-bG | *-minC-FP-T2A-NT-W-S | *-RSV-FP-I2-NT-W-bG | *-SV40-luc-E2A-NT-W-bG |
| *-H68-RFP-W-bG | *-minC-FP-T2A-CR-W-S | *-RSV-FP-I2-CR-W-bG | *-SV40-luc-E2A-CR-W-bG |
| *-H68-fRFP-W-bG | *-minC-FP-T2A-chR-W-S | *-RSV-FP-I2-chR-W-bG | *-SV40-luc-E2A-chR-W-bG |
| *-H68-YFP-W-bG | *-minC-FP-T2A-gRNA-W-S | *-RSV-FP-I2-gRNA-W-bG | *-SV40-luc-E2A-gRNA-W-bG |
| *-H68-Luc-W-bG | *-minC-FP-T2A-Nuc-W-S | *-RSV-FP-I2-Nuc-W-bG | *-SV40-luc-E2A-Nuc-W-bG |
| *-RSV-BFP-W-bG | *-mut-FP-T2A-enz-W-S | *-minB-FP-I2-enz-W-S | *-H68-luc-E2A-enz-W-bG |
| *-RSV-CFP-W-bG | *-mut-FP-T2A-TF-W-S | *-minB-FP-I2-TF-W-S | *-H68-luc-E2A-TF-W-bG |
| *-RSV-GFP-W-bG | *-mut-FP-T2A-rec-W-S | *-minB-FP-I2-rec-W-S | *-H68-luc-E2A-rec-W-bG |
| *-RSV-OFP-W-bG | *-mut-FP-T2A-CTP-W-S | *-minB-FP-I2-CTP-W-S | *-H68-luc-E2A-CTP-W-bG |
| *-RSV-RFP-W-bG | *-mut-FP-T2A-SM-W-S | *-minB-FP-I2-SM-W-S | *-H68-luc-E2A-SM-W-bG |
| *-RSV-fRFP-W-bG | *-mut-FP-T2A-NT-W-S | *-minB-FP-I2-NT-W-S | *-H68-luc-E2A-NT-W-bG |
| *-RSV-YFP-W-bG | *-mut-FP-T2A-CR-W-S | *-minB-FP-I2-CR-W-S | *-H68-luc-E2A-CR-W-bG |
| *-RSV-Luc-W-bG | *-mut-FP-T2A-chR-W-S | *-minB-FP-I2-chR-W-S | *-H68-luc-E2A-chR-W-bG |
| *-CMV-BFP-W-S | *-mut-FP-T2A-gRNA-W-S | *-minB-FP-I2-gRNA-W-S | *-H68-luc-E2A-gRNA-W-bG |
| *-CMV-CFP-W-S | *-mut-FP-T2A-Nuc-W-S | *-minB-FP-I2-Nuc-W-S | *-H68-luc-E2A-Nuc-W-bG |
| *-CMV-GFP-W-S | *-minR-FP-T2A-enz-W-S | *-minC-FP-I2-enz-W-S | *-RSV-luc-E2A-enz-W-bG |
| *-CMV-OFP-W-S | *-minR-FP-T2A-TF-W-S | *-minC-FP-I2-TF-W-S | *-RSV-luc-E2A-TF-W-bG |
| *-CMV-RFP-W-S | *-minR-FP-T2A-rec-W-S | *-minC-FP-I2-rec-W-S | *-RSV-luc-E2A-rec-W-bG |
| *-CMV-fRFP-W-S | *-minR-FP-T2A-CTP-W-S | *-minC-FP-I2-CTP-W-S | *-RSV-luc-E2A-CTP-W-bG |
| *-CMV-YFP-W-S | *-minR-FP-T2A-SM-W-S | *-minC-FP-I2-SM-W-S | *-RSV-luc-E2A-SM-W-bG |
| *-CMV-Luc-W-S | *-minR-FP-T2A-NT-W-S | *-minC-FP-I2-NT-W-S | *-RSV-luc-E2A-NT-W-bG |
| *-SV40-BFP-W-S | *-minR-FP-T2A-CR-W-S | *-minC-FP-I2-CR-W-S | *-RSV-luc-E2A-CR-W-bG |
| *-SV40-CFP-W-S | *-minR-FP-T2A-chR-W-S | *-minC-FP-I2-chR-W-S | *-RSV-luc-E2A-chR-W-bG |
| *-SV40-GFP-W-S | *-minR-FP-T2A-gRNA-W-S | *-minC-FP-I2-gRNA-W-S | *-RSV-luc-E2A-gRNA-W-bG |
| *-SV40-OFP-W-S | *-minR-FP-T2A-Nuc-W-S | *-minC-FP-I2-Nuc-W-S | *-RSV-luc-E2A-Nuc-W-bG |
| *-SV40-RFP-W-S | *-CMV-FP-T2A-enz-W-S | *-mut-FP-I2-enz-W-S | *-minB-luc-E2A-enz-W-S |
| *-SV40-fRFP-W-S | *-CMV-FP-T2A-TF-W-S | *-mut-FP-I2-TF-W-S | *-minB-luc-E2A-TF-W-S |
| *-SV40-YFP-W-S | *-CMV-FP-T2A-rec-W-S | *-mut-FP-I2-rec-W-S | *-minB-luc-E2A-rec-W-S |
| *-SV40-Luc-W-S | *-CMV-FP-T2A-CTP-W-S | *-mut-FP-I2-CTP-W-S | *-minB-luc-E2A-CTP-W-S |
| *-H68-BFP-W-S | *-CMV-FP-T2A-SM-W-S | *-mut-FP-I2-SM-W-S | *-minB-luc-E2A-SM-W-S |

FIG. 16 cont'd

| | | | |
|---|---|---|---|
| *-H68-CFP-W-S | *-CMV-FP-T2A-NT-W-S | *-mut-FP-I2-NT-W-S | *-minB-luc-E2A-NT-W-S |
| *-H68-GFP-W-S | *-CMV-FP-T2A-CR-W-S | *-mut-FP-I2-CR-W-S | *-minB-luc-E2A-CR-W-S |
| *-H68-OFP-W-S | *-CMV-FP-T2A-chR-W-S | *-mut-FP-I2-chR-W-S | *-minB-luc-E2A-chR-W-S |
| *-H68-RFP-W-S | *-CMV-FP-T2A-gRNA-W-S | *-mut-FP-I2-gRNA-W-S | *-minB-luc-E2A-gRNA-W-S |
| *-H68-fRFP-W-S | *-CMV-FP-T2A-Nuc-W-S | *-mut-FP-I2-Nuc-W-S | *-minB-luc-E2A-Nuc-W-S |
| *-H68-YFP-W-S | *-SV40-FP-T2A-enz-W-S | *-minR-FP-I2-enz-W-S | *-minC-luc-E2A-enz-W-S |
| *-H68-Luc-W-S | *-SV40-FP-T2A-TF-W-S | *-minR-FP-I2-TF-W-S | *-minC-luc-E2A-TF-W-S |
| *-RSV-BFP-W-S | *-SV40-FP-T2A-rec-W-S | *-minR-FP-I2-rec-W-S | *-minC-luc-E2A-rec-W-S |
| *-RSV-CFP-W-S | *-SV40-FP-T2A-CTP-W-S | *-minR-FP-I2-CTP-W-S | *-minC-luc-E2A-CTP-W-S |
| *-RSV-GFP-W-S | *-SV40-FP-T2A-SM-W-S | *-minR-FP-I2-SM-W-S | *-minC-luc-E2A-SM-W-S |
| *-RSV-OFP-W-S | *-SV40-FP-T2A-NT-W-S | *-minR-FP-I2-NT-W-S | *-minC-luc-E2A-NT-W-S |
| *-RSV-RFP-W-S | *-SV40-FP-T2A-CR-W-S | *-minR-FP-I2-CR-W-S | *-minC-luc-E2A-CR-W-S |
| *-RSV-fRFP-W-S | *-SV40-FP-T2A-chR-W-S | *-minR-FP-I2-chR-W-S | *-minC-luc-E2A-chR-W-S |
| *-RSV-YFP-W-S | *-SV40-FP-T2A-gRNA-W-S | *-minR-FP-I2-gRNA-W-S | *-minC-luc-E2A-gRNA-W-S |
| *-RSV-Luc-W-S | *-SV40-FP-T2A-Nuc-W-S | *-minR-FP-I2-Nuc-W-S | *-minC-luc-E2A-Nuc-W-S |
| *-minB-enz-W | *-H68-FP-T2A-enz-W-S | *-CMV-FP-I2-enz-W-S | *-mut-luc-E2A-enz-W-S |
| *-minB-TF-W | *-H68-FP-T2A-TF-W-S | *-CMV-FP-I2-TF-W-S | *-mut-luc-E2A-TF-W-S |
| *-minB-rec-W | *-H68-FP-T2A-rec-W-S | *-CMV-FP-I2-rec-W-S | *-mut-luc-E2A-rec-W-S |
| *-minB-CTP-W | *-H68-FP-T2A-CTP-W-S | *-CMV-FP-I2-CTP-W-S | *-mut-luc-E2A-CTP-W-S |
| *-minB-SM-W | *-H68-FP-T2A-SM-W-S | *-CMV-FP-I2-SM-W-S | *-mut-luc-E2A-SM-W-S |
| *-minB-NT-W | *-H68-FP-T2A-NT-W-S | *-CMV-FP-I2-NT-W-S | *-mut-luc-E2A-NT-W-S |
| *-minB-CR-W | *-H68-FP-T2A-CR-W-S | *-CMV-FP-I2-CR-W-S | *-mut-luc-E2A-CR-W-S |
| *-minB-chR-W | *-H68-FP-T2A-chR-W-S | *-CMV-FP-I2-chR-W-S | *-mut-luc-E2A-chR-W-S |
| *-minB-gRNA-W | *-H68-FP-T2A-gRNA-W-S | *-CMV-FP-I2-gRNA-W-S | *-mut-luc-E2A-gRNA-W-S |
| *-minB-Nuc-W | *-H68-FP-T2A-Nuc-W-S | *-CMV-FP-I2-Nuc-W-S | *-mut-luc-E2A-Nuc-W-S |
| *-minC-enz-W | *-RSV-FP-T2A-enz-W-S | *-SV40-FP-I2-enz-W-S | *-minR-luc-E2A-enz-W-S |
| *-minC-TF-W | *-RSV-FP-T2A-TF-W-S | *-SV40-FP-I2-TF-W-S | *-minR-luc-E2A-TF-W-S |
| *-minC-rec-W | *-RSV-FP-T2A-rec-W-S | *-SV40-FP-I2-rec-W-S | *-minR-luc-E2A-rec-W-S |
| *-minC-CTP-W | *-RSV-FP-T2A-CTP-W-S | *-SV40-FP-I2-CTP-W-S | *-minR-luc-E2A-CTP-W-S |
| *-minC-SM-W | *-RSV-FP-T2A-SM-W-S | *-SV40-FP-I2-SM-W-S | *-minR-luc-E2A-SM-W-S |
| *-minC-NT-W | *-RSV-FP-T2A-NT-W-S | *-SV40-FP-I2-NT-W-S | *-minR-luc-E2A-NT-W-S |
| *-minC-CR-W | *-RSV-FP-T2A-CR-W-S | *-SV40-FP-I2-CR-W-S | *-minR-luc-E2A-CR-W-S |
| *-minC-chR-W | *-RSV-FP-T2A-chR-W-S | *-SV40-FP-I2-chR-W-S | *-minR-luc-E2A-chR-W-S |
| *-minC-gRNA-W | *-RSV-FP-T2A-gRNA-W-S | *-SV40-FP-I2-gRNA-W-S | *-minR-luc-E2A-gRNA-W-S |

FIG. 16 cont'd

| | | | |
|---|---|---|---|
| *-minC-Nuc-W | *-RSV-FP-T2A-Nuc-W-S | *-SV40-FP-I2-Nuc-W-S | *-minR-luc-E2A-Nuc-W-S |
| *-mut-enz-W | *-minB-FP-E2A-enz-W | *-H68-FP-I2-enz-W-S | *-CMV-luc-E2A-enz-W-S |
| *-mut-TF-W | *-minB-FP-E2A-TF-W | *-H68-FP-I2-TF-W-S | *-CMV-luc-E2A-TF-W-S |
| *-mut-rec-W | *-minB-FP-E2A-rec-W | *-H68-FP-I2-rec-W-S | *-CMV-luc-E2A-rec-W-S |
| *-mut-CTP-W | *-minB-FP-E2A-CTP-W | *-H68-FP-I2-CTP-W-S | *-CMV-luc-E2A-CTP-W-S |
| *-mut-SM-W | *-minB-FP-E2A-SM-W | *-H68-FP-I2-SM-W-S | *-CMV-luc-E2A-SM-W-S |
| *-mut-NT-W | *-minB-FP-E2A-NT-W | *-H68-FP-I2-NT-W-S | *-CMV-luc-E2A-NT-W-S |
| *-mut-CR-W | *-minB-FP-E2A-CR-W | *-H68-FP-I2-CR-W-S | *-CMV-luc-E2A-CR-W-S |
| *-mut-chR-W | *-minB-FP-E2A-chR-W | *-H68-FP-I2-chR-W-S | *-CMV-luc-E2A-chR-W-S |
| *-mut-gRNA-W | *-minB-FP-E2A-gRNA-W | *-H68-FP-I2-gRNA-W-S | *-CMV-luc-E2A-gRNA-W-S |
| *-mut-Nuc-W | *-minB-FP-E2A-Nuc-W | *-H68-FP-I2-Nuc-W-S | *-CMV-luc-E2A-Nuc-W-S |
| *-minR-enz-W | *-minC-FP-E2A-enz-W | *-RSV-FP-I2-enz-W-S | *-SV40-luc-E2A-enz-W-S |
| *-minR-TF-W | *-minC-FP-E2A-TF-W | *-RSV-FP-I2-TF-W-S | *-SV40-luc-E2A-TF-W-S |
| *-minR-rec-W | *-minC-FP-E2A-rec-W | *-RSV-FP-I2-rec-W-S | *-SV40-luc-E2A-rec-W-S |
| *-minR-CTP-W | *-minC-FP-E2A-CTP-W | *-RSV-FP-I2-CTP-W-S | *-SV40-luc-E2A-CTP-W-S |
| *-minR-SM-W | *-minC-FP-E2A-SM-W | *-RSV-FP-I2-SM-W-S | *-SV40-luc-E2A-SM-W-S |
| *-minR-NT-W | *-minC-FP-E2A-NT-W | *-RSV-FP-I2-NT-W-S | *-SV40-luc-E2A-NT-W-S |
| *-minR-CR-W | *-minC-FP-E2A-CR-W | *-RSV-FP-I2-CR-W-S | *-SV40-luc-E2A-CR-W-S |
| *-minR-chR-W | *-minC-FP-E2A-chR-W | *-RSV-FP-I2-chR-W-S | *-SV40-luc-E2A-chR-W-S |
| *-minR-gRNA-W | *-minC-FP-E2A-gRNA-W | *-RSV-FP-I2-gRNA-W-S | *-SV40-luc-E2A-gRNA-W-S |
| *-minR-Nuc-W | *-minC-FP-E2A-Nuc-W | *-RSV-FP-I2-Nuc-W-S | *-SV40-luc-E2A-Nuc-W-S |
| *-CMV-enz-W | *-mut-FP-E2A-enz-W | *-minB-luc-P2A-enz-W | *-H68-luc-E2A-enz-W-S |
| *-CMV-TF-W | *-mut-FP-E2A-TF-W | *-minB-luc-P2A-TF-W | *-H68-luc-E2A-TF-W-S |
| *-CMV-rec-W | *-mut-FP-E2A-rec-W | *-minB-luc-P2A-rec-W | *-H68-luc-E2A-rec-W-S |
| *-CMV-CTP-W | *-mut-FP-E2A-CTP-W | *-minB-luc-P2A-CTP-W | *-H68-luc-E2A-CTP-W-S |
| *-CMV-SM-W | *-mut-FP-E2A-SM-W | *-minB-luc-P2A-SM-W | *-H68-luc-E2A-SM-W-S |
| *-CMV-NT-W | *-mut-FP-E2A-NT-W | *-minB-luc-P2A-NT-W | *-H68-luc-E2A-NT-W-S |
| *-CMV-CR-W | *-mut-FP-E2A-CR-W | *-minB-luc-P2A-CR-W | *-H68-luc-E2A-CR-W-S |
| *-CMV-chR-W | *-mut-FP-E2A-chR-W | *-minB-luc-P2A-chR-W | *-H68-luc-E2A-chR-W-S |
| *-CMV-gRNA-W | *-mut-FP-E2A-gRNA-W | *-minB-luc-P2A-gRNA-W | *-H68-luc-E2A-gRNA-W-S |
| *-CMV-Nuc-W | *-mut-FP-E2A-Nuc-W | *-minB-luc-P2A-Nuc-W | *-H68-luc-E2A-Nuc-W-S |
| *-SV40-enz-W | *-minR-FP-E2A-enz-W | *-minC-luc-P2A-enz-W | *-RSV-luc-E2A-enz-W-S |
| *-SV40-TF-W | *-minR-FP-E2A-TF-W | *-minC-luc-P2A-TF-W | *-RSV-luc-E2A-TF-W-S |
| *-SV40-rec-W | *-minR-FP-E2A-rec-W | *-minC-luc-P2A-rec-W | *-RSV-luc-E2A-rec-W-S |

FIG. 16 cont'd

| | | | |
|---|---|---|---|
| *-SV40-CTP-W | *-minR-FP-E2A-CTP-W | *-minC-luc-P2A-CTP-W | *-RSV-luc-E2A-CTP-W-S |
| *-SV40-SM-W | *-minR-FP-E2A-SM-W | *-minC-luc-P2A-SM-W | *-RSV-luc-E2A-SM-W-S |
| *-SV40-NT-W | *-minR-FP-E2A-NT-W | *-minC-luc-P2A-NT-W | *-RSV-luc-E2A-NT-W-S |
| *-SV40-CR-W | *-minR-FP-E2A-CR-W | *-minC-luc-P2A-CR-W | *-RSV-luc-E2A-CR-W-S |
| *-SV40-chR-W | *-minR-FP-E2A-chR-W | *-minC-luc-P2A-chR-W | *-RSV-luc-E2A-chR-W-S |
| *-SV40-gRNA-W | *-minR-FP-E2A-gRNA-W | *-minC-luc-P2A-gRNA-W | *-RSV-luc-E2A-gRNA-W-S |
| *-SV40-Nuc-W | *-minR-FP-E2A-Nuc-W | *-minC-luc-P2A-Nuc-W | *-RSV-luc-E2A-Nuc-W-S |
| *-H68-enz-W | *-CMV-FP-E2A-enz-W | *-mut-luc-P2A-enz-W | *-minB-luc-F2A-enz-W |
| *-H68-TF-W | *-CMV-FP-E2A-TF-W | *-mut-luc-P2A-TF-W | *-minB-luc-F2A-TF-W |
| *-H68-rec-W | *-CMV-FP-E2A-rec-W | *-mut-luc-P2A-rec-W | *-minB-luc-F2A-rec-W |
| *-H68-CTP-W | *-CMV-FP-E2A-CTP-W | *-mut-luc-P2A-CTP-W | *-minB-luc-F2A-CTP-W |
| *-H68-SM-W | *-CMV-FP-E2A-SM-W | *-mut-luc-P2A-SM-W | *-minB-luc-F2A-SM-W |
| *-H68-NT-W | *-CMV-FP-E2A-NT-W | *-mut-luc-P2A-NT-W | *-minB-luc-F2A-NT-W |
| *-H68-CR-W | *-CMV-FP-E2A-CR-W | *-mut-luc-P2A-CR-W | *-minB-luc-F2A-CR-W |
| *-H68-chR-W | *-CMV-FP-E2A-chR-W | *-mut-luc-P2A-chR-W | *-minB-luc-F2A-chR-W |
| *-H68-gRNA-W | *-CMV-FP-E2A-gRNA-W | *-mut-luc-P2A-gRNA-W | *-minB-luc-F2A-gRNA-W |
| *-H68-Nuc-W | *-CMV-FP-E2A-Nuc-W | *-mut-luc-P2A-Nuc-W | *-minB-luc-F2A-Nuc-W |
| *-RSV-enz-W | *-SV40-FP-E2A-enz-W | *-minR-luc-P2A-enz-W | *-minC-luc-F2A-enz-W |
| *-RSV-TF-W | *-SV40-FP-E2A-TF-W | *-minR-luc-P2A-TF-W | *-minC-luc-F2A-TF-W |
| *-RSV-rec-W | *-SV40-FP-E2A-rec-W | *-minR-luc-P2A-rec-W | *-minC-luc-F2A-rec-W |
| *-RSV-CTP-W | *-SV40-FP-E2A-CTP-W | *-minR-luc-P2A-CTP-W | *-minC-luc-F2A-CTP-W |
| *-RSV-SM-W | *-SV40-FP-E2A-SM-W | *-minR-luc-P2A-SM-W | *-minC-luc-F2A-SM-W |
| *-RSV-NT-W | *-SV40-FP-E2A-NT-W | *-minR-luc-P2A-NT-W | *-minC-luc-F2A-NT-W |
| *-RSV-CR-W | *-SV40-FP-E2A-CR-W | *-minR-luc-P2A-CR-W | *-minC-luc-F2A-CR-W |
| *-RSV-chR-W | *-SV40-FP-E2A-chR-W | *-minR-luc-P2A-chR-W | *-minC-luc-F2A-chR-W |
| *-RSV-gRNA-W | *-SV40-FP-E2A-gRNA-W | *-minR-luc-P2A-gRNA-W | *-minC-luc-F2A-gRNA-W |
| *-RSV-Nuc-W | *-SV40-FP-E2A-Nuc-W | *-minR-luc-P2A-Nuc-W | *-minC-luc-F2A-Nuc-W |
| *-minB-enz-S | *-H68-FP-E2A-enz-W | *-CMV-luc-P2A-enz-W | *-mut-luc-F2A-enz-W |
| *-minB-TF-S | *-H68-FP-E2A-TF-W | *-CMV-luc-P2A-TF-W | *-mut-luc-F2A-TF-W |
| *-minB-rec-S | *-H68-FP-E2A-rec-W | *-CMV-luc-P2A-rec-W | *-mut-luc-F2A-rec-W |
| *-minB-CTP-S | *-H68-FP-E2A-CTP-W | *-CMV-luc-P2A-CTP-W | *-mut-luc-F2A-CTP-W |
| *-minB-SM-S | *-H68-FP-E2A-SM-W | *-CMV-luc-P2A-SM-W | *-mut-luc-F2A-SM-W |
| *-minB-NT-S | *-H68-FP-E2A-NT-W | *-CMV-luc-P2A-NT-W | *-mut-luc-F2A-NT-W |
| *-minB-CR-S | *-H68-FP-E2A-CR-W | *-CMV-luc-P2A-CR-W | *-mut-luc-F2A-CR-W |

FIG. 16 cont'd

| | | | |
|---|---|---|---|
| *-minB-chR-S | *-H68-FP-E2A-chR-W | *-CMV-luc-P2A-chR-W | *-mut-luc-F2A-chR-W |
| *-minB-gRNA-S | *-H68-FP-E2A-gRNA-W | *-CMV-luc-P2A-gRNA-W | *-mut-luc-F2A-gRNA-W |
| *-minB-Nuc-S | *-H68-FP-E2A-Nuc-W | *-CMV-luc-P2A-Nuc-W | *-mut-luc-F2A-Nuc-W |
| *-minC-enz-S | *-RSV-FP-E2A-enz-W | *-SV40-luc-P2A-enz-W | *-minR-luc-F2A-enz-W |
| *-minC-TF-S | *-RSV-FP-E2A-TF-W | *-SV40-luc-P2A-TF-W | *-minR-luc-F2A-TF-W |
| *-minC-rec-S | *-RSV-FP-E2A-rec-W | *-SV40-luc-P2A-rec-W | *-minR-luc-F2A-rec-W |
| *-minC-CTP-S | *-RSV-FP-E2A-CTP-W | *-SV40-luc-P2A-CTP-W | *-minR-luc-F2A-CTP-W |
| *-minC-SM-S | *-RSV-FP-E2A-SM-W | *-SV40-luc-P2A-SM-W | *-minR-luc-F2A-SM-W |
| *-minC-NT-S | *-RSV-FP-E2A-NT-W | *-SV40-luc-P2A-NT-W | *-minR-luc-F2A-NT-W |
| *-minC-CR-S | *-RSV-FP-E2A-CR-W | *-SV40-luc-P2A-CR-W | *-minR-luc-F2A-CR-W |
| *-minC-chR-S | *-RSV-FP-E2A-chR-W | *-SV40-luc-P2A-chR-W | *-minR-luc-F2A-chR-W |
| *-minC-gRNA-S | *-RSV-FP-E2A-gRNA-W | *-SV40-luc-P2A-gRNA-W | *-minR-luc-F2A-gRNA-W |
| *-minC-Nuc-S | *-RSV-FP-E2A-Nuc-W | *-SV40-luc-P2A-Nuc-W | *-minR-luc-F2A-Nuc-W |
| *-mut-enz-S | *-minB-FP-E2A-enz-bG | *-H68-luc-P2A-enz-W | *-CMV-luc-F2A-enz-W |
| *-mut-TF-S | *-minB-FP-E2A-TF-bG | *-H68-luc-P2A-TF-W | *-CMV-luc-F2A-TF-W |
| *-mut-rec-S | *-minB-FP-E2A-rec-bG | *-H68-luc-P2A-rec-W | *-CMV-luc-F2A-rec-W |
| *-mut-CTP-S | *-minB-FP-E2A-CTP-bG | *-H68-luc-P2A-CTP-W | *-CMV-luc-F2A-CTP-W |
| *-mut-SM-S | *-minB-FP-E2A-SM-bG | *-H68-luc-P2A-SM-W | *-CMV-luc-F2A-SM-W |
| *-mut-NT-S | *-minB-FP-E2A-NT-bG | *-H68-luc-P2A-NT-W | *-CMV-luc-F2A-NT-W |
| *-mut-CR-S | *-minB-FP-E2A-CR-bG | *-H68-luc-P2A-CR-W | *-CMV-luc-F2A-CR-W |
| *-mut-chR-S | *-minB-FP-E2A-chR-bG | *-H68-luc-P2A-chR-W | *-CMV-luc-F2A-chR-W |
| *-mut-gRNA-S | *-minB-FP-E2A-gRNA-bG | *-H68-luc-P2A-gRNA-W | *-CMV-luc-F2A-gRNA-W |
| *-mut-Nuc-S | *-minB-FP-E2A-Nuc-bG | *-H68-luc-P2A-Nuc-W | *-CMV-luc-F2A-Nuc-W |
| *-minR-enz-S | *-minC-FP-E2A-enz-bG | *-RSV-luc-P2A-enz-W | *-SV40-luc-F2A-enz-W |
| *-minR-TF-S | *-minC-FP-E2A-TF-bG | *-RSV-luc-P2A-TF-W | *-SV40-luc-F2A-TF-W |
| *-minR-rec-S | *-minC-FP-E2A-rec-bG | *-RSV-luc-P2A-rec-W | *-SV40-luc-F2A-rec-W |
| *-minR-CTP-S | *-minC-FP-E2A-CTP-bG | *-RSV-luc-P2A-CTP-W | *-SV40-luc-F2A-CTP-W |
| *-minR-SM-S | *-minC-FP-E2A-SM-bG | *-RSV-luc-P2A-SM-W | *-SV40-luc-F2A-SM-W |
| *-minR-NT-S | *-minC-FP-E2A-NT-bG | *-RSV-luc-P2A-NT-W | *-SV40-luc-F2A-NT-W |
| *-minR-CR-S | *-minC-FP-E2A-CR-bG | *-RSV-luc-P2A-CR-W | *-SV40-luc-F2A-CR-W |
| *-minR-chR-S | *-minC-FP-E2A-chR-bG | *-RSV-luc-P2A-chR-W | *-SV40-luc-F2A-chR-W |
| *-minR-gRNA-S | *-minC-FP-E2A-gRNA-bG | *-RSV-luc-P2A-gRNA-W | *-SV40-luc-F2A-gRNA-W |
| *-minR-Nuc-S | *-minC-FP-E2A-Nuc-bG | *-RSV-luc-P2A-Nuc-W | *-SV40-luc-F2A-Nuc-W |
| *-CMV-enz-S | *-mut-FP-E2A-enz-bG | *-minB-luc-P2A-enz-bG | *-H68-luc-F2A-enz-W |

FIG. 16 cont'd

| | | | |
|---|---|---|---|
| *-CMV-TF-S | *-mut-FP-E2A-TF-bG | *-minB-luc-P2A-TF-bG | *-H68-luc-F2A-TF-W |
| *-CMV-rec-S | *-mut-FP-E2A-rec-bG | *-minB-luc-P2A-rec-bG | *-H68-luc-F2A-rec-W |
| *-CMV-CTP-S | *-mut-FP-E2A-CTP-bG | *-minB-luc-P2A-CTP-bG | *-H68-luc-F2A-CTP-W |
| *-CMV-SM-S | *-mut-FP-E2A-SM-bG | *-minB-luc-P2A-SM-bG | *-H68-luc-F2A-SM-W |
| *-CMV-NT-S | *-mut-FP-E2A-NT-bG | *-minB-luc-P2A-NT-bG | *-H68-luc-F2A-NT-W |
| *-CMV-CR-S | *-mut-FP-E2A-CR-bG | *-minB-luc-P2A-CR-bG | *-H68-luc-F2A-CR-W |
| *-CMV-chR-S | *-mut-FP-E2A-chR-bG | *-minB-luc-P2A-chR-bG | *-H68-luc-F2A-chR-W |
| *-CMV-gRNA-S | *-mut-FP-E2A-gRNA-bG | *-minB-luc-P2A-gRNA-bG | *-H68-luc-F2A-gRNA-W |
| *-CMV-Nuc-S | *-mut-FP-E2A-Nuc-bG | *-minB-luc-P2A-Nuc-bG | *-H68-luc-F2A-Nuc-W |
| *-SV40-enz-S | *-minR-FP-E2A-enz-bG | *-minC-luc-P2A-enz-bG | *-RSV-luc-F2A-enz-W |
| *-SV40-TF-S | *-minR-FP-E2A-TF-bG | *-minC-luc-P2A-TF-bG | *-RSV-luc-F2A-TF-W |
| *-SV40-rec-S | *-minR-FP-E2A-rec-bG | *-minC-luc-P2A-rec-bG | *-RSV-luc-F2A-rec-W |
| *-SV40-CTP-S | *-minR-FP-E2A-CTP-bG | *-minC-luc-P2A-CTP-bG | *-RSV-luc-F2A-CTP-W |
| *-SV40-SM-S | *-minR-FP-E2A-SM-bG | *-minC-luc-P2A-SM-bG | *-RSV-luc-F2A-SM-W |
| *-SV40-NT-S | *-minR-FP-E2A-NT-bG | *-minC-luc-P2A-NT-bG | *-RSV-luc-F2A-NT-W |
| *-SV40-CR-S | *-minR-FP-E2A-CR-bG | *-minC-luc-P2A-CR-bG | *-RSV-luc-F2A-CR-W |
| *-SV40-chR-S | *-minR-FP-E2A-chR-bG | *-minC-luc-P2A-chR-bG | *-RSV-luc-F2A-chR-W |
| *-SV40-gRNA-S | *-minR-FP-E2A-gRNA-bG | *-minC-luc-P2A-gRNA-bG | *-RSV-luc-F2A-gRNA-W |
| *-SV40-Nuc-S | *-minR-FP-E2A-Nuc-bG | *-minC-luc-P2A-Nuc-bG | *-RSV-luc-F2A-Nuc-W |
| *-H68-enz-S | *-CMV-FP-E2A-enz-bG | *-mut-luc-P2A-enz-bG | *-minB-luc-F2A-enz-bG |
| *-H68-TF-S | *-CMV-FP-E2A-TF-bG | *-mut-luc-P2A-TF-bG | *-minB-luc-F2A-TF-bG |
| *-H68-rec-S | *-CMV-FP-E2A-rec-bG | *-mut-luc-P2A-rec-bG | *-minB-luc-F2A-rec-bG |
| *-H68-CTP-S | *-CMV-FP-E2A-CTP-bG | *-mut-luc-P2A-CTP-bG | *-minB-luc-F2A-CTP-bG |
| *-H68-SM-S | *-CMV-FP-E2A-SM-bG | *-mut-luc-P2A-SM-bG | *-minB-luc-F2A-SM-bG |
| *-H68-NT-S | *-CMV-FP-E2A-NT-bG | *-mut-luc-P2A-NT-bG | *-minB-luc-F2A-NT-bG |
| *-H68-CR-S | *-CMV-FP-E2A-CR-bG | *-mut-luc-P2A-CR-bG | *-minB-luc-F2A-CR-bG |
| *-H68-chR-S | *-CMV-FP-E2A-chR-bG | *-mut-luc-P2A-chR-bG | *-minB-luc-F2A-chR-bG |
| *-H68-gRNA-S | *-CMV-FP-E2A-gRNA-bG | *-mut-luc-P2A-gRNA-bG | *-minB-luc-F2A-gRNA-bG |
| *-H68-Nuc-S | *-CMV-FP-E2A-Nuc-bG | *-mut-luc-P2A-Nuc-bG | *-minB-luc-F2A-Nuc-bG |
| *-RSV-enz-S | *-SV40-FP-E2A-enz-bG | *-minR-luc-P2A-enz-bG | *-minC-luc-F2A-enz-bG |
| *-RSV-TF-S | *-SV40-FP-E2A-TF-bG | *-minR-luc-P2A-TF-bG | *-minC-luc-F2A-TF-bG |
| *-RSV-rec-S | *-SV40-FP-E2A-rec-bG | *-minR-luc-P2A-rec-bG | *-minC-luc-F2A-rec-bG |
| *-RSV-CTP-S | *-SV40-FP-E2A-CTP-bG | *-minR-luc-P2A-CTP-bG | *-minC-luc-F2A-CTP-bG |
| *-RSV-SM-S | *-SV40-FP-E2A-SM-bG | *-minR-luc-P2A-SM-bG | *-minC-luc-F2A-SM-bG |

FIG. 16 cont'd

| | | | |
|---|---|---|---|
| *-RSV-NT-S | *-SV40-FP-E2A-NT-bG | *-minR-luc-P2A-NT-bG | *-minC-luc-F2A-NT-bG |
| *-RSV-CR-S | *-SV40-FP-E2A-CR-bG | *-minR-luc-P2A-CR-bG | *-minC-luc-F2A-CR-bG |
| *-RSV-chR-S | *-SV40-FP-E2A-chR-bG | *-minR-luc-P2A-chR-bG | *-minC-luc-F2A-chR-bG |
| *-RSV-gRNA-S | *-SV40-FP-E2A-gRNA-bG | *-minR-luc-P2A-gRNA-bG | *-minC-luc-F2A-gRNA-bG |
| *-RSV-Nuc-S | *-SV40-FP-E2A-Nuc-bG | *-minR-luc-P2A-Nuc-bG | *-minC-luc-F2A-Nuc-bG |
| *-minB-enz-W-S | *-H68-FP-E2A-enz-bG | *-CMV-luc-P2A-enz-bG | *-mut-luc-F2A-enz-bG |
| *-minB-TF-W-S | *-H68-FP-E2A-TF-bG | *-CMV-luc-P2A-TF-bG | *-mut-luc-F2A-TF-bG |
| *-minB-rec-W-S | *-H68-FP-E2A-rec-bG | *-CMV-luc-P2A-rec-bG | *-mut-luc-F2A-rec-bG |
| *-minB-CTP-W-S | *-H68-FP-E2A-CTP-bG | *-CMV-luc-P2A-CTP-bG | *-mut-luc-F2A-CTP-bG |
| *-minB-SM-W-S | *-H68-FP-E2A-SM-bG | *-CMV-luc-P2A-SM-bG | *-mut-luc-F2A-SM-bG |
| *-minB-NT-W-S | *-H68-FP-E2A-NT-bG | *-CMV-luc-P2A-NT-bG | *-mut-luc-F2A-NT-bG |
| *-minB-CR-W-S | *-H68-FP-E2A-CR-bG | *-CMV-luc-P2A-CR-bG | *-mut-luc-F2A-CR-bG |
| *-minB-chR-W-S | *-H68-FP-E2A-chR-bG | *-CMV-luc-P2A-chR-bG | *-mut-luc-F2A-chR-bG |
| *-minB-gRNA-W-S | *-H68-FP-E2A-gRNA-bG | *-CMV-luc-P2A-gRNA-bG | *-mut-luc-F2A-gRNA-bG |
| *-minB-Nuc-W-S | *-H68-FP-E2A-Nuc-bG | *-CMV-luc-P2A-Nuc-bG | *-mut-luc-F2A-Nuc-bG |
| *-minC-enz-W-S | *-RSV-FP-E2A-enz-bG | *-SV40-luc-P2A-enz-bG | *-minR-luc-F2A-enz-bG |
| *-minC-TF-W-S | *-RSV-FP-E2A-TF-bG | *-SV40-luc-P2A-TF-bG | *-minR-luc-F2A-TF-bG |
| *-minC-rec-W-S | *-RSV-FP-E2A-rec-bG | *-SV40-luc-P2A-rec-bG | *-minR-luc-F2A-rec-bG |
| *-minC-CTP-W-S | *-RSV-FP-E2A-CTP-bG | *-SV40-luc-P2A-CTP-bG | *-minR-luc-F2A-CTP-bG |
| *-minC-SM-W-S | *-RSV-FP-E2A-SM-bG | *-SV40-luc-P2A-SM-bG | *-minR-luc-F2A-SM-bG |
| *-minC-NT-W-S | *-RSV-FP-E2A-NT-bG | *-SV40-luc-P2A-NT-bG | *-minR-luc-F2A-NT-bG |
| *-minC-CR-W-S | *-RSV-FP-E2A-CR-bG | *-SV40-luc-P2A-CR-bG | *-minR-luc-F2A-CR-bG |
| *-minC-chR-W-S | *-RSV-FP-E2A-chR-bG | *-SV40-luc-P2A-chR-bG | *-minR-luc-F2A-chR-bG |
| *-minC-gRNA-W-S | *-RSV-FP-E2A-gRNA-bG | *-SV40-luc-P2A-gRNA-bG | *-minR-luc-F2A-gRNA-bG |
| *-minC-Nuc-W-S | *-RSV-FP-E2A-Nuc-bG | *-SV40-luc-P2A-Nuc-bG | *-minR-luc-F2A-Nuc-bG |
| *-mut-enz-W-S | *-minB-FP-E2A-enz-S | *-H68-luc-P2A-enz-bG | *-CMV-luc-F2A-enz-bG |
| *-mut-TF-W-S | *-minB-FP-E2A-TF-S | *-H68-luc-P2A-TF-bG | *-CMV-luc-F2A-TF-bG |
| *-mut-rec-W-S | *-minB-FP-E2A-rec-S | *-H68-luc-P2A-rec-bG | *-CMV-luc-F2A-rec-bG |
| *-mut-CTP-W-S | *-minB-FP-E2A-CTP-S | *-H68-luc-P2A-CTP-bG | *-CMV-luc-F2A-CTP-bG |
| *-mut-SM-W-S | *-minB-FP-E2A-SM-S | *-H68-luc-P2A-SM-bG | *-CMV-luc-F2A-SM-bG |
| *-mut-NT-W-S | *-minB-FP-E2A-NT-S | *-H68-luc-P2A-NT-bG | *-CMV-luc-F2A-NT-bG |
| *-mut-CR-W-S | *-minB-FP-E2A-CR-S | *-H68-luc-P2A-CR-bG | *-CMV-luc-F2A-CR-bG |
| *-mut-chR-W-S | *-minB-FP-E2A-chR-S | *-H68-luc-P2A-chR-bG | *-CMV-luc-F2A-chR-bG |
| *-mut-gRNA-W-S | *-minB-FP-E2A-gRNA-S | *-H68-luc-P2A-gRNA-bG | *-CMV-luc-F2A-gRNA-bG |

FIG. 16 cont'd

| | | | |
|---|---|---|---|
| *-mut-Nuc-W-S | *-minB-FP-E2A-Nuc-S | *-H68-luc-P2A-Nuc-bG | *-CMV-luc-F2A-Nuc-bG |
| *-minR-enz-W-S | *-minC-FP-E2A-enz-S | *-RSV-luc-P2A-enz-bG | *-SV40-luc-F2A-enz-bG |
| *-minR-TF-W-S | *-minC-FP-E2A-TF-S | *-RSV-luc-P2A-TF-bG | *-SV40-luc-F2A-TF-bG |
| *-minR-rec-W-S | *-minC-FP-E2A-rec-S | *-RSV-luc-P2A-rec-bG | *-SV40-luc-F2A-rec-bG |
| *-minR-CTP-W-S | *-minC-FP-E2A-CTP-S | *-RSV-luc-P2A-CTP-bG | *-SV40-luc-F2A-CTP-bG |
| *-minR-SM-W-S | *-minC-FP-E2A-SM-S | *-RSV-luc-P2A-SM-bG | *-SV40-luc-F2A-SM-bG |
| *-minR-NT-W-S | *-minC-FP-E2A-NT-S | *-RSV-luc-P2A-NT-bG | *-SV40-luc-F2A-NT-bG |
| *-minR-CR-W-S | *-minC-FP-E2A-CR-S | *-RSV-luc-P2A-CR-bG | *-SV40-luc-F2A-CR-bG |
| *-minR-chR-W-S | *-minC-FP-E2A-chR-S | *-RSV-luc-P2A-chR-bG | *-SV40-luc-F2A-chR-bG |
| *-minR-gRNA-W-S | *-minC-FP-E2A-gRNA-S | *-RSV-luc-P2A-gRNA-bG | *-SV40-luc-F2A-gRNA-bG |
| *-minR-Nuc-W-S | *-minC-FP-E2A-Nuc-S | *-RSV-luc-P2A-Nuc-bG | *-SV40-luc-F2A-Nuc-bG |
| *-minB-enz-bG | *-mut-FP-E2A-enz-S | *-minB-luc-P2A-enz-S | *-H68-luc-F2A-enz-bG |
| *-minB-TF-bG | *-mut-FP-E2A-TF-S | *-minB-luc-P2A-TF-S | *-H68-luc-F2A-TF-bG |
| *-minB-rec-bG | *-mut-FP-E2A-rec-S | *-minB-luc-P2A-rec-S | *-H68-luc-F2A-rec-bG |
| *-minB-CTP-bG | *-mut-FP-E2A-CTP-S | *-minB-luc-P2A-CTP-S | *-H68-luc-F2A-CTP-bG |
| *-minB-SM-bG | *-mut-FP-E2A-SM-S | *-minB-luc-P2A-SM-S | *-H68-luc-F2A-SM-bG |
| *-minB-NT-bG | *-mut-FP-E2A-NT-S | *-minB-luc-P2A-NT-S | *-H68-luc-F2A-NT-bG |
| *-minB-CR-bG | *-mut-FP-E2A-CR-S | *-minB-luc-P2A-CR-S | *-H68-luc-F2A-CR-bG |
| *-minB-chR-bG | *-mut-FP-E2A-chR-S | *-minB-luc-P2A-chR-S | *-H68-luc-F2A-chR-bG |
| *-minB-gRNA-bG | *-mut-FP-E2A-gRNA-S | *-minB-luc-P2A-gRNA-S | *-H68-luc-F2A-gRNA-bG |
| *-minB-Nuc-bG | *-mut-FP-E2A-Nuc-S | *-minB-luc-P2A-Nuc-S | *-H68-luc-F2A-Nuc-bG |
| *-minC-enz-bG | *-minR-FP-E2A-enz-S | *-minC-luc-P2A-enz-S | *-RSV-luc-F2A-enz-bG |
| *-minC-TF-bG | *-minR-FP-E2A-TF-S | *-minC-luc-P2A-TF-S | *-RSV-luc-F2A-TF-bG |
| *-minC-rec-bG | *-minR-FP-E2A-rec-S | *-minC-luc-P2A-rec-S | *-RSV-luc-F2A-rec-bG |
| *-minC-CTP-bG | *-minR-FP-E2A-CTP-S | *-minC-luc-P2A-CTP-S | *-RSV-luc-F2A-CTP-bG |
| *-minC-SM-bG | *-minR-FP-E2A-SM-S | *-minC-luc-P2A-SM-S | *-RSV-luc-F2A-SM-bG |
| *-minC-NT-bG | *-minR-FP-E2A-NT-S | *-minC-luc-P2A-NT-S | *-RSV-luc-F2A-NT-bG |
| *-minC-CR-bG | *-minR-FP-E2A-CR-S | *-minC-luc-P2A-CR-S | *-RSV-luc-F2A-CR-bG |
| *-minC-chR-bG | *-minR-FP-E2A-chR-S | *-minC-luc-P2A-chR-S | *-RSV-luc-F2A-chR-bG |
| *-minC-gRNA-bG | *-minR-FP-E2A-gRNA-S | *-minC-luc-P2A-gRNA-S | *-RSV-luc-F2A-gRNA-bG |
| *-minC-Nuc-bG | *-minR-FP-E2A-Nuc-S | *-minC-luc-P2A-Nuc-S | *-RSV-luc-F2A-Nuc-bG |
| *-mut-enz-bG | *-CMV-FP-E2A-enz-S | *-mut-luc-P2A-enz-S | *-minB-luc-F2A-enz-S |
| *-mut-TF-bG | *-CMV-FP-E2A-TF-S | *-mut-luc-P2A-TF-S | *-minB-luc-F2A-TF-S |
| *-mut-rec-bG | *-CMV-FP-E2A-rec-S | *-mut-luc-P2A-rec-S | *-minB-luc-F2A-rec-S |

FIG. 16 cont'd

| | | | |
|---|---|---|---|
| *-mut-CTP-bG | *-CMV-FP-E2A-CTP-S | *-mut-luc-P2A-CTP-S | *-minB-luc-F2A-CTP-S |
| *-mut-SM-bG | *-CMV-FP-E2A-SM-S | *-mut-luc-P2A-SM-S | *-minB-luc-F2A-SM-S |
| *-mut-NT-bG | *-CMV-FP-E2A-NT-S | *-mut-luc-P2A-NT-S | *-minB-luc-F2A-NT-S |
| *-mut-CR-bG | *-CMV-FP-E2A-CR-S | *-mut-luc-P2A-CR-S | *-minB-luc-F2A-CR-S |
| *-mut-chR-bG | *-CMV-FP-E2A-chR-S | *-mut-luc-P2A-chR-S | *-minB-luc-F2A-chR-S |
| *-mut-gRNA-bG | *-CMV-FP-E2A-gRNA-S | *-mut-luc-P2A-gRNA-S | *-minB-luc-F2A-gRNA-S |
| *-mut-Nuc-bG | *-CMV-FP-E2A-Nuc-S | *-mut-luc-P2A-Nuc-S | *-minB-luc-F2A-Nuc-S |
| *-minR-enz-bG | *-SV40-FP-E2A-enz-S | *-minR-luc-P2A-enz-S | *-minC-luc-F2A-enz-S |
| *-minR-TF-bG | *-SV40-FP-E2A-TF-S | *-minR-luc-P2A-TF-S | *-minC-luc-F2A-TF-S |
| *-minR-rec-bG | *-SV40-FP-E2A-rec-S | *-minR-luc-P2A-rec-S | *-minC-luc-F2A-rec-S |
| *-minR-CTP-bG | *-SV40-FP-E2A-CTP-S | *-minR-luc-P2A-CTP-S | *-minC-luc-F2A-CTP-S |
| *-minR-SM-bG | *-SV40-FP-E2A-SM-S | *-minR-luc-P2A-SM-S | *-minC-luc-F2A-SM-S |
| *-minR-NT-bG | *-SV40-FP-E2A-NT-S | *-minR-luc-P2A-NT-S | *-minC-luc-F2A-NT-S |
| *-minR-CR-bG | *-SV40-FP-E2A-CR-S | *-minR-luc-P2A-CR-S | *-minC-luc-F2A-CR-S |
| *-minR-chR-bG | *-SV40-FP-E2A-chR-S | *-minR-luc-P2A-chR-S | *-minC-luc-F2A-chR-S |
| *-minR-gRNA-bG | *-SV40-FP-E2A-gRNA-S | *-minR-luc-P2A-gRNA-S | *-minC-luc-F2A-gRNA-S |
| *-minR-Nuc-bG | *-SV40-FP-E2A-Nuc-S | *-minR-luc-P2A-Nuc-S | *-minC-luc-F2A-Nuc-S |
| *-CMV-enz-bG | *-H68-FP-E2A-enz-S | *-CMV-luc-P2A-enz-S | *-mut-luc-F2A-enz-S |
| *-CMV-TF-bG | *-H68-FP-E2A-TF-S | *-CMV-luc-P2A-TF-S | *-mut-luc-F2A-TF-S |
| *-CMV-rec-bG | *-H68-FP-E2A-rec-S | *-CMV-luc-P2A-rec-S | *-mut-luc-F2A-rec-S |
| *-CMV-CTP-bG | *-H68-FP-E2A-CTP-S | *-CMV-luc-P2A-CTP-S | *-mut-luc-F2A-CTP-S |
| *-CMV-SM-bG | *-H68-FP-E2A-SM-S | *-CMV-luc-P2A-SM-S | *-mut-luc-F2A-SM-S |
| *-CMV-NT-bG | *-H68-FP-E2A-NT-S | *-CMV-luc-P2A-NT-S | *-mut-luc-F2A-NT-S |
| *-CMV-CR-bG | *-H68-FP-E2A-CR-S | *-CMV-luc-P2A-CR-S | *-mut-luc-F2A-CR-S |
| *-CMV-chR-bG | *-H68-FP-E2A-chR-S | *-CMV-luc-P2A-chR-S | *-mut-luc-F2A-chR-S |
| *-CMV-gRNA-bG | *-H68-FP-E2A-gRNA-S | *-CMV-luc-P2A-gRNA-S | *-mut-luc-F2A-gRNA-S |
| *-CMV-Nuc-bG | *-H68-FP-E2A-Nuc-S | *-CMV-luc-P2A-Nuc-S | *-mut-luc-F2A-Nuc-S |
| *-SV40-enz-bG | *-RSV-FP-E2A-enz-S | *-SV40-luc-P2A-enz-S | *-minR-luc-F2A-enz-S |
| *-SV40-TF-bG | *-RSV-FP-E2A-TF-S | *-SV40-luc-P2A-TF-S | *-minR-luc-F2A-TF-S |
| *-SV40-rec-bG | *-RSV-FP-E2A-rec-S | *-SV40-luc-P2A-rec-S | *-minR-luc-F2A-rec-S |
| *-SV40-CTP-bG | *-RSV-FP-E2A-CTP-S | *-SV40-luc-P2A-CTP-S | *-minR-luc-F2A-CTP-S |
| *-SV40-SM-bG | *-RSV-FP-E2A-SM-S | *-SV40-luc-P2A-SM-S | *-minR-luc-F2A-SM-S |
| *-SV40-NT-bG | *-RSV-FP-E2A-NT-S | *-SV40-luc-P2A-NT-S | *-minR-luc-F2A-NT-S |
| *-SV40-CR-bG | *-RSV-FP-E2A-CR-S | *-SV40-luc-P2A-CR-S | *-minR-luc-F2A-CR-S |

FIG. 16 cont'd

| | | | |
|---|---|---|---|
| *-SV40-chR-bG | *-RSV-FP-E2A-chR-S | *-SV40-luc-P2A-chR-S | *-minR-luc-F2A-chR-S |
| *-SV40-gRNA-bG | *-RSV-FP-E2A-gRNA-S | *-SV40-luc-P2A-gRNA-S | *-minR-luc-F2A-gRNA-S |
| *-SV40-Nuc-bG | *-RSV-FP-E2A-Nuc-S | *-SV40-luc-P2A-Nuc-S | *-minR-luc-F2A-Nuc-S |
| *-H68-enz-bG | *-minB-FP-E2A-enz-W-bG | *-H68-luc-P2A-enz-S | *-CMV-luc-F2A-enz-S |
| *-H68-TF-bG | *-minB-FP-E2A-TF-W-bG | *-H68-luc-P2A-TF-S | *-CMV-luc-F2A-TF-S |
| *-H68-rec-bG | *-minB-FP-E2A-rec-W-bG | *-H68-luc-P2A-rec-S | *-CMV-luc-F2A-rec-S |
| *-H68-CTP-bG | *-minB-FP-E2A-CTP-W-bG | *-H68-luc-P2A-CTP-S | *-CMV-luc-F2A-CTP-S |
| *-H68-SM-bG | *-minB-FP-E2A-SM-W-bG | *-H68-luc-P2A-SM-S | *-CMV-luc-F2A-SM-S |
| *-H68-NT-bG | *-minB-FP-E2A-NT-W-bG | *-H68-luc-P2A-NT-S | *-CMV-luc-F2A-NT-S |
| *-H68-CR-bG | *-minB-FP-E2A-CR-W-bG | *-H68-luc-P2A-CR-S | *-CMV-luc-F2A-CR-S |
| *-H68-chR-bG | *-minB-FP-E2A-chR-W-bG | *-H68-luc-P2A-chR-S | *-CMV-luc-F2A-chR-S |
| *-H68-gRNA-bG | *-minB-FP-E2A-gRNA-W-bG | *-H68-luc-P2A-gRNA-S | *-CMV-luc-F2A-gRNA-S |
| *-H68-Nuc-bG | *-minB-FP-E2A-Nuc-W-bG | *-H68-luc-P2A-Nuc-S | *-CMV-luc-F2A-Nuc-S |
| *-RSV-enz-bG | *-minC-FP-E2A-enz-W-bG | *-RSV-luc-P2A-enz-S | *-SV40-luc-F2A-enz-S |
| *-RSV-TF-bG | *-minC-FP-E2A-TF-W-bG | *-RSV-luc-P2A-TF-S | *-SV40-luc-F2A-TF-S |
| *-RSV-rec-bG | *-minC-FP-E2A-rec-W-bG | *-RSV-luc-P2A-rec-S | *-SV40-luc-F2A-rec-S |
| *-RSV-CTP-bG | *-minC-FP-E2A-CTP-W-bG | *-RSV-luc-P2A-CTP-S | *-SV40-luc-F2A-CTP-S |
| *-RSV-SM-bG | *-minC-FP-E2A-SM-W-bG | *-RSV-luc-P2A-SM-S | *-SV40-luc-F2A-SM-S |
| *-RSV-NT-bG | *-minC-FP-E2A-NT-W-bG | *-RSV-luc-P2A-NT-S | *-SV40-luc-F2A-NT-S |
| *-RSV-CR-bG | *-minC-FP-E2A-CR-W-bG | *-RSV-luc-P2A-CR-S | *-SV40-luc-F2A-CR-S |
| *-RSV-chR-bG | *-minC-FP-E2A-chR-W-bG | *-RSV-luc-P2A-chR-S | *-SV40-luc-F2A-chR-S |
| *-RSV-gRNA-bG | *-minC-FP-E2A-gRNA-W-bG | *-RSV-luc-P2A-gRNA-S | *-SV40-luc-F2A-gRNA-S |
| *-RSV-Nuc-bG | *-minC-FP-E2A-Nuc-W-bG | *-RSV-luc-P2A-Nuc-S | *-SV40-luc-F2A-Nuc-S |
| *-minB-enz-W-bG | *-mut-FP-E2A-enz-W-bG | *-minB-luc-P2A-enz-W-bG | *-H68-luc-F2A-enz-S |
| *-minB-TF-W-bG | *-mut-FP-E2A-TF-W-bG | *-minB-luc-P2A-TF-W-bG | *-H68-luc-F2A-TF-S |
| *-minB-rec-W-bG | *-mut-FP-E2A-rec-W-bG | *-minB-luc-P2A-rec-W-bG | *-H68-luc-F2A-rec-S |
| *-minB-CTP-W-bG | *-mut-FP-E2A-CTP-W-bG | *-minB-luc-P2A-CTP-W-bG | *-H68-luc-F2A-CTP-S |
| *-minB-SM-W-bG | *-mut-FP-E2A-SM-W-bG | *-minB-luc-P2A-SM-W-bG | *-H68-luc-F2A-SM-S |
| *-minB-NT-W-bG | *-mut-FP-E2A-NT-W-bG | *-minB-luc-P2A-NT-W-bG | *-H68-luc-F2A-NT-S |
| *-minB-CR-W-bG | *-mut-FP-E2A-CR-W-bG | *-minB-luc-P2A-CR-W-bG | *-H68-luc-F2A-CR-S |
| *-minB-chR-W-bG | *-mut-FP-E2A-chR-W-bG | *-minB-luc-P2A-chR-W-bG | *-H68-luc-F2A-chR-S |
| *-minB-gRNA-W-bG | *-mut-FP-E2A-gRNA-W-bG | *-minB-luc-P2A-gRNA-W-bG | *-H68-luc-F2A-gRNA-S |
| *-minB-Nuc-W-bG | *-mut-FP-E2A-Nuc-W-bG | *-minB-luc-P2A-Nuc-W-bG | *-H68-luc-F2A-Nuc-S |
| *-minC-enz-W-bG | *-minR-FP-E2A-enz-W-bG | *-minC-luc-P2A-enz-W-bG | *-RSV-luc-F2A-enz-S |

FIG. 16 cont'd

| | | | |
|---|---|---|---|
| *-minC-TF-W-bG | *-minR-FP-E2A-TF-W-bG | *-minC-luc-P2A-TF-W-bG | *-RSV-luc-F2A-TF-S |
| *-minC-rec-W-bG | *-minR-FP-E2A-rec-W-bG | *-minC-luc-P2A-rec-W-bG | *-RSV-luc-F2A-rec-S |
| *-minC-CTP-W-bG | *-minR-FP-E2A-CTP-W-bG | *-minC-luc-P2A-CTP-W-bG | *-RSV-luc-F2A-CTP-S |
| *-minC-SM-W-bG | *-minR-FP-E2A-SM-W-bG | *-minC-luc-P2A-SM-W-bG | *-RSV-luc-F2A-SM-S |
| *-minC-NT-W-bG | *-minR-FP-E2A-NT-W-bG | *-minC-luc-P2A-NT-W-bG | *-RSV-luc-F2A-NT-S |
| *-minC-CR-W-bG | *-minR-FP-E2A-CR-W-bG | *-minC-luc-P2A-CR-W-bG | *-RSV-luc-F2A-CR-S |
| *-minC-chR-W-bG | *-minR-FP-E2A-chR-W-bG | *-minC-luc-P2A-chR-W-bG | *-RSV-luc-F2A-chR-S |
| *-minC-gRNA-W-bG | *-minR-FP-E2A-gRNA-W-bG | *-minC-luc-P2A-gRNA-W-bG | *-RSV-luc-F2A-gRNA-S |
| *-minC-Nuc-W-bG | *-minR-FP-E2A-Nuc-W-bG | *-minC-luc-P2A-Nuc-W-bG | *-RSV-luc-F2A-Nuc-S |
| *-mut-enz-W-bG | *-CMV-FP-E2A-enz-W-bG | *-mut-luc-P2A-enz-W-bG | *-minB-luc-F2A-enz-W-bG |
| *-mut-TF-W-bG | *-CMV-FP-E2A-TF-W-bG | *-mut-luc-P2A-TF-W-bG | *-minB-luc-F2A-TF-W-bG |
| *-mut-rec-W-bG | *-CMV-FP-E2A-rec-W-bG | *-mut-luc-P2A-rec-W-bG | *-minB-luc-F2A-rec-W-bG |
| *-mut-CTP-W-bG | *-CMV-FP-E2A-CTP-W-bG | *-mut-luc-P2A-CTP-W-bG | *-minB-luc-F2A-CTP-W-bG |
| *-mut-SM-W-bG | *-CMV-FP-E2A-SM-W-bG | *-mut-luc-P2A-SM-W-bG | *-minB-luc-F2A-SM-W-bG |
| *-mut-NT-W-bG | *-CMV-FP-E2A-NT-W-bG | *-mut-luc-P2A-NT-W-bG | *-minB-luc-F2A-NT-W-bG |
| *-mut-CR-W-bG | *-CMV-FP-E2A-CR-W-bG | *-mut-luc-P2A-CR-W-bG | *-minB-luc-F2A-CR-W-bG |
| *-mut-chR-W-bG | *-CMV-FP-E2A-chR-W-bG | *-mut-luc-P2A-chR-W-bG | *-minB-luc-F2A-chR-W-bG |
| *-mut-gRNA-W-bG | *-CMV-FP-E2A-gRNA-W-bG | *-mut-luc-P2A-gRNA-W-bG | *-minB-luc-F2A-gRNA-W-bG |
| *-mut-Nuc-W-bG | *-CMV-FP-E2A-Nuc-W-bG | *-mut-luc-P2A-Nuc-W-bG | *-minB-luc-F2A-Nuc-W-bG |
| *-minR-enz-W-bG | *-SV40-FP-E2A-enz-W-bG | *-minR-luc-P2A-enz-W-bG | *-minC-luc-F2A-enz-W-bG |
| *-minR-TF-W-bG | *-SV40-FP-E2A-TF-W-bG | *-minR-luc-P2A-TF-W-bG | *-minC-luc-F2A-TF-W-bG |
| *-minR-rec-W-bG | *-SV40-FP-E2A-rec-W-bG | *-minR-luc-P2A-rec-W-bG | *-minC-luc-F2A-rec-W-bG |
| *-minR-CTP-W-bG | *-SV40-FP-E2A-CTP-W-bG | *-minR-luc-P2A-CTP-W-bG | *-minC-luc-F2A-CTP-W-bG |
| *-minR-SM-W-bG | *-SV40-FP-E2A-SM-W-bG | *-minR-luc-P2A-SM-W-bG | *-minC-luc-F2A-SM-W-bG |
| *-minR-NT-W-bG | *-SV40-FP-E2A-NT-W-bG | *-minR-luc-P2A-NT-W-bG | *-minC-luc-F2A-NT-W-bG |
| *-minR-CR-W-bG | *-SV40-FP-E2A-CR-W-bG | *-minR-luc-P2A-CR-W-bG | *-minC-luc-F2A-CR-W-bG |
| *-minR-chR-W-bG | *-SV40-FP-E2A-chR-W-bG | *-minR-luc-P2A-chR-W-bG | *-minC-luc-F2A-chR-W-bG |
| *-minR-gRNA-W-bG | *-SV40-FP-E2A-gRNA-W-bG | *-minR-luc-P2A-gRNA-W-bG | *-minC-luc-F2A-gRNA-W-bG |
| *-minR-Nuc-W-bG | *-SV40-FP-E2A-Nuc-W-bG | *-minR-luc-P2A-Nuc-W-bG | *-minC-luc-F2A-Nuc-W-bG |
| *-CMV-enz-W-bG | *-H68-FP-E2A-enz-W-bG | *-CMV-luc-P2A-enz-W-bG | *-mut-luc-F2A-enz-W-bG |
| *-CMV-TF-W-bG | *-H68-FP-E2A-TF-W-bG | *-CMV-luc-P2A-TF-W-bG | *-mut-luc-F2A-TF-W-bG |
| *-CMV-rec-W-bG | *-H68-FP-E2A-rec-W-bG | *-CMV-luc-P2A-rec-W-bG | *-mut-luc-F2A-rec-W-bG |
| *-CMV-CTP-W-bG | *-H68-FP-E2A-CTP-W-bG | *-CMV-luc-P2A-CTP-W-bG | *-mut-luc-F2A-CTP-W-bG |
| *-CMV-SM-W-bG | *-H68-FP-E2A-SM-W-bG | *-CMV-luc-P2A-SM-W-bG | *-mut-luc-F2A-SM-W-bG |

FIG. 16 cont'd

| | | | |
|---|---|---|---|
| *-CMV-NT-W-bG | *-H68-FP-E2A-NT-W-bG | *-CMV-luc-P2A-NT-W-bG | *-mut-luc-F2A-NT-W-bG |
| *-CMV-CR-W-bG | *-H68-FP-E2A-CR-W-bG | *-CMV-luc-P2A-CR-W-bG | *-mut-luc-F2A-CR-W-bG |
| *-CMV-chR-W-bG | *-H68-FP-E2A-chR-W-bG | *-CMV-luc-P2A-chR-W-bG | *-mut-luc-F2A-chR-W-bG |
| *-CMV-gRNA-W-bG | *-H68-FP-E2A-gRNA-W-bG | *-CMV-luc-P2A-gRNA-W-bG | *-mut-luc-F2A-gRNA-W-bG |
| *-CMV-Nuc-W-bG | *-H68-FP-E2A-Nuc-W-bG | *-CMV-luc-P2A-Nuc-W-bG | *-mut-luc-F2A-Nuc-W-bG |
| *-SV40-enz-W-bG | *-RSV-FP-E2A-enz-W-bG | *-SV40-luc-P2A-enz-W-bG | *-minR-luc-F2A-enz-W-bG |
| *-SV40-TF-W-bG | *-RSV-FP-E2A-TF-W-bG | *-SV40-luc-P2A-TF-W-bG | *-minR-luc-F2A-TF-W-bG |
| *-SV40-rec-W-bG | *-RSV-FP-E2A-rec-W-bG | *-SV40-luc-P2A-rec-W-bG | *-minR-luc-F2A-rec-W-bG |
| *-SV40-CTP-W-bG | *-RSV-FP-E2A-CTP-W-bG | *-SV40-luc-P2A-CTP-W-bG | *-minR-luc-F2A-CTP-W-bG |
| *-SV40-SM-W-bG | *-RSV-FP-E2A-SM-W-bG | *-SV40-luc-P2A-SM-W-bG | *-minR-luc-F2A-SM-W-bG |
| *-SV40-NT-W-bG | *-RSV-FP-E2A-NT-W-bG | *-SV40-luc-P2A-NT-W-bG | *-minR-luc-F2A-NT-W-bG |
| *-SV40-CR-W-bG | *-RSV-FP-E2A-CR-W-bG | *-SV40-luc-P2A-CR-W-bG | *-minR-luc-F2A-CR-W-bG |
| *-SV40-chR-W-bG | *-RSV-FP-E2A-chR-W-bG | *-SV40-luc-P2A-chR-W-bG | *-minR-luc-F2A-chR-W-bG |
| *-SV40-gRNA-W-bG | *-RSV-FP-E2A-gRNA-W-bG | *-SV40-luc-P2A-gRNA-W-bG | *-minR-luc-F2A-gRNA-W-bG |
| *-SV40-Nuc-W-bG | *-RSV-FP-E2A-Nuc-W-bG | *-SV40-luc-P2A-Nuc-W-bG | *-minR-luc-F2A-Nuc-W-bG |
| *-H68-enz-W-bG | *-minB-FP-E2A-enz-W-S | *-H68-luc-P2A-enz-W-bG | *-CMV-luc-F2A-enz-W-bG |
| *-H68-TF-W-bG | *-minB-FP-E2A-TF-W-S | *-H68-luc-P2A-TF-W-bG | *-CMV-luc-F2A-TF-W-bG |
| *-H68-rec-W-bG | *-minB-FP-E2A-rec-W-S | *-H68-luc-P2A-rec-W-bG | *-CMV-luc-F2A-rec-W-bG |
| *-H68-CTP-W-bG | *-minB-FP-E2A-CTP-W-S | *-H68-luc-P2A-CTP-W-bG | *-CMV-luc-F2A-CTP-W-bG |
| *-H68-SM-W-bG | *-minB-FP-E2A-SM-W-S | *-H68-luc-P2A-SM-W-bG | *-CMV-luc-F2A-SM-W-bG |
| *-H68-NT-W-bG | *-minB-FP-E2A-NT-W-S | *-H68-luc-P2A-NT-W-bG | *-CMV-luc-F2A-NT-W-bG |
| *-H68-CR-W-bG | *-minB-FP-E2A-CR-W-S | *-H68-luc-P2A-CR-W-bG | *-CMV-luc-F2A-CR-W-bG |
| *-H68-chR-W-bG | *-minB-FP-E2A-chR-W-S | *-H68-luc-P2A-chR-W-bG | *-CMV-luc-F2A-chR-W-bG |
| *-H68-gRNA-W-bG | *-minB-FP-E2A-gRNA-W-S | *-H68-luc-P2A-gRNA-W-bG | *-CMV-luc-F2A-gRNA-W-bG |
| *-H68-Nuc-W-bG | *-minB-FP-E2A-Nuc-W-S | *-H68-luc-P2A-Nuc-W-bG | *-CMV-luc-F2A-Nuc-W-bG |
| *-RSV-enz-W-bG | *-minC-FP-E2A-enz-W-S | *-RSV-luc-P2A-enz-W-bG | *-SV40-luc-F2A-enz-W-bG |
| *-RSV-TF-W-bG | *-minC-FP-E2A-TF-W-S | *-RSV-luc-P2A-TF-W-bG | *-SV40-luc-F2A-TF-W-bG |
| *-RSV-rec-W-bG | *-minC-FP-E2A-rec-W-S | *-RSV-luc-P2A-rec-W-bG | *-SV40-luc-F2A-rec-W-bG |
| *-RSV-CTP-W-bG | *-minC-FP-E2A-CTP-W-S | *-RSV-luc-P2A-CTP-W-bG | *-SV40-luc-F2A-CTP-W-bG |
| *-RSV-SM-W-bG | *-minC-FP-E2A-SM-W-S | *-RSV-luc-P2A-SM-W-bG | *-SV40-luc-F2A-SM-W-bG |
| *-RSV-NT-W-bG | *-minC-FP-E2A-NT-W-S | *-RSV-luc-P2A-NT-W-bG | *-SV40-luc-F2A-NT-W-bG |
| *-RSV-CR-W-bG | *-minC-FP-E2A-CR-W-S | *-RSV-luc-P2A-CR-W-bG | *-SV40-luc-F2A-CR-W-bG |
| *-RSV-chR-W-bG | *-minC-FP-E2A-chR-W-S | *-RSV-luc-P2A-chR-W-bG | *-SV40-luc-F2A-chR-W-bG |
| *-RSV-gRNA-W-bG | *-minC-FP-E2A-gRNA-W-S | *-RSV-luc-P2A-gRNA-W-bG | *-SV40-luc-F2A-gRNA-W-bG |

FIG. 16 cont'd

| | | | |
|---|---|---|---|
| *-RSV-Nuc-W-bG | *-minC-FP-E2A-Nuc-W-S | *-RSV-luc-P2A-Nuc-W-bG | *-SV40-luc-F2A-Nuc-W-bG |
| *-CMV-enz-W-S | *-mut-FP-E2A-enz-W-S | *-minB-luc-P2A-enz-W-S | *-H68-luc-F2A-enz-W-bG |
| *-CMV-TF-W-S | *-mut-FP-E2A-TF-W-S | *-minB-luc-P2A-TF-W-S | *-H68-luc-F2A-TF-W-bG |
| *-CMV-rec-W-S | *-mut-FP-E2A-rec-W-S | *-minB-luc-P2A-rec-W-S | *-H68-luc-F2A-rec-W-bG |
| *-CMV-CTP-W-S | *-mut-FP-E2A-CTP-W-S | *-minB-luc-P2A-CTP-W-S | *-H68-luc-F2A-CTP-W-bG |
| *-CMV-SM-W-S | *-mut-FP-E2A-SM-W-S | *-minB-luc-P2A-SM-W-S | *-H68-luc-F2A-SM-W-bG |
| *-CMV-NT-W-S | *-mut-FP-E2A-NT-W-S | *-minB-luc-P2A-NT-W-S | *-H68-luc-F2A-NT-W-bG |
| *-CMV-CR-W-S | *-mut-FP-E2A-CR-W-S | *-minB-luc-P2A-CR-W-S | *-H68-luc-F2A-CR-W-bG |
| *-CMV-chR-W-S | *-mut-FP-E2A-chR-W-S | *-minB-luc-P2A-chR-W-S | *-H68-luc-F2A-chR-W-bG |
| *-CMV-gRNA-W-S | *-mut-FP-E2A-gRNA-W-S | *-minB-luc-P2A-gRNA-W-S | *-H68-luc-F2A-gRNA-W-bG |
| *-CMV-Nuc-W-S | *-mut-FP-E2A-Nuc-W-S | *-minB-luc-P2A-Nuc-W-S | *-H68-luc-F2A-Nuc-W-bG |
| *-SV40-enz-W-S | *-minR-FP-E2A-enz-W-S | *-minC-luc-P2A-enz-W-S | *-RSV-luc-F2A-enz-W-bG |
| *-SV40-TF-W-S | *-minR-FP-E2A-TF-W-S | *-minC-luc-P2A-TF-W-S | *-RSV-luc-F2A-TF-W-bG |
| *-SV40-rec-W-S | *-minR-FP-E2A-rec-W-S | *-minC-luc-P2A-rec-W-S | *-RSV-luc-F2A-rec-W-bG |
| *-SV40-CTP-W-S | *-minR-FP-E2A-CTP-W-S | *-minC-luc-P2A-CTP-W-S | *-RSV-luc-F2A-CTP-W-bG |
| *-SV40-SM-W-S | *-minR-FP-E2A-SM-W-S | *-minC-luc-P2A-SM-W-S | *-RSV-luc-F2A-SM-W-bG |
| *-SV40-NT-W-S | *-minR-FP-E2A-NT-W-S | *-minC-luc-P2A-NT-W-S | *-RSV-luc-F2A-NT-W-bG |
| *-SV40-CR-W-S | *-minR-FP-E2A-CR-W-S | *-minC-luc-P2A-CR-W-S | *-RSV-luc-F2A-CR-W-bG |
| *-SV40-chR-W-S | *-minR-FP-E2A-chR-W-S | *-minC-luc-P2A-chR-W-S | *-RSV-luc-F2A-chR-W-bG |
| *-SV40-gRNA-W-S | *-minR-FP-E2A-gRNA-W-S | *-minC-luc-P2A-gRNA-W-S | *-RSV-luc-F2A-gRNA-W-bG |
| *-SV40-Nuc-W-S | *-minR-FP-E2A-Nuc-W-S | *-minC-luc-P2A-Nuc-W-S | *-RSV-luc-F2A-Nuc-W-bG |
| *-H68-enz-W-S | *-CMV-FP-E2A-enz-W-S | *-mut-luc-P2A-enz-W-S | *-minB-luc-F2A-enz-W-S |
| *-H68-TF-W-S | *-CMV-FP-E2A-TF-W-S | *-mut-luc-P2A-TF-W-S | *-minB-luc-F2A-TF-W-S |
| *-H68-rec-W-S | *-CMV-FP-E2A-rec-W-S | *-mut-luc-P2A-rec-W-S | *-minB-luc-F2A-rec-W-S |
| *-H68-CTP-W-S | *-CMV-FP-E2A-CTP-W-S | *-mut-luc-P2A-CTP-W-S | *-minB-luc-F2A-CTP-W-S |
| *-H68-SM-W-S | *-CMV-FP-E2A-SM-W-S | *-mut-luc-P2A-SM-W-S | *-minB-luc-F2A-SM-W-S |
| *-H68-NT-W-S | *-CMV-FP-E2A-NT-W-S | *-mut-luc-P2A-NT-W-S | *-minB-luc-F2A-NT-W-S |
| *-H68-CR-W-S | *-CMV-FP-E2A-CR-W-S | *-mut-luc-P2A-CR-W-S | *-minB-luc-F2A-CR-W-S |
| *-H68-chR-W-S | *-CMV-FP-E2A-chR-W-S | *-mut-luc-P2A-chR-W-S | *-minB-luc-F2A-chR-W-S |
| *-H68-gRNA-W-S | *-CMV-FP-E2A-gRNA-W-S | *-mut-luc-P2A-gRNA-W-S | *-minB-luc-F2A-gRNA-W-S |
| *-H68-Nuc-W-S | *-CMV-FP-E2A-Nuc-W-S | *-mut-luc-P2A-Nuc-W-S | *-minB-luc-F2A-Nuc-W-S |
| *-RSV-enz-W-S | *-SV40-FP-E2A-enz-W-S | *-minR-luc-P2A-enz-W-S | *-minC-luc-F2A-enz-W-S |
| *-RSV-TF-W-S | *-SV40-FP-E2A-TF-W-S | *-minR-luc-P2A-TF-W-S | *-minC-luc-F2A-TF-W-S |
| *-RSV-rec-W-S | *-SV40-FP-E2A-rec-W-S | *-minR-luc-P2A-rec-W-S | *-minC-luc-F2A-rec-W-S |

FIG. 16 cont'd

| | | | |
|---|---|---|---|
| *-RSV-CTP-W-S | *-SV40-FP-E2A-CTP-W-S | *-minR-luc-P2A-CTP-W-S | *-minC-luc-F2A-CTP-W-S |
| *-RSV-SM-W-S | *-SV40-FP-E2A-SM-W-S | *-minR-luc-P2A-SM-W-S | *-minC-luc-F2A-SM-W-S |
| *-RSV-NT-W-S | *-SV40-FP-E2A-NT-W-S | *-minR-luc-P2A-NT-W-S | *-minC-luc-F2A-NT-W-S |
| *-RSV-CR-W-S | *-SV40-FP-E2A-CR-W-S | *-minR-luc-P2A-CR-W-S | *-minC-luc-F2A-CR-W-S |
| *-RSV-chR-W-S | *-SV40-FP-E2A-chR-W-S | *-minR-luc-P2A-chR-W-S | *-minC-luc-F2A-chR-W-S |
| *-RSV-gRNA-W-S | *-SV40-FP-E2A-gRNA-W-S | *-minR-luc-P2A-gRNA-W-S | *-minC-luc-F2A-gRNA-W-S |
| *-RSV-Nuc-W-S | *-SV40-FP-E2A-Nuc-W-S | *-minR-luc-P2A-Nuc-W-S | *-minC-luc-F2A-Nuc-W-S |
| *-minB-FP-P2A-enz-W | *-H68-FP-E2A-enz-W-S | *-CMV-luc-P2A-enz-W-S | *-mut-luc-F2A-enz-W-S |
| *-minB-FP-P2A-TF-W | *-H68-FP-E2A-TF-W-S | *-CMV-luc-P2A-TF-W-S | *-mut-luc-F2A-TF-W-S |
| *-minB-FP-P2A-rec-W | *-H68-FP-E2A-rec-W-S | *-CMV-luc-P2A-rec-W-S | *-mut-luc-F2A-rec-W-S |
| *-minB-FP-P2A-CTP-W | *-H68-FP-E2A-CTP-W-S | *-CMV-luc-P2A-CTP-W-S | *-mut-luc-F2A-CTP-W-S |
| *-minB-FP-P2A-SM-W | *-H68-FP-E2A-SM-W-S | *-CMV-luc-P2A-SM-W-S | *-mut-luc-F2A-SM-W-S |
| *-minB-FP-P2A-NT-W | *-H68-FP-E2A-NT-W-S | *-CMV-luc-P2A-NT-W-S | *-mut-luc-F2A-NT-W-S |
| *-minB-FP-P2A-CR-W | *-H68-FP-E2A-CR-W-S | *-CMV-luc-P2A-CR-W-S | *-mut-luc-F2A-CR-W-S |
| *-minB-FP-P2A-chR-W | *-H68-FP-E2A-chR-W-S | *-CMV-luc-P2A-chR-W-S | *-mut-luc-F2A-chR-W-S |
| *-minB-FP-P2A-gRNA-W | *-H68-FP-E2A-gRNA-W-S | *-CMV-luc-P2A-gRNA-W-S | *-mut-luc-F2A-gRNA-W-S |
| *-minB-FP-P2A-Nuc-W | *-H68-FP-E2A-Nuc-W-S | *-CMV-luc-P2A-Nuc-W-S | *-mut-luc-F2A-Nuc-W-S |
| *-minC-FP-P2A-enz-W | *-RSV-FP-E2A-enz-W-S | *-SV40-luc-P2A-enz-W-S | *-minR-luc-F2A-enz-W-S |
| *-minC-FP-P2A-TF-W | *-RSV-FP-E2A-TF-W-S | *-SV40-luc-P2A-TF-W-S | *-minR-luc-F2A-TF-W-S |
| *-minC-FP-P2A-rec-W | *-RSV-FP-E2A-rec-W-S | *-SV40-luc-P2A-rec-W-S | *-minR-luc-F2A-rec-W-S |
| *-minC-FP-P2A-CTP-W | *-RSV-FP-E2A-CTP-W-S | *-SV40-luc-P2A-CTP-W-S | *-minR-luc-F2A-CTP-W-S |
| *-minC-FP-P2A-SM-W | *-RSV-FP-E2A-SM-W-S | *-SV40-luc-P2A-SM-W-S | *-minR-luc-F2A-SM-W-S |
| *-minC-FP-P2A-NT-W | *-RSV-FP-E2A-NT-W-S | *-SV40-luc-P2A-NT-W-S | *-minR-luc-F2A-NT-W-S |
| *-minC-FP-P2A-CR-W | *-RSV-FP-E2A-CR-W-S | *-SV40-luc-P2A-CR-W-S | *-minR-luc-F2A-CR-W-S |
| *-minC-FP-P2A-chR-W | *-RSV-FP-E2A-chR-W-S | *-SV40-luc-P2A-chR-W-S | *-minR-luc-F2A-chR-W-S |
| *-minC-FP-P2A-gRNA-W | *-RSV-FP-E2A-gRNA-W-S | *-SV40-luc-P2A-gRNA-W-S | *-minR-luc-F2A-gRNA-W-S |
| *-minC-FP-P2A-Nuc-W | *-RSV-FP-E2A-Nuc-W-S | *-SV40-luc-P2A-Nuc-W-S | *-minR-luc-F2A-Nuc-W-S |
| *-mut-FP-P2A-enz-W | *-minB-FP-F2A-enz-W | *-H68-luc-P2A-enz-W-S | *-CMV-luc-F2A-enz-W-S |
| *-mut-FP-P2A-TF-W | *-minB-FP-F2A-TF-W | *-H68-luc-P2A-TF-W-S | *-CMV-luc-F2A-TF-W-S |
| *-mut-FP-P2A-rec-W | *-minB-FP-F2A-rec-W | *-H68-luc-P2A-rec-W-S | *-CMV-luc-F2A-rec-W-S |
| *-mut-FP-P2A-CTP-W | *-minB-FP-F2A-CTP-W | *-H68-luc-P2A-CTP-W-S | *-CMV-luc-F2A-CTP-W-S |
| *-mut-FP-P2A-SM-W | *-minB-FP-F2A-SM-W | *-H68-luc-P2A-SM-W-S | *-CMV-luc-F2A-SM-W-S |
| *-mut-FP-P2A-NT-W | *-minB-FP-F2A-NT-W | *-H68-luc-P2A-NT-W-S | *-CMV-luc-F2A-NT-W-S |
| *-mut-FP-P2A-CR-W | *-minB-FP-F2A-CR-W | *-H68-luc-P2A-CR-W-S | *-CMV-luc-F2A-CR-W-S |

FIG. 16 cont'd

| | | | |
|---|---|---|---|
| *-mut-FP-P2A-chR-W | *-minB-FP-F2A-chR-W | *-H68-luc-P2A-chR-W-S | *-CMV-luc-F2A-chR-W-S |
| *-mut-FP-P2A-gRNA-W | *-minB-FP-F2A-gRNA-W | *-H68-luc-P2A-gRNA-W-S | *-CMV-luc-F2A-gRNA-W-S |
| *-mut-FP-P2A-Nuc-W | *-minB-FP-F2A-Nuc-W | *-H68-luc-P2A-Nuc-W-S | *-CMV-luc-F2A-Nuc-W-S |
| *-minR-FP-P2A-enz-W | *-minC-FP-F2A-enz-W | *-RSV-luc-P2A-enz-W-S | *-SV40-luc-F2A-enz-W-S |
| *-minR-FP-P2A-TF-W | *-minC-FP-F2A-TF-W | *-RSV-luc-P2A-TF-W-S | *-SV40-luc-F2A-TF-W-S |
| *-minR-FP-P2A-rec-W | *-minC-FP-F2A-rec-W | *-RSV-luc-P2A-rec-W-S | *-SV40-luc-F2A-rec-W-S |
| *-minR-FP-P2A-CTP-W | *-minC-FP-F2A-CTP-W | *-RSV-luc-P2A-CTP-W-S | *-SV40-luc-F2A-CTP-W-S |
| *-minR-FP-P2A-SM-W | *-minC-FP-F2A-SM-W | *-RSV-luc-P2A-SM-W-S | *-SV40-luc-F2A-SM-W-S |
| *-minR-FP-P2A-NT-W | *-minC-FP-F2A-NT-W | *-RSV-luc-P2A-NT-W-S | *-SV40-luc-F2A-NT-W-S |
| *-minR-FP-P2A-CR-W | *-minC-FP-F2A-CR-W | *-RSV-luc-P2A-CR-W-S | *-SV40-luc-F2A-CR-W-S |
| *-minR-FP-P2A-chR-W | *-minC-FP-F2A-chR-W | *-RSV-luc-P2A-chR-W-S | *-SV40-luc-F2A-chR-W-S |
| *-minR-FP-P2A-gRNA-W | *-minC-FP-F2A-gRNA-W | *-RSV-luc-P2A-gRNA-W-S | *-SV40-luc-F2A-gRNA-W-S |
| *-minR-FP-P2A-Nuc-W | *-minC-FP-F2A-Nuc-W | *-RSV-luc-P2A-Nuc-W-S | *-SV40-luc-F2A-Nuc-W-S |
| *-CMV-FP-P2A-enz-W | *-mut-FP-F2A-enz-W | *-minB-luc-T2A-enz-W | *-H68-luc-F2A-enz-W-S |
| *-CMV-FP-P2A-TF-W | *-mut-FP-F2A-TF-W | *-minB-luc-T2A-TF-W | *-H68-luc-F2A-TF-W-S |
| *-CMV-FP-P2A-rec-W | *-mut-FP-F2A-rec-W | *-minB-luc-T2A-rec-W | *-H68-luc-F2A-rec-W-S |
| *-CMV-FP-P2A-CTP-W | *-mut-FP-F2A-CTP-W | *-minB-luc-T2A-CTP-W | *-H68-luc-F2A-CTP-W-S |
| *-CMV-FP-P2A-SM-W | *-mut-FP-F2A-SM-W | *-minB-luc-T2A-SM-W | *-H68-luc-F2A-SM-W-S |
| *-CMV-FP-P2A-NT-W | *-mut-FP-F2A-NT-W | *-minB-luc-T2A-NT-W | *-H68-luc-F2A-NT-W-S |
| *-CMV-FP-P2A-CR-W | *-mut-FP-F2A-CR-W | *-minB-luc-T2A-CR-W | *-H68-luc-F2A-CR-W-S |
| *-CMV-FP-P2A-chR-W | *-mut-FP-F2A-chR-W | *-minB-luc-T2A-chR-W | *-H68-luc-F2A-chR-W-S |
| *-CMV-FP-P2A-gRNA-W | *-mut-FP-F2A-gRNA-W | *-minB-luc-T2A-gRNA-W | *-H68-luc-F2A-gRNA-W-S |
| *-CMV-FP-P2A-Nuc-W | *-mut-FP-F2A-Nuc-W | *-minB-luc-T2A-Nuc-W | *-H68-luc-F2A-Nuc-W-S |
| *-SV40-FP-P2A-enz-W | *-minR-FP-F2A-enz-W | *-minC-luc-T2A-enz-W | *-RSV-luc-F2A-enz-W-S |
| *-SV40-FP-P2A-TF-W | *-minR-FP-F2A-TF-W | *-minC-luc-T2A-TF-W | *-RSV-luc-F2A-TF-W-S |
| *-SV40-FP-P2A-rec-W | *-minR-FP-F2A-rec-W | *-minC-luc-T2A-rec-W | *-RSV-luc-F2A-rec-W-S |
| *-SV40-FP-P2A-CTP-W | *-minR-FP-F2A-CTP-W | *-minC-luc-T2A-CTP-W | *-RSV-luc-F2A-CTP-W-S |
| *-SV40-FP-P2A-SM-W | *-minR-FP-F2A-SM-W | *-minC-luc-T2A-SM-W | *-RSV-luc-F2A-SM-W-S |
| *-SV40-FP-P2A-NT-W | *-minR-FP-F2A-NT-W | *-minC-luc-T2A-NT-W | *-RSV-luc-F2A-NT-W-S |
| *-SV40-FP-P2A-CR-W | *-minR-FP-F2A-CR-W | *-minC-luc-T2A-CR-W | *-RSV-luc-F2A-CR-W-S |
| *-SV40-FP-P2A-chR-W | *-minR-FP-F2A-chR-W | *-minC-luc-T2A-chR-W | *-RSV-luc-F2A-chR-W-S |
| *-SV40-FP-P2A-gRNA-W | *-minR-FP-F2A-gRNA-W | *-minC-luc-T2A-gRNA-W | *-RSV-luc-F2A-gRNA-W-S |
| *-SV40-FP-P2A-Nuc-W | *-minR-FP-F2A-Nuc-W | *-minC-luc-T2A-Nuc-W | *-RSV-luc-F2A-Nuc-W-S |
| *-H68-FP-P2A-enz-W | *-CMV-FP-F2A-enz-W | *-mut-luc-T2A-enz-W | *-minB-luc-I2-enz-W |

FIG. 16 cont'd

| | | | |
|---|---|---|---|
| *-H68-FP-P2A-TF-W | *-CMV-FP-F2A-TF-W | *-mut-luc-T2A-TF-W | *-minB-luc-I2-TF-W |
| *-H68-FP-P2A-rec-W | *-CMV-FP-F2A-rec-W | *-mut-luc-T2A-rec-W | *-minB-luc-I2-rec-W |
| *-H68-FP-P2A-CTP-W | *-CMV-FP-F2A-CTP-W | *-mut-luc-T2A-CTP-W | *-minB-luc-I2-CTP-W |
| *-H68-FP-P2A-SM-W | *-CMV-FP-F2A-SM-W | *-mut-luc-T2A-SM-W | *-minB-luc-I2-SM-W |
| *-H68-FP-P2A-NT-W | *-CMV-FP-F2A-NT-W | *-mut-luc-T2A-NT-W | *-minB-luc-I2-NT-W |
| *-H68-FP-P2A-CR-W | *-CMV-FP-F2A-CR-W | *-mut-luc-T2A-CR-W | *-minB-luc-I2-CR-W |
| *-H68-FP-P2A-chR-W | *-CMV-FP-F2A-chR-W | *-mut-luc-T2A-chR-W | *-minB-luc-I2-chR-W |
| *-H68-FP-P2A-gRNA-W | *-CMV-FP-F2A-gRNA-W | *-mut-luc-T2A-gRNA-W | *-minB-luc-I2-gRNA-W |
| *-H68-FP-P2A-Nuc-W | *-CMV-FP-F2A-Nuc-W | *-mut-luc-T2A-Nuc-W | *-minB-luc-I2-Nuc-W |
| *-RSV-FP-P2A-enz-W | *-SV40-FP-F2A-enz-W | *-minR-luc-T2A-enz-W | *-minC-luc-I2-enz-W |
| *-RSV-FP-P2A-TF-W | *-SV40-FP-F2A-TF-W | *-minR-luc-T2A-TF-W | *-minC-luc-I2-TF-W |
| *-RSV-FP-P2A-rec-W | *-SV40-FP-F2A-rec-W | *-minR-luc-T2A-rec-W | *-minC-luc-I2-rec-W |
| *-RSV-FP-P2A-CTP-W | *-SV40-FP-F2A-CTP-W | *-minR-luc-T2A-CTP-W | *-minC-luc-I2-CTP-W |
| *-RSV-FP-P2A-SM-W | *-SV40-FP-F2A-SM-W | *-minR-luc-T2A-SM-W | *-minC-luc-I2-SM-W |
| *-RSV-FP-P2A-NT-W | *-SV40-FP-F2A-NT-W | *-minR-luc-T2A-NT-W | *-minC-luc-I2-NT-W |
| *-RSV-FP-P2A-CR-W | *-SV40-FP-F2A-CR-W | *-minR-luc-T2A-CR-W | *-minC-luc-I2-CR-W |
| *-RSV-FP-P2A-chR-W | *-SV40-FP-F2A-chR-W | *-minR-luc-T2A-chR-W | *-minC-luc-I2-chR-W |
| *-RSV-FP-P2A-gRNA-W | *-SV40-FP-F2A-gRNA-W | *-minR-luc-T2A-gRNA-W | *-minC-luc-I2-gRNA-W |
| *-RSV-FP-P2A-Nuc-W | *-SV40-FP-F2A-Nuc-W | *-minR-luc-T2A-Nuc-W | *-minC-luc-I2-Nuc-W |
| *-minB-FP-P2A-enz-bG | *-H68-FP-F2A-enz-W | *-CMV-luc-T2A-enz-W | *-mut-luc-I2-enz-W |
| *-minB-FP-P2A-TF-bG | *-H68-FP-F2A-TF-W | *-CMV-luc-T2A-TF-W | *-mut-luc-I2-TF-W |
| *-minB-FP-P2A-rec-bG | *-H68-FP-F2A-rec-W | *-CMV-luc-T2A-rec-W | *-mut-luc-I2-rec-W |
| *-minB-FP-P2A-CTP-bG | *-H68-FP-F2A-CTP-W | *-CMV-luc-T2A-CTP-W | *-mut-luc-I2-CTP-W |
| *-minB-FP-P2A-SM-bG | *-H68-FP-F2A-SM-W | *-CMV-luc-T2A-SM-W | *-mut-luc-I2-SM-W |
| *-minB-FP-P2A-NT-bG | *-H68-FP-F2A-NT-W | *-CMV-luc-T2A-NT-W | *-mut-luc-I2-NT-W |
| *-minB-FP-P2A-CR-bG | *-H68-FP-F2A-CR-W | *-CMV-luc-T2A-CR-W | *-mut-luc-I2-CR-W |
| *-minB-FP-P2A-chR-bG | *-H68-FP-F2A-chR-W | *-CMV-luc-T2A-chR-W | *-mut-luc-I2-chR-W |
| *-minB-FP-P2A-gRNA-bG | *-H68-FP-F2A-gRNA-W | *-CMV-luc-T2A-gRNA-W | *-mut-luc-I2-gRNA-W |
| *-minB-FP-P2A-Nuc-bG | *-H68-FP-F2A-Nuc-W | *-CMV-luc-T2A-Nuc-W | *-mut-luc-I2-Nuc-W |
| *-minC-FP-P2A-enz-bG | *-RSV-FP-F2A-enz-W | *-SV40-luc-T2A-enz-W | *-minR-luc-I2-enz-W |
| *-minC-FP-P2A-TF-bG | *-RSV-FP-F2A-TF-W | *-SV40-luc-T2A-TF-W | *-minR-luc-I2-TF-W |
| *-minC-FP-P2A-rec-bG | *-RSV-FP-F2A-rec-W | *-SV40-luc-T2A-rec-W | *-minR-luc-I2-rec-W |
| *-minC-FP-P2A-CTP-bG | *-RSV-FP-F2A-CTP-W | *-SV40-luc-T2A-CTP-W | *-minR-luc-I2-CTP-W |
| *-minC-FP-P2A-SM-bG | *-RSV-FP-F2A-SM-W | *-SV40-luc-T2A-SM-W | *-minR-luc-I2-SM-W |

FIG. 16 cont'd

| | | | |
|---|---|---|---|
| *-minC-FP-P2A-NT-bG | *-RSV-FP-F2A-NT-W | *-SV40-luc-T2A-NT-W | *-minR-luc-I2-NT-W |
| *-minC-FP-P2A-CR-bG | *-RSV-FP-F2A-CR-W | *-SV40-luc-T2A-CR-W | *-minR-luc-I2-CR-W |
| *-minC-FP-P2A-chR-bG | *-RSV-FP-F2A-chR-W | *-SV40-luc-T2A-chR-W | *-minR-luc-I2-chR-W |
| *-minC-FP-P2A-gRNA-bG | *-RSV-FP-F2A-gRNA-W | *-SV40-luc-T2A-gRNA-W | *-minR-luc-I2-gRNA-W |
| *-minC-FP-P2A-Nuc-bG | *-RSV-FP-F2A-Nuc-W | *-SV40-luc-T2A-Nuc-W | *-minR-luc-I2-Nuc-W |
| *-mut-FP-P2A-enz-bG | *-minB-FP-F2A-enz-bG | *-H68-luc-T2A-enz-W | *-CMV-luc-I2-enz-W |
| *-mut-FP-P2A-TF-bG | *-minB-FP-F2A-TF-bG | *-H68-luc-T2A-TF-W | *-CMV-luc-I2-TF-W |
| *-mut-FP-P2A-rec-bG | *-minB-FP-F2A-rec-bG | *-H68-luc-T2A-rec-W | *-CMV-luc-I2-rec-W |
| *-mut-FP-P2A-CTP-bG | *-minB-FP-F2A-CTP-bG | *-H68-luc-T2A-CTP-W | *-CMV-luc-I2-CTP-W |
| *-mut-FP-P2A-SM-bG | *-minB-FP-F2A-SM-bG | *-H68-luc-T2A-SM-W | *-CMV-luc-I2-SM-W |
| *-mut-FP-P2A-NT-bG | *-minB-FP-F2A-NT-bG | *-H68-luc-T2A-NT-W | *-CMV-luc-I2-NT-W |
| *-mut-FP-P2A-CR-bG | *-minB-FP-F2A-CR-bG | *-H68-luc-T2A-CR-W | *-CMV-luc-I2-CR-W |
| *-mut-FP-P2A-chR-bG | *-minB-FP-F2A-chR-bG | *-H68-luc-T2A-chR-W | *-CMV-luc-I2-chR-W |
| *-mut-FP-P2A-gRNA-bG | *-minB-FP-F2A-gRNA-bG | *-H68-luc-T2A-gRNA-W | *-CMV-luc-I2-gRNA-W |
| *-mut-FP-P2A-Nuc-bG | *-minB-FP-F2A-Nuc-bG | *-H68-luc-T2A-Nuc-W | *-CMV-luc-I2-Nuc-W |
| *-minR-FP-P2A-enz-bG | *-minC-FP-F2A-enz-bG | *-RSV-luc-T2A-enz-W | *-SV40-luc-I2-enz-W |
| *-minR-FP-P2A-TF-bG | *-minC-FP-F2A-TF-bG | *-RSV-luc-T2A-TF-W | *-SV40-luc-I2-TF-W |
| *-minR-FP-P2A-rec-bG | *-minC-FP-F2A-rec-bG | *-RSV-luc-T2A-rec-W | *-SV40-luc-I2-rec-W |
| *-minR-FP-P2A-CTP-bG | *-minC-FP-F2A-CTP-bG | *-RSV-luc-T2A-CTP-W | *-SV40-luc-I2-CTP-W |
| *-minR-FP-P2A-SM-bG | *-minC-FP-F2A-SM-bG | *-RSV-luc-T2A-SM-W | *-SV40-luc-I2-SM-W |
| *-minR-FP-P2A-NT-bG | *-minC-FP-F2A-NT-bG | *-RSV-luc-T2A-NT-W | *-SV40-luc-I2-NT-W |
| *-minR-FP-P2A-CR-bG | *-minC-FP-F2A-CR-bG | *-RSV-luc-T2A-CR-W | *-SV40-luc-I2-CR-W |
| *-minR-FP-P2A-chR-bG | *-minC-FP-F2A-chR-bG | *-RSV-luc-T2A-chR-W | *-SV40-luc-I2-chR-W |
| *-minR-FP-P2A-gRNA-bG | *-minC-FP-F2A-gRNA-bG | *-RSV-luc-T2A-gRNA-W | *-SV40-luc-I2-gRNA-W |
| *-minR-FP-P2A-Nuc-bG | *-minC-FP-F2A-Nuc-bG | *-RSV-luc-T2A-Nuc-W | *-SV40-luc-I2-Nuc-W |
| *-CMV-FP-P2A-enz-bG | *-mut-FP-F2A-enz-bG | *-minB-luc-T2A-enz-bG | *-H68-luc-I2-enz-W |
| *-CMV-FP-P2A-TF-bG | *-mut-FP-F2A-TF-bG | *-minB-luc-T2A-TF-bG | *-H68-luc-I2-TF-W |
| *-CMV-FP-P2A-rec-bG | *-mut-FP-F2A-rec-bG | *-minB-luc-T2A-rec-bG | *-H68-luc-I2-rec-W |
| *-CMV-FP-P2A-CTP-bG | *-mut-FP-F2A-CTP-bG | *-minB-luc-T2A-CTP-bG | *-H68-luc-I2-CTP-W |
| *-CMV-FP-P2A-SM-bG | *-mut-FP-F2A-SM-bG | *-minB-luc-T2A-SM-bG | *-H68-luc-I2-SM-W |
| *-CMV-FP-P2A-NT-bG | *-mut-FP-F2A-NT-bG | *-minB-luc-T2A-NT-bG | *-H68-luc-I2-NT-W |
| *-CMV-FP-P2A-CR-bG | *-mut-FP-F2A-CR-bG | *-minB-luc-T2A-CR-bG | *-H68-luc-I2-CR-W |
| *-CMV-FP-P2A-chR-bG | *-mut-FP-F2A-chR-bG | *-minB-luc-T2A-chR-bG | *-H68-luc-I2-chR-W |
| *-CMV-FP-P2A-gRNA-bG | *-mut-FP-F2A-gRNA-bG | *-minB-luc-T2A-gRNA-bG | *-H68-luc-I2-gRNA-W |

FIG. 16 cont'd

| | | | |
|---|---|---|---|
| *-CMV-FP-P2A-Nuc-bG | *-mut-FP-F2A-Nuc-bG | *-minB-luc-T2A-Nuc-bG | *-H68-luc-I2-Nuc-W |
| *-SV40-FP-P2A-enz-bG | *-minR-FP-F2A-enz-bG | *-minC-luc-T2A-enz-bG | *-RSV-luc-I2-enz-W |
| *-SV40-FP-P2A-TF-bG | *-minR-FP-F2A-TF-bG | *-minC-luc-T2A-TF-bG | *-RSV-luc-I2-TF-W |
| *-SV40-FP-P2A-rec-bG | *-minR-FP-F2A-rec-bG | *-minC-luc-T2A-rec-bG | *-RSV-luc-I2-rec-W |
| *-SV40-FP-P2A-CTP-bG | *-minR-FP-F2A-CTP-bG | *-minC-luc-T2A-CTP-bG | *-RSV-luc-I2-CTP-W |
| *-SV40-FP-P2A-SM-bG | *-minR-FP-F2A-SM-bG | *-minC-luc-T2A-SM-bG | *-RSV-luc-I2-SM-W |
| *-SV40-FP-P2A-NT-bG | *-minR-FP-F2A-NT-bG | *-minC-luc-T2A-NT-bG | *-RSV-luc-I2-NT-W |
| *-SV40-FP-P2A-CR-bG | *-minR-FP-F2A-CR-bG | *-minC-luc-T2A-CR-bG | *-RSV-luc-I2-CR-W |
| *-SV40-FP-P2A-chR-bG | *-minR-FP-F2A-chR-bG | *-minC-luc-T2A-chR-bG | *-RSV-luc-I2-chR-W |
| *-SV40-FP-P2A-gRNA-bG | *-minR-FP-F2A-gRNA-bG | *-minC-luc-T2A-gRNA-bG | *-RSV-luc-I2-gRNA-W |
| *-SV40-FP-P2A-Nuc-bG | *-minR-FP-F2A-Nuc-bG | *-minC-luc-T2A-Nuc-bG | *-RSV-luc-I2-Nuc-W |
| *-H68-FP-P2A-enz-bG | *-CMV-FP-F2A-enz-bG | *-mut-luc-T2A-enz-bG | *-minB-luc-I2-enz-bG |
| *-H68-FP-P2A-TF-bG | *-CMV-FP-F2A-TF-bG | *-mut-luc-T2A-TF-bG | *-minB-luc-I2-TF-bG |
| *-H68-FP-P2A-rec-bG | *-CMV-FP-F2A-rec-bG | *-mut-luc-T2A-rec-bG | *-minB-luc-I2-rec-bG |
| *-H68-FP-P2A-CTP-bG | *-CMV-FP-F2A-CTP-bG | *-mut-luc-T2A-CTP-bG | *-minB-luc-I2-CTP-bG |
| *-H68-FP-P2A-SM-bG | *-CMV-FP-F2A-SM-bG | *-mut-luc-T2A-SM-bG | *-minB-luc-I2-SM-bG |
| *-H68-FP-P2A-NT-bG | *-CMV-FP-F2A-NT-bG | *-mut-luc-T2A-NT-bG | *-minB-luc-I2-NT-bG |
| *-H68-FP-P2A-CR-bG | *-CMV-FP-F2A-CR-bG | *-mut-luc-T2A-CR-bG | *-minB-luc-I2-CR-bG |
| *-H68-FP-P2A-chR-bG | *-CMV-FP-F2A-chR-bG | *-mut-luc-T2A-chR-bG | *-minB-luc-I2-chR-bG |
| *-H68-FP-P2A-gRNA-bG | *-CMV-FP-F2A-gRNA-bG | *-mut-luc-T2A-gRNA-bG | *-minB-luc-I2-gRNA-bG |
| *-H68-FP-P2A-Nuc-bG | *-CMV-FP-F2A-Nuc-bG | *-mut-luc-T2A-Nuc-bG | *-minB-luc-I2-Nuc-bG |
| *-RSV-FP-P2A-enz-bG | *-SV40-FP-F2A-enz-bG | *-minR-luc-T2A-enz-bG | *-minC-luc-I2-enz-bG |
| *-RSV-FP-P2A-TF-bG | *-SV40-FP-F2A-TF-bG | *-minR-luc-T2A-TF-bG | *-minC-luc-I2-TF-bG |
| *-RSV-FP-P2A-rec-bG | *-SV40-FP-F2A-rec-bG | *-minR-luc-T2A-rec-bG | *-minC-luc-I2-rec-bG |
| *-RSV-FP-P2A-CTP-bG | *-SV40-FP-F2A-CTP-bG | *-minR-luc-T2A-CTP-bG | *-minC-luc-I2-CTP-bG |
| *-RSV-FP-P2A-SM-bG | *-SV40-FP-F2A-SM-bG | *-minR-luc-T2A-SM-bG | *-minC-luc-I2-SM-bG |
| *-RSV-FP-P2A-NT-bG | *-SV40-FP-F2A-NT-bG | *-minR-luc-T2A-NT-bG | *-minC-luc-I2-NT-bG |
| *-RSV-FP-P2A-CR-bG | *-SV40-FP-F2A-CR-bG | *-minR-luc-T2A-CR-bG | *-minC-luc-I2-CR-bG |
| *-RSV-FP-P2A-chR-bG | *-SV40-FP-F2A-chR-bG | *-minR-luc-T2A-chR-bG | *-minC-luc-I2-chR-bG |
| *-RSV-FP-P2A-gRNA-bG | *-SV40-FP-F2A-gRNA-bG | *-minR-luc-T2A-gRNA-bG | *-minC-luc-I2-gRNA-bG |
| *-RSV-FP-P2A-Nuc-bG | *-SV40-FP-F2A-Nuc-bG | *-minR-luc-T2A-Nuc-bG | *-minC-luc-I2-Nuc-bG |
| *-minB-FP-P2A-enz-S | *-H68-FP-F2A-enz-bG | *-CMV-luc-T2A-enz-bG | *-mut-luc-I2-enz-bG |
| *-minB-FP-P2A-TF-S | *-H68-FP-F2A-TF-bG | *-CMV-luc-T2A-TF-bG | *-mut-luc-I2-TF-bG |
| *-minB-FP-P2A-rec-S | *-H68-FP-F2A-rec-bG | *-CMV-luc-T2A-rec-bG | *-mut-luc-I2-rec-bG |

FIG. 16 cont'd

| | | | |
|---|---|---|---|
| *-minB-FP-P2A-CTP-S | *-H68-FP-F2A-CTP-bG | *-CMV-luc-T2A-CTP-bG | *-mut-luc-I2-CTP-bG |
| *-minB-FP-P2A-SM-S | *-H68-FP-F2A-SM-bG | *-CMV-luc-T2A-SM-bG | *-mut-luc-I2-SM-bG |
| *-minB-FP-P2A-NT-S | *-H68-FP-F2A-NT-bG | *-CMV-luc-T2A-NT-bG | *-mut-luc-I2-NT-bG |
| *-minB-FP-P2A-CR-S | *-H68-FP-F2A-CR-bG | *-CMV-luc-T2A-CR-bG | *-mut-luc-I2-CR-bG |
| *-minB-FP-P2A-chR-S | *-H68-FP-F2A-chR-bG | *-CMV-luc-T2A-chR-bG | *-mut-luc-I2-chR-bG |
| *-minB-FP-P2A-gRNA-S | *-H68-FP-F2A-gRNA-bG | *-CMV-luc-T2A-gRNA-bG | *-mut-luc-I2-gRNA-bG |
| *-minB-FP-P2A-Nuc-S | *-H68-FP-F2A-Nuc-bG | *-CMV-luc-T2A-Nuc-bG | *-mut-luc-I2-Nuc-bG |
| *-minC-FP-P2A-enz-S | *-RSV-FP-F2A-enz-bG | *-SV40-luc-T2A-enz-bG | *-minR-luc-I2-enz-bG |
| *-minC-FP-P2A-TF-S | *-RSV-FP-F2A-TF-bG | *-SV40-luc-T2A-TF-bG | *-minR-luc-I2-TF-bG |
| *-minC-FP-P2A-rec-S | *-RSV-FP-F2A-rec-bG | *-SV40-luc-T2A-rec-bG | *-minR-luc-I2-rec-bG |
| *-minC-FP-P2A-CTP-S | *-RSV-FP-F2A-CTP-bG | *-SV40-luc-T2A-CTP-bG | *-minR-luc-I2-CTP-bG |
| *-minC-FP-P2A-SM-S | *-RSV-FP-F2A-SM-bG | *-SV40-luc-T2A-SM-bG | *-minR-luc-I2-SM-bG |
| *-minC-FP-P2A-NT-S | *-RSV-FP-F2A-NT-bG | *-SV40-luc-T2A-NT-bG | *-minR-luc-I2-NT-bG |
| *-minC-FP-P2A-CR-S | *-RSV-FP-F2A-CR-bG | *-SV40-luc-T2A-CR-bG | *-minR-luc-I2-CR-bG |
| *-minC-FP-P2A-chR-S | *-RSV-FP-F2A-chR-bG | *-SV40-luc-T2A-chR-bG | *-minR-luc-I2-chR-bG |
| *-minC-FP-P2A-gRNA-S | *-RSV-FP-F2A-gRNA-bG | *-SV40-luc-T2A-gRNA-bG | *-minR-luc-I2-gRNA-bG |
| *-minC-FP-P2A-Nuc-S | *-RSV-FP-F2A-Nuc-bG | *-SV40-luc-T2A-Nuc-bG | *-minR-luc-I2-Nuc-bG |
| *-mut-FP-P2A-enz-S | *-minB-FP-F2A-enz-S | *-H68-luc-T2A-enz-bG | *-CMV-luc-I2-enz-bG |
| *-mut-FP-P2A-TF-S | *-minB-FP-F2A-TF-S | *-H68-luc-T2A-TF-bG | *-CMV-luc-I2-TF-bG |
| *-mut-FP-P2A-rec-S | *-minB-FP-F2A-rec-S | *-H68-luc-T2A-rec-bG | *-CMV-luc-I2-rec-bG |
| *-mut-FP-P2A-CTP-S | *-minB-FP-F2A-CTP-S | *-H68-luc-T2A-CTP-bG | *-CMV-luc-I2-CTP-bG |
| *-mut-FP-P2A-SM-S | *-minB-FP-F2A-SM-S | *-H68-luc-T2A-SM-bG | *-CMV-luc-I2-SM-bG |
| *-mut-FP-P2A-NT-S | *-minB-FP-F2A-NT-S | *-H68-luc-T2A-NT-bG | *-CMV-luc-I2-NT-bG |
| *-mut-FP-P2A-CR-S | *-minB-FP-F2A-CR-S | *-H68-luc-T2A-CR-bG | *-CMV-luc-I2-CR-bG |
| *-mut-FP-P2A-chR-S | *-minB-FP-F2A-chR-S | *-H68-luc-T2A-chR-bG | *-CMV-luc-I2-chR-bG |
| *-mut-FP-P2A-gRNA-S | *-minB-FP-F2A-gRNA-S | *-H68-luc-T2A-gRNA-bG | *-CMV-luc-I2-gRNA-bG |
| *-mut-FP-P2A-Nuc-S | *-minB-FP-F2A-Nuc-S | *-H68-luc-T2A-Nuc-bG | *-CMV-luc-I2-Nuc-bG |
| *-minR-FP-P2A-enz-S | *-minC-FP-F2A-enz-S | *-RSV-luc-T2A-enz-bG | *-SV40-luc-I2-enz-bG |
| *-minR-FP-P2A-TF-S | *-minC-FP-F2A-TF-S | *-RSV-luc-T2A-TF-bG | *-SV40-luc-I2-TF-bG |
| *-minR-FP-P2A-rec-S | *-minC-FP-F2A-rec-S | *-RSV-luc-T2A-rec-bG | *-SV40-luc-I2-rec-bG |
| *-minR-FP-P2A-CTP-S | *-minC-FP-F2A-CTP-S | *-RSV-luc-T2A-CTP-bG | *-SV40-luc-I2-CTP-bG |
| *-minR-FP-P2A-SM-S | *-minC-FP-F2A-SM-S | *-RSV-luc-T2A-SM-bG | *-SV40-luc-I2-SM-bG |
| *-minR-FP-P2A-NT-S | *-minC-FP-F2A-NT-S | *-RSV-luc-T2A-NT-bG | *-SV40-luc-I2-NT-bG |
| *-minR-FP-P2A-CR-S | *-minC-FP-F2A-CR-S | *-RSV-luc-T2A-CR-bG | *-SV40-luc-I2-CR-bG |

FIG. 16 cont'd

| | | | |
|---|---|---|---|
| *-minR-FP-P2A-chR-S | *-minC-FP-F2A-chR-S | *-RSV-luc-T2A-chR-bG | *-SV40-luc-I2-chR-bG |
| *-minR-FP-P2A-gRNA-S | *-minC-FP-F2A-gRNA-S | *-RSV-luc-T2A-gRNA-bG | *-SV40-luc-I2-gRNA-bG |
| *-minR-FP-P2A-Nuc-S | *-minC-FP-F2A-Nuc-S | *-RSV-luc-T2A-Nuc-bG | *-SV40-luc-I2-Nuc-bG |
| *-CMV-FP-P2A-enz-S | *-mut-FP-F2A-enz-S | *-minB-luc-T2A-enz-S | *-H68-luc-I2-enz-bG |
| *-CMV-FP-P2A-TF-S | *-mut-FP-F2A-TF-S | *-minB-luc-T2A-TF-S | *-H68-luc-I2-TF-bG |
| *-CMV-FP-P2A-rec-S | *-mut-FP-F2A-rec-S | *-minB-luc-T2A-rec-S | *-H68-luc-I2-rec-bG |
| *-CMV-FP-P2A-CTP-S | *-mut-FP-F2A-CTP-S | *-minB-luc-T2A-CTP-S | *-H68-luc-I2-CTP-bG |
| *-CMV-FP-P2A-SM-S | *-mut-FP-F2A-SM-S | *-minB-luc-T2A-SM-S | *-H68-luc-I2-SM-bG |
| *-CMV-FP-P2A-NT-S | *-mut-FP-F2A-NT-S | *-minB-luc-T2A-NT-S | *-H68-luc-I2-NT-bG |
| *-CMV-FP-P2A-CR-S | *-mut-FP-F2A-CR-S | *-minB-luc-T2A-CR-S | *-H68-luc-I2-CR-bG |
| *-CMV-FP-P2A-chR-S | *-mut-FP-F2A-chR-S | *-minB-luc-T2A-chR-S | *-H68-luc-I2-chR-bG |
| *-CMV-FP-P2A-gRNA-S | *-mut-FP-F2A-gRNA-S | *-minB-luc-T2A-gRNA-S | *-H68-luc-I2-gRNA-bG |
| *-CMV-FP-P2A-Nuc-S | *-mut-FP-F2A-Nuc-S | *-minB-luc-T2A-Nuc-S | *-H68-luc-I2-Nuc-bG |
| *-SV40-FP-P2A-enz-S | *-minR-FP-F2A-enz-S | *-minC-luc-T2A-enz-S | *-RSV-luc-I2-enz-bG |
| *-SV40-FP-P2A-TF-S | *-minR-FP-F2A-TF-S | *-minC-luc-T2A-TF-S | *-RSV-luc-I2-TF-bG |
| *-SV40-FP-P2A-rec-S | *-minR-FP-F2A-rec-S | *-minC-luc-T2A-rec-S | *-RSV-luc-I2-rec-bG |
| *-SV40-FP-P2A-CTP-S | *-minR-FP-F2A-CTP-S | *-minC-luc-T2A-CTP-S | *-RSV-luc-I2-CTP-bG |
| *-SV40-FP-P2A-SM-S | *-minR-FP-F2A-SM-S | *-minC-luc-T2A-SM-S | *-RSV-luc-I2-SM-bG |
| *-SV40-FP-P2A-NT-S | *-minR-FP-F2A-NT-S | *-minC-luc-T2A-NT-S | *-RSV-luc-I2-NT-bG |
| *-SV40-FP-P2A-CR-S | *-minR-FP-F2A-CR-S | *-minC-luc-T2A-CR-S | *-RSV-luc-I2-CR-bG |
| *-SV40-FP-P2A-chR-S | *-minR-FP-F2A-chR-S | *-minC-luc-T2A-chR-S | *-RSV-luc-I2-chR-bG |
| *-SV40-FP-P2A-gRNA-S | *-minR-FP-F2A-gRNA-S | *-minC-luc-T2A-gRNA-S | *-RSV-luc-I2-gRNA-bG |
| *-SV40-FP-P2A-Nuc-S | *-minR-FP-F2A-Nuc-S | *-minC-luc-T2A-Nuc-S | *-RSV-luc-I2-Nuc-bG |
| *-H68-FP-P2A-enz-S | *-CMV-FP-F2A-enz-S | *-mut-luc-T2A-enz-S | *-minB-luc-I2-enz-S |
| *-H68-FP-P2A-TF-S | *-CMV-FP-F2A-TF-S | *-mut-luc-T2A-TF-S | *-minB-luc-I2-TF-S |
| *-H68-FP-P2A-rec-S | *-CMV-FP-F2A-rec-S | *-mut-luc-T2A-rec-S | *-minB-luc-I2-rec-S |
| *-H68-FP-P2A-CTP-S | *-CMV-FP-F2A-CTP-S | *-mut-luc-T2A-CTP-S | *-minB-luc-I2-CTP-S |
| *-H68-FP-P2A-SM-S | *-CMV-FP-F2A-SM-S | *-mut-luc-T2A-SM-S | *-minB-luc-I2-SM-S |
| *-H68-FP-P2A-NT-S | *-CMV-FP-F2A-NT-S | *-mut-luc-T2A-NT-S | *-minB-luc-I2-NT-S |
| *-H68-FP-P2A-CR-S | *-CMV-FP-F2A-CR-S | *-mut-luc-T2A-CR-S | *-minB-luc-I2-CR-S |
| *-H68-FP-P2A-chR-S | *-CMV-FP-F2A-chR-S | *-mut-luc-T2A-chR-S | *-minB-luc-I2-chR-S |
| *-H68-FP-P2A-gRNA-S | *-CMV-FP-F2A-gRNA-S | *-mut-luc-T2A-gRNA-S | *-minB-luc-I2-gRNA-S |
| *-H68-FP-P2A-Nuc-S | *-CMV-FP-F2A-Nuc-S | *-mut-luc-T2A-Nuc-S | *-minB-luc-I2-Nuc-S |
| *-RSV-FP-P2A-enz-S | *-SV40-FP-F2A-enz-S | *-minR-luc-T2A-enz-S | *-minC-luc-I2-enz-S |

FIG. 16 cont'd

| | | | |
|---|---|---|---|
| *-RSV-FP-P2A-TF-S | *-SV40-FP-F2A-TF-S | *-minR-luc-T2A-TF-S | *-minC-luc-I2-TF-S |
| *-RSV-FP-P2A-rec-S | *-SV40-FP-F2A-rec-S | *-minR-luc-T2A-rec-S | *-minC-luc-I2-rec-S |
| *-RSV-FP-P2A-CTP-S | *-SV40-FP-F2A-CTP-S | *-minR-luc-T2A-CTP-S | *-minC-luc-I2-CTP-S |
| *-RSV-FP-P2A-SM-S | *-SV40-FP-F2A-SM-S | *-minR-luc-T2A-SM-S | *-minC-luc-I2-SM-S |
| *-RSV-FP-P2A-NT-S | *-SV40-FP-F2A-NT-S | *-minR-luc-T2A-NT-S | *-minC-luc-I2-NT-S |
| *-RSV-FP-P2A-CR-S | *-SV40-FP-F2A-CR-S | *-minR-luc-T2A-CR-S | *-minC-luc-I2-CR-S |
| *-RSV-FP-P2A-chR-S | *-SV40-FP-F2A-chR-S | *-minR-luc-T2A-chR-S | *-minC-luc-I2-chR-S |
| *-RSV-FP-P2A-gRNA-S | *-SV40-FP-F2A-gRNA-S | *-minR-luc-T2A-gRNA-S | *-minC-luc-I2-gRNA-S |
| *-RSV-FP-P2A-Nuc-S | *-SV40-FP-F2A-Nuc-S | *-minR-luc-T2A-Nuc-S | *-minC-luc-I2-Nuc-S |
| *-minB-FP-P2A-enz-W-bG | *-H68-FP-F2A-enz-S | *-CMV-luc-T2A-enz-S | *-mut-luc-I2-enz-S |
| *-minB-FP-P2A-TF-W-bG | *-H68-FP-F2A-TF-S | *-CMV-luc-T2A-TF-S | *-mut-luc-I2-TF-S |
| *-minB-FP-P2A-rec-W-bG | *-H68-FP-F2A-rec-S | *-CMV-luc-T2A-rec-S | *-mut-luc-I2-rec-S |
| *-minB-FP-P2A-CTP-W-bG | *-H68-FP-F2A-CTP-S | *-CMV-luc-T2A-CTP-S | *-mut-luc-I2-CTP-S |
| *-minB-FP-P2A-SM-W-bG | *-H68-FP-F2A-SM-S | *-CMV-luc-T2A-SM-S | *-mut-luc-I2-SM-S |
| *-minB-FP-P2A-NT-W-bG | *-H68-FP-F2A-NT-S | *-CMV-luc-T2A-NT-S | *-mut-luc-I2-NT-S |
| *-minB-FP-P2A-CR-W-bG | *-H68-FP-F2A-CR-S | *-CMV-luc-T2A-CR-S | *-mut-luc-I2-CR-S |
| *-minB-FP-P2A-chR-W-bG | *-H68-FP-F2A-chR-S | *-CMV-luc-T2A-chR-S | *-mut-luc-I2-chR-S |
| *-minB-FP-P2A-gRNA-W-bG | *-H68-FP-F2A-gRNA-S | *-CMV-luc-T2A-gRNA-S | *-mut-luc-I2-gRNA-S |
| *-minB-FP-P2A-Nuc-W-bG | *-H68-FP-F2A-Nuc-S | *-CMV-luc-T2A-Nuc-S | *-mut-luc-I2-Nuc-S |
| *-minC-FP-P2A-enz-W-bG | *-RSV-FP-F2A-enz-S | *-SV40-luc-T2A-enz-S | *-minR-luc-I2-enz-S |
| *-minC-FP-P2A-TF-W-bG | *-RSV-FP-F2A-TF-S | *-SV40-luc-T2A-TF-S | *-minR-luc-I2-TF-S |
| *-minC-FP-P2A-rec-W-bG | *-RSV-FP-F2A-rec-S | *-SV40-luc-T2A-rec-S | *-minR-luc-I2-rec-S |
| *-minC-FP-P2A-CTP-W-bG | *-RSV-FP-F2A-CTP-S | *-SV40-luc-T2A-CTP-S | *-minR-luc-I2-CTP-S |
| *-minC-FP-P2A-SM-W-bG | *-RSV-FP-F2A-SM-S | *-SV40-luc-T2A-SM-S | *-minR-luc-I2-SM-S |
| *-minC-FP-P2A-NT-W-bG | *-RSV-FP-F2A-NT-S | *-SV40-luc-T2A-NT-S | *-minR-luc-I2-NT-S |
| *-minC-FP-P2A-CR-W-bG | *-RSV-FP-F2A-CR-S | *-SV40-luc-T2A-CR-S | *-minR-luc-I2-CR-S |
| *-minC-FP-P2A-chR-W-bG | *-RSV-FP-F2A-chR-S | *-SV40-luc-T2A-chR-S | *-minR-luc-I2-chR-S |
| *-minC-FP-P2A-gRNA-W-bG | *-RSV-FP-F2A-gRNA-S | *-SV40-luc-T2A-gRNA-S | *-minR-luc-I2-gRNA-S |
| *-minC-FP-P2A-Nuc-W-bG | *-RSV-FP-F2A-Nuc-S | *-SV40-luc-T2A-Nuc-S | *-minR-luc-I2-Nuc-S |
| *-mut-FP-P2A-enz-W-bG | *-minB-FP-F2A-enz-W-bG | *-H68-luc-T2A-enz-S | *-CMV-luc-I2-enz-S |
| *-mut-FP-P2A-TF-W-bG | *-minB-FP-F2A-TF-W-bG | *-H68-luc-T2A-TF-S | *-CMV-luc-I2-TF-S |
| *-mut-FP-P2A-rec-W-bG | *-minB-FP-F2A-rec-W-bG | *-H68-luc-T2A-rec-S | *-CMV-luc-I2-rec-S |
| *-mut-FP-P2A-CTP-W-bG | *-minB-FP-F2A-CTP-W-bG | *-H68-luc-T2A-CTP-S | *-CMV-luc-I2-CTP-S |
| *-mut-FP-P2A-SM-W-bG | *-minB-FP-F2A-SM-W-bG | *-H68-luc-T2A-SM-S | *-CMV-luc-I2-SM-S |

FIG. 16 cont'd

| | | | |
|---|---|---|---|
| *-mut-FP-P2A-NT-W-bG | *-minB-FP-F2A-NT-W-bG | *-H68-luc-T2A-NT-S | *-CMV-luc-I2-NT-S |
| *-mut-FP-P2A-CR-W-bG | *-minB-FP-F2A-CR-W-bG | *-H68-luc-T2A-CR-S | *-CMV-luc-I2-CR-S |
| *-mut-FP-P2A-chR-W-bG | *-minB-FP-F2A-chR-W-bG | *-H68-luc-T2A-chR-S | *-CMV-luc-I2-chR-S |
| *-mut-FP-P2A-gRNA-W-bG | *-minB-FP-F2A-gRNA-W-bG | *-H68-luc-T2A-gRNA-S | *-CMV-luc-I2-gRNA-S |
| *-mut-FP-P2A-Nuc-W-bG | *-minB-FP-F2A-Nuc-W-bG | *-H68-luc-T2A-Nuc-S | *-CMV-luc-I2-Nuc-S |
| *-minR-FP-P2A-enz-W-bG | *-minC-FP-F2A-enz-W-bG | *-RSV-luc-T2A-enz-S | *-SV40-luc-I2-enz-S |
| *-minR-FP-P2A-TF-W-bG | *-minC-FP-F2A-TF-W-bG | *-RSV-luc-T2A-TF-S | *-SV40-luc-I2-TF-S |
| *-minR-FP-P2A-rec-W-bG | *-minC-FP-F2A-rec-W-bG | *-RSV-luc-T2A-rec-S | *-SV40-luc-I2-rec-S |
| *-minR-FP-P2A-CTP-W-bG | *-minC-FP-F2A-CTP-W-bG | *-RSV-luc-T2A-CTP-S | *-SV40-luc-I2-CTP-S |
| *-minR-FP-P2A-SM-W-bG | *-minC-FP-F2A-SM-W-bG | *-RSV-luc-T2A-SM-S | *-SV40-luc-I2-SM-S |
| *-minR-FP-P2A-NT-W-bG | *-minC-FP-F2A-NT-W-bG | *-RSV-luc-T2A-NT-S | *-SV40-luc-I2-NT-S |
| *-minR-FP-P2A-CR-W-bG | *-minC-FP-F2A-CR-W-bG | *-RSV-luc-T2A-CR-S | *-SV40-luc-I2-CR-S |
| *-minR-FP-P2A-chR-W-bG | *-minC-FP-F2A-chR-W-bG | *-RSV-luc-T2A-chR-S | *-SV40-luc-I2-chR-S |
| *-minR-FP-P2A-gRNA-W-bG | *-minC-FP-F2A-gRNA-W-bG | *-RSV-luc-T2A-gRNA-S | *-SV40-luc-I2-gRNA-S |
| *-minR-FP-P2A-Nuc-W-bG | *-minC-FP-F2A-Nuc-W-bG | *-RSV-luc-T2A-Nuc-S | *-SV40-luc-I2-Nuc-S |
| *-CMV-FP-P2A-enz-W-bG | *-mut-FP-F2A-enz-W-bG | *-minB-luc-T2A-enz-W-bG | *-H68-luc-I2-enz-S |
| *-CMV-FP-P2A-TF-W-bG | *-mut-FP-F2A-TF-W-bG | *-minB-luc-T2A-TF-W-bG | *-H68-luc-I2-TF-S |
| *-CMV-FP-P2A-rec-W-bG | *-mut-FP-F2A-rec-W-bG | *-minB-luc-T2A-rec-W-bG | *-H68-luc-I2-rec-S |
| *-CMV-FP-P2A-CTP-W-bG | *-mut-FP-F2A-CTP-W-bG | *-minB-luc-T2A-CTP-W-bG | *-H68-luc-I2-CTP-S |
| *-CMV-FP-P2A-SM-W-bG | *-mut-FP-F2A-SM-W-bG | *-minB-luc-T2A-SM-W-bG | *-H68-luc-I2-SM-S |
| *-CMV-FP-P2A-NT-W-bG | *-mut-FP-F2A-NT-W-bG | *-minB-luc-T2A-NT-W-bG | *-H68-luc-I2-NT-S |
| *-CMV-FP-P2A-CR-W-bG | *-mut-FP-F2A-CR-W-bG | *-minB-luc-T2A-CR-W-bG | *-H68-luc-I2-CR-S |
| *-CMV-FP-P2A-chR-W-bG | *-mut-FP-F2A-chR-W-bG | *-minB-luc-T2A-chR-W-bG | *-H68-luc-I2-chR-S |
| *-CMV-FP-P2A-gRNA-W-bG | *-mut-FP-F2A-gRNA-W-bG | *-minB-luc-T2A-gRNA-W-bG | *-H68-luc-I2-gRNA-S |
| *-CMV-FP-P2A-Nuc-W-bG | *-mut-FP-F2A-Nuc-W-bG | *-minB-luc-T2A-Nuc-W-bG | *-H68-luc-I2-Nuc-S |
| *-SV40-FP-P2A-enz-W-bG | *-minR-FP-F2A-enz-W-bG | *-minC-luc-T2A-enz-W-bG | *-RSV-luc-I2-enz-S |
| *-SV40-FP-P2A-TF-W-bG | *-minR-FP-F2A-TF-W-bG | *-minC-luc-T2A-TF-W-bG | *-RSV-luc-I2-TF-S |
| *-SV40-FP-P2A-rec-W-bG | *-minR-FP-F2A-rec-W-bG | *-minC-luc-T2A-rec-W-bG | *-RSV-luc-I2-rec-S |
| *-SV40-FP-P2A-CTP-W-bG | *-minR-FP-F2A-CTP-W-bG | *-minC-luc-T2A-CTP-W-bG | *-RSV-luc-I2-CTP-S |
| *-SV40-FP-P2A-SM-W-bG | *-minR-FP-F2A-SM-W-bG | *-minC-luc-T2A-SM-W-bG | *-RSV-luc-I2-SM-S |
| *-SV40-FP-P2A-NT-W-bG | *-minR-FP-F2A-NT-W-bG | *-minC-luc-T2A-NT-W-bG | *-RSV-luc-I2-NT-S |
| *-SV40-FP-P2A-CR-W-bG | *-minR-FP-F2A-CR-W-bG | *-minC-luc-T2A-CR-W-bG | *-RSV-luc-I2-CR-S |
| *-SV40-FP-P2A-chR-W-bG | *-minR-FP-F2A-chR-W-bG | *-minC-luc-T2A-chR-W-bG | *-RSV-luc-I2-chR-S |
| *-SV40-FP-P2A-gRNA-W-bG | *-minR-FP-F2A-gRNA-W-bG | *-minC-luc-T2A-gRNA-W-bG | *-RSV-luc-I2-gRNA-S |

FIG. 16 cont'd

| | | | |
|---|---|---|---|
| *-SV40-FP-P2A-Nuc-W-bG | *-minR-FP-F2A-Nuc-W-bG | *-minC-luc-T2A-Nuc-W-bG | *-RSV-luc-I2-Nuc-S |
| *-H68-FP-P2A-enz-W-bG | *-CMV-FP-F2A-enz-W-bG | *-mut-luc-T2A-enz-W-bG | *-minB-luc-I2-enz-W-bG |
| *-H68-FP-P2A-TF-W-bG | *-CMV-FP-F2A-TF-W-bG | *-mut-luc-T2A-TF-W-bG | *-minB-luc-I2-TF-W-bG |
| *-H68-FP-P2A-rec-W-bG | *-CMV-FP-F2A-rec-W-bG | *-mut-luc-T2A-rec-W-bG | *-minB-luc-I2-rec-W-bG |
| *-H68-FP-P2A-CTP-W-bG | *-CMV-FP-F2A-CTP-W-bG | *-mut-luc-T2A-CTP-W-bG | *-minB-luc-I2-CTP-W-bG |
| *-H68-FP-P2A-SM-W-bG | *-CMV-FP-F2A-SM-W-bG | *-mut-luc-T2A-SM-W-bG | *-minB-luc-I2-SM-W-bG |
| *-H68-FP-P2A-NT-W-bG | *-CMV-FP-F2A-NT-W-bG | *-mut-luc-T2A-NT-W-bG | *-minB-luc-I2-NT-W-bG |
| *-H68-FP-P2A-CR-W-bG | *-CMV-FP-F2A-CR-W-bG | *-mut-luc-T2A-CR-W-bG | *-minB-luc-I2-CR-W-bG |
| *-H68-FP-P2A-chR-W-bG | *-CMV-FP-F2A-chR-W-bG | *-mut-luc-T2A-chR-W-bG | *-minB-luc-I2-chR-W-bG |
| *-H68-FP-P2A-gRNA-W-bG | *-CMV-FP-F2A-gRNA-W-bG | *-mut-luc-T2A-gRNA-W-bG | *-minB-luc-I2-gRNA-W-bG |
| *-H68-FP-P2A-Nuc-W-bG | *-CMV-FP-F2A-Nuc-W-bG | *-mut-luc-T2A-Nuc-W-bG | *-minB-luc-I2-Nuc-W-bG |
| *-RSV-FP-P2A-enz-W-bG | *-SV40-FP-F2A-enz-W-bG | *-minR-luc-T2A-enz-W-bG | *-minC-luc-I2-enz-W-bG |
| *-RSV-FP-P2A-TF-W-bG | *-SV40-FP-F2A-TF-W-bG | *-minR-luc-T2A-TF-W-bG | *-minC-luc-I2-TF-W-bG |
| *-RSV-FP-P2A-rec-W-bG | *-SV40-FP-F2A-rec-W-bG | *-minR-luc-T2A-rec-W-bG | *-minC-luc-I2-rec-W-bG |
| *-RSV-FP-P2A-CTP-W-bG | *-SV40-FP-F2A-CTP-W-bG | *-minR-luc-T2A-CTP-W-bG | *-minC-luc-I2-CTP-W-bG |
| *-RSV-FP-P2A-SM-W-bG | *-SV40-FP-F2A-SM-W-bG | *-minR-luc-T2A-SM-W-bG | *-minC-luc-I2-SM-W-bG |
| *-RSV-FP-P2A-NT-W-bG | *-SV40-FP-F2A-NT-W-bG | *-minR-luc-T2A-NT-W-bG | *-minC-luc-I2-NT-W-bG |
| *-RSV-FP-P2A-CR-W-bG | *-SV40-FP-F2A-CR-W-bG | *-minR-luc-T2A-CR-W-bG | *-minC-luc-I2-CR-W-bG |
| *-RSV-FP-P2A-chR-W-bG | *-SV40-FP-F2A-chR-W-bG | *-minR-luc-T2A-chR-W-bG | *-minC-luc-I2-chR-W-bG |
| *-RSV-FP-P2A-gRNA-W-bG | *-SV40-FP-F2A-gRNA-W-bG | *-minR-luc-T2A-gRNA-W-bG | *-minC-luc-I2-gRNA-W-bG |
| *-RSV-FP-P2A-Nuc-W-bG | *-SV40-FP-F2A-Nuc-W-bG | *-minR-luc-T2A-Nuc-W-bG | *-minC-luc-I2-Nuc-W-bG |
| *-minB-FP-P2A-enz-W-S | *-H68-FP-F2A-enz-W-bG | *-CMV-luc-T2A-enz-W-bG | *-mut-luc-I2-enz-W-bG |
| *-minB-FP-P2A-TF-W-S | *-H68-FP-F2A-TF-W-bG | *-CMV-luc-T2A-TF-W-bG | *-mut-luc-I2-TF-W-bG |
| *-minB-FP-P2A-rec-W-S | *-H68-FP-F2A-rec-W-bG | *-CMV-luc-T2A-rec-W-bG | *-mut-luc-I2-rec-W-bG |
| *-minB-FP-P2A-CTP-W-S | *-H68-FP-F2A-CTP-W-bG | *-CMV-luc-T2A-CTP-W-bG | *-mut-luc-I2-CTP-W-bG |
| *-minB-FP-P2A-SM-W-S | *-H68-FP-F2A-SM-W-bG | *-CMV-luc-T2A-SM-W-bG | *-mut-luc-I2-SM-W-bG |
| *-minB-FP-P2A-NT-W-S | *-H68-FP-F2A-NT-W-bG | *-CMV-luc-T2A-NT-W-bG | *-mut-luc-I2-NT-W-bG |
| *-minB-FP-P2A-CR-W-S | *-H68-FP-F2A-CR-W-bG | *-CMV-luc-T2A-CR-W-bG | *-mut-luc-I2-CR-W-bG |
| *-minB-FP-P2A-chR-W-S | *-H68-FP-F2A-chR-W-bG | *-CMV-luc-T2A-chR-W-bG | *-mut-luc-I2-chR-W-bG |
| *-minB-FP-P2A-gRNA-W-S | *-H68-FP-F2A-gRNA-W-bG | *-CMV-luc-T2A-gRNA-W-bG | *-mut-luc-I2-gRNA-W-bG |
| *-minB-FP-P2A-Nuc-W-S | *-H68-FP-F2A-Nuc-W-bG | *-CMV-luc-T2A-Nuc-W-bG | *-mut-luc-I2-Nuc-W-bG |
| *-minC-FP-P2A-enz-W-S | *-RSV-FP-F2A-enz-W-bG | *-SV40-luc-T2A-enz-W-bG | *-minR-luc-I2-enz-W-bG |
| *-minC-FP-P2A-TF-W-S | *-RSV-FP-F2A-TF-W-bG | *-SV40-luc-T2A-TF-W-bG | *-minR-luc-I2-TF-W-bG |
| *-minC-FP-P2A-rec-W-S | *-RSV-FP-F2A-rec-W-bG | *-SV40-luc-T2A-rec-W-bG | *-minR-luc-I2-rec-W-bG |

FIG. 16 cont'd

| | | | |
|---|---|---|---|
| *-minC-FP-P2A-CTP-W-S | *-RSV-FP-F2A-CTP-W-bG | *-SV40-luc-T2A-CTP-W-bG | *-minR-luc-I2-CTP-W-bG |
| *-minC-FP-P2A-SM-W-S | *-RSV-FP-F2A-SM-W-bG | *-SV40-luc-T2A-SM-W-bG | *-minR-luc-I2-SM-W-bG |
| *-minC-FP-P2A-NT-W-S | *-RSV-FP-F2A-NT-W-bG | *-SV40-luc-T2A-NT-W-bG | *-minR-luc-I2-NT-W-bG |
| *-minC-FP-P2A-CR-W-S | *-RSV-FP-F2A-CR-W-bG | *-SV40-luc-T2A-CR-W-bG | *-minR-luc-I2-CR-W-bG |
| *-minC-FP-P2A-chR-W-S | *-RSV-FP-F2A-chR-W-bG | *-SV40-luc-T2A-chR-W-bG | *-minR-luc-I2-chR-W-bG |
| *-minC-FP-P2A-gRNA-W-S | *-RSV-FP-F2A-gRNA-W-bG | *-SV40-luc-T2A-gRNA-W-bG | *-minR-luc-I2-gRNA-W-bG |
| *-minC-FP-P2A-Nuc-W-S | *-RSV-FP-F2A-Nuc-W-bG | *-SV40-luc-T2A-Nuc-W-bG | *-minR-luc-I2-Nuc-W-bG |
| *-mut-FP-P2A-enz-W-S | *-minB-FP-F2A-enz-W-S | *-H68-luc-T2A-enz-W-bG | *-CMV-luc-I2-enz-W-bG |
| *-mut-FP-P2A-TF-W-S | *-minB-FP-F2A-TF-W-S | *-H68-luc-T2A-TF-W-bG | *-CMV-luc-I2-TF-W-bG |
| *-mut-FP-P2A-rec-W-S | *-minB-FP-F2A-rec-W-S | *-H68-luc-T2A-rec-W-bG | *-CMV-luc-I2-rec-W-bG |
| *-mut-FP-P2A-CTP-W-S | *-minB-FP-F2A-CTP-W-S | *-H68-luc-T2A-CTP-W-bG | *-CMV-luc-I2-CTP-W-bG |
| *-mut-FP-P2A-SM-W-S | *-minB-FP-F2A-SM-W-S | *-H68-luc-T2A-SM-W-bG | *-CMV-luc-I2-SM-W-bG |
| *-mut-FP-P2A-NT-W-S | *-minB-FP-F2A-NT-W-S | *-H68-luc-T2A-NT-W-bG | *-CMV-luc-I2-NT-W-bG |
| *-mut-FP-P2A-CR-W-S | *-minB-FP-F2A-CR-W-S | *-H68-luc-T2A-CR-W-bG | *-CMV-luc-I2-CR-W-bG |
| *-mut-FP-P2A-chR-W-S | *-minB-FP-F2A-chR-W-S | *-H68-luc-T2A-chR-W-bG | *-CMV-luc-I2-chR-W-bG |
| *-mut-FP-P2A-gRNA-W-S | *-minB-FP-F2A-gRNA-W-S | *-H68-luc-T2A-gRNA-W-bG | *-CMV-luc-I2-gRNA-W-bG |
| *-mut-FP-P2A-Nuc-W-S | *-minB-FP-F2A-Nuc-W-S | *-H68-luc-T2A-Nuc-W-bG | *-CMV-luc-I2-Nuc-W-bG |
| *-minR-FP-P2A-enz-W-S | *-minC-FP-F2A-enz-W-S | *-RSV-luc-T2A-enz-W-bG | *-SV40-luc-I2-enz-W-bG |
| *-minR-FP-P2A-TF-W-S | *-minC-FP-F2A-TF-W-S | *-RSV-luc-T2A-TF-W-bG | *-SV40-luc-I2-TF-W-bG |
| *-minR-FP-P2A-rec-W-S | *-minC-FP-F2A-rec-W-S | *-RSV-luc-T2A-rec-W-bG | *-SV40-luc-I2-rec-W-bG |
| *-minR-FP-P2A-CTP-W-S | *-minC-FP-F2A-CTP-W-S | *-RSV-luc-T2A-CTP-W-bG | *-SV40-luc-I2-CTP-W-bG |
| *-minR-FP-P2A-SM-W-S | *-minC-FP-F2A-SM-W-S | *-RSV-luc-T2A-SM-W-bG | *-SV40-luc-I2-SM-W-bG |
| *-minR-FP-P2A-NT-W-S | *-minC-FP-F2A-NT-W-S | *-RSV-luc-T2A-NT-W-bG | *-SV40-luc-I2-NT-W-bG |
| *-minR-FP-P2A-CR-W-S | *-minC-FP-F2A-CR-W-S | *-RSV-luc-T2A-CR-W-bG | *-SV40-luc-I2-CR-W-bG |
| *-minR-FP-P2A-chR-W-S | *-minC-FP-F2A-chR-W-S | *-RSV-luc-T2A-chR-W-bG | *-SV40-luc-I2-chR-W-bG |
| *-minR-FP-P2A-gRNA-W-S | *-minC-FP-F2A-gRNA-W-S | *-RSV-luc-T2A-gRNA-W-bG | *-SV40-luc-I2-gRNA-W-bG |
| *-minR-FP-P2A-Nuc-W-S | *-minC-FP-F2A-Nuc-W-S | *-RSV-luc-T2A-Nuc-W-bG | *-SV40-luc-I2-Nuc-W-bG |
| *-CMV-FP-P2A-enz-W-S | *-mut-FP-F2A-enz-W-S | *-minB-luc-T2A-enz-W-S | *-H68-luc-I2-enz-W-bG |
| *-CMV-FP-P2A-TF-W-S | *-mut-FP-F2A-TF-W-S | *-minB-luc-T2A-TF-W-S | *-H68-luc-I2-TF-W-bG |
| *-CMV-FP-P2A-rec-W-S | *-mut-FP-F2A-rec-W-S | *-minB-luc-T2A-rec-W-S | *-H68-luc-I2-rec-W-bG |
| *-CMV-FP-P2A-CTP-W-S | *-mut-FP-F2A-CTP-W-S | *-minB-luc-T2A-CTP-W-S | *-H68-luc-I2-CTP-W-bG |
| *-CMV-FP-P2A-SM-W-S | *-mut-FP-F2A-SM-W-S | *-minB-luc-T2A-SM-W-S | *-H68-luc-I2-SM-W-bG |
| *-CMV-FP-P2A-NT-W-S | *-mut-FP-F2A-NT-W-S | *-minB-luc-T2A-NT-W-S | *-H68-luc-I2-NT-W-bG |
| *-CMV-FP-P2A-CR-W-S | *-mut-FP-F2A-CR-W-S | *-minB-luc-T2A-CR-W-S | *-H68-luc-I2-CR-W-bG |

FIG. 16 cont'd

| | | | |
|---|---|---|---|
| *-CMV-FP-P2A-chR-W-S | *-mut-FP-F2A-chR-W-S | *-minB-luc-T2A-chR-W-S | *-H68-luc-I2-chR-W-bG |
| *-CMV-FP-P2A-gRNA-W-S | *-mut-FP-F2A-gRNA-W-S | *-minB-luc-T2A-gRNA-W-S | *-H68-luc-I2-gRNA-W-bG |
| *-CMV-FP-P2A-Nuc-W-S | *-mut-FP-F2A-Nuc-W-S | *-minB-luc-T2A-Nuc-W-S | *-H68-luc-I2-Nuc-W-bG |
| *-SV40-FP-P2A-enz-W-S | *-minR-FP-F2A-enz-W-S | *-minC-luc-T2A-enz-W-S | *-RSV-luc-I2-enz-W-bG |
| *-SV40-FP-P2A-TF-W-S | *-minR-FP-F2A-TF-W-S | *-minC-luc-T2A-TF-W-S | *-RSV-luc-I2-TF-W-bG |
| *-SV40-FP-P2A-rec-W-S | *-minR-FP-F2A-rec-W-S | *-minC-luc-T2A-rec-W-S | *-RSV-luc-I2-rec-W-bG |
| *-SV40-FP-P2A-CTP-W-S | *-minR-FP-F2A-CTP-W-S | *-minC-luc-T2A-CTP-W-S | *-RSV-luc-I2-CTP-W-bG |
| *-SV40-FP-P2A-SM-W-S | *-minR-FP-F2A-SM-W-S | *-minC-luc-T2A-SM-W-S | *-RSV-luc-I2-SM-W-bG |
| *-SV40-FP-P2A-NT-W-S | *-minR-FP-F2A-NT-W-S | *-minC-luc-T2A-NT-W-S | *-RSV-luc-I2-NT-W-bG |
| *-SV40-FP-P2A-CR-W-S | *-minR-FP-F2A-CR-W-S | *-minC-luc-T2A-CR-W-S | *-RSV-luc-I2-CR-W-bG |
| *-SV40-FP-P2A-chR-W-S | *-minR-FP-F2A-chR-W-S | *-minC-luc-T2A-chR-W-S | *-RSV-luc-I2-chR-W-bG |
| *-SV40-FP-P2A-gRNA-W-S | *-minR-FP-F2A-gRNA-W-S | *-minC-luc-T2A-gRNA-W-S | *-RSV-luc-I2-gRNA-W-bG |
| *-SV40-FP-P2A-Nuc-W-S | *-minR-FP-F2A-Nuc-W-S | *-minC-luc-T2A-Nuc-W-S | *-RSV-luc-I2-Nuc-W-bG |
| *-H68-FP-P2A-enz-W-S | *-CMV-FP-F2A-enz-W-S | *-mut-luc-T2A-enz-W-S | *-minB-luc-I2-enz-W-S |
| *-H68-FP-P2A-TF-W-S | *-CMV-FP-F2A-TF-W-S | *-mut-luc-T2A-TF-W-S | *-minB-luc-I2-TF-W-S |
| *-H68-FP-P2A-rec-W-S | *-CMV-FP-F2A-rec-W-S | *-mut-luc-T2A-rec-W-S | *-minB-luc-I2-rec-W-S |
| *-H68-FP-P2A-CTP-W-S | *-CMV-FP-F2A-CTP-W-S | *-mut-luc-T2A-CTP-W-S | *-minB-luc-I2-CTP-W-S |
| *-H68-FP-P2A-SM-W-S | *-CMV-FP-F2A-SM-W-S | *-mut-luc-T2A-SM-W-S | *-minB-luc-I2-SM-W-S |
| *-H68-FP-P2A-NT-W-S | *-CMV-FP-F2A-NT-W-S | *-mut-luc-T2A-NT-W-S | *-minB-luc-I2-NT-W-S |
| *-H68-FP-P2A-CR-W-S | *-CMV-FP-F2A-CR-W-S | *-mut-luc-T2A-CR-W-S | *-minB-luc-I2-CR-W-S |
| *-H68-FP-P2A-chR-W-S | *-CMV-FP-F2A-chR-W-S | *-mut-luc-T2A-chR-W-S | *-minB-luc-I2-chR-W-S |
| *-H68-FP-P2A-gRNA-W-S | *-CMV-FP-F2A-gRNA-W-S | *-mut-luc-T2A-gRNA-W-S | *-minB-luc-I2-gRNA-W-S |
| *-H68-FP-P2A-Nuc-W-S | *-CMV-FP-F2A-Nuc-W-S | *-mut-luc-T2A-Nuc-W-S | *-minB-luc-I2-Nuc-W-S |
| *-RSV-FP-P2A-enz-W-S | *-SV40-FP-F2A-enz-W-S | *-minR-luc-T2A-enz-W-S | *-minC-luc-I2-enz-W-S |
| *-RSV-FP-P2A-TF-W-S | *-SV40-FP-F2A-TF-W-S | *-minR-luc-T2A-TF-W-S | *-minC-luc-I2-TF-W-S |
| *-RSV-FP-P2A-rec-W-S | *-SV40-FP-F2A-rec-W-S | *-minR-luc-T2A-rec-W-S | *-minC-luc-I2-rec-W-S |
| *-RSV-FP-P2A-CTP-W-S | *-SV40-FP-F2A-CTP-W-S | *-minR-luc-T2A-CTP-W-S | *-minC-luc-I2-CTP-W-S |
| *-RSV-FP-P2A-SM-W-S | *-SV40-FP-F2A-SM-W-S | *-minR-luc-T2A-SM-W-S | *-minC-luc-I2-SM-W-S |
| *-RSV-FP-P2A-NT-W-S | *-SV40-FP-F2A-NT-W-S | *-minR-luc-T2A-NT-W-S | *-minC-luc-I2-NT-W-S |
| *-RSV-FP-P2A-CR-W-S | *-SV40-FP-F2A-CR-W-S | *-minR-luc-T2A-CR-W-S | *-minC-luc-I2-CR-W-S |
| *-RSV-FP-P2A-chR-W-S | *-SV40-FP-F2A-chR-W-S | *-minR-luc-T2A-chR-W-S | *-minC-luc-I2-chR-W-S |
| *-RSV-FP-P2A-gRNA-W-S | *-SV40-FP-F2A-gRNA-W-S | *-minR-luc-T2A-gRNA-W-S | *-minC-luc-I2-gRNA-W-S |
| *-RSV-FP-P2A-Nuc-W-S | *-SV40-FP-F2A-Nuc-W-S | *-minR-luc-T2A-Nuc-W-S | *-minC-luc-I2-Nuc-W-S |
| *-minB-FP-T2A-enz-W | *-H68-FP-F2A-enz-W-S | *-CMV-luc-T2A-enz-W-S | *-mut-luc-I2-enz-W-S |

FIG. 16 cont'd

| | | | |
|---|---|---|---|
| *-minB-FP-T2A-TF-W | *-H68-FP-F2A-TF-W-S | *-CMV-luc-T2A-TF-W-S | *-mut-luc-I2-TF-W-S |
| *-minB-FP-T2A-rec-W | *-H68-FP-F2A-rec-W-S | *-CMV-luc-T2A-rec-W-S | *-mut-luc-I2-rec-W-S |
| *-minB-FP-T2A-CTP-W | *-H68-FP-F2A-CTP-W-S | *-CMV-luc-T2A-CTP-W-S | *-mut-luc-I2-CTP-W-S |
| *-minB-FP-T2A-SM-W | *-H68-FP-F2A-SM-W-S | *-CMV-luc-T2A-SM-W-S | *-mut-luc-I2-SM-W-S |
| *-minB-FP-T2A-NT-W | *-H68-FP-F2A-NT-W-S | *-CMV-luc-T2A-NT-W-S | *-mut-luc-I2-NT-W-S |
| *-minB-FP-T2A-CR-W | *-H68-FP-F2A-CR-W-S | *-CMV-luc-T2A-CR-W-S | *-mut-luc-I2-CR-W-S |
| *-minB-FP-T2A-chR-W | *-H68-FP-F2A-chR-W-S | *-CMV-luc-T2A-chR-W-S | *-mut-luc-I2-chR-W-S |
| *-minB-FP-T2A-gRNA-W | *-H68-FP-F2A-gRNA-W-S | *-CMV-luc-T2A-gRNA-W-S | *-mut-luc-I2-gRNA-W-S |
| *-minB-FP-T2A-Nuc-W | *-H68-FP-F2A-Nuc-W-S | *-CMV-luc-T2A-Nuc-W-S | *-mut-luc-I2-Nuc-W-S |
| *-minC-FP-T2A-enz-W | *-RSV-FP-F2A-enz-W-S | *-SV40-luc-T2A-enz-W-S | *-minR-luc-I2-enz-W-S |
| *-minC-FP-T2A-TF-W | *-RSV-FP-F2A-TF-W-S | *-SV40-luc-T2A-TF-W-S | *-minR-luc-I2-TF-W-S |
| *-minC-FP-T2A-rec-W | *-RSV-FP-F2A-rec-W-S | *-SV40-luc-T2A-rec-W-S | *-minR-luc-I2-rec-W-S |
| *-minC-FP-T2A-CTP-W | *-RSV-FP-F2A-CTP-W-S | *-SV40-luc-T2A-CTP-W-S | *-minR-luc-I2-CTP-W-S |
| *-minC-FP-T2A-SM-W | *-RSV-FP-F2A-SM-W-S | *-SV40-luc-T2A-SM-W-S | *-minR-luc-I2-SM-W-S |
| *-minC-FP-T2A-NT-W | *-RSV-FP-F2A-NT-W-S | *-SV40-luc-T2A-NT-W-S | *-minR-luc-I2-NT-W-S |
| *-minC-FP-T2A-CR-W | *-RSV-FP-F2A-CR-W-S | *-SV40-luc-T2A-CR-W-S | *-minR-luc-I2-CR-W-S |
| *-minC-FP-T2A-chR-W | *-RSV-FP-F2A-chR-W-S | *-SV40-luc-T2A-chR-W-S | *-minR-luc-I2-chR-W-S |
| *-minC-FP-T2A-gRNA-W | *-RSV-FP-F2A-gRNA-W-S | *-SV40-luc-T2A-gRNA-W-S | *-minR-luc-I2-gRNA-W-S |
| *-minC-FP-T2A-Nuc-W | *-RSV-FP-F2A-Nuc-W-S | *-SV40-luc-T2A-Nuc-W-S | *-minR-luc-I2-Nuc-W-S |
| *-mut-FP-T2A-enz-W | *-minB-FP-I2-enz-W | *-H68-luc-T2A-enz-W-S | *-CMV-luc-I2-enz-W-S |
| *-mut-FP-T2A-TF-W | *-minB-FP-I2-TF-W | *-H68-luc-T2A-TF-W-S | *-CMV-luc-I2-TF-W-S |
| *-mut-FP-T2A-rec-W | *-minB-FP-I2-rec-W | *-H68-luc-T2A-rec-W-S | *-CMV-luc-I2-rec-W-S |
| *-mut-FP-T2A-CTP-W | *-minB-FP-I2-CTP-W | *-H68-luc-T2A-CTP-W-S | *-CMV-luc-I2-CTP-W-S |
| *-mut-FP-T2A-SM-W | *-minB-FP-I2-SM-W | *-H68-luc-T2A-SM-W-S | *-CMV-luc-I2-SM-W-S |
| *-mut-FP-T2A-NT-W | *-minB-FP-I2-NT-W | *-H68-luc-T2A-NT-W-S | *-CMV-luc-I2-NT-W-S |
| *-mut-FP-T2A-CR-W | *-minB-FP-I2-CR-W | *-H68-luc-T2A-CR-W-S | *-CMV-luc-I2-CR-W-S |
| *-mut-FP-T2A-chR-W | *-minB-FP-I2-chR-W | *-H68-luc-T2A-chR-W-S | *-CMV-luc-I2-chR-W-S |
| *-mut-FP-T2A-gRNA-W | *-minB-FP-I2-gRNA-W | *-H68-luc-T2A-gRNA-W-S | *-CMV-luc-I2-gRNA-W-S |
| *-mut-FP-T2A-Nuc-W | *-minB-FP-I2-Nuc-W | *-H68-luc-T2A-Nuc-W-S | *-CMV-luc-I2-Nuc-W-S |
| *-minR-FP-T2A-enz-W | *-minC-FP-I2-enz-W | *-RSV-luc-T2A-enz-W-S | *-SV40-luc-I2-enz-W-S |
| *-minR-FP-T2A-TF-W | *-minC-FP-I2-TF-W | *-RSV-luc-T2A-TF-W-S | *-SV40-luc-I2-TF-W-S |
| *-minR-FP-T2A-rec-W | *-minC-FP-I2-rec-W | *-RSV-luc-T2A-rec-W-S | *-SV40-luc-I2-rec-W-S |
| *-minR-FP-T2A-CTP-W | *-minC-FP-I2-CTP-W | *-RSV-luc-T2A-CTP-W-S | *-SV40-luc-I2-CTP-W-S |
| *-minR-FP-T2A-SM-W | *-minC-FP-I2-SM-W | *-RSV-luc-T2A-SM-W-S | *-SV40-luc-I2-SM-W-S |

FIG. 16 cont'd

| | | | |
|---|---|---|---|
| *-minR-FP-T2A-NT-W | *-minC-FP-I2-NT-W | *-RSV-luc-T2A-NT-W-S | *-SV40-luc-I2-NT-W-S |
| *-minR-FP-T2A-CR-W | *-minC-FP-I2-CR-W | *-RSV-luc-T2A-CR-W-S | *-SV40-luc-I2-CR-W-S |
| *-minR-FP-T2A-chR-W | *-minC-FP-I2-chR-W | *-RSV-luc-T2A-chR-W-S | *-SV40-luc-I2-chR-W-S |
| *-minR-FP-T2A-gRNA-W | *-minC-FP-I2-gRNA-W | *-RSV-luc-T2A-gRNA-W-S | *-SV40-luc-I2-gRNA-W-S |
| *-minR-FP-T2A-Nuc-W | *-minC-FP-I2-Nuc-W | *-RSV-luc-T2A-Nuc-W-S | *-SV40-luc-I2-Nuc-W-S |
| *-CMV-FP-T2A-enz-W | *-mut-FP-I2-enz-W | *-minB-luc-E2A-enz-W | *-H68-luc-I2-enz-W-S |
| *-CMV-FP-T2A-TF-W | *-mut-FP-I2-TF-W | *-minB-luc-E2A-TF-W | *-H68-luc-I2-TF-W-S |
| *-CMV-FP-T2A-rec-W | *-mut-FP-I2-rec-W | *-minB-luc-E2A-rec-W | *-H68-luc-I2-rec-W-S |
| *-CMV-FP-T2A-CTP-W | *-mut-FP-I2-CTP-W | *-minB-luc-E2A-CTP-W | *-H68-luc-I2-CTP-W-S |
| *-CMV-FP-T2A-SM-W | *-mut-FP-I2-SM-W | *-minB-luc-E2A-SM-W | *-H68-luc-I2-SM-W-S |
| *-CMV-FP-T2A-NT-W | *-mut-FP-I2-NT-W | *-minB-luc-E2A-NT-W | *-H68-luc-I2-NT-W-S |
| *-CMV-FP-T2A-CR-W | *-mut-FP-I2-CR-W | *-minB-luc-E2A-CR-W | *-H68-luc-I2-CR-W-S |
| *-CMV-FP-T2A-chR-W | *-mut-FP-I2-chR-W | *-minB-luc-E2A-chR-W | *-H68-luc-I2-chR-W-S |
| *-CMV-FP-T2A-gRNA-W | *-mut-FP-I2-gRNA-W | *-minB-luc-E2A-gRNA-W | *-H68-luc-I2-gRNA-W-S |
| *-CMV-FP-T2A-Nuc-W | *-mut-FP-I2-Nuc-W | *-minB-luc-E2A-Nuc-W | *-H68-luc-I2-Nuc-W-S |
| *-SV40-FP-T2A-enz-W | *-minR-FP-I2-enz-W | *-minC-luc-E2A-enz-W | *-RSV-luc-I2-enz-W-S |
| *-SV40-FP-T2A-TF-W | *-minR-FP-I2-TF-W | *-minC-luc-E2A-TF-W | *-RSV-luc-I2-TF-W-S |
| *-SV40-FP-T2A-rec-W | *-minR-FP-I2-rec-W | *-minC-luc-E2A-rec-W | *-RSV-luc-I2-rec-W-S |
| *-SV40-FP-T2A-CTP-W | *-minR-FP-I2-CTP-W | *-minC-luc-E2A-CTP-W | *-RSV-luc-I2-CTP-W-S |
| *-SV40-FP-T2A-SM-W | *-minR-FP-I2-SM-W | *-minC-luc-E2A-SM-W | *-RSV-luc-I2-SM-W-S |
| *-SV40-FP-T2A-NT-W | *-minR-FP-I2-NT-W | *-minC-luc-E2A-NT-W | *-RSV-luc-I2-NT-W-S |
| *-SV40-FP-T2A-CR-W | *-minR-FP-I2-CR-W | *-minC-luc-E2A-CR-W | *-RSV-luc-I2-CR-W-S |
| *-SV40-FP-T2A-chR-W | *-minR-FP-I2-chR-W | *-minC-luc-E2A-chR-W | *-RSV-luc-I2-chR-W-S |
| *-SV40-FP-T2A-gRNA-W | *-minR-FP-I2-gRNA-W | *-minC-luc-E2A-gRNA-W | *-RSV-luc-I2-gRNA-W-S |
| *-SV40-FP-T2A-Nuc-W | *-minR-FP-I2-Nuc-W | *-minC-luc-E2A-Nuc-W | *-RSV-luc-I2-Nuc-W-S |
| *-minB-IT-W | *-minB-IT-bG | *-minB-IT-S | *-minB-IT-W-bG |
| *-minC-IT-W | *-minC-IT-bG | *-minC-IT-S | *-minC-IT-W-bG |
| *-mut-IT-W | *-mut-IT-bG | *-mut-IT-S | *-mut-IT-W-bG |
| *-minR-IT-W | *-minR-IT-bG | *-minR-IT-S | *-minR-IT-W-bG |
| *-CMV-IT-W | *-CMV-IT-bG | *-CMV-IT-S | *-CMV-IT-W-bG |
| *-SV40-IT-W | *-SV40-IT-bG | *-SV40-IT-S | *-SV40-IT-W-bG |
| *-H68-IT-W | *-H68-IT-bG | *-H68-IT-S | *-H68-IT-W-bG |
| *-RSV-IT-W | *-RSV-IT-bG | *-RSV-IT-S | *-RSV-IT-W-bG |
| *-minB-IT-W-S | *-minB-luc-P2A-IT-W | *-minB-luc-P2A-IT-bG | *-minB-luc-P2A-IT-S |

FIG. 16 cont'd

| | | | |
|---|---|---|---|
| *-minC-IT-W-S | *-minC-luc-P2A-IT-W | *-minC-luc-P2A-IT-bG | *-minC-luc-P2A-IT-S |
| *-mut-IT-W-S | *-mut-luc-P2A-IT-W | *-mut-luc-P2A-IT-bG | *-mut-luc-P2A-IT-S |
| *-minR-IT-W-S | *-minR-luc-P2A-IT-W | *-minR-luc-P2A-IT-bG | *-minR-luc-P2A-IT-S |
| *-CMV-IT-W-S | *-CMV-luc-P2A-IT-W | *-CMV-luc-P2A-IT-bG | *-CMV-luc-P2A-IT-S |
| *-SV40-IT-W-S | *-SV40-luc-P2A-IT-W | *-SV40-luc-P2A-IT-bG | *-SV40-luc-P2A-IT-S |
| *-H68-IT-W-S | *-H68-luc-P2A-IT-W | *-H68-luc-P2A-IT-bG | *-H68-luc-P2A-IT-S |
| *-RSV-IT-W-S | *-RSV-luc-P2A-IT-W | *-RSV-luc-P2A-IT-bG | *-RSV-luc-P2A-IT-S |
| *-minB-luc-P2A-IT-W-bG | *-minB-luc-P2A-IT-W-S | *-minB-FP-P2A-IT-W | *-minB-FP-P2A-IT-bG |
| *-minC-luc-P2A-IT-W-bG | *-minC-luc-P2A-IT-W-S | *-minC-FP-P2A-IT-W | *-minC-FP-P2A-IT-bG |
| *-mut-luc-P2A-IT-W-bG | *-mut-luc-P2A-IT-W-S | *-mut-FP-P2A-IT-W | *-mut-FP-P2A-IT-bG |
| *-minR-luc-P2A-IT-W-bG | *-minR-luc-P2A-IT-W-S | *-minR-FP-P2A-IT-W | *-minR-FP-P2A-IT-bG |
| *-CMV-luc-P2A-IT-W-bG | *-CMV-luc-P2A-IT-W-S | *-CMV-FP-P2A-IT-W | *-CMV-FP-P2A-IT-bG |
| *-SV40-luc-P2A-IT-W-bG | *-SV40-luc-P2A-IT-W-S | *-SV40-FP-P2A-IT-W | *-SV40-FP-P2A-IT-bG |
| *-H68-luc-P2A-IT-W-bG | *-H68-luc-P2A-IT-W-S | *-H68-FP-P2A-IT-W | *-H68-FP-P2A-IT-bG |
| *-RSV-luc-P2A-IT-W-bG | *-RSV-luc-P2A-IT-W-S | *-RSV-FP-P2A-IT-W | *-RSV-FP-P2A-IT-bG |
| *-minB-FP-P2A-IT-S | *-minB-FP-P2A-IT-W-bG | *-minB-FP-P2A-IT-W-S | *-minB-luc-T2A-IT-W |
| *-minC-FP-P2A-IT-S | *-minC-FP-P2A-IT-W-bG | *-minC-FP-P2A-IT-W-S | *-minC-luc-T2A-IT-W |
| *-mut-FP-P2A-IT-S | *-mut-FP-P2A-IT-W-bG | *-mut-FP-P2A-IT-W-S | *-mut-luc-T2A-IT-W |
| *-minR-FP-P2A-IT-S | *-minR-FP-P2A-IT-W-bG | *-minR-FP-P2A-IT-W-S | *-minR-luc-T2A-IT-W |
| *-CMV-FP-P2A-IT-S | *-CMV-FP-P2A-IT-W-bG | *-CMV-FP-P2A-IT-W-S | *-CMV-luc-T2A-IT-W |
| *-SV40-FP-P2A-IT-S | *-SV40-FP-P2A-IT-W-bG | *-SV40-FP-P2A-IT-W-S | *-SV40-luc-T2A-IT-W |
| *-H68-FP-P2A-IT-S | *-H68-FP-P2A-IT-W-bG | *-H68-FP-P2A-IT-W-S | *-H68-luc-T2A-IT-W |
| *-RSV-FP-P2A-IT-S | *-RSV-FP-P2A-IT-W-bG | *-RSV-FP-P2A-IT-W-S | *-RSV-luc-T2A-IT-W |
| *-minB-luc-T2A-IT-bG | *-minB-luc-T2A-IT-S | *-minB-luc-T2A-IT-W-bG | *-minB-luc-T2A-IT-W-S |
| *-minC-luc-T2A-IT-bG | *-minC-luc-T2A-IT-S | *-minC-luc-T2A-IT-W-bG | *-minC-luc-T2A-IT-W-S |
| *-mut-luc-T2A-IT-bG | *-mut-luc-T2A-IT-S | *-mut-luc-T2A-IT-W-bG | *-mut-luc-T2A-IT-W-S |
| *-minR-luc-T2A-IT-bG | *-minR-luc-T2A-IT-S | *-minR-luc-T2A-IT-W-bG | *-minR-luc-T2A-IT-W-S |
| *-CMV-luc-T2A-IT-bG | *-CMV-luc-T2A-IT-S | *-CMV-luc-T2A-IT-W-bG | *-CMV-luc-T2A-IT-W-S |
| *-SV40-luc-T2A-IT-bG | *-SV40-luc-T2A-IT-S | *-SV40-luc-T2A-IT-W-bG | *-SV40-luc-T2A-IT-W-S |
| *-H68-luc-T2A-IT-bG | *-H68-luc-T2A-IT-S | *-H68-luc-T2A-IT-W-bG | *-H68-luc-T2A-IT-W-S |
| *-RSV-luc-T2A-IT-bG | *-RSV-luc-T2A-IT-S | *-RSV-luc-T2A-IT-W-bG | *-RSV-luc-T2A-IT-W-S |
| *-minB-FP-T2A-IT-W | *-minB-FP-T2A-IT-bG | *-minB-FP-T2A-IT-S | *-minB-FP-T2A-IT-W-bG |
| *-minC-FP-T2A-IT-W | *-minC-FP-T2A-IT-bG | *-minC-FP-T2A-IT-S | *-minC-FP-T2A-IT-W-bG |
| *-mut-FP-T2A-IT-W | *-mut-FP-T2A-IT-bG | *-mut-FP-T2A-IT-S | *-mut-FP-T2A-IT-W-bG |

FIG. 16 cont'd

| | | | |
|---|---|---|---|
| *-minR-FP-T2A-IT-W | *-minR-FP-T2A-IT-bG | *-minR-FP-T2A-IT-S | *-minR-FP-T2A-IT-W-bG |
| *-CMV-FP-T2A-IT-W | *-CMV-FP-T2A-IT-bG | *-CMV-FP-T2A-IT-S | *-CMV-FP-T2A-IT-W-bG |
| *-SV40-FP-T2A-IT-W | *-SV40-FP-T2A-IT-bG | *-SV40-FP-T2A-IT-S | *-SV40-FP-T2A-IT-W-bG |
| *-H68-FP-T2A-IT-W | *-H68-FP-T2A-IT-bG | *-H68-FP-T2A-IT-S | *-H68-FP-T2A-IT-W-bG |
| *-RSV-FP-T2A-IT-W | *-RSV-FP-T2A-IT-bG | *-RSV-FP-T2A-IT-S | *-RSV-FP-T2A-IT-W-bG |
| *-minB-FP-T2A-IT-W-S | *-minB-luc-E2A-IT-W | *-minB-luc-E2A-IT-bG | *-minB-luc-E2A-IT-S |
| *-minC-FP-T2A-IT-W-S | *-minC-luc-E2A-IT-W | *-minC-luc-E2A-IT-bG | *-minC-luc-E2A-IT-S |
| *-mut-FP-T2A-IT-W-S | *-mut-luc-E2A-IT-W | *-mut-luc-E2A-IT-bG | *-mut-luc-E2A-IT-S |
| *-minR-FP-T2A-IT-W-S | *-minR-luc-E2A-IT-W | *-minR-luc-E2A-IT-bG | *-minR-luc-E2A-IT-S |
| *-CMV-FP-T2A-IT-W-S | *-CMV-luc-E2A-IT-W | *-CMV-luc-E2A-IT-bG | *-CMV-luc-E2A-IT-S |
| *-SV40-FP-T2A-IT-W-S | *-SV40-luc-E2A-IT-W | *-SV40-luc-E2A-IT-bG | *-SV40-luc-E2A-IT-S |
| *-H68-FP-T2A-IT-W-S | *-H68-luc-E2A-IT-W | *-H68-luc-E2A-IT-bG | *-H68-luc-E2A-IT-S |
| *-RSV-FP-T2A-IT-W-S | *-RSV-luc-E2A-IT-W | *-RSV-luc-E2A-IT-bG | *-RSV-luc-E2A-IT-S |
| *-minB-luc-E2A-IT-W-bG | *-minB-luc-E2A-IT-W-S | *-minB-FP-E2A-IT-W | *-minB-FP-E2A-IT-bG |
| *-minC-luc-E2A-IT-W-bG | *-minC-luc-E2A-IT-W-S | *-minC-FP-E2A-IT-W | *-minC-FP-E2A-IT-bG |
| *-mut-luc-E2A-IT-W-bG | *-mut-luc-E2A-IT-W-S | *-mut-FP-E2A-IT-W | *-mut-FP-E2A-IT-bG |
| *-minR-luc-E2A-IT-W-bG | *-minR-luc-E2A-IT-W-S | *-minR-FP-E2A-IT-W | *-minR-FP-E2A-IT-bG |
| *-CMV-luc-E2A-IT-W-bG | *-CMV-luc-E2A-IT-W-S | *-CMV-FP-E2A-IT-W | *-CMV-FP-E2A-IT-bG |
| *-SV40-luc-E2A-IT-W-bG | *-SV40-luc-E2A-IT-W-S | *-SV40-FP-E2A-IT-W | *-SV40-FP-E2A-IT-bG |
| *-H68-luc-E2A-IT-W-bG | *-H68-luc-E2A-IT-W-S | *-H68-FP-E2A-IT-W | *-H68-FP-E2A-IT-bG |
| *-RSV-luc-E2A-IT-W-bG | *-RSV-luc-E2A-IT-W-S | *-RSV-FP-E2A-IT-W | *-RSV-FP-E2A-IT-bG |
| *-minB-FP-E2A-IT-S | *-minB-FP-E2A-IT-W-bG | *-minB-FP-E2A-IT-W-S | *-minB-luc-F2A-IT-W |
| *-minC-FP-E2A-IT-S | *-minC-FP-E2A-IT-W-bG | *-minC-FP-E2A-IT-W-S | *-minC-luc-F2A-IT-W |
| *-mut-FP-E2A-IT-S | *-mut-FP-E2A-IT-W-bG | *-mut-FP-E2A-IT-W-S | *-mut-luc-F2A-IT-W |
| *-minR-FP-E2A-IT-S | *-minR-FP-E2A-IT-W-bG | *-minR-FP-E2A-IT-W-S | *-minR-luc-F2A-IT-W |
| *-CMV-FP-E2A-IT-S | *-CMV-FP-E2A-IT-W-bG | *-CMV-FP-E2A-IT-W-S | *-CMV-luc-F2A-IT-W |
| *-SV40-FP-E2A-IT-S | *-SV40-FP-E2A-IT-W-bG | *-SV40-FP-E2A-IT-W-S | *-SV40-luc-F2A-IT-W |
| *-H68-FP-E2A-IT-S | *-H68-FP-E2A-IT-W-bG | *-H68-FP-E2A-IT-W-S | *-H68-luc-F2A-IT-W |
| *-RSV-FP-E2A-IT-S | *-RSV-FP-E2A-IT-W-bG | *-RSV-FP-E2A-IT-W-S | *-RSV-luc-F2A-IT-W |
| *-minB-luc-F2A-IT-bG | *-minB-luc-F2A-IT-S | *-minB-luc-F2A-IT-W-bG | *-minB-luc-F2A-IT-W-S |
| *-minC-luc-F2A-IT-bG | *-minC-luc-F2A-IT-S | *-minC-luc-F2A-IT-W-bG | *-minC-luc-F2A-IT-W-S |
| *-mut-luc-F2A-IT-bG | *-mut-luc-F2A-IT-S | *-mut-luc-F2A-IT-W-bG | *-mut-luc-F2A-IT-W-S |
| *-minR-luc-F2A-IT-bG | *-minR-luc-F2A-IT-S | *-minR-luc-F2A-IT-W-bG | *-minR-luc-F2A-IT-W-S |
| *-CMV-luc-F2A-IT-bG | *-CMV-luc-F2A-IT-S | *-CMV-luc-F2A-IT-W-bG | *-CMV-luc-F2A-IT-W-S |

FIG. 16 cont'd

| | | | |
|---|---|---|---|
| *-SV40-luc-F2A-IT-bG | *-SV40-luc-F2A-IT-S | *-SV40-luc-F2A-IT-W-bG | *-SV40-luc-F2A-IT-W-S |
| *-H68-luc-F2A-IT-bG | *-H68-luc-F2A-IT-S | *-H68-luc-F2A-IT-W-bG | *-H68-luc-F2A-IT-W-S |
| *-RSV-luc-F2A-IT-bG | *-RSV-luc-F2A-IT-S | *-RSV-luc-F2A-IT-W-bG | *-RSV-luc-F2A-IT-W-S |
| *-minB-FP-F2A-IT-W | *-minB-FP-F2A-IT-bG | *-minB-FP-F2A-IT-S | *-minB-FP-F2A-IT-W-bG |
| *-minC-FP-F2A-IT-W | *-minC-FP-F2A-IT-bG | *-minC-FP-F2A-IT-S | *-minC-FP-F2A-IT-W-bG |
| *-mut-FP-F2A-IT-W | *-mut-FP-F2A-IT-bG | *-mut-FP-F2A-IT-S | *-mut-FP-F2A-IT-W-bG |
| *-minR-FP-F2A-IT-W | *-minR-FP-F2A-IT-bG | *-minR-FP-F2A-IT-S | *-minR-FP-F2A-IT-W-bG |
| *-CMV-FP-F2A-IT-W | *-CMV-FP-F2A-IT-bG | *-CMV-FP-F2A-IT-S | *-CMV-FP-F2A-IT-W-bG |
| *-SV40-FP-F2A-IT-W | *-SV40-FP-F2A-IT-bG | *-SV40-FP-F2A-IT-S | *-SV40-FP-F2A-IT-W-bG |
| *-H68-FP-F2A-IT-W | *-H68-FP-F2A-IT-bG | *-H68-FP-F2A-IT-S | *-H68-FP-F2A-IT-W-bG |
| *-RSV-FP-F2A-IT-W | *-RSV-FP-F2A-IT-bG | *-RSV-FP-F2A-IT-S | *-RSV-FP-F2A-IT-W-bG |
| *-minB-FP-F2A-IT-W-S | *-minB-luc-I2-IT-W | *-minB-luc-I2-IT-bG | *-minB-luc-I2-IT-S |
| *-minC-FP-F2A-IT-W-S | *-minC-luc-I2-IT-W | *-minC-luc-I2-IT-bG | *-minC-luc-I2-IT-S |
| *-mut-FP-F2A-IT-W-S | *-mut-luc-I2-IT-W | *-mut-luc-I2-IT-bG | *-mut-luc-I2-IT-S |
| *-minR-FP-F2A-IT-W-S | *-minR-luc-I2-IT-W | *-minR-luc-I2-IT-bG | *-minR-luc-I2-IT-S |
| *-CMV-FP-F2A-IT-W-S | *-CMV-luc-I2-IT-W | *-CMV-luc-I2-IT-bG | *-CMV-luc-I2-IT-S |
| *-SV40-FP-F2A-IT-W-S | *-SV40-luc-I2-IT-W | *-SV40-luc-I2-IT-bG | *-SV40-luc-I2-IT-S |
| *-H68-FP-F2A-IT-W-S | *-H68-luc-I2-IT-W | *-H68-luc-I2-IT-bG | *-H68-luc-I2-IT-S |
| *-RSV-FP-F2A-IT-W-S | *-RSV-luc-I2-IT-W | *-RSV-luc-I2-IT-bG | *-RSV-luc-I2-IT-S |
| *-minB-luc-I2-IT-W-bG | *-minB-luc-I2-IT-W-S | *-minB-FP-I2-IT-W | *-minB-FP-I2-IT-bG |
| *-minC-luc-I2-IT-W-bG | *-minC-luc-I2-IT-W-S | *-minC-FP-I2-IT-W | *-minC-FP-I2-IT-bG |
| *-mut-luc-I2-IT-W-bG | *-mut-luc-I2-IT-W-S | *-mut-FP-I2-IT-W | *-mut-FP-I2-IT-bG |
| *-minR-luc-I2-IT-W-bG | *-minR-luc-I2-IT-W-S | *-minR-FP-I2-IT-W | *-minR-FP-I2-IT-bG |
| *-CMV-luc-I2-IT-W-bG | *-CMV-luc-I2-IT-W-S | *-CMV-FP-I2-IT-W | *-CMV-FP-I2-IT-bG |
| *-SV40-luc-I2-IT-W-bG | *-SV40-luc-I2-IT-W-S | *-SV40-FP-I2-IT-W | *-SV40-FP-I2-IT-bG |
| *-H68-luc-I2-IT-W-bG | *-H68-luc-I2-IT-W-S | *-H68-FP-I2-IT-W | *-H68-FP-I2-IT-bG |
| *-RSV-luc-I2-IT-W-bG | *-RSV-luc-I2-IT-W-S | *-RSV-FP-I2-IT-W | *-RSV-FP-I2-IT-bG |
| *-minB-FP-I2-IT-S | *-minB-FP-I2-IT-W-bG | *-minB-FP-I2-IT-W-S | *-CMV-FP-I2-IT-S |
| *-minC-FP-I2-IT-S | *-minC-FP-I2-IT-W-bG | *-minC-FP-I2-IT-W-S | *-SV40-FP-I2-IT-S |
| *-mut-FP-I2-IT-S | *-mut-FP-I2-IT-W-bG | *-mut-FP-I2-IT-W-S | *-H68-FP-I2-IT-S |
| *-minR-FP-I2-IT-S | *-minR-FP-I2-IT-W-bG | *-minR-FP-I2-IT-W-S | *-RSV-FP-I2-IT-S |
| *-CMV-FP-I2-IT-W-bG | *-CMV-FP-I2-IT-W-S | *-H68-FP-I2-IT-W-bG | *-H68-FP-I2-IT-W-S |
| *-SV40-FP-I2-IT-W-bG | *-SV40-FP-I2-IT-W-S | *-RSV-FP-I2-IT-W-bG | *-RSV-FP-I2-IT-W-S |

FIG. 17 hDLX I56i enhancer:
TATGCACTCACAGTGGTTTGGCATGCATCTGGTGAATTTTTTTTAACGAAAAATTAGTGTTG
GTTTCGATGTATGGTAGCATTCTCCCTAACGTAATTTGAATAATTCAGCAAAGCCCCACTAC
CAGCTGTACTTCTGCAGCCTCTTCCATTCTTTTCAGCATTATAATTTTGGTTAATTTTCAATT
TTAGGTCCTACGTCTCTGCAATTTGTGTATGAATAACAGAATAATTTCCCTCTTTTGTTTCGC
CTTTCCTGTTCCTGAATCTAAATAAAGATGGCTTTTTAGTATTAAAAGTGGAAGAAAATTACA
GGTAATTATCTTTGACGGTAAAAACGCTGTAATCAGCGGGCTACATGAAAAATTACTCTAAT
TATGGCTGCATTTAAGAGAATGGAAAAAAACCTTCTTGTGGATAAAAACCTTAAATTGTCCC
CAATGTCTGCTTCAAATTGGATGGCACTGCAGCTGGAGGCTTTGTTCAGAATTGATCCTGG
GGAGCTACGAACCCAAAGTTTCACAGTAGG (SEQ ID NO: 1)

Core of the hDLX I56i enhancer:
CTAAATAAAGATGGCTTTTTAGTATTAAAAGTGGAAGAAAATTACAGGTAATTATCTTTGACG
GTAAAAACGCTGTAATCAGCGGGCTACATGAAAAATTACTCTAATTATGGCTGCATTTAAGA
GAATGG (SEQ ID NO: 2)

3xhI56iCore, Triply Concatamerized Core of the hDLX I56i enhancer:
CTAAATAAAGATGGCTTTTTAGTATTAAAAGTGGAAGAAAATTACAGGTAATTATCTTTGACG
GTAAAAACGCTGTAATCAGCGGGCTACATGAAAAATTACTCTAATTATGGCTGCATTTAAGA
GAATGGCTAAATAAAGATGGCTTTTTAGTATTAAAAGTGGAAGAAAATTACAGGTAATTATC
TTTGACGGTAAAAACGCTGTAATCAGCGGGCTACATGAAAAATTACTCTAATTATGGCTGCA
TTTAAGAGAATGGCTAAATAAAGATGGCTTTTTAGTATTAAAAGTGGAAGAAAATTACAGGT
AATTATCTTTGACGGTAAAAACGCTGTAATCAGCGGGCTACATGAAAAATTACTCTAATTAT
GGCTGCATTTAAGAGAATGG (SEQ ID NO: 3)

Murine I56i Enhancer (core is the same as human):
TATACACTCACAGTGGTTTGGCATATATTTGGTGAAATTTTTTAAGGAAAAATTAGTGTTGGT
TTCGATATATGGTAGCTTTTTCTCTAACATAATTTGAATAATTCAGCAAAGCCCTACTACCAG
CTGTACTTCTGCAGCCTCTTCCATTCTTTCCAGCATTATAATTTTGGTTAATTTTCAATTTTA
GGTCCTACGTCTCTGCAATTTGTGTATGAATAACAGAATAATTTCCCTCTTTTGTTTCGCCTT
TCCTGTTCCTGAATCTAAATAAAGATGGCTTTTTAGTATTAAAAGTGGAAGAAAATTACAGG
TAATTATCTTTGACGGTAAAAACGCTGTAATCAGCGGGCTACATGAAAAATTACTCTAATTA
TGGCTGCATTTAAGAGAATGGAAAAAAACCTTCTTGTGGATAAAAACCTTAAATTGTCCCCA
ATGTCTGCTTCAAATTGGATGGCACTGCAGCTGGAGGCTTTGTTCAGAATTGATCCTGGGG
AGCTACGAACCCAAAGTTTCACAGTAGG (SEQ ID NO: 4)

Zebrafish I46i Enhancer:
ACATTGTAATTTTAGATAATATCCCAAGCGTTCACTCTCCTCGGCAATTTGTACATGAATAAC
CGAATAATTTCATCTTTTGTTTCGTCTTTGCCACTTCAAATCCAAATAAAGATGCCTTTTAGT
ATTAAAAGTGGTAGAAAATTACAGGTAATTATCTTTGACGGTAAAAACGCTGTAATCAGCGG
GCTACATCAAAAATTACCCTAATTATGTCTGCATTTATGAGAATGGAAAAAAACCCTCTCTT
GGATAAAACCCATAAATTGTCCCAAATATCT (SEQ ID NO: 5)

Core of the Zebrafish I46i Enhancer:
CCAAATAAAGATGCCTTTTAGTATTAAAAGTGGTAGAAAATTACAGGTAATTATCTTTGACG
GTAAAAACGCTGTAATCAGCGGGCTACATCAAAAATTACCCTAATTATGTCTGCATTTATGA
GAATGG (SEQ ID NO: 6)

FIG. 17 cont'd

3x Concatamerized Core of the Zebrafish I46i Enhancer:
CCAAATAAAGATGCCTTTTAGTATTAAAAGTGGTAGAAAATTACAGGTAATTATCTTTGACG
GTAAAAACGCTGTAATCAGCGGGCTACATCAAAAATTACCCTAATTATGTCTGCATTTATGA
GAATGGCCAAATAAAGATGCCTTTTAGTATTAAAAGTGGTAGAAAATTACAGGTAATTATCT
TTGACGGTAAAAACGCTGTAATCAGCGGGCTACATCAAAAATTACCCTAATTATGTCTGCAT
TTATGAGAATGGCCAAATAAAGATGCCTTTTAGTATTAAAAGTGGTAGAAAATTACAGGTAA
TTATCTTTGACGGTAAAAACGCTGTAATCAGCGGGCTACATCAAAAATTACCCTAATTATGT
CTGCATTTATGAGAATGG (SEQ ID NO: 7)

Beta-Globin Minimal Promoter (pBGmin/minBGlobin/minBGprom):
GGGCTGGGCATAAAAGTCAGGGCAGAGCCATCTATTGCTTACATTTGCTTCTG (SEQ ID NO: 8)

minCMV Promoter:
GAGGTAGGCGTGTACGGTGGGAGGCCTATATAAGCAGAGCTCGTTTAGTGAACCGTCAGA
TCGCCTGG (SEQ ID NO: 9)

Mutated minCMV Promoter (SacI RE site removed):
GAGGTAGGCGTGTACGGTGGGAGGCCTATATAAGCAGAGCTGGTTTAGTGAACCGTCAGA
TCGCCTGG (SEQ ID NO: 10)

minRho Promoter:
GATTCAGCCGGGAGCTTAGGGAGGGGAGGTCACTTCATAAGGGCCTGGGGGGGGAGTTG
GAGCCACGAGTCGTCCAGCCGGAGCCCCGTGTGGCTGAGCTCCGGCCTCAGAAGCATCC
CC (SEQ ID NO: 11)

Hsp68 minimal Promoter (proHsp68):
CAGGAACATCCAAACTGAGCAGCCGGGGTCCCCCCCACCCCCCACCCCGCCCCACGCGG
CAACTTTGAGCCTGTGCTGGGACAGAGCCTCTAGTTCCTAAATTAGTCCATGAGGTCAGAG
GCAGCACTGCCATTGTAACGCGATTGGAGAGGATCACGTCACCGGACACGCCCCCAGGC
ATCTCCCTGGGTCTCCTAAACTTGGCGGGGAGAAGTTTTAGCCCTTAAGTTTTAGCCTTTAA
CCCCCATATTCAGAACTGTGCGAGTTGGCGAAACCCCACAAATCACAACAAACTGTACACA
ACACCGAGCTAGAGGTGATCTTTCTTGTCCATTCCACACAGGCCTTAGTAATGCGTCGCCA
TAGCAACAGTGTCACTAGTAGCACCAGCACTTCCCCACACCCTCCCCCTCAGGAATCCGTA
CTCTCCAGTGAACCCCAGAAACCTCTGGAGAGTTCTGGACAAGGGCGGAACCCACAACTC
CGATTACTCAAGGGAGGCGGGGAAGCTCCACCAGACGCGAAACTGCTGGAAGATTCCTG
GCCCCAAGGCCTCCTCCGGCTCGCTGATTGGCCCAGCGGAGAGTGGGCGGGGCCGGTG
AAGACTCCTTAAAGGCGCAGGGCGGCGAGCAGGTCACCAGACGCTGACAGCTACTCAGA
ACCAAATCTGGTTCCATCCAGAGACAAGCGAAGACAAGAGAAGCAGAGCGAGCGGCGCGT
TCCCGATCCTCGGCCAGGACCAGCCTTCCCCAGAGCATCCCTGCCGCGGAGCGCAACCT
TCCCAGGAGCATCCCTGCCGCGGAGCGCAACTTTCCCCGGAGCATCCACGCCGCGGAGC
GCAGCCTTCCAGAAGCAGAGCGCGGCGCC (SEQ ID NO: 12)

FIG. 17 cont'd

SYFP2:
ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACCT
ACGGCAAGCTGACCCTGAAGCTGATCTGCACCACCGGCAAGCTGCCCGTGCCCTGGCCC
ACCCTCGTGACCACCCTGGGCTACGGCGTGCAGTGCTTCGCCCGCTACCCCGACCACAT
GAAGCAGCACGACTTCTTCAAGTCCGCCATGCCCGAAGGCTACGTCCAGGAGCGCACCAT
CTTCTTCAAGGACGACGGCAACTACAAGACCCGCGCCGAGGTGAAGTTCGAGGGCGACA
CCCTGGTGAACCGCATCGAGCTGAAGGGCATCGACTTCAAGGAGGACGGCAACATCCTG
GGGCACAAGCTGGAGTACAACTACAACAGCCACAACGTCTATATCACCGCCGACAAGCAG
AAGAACGGCATCAAGGCCAACTTCAAGATCCGCCACAACATCGAGGACGGCGGCGTGCA
GCTCGCCGACCACTACCAGCAGAACACCCCCATCGGCGACGGCCCCGTGCTGCTGCCCG
ACAACCACTACCTGAGCTACCAGTCCAAGCTGAGCAAAGACCCCAACGAGAAGCGCGATC
ACATGGTCCTGCTGGAGTTCGTGACCGCCGCCGGGATCACTCTCGGCATGGACGAGCTGT
ACAAGTAA (SEQ ID NO: 13)

EGFP:
ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACCT
ACGGCAAGCTGACCCTGAAGTTCATCTGCACCACCGGCAAGCTGCCCGTGCCCTGGCCCA
CCCTCGTGACCACCCTGACCTACGGCGTGCAGTGCTTCAGCCGCTACCCCGACCACATGA
AGCAGCACGACTTCTTCAAGTCCGCCATGCCCGAAGGCTACGTCCAGGAGCGCACCATCT
TCTTCAAGGACGACGGCAACTACAAGACCCGCGCCGAGGTGAAGTTCGAGGGCGACACC
CTGGTGAACCGCATCGAGCTGAAGGGCATCGACTTCAAGGAGGACGGCAACATCCTGGG
GCACAAGCTGGAGTACAACTACAACAGCCACAACGTCTATATCATGGCCGACAAGCAGAA
GAACGGCATCAAGGTGAACTTCAAGATCCGCCACAACATCGAGGACGGCAGCGTGCAGCT
CGCCGACCACTACCAGCAGAACACCCCCATCGGCGACGGCCCCGTGCTGCTGCCCGACA
ACCACTACCTGAGCACCCAGTCCGCCCTGAGCAAAGACCCCAACGAGAAGCGCGATCACA
TGGTCCTGCTGGAGTTCGTGACCGCCGCCGGGATCACTCTCGGCATGGACGAGCTGTACA
AGTAA (SEQ ID NO: 14)

Optimized Flp recombinase (FlpO):
ATGGCTCCTAAGAAGAAGAGGAAGGTGATGAGCCAGTTCGACATCCTGTGCAAGACCCCC
CCCAAGGTGCTGGTGCGGCAGTTCGTGGAGAGATTCGAGAGGCCCAGCGGCGAGAAGAT
CGCCAGCTGTGCCGCCGAGCTGACCTACCTGTGCTGGATGATCACCCACAACGGCACCG
CCATCAAGAGGGCCACCTTCATGAGCTACAACACCATCATCAGCAACAGCCTGAGCTTCGA
CATCGTGAACAAGAGCCTGCAGTTCAAGTACAAGACCCAGAAGGCCACCATCCTGGAGGC
CAGCCTGAAGAAGCTGATCCCCGCCTGGGAGTTCACCATCATCCCTTACAACGGCCAGAA
GCACCAGAGCGACATCACCGACATCGTGTCCAGCCTGCAGCTGCAGTTCGAGAGCAGCG
AGGAGGCCGACAAGGGCAACAGCCACAGCAAGAAGATGCTGAAGGCCCTGCTGTCCGAG
GGCGAGAGCATCTGGGAGATCACCGAGAAGATCCTGAACAGCTTCGAGTACACCAGCAGG
TTCACCAAGACCAAGACCCTGTACCAGTTCCTGTTCCTGGCCACATTCATCAACTGCGGCA
GGTTCAGCGACATCAAGAACGTGGACCCCAAGAGCTTCAAGCTGGTGCAGAACAAGTACC
TGGGCGTGATCATTCAGTGCCTGGTGACCGAGACCAAGACAAGCGTGTCCAGGCACATCT
ACTTTTTCAGCGCCAGAGGCAGGATCGACCCCCTGGTGTACCTGGACGAGTTCCTGAGGA
ACAGCGAGCCCGTGCTGAAGAGAGTGAACAGGACCGGCAACAGCAGCAGCAACAAGCAG
GAGTACCAGCTGCTGAAGGACAACCTGGTGCGCAGCTACAACAAGGCCCTGAAGAAGAAC
GCCCCCTACCCCATCTTCGCTATCAAGAACGGCCCTAAGAGCCACATCGGCAGGCACCTG
ATGACCAGCTTTCTGAGCATGAAGGGCCTGACCGAGCTGACAAACGTGGTGGGCAACTGG
AGCGACAAGAGGGCCTCCGCCGTGGCCAGGACCACCTACACCCACCAGATCACCGCCAT

FIG. 17 cont'd

CCCCGACCACTACTTCGCCCTGGTGTCCAGGTACTACGCCTACGACCCCATCAGCAAGGA
GATGATCGCCCTGAAGGACGAGACCAACCCCATCGAGGAGTGGCAGCACATCGAGCAGC
TGAAGGGCAGCGCCGAGGGCAGCATCAGATACCCCGCCTGGAACGGCATCATCAGCCAG
GAGGTGCTGGACTACCTGAGCAGCTACATCAACAGGCGGATCTGA (SEQ ID NO: 15)

Improved Cre recombinase (iCre):
ATGGTGCCCAAGAAGAAGAGGAAAGTCTCCAACCTGCTGACTGTGCACCAAAACCTGCCT
GCCCTCCCTGTGGATGCCACCTCTGATGAAGTCAGGAAGAACCTGATGGACATGTTCAGG
GACAGGCAGGCCTTCTCTGAACACACCTGGAAGATGCTCCTGTCTGTGTGCAGATCCTGG
GCTGCCTGGTGCAAGCTGAACAACAGGAAATGGTTCCCTGCTGAACCTGAGGATGTGAGG
GACTACCTCCTGTACCTGCAAGCCAGAGGCCTGGCTGTGAAGACCATCCAACAGCACCTG
GGCCAGCTCAACATGCTGCACAGGAGATCTGGCCTGCCTCGCCCTTCTGACTCCAATGCT
GTGTCCCTGGTGATGAGGAGAATCAGAAAGGAGAATGTGGATGCTGGGGAGAGAGCCAA
GCAGGCCCTGGCCTTTGAACGCACTGACTTTGACCAAGTCAGATCCCTGATGGAGAACTC
TGACAGATGCCAGGACATCAGGAACCTGGCCTTCCTGGGCATTGCCTACAACACCCTGCT
GCGCATTGCCGAAATTGCCAGAATCAGAGTGAAGGACATCTCCCGCACCGATGGTGGGAG
AATGCTGATCCACATTGGCAGGACCAAGACCCTGGTGTCCACAGCTGGTGTGGAGAAGGC
CCTGTCCCTGGGGGTTACCAAGCTGGTGGAGAGATGGATCTCTGTGTCTGGTGTGGCTGA
TGACCCCAACAACTACCTGTTCTGCCGGGTCAGAAAGAATGGTGTGGCTGCCCCTTCTGC
CACCTCCCAACTGTCCACCCGGGCCCTGGAAGGGATCTTTGAGGCCACCCACCGCCTGAT
CTATGGTGCCAAGGATGACTCTGGGCAGAGATACCTGGCCTGGTCTGGCCACTCTGCCAG
AGTGGGTGCTGCCAGGGACATGGCCAGGGCTGGTGTGTCCATCCCTGAAATCATGCAGG
CTGGTGGCTGGACCAATGTGAACATTGTGATGAACTACATCAGAAACCTGGACTCTGAGAC
TGGGGCCATGGTGAGGCTGCTCGAGGATGGGGACTAA (SEQ ID NO: 16)

NavMs, endogenous sequence:
ATGTCACGCAAAATAAGAGATTTAATCGAATCCAAACGCTTTCAAAACGTCATCACCGCCAT
TATTGTGCTCAATGGCGCTGTGCTGGGTCTGCTGACCGATACAACCCTATCGGCCTCCAG
CCAAAACCTGCTGGAGCGTGTGGATCAACTTTGTCTGACTATCTTTATTGTTGAAATATCCC
TGAAAATATACGCCTATGGCGTGCGAGGCTTTTTCCGCAGCGGCTGGAATCTGTTTGATTT
TGTGATTGTGGCCATCGCGCTTATGCCCGCCCAGGGTAGCCTATCGGTGCTGCGAACCTT
CCGTATATTCCGCGTCATGCGGCTCGTATCGGTCATACCAACCATGCGAAGAGTGGTGCA
AGGCATGCTCTTGGCACTGCCCGGCGTGGGATCGGTAGCGGCACTGTTGACGGTGGTCT
TCTATATTGCGGCTGTCATGGCCACCAATCTCTACGGGGCAACCTTCCCTGAATGGTTTGG
TGATCTTAGCAAGAGCCTGTACACACTATTTCAGGTGATGACCTTAGAGTCATGGTCTATG
GGCATTGTGCGTCCAGTGATGAACGTTCATCCCAACGCATGGGTTTTTTTCATCCCCTTCA
TCATGCTCACCACCTTTACCGTGCTCAACCTGTTTATTGGCATTATTGTAGATGCCATGGCC
ATCACCAAGGAACAGGAGGAAGAGGCCAAAACCGGCCACCACCAAGAGCCTATTAGCCAA
ACATTGCTCCATCTGGGAGATCGCCTAGATAGGATCGAAAAGCAGCTTGCGCAAAACAAC
GAGCTCTTACAACGACAACAGCCGCAAAAAAAATAG (SEQ ID NO: 17)

NavMs, codon optimized, with N-terminal 3x HA tag and linker:
ATGGTTTATCCGTATGATGTTCCTGACTATGCAGGATCCTATCCTTATGATGTTCCCGATTA
CGCTGGTTCTTACCCTTACGATGTTCCCGATTATGCCAGTTCTGGATTGGTGCCACGAGGC
AGCCACATGAGCCGGAAGATCAGAGATCTTATCGAATCTAAGAGATTTCAGAATGTTATTAC
CGCGATAATCGTACTCAACGGGGCGGTGCTCGGTCTCCTCACCGATACCACATTGAGCGC
TTCTAGCCAGAACCTGCTCGAAAGGGTTGACCAACTGTGCCTGACAATTTTTATCGTGGAA
ATTAGCTTGAAAATTTACGCCTACGGCGTTCGCGGTTTTTTCCGGAGCGGTTGGAATCTTTT
TGACTTCGTTATCGTTGCCATCGCGCTCATGCCCGCACAGGGTTCTTTGTCTGTGTTGAGG

FIG. 17 cont'd

ACATTCCGAATATTTCGCGTGATGCGCTTGGTATCCGTGATCCCTACGATGCGCCGCGTCG
TACAAGGAATGTTGCTGGCTCTCCCCGGCGTCGGGAGCGTTGCTGCCCTCCTTACCGTGG
TATTTTACATAGCGGCGGTTATGGCTACTAATCTTTACGGAGCTACCTTCCCGGAGTGGTT
CGGGGATTTGTCCAAGAGCCTCTATACATTGTTTCAAGTTATGACCCTGGAGTCCTGGTCT
ATGGGCATTGTCCGGCCCGTAATGAACGTACACCCAAATGCGTGGGTGTTTTTCATTCCAT
TCATCATGCTGACTACCTTTACCGTGCTGAACTTGTTCATTGGGATTATCGTGGATGCGATG
GCCATCACTAAGGAGCAAGAAGAAGAGGCTAAAACTGGCCACCACCAAGAGCCAATTTCT
CAAACCCTCTTGCATCTCGGGGACCGACTGGACCGCATTGAGAAGCAACTCGCGCAGAAC
AATGAGCTGTTGCAGCGACAGCAACCTCAAAAAAAATAA (SEQ ID NO: 18)

NavMs, codon optimized, with N-terminal His tag and linker:

ATGGGCAGCAGCCATCATCATCATCATCACAGCAGCGGCCTGGTGCCGCGCGGCAGCCA
TATGTCACGCAAAATCCGCGATTTAATCGAATCCAAACGCTTTCAAAACGTCATCACCGCCA
TTATTGTGCTCAATGGCGCTGTGCTGGGTCTGCTGACCGATACAACCCTGTCGGCCTCCA
GCCAAAACCTGCTGGAGCGTGTGGATCAACTTTGTCTGACTATCTTTATTGTTGAAATCTCC
CTGAAAATCTACGCCTATGGCGTGCGCGGCTTTTTCCGCAGCGGCTGGAATCTGTTTGATT
TTGTGATTGTGGCCATCGCGCTTATGCCGGCCCAGGGTAGCCTGTCGGTGCTGCGTACCT
TCCGTATCTTCCGCGTCATGCGCCTCGTATCGGTCATCCCAACCATGCGCCGTGTGGTGC
AAGGCATGCTCTTGGCACTGCCGGGCGTGGGCTCGGTAGCGGCACTGTTGACGGTGGTC
TTCTATATTGCGGCTGTCATGGCCACCAATCTCTACGGGGCAACCTTCCCTGAATGGTTTG
GTGATCTTAGCAAGAGCCTGTACACACTGTTTCAGGTGATGACCTTAGAGTCATGGTCTAT
GGGCATTGTGCGTCCAGTGATGAACGTTCATCCGAACGCATGGGTTTTTTTCATCCCGTTC
ATCATGCTCACCACCTTTACCGTGCTCAACCTGTTTATTGGCATTATTGTAGATGCAATGGC
AATCACCAAGGAACAGGAGGAAGAGGCCAAAACCGGTCACCATCAAGAACCTATTTCTCAA
ACTCTTCTTCATCTTGGTGATCGTCTTGATCGTATTGAAAAACAACTTGCTCAAAATAATGAA
CTTCTTCAACGTCAACAACCTCAAAAAAAATAA (SEQ ID NO: 19)

NavBp, endogenous sequence:

ATGGAAAACAATCCAGCCGAACAACAAGTTCCACCATTAGTAGCCTTAGCTCAGCGTATCG
TCTTTCATAAGGCCTTTACCCCAACTATTATTACCTTGATTATCATTAATGCCATTATTGTAG
GCCTTGAAACATATCCTACTGTTTATCAAGGTTATAATGATTGGTTCTACGCAGCAGATTTA
GCCTTACTTTGGATTTTTACAATTGAGATTACACTGCGTTTTATCGCAGCGAGACCGACTAA
ATCTTTTTTTAAAAGCAGCTGGAACTGGTTTGATTTATTAATCGTTCTTGCCGGTCATGTCTT
TGCCGGTGCTCATTTTGTAACGGTTCTTCGTATCCTGCGCGTTCTTCGCGTATTACGTGCC
ATTTCTGTCATTCCTTCTCTGCGTCGTTTAGTCGATGCTTTGCTGATGACCATCCCGGCTTT
AGGAAACATTATGATCCTGATGGGAATTATTTTCTATATTTTCGCTGTGATTGGAACGATGT
TATTTGCTTCTGTAGCACCTGAGTACTTTGGTAACTTACAGCTTTCTTTATTAACATTATTCC
AAGTTGTTACACTTGAATCTTGGGCAAGCGGTGTCATGAGGCCGATTTTTGCAGAGGTTTG
GTGGTCTTGGATTTATTTTGTCATCTTTATTTTAGTAGGGACATTTATTGTCTTTAACTTATTT
ATCGGTGTTATCGTTAATAACGTTGAAAAAGCAAACGAAGAAGAACTCAAATCAGAATTAGA
TGATAAAGAGGCAGATACAAAAGAAGAGCTTGCTTCTCTGCGTAATGAAGTAGCAGAGATG
AAAGACCTCATTAAACAAATGCATAAACAGCAAACAAAAAAAGGGTAA (SEQ ID NO: 20)

NavBp, codon optimized, with N-terminal 3x HA tag:

ATGGTTTACCCGTATGATGTCCCGGATTACGCTGGCAGCTACCCATACGATGTACCCGACT
ATGCCGGCAGTTATCCCTACGACGTCCCTGACTACGCAGAAAACAACCCAGCCGAACAGC
AAGTCCCACCCCTCGTGGCGCTCGCCCAACGCATAGTATTTCACAAGGCGTTTACGCCGA
CGATAATCACCCTCATCATTATTAATGCGATCATTGTGGGACTCGAGACATACCCAACGGTT
TACCAGGGTTACAATGATTGGTTCTATGCTGCCGACCTTGCTTTGTTGTGGATATTCACTAT

FIG. 17 cont'd

TGAAATCACGCTCCGATTCATCGCCGCCCGACCGACGAAGAGTTTCTTCAAGTCTAGCTGG
AACTGGTTTGATCTGCTTATCGTATTGGCGGCCACGTCTTCGCTGGCGCCCATTTTGTTA
CGGTGCTTAGGATCCTCCGCGTCCTGAGGGTCCTCAGAGCTATCTCAGTCATACCCAGTC
TCCGGCGGCTGGTTGACGCACTTTTGATGACAATCCCAGCACTCGGTAACATCATGATACT
GATGGGGATTATTTTTACATATTCGCGGTTATCGGGACGATGCTCTTTGCATCAGTAGCG
CCAGAATACTTTGGCAATTTGCAGCTGTCTCTGCTTACACTGTTCCAAGTGGTTACGCTGG
AAAGTTGGGCTAGTGGGGTTATGCGACCTATTTTTGCCGAAGTCTGGTGGTCTTGGATCTA
TTTTGTAATCTTTATTCTCGTGGGAACTTTCATAGTATTTAACCTTTTCATTGGCGTCATCGT
GAACAATGTGGAAAAAGCTAACGAAGAGGAACTGAAAAGCGAACTGGATGATAAAGAGGC
TGATACAAAAGAAGAACTGGCATCATTGCGAAACGAGGTGGCAGAAATGAAGGATCTCATA
AAACAGATGCATAAACAGCAAACAAAAAAGGGTTAA (SEQ ID NO: 21)

NavSheP-D60N, codon optimized, with N-terminal 3x HA tag:

ATGGTTTACCCGTATGATGTCCCGGATTACGCTGGCAGCTACCCATACGATGTACCCGACT
ATGCCGGCAGTTATCCCTACGACGTCCCTGACTACGCATCTACGTCCCTTTTGAATGCGCC
TACCGGCCTTCAAGCTAGAGTCATTAATCTCGTCGAACAAAACTGGTTTGGACACTTTATAC
TGACTCTCATACTCATTAATGCTGTGCAGCTTGGAATGGAAACTAGCGCCAGCCTCATGGC
ACAATATGGCGCGCTGCTTATGTCCTTGAATAAGGTCCTTCTCTCTGTGTTCGTGGTCGAA
CTGCTGCTCCGGATTTATGCGTATCGGGGCAAGTTTTTTAAGGACCCGTGGAATGTGTTTG
ACTTCACTGTTATTGTTATTGCTCTGATTCCTGCATCTGGCCCATTGGCTGTCCTCCGCTCC
CTCCGAGTTCTCCGCGTCTTGAGGGTTCTGACGATTGTCCCCAGCATGAAAAGAGTAGTGT
CAGCACTGCTTGGGAGCTTGCCCGGGTTGGCCTCCATTGCAACCGTGCTTCTGTTGATCT
ATTACGTTTTCGCTGTGATCGCCACTAAAATTTTCGGGGATGCTTTTCCGGAATGGTTCGG
GACGATAGCGGACTCCTTCTATACCCTTTTTCAAATTATGACCTTGGAAAGTTGGTCTATGG
GGATCTCTAGGCCAGTGATGGAGGTGTACCCTTACGCTTGGGTATTCTTTGTGCCCTTTAT
TCTTGTTGCTACTTTTACCATGCTTAACCTTTTCATCGCCATCATAGTGAATACTATGCAGAC
ATTCTCTGACGAGGAACATGCTCTGGAGCGAGAGCAAGATAAACAGATCTTGGAACAGGA
GCAGAGACAAATGCACGAGGAACTGAAGGCCATTCGACTCGAGCTTCAGCAACTCCAAAC
CCTTTTGCGAAATGCGGCTGGGGACTCCTCCAATGTCTCCACAAAGGGCAATATCGGCTC
AGACTAA (SEQ ID NO: 22)

NavSheP endogenous sequence:

ATGAGTACATCTTTACTTAACGCGCCAACGGGTTTGCAGGCACGAGTGATTAACTTGGTTG
AGCAAAACTGGTTTGGTCATTTTATTTTGACATTGATTTTAATCAACGCGGTGCAGTTAGGT
ATGGAGACCTCAGCCAGCCTGATGGCGCAATACGGTGCTTTGTTGATGAGTCTTGATAAG
GTGCTGCTGAGTGTATTTGTGGTGGAGTTATTGCTGCGGATTTATGCCTACAGGGGGAAAT
TTTTTAAAGACCCTTGGAACGTGTTCGATTTTACCGTGATAGTGATAGCACTGATCCCTGCA
TCTGGGCCATTGGCTGTCCTGCGTTCGCTCAGGGTATTGCGGGTGCTGAGAGTGTTAACA
ATTGTGCCATCAATGAAACGGGTGGTGTCTGCGCTGTTGGGATCACTTCCTGGATTGGCAT
CGATCGCCACAGTATTACTGCTGATTTATTATGTGTTTGCGGTGATCGCTACCAAAATTTTT
GGCGATGCATTCCCTGAATGGTTTGGCACTATTGCTGACTCATTTTATACCCTATTTCAAAT
AATGACGCTTGAAAGCTGGTCTATGGGAATTTCGCGGCCAGTGATGGAAGTCTACCCTTAT
GCTTGGGTATTTTTCGTACCATTTATTCTGGTAGCGACTTTCACAATGCTAAATTTGTTTATT
GCGATTATCGTCAATACCATGCAAACCTTCAGCGACGAAGAGCATGCATTAGAGCGTGAGC
AAGACAAACAAATCTTAGAGCAGGAACAAAGACAAATGCACGAGGAGTTGAAAGCCATCAG
ACTCGAGCTACAACAATTACAAACCTTGCTGCGCAATGCTGCTGGTGATTCTTCTAATGTGT
CGACAAAGGGAAACATTGGTTCTGACTAA (SEQ ID NO: 23)

WPRE3:

FIG. 17 cont'd

ATAATCAACCTCTGGATTACAAAATTTGTGAAAGATTGACTGGTATTCTTAACTATGTTGCTC
CTTTTACGCTATGTGGATACGCTGCTTTAATGCCTTTGTATCATGCTATTGCTTCCCGTATG
GCTTTCATTTTCTCCTCCTTGTATAAATCCTGGTTAGTTCTTGCCACGGCGGAACTCATCGC
CGCCTGCCTTGCCCGCTGCTGGACAGGGGCTCGGCTGTTGGGCACTGACAATTCCGTGG
(SEQ ID NO: 24)

BGHpA:
CGACTGTGCCTTCTAGTTGCCAGCCATCTGTTGTTTGCCCCTCCCCCGTGCCTTCCTTGAC
CCTGGAAGGTGCCACTCCCACTGTCCTTTCCTAATAAAATGAGGAAATTGCATCGCATTGT
CTGAGTAGGTGTCATTCTATTCTGGGGGGTGGGGTGGGGCAGGACAGCAAGGGGGAGGA
TTGGGAAGACAATAGCAGGCATG (SEQ ID NO: 25)

P2A Encoding Sequence:
GGCAGCGGCGCCACCAACTTCAGCCTGCTGAAGCAGGCCGGCGACGTGGAGGAGAACCC
CGGCCCCGGAGCTAGCGGA (SEQ ID NO: 26)

P2A:
(GSG)ATNFSLLKQAGDVEENPGPGASG (SEQ ID NO: 27)

T2A:
(GSG)EGRGSLLTCGDVEENPGP (SEQ ID NO: 28)

E2A:
(GSG)QCTNYALLKLAGDVESNPGPP (SEQ ID NO: 29)

F2A:
(GSG)VKQTLNFDLLKLAGDVESNPGP (SEQ ID NO: 30)

N-terminal 3XHA tag (DNA):
ATGGTTTACCCGTATGATGTCCCGGATTACGCTGGCAGCTACCCATACGATGTACCCGACT
ATGCCGGCAGTTATCCCTACGACGTCCCTGACTACGCA (SEQ ID NO: 31)

N-terminal 3XHA tag (Protein):
MVYPYDVPDYAGSYPYDVPDYAGSYPYDVPDYA (SEQ ID NO: 32)

PHP.eB capsid:
AAV9 capsid except that amino acids starting at residue 586: SAQA (SEQ ID NO: 98) are changed to SDGTLAVPFKA (SEQ ID NO: 33) to form
MAADGYLPDWLEDNLSEGIREWWALKPGAPQPKANQQHQDNARGLVLPGYKYLGPGNGLDK
GEPVNAADAAALEHDKAYDQQLKAGDNPYLKYNHADAEFQERLKEDTSFGGNLGRAVFQAKK
RLLEPLGLVEEAAKTAPGKKRPVEQSPQEPDSSAGIGKSGAQPAKKRLNFGQTGDTESVPDP
QPIGEPPAAPSGVGSLTMASGGGAPVADNNEGADGVGSSSGNWHCDSQWLGDRVITTSTRT
WALPTYNNHLYKQISNSTSGGSSNDNAYFGYSTPWGYFDFNRFHCHFSPRDWQRLINNNWG
FRPKRLNFKLFNIQVKEVTDNNGVKTIANNLTSTVQVFTDSDYQLPYVLGSAHEGCLPPFPADV
FMIPQYGYLTLNDGSQAVGRSSFYCLEYFPSQMLRTGNNFQFSYEFENVPFHSSYAHSQSLD
RLMNPLIDQYLYYLSKTINGSGQNQQTLKFSVAGPSNMAVQGRNYIPGPSYRQQRVSTTVTQN
NNSEFAWPGASSWALNGRNSLMNPGPAMASHKEGEDRFFPLSGSLIFGKQGTGRDNVDADK
VMITNEEEIKTTNPVATESYGQVATNHQSDGTLAVPFKAQAQTGWVQNQGILPGMVWQDRDV
YLQGPIWAKIPHTDGNFHPSPLMGGFGMKHPPPQILIKNTPVPADPPTAFNKDKLNSFITQYST

FIG. 17 cont'd

GQVSVEIEWELQKENSKRWNPEIQYTSNYYKSNNVEFAVNTEGVYSEPRPIGTRYLTRNL
(SEQ ID NO: 90)

AAV9 VP1 capsid protein:
MAADGYLPDWLEDNLSEGIREWWALKPGAPQPKANQQHQDNARGLVLPGYKYLGPGNGLDK
GEPVNAADAAALEHDKAYDQQLKAGDNPYLKYNHADAEFQERLKEDTSFGGNLGRAVFQAKK
RLLEPLGLVEEAAKTAPGKKRPVEQSPQEPDSSAGIGKSGAQPAKKRLNFGQTGDTESVPDP
QPIGEPPAAPSGVGSLTMASGGGAPVADNNEGADGVGSSSGNWHCDSQWLGDRVITTSTRT
WALPTYNNHLYKQISNSTSGGSSNDNAYFGYSTPWGYFDFNRFHCHFSPRDWQRLINNNWG
FRPKRLNFKLFNIQVKEVTDNNGVKTIANNLTSTVQVFTDSDYQLPYVLGSAHEGCLPPFPADV
FMIPQYGYLTLNDGSQAVGRSSFYCLEYFPSQMLRTGNNFQFSYEFENVPFHSSYAHSQSLD
RLMNPLIDQYLYYLSKTINGSGQNQQTLKFSVAGPSNMAVQGRNYIPGPSYRQQRVSTTVTQN
NNSEFAWPGASSWALNGRNSLMNPGPAMASHKEGEDRFFPLSGSLIFGKQGTGRDNVDADK
VMITNEEEIKTTNPVATESYGQVATNHQSAQAQAQTGWVQNQGILPGMVWQDRDVYLQGPIW
AKIPHTDGNFHPSPLMGGFGMKHPPPQILIKNTPVPADPPTAFNKDKLNSFITQYSTGQVSVEIE
WELQKENSKRWNPEIQYTSNYYKSNNVEFAVNTEGVYSEPRPIGTRYLTRNL (SEQ ID NO:
34)

tet-Transactivator version 2 (tTA2):
ATGTCTAGACTGGACAAGAGCAAAGTCATAAACTCTGCTCTGGAATTACTCAATGAAGTCG
GTATCGAAGGCCTGACGACAAGGAAACTCGCTCAAAAGCTGGGAGTTGAGCAGCCTACCC
TGTACTGGCACGTGAAGAACAAGCGGGCCCTGCTCGATGCCCTGGCAATCGAGATGCTGG
ACAGGCATCATACCCACTTCTGCCCCCTGGAAGGCGAGTCATGGCAAGACTTTCTGCGGA
ACAACGCCAAGTCATTCCGCTGTGCTCTCCTCTCACATCGCGACGGGGCTAAAGTGCATCT
CGGCACCCGCCCAACAGAGAAACAGTACGAAACCCTGGAAAATCAGCTCGCGTTCCTGTG
TCAGCAAGGCTTCTCCCTGGAGAACGCACTGTACGCTCTGTCCGCCGTGGGCCACTTTAC
ACTGGGCTGCGTATTGGAGGATCAGGAGCATCAAGTAGCAAAAGAGGAAAGAGAGACACC
TACCACCGATTCTATGCCCCCACTTCTGAGACAAGCAATTGAGCTGTTCGACCATCAGGGA
GCCGAACCTGCCTTCCTTTTCGGCCTGGAACTAATCATATGTGGCCTGGAGAAACAGCTAA
AGTGCGAAAGCGGCGGGCCGGCCGACGCCCTTGACGATTTTGACTTAGACATGCTCCCAG
CCGATGCCCTTGACGACTTTGACCTTGATATGCTGCCTGCTGACGCTCTTGACGATTTTGA
CCTTGACATGCTCCCCGGGTAA (SEQ ID NO: 35)

CN1367 - The portion between L-ITR and R-ITR: positions 142-2984:
GCGGCCGCACGCGTATAGGTACCGAGCTCTATGCACTCACAGTGGTTTGGCATGCATCTG
GTGAATTTTTTTTAACGAAAAATTAGTGTTGGTTTCGATGTATGGTAGCATTCTCCCTAACGT
AATTTGAATAATTCAGCAAAGCCCCACTACCAGCTGTACTTCTGCAGCCTCTTCCATTCTTT
TCAGCATTATAATTTTGGTTAATTTTCAATTTTAGGTCCTACGTCTCTGCAATTTGTGTATGA
ATAACAGAATAATTTCCCTCTTTTGTTTCGCCTTTCCTGTTCCTGAATCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGAAAAAAACC
TTCTTGTGGATAAAAACCTTAAATTGTCCCCAATGTCTGCTTCAAATTGGATGGCACTGCAG
CTGGAGGCTTTGTTCAGAATTGATCCTGGGGAGCTACGAACCCAAAGTTTCACAGTAGGGA
GCTCGGGCTGGGCATAAAAGTCAGGGCAGAGCCATCTATTGCTTACATTTGCTTCTGGGAT
CCAGATCTTTCGAAGCTAGCGCTACCGGTCGCCACCATGGGCAGCAGCCATCATCATCAT
CATCACAGCAGCGGCCTGGTGCCGCGCGGCAGCCATATGTCACGCAAAATCCGCGATTTA
ATCGAATCCAAACGCTTTCAAAACGTCATCACCGCCATTATTGTGCTCAATGGCGCTGTGC
TGGGTCTGCTGACCGATACAACCCTGTCGGCCTCCAGCCAAAACCTGCTGGAGCGTGTGG

FIG. 17 cont'd

ATCAACTTTGTCTGACTATCTTTATTGTTGAAATCTCCCTGAAAATCTACGCCTATGGCGTG
CGCGGCTTTTTCCGCAGCGGCTGGAATCTGTTTGATTTTGTGATTGTGGCCATCGCGCTTA
TGCCGGCCCAGGGTAGCCTGTCGGTGCTGCGTACCTTCCGTATCTTCCGCGTCATGCGCC
TCGTATCGGTCATCCCAACCATGCGCCGTGTGGTGCAAGGCATGCTCTTGGCACTGCCGG
GCGTGGGCTCGGTAGCGGCACTGTTGACGGTGGTCTTCTATATTGCGGCTGTCATGGCCA
CCAATCTCTACGGGGCAACCTTCCCTGAATGGTTTGGTGATCTTAGCAAGAGCCTGTACAC
ACTGTTTCAGGTGATGACCTTAGAGTCATGGTCTATGGGCATTGTGCGTCCAGTGATGAAC
GTTCATCCGAACGCATGGGTTTTTTCATCCCGTTCATCATGCTCACCACCTTTACCGTGCT
CAACCTGTTTATTGGCATTATTGTAGATGCAATGGCAATCACCAAGGAACAGGAGGAAGAG
GCCAAAACCGGTCACCATCAAGAACCTATTTCTCAAACTCTTCTTCATCTTGGTGATCGTCT
TGATCGTATTGAAAAACAACTTGCTCAAAATAATGAACTTCTTCAACGTCAACAACCTCAAA
AAAAAGGCAGCGGCGCCACCAACTTCAGCCTGCTGAAGCAGGCCGGCGACGTGGAGGAG
AACCCCGGCCCCATGGTGAGCAAGGGCGAGGAGCTGTTCACCGGGGTGGTGCCCATCCT
GGTCGAGCTGGACGGCGACGTAAACGGCCACAAGTTCAGCGTGTCCGGCGAGGGCGAG
GGCGATGCCACCTACGGCAAGCTGACCCTGAAGCTGATCTGCACCACCGGCAAGCTGCC
CGTGCCCTGGCCCACCCTCGTGACCACCCTGGGCTACGGCGTGCAGTGCTTCGCCCGCT
ACCCCGACCACATGAAGCAGCACGACTTCTTCAAGTCCGCCATGCCCGAAGGCTACGTCC
AGGAGCGCACCATCTTCTTCAAGGACGACGGCAACTACAAGACCCGCGCCGAGGTGAAGT
TCGAGGGCGACACCCTGGTGAACCGCATCGAGCTGAAGGGCATCGACTTCAAGGAGGAC
GGCAACATCCTGGGGCACAAGCTGGAGTACAACTACAACAGCCACAACGTCTATATCACC
GCCGACAAGCAGAAGAACGGCATCAAGGCCAACTTCAAGATCCGCCACAACATCGAGGAC
GGCGGCGTGCAGCTCGCCGACCACTACCAGCAGAACACCCCCATCGGCGACGGCCCCGT
GCTGCTGCCCGACAACCACTACCTGAGCTACCAGTCCAAGCTGAGCAAAGACCCCAACGA
GAAGCGCGATCACATGGTCCTGCTGGAGTTCGTGACCGCCGCCGGGATCACTCTCGGCAT
GGACGAGCTGTACAAGTAAGTCGACGGCGCGCCGCGGCCGCGAATTCGATATCATAATCA
ACCTCTGGATTACAAAATTTGTGAAAGATTGACTGGTATTCTTAACTATGTTGCTCCTTTTAC
GCTATGTGGATACGCTGCTTTAATGCCTTTGTATCATGCTATTGCTTCCCGTATGGCTTTCA
TTTTCTCCTCCTTGTATAAATCCTGGTTAGTTCTTGCCACGGCGGAACTCATCGCCGCCTG
CCTTGCCCGCTGCTGGACAGGGGCTCGGCTGTTGGGCACTGACAATTCCGTGGCTCGAG
AGATCTTCGACTGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAGGAAATTGCATC
GCATTGTCTGAGTAGGTGTCATTCTATTCTGGGGGGTGGGGTGGGGCAGGACAGCAAGG
GGGAGGATTGGGAAGACAATAGCAGGCATGCACGTGCGGACCGAGCGGCCGC (SEQ ID NO: 36)

CN1500 - The portion between L-ITR and R-ITR: positions 142-2976:

GCGGCCGCACGCGTGGTACCCTAAATAAAGATGGCTTTTTAGTATTAAAAGTGGAAGAAAA
TTACAGGTAATTATCTTTGACGGTAAAAACGCTGTAATCAGCGGGCTACATGAAAAATTACT
CTAATTATGGCTGCATTTAAGAGAATGGCTAAATAAAGATGGCTTTTTAGTATTAAAAGTGG
AAGAAAATTACAGGTAATTATCTTTGACGGTAAAAACGCTGTAATCAGCGGGCTACATGAAA
AATTACTCTAATTATGGCTGCATTTAAGAGAATGGCTAAATAAAGATGGCTTTTTAGTATTAA
AAGTGGAAGAAAATTACAGGTAATTATCTTTGACGGTAAAAACGCTGTAATCAGCGGGCTA
CATGAAAAATTACTCTAATTATGGCTGCATTTAAGAGAATGGAGCTCGGGCTGGTCGACAC
AATTGGAGGTAGGCGTGTACGGTGGGAGGCCTATATAAGCAGAGCTCGTTTAGTGAACCG
TCAGATCGCCTGGAGGATCCTTCGAAAAGCTTGCTACCGGTCGCCACCATGGTCAGCAAG
GGCGAGGAGCTGTTCACCGGGGTGGTGCCCATCCTGGTCGAGCTGGACGGCGACGTCAA
TGGCCACAAGTTCAGCGTGTCCGGCGAGGGCGAGGGCGATGCCACCTACGGCAAGCTGA
CCCTGAAGCTGATCTGCACCACCGGCAAGCTGCCCGTGCCCTGGCCCACCCTCGTGACC
ACCCTGGGCTACGGCGTGCAGTGCTTCGCCCGCTACCCCGACCACATGAAGCAGCACGA

FIG. 17 cont'd

CTTCTTCAAGTCCGCCATGCCCGAAGGCTACGTCCAGGAGCGCACCATCTTCTTCAAAGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACTACAACAGCCACAACGTCTATATCACCGCCGACAAGCAGAAGAACGGCATCAA
GGCCAACTTCAAGATCCGCCACAACATCGAGGACGGCGGCGTGCAGCTCGCCGACCACT
ACCAGCAGAACACCCCCATCGGCGACGGCCCCGTGCTGCTGCCCGACAACCACTACCTG
AGCTACCAGTCCAAGCTGAGCAAAGACCCCAACGAGAAGCGCGATCACATGGTCCTGCTG
GAGTTCGTGACCGCCGCCGGGATCACTCTCGGCATGGACGAGCTGTACAAAGGCAGCGG
CGCCACCAACTTCAGCCTGCTGAAGCAGGCCGGCGACGTGGAGGAGAACCCCGGCCCCG
GAGCTAGCGGAATGGTTTACCCGTATGATGTCCCGGATTACGCTGGCAGCTACCCATACG
ATGTACCCGACTATGCCGGCAGTTATCCCTACGACGTCCCTGACTACGCATCTACGTCCCT
TTTGAATGCGCCTACCGGCCTTCAAGCTAGAGTCATTAATCTCGTCGAACAAAACTGGTTT
GGACACTTTATACTGACTCTCATACTCATTAATGCTGTGCAGCTTGGAATGGAAACTAGCG
CCAGCCTCATGGCACAATATGGCGCGCTGCTTATGTCCTTGAATAAGGTCCTTCTCTCTGT
GTTCGTGGTCGAACTGCTGCTCCGGATTTATGCGTATCGGGGCAAGTTTTTAAGGACCCG
TGGAATGTGTTTGACTTCACTGTTATTGTTATTGCTCTGATTCCTGCATCTGGCCCATTGGC
TGTCCTCCGCTCCCTCCGAGTTCTCCGCGTCTTGAGGGTTCTGACGATTGTCCCCAGCAT
GAAAAGAGTAGTGTCAGCACTGCTTGGGAGCTTGCCCGGGTTGGCCTCCATTGCAACCGT
GCTTCTGTTGATCTATTACGTTTTCGCTGTGATCGCCACTAAAATTTTCGGGGATGCTTTTC
CGGAATGGTTCGGGACGATAGCGGACTCCTTCTATACCCTTTTTCAAATTATGACCTTGGA
AAGTTGGTCTATGGGGATCTCTAGGCCAGTGATGGAGGTGTACCCTTACGCTTGGGTATTC
TTTGTGCCCTTTATTCTTGTTGCTACTTTTACCATGCTTAACCTTTTCATCGCCATCATAGTG
AATACTATGCAGACATTCTCTGACGAGGAACATGCTCTGGAGCGAGAGCAAGATAAACAGA
TCTTGGAACAGGAGCAGAGACAAATGCACGAGGAACTGAAGGCCATTCGACTCGAGCTTC
AGCAACTCCAAACCCTTTTGCGAAATGCGGCTGGGGACTCCTCCAATGTCTCCACAAAGG
GCAATATCGGCTCAGACTAATGACCGCGGCCGCGAATTCGATATCATAATCAACCTCTGGA
TTACAAAATTTGTGAAAGATTGACTGGTATTCTTAACTATGTTGCTCCTTTTACGCTATGTGG
ATACGCTGCTTTAATGCCTTTGTATCATGCTATTGCTTCCCGTATGGCTTTCATTTTCTCCTC
CTTGTATAAATCCTGGTTAGTTCTTGCCACGGCGGAACTCATCGCCGCCTGCCTTGCCCGC
TGCTGGACAGGGGCTCGGCTGTTGGGCACTGACAATTCCGTGGCTCGAGAGATCTTCGAC
TGTGCCTTCTAGTTGCCAGCCATCTGTTGTTTGCCCCTCCCCCGTGCCTTCCTTGACCCTG
GAAGGTGCCACTCCCACTGTCCTTTCCTAATAAAATGAGGAAATTGCATCGCATTGTCTGA
GTAGGTGTCATTCTATTCTGGGGGGTGGGGTGGGGCAGGACAGCAAGGGGGAGGATTGG
GAAGACAATAGCAGGCATGAGATCTCACGTGCGGACCGAGCGGCCGC (SEQ ID NO: 37)

CN1498 - The portion between L-ITR and R-ITR: positions 142-2943:

GCGGCCGCACGCGTGGTACCCTAAATAAAGATGGCTTTTTAGTATTAAAAGTGGAAGAAAA
TTACAGGTAATTATCTTTGACGGTAAAAACGCTGTAATCAGCGGGCTACATGAAAAATTACT
CTAATTATGGCTGCATTTAAGAGAATGGCTAAATAAAGATGGCTTTTTAGTATTAAAAGTGG
AAGAAAATTACAGGTAATTATCTTTGACGGTAAAAACGCTGTAATCAGCGGGCTACATGAAA
AATTACTCTAATTATGGCTGCATTTAAGAGAATGGCTAAATAAAGATGGCTTTTTAGTATTAA
AAGTGGAAGAAAATTACAGGTAATTATCTTTGACGGTAAAAACGCTGTAATCAGCGGGCTA
CATGAAAAATTACTCTAATTATGGCTGCATTTAAGAGAATGGAGCTCGGGCTGGTCGACAC
AATTGGAGGTAGGCGTGTACGGTGGGAGGCCTATATAAGCAGAGCTCGTTTAGTGAACCG
TCAGATCGCCTGGAGGATCCTTCGAAAAGCTTGCTACCGGTCGCCACCATGGTCAGCAAG
GGCGAGGAGCTGTTCACCGGGGTGGTGCCCATCCTGGTCGAGCTGGACGGCGACGTCAA
TGGCCACAAGTTCAGCGTGTCCGGCGAGGGCGAGGGCGATGCCACCTACGGCAAGCTGA
CCCTGAAGCTGATCTGCACCACCGGCAAGCTGCCCGTGCCCTGGCCCACCCTCGTGACC
ACCCTGGGCTACGGCGTGCAGTGCTTCGCCCGCTACCCCGACCACATGAAGCAGCACGA

FIG. 17 cont'd

CTTCTTCAAGTCCGCCATGCCCGAAGGCTACGTCCAGGAGCGCACCATCTTCTTCAAAGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACTACAACAGCCACAACGTCTATATCACCGCCGACAAGCAGAAGAACGGCATCAA
GGCCAACTTCAAGATCCGCCACAACATCGAGGACGGCGGCGTGCAGCTCGCCGACCACT
ACCAGCAGAACACCCCCATCGGCGACGGCCCCGTGCTGCTGCCCGACAACCACTACCTG
AGCTACCAGTCCAAGCTGAGCAAAGACCCCAACGAGAAGCGCGATCACATGGTCCTGCTG
GAGTTCGTGACCGCCGCCGGGATCACTCTCGGCATGGACGAGCTGTACAAGGCAGCGG
CGCCACCAACTTCAGCCTGCTGAAGCAGGCCGGCGACGTGGAGGAGAACCCCGGCCCCG
GAGCTAGCGGAATGGTTTACCCGTATGATGTCCCGGATTACGCTGGCAGCTACCCATACG
ATGTACCCGACTATGCCGGCAGTTATCCCTACGACGTCCCTGACTACGCAGAAAACAACCC
AGCCGAACAGCAAGTCCCACCCCTCGTGGCGCTCGCCCAACGCATAGTATTTCACAAGGC
GTTTACGCCGACGATAATCACCCTCATCATTATTAATGCGATCATTGTGGGACTCGAGACAT
ACCCAACGGTTTACCAGGGTTACAATGATTGGTTCTATGCTGCCGACCTTGCTTTGTTGTG
GATATTCACTATTGAAATCACGCTCCGATTCATCGCCGCCCGACCGACGAAGAGTTTCTTC
AAGTCTAGCTGGAACTGGTTTGATCTGCTTATCGTATTGGCGGGCCACGTCTTCGCTGGCG
CCCATTTTGTTACGGTGCTTAGGATCCTCCGCGTCCTGAGGGTCCTCAGAGCTATCTCAGT
CATACCCAGTCTCCGGCGGCTGGTTGACGCACTTTTGATGACAATCCCAGCACTCGGTAA
CATCATGATACTGATGGGGATTATTTTTACATATTCGCGGTTATCGGGACGATGCTCTTTG
CATCAGTAGCGCCAGAATACTTTGGCAATTTGCAGCTGTCTCTGCTTACACTGTTCCAAGT
GGTTACGCTGGAAAGTTGGGCTAGTGGGGTTATGCGACCTATTTTTGCCGAAGTCTGGTG
GTCTTGGATCTATTTTGTAATCTTTATTCTCGTGGGAACTTTCATAGTATTTAACCTTTTCATT
GGCGTCATCGTGAACAATGTGGAAAAAGCTAACGAAGAGGAACTGAAAAGCGAACTGGAT
GATAAAGAGGCTGATACAAAAGAAGAACTGGCATCATTGCGAAACGAGGTGGCAGAAATG
AAGGATCTCATAAAACAGATGCATAAACAGCAAACAAAAAAGGGTTAATGACCGCGGCCGC
GAATTCGATATCATAATCAACCTCTGGATTACAAAATTTGTGAAAGATTGACTGGTATTCTTA
ACTATGTTGCTCCTTTTACGCTATGTGGATACGCTGCTTTAATGCCTTTGTATCATGCTATT
GCTTCCCGTATGGCTTTCATTTTCTCCTCCTTGTATAAATCCTGGTTAGTTCTTGCCACGGC
GGAACTCATCGCCGCCTGCCTTGCCCGCTGCTGGACAGGGGCTCGGCTGTTGGGCACTG
ACAATTCCGTGGCTCGAGAGATCTTCGACTGTGCCTTCTAGTTGCCAGCCATCTGTTGTTT
GCCCCTCCCCCGTGCCTTCCTTGACCCTGGAAGGTGCCACTCCCACTGTCCTTTCCTAATA
AAATGAGGAAATTGCATCGCATTGTCTGAGTAGGTGTCATTCTATTCTGGGGGGTGGGGTG
GGGCAGGACAGCAAGGGGGAGGATTGGGAAGACAATAGCAGGCATGAGATCTCACGTGC
GGACCGAGCGGCCGC (SEQ ID NO: 38)

CN1499 - The portion between L-ITR and R-ITR: positions 142-2946:

GCGGCCGCACGCGTGGTACCCTAAATAAAGATGGCTTTTTAGTATTAAAAGTGGAAGAAAA
TTACAGGTAATTATCTTTGACGGTAAAAACGCTGTAATCAGCGGGCTACATGAAAAATTACT
CTAATTATGGCTGCATTTAAGAGAATGGCTAAATAAAGATGGCTTTTTAGTATTAAAAGTGG
AAGAAAATTACAGGTAATTATCTTTGACGGTAAAAACGCTGTAATCAGCGGGCTACATGAAA
AATTACTCTAATTATGGCTGCATTTAAGAGAATGGCTAAATAAAGATGGCTTTTTAGTATTAA
AAGTGGAAGAAAATTACAGGTAATTATCTTTGACGGTAAAAACGCTGTAATCAGCGGGCTA
CATGAAAAATTACTCTAATTATGGCTGCATTTAAGAGAATGGAGCTCGGGCTGGTCGACAC
AATTGGAGGTAGGCGTGTACGGTGGGAGGCCTATATAAGCAGAGCTCGTTTAGTGAACCG
TCAGATCGCCTGGAGGATCCTTCGAAAAGCTTGCTACCGGTCGCCACCATGGTCAGCAAG
GGCGAGGAGCTGTTCACCGGGGTGGTGCCCATCCTGGTCGAGCTGGACGGCGACGTCAA
TGGCCACAAGTTCAGCGTGTCCGGCGAGGGCGAGGGCGATGCCACCTACGGCAAGCTGA
CCCTGAAGCTGATCTGCACCACCGGCAAGCTGCCCGTGCCCTGGCCCACCCTCGTGACC
ACCCTGGGCTACGGCGTGCAGTGCTTCGCCCGCTACCCCGACCACATGAAGCAGCACGA

FIG. 17 cont'd

CTTCTTCAAGTCCGCCATGCCCGAAGGCTACGTCCAGGAGCGCACCATCTTCTTCAAAGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACTACAACAGCCACAACGTCTATATCACCGCCGACAAGCAGAAGAACGGCATCAA
GGCCAACTTCAAGATCCGCCACAACATCGAGGACGGCGGCGTGCAGCTCGCCGACCACT
ACCAGCAGAACACCCCCATCGGCGACGGCCCCGTGCTGCTGCCCGACAACCACTACCTG
AGCTACCAGTCCAAGCTGAGCAAAGACCCCAACGAGAAGCGCGATCACATGGTCCTGCTG
GAGTTCGTGACCGCCGCCGGGATCACTCTCGGCATGGACGAGCTGTACAAAGGCAGCGG
CGCCACCAACTTCAGCCTGCTGAAGCAGGCCGGCGACGTGGAGGAGAACCCCGGCCCCG
GAGCTAGCGGAATGGTTTATCCGTATGATGTTCCTGACTATGCAGGATCCTATCCTTATGAT
GTTCCCGATTACGCTGGTTCTTACCCTTACGATGTTCCCGATTATGCCAGTTCTGGATTGGT
GCCACGAGGCAGCCACATGAGCCGGAAGATCAGAGATCTTATCGAATCTAAGAGATTTCA
GAATGTTATTACCGCGATAATCGTACTCAACGGGGCGGTGCTCGGTCTCCTCACCGATACC
ACATTGAGCGCTTCTAGCCAGAACCTGCTCGAAAGGGTTGACCAACTGTGCCTGACAATTT
TTATCGTGGAAATTAGCTTGAAAATTTACGCCTACGGCGTTCGCGGTTTTTTCCGGAGCGG
TTGGAATCTTTTTGACTTCGTTATCGTTGCCATCGCGCTCATGCCCGCACAGGGTTCTTTGT
CTGTGTTGAGGACATTCCGAATATTTCGCGTGATGCGCTTGGTATCCGTGATCCCTACGAT
GCGCCGCGTCGTACAAGGAATGTTGCTGGCTCTCCCCGGCGTCGGGAGCGTTGCTGCCC
TCCTTACCGTGGTATTTTACATAGCGGCGGTTATGGCTACTAATCTTTACGGAGCTACCTTC
CCGGAGTGGTTCGGGGATTTGTCCAAGAGCCTCTATACATTGTTTCAAGTTATGACCCTGG
AGTCCTGGTCTATGGGCATTGTCCGGCCCGTAATGAACGTACACCCAAATGCGTGGGTGT
TTTTCATTCCATTCATCATGCTGACTACCTTTACCGTGCTGAACTTGTTCATTGGGATTATCG
TGGATGCGATGGCCATCACTAAGGAGCAAGAAGAAGAGGCTAAAACTGGCCACCACCAAG
AGCCAATTTCTCAAACCCTCTTGCATCTCGGGGACCGACTGGACCGCATTGAGAAGCAACT
CGCGCAGAACAATGAGCTGTTGCAGCGACAGCAACCTCAAAAAAAATAATGACCGCGGCC
GCGAATTCGATATCATAATCAACCTCTGGATTACAAAATTTGTGAAAGATTGACTGGTATTC
TTAACTATGTTGCTCCTTTTACGCTATGTGGATACGCTGCTTTAATGCCTTTGTATCATGCTA
TTGCTTCCCGTATGGCTTTCATTTTCTCCTCCTTGTATAAATCCTGGTTAGTTCTTGCCACG
GCGGAACTCATCGCCGCCTGCCTTGCCCGCTGCTGGACAGGGGCTCGGCTGTTGGGCAC
TGACAATTCCGTGGCTCGAGAGATCTTCGACTGTGCCTTCTAGTTGCCAGCCATCTGTTGT
TTGCCCCTCCCCCGTGCCTTCCTTGACCCTGGAAGGTGCCACTCCCACTGTCCTTTCCTAA
TAAAATGAGGAAATTGCATCGCATTGTCTGAGTAGGTGTCATTCTATTCTGGGGGGTGGGG
TGGGGCAGGACAGCAAGGGGGAGGATTGGGAAGACAATAGCAGGCATGAGATCTCACGT
GCGGACCGAGCGGCCGC (SEQ ID NO: 39)

CN1244 - The portion between L-ITR and R-ITR: positions 142-2042:
GCGGCCGCACGCGTATAGGTACCGAGCTCTATGCACTCACAGTGGTTTGGCATGCATCTG
GTGAATTTTTTTTAACGAAAAATTAGTGTTGGTTTCGATGTATGGTAGCATTCTCCCTAACGT
AATTTGAATAATTCAGCAAAGCCCCACTACCAGCTGTACTTCTGCAGCCTCTTCCATTCTTT
TCAGCATTATAATTTTGGTTAATTTTCAATTTTAGGTCCTACGTCTCTGCAATTTGTGTATGA
ATAACAGAATAATTTCCCTCTTTTGTTTCGCCTTTCCTGTTCCTGAATCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGAAAAAAACC
TTCTTGTGGATAAAAACCTTAAATTGTCCCCAATGTCTGCTTCAAATTGGATGGCACTGCAG
CTGGAGGCTTTGTTCAGAATTGATCCTGGGGAGCTACGAACCCAAAGTTTCACAGTAGGGA
GCTCGGGCTGGGCATAAAAGTCAGGGCAGAGCCATCTATTGCTTACATTTGCTTCTGGGAT
CCAGATCTTTCGAAGCTAGCGCTACCGGTCGCCACCATGGTGAGCAAGGGCGAGGAGCT
GTTCACCGGGGTGGTGCCCATCCTGGTCGAGCTGGACGGCGACGTAAACGGCCACAAGT
TCAGCGTGTCCGGCGAGGGCGAGGGCGATGCCACCTACGGCAAGCTGACCCTGAAGCTG

FIG. 17 cont'd

ATCTGCACCACCGGCAAGCTGCCCGTGCCCTGGCCCACCCTCGTGACCACCCTGGGCTA
CGGCGTGCAGTGCTTCGCCCGCTACCCCGACCACATGAAGCAGCACGACTTCTTCAAGTC
CGCCATGCCCGAAGGCTACGTCCAGGAGCGCACCATCTTCTTCAAGGACGACGGCAACTA
CAAGACCCGCGCCGAGGTGAAGTTCGAGGGCGACACCCTGGTGAACCGCATCGAGCTGA
AGGGCATCGACTTCAAGGAGGACGGCAACATCCTGGGGCACAAGCTGGAGTACAACTACA
ACAGCCACAACGTCTATATCACCGCCGACAAGCAGAAGAACGGCATCAAGGCCAACTTCA
AGATCCGCCACAACATCGAGGACGGCGGCGTGCAGCTCGCCGACCACTACCAGCAGAAC
ACCCCCATCGGCGACGGCCCCGTGCTGCTGCCCGACAACCACTACCTGAGCTACCAGTC
CAAGCTGAGCAAAGACCCCAACGAGAAGCGCGATCACATGGTCCTGCTGGAGTTCGTGAC
CGCCGCCGGGATCACTCTCGGCATGGACGAGCTGTACAAGTAAGTCGACGGCGCGCCGC
GGCCGCGAATTCGATATCATAATCAACCTCTGGATTACAAAATTTGTGAAAGATTGACTGGT
ATTCTTAACTATGTTGCTCCTTTTACGCTATGTGGATACGCTGCTTTAATGCCTTTGTATCAT
GCTATTGCTTCCCGTATGGCTTTCATTTTCTCCTCCTTGTATAAATCCTGGTTAGTTCTTGCC
ACGGCGGAACTCATCGCCGCCTGCCTTGCCCGCTGCTGGACAGGGGCTCGGCTGTTGGG
CACTGACAATTCCGTGGCTCGAGAGATCTTCGACTGTGCCTTCTAGTTGCCAGCCATCTGT
TGTTTGCCCCTCCCCCGTGCCTTCCTTGACCCTGGAAGGTGCCACTCCCACTGTCCTTTCC
TAATAAAATGAGGAAATTGCATCGCATTGTCTGAGTAGGTGTCATTCTATTCTGGGGGGTG
GGGTGGGGCAGGACAGCAAGGGGGAGGATTGGGAAGACAATAGCAGGCATGAGATCTCA
CGTGCGGACCGAGCGGCCGC (SEQ ID NO: 40)

CN1389 - The portion between L-ITR and R-ITR corresponds to positions 142-1897:

CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTTCGCCTTTCCTGTTCCTGAAT
CTAAATAAAGATGGCTTTTTAGTATTAAAAGTGGAAGAAAATTACAGGTAATTATCTTTGACG
GTAAAAACGCTGTAATCAGCGGGCTACATGAAAAATTACTCTAATTATGGCTGCATTTAAGA
GAATGGACCTGCAGGGAGCTCGGGCTGGGCATAAAAGTCAGGGCAGAGCCATCTATTGCT
TACATTTGCTTCTGGGATCCAGATCTTTCGAAGCTAGCGCTACCGGTCGCCACCATGGTGA
GCAAGGGCGAGGAGCTGTTCACCGGGGTGGTGCCCATCCTGGTCGAGCTGGACGGCGAC
GTAAACGGCCACAAGTTCAGCGTGTCCGGCGAGGGCGAGGGCGATGCCACCTACGGCAA
GCTGACCCTGAAGCTGATCTGCACCACCGGCAAGCTGCCCGTGCCCTGGCCCACCCTCG
TGACCACCCTGGGCTACGGCGTGCAGTGCTTCGCCCGCTACCCCGACCACATGAAGCAG
CACGACTTCTTCAAGTCCGCCATGCCCGAAGGCTACGTCCAGGAGCGCACCATCTTCTTC
AAGGACGACGGCAACTACAAGACCCGCGCCGAGGTGAAGTTCGAGGGCGACACCCTGGT
GAACCGCATCGAGCTGAAGGGCATCGACTTCAAGGAGGACGGCAACATCCTGGGGCACA
AGCTGGAGTACAACTACAACAGCCACAACGTCTATATCACCGCCGACAAGCAGAAGAACG
GCATCAAGGCCAACTTCAAGATCCGCCACAACATCGAGGACGGCGGCGTGCAGCTCGCC
GACCACTACCAGCAGAACACCCCCATCGGCGACGGCCCCGTGCTGCTGCCCGACAACCA
CTACCTGAGCTACCAGTCCAAGCTGAGCAAAGACCCCAACGAGAAGCGCGATCACATGGT
CCTGCTGGAGTTCGTGACCGCCGCCGGGATCACTCTCGGCATGGACGAGCTGTACAAGTA
AGTCGACGGCGCGCCGCGGCCGCGAATTCGATATCATAATCAACCTCTGGATTACAAAATT
TGTGAAAGATTGACTGGTATTCTTAACTATGTTGCTCCTTTTACGCTATGTGGATACGCTGC
TTTAATGCCTTTGTATCATGCTATTGCTTCCCGTATGGCTTTCATTTTCTCCTCCTTGTATAA
ATCCTGGTTAGTTCTTGCCACGGCGGAACTCATCGCCGCCTGCCTTGCCCGCTGCTGGAC
AGGGGCTCGGCTGTTGGGCACTGACAATTCCGTGGCTCGAGAGATCTTCGACTGTGCCTT
CTAGTTGCCAGCCATCTGTTGTTTGCCCCTCCCCCGTGCCTTCCTTGACCCTGGAAGGTGC
CACTCCCACTGTCCTTTCCTAATAAAATGAGGAAATTGCATCGCATTGTCTGAGTAGGTGTC
ATTCTATTCTGGGGGGTGGGGTGGGGCAGGACAGCAAGGGGGAGGATTGGGAAGACAAT
AGCAGGCATGAGATCTCACGTGCGGACCGAGCGGCCGCAGGAACCCCTAGTGATGGAGT

FIG. 17 cont'd

TGGCCACTCCCTCTCTGCGCGCTCGCTCGCTCACTGAGGCCGGGCGACCAAAGGTCGCC
CGACGCCCGGGCTTTGCCCGGGCGGCCTCAGTGAGCGAGCGAGCGCGCAGCTGCCTGC
AGGGGCGCCTGATGCGGTATTTTCTCCTTACGCATCTGTGCGGTATTTCACACCGCATACG
TCAAAGCAACCATAGTACGCGCCCTGTAGCGGCGCATTAAGCGCGGCGGGTGTGGTGGTT
ACGCGCAGCGTGACCGCTACACTTGCCAGCGCCCTAGCGCCCGCTCCTTTCGCTTTCTTC
CCTTCCTTTCTCGCCACGTTCGCCGGCTTTCCCCGTCAAGCTCTAAATCGGGGGCTCCCTT
TAGGGTTCCGATTTAGTGCTTTACGGCACCTCGACCCCAAAAAACTTGATTTGGGTGATGG
TTCACGTAGTGGGCCATCGCCCTGATAGACGGTTTTTCGCCCTTTGACGTTGGAGTCCACG
TTCTTTAATAGTGGACTCTTGTTCCAAACTGGAACAACACTCAACCCTATCTCGGGCTATTC
TTTTGATTTATAAGGGATTTTGCCGATTTCGGCCTATTGGTTAAAAAATGAGCTGATTTAACA
AAAATTTAACGCGAATTTTAACAAAATATTAACGTTTACAATTTTATGGTGCACTCTCAGTAC
AATCTGCTCTGATGCCGCATAGTTAAGCCAGCCCCGACACCCGCCAACACCCGCTGACGC
GCCCTGACGGGCTTGTCTGCTCCCGGCATCCGCTTACAGACAAGCTGTGACCGTCTCCGG
GAGCTGCATGTGTCAGAGGTTTTCACCGTCATCACCGAAACGCGCGAGACGAAAGGGCCT
CGTGATACGCCTATTTTTATAGGTTAATGTCATGATAATAATGGTTTCTTAGACGTCAGGTG
GCACTTTTCGGGGAAATGTGCGCGGAACCCCTATTTGTTTATTTTTCTAAATACATTCAAAT
ATGTATCCGCTCATGAGACAATAACCCTGATAAATGCTTCAATAATATTGAAAAAGGAAGAG
TATGAGTATTCAACATTTCCGTGTCGCCCTTATTCCCTTTTTTGCGGCATTTTGCCTTCCTGT
TTTTGCTCACCCAGAAACGCTGGTGAAAGTAAAAGATGCTGAAGATCAGTTGGGTGCACGA
GTGGGTTACATCGAACTGGATCTCAACAGCGGTAAGATCCTTGAGAGTTTTCGCCCCGAAG
AACGTTTTCCAATGATGAGCACTTTTAAAGTTCTGCTATGTGGCGCGGTATTATCCCGTATT
GACGCCGGGCAAGAGCAACTCGGTCGCCGCATACACTATTCTCAGAATGACTTGGTTGAG
TACTCACCAGTCACAGAAAAGCATCTTACGGATGGCATGACAGTAAGAGAATTATGCAGTG
CTGCCATAACCATGAGTGATAACACTGCGGCCAACTTACTTCTGACAACGATCGGAGGACC
GAAGGAGCTAACCGCTTTTTTGCACAACATGGGGGATCATGTAACTCGCCTTGATCGTTGG
GAACCGGAGCTGAATGAAGCCATACCAAACGACGAGCGTGACACCACGATGCCTGTAGCA
ATGGCAACAACGTTGCGCAAACTATTAACTGGCGAACTACTTACTCTAGCTTCCCGGCAAC
AATTAATAGACTGGATGGAGGCGGATAAAGTTGCAGGACCACTTCTGCGCTCGGCCCTTC
CGGCTGGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGACGGGGA
GTCAGGCAACTATGGATGAACGAAATAGACAGATCGCTGAGATAGGTGCCTCACTGATTAA
GCATTGGTAACTGTCAGACCAAGTTTACTCATATATACTTTAGATTGATTTAAAACTTCATTT
TTAATTTAAAAGGATCTAGGTGAAGATCCTTTTTGATAATCTCATGACCAAAATCCCTTAACG
TGAGTTTTCGTTCCACTGAGCGTCAGACCCCGTAGAAAAGATCAAAGGATCTTCTTGAGAT
CCTTTTTTTCTGCGCGTAATCTGCTGCTTGCAAACAAAAAAACCACCGCTACCAGCGGTGG
TTTGTTTGCCGGATCAAGAGCTACCAACTCTTTTTCCGAAGGTAACTGGCTTCAGCAGAGC
GCAGATACCAAATACTGTCCTTCTAGTGTAGCCGTAGTTAGGCCACCACTTCAAGAACTCT
GTAGCACCGCCTACATACCTCGCTCTGCTAATCCTGTTACCAGTGGCTGCTGCCAGTGGC
GATAAGTCGTGTCTTACCGGGTTGGACTCAAGACGATAGTTACCGGATAAGGCGCAGCGG
TCGGGCTGAACGGGGGGTTCGTGCACACAGCCCAGCTTGGAGCGAACGACCTACACCGA
ACTGAGATACCTACAGCGTGAGCTATGAGAAAGCGCCACGCTTCCCGAAGGGAGAAAGGC
GGACAGGTATCCGGTAAGCGGCAGGGTCGGAACAGGAGAGCGCACGAGGGAGCTTCCAG
GGGGAAACGCCTGGTATCTTTATAGTCCTGTCGGGTTTCGCCACCTCTGACTTGAGCGTC
GATTTTTGTGATGCTCGTCAGGGGGGCGGAGCCTATGGAAAAACGCCAGCAACGCGGCCT
TTTTACGGTTCCTGGCCTTTTGCTGGCCTTTTGCTCACATGT (SEQ ID NO: 41)

CN1390 - The portion between L-ITR and R-ITR corresponds to positions 142-1660:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG

FIG. 17 cont'd

GCCAACTCCATCACTAGGGGTTCCTGCGGCCGCACGCGTGGTACCCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGCTAAATAAA
GATGGCTTTTTAGTATTAAAAGTGGAAGAAAATTACAGGTAATTATCTTTGACGGTAAAAAC
GCTGTAATCAGCGGGCTACATGAAAAATTACTCTAATTATGGCTGCATTTAAGAGAATGGCT
AAATAAAGATGGCTTTTTAGTATTAAAAGTGGAAGAAAATTACAGGTAATTATCTTTGACGGT
AAAAACGCTGTAATCAGCGGGCTACATGAAAAATTACTCTAATTATGGCTGCATTTAAGAGA
ATGGAGCTCGGGCTGGGCATAAAAGTCAGGGCAGAGCCATCTATTGCTTACATTTGCTTCT
GGGATCCAGATCTTTCGAAGCTAGCGCTACCGGTCGCCACCATGGTGAGCAAGGGCGAG
GAGCTGTTCACCGGGGTGGTGCCCATCCTGGTCGAGCTGGACGGCGACGTAAACGGCCA
CAAGTTCAGCGTGTCCGGCGAGGGCGAGGGCGATGCCACCTACGGCAAGCTGACCCTGA
AGCTGATCTGCACCACCGGCAAGCTGCCCGTGCCCTGGCCCACCCTCGTGACCACCCTG
GGCTACGGCGTGCAGTGCTTCGCCCGCTACCCCGACCACATGAAGCAGCACGACTTCTTC
AAGTCCGCCATGCCCGAAGGCTACGTCCAGGAGCGCACCATCTTCTTCAAGGACGACGGC
AACTACAAGACCCGCGCCGAGGTGAAGTTCGAGGGCGACACCCTGGTGAACCGCATCGA
GCTGAAGGGCATCGACTTCAAGGAGGACGGCAACATCCTGGGGCACAAGCTGGAGTACA
ACTACAACAGCCACAACGTCTATATCACCGCCGACAAGCAGAAGAACGGCATCAAGGCCA
ACTTCAAGATCCGCCACAACATCGAGGACGGCGGCGTGCAGCTCGCCGACCACTACCAG
CAGAACACCCCCATCGGCGACGGCCCCGTGCTGCTGCCCGACAACCACTACCTGAGCTA
CCAGTCCAAGCTGAGCAAAGACCCCAACGAGAAGCGCGATCACATGGTCCTGCTGGAGTT
CGTGACCGCCGCCGGGATCACTCTCGGCATGGACGAGCTGTACAAGTAAGTCGACGGCG
CGCCGCGGCCGCGAATTCGATATCATAATCAACCTCTGGATTACAAAATTTGTGAAAGATT
GACTGGTATTCTTAACTATGTTGCTCCTTTTACGCTATGTGGATACGCTGCTTTAATGCCTT
TGTATCATGCTATTGCTTCCCGTATGGCTTTCATTTTCTCCTCCTTGTATAAATCCTGGTTAG
TTCTTGCCACGGCGGAACTCATCGCCGCCTGCCTTGCCCGCTGCTGGACAGGGGCTCGG
CTGTTGGGCACTGACAATTCCGTGGCTCGAGAGATCTTCGACTGTGCCTTCTAGTTGCCAG
CCATCTGTTGTTTGCCCCTCCCCCGTGCCTTCCTTGACCCTGGAAGGTGCCACTCCCACTG
TCCTTTCCTAATAAAATGAGGAAATTGCATCGCATTGTCTGAGTAGGTGTCATTCTATTCTG
GGGGGTGGGGTGGGGCAGGACAGCAAGGGGGAGGATTGGGAAGACAATAGCAGGCATG
AGATCTCACGTGCGGACCGAGCGGCCGCAGGAACCCCTAGTGATGGAGTTGGCCACTCC
CTCTCTGCGCGCTCGCTCGCTCACTGAGGCCGGGCGACCAAAGGTCGCCCGACGCCCGG
GCTTTGCCCGGGCGGCCTCAGTGAGCGAGCGAGCGCGCAGCTGCCTGCAGGGGCGCCT
GATGCGGTATTTTCTCCTTACGCATCTGTGCGGTATTTCACACCGCATACGTCAAAGCAAC
CATAGTACGCGCCCTGTAGCGGCGCATTAAGCGCGGCGGGTGTGGTGGTTACGCGCAGC
GTGACCGCTACACTTGCCAGCGCCCTAGCGCCCGCTCCTTTCGCTTTCTTCCCTTCCTTTC
TCGCCACGTTCGCCGGCTTTCCCCGTCAAGCTCTAAATCGGGGGCTCCCTTTAGGGTTCC
GATTTAGTGCTTTACGGCACCTCGACCCCAAAAAACTTGATTTGGGTGATGGTTCACGTAG
TGGGCCATCGCCCTGATAGACGGTTTTTCGCCCTTTGACGTTGGAGTCCACGTTCTTTAAT
AGTGGACTCTTGTTCCAAACTGGAACAACACTCAACCCTATCTCGGGCTATTCTTTTGATTT
ATAAGGGATTTTGCCGATTTCGGCCTATTGGTTAAAAAATGAGCTGATTTAACAAAAATTTA
ACGCGAATTTTAACAAAATATTAACGTTTACAATTTTATGGTGCACTCTCAGTACAATCTGCT
CTGATGCCGCATAGTTAAGCCAGCCCCGACACCCGCCAACACCCGCTGACGCGCCCTGA
CGGGCTTGTCTGCTCCCGGCATCCGCTTACAGACAAGCTGTGACCGTCTCCGGGAGCTGC
ATGTGTCAGAGGTTTTCACCGTCATCACCGAAACGCGCGAGACGAAAGGGCCTCGTGATA
CGCCTATTTTTATAGGTTAATGTCATGATAATAATGGTTTCTTAGACGTCAGGTGGCACTTTT
CGGGGAAATGTGCGCGGAACCCCTATTTGTTTATTTTTCTAAATACATTCAAATATGTATCC
GCTCATGAGACAATAACCCTGATAAATGCTTCAATAATATTGAAAAAGGAAGAGTATGAGTA
TTCAACATTTCCGTGTCGCCCTTATTCCCTTTTTTGCGGCATTTTGCCTTCCTGTTTTTGCTC
ACCCAGAAACGCTGGTGAAAGTAAAAGATGCTGAAGATCAGTTGGGTGCACGAGTGGGTT

FIG. 17 cont'd

ACATCGAACTGGATCTCAACAGCGGTAAGATCCTTGAGAGTTTTCGCCCCGAAGAACGTTT
TCCAATGATGAGCACTTTTAAAGTTCTGCTATGTGGCGCGGTATTATCCCGTATTGACGCC
GGGCAAGAGCAACTCGGTCGCCGCATACACTATTCTCAGAATGACTTGGTTGAGTACTCAC
CAGTCACAGAAAAGCATCTTACGGATGGCATGACAGTAAGAGAATTATGCAGTGCTGCCAT
AACCATGAGTGATAACACTGCGGCCAACTTACTTCTGACAACGATCGGAGGACCGAAGGA
GCTAACCGCTTTTTTGCACAACATGGGGGATCATGTAACTCGCCTTGATCGTTGGGAACCG
GAGCTGAATGAAGCCATACCAAACGACGAGCGTGACACCACGATGCCTGTAGCAATGGCA
ACAACGTTGCGCAAACTATTAACTGGCGAACTACTTACTCTAGCTTCCCGGCAACAATTAAT
AGACTGGATGGAGGCGGATAAAGTTGCAGGACCACTTCTGCGCTCGGCCCTTCCGGCTG
GCTGGTTTATTGCTGATAAATCTGGAGCCGGTGAGCGTGGGTCTCGCGGTATCATTGCAG
CACTGGGGCCAGATGGTAAGCCCTCCCGTATCGTAGTTATCTACACGACGGGGAGTCAGG
CAACTATGGATGAACGAAATAGACAGATCGCTGAGATAGGTGCCTCACTGATTAAGCATTG
GTAACTGTCAGACCAAGTTTACTCATATATACTTTAGATTGATTTAAAACTTCATTTTTAATTT
AAAAGGATCTAGGTGAAGATCCTTTTTGATAATCTCATGACCAAAATCCCTTAACGTGAGTT
TTCGTTCCACTGAGCGTCAGACCCCGTAGAAAAGATCAAAGGATCTTCTTGAGATCCTTTTT
TTCTGCGCGTAATCTGCTGCTTGCAAACAAAAAAACCACCGCTACCAGCGGTGGTTTGTTT
GCCGGATCAAGAGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAACTCTGTAGCAC
CGCCTACATACCTCGCTCTGCTAATCCTGTTACCAGTGGCTGCTGCCAGTGGCGATAAGTC
GTGTCTTACCGGGTTGGACTCAAGACGATAGTTACCGGATAAGGCGCAGCGGTCGGGCTG
AACGGGGGGTTCGTGCACACAGCCCAGCTTGGAGCGAACGACCTACACCGAACTGAGATA
CCTACAGCGTGAGCTATGAGAAAGCGCCACGCTTCCCGAAGGGAGAAAGGCGGACAGGT
ATCCGGTAAGCGGCAGGGTCGGAACAGGAGAGCGCACGAGGGAGCTTCCAGGGGGAAA
CGCCTGGTATCTTTATAGTCCTGTCGGGTTTCGCCACCTCTGACTTGAGCGTCGATTTTTG
TGATGCTCGTCAGGGGGGCGGAGCCTATGGAAAAACGCCAGCAACGCGGCCTTTTTACG
GTTCCTGGCCTTTTGCTGGCCTTTTGCTCACATGT (SEQ ID NO: 42)

CN1203 - The portion between L-ITR and R-ITR corresponds to positions 183-2052:

AAAGCTTCCCGGGGGGATCTGGGCCACTCCCTCTCTGCGCGCTCGCTCGCTCACTGAGG
CCGGGCGACCAAAGGTCGCCCGACGCCCGGGCTTTGCCCGGGCGGCCTCAGTGAGCGA
GCGAGCGCGCAGAGAGGGAGTGGCCAACTCCATCACTAGGGGTTCCTGGAGGGGTGGAG
TCGTGACCTAGGACGCGTATAGGTACCGAGCTCTATGCACTCACAGTGGTTTGGCATGCAT
CTGGTGAATTTTTTTTAACGAAAAATTAGTGTTGGTTTCGATGTATGGTAGCATTCTCCCTAA
CGTAATTTGAATAATTCAGCAAAGCCCCACTACCAGCTGTACTTCTGCAGCCTCTTCCATTC
TTTTCAGCATTATAATTTTGGTTAATTTTCAATTTTAGGTCCTACGTCTCTGCAATTTGTGTAT
GAATAACAGAATAATTTCCCTCTTTTGTTTCGCCTTTCCTGTTCCTGAATCTAAATAAAGATG
GCTTTTTAGTATTAAAAGTGGAAGAAAATTACAGGTAATTATCTTTGACGGTAAAAACGCTG
TAATCAGCGGGCTACATGAAAAATTACTCTAATTATGGCTGCATTTAAGAGAATGGAAAAAA
ACCTTCTTGTGGATAAAAACCTTAAATTGTCCCCAATGTCTGCTTCAAATTGGATGGCACTG
CAGCTGGAGGCTTTGTTCAGAATTGATCCTGGGGAGCTACGAACCCAAAGTTTCACAGTAG
GGAGCTCGGGCTGGGCATAAAAGTCAGGGCAGAGCCATCTATTGCTTACATTTGCTTCTG
GGATCCAGATCTTTCGAAGCTAGCGCTACCGGTCGCCACCATGGTGAGCAAGGGCGAGG
AGCTGTTCACCGGGGTGGTGCCCATCCTGGTCGAGCTGGACGGCGACGTAAACGGCCAC
AAGTTCAGCGTGTCCGGCGAGGGCGAGGGCGATGCCACCTACGGCAAGCTGACCCTGAA
GCTGATCTGCACCACCGGCAAGCTGCCCGTGCCCTGGCCCACCCTCGTGACCACCCTGG
GCTACGGCGTGCAGTGCTTCGCCCGCTACCCCGACCACATGAAGCAGCACGACTTCTTCA
AGTCCGCCATGCCCGAAGGCTACGTCCAGGAGCGCACCATCTTCTTCAAGGACGACGGCA
ACTACAAGACCCGCGCCGAGGTGAAGTTCGAGGGCGACACCCTGGTGAACCGCATCGAG
CTGAAGGGCATCGACTTCAAGGAGGACGGCAACATCCTGGGGCACAAGCTGGAGTACAAC

FIG. 17 cont'd

TACAACAGCCACAACGTCTATATCACCGCCGACAAGCAGAAGAACGGCATCAAGGCCAAC
TTCAAGATCCGCCACAACATCGAGGACGGCGGCGTGCAGCTCGCCGACCACTACCAGCA
GAACACCCCCATCGGCGACGGCCCCGTGCTGCTGCCCGACAACCACTACCTGAGCTACC
AGTCCAAGCTGAGCAAAGACCCCAACGAGAAGCGCGATCACATGGTCCTGCTGGAGTTCG
TGACCGCCGCCGGGATCACTCTCGGCATGGACGAGCTGTACAAGTAAGTCGACGGCGCG
CCGCGGCCGCGAATTCGATATCATAATCAACCTCTGGATTACAAAATTTGTGAAAGATTGA
CTGGTATTCTTAACTATGTTGCTCCTTTTACGCTATGTGGATACGCTGCTTTAATGCCTTTGT
ATCATGCTATTGCTTCCCGTATGGCTTTCATTTTCTCCTCCTTGTATAAATCCTGGTTAGTTC
TTGCCACGGCGGAACTCATCGCCGCCTGCCTTGCCCGCTGCTGGACAGGGGCTCGGCTG
TTGGGCACTGACAATTCCGTGGCTCGAGCGACTGTGCCTTCTAGTTGCCAGCCATCTGTTG
TTTGCCCCTCCCCCGTGCCTTCCTTGACCCTGGAAGGTGCCACTCCCACTGTCCTTTCCTA
ATAAAATGAGGAAATTGCATCGCATTGTCTGAGTAGGTGTCATTCTATTCTGGGGGGTGGG
GTGGGGCAGGACAGCAAGGGGGAGGATTGGGAAGACAATAGCAGGCATGACTAGTCCAC
TCCCTCTCTGCGCGCTCGCTCGCTCACTGAGGCCGGGCGACCAAAGGTCGCCCGACGCC
CGGGCTTTGCCCGGGCGGCCTCAGTGAGCGAGCGAGCGCGCAGAGAGGGACAGATCCG
GGCCCGCATGCGTCGACAATTCACTGGCCGTCGTTTTACAACGTCGTGACTGGGAAAACC
CTGGCGTTACCCAACTTAATCGCCTTGCAGCACATCCCCCTTTCGCCAGCTGGCGTAATAG
CGAAGAGGCCCGCACCGATCGCCCTTCCCAACAGTTGCGCAGCCTGAATGGCGAATGGC
GCCTGATGCGGTATTTTCTCCTTACGCATCTGTGCGGTATTTCACACCGCATATGGTGCAC
TCTCAGTACAATCTGCTCTGATGCCGCATAGTTAAGCCAGCCCCGACACCCGCCAACACC
CGCTGACGCGCCCTGACGGGCTTGTCTGCTCCCGGCATCCGCTTACAGACAAGCTGTGAC
CGTCTCCGGGAGCTGCATGTGTCAGAGGTTTTCACCGTCATCACCGAAACGCGCGAGACG
AAAGGGCCTCGTGATACGCCTATTTTTATAGGTTAATGTCATGATAATAATGGTTTCTTAGA
CGTCAGGTGGCACTTTTCGGGGAAATGTGCGCGGAACCCCTATTTGTTTATTTTTCTAAATA
CATTCAAATATGTATCCGCTCATGAGACAATAACCCTGATAAATGCTTCAATAATATTGAAAA
AGGAAGAGTATGAGTATTCAACATTTCCGTGTCGCCCTTATTCCCTTTTTTGCGGCATTTTG
CCTTCCTGTTTTTGCTCACCCAGAAACGCTGGTGAAAGTAAAAGATGCTGAAGATCAGTTG
GGTGCACGAGTGGGTTACATCGAACTGGATCTCAACAGCGGTAAGATCCTTGAGAGTTTTC
GCCCCGAAGAACGTTTTCCAATGATGAGCACTTTTAAAGTTCTGCTATGTGGCGCGGTATT
ATCCCGTATTGACGCCGGGCAAGAGCAACTCGGTCGCCGCATACACTATTCTCAGAATGA
CTTGGTTGAGTACTCACCAGTCACAGAAAAGCATCTTACGGATGGCATGACAGTAAGAGAA
TTATGCAGTGCTGCCATAACCATGAGTGATAACACTGCGGCCAACTTACTTCTGACAACGA
TCGGAGGACCGAAGGAGCTAACCGCTTTTTTGCACAACATGGGGGATCATGTAACTCGCC
TTGATCGTTGGGAACCGGAGCTGAATGAAGCCATACCAAACGACGAGCGTGACACCACGA
TGCCTGTAGCAATGGCAACAACGTTGCGCAAACTATTAACTGGCGAACTACTTACTCTAGC
TTCCCGGCAACAATTAATAGACTGGATGGAGGCGGATAAAGTTGCAGGACCACTTCTGCG
CTCGGCCCTTCCGGCTGGCTGGTTTATTGCTGATAAATCTGGAGCCGGTGAGCGTGGGTC
TCGCGGTATCATTGCAGCACTGGGGCCAGATGGTAAGCCCTCCCGTATCGTAGTTATCTAC
ACGACGGGGAGTCAGGCAACTATGGATGAACGAAATAGACAGATCGCTGAGATAGGTGCC
TCACTGATTAAGCATTGGTAACTGTCAGACCAAGTTTACTCATATATACTTTAGATTGATTTA
AAACTTCATTTTTAATTTAAAAGGATCTAGGTGAAGATCCTTTTTGATAATCTCATGACCAAA
ATCCCTTAACGTGAGTTTTCGTTCCACTGAGCGTCAGACCCCGTAGAAAAGATCAAAGGAT
CTTCTTGAGATCCTTTTTTTCTGCGCGTAATCTGCTGCTTGCAAACAAAAAAACCACCGCTA
CCAGCGGTGGTTTGTTTGCCGGATCAAGAGCTACCAACTCTTTTTCCGAAGGTAACTGGCT
TCAGCAGAGCGCAGATACCAAATACTGTTCTTCTAGTGTAGCCGTAGTTAGGCCACCACTT
CAAGAACTCTGTAGCACCGCCTACATACCTCGCTCTGCTAATCCTGTTACCAGTGGCTGCT
GCCAGTGGCGATAAGTCGTGTCTTACCGGGTTGGACTCAAGACGATAGTTACCGGATAAG
GCGCAGCGGTCGGGCTGAACGGGGGGTTCGTGCACACAGCCCAGCTTGGAGCGAACGA
CCTACACCGAACTGAGATACCTACAGCGTGAGCTATGAGAAAGCGCCACGCTTCCCGAAG

FIG. 17 cont'd

GGAGAAAGGCGGACAGGTATCCGGTAAGCGGCAGGGTCGGAACAGGAGAGCGCACGAG
GGAGCTTCCAGGGGGAAACGCCTGGTATCTTTATAGTCCTGTCGGGTTTCGCCACCTCTG
ACTTGAGCGTCGATTTTTGTGATGCTCGTCAGGGGGGCGGAGCCTATGGAAAAACGCCAG
CAACGCGGCCTTTTTACGGTTCCTGGCCTTTTGCTGGCCTTTTGCTCACATGTTCTTTCCTG
CGTTATCCCCTGATTCTGTGGATAACCGTATTACCGCCTTTGAGTGAGCTGATACCGCTCG
CCGCAGCCGAACGACCGAGCGCAGCGAGTCAGTGAGCGAGGAAGCGGAAGAGCGCCCA
ATACGCAAACCGCCTCTCCCCGCGCGTTGGCCGATTCATTAATGCAGCTGGCACGACAGG
TTTCCCGACTGGAAAGCGGGCAGTGAGCGCAACGCAATTAATGTGAGTTAGCTCACTCATT
AGGCACCCCAGGCTTTACACTTTATGCTTCCGGCTCGTATGTTGTGTGGAATTGTGAGCGG
ATAACAATTTCACACAGGAAACAGCTATGACCATGATTACGCCAAGCTCTCGAGATCTAG
(SEQ ID NO: 43)

Lactase [Homo sapiens], GenBank: EAX11622.1:
MELSWHVVFIALLSFSCWGSDWESDRNFISTAGPLTNDLLHNLSGLLGDQSSNFVAGDKDMYV
CHQPLPTFLPEYFSSLHASQITHYKVFLSWAQLLPAGSTQNPDEKTVQCYRRLLKALKTARLQP
MVILHHQTLPASTLRRTEAFADLFADYATFAFHSFGDLVGIWFTFSDLEEVIKELPHQESRASQL
QTLSDAHRKAYEIYHESYAFQGGKLSVVLRAEDIPELLLEPPISALAQDTVDFLSLDLSYECQNE
ASLRQKLSKLQTIEPKVKVFIFNLKLPDCPSTMKNPASLLFSLFEAINKDQVLTIGFDINEFLSCSS
SSKKSMSCSLTGSLALQPDQQQDHETTDSSPASAYQRVWEAFANQSRAERDAFLQDTFPEGF
LWGASTGAFNVEGGWAEGGRGVSIWDPRRPLNTTEGQATLEVASDSYHKVASDVALLCGLR
AQVYKFSISWSRIFPMGHGSSPSLPGVAYYNKLIDRLQDAGIEPMATLFHWDLPQALQDHGGW
QNESVVDAFLDYAAFCFSTFGDRVKLWVTFHEPWVMSYAGYGTGQHPPGISDPGVASFKVAH
LVLKAHARTWHHYNSHHRPQQQGHVGIVLNSDWAEPLSPERPEDLRASERFLHFMLGWFAH
PVFVDGDYPATLRTQIQQMNRQCSHPVAQLPEFTEAEKQLLKGSADFLGLSHYTSRLISNAPQ
NTCIPSYDTIGGFSQHVNHVWPQTSSSWIRVVPWGIRRLLQFVSLEYTRGKVPIYLAGNGMPIG
ESENLFDDSLRVDYFNQYINEVLKAIKEDSVDVRSYIARSLIDGFEGPSGYSQRFGLHHVNFSD
SSKSRTPRKSAYFFTSIIEKNGFLTKGAKRLLPPNTVNLPSKVRAFTFPSEVPSKAKVVWEKFSS
QPKFERDLFYHGTFRDDFLWGVSSSAYQIEGAWDADGKGPSIWDNFTHTPGSNVKDNATGDI
ACDSYHQLDADLNMLRALKVKAYRFSISWSRIFPTGRNSSINSHGVDYYNRLINGLVASNIFPM
VTLFHWDLPQALQDIGGWENPALIDLFDSYADFCFQTFGDRVKFWMTFNEPMYLAWLGYGSG
EFPPGVKDPGWAPYRIAHAVIKAHARVYHTYDEKYRQEQKGVISLSLSTHWAEPKSPGVPRDV
EAADRMLQFSLGWFAHPIFRNGDYPDTMKWKVGNRSELQHLATSRLPSFTEEEKRFIRATADV
FCLNTYYSRIVQHKTPRLNPPSYEDDQEMAEEEDPSWPSTAMNRAAPWGTRRLLNWIKEEYG
DIPIYITENGVGLTNPNTEDTDRIFYHKTYINEALKAYRLDGIDLRGYVAWSLMDNFEWLNGYTV
KFGLYHVDFNNTNRPRTARASARYYTEVITNNGMPLAREDEFLYGRFPEGFIWSAASAAYQIE
GAWRADGKGLSIWDTFSHTPLRVENDAIGDVACDSYHKIAEDLVTLQNLGVSHYRFSISWSRIL
PDGTTRYINEAGLNYYVRLIDTLLAASIQPQVTIYHWDLPQTLQDVGGWENETIVQRFKEYADVL
FQRLGDKVKFWITLNEPFVIAYQGYGYGTAAPGVSNRPGTAPYIVGHNLIKAHAEAWHLYNDVY
RASQGGVISITISSDWAEPRDPSNQEDVEAARRYVQFMGGWFAHPIFKNGDYNEVMKTRIRDR
SLAAGLNKSRLPEFTESEKRRINGTYDFFGFNHYTTVLAYNLNYATAISSFDADRGVASIADRS
WPDSGSFWLKMTPFGFRRILNWLKEEYNDPPIYVTENGVSQREETDLNDTARIYYLRTYINEAL
KAVQDKVDLRGYTVWSAMDNFEWATGFSERFGLHFVNYSDPSLPRIPKASAKFYASVVRCNG
FPDPATGPHACLHQPDAGPTISPVRQEEVQFLGLMLGTTEAQTALYVLFSLVLLGVCGLAFLSY
KYCKRSKQGKTQRSQQELSPVSSF (SEQ ID NO: 44)

Lipase [Homo sapiens], GenBank: AAA60129.1:
MLPLWTLSLLLGAVAGKEVCYERLGCFSDDSPWSGITERPLHILPWSPKDVNTRFLLYTNENPN
NFQEVAADSSSISGSNFKTNRKTRFIIHGFIDKGEENWLANVCKNLFKVESVNCICVDWKGGSR
TGYTQASQNIRIVGAEVAYFVEFLQSAFGYSPSNVHVIGHSLGAHAAGEAGRRTNGTIGRITGL

FIG. 17 cont'd

DPAEPCFQGTPELVRLDPSDAKFVDVIHTDGAPIVPNLGFGMSQVVGHLDFFPNGGVEMPGC
KKNILSQIVDIDGIWEGTRDFAACNHLRSYKYYTDSIVNPDGFAGFPCASYNVFTANKCFPCPS
GGCPQMGHYADRYPGKTNDVGQKFYLDTGDASNFARWRYKVSVTLSGKKVTGHILVSLFGNK
GNSKQYEIFKGTLKPDSTHSNEFDSDVDVGDLQMVKFIWYNNVINPTLPRVGASKIIVETNVGK
QFNFCSPETVREEVLLTLTPC (SEQ ID NO:45)

Helicase [Homo sapiens], GenBank: AMD82207.1:
MSISSLFGGRYDNKFLLNMSSAPKIELIVDKVASLSEGRLEGRLPEDWFRHIMDPETEFNSEFA
DALCIGIDEFAQPLPFLPFKALLVTGTAGAGKTNSIQTLAANLDCIVTATTSIAAQNLSVVLNRSKS
AQVKTIFKTFGFNSSHVSMSERQSYIANDERSIQIQQKQDLSIYWNVISDIADRALGAVACKTKE
LPDLCESSVIVIDEAGVILRHILHTVVFFYWFYNALYKTPLYEDGIVPCIVCVGSPTQSNALVTSFN
PLTQNKDVKRGIDVLSALICDDVLSKYCEVDNNWIIFVNNKRCADHAFGDFLKHIEFGLPLKPELI
EYVDQFVKPASYIRNPMNEIETTRLFLSHNEVKNYFRSLHEQVEVTNRNNLFVFPVYFLIKNKTF
EDYKSEIGNFSLEIEPWFKSNIHRLNTYSQFADQDLSKTVQLEEIVLEDGSVEETLITCHLKHIRN
SSIGVTSKIKASTVGFSGTYEKFVELLQSDLFIEKTSCDQTIHAYSFLSGLMFGGMYSFCCSKFT
TPEVLMEIKNIKMPSIEFLESEMSRMSPDVQTVETDERYDFGLVDDGLSDVDLLEIDPCGDPFFT
RYSKLPLTNSLSFEEISLLYTTFKDIFISRFAILQKHTKGKFGKTLLVTYNRNNVSRKQCGEIYSHL
KSFYGMLTYAIPANNYTLEGYTNDNVVHLGTDKQLPQILYKKGLPRLVIKDEMGFISVLDNNVSK
FIDVVNGQSFHLCTTVDYATVSKVSMTITKSQGLSIQKVAIDFGSDPKNLKLSSIYVGMSRVTDP
NNLIMNVNPLRLNYENDNFIAPHIVKALKNENTMLIF (SEQ ID NO: 46)

Amylase [Homo sapiens], GenBank: AAA51724.1:
MKFFLLLFTIGFCWAQYSPNTQQGRTSIVHLFEWRWVDIALECERYLAPKGFGGVQVSPPNEN
VAIYNPFRPWWERYQPVSYKLCTRSGNEDEFRNMVTRCNNVGVRIYVDAVINHMCGNAVSAG
TSSTCGSYFNPGSRDFPAVPYSGWDFNDGKCKTGSGDIENYNDATQVRDCRLTGLLDLALEK
DYVRSKIAEYMNHLIDIGVAGFRLDASKHMWPGDIKAILDKLHNLNSNWFPAGSKPFIYQEVIDL
GGEPIKSSDYFGNGRVTEFKYGAKLGTVIRKWNGEKMSYLKNWGEGWGFVPSDRALVFVDN
HDNQRGHGAGGASILTFWDARLYKMAVGFMLAHPYGFTRVMSSYRWPRQFQNGNDVNDWV
GPPNNNGVIKEVTINPDTTCGNDWVCEHRWRQIRNMVIFRNVVDGQPFTNWYDNGSNQVAF
GRGNRGFIVFNNDDWSFSLTLQTGLPAGTYCDVISGDKINGNCTGIKIYVSDDGKAHFSISNSA
EDPFIAIHAESKL (SEQ ID NO: 47)

Alpha-glucosidase [Homo sapiens], GenBank: ABI53718.1:
MGVRHPPCSHRLLAVCALVSLATAALLGHILLHDFLLVPRELSGSSPVLEETHPAHQQGASRPG
PRDAQAHPGRPRAVPTQCDVPPNSRFDCAPDKAITQEQCEARGCCYIPAKQGLQGAQMGQP
WCFFPPSYPSYKLENLSSSEMGYTATLTRTTPTFFPKDILTLRLDVMMETENRLHFTIKDPANR
RYEVPLETPRVHSRAPSPLYSVEFSEEPFGVIVHRQLDGRVLLNTTVAPLFFADQFLQLSTSLP
SQYITGLAEHLSPLMLSTSWTRITLWNRDLAPTPGANLYGSHPFYLALEDGGSAHGVFLLNSNA
MDVVLQPSPALSWRSTGGILDVYIFLGPEPKSVVQQYLDVVGYPFMPPYWGLGFHLCRWGYS
STAITRQVVENMTRAHFPLDVQWNDLDYMDSRRDFTFNKDGFRDFPAMVQELHQGGRRYMM
IVDPAISSSGPAGSYRLYDEGLRRGVFITNETGQPLIGKVWPGSTAFPDFTNPTALAWWEDMV
AEFHDQVPFDGMWIDMNEPSNFIRGSEDGCPNNELENPPYVPGVVGGTLQAATICASSHQFL
STHYNLHNLYGLTEAIASHRALVKARGTRPFVISRSTFAGHGRYAGHWTGDVWSSWEQLASS
VPEILQFNLLGVPLVGADVCGFLGNTSEELCVRWTQLGAFYPFMRNHNSLLSLPQEPYSFSEP
AQQAMRKALTLRYALLPHLYTLFHQAHVAGETVARPLFLEFPKDSSTWTVDHQLLWGEALLITP
VLQAGKAEVTGYFPLGTWYDLQTVPIEALGSLPPPPAAPREPAIHSEGQWVTLPAPLDTINVHL
RAGYIIPLQGPGLTTTESRQQPMALAVALTKGGEARGELFWDDGESLEVLERGAYTQVIFLARN
NTIVNELVRVTSEGAGLQLQKVTVLGVATAPQQVLSNGVPVSNFTYSPDTKVLDICVSLLMGEQ
FLVSWC (SEQ ID NO: 48)

FIG. 17 cont'd

Transcription factor SP1 [Homo sapiens], UniProtKB/Swiss-Prot: P08047.3:
MSDQDHSMDEMTAVVKIEKGVGGNNGGNGNGGGAFSQARSSSTGSSSSTGGGGQESQPSP
LALLAATCSRIESPNENSNNSQGPSQSGGTGELDLTATQLSQGANGWQIISSSSGATPTSKEQ
SGSSTNGSNGSESSKNRTVSGGQYVVAAAPNLQNQQVLTGLPGVMPNIQYQVIPQFQTVDGQ
QLQFAATGAQVQQDGSGQIQIIPGANQQIITNRGSGGNIIAAMPNLLQQAVPLQGLANNVLSGQ
TQYVTNVPVALNGNITLLPVNSVSAATLTPSSQAVTISSSGSQESGSQPVTSGTTISSASLVSSQ
ASSSSFFTNANSYSTTTTTSNMGIMNFTTSGSSGTNSQGQTPQRVSGLQGSDALNIQQNQTS
GGSLQAGQQKEGEQNQQTQQQQILIQPQLVQGGQALQALQAAPLSGQTFTTQAISQETLQNL
QLQAVPNSGPIIIRTPTVGPNGQVSWQTLQLQNLQVQNPQAQTITLAPMQGVSLGQTSSSNTT
LTPIASAASIPAGTVTVNAAQLSSMPGLQTINLSALGTSGIQVHPIQGLPLAIANAPGDHGAQLGL
HGAGGDGIHDDTAGGEEGENSPDAQPQAGRRTRREACTCPYCKDSEGRGSGDPGKKKQHIC
HIQGCGKVYGKTSHLRAHLRWHTGERPFMCTWSYCGKRFTRSDELQRHKRTHTGEKKFACP
ECPKRFMRSDHLSKHIKTHQNKKGGPGVALSVGTLPLDSGAGSEGSGTATPSALITTNMVAME
AICPEGIARLANSGINVMQVADLQSINISGNGF (SEQ ID NO: 49)

Transcription factor AP-1 [Homo sapiens], NP_002219.1:
MTAKMETTFYDDALNASFLPSESGPYGYSNPKILKQSMTLNLADPVGSLKPHLRAKNSDLLTSP
DVGLLKLASPELERLIIQSSNGHITTTPTPTQFLCPKNVTDEQEGFAEGFVRALAELHSQNTLPS
VTSAAQPVNGAGMVAPAVASVAGGSGSGGFSASLHSEPPVYANLSNFNPGALSSGGGAPSY
GAAGLAFPAQPQQQQQPPHHLPQQMPVQHPRLQALKEEPQTVPEMPGETPPLSPIDMESQE
RIKAERKRMRNRIAASKCRKRKLERIARLEEKVKTLKAQNSELASTANMLREQVAQLKQKVMN
HVNSGCQLMLTQQLQTF (SEQ ID NO: 50)

Heat shock factor protein 1, UniProtKB/Swiss-Prot: Q00613.1:
MDLPVGPGAAGPSNVPAFLTKLWTLVSDPDTDALICWSPSGNSFHVFDQGQFAKEVLPKYFK
HNNMASFVRQLNMYGFRKVVHIEQGGLVKPERDDTEFQHPCFLRGQEQLLENIKRKVTSVSTL
KSEDIKIRQDSVTKLLTDVQLMKGKQECMDSKLLAMKHENEALWREVASLRQKHAQQQKVVN
KLIQFLISLVQSNRILGVKRKIPLMLNDSGSAHSMPKYSRQFSLEHVHGSGPYSAPSPAYSSSSL
YAPDAVASSGPIISDITELAPASPMASPGGSIDERPLSSSPLVRVKEEPPSPPQSPRVEEASPGR
PSSVDTLLSPTALIDSILRESEPAPASVTALTDARGHTDTEGRPPSPPPTSTPEKCLSVACLDKN
ELSDHLDAMDSNLDNLQTMLSSHGFSVDTSALLDLFSPSVTVPDMSLPDLDSSLASIQELLSPQ
EPPRPPEAENSSPDSGKQLVHYTAQPLFLLDPGSVDTGSNDLPVLFELGEGSYFSEGDGFAED
PTISLLTGSEPPKAKDPTVS (SEQ ID NO: 51)

CCAAT/enhancer-binding protein (C/EBP) beta isoform a [Homo sapiens], NP_005185.2:
MQRLVAWDPACLPLPPPPPAFKSMEVANFYYEADCLAAAYGGKAAPAAPPAARPGPRPPAGE
LGSIGDHERAIDFSPYLEPLGAPQAPAPATATDTFEAAPPAPAPAPASSGQHHDFLSDLFSDDY
GGKNCKKPAEYGYVSLGRLGAAKGALHPGCFAPLHPPPPPPPPPAELKAEPGFEPADCKRKE
EAGAPGGGAGMAAGFPYALRAYLGYQAVPSGSSGSLSTSSSSSPPGTPSPADAKAPPTACYA
GAAPAPSQVKSKAKKTVDKHSDEYKIRRERNNIAVRKSRDKAKMRNLETQHKVLELTAENERL
QKKVEQLSRELSTLRNLFKQLPEPLLASSGHC (SEQ ID NO: 52)

Octamer-binding protein 1 (Oct-1), UniProtKB/Swiss-Prot: P14859.2:
MNNPSETSKPSMESGDGNTGTQTNGLDFQKQPVPVGGAISTAQAQAFLGHLHQVQLAGTSLQ
AAAQSLNVQSKSNEESGDSQQPSQPSQQPSVQAAIPQTQLMLAGGQITGLTLTPAQQQLLLQ
QAQAQAQLLAAAVQQHSASQQHSAAGATISASAATPMTQIPLSQPIQIAQDLQQLQQLQQQNL
NLQQFVLVHPTTNLQPAQFIISQTPQGQQGLLQAQNLLTQLPQQSQANLLQSQPSITLTSQPAT
PTRTIAATPIQTLPQSQSTPKRIDTPSLEEPSDLEELEQFAKTFKQRRIKLGFTQGDVGLAMGKL

FIG. 17 cont'd

YGNDFSQTTISRFEALNLSFKNMCKLKPLLEKWLNDAENLSSDSSLSSPSALNSPGIEGLSRRR
KKRTSIETNIRVALEKSFLENQKPTSEEITMIADQLNMEKEVIRVWFCNRRQKEKRINPPSSGGT
SSSPIKAIFPSPTSLVATTPSLVTSSAATTLTVSPVLPLTSAAVTNLSVTGTSDTTSNNTATVISTA
PPASSAVTSPSLSPSPSASASTSEASSASETSTTQTTSTPLSSPLGTSQVMVTASGLQTAAAAA
LQGAAQLPANASLAAMAAAAGLNPSLMAPSQFAAGGALLSLNPGTLSGALSPALMSNSTLATI
QALASGGSLPITSLDATGNLVFANAGGAPNIVTAPLFLNPQNLSLLTSNPVSLVSAAAASAGNSA
PVASLHATSTSAESIQNSLFTVASASGAASTTTTASKAQ (SEQ ID NO: 53)

Transforming growth factor receptor beta 1 [Homo sapiens], GenBank: CAF02096.2:
MEAAVAAPRPRLLLLVLAAAAAAAAALLPGATALQCFCHLCTKDNFTCVTDGLCFVSVTETTDK
VIHNSMCIAEIDLIPRDRPFVCAPSSKTGSVTTTYCCNQDHCNKIELPTTGPFSVKSSPGLGPVE
LAAVIAGPVCFVCISLMLMVYICHNRTVIHHRVPNEEDPSLDRPFISEGTTLKDLIYDMTTSGSGS
GLPLLVQRTIARTIVLQESIGKGRFGEVWRGKWRGEEVAVKIFSSREERSWFREAEIYQTVMLR
HENILGFIAADNKDNGTWTQLWLVSDYHEHGSLFDYLNRYTVTVEGMIKLALSTASGLAHLHME
IVGTQGKPAIAHRDLKSKNILVKKNGTCCIADLGLAVRHDSATDTIDIAPNHRVGTKRYMAPEVL
DDSINMKHFESFKRADIYAMGLVFWEIARRCSIGGIHEDYQLPYYDLVPSDPSVEEMRKVVCEQ
KLRPNIPNRWQSCEALRVMAKIMRECWYANGAARLTALRIKKTLSQLSQQEGIKM (SEQ ID NO: 54)

Platelet-derived growth factor receptor [Homo sapiens], GenBank: AAA60049.1:
MRLPGAMPALALKGELLLLSLLLLLEPQISQGLVVTPPGPELVLNVSSTFVLTCSGSAPVVWER
MSQEPPQEMAKAQDGTFSSVLTLTNLTGLDTGEYFCTHNDSRGLETDERKRLYIFVPDPTVGF
LPNDAEELFIFLTEITEITIPCRVTDPQLVVTLHEKKGDVALPVPYDHQRGFSGIFEDRSYICKTTI
GDREVDSDAYYVYRLQVSSINVSVNAVQTVVRQGENITLMCIVIGNEVVNFEWTYPRKESGRL
VEPVTDFLLDMPYHIRSILHIPSAELEDSGTYTCNVTESVNDHQDEKAINITVVESGYVRLLGEV
GTLQFAELHRSRTLQVVFEAYPPPTVLWFKDNRTLGDSSAGEIALSTRNVSETRYVSELTLVRV
KVAEAGHYTMRAFHEDAEVQLSFQLQINVPVRVLELSESHPDSGEQTVRCRGRGMPQPNIIWS
ACRDLKRCPRELPPTLLGNSSEEESQLETNVTYWEEEQEFEVVSTLRLQHVDRPLSVRCTLRN
AVGQDTQEVIVVPHSLPFKVVVISAILALVVLTIISLIILIMLWQKKPRYEIRWKVIESVSSDGHEYIY
VDPMQLPYDSTWELPRDQLVLGRTLGSGAFGQVVEATAHGLSHSQATMKVAVKMLKSTARSS
EKQALMSELKIMSHLGPHLNVVNLLGACTKGGPIYIITEYCRYGDLVDYLHRNKHTFLQHHSDK
RRPPSAELYSNALPVGLPLPSHVSLTGESDGGYMDMSKDESVDYVPMLDMKGDVKYADIESS
NYMAPYDNYVPSAPERTCRATLINESPVLSYMDLVGFSYQVANGMEFLASKNCVHRDLAARN
VLICEGKLVKICDFGLARDIMRDSNYISKGSTFLPLKWMAPESIFNSLYTTLSDVWSFGILLWEIF
TLGGTPYPELPMNEQFYNAIKRGYRMAQPAHASDEIYEIMQKCWEEKFEIRPPFSQLVLLLERL
LGEGYKKKYQQVDEEFLRSDHPAILRSQARLPGFHGLRSPLDTSSVLYTAVQPNEGDNDYIIPL
PDPKPEVADEGPLEGSPSLASSTLNEVNTSSTISCDSPLEPQDEPEPEPQLELQVEPEPELEQL
PDSGCPAPRAEAEDSFL (SEQ ID NO: 55)

Epidermal growth factor receptor [Homo sapiens], GenBank: CAA25240.1:
MRPSGTAGAALLALLAALCPASRALEEKKVCQGTSNKLTQLGTFEDHFLSLQRMFNNCEVVLG
NLEITYVQRNYDLSFLKTIQEVAGYVLIALNTVERIPLENLQIIRGNMYYENSYALAVLSNYDANKT
GLKELPMRNLQEILHGAVRFSNNPALCNVESIQWRDIVSSDFLSNMSMDFQNHLGSCQKCDPS
CPNGSCWGAGEENCQKLTKIICAQQCSGRCRGKSPSDCCHNQCAAGCTGPRESDCLVCRKF
RDEATCKDTCPPLMLYNPTTYQMDVNPEGKYSFGATCVKKCPRNYVVTDHGSCVRACGADS
YEMEEDGVRKCKKCEGPCRKVCNGIGIGEFKDSLSINATNIKHFKNCTSISGDLHILPVAFRGDS
FTHTPPLDPQELDILKTVKEITGFLLIQAWPENRTDLHAFENLEIIRGRTKQHGQFSLAVVSLNITS
LGLRSLKEISDGDVIISGNKNLCYANTINWKKLFGTSGQKTKIISNRGENSCKATGQVCHALCSP
EGCWGPEPRDCVSCRNVSRGRECVDKCKLLEGEPREFVENSECIQCHPECLPQAMNITCTGR

FIG. 17 cont'd

GPDNCIQCAHYIDGPHCVKTCPAGVMGENNTLVWKYADAGHVCHLCHPNCTYGCTGPGLEG
CPTNGPKIPSIATGMVGALLLLLVVALGIGLFMRRRHIVRKRTLRRLLQERELVEPLTPSGEAPN
QALLRILKETEFKKIKVLGSGAFGTVYKGLWIPEGEKVKIPVAIKELREATSPKANKEILDEAYVM
ASVDNPHVCRLLGICLTSTVQLITQLMPFGCLLDYVREHKDNIGSQYLLNWCVQIAKGMNYLED
RRLVHRDLAARNVLVKTPQHVKITDFGLAKLLGAEEKEYHAEGGKVPIKWMALESILHRIYTHQS
DVWSYGVTVWELMTFGSKPYDGIPASEISSILEKGERLPQPPICTIDVYMIMVKCWMIDADSRP
KFRELIIEFSKMARDPQRYLVIQGDERMHLPSPTDSNFYRALMDEEDMDDVVDADEYLIPQQGF
FSSPSTSRTPLLSSLSATSNNSTVACIDRNGLQSCPIKEDSFLQRYSSDPTGALTEDSIDDTFLP
VPEYINQSVPKRPAGSVQNPVYHNQPLNPAPSRDPHYQDPHSTAVGNPEYLNTVQPTCVNST
FDSPAHWAQKGSHQISLDNPDYQQDFFPKEAKPNGIFKGSTAENAEYLRVAPQSSEFIGA
(SEQ ID NO: 56)

Vascular endothelial growth factor receptor [Homo sapiens], GenBank: AAC16449.2:
MVSYWDTGVLLCALLSCLLLTGSSSGSKLKDPELSLKGTQHIMQAGQTLHLQCRGEAAHKWSL
PEMVSKESERLSITKSACGRNGKQFCSTLTLNTAQANHTGFYSCKYLAVPTSKKKETESAIYIFI
SDTGRPFVEMYSEIPEIIHMTEGRELVIPCRVTSPNITVTLKKFPLDTLIPDGKRIIWDSRKGFIISN
ATYKEIGLLTCEATVNGHLYKTNYLTHRQTNTIIDVQISTPRPVKLLRGHTLVLNCTATTPLNTRV
QMTWSYPDEKNKRASVRRRIDQSNSHANIFYSVLTIDKMQNKDKGLYTCRVRSGPSFKSVNTS
VHIYDKAFITVKHRKQQVLETVAGKRSYRLSMKVKAFPSPEVVWLKDGLPATEKSARYLTRGYS
LIIKDVTEEDAGNYTILLSIKQSNVFKNLTATLIVNVKPQIYEKAVSSFPDPALYPLGSRQILTCTAY
GIPQPTIKWFWHPCNHNHSEARCDFCSNNEESSILDADSNMGNRIESITQRMAIIEGKNKMAST
LVVADSRISGIYICIASNKVGTVGRNISFYITDVPNGFHVNLEKMPTEGEDLKLSCTVNKFLYRDV
TWILLRTVNNRTMHYSISKQKMAITKEHSITLNLTIMNVSLQDSGTYACRARNVYTGEEILQKKEI
TIRDQEAPYLLRNLSDHTVAISSSTTLDCHANGVPEPQITWFKNNHKIQQEPGIILGPGSSTLFIE
RVTEEDEGVYHCKATNQKGSVESSAYLTVQGTSDKSNLELITLTCTCVAATLFWLLLTLFIRKMK
RSSSEIKTDYLSIIMDPDEVPLDEQCERLPYDASKWEFARERLKLGKSLGRGAFGKVVQASAFG
IKKSPTCRTVAVKMLKEGATASEYKALMTELKILTHIGHHLNVVNLLGACTKQGGPLMVIVEYCK
YGNLSNYLKSKRDLFFLNKDAALHMEPKKEKMEPGLEQGKKPRLDSVTSSESFASSGFQEDKS
LSDVEEEEDSDGFYKEPITMEDLISYSFQVARGMEFLSSRKCIHRDLAARNILLSENNVVKICDF
GLARDIYKNPDYVRKGDTRLPLKWMAPESIFDKIYSTKSDVWSYGVLLWEIFSLGGSPYPGVQ
MDEDFCSRLREGMRMRAPEYSTPEIYQIMLDCWHRDPKERPRFAELVEKLGDLLQANVQQDG
KDYIPINAILTGNSGFTYSTPAFSEDFFKESISAPKFNSGSSDDVRYVNAFKFMSLERIKTFEELL
PNATSMFDDYQGDSSTLLASPMLKRFTWTDSKPKASLKIDLRVTSKSKESGLSDVSRPSFCHS
SCGHVSEGKRRFTYDHAELERKIACCSPPPDYNSVVLYSTPPI (SEQ ID NO: 57)

Interleukin 8 receptor alpha [Homo sapiens], GenBank: AAB59436.1:
MSNITDPQMWDFDDLNFTGMPPADEDYSPCMLETETLNKYVVIIAYALVFLLSLLGNSLVMLVIL
YSRVGRSVTDVYLLNLALADLLFALTLPIWAASKVNGWIFGTFLCKVVSLLKEVNFYSGILLLACI
SVDRYLAIVHATRTLTQKRHLVKFVCLGCWGLSMNLSLPFFLFRQAYHPNNSSPVCYEVLGND
TAKWRMVLRILPHTFGFIVPLFVMLFCYGFTLRTLFKAHMGQKHRAMRVIFAVVLIFLLCWLPYN
LVLLADTLMRTQVIQESCERRNNIGRALDATEILGFLHSCLNPIIYAFIGQNFRHGFLKILAMHGLV
SKEFLARHRVTSYTSSSVNVSSNL (SEQ ID NO: 58)

Caveolin [Homo sapiens], GenBank: CAA79476.1:

FIG. 17 cont'd

MSGGKYVDSEGHLYTVPIREQGNIYKPNNKAMADELSEKQVYDAHTKEIDLVNRDPKHLNDDV
VKIDFEDVIAEPEGTHSFHGIWKASFTTFTVTKYWFYRLLSALFGIPMALIWGIYFAILSFLHIWAV
VPCIKSFLIEIQCTSRVYSIYVHTVCDPLFEAVGKIFSNVRINLQKEI (SEQ ID NO: 59)

Dynamin [Homo sapiens], GenBank: AAA88025.1:
MGNRGMEELIPLVNKLQDAFSSIGQSCHLDLPQIAVVGGQSAGKSSVLENFVGRDFLPRGSGI
VTRRPLILQLIFSKTEHAEFLHCKSKKFTDFDEVRQEIEAETDRVTGTNKGISPVPINLRVYSPHV
LNLTLIDLPGITKVPVGDQPPDIEYRVKDMILQFISRESSLILAVTPANMDLANSDALKLAKEVDP
QGLRTIGVITKLDLMDEGTDARDVLENKLLPLRRGYIGVVNRSQKDIEGKKDIRAALAAERKFFL
SHPAYRHMADRMGTPHLQKTLNQQLTNHIRESLPALRSKLQSQLLSLEKEVEEYKIFRPDDPTP
KTKALLQMVQQFGVDFEKRIEGSGDQVDTLELSGGARINRIFHERFPFELVKMEFDEKDLRREI
SYAIKNIHGVRTGLFTPDLAFEAIVKKQVVKLKEPCLKCVDLVIQELINTVRQCTSKLSSYPRLRE
ETERIVTTYIREREGRTKDQILLLIDIEQSYINTNHEDFIGFANAQQRSTQLNKKRAIPNQVIRRGW
LTINNISLMKGGSKEYWFVLTAESLSWYKDEEEKEKKYMLPLDNLKIRDVEKGFMSNKHVFAIF
NTEQRNVYKDLRQIELACDSQEDVDSWKASFLRAGVYPEKDQAENEDGAQENTFSMDPQLER
QVETIRNLVDSYVAIINKSIRDLMPKTIMHLMINNTKAFIHHELLAYLYSSADQSSLMEESADQAQ
RRDDMLRMYHALKEALNIIGDISTSTVSTPVPPPVDDTWLQSASSHSPTPQRRPVSSIHPPGRP
PAVRGPTPGPPLIPVPVGAAASFSAPPIPSRPGPQSVFANSDLFPAPPQIPSRPVRIPPGIPPGV
PSRRPPAAPSRPTIIRPAEPSLLD (SEQ ID NO: 60)

Clathrin heavy chain 1 isoform 1 [Homo sapiens], NP_004850.1:
MAQILPIRFQEHLQLQNLGINPANIGFSTLTMESDKFICIREKVGEQAQVVIIDMNDPSNPIRRPIS
ADSAIMNPASKVIALKAGKTLQIFNIEMKSKMKAHTMTDDVTFWKWISLNTVALVTDNAVYHWS
MEGESQPVKMFDRHSSLAGCQIINYRTDAKQKWLLLTGISAQQNRVVGAMQLYSVDRKVSQPI
EGHAASFAQFKMEGNAEESTLFCFAVRGQAGGKLHIIEVGTPPTGNQPFPKKAVDVFFPPEAQ
NDFPVAMQISEKHDVVFLITKYGYIHLYDLETGTCIYMNRISGETIFVTAPHEATAGIIGVNRKGQ
VLSVCVEEENIIPYITNVLQNPDLALRMAVRNNLAGAEELFARKFNALFAQGNYSEAAKVAANAP
KGILRTPDTIRRFQSVPAQPGQTSPLLQYFGILLDQGQLNKYESLELCRPVLQQGRKQLLEKWL
KEDKLECSEELGDLVKSVDPTLALSVYLRANVPNKVIQCFAETGQVQKIVLYAKKVGYTPDWIFL
LRNVMRISPDQGQQFAQMLVQDEEPLADITQIVDVFMEYNLIQQCTAFLLDALKNNRPSEGPLQ
TRLLEMNLMHAPQVADAILGNQMFTHYDRAHIAQLCEKAGLLQRALEHFTDLYDIKRAVVHTHL
LNPEWLVNYFGSLSVEDSLECLRAMLSANIRQNLQICVQVASKYHEQLSTQSLIELFESFKSFE
GLFYFLGSIVNFSQDPDVHFKYIQAACKTGQIKEVERICRESNCYDPERVKNFLKEAKLTDQLPL
IIVCDRFDFVHDLVLYLYRNNLQKYIEIYVQKVNPSRLPVVIGGLLDVDCSEDVIKNLILVVRGQFS
TDELVAEVEKRNRLKLLLPWLEARIHEGCEEPATHNALAKIYIDSNNNPERFLRENPYYDSRVV
GKYCEKRDPHLACVAYERGQCDLELINVCNENSLFKSLSRYLVRRKDPELWGSVLLESNPYRR
PLIDQVVQTALSETQDPEEVSVTVKAFMTADLPNELIELLEKIVLDNSVFSEHRNLQNLLILTAIKA
DRTRVMEYINRLDNYDAPDIANIAISNELFEEAFAIFRKFDVNTSAVQVLIEHIGNLDRAYEFAER
CNEPAVWSQLAKAQLQKGMVKEAIDSYIKADDPSSYMEVVQAANTSGNWEELVKYLQMARKK
ARESYVETELIFALAKTNRLAELEEFINGPNNAHIQQVGDRCYDEKMYDAAKLLYNNVSNFGRL
ASTLVHLGEYQAAVDGARKANSTRTWKEVCFACVDGKEFRLAQMCGLHIVVHADELEELINYY
QDRGYFEELITMLEAALGLERAHMGMFTELAILYSKFKPQKMREHLELFWSRVNIPKVLRAAEQ
AHLWAELVFLYDKYEEYDNAIITMMNHPTDAWKEGQFKDIITKVANVELYYRAIQFYLEFKPLLL
NDLLMVLSPRLDHTRAVNYFSKVKQLPLVKPYLRSVQNHNNKSVNESLNNLFITEEDYQALRTS
IDAYDNFDNISLAQRLEKHELIEFRRIAAYLFKGNNRWKQSVELCKKDSLYKDAMQYASESKDT
ELAEELLQWFLQEEKRECFGACLFTCYDLLRPDVVLETAWRHNIMDFAMPYFIQVMKEYLTKV
DKLDASESLRKEEEQATETQPIVYGQPQLMLTAGPSVAVPPQAPFGYGYTAPPYGQPQPGFG
YSM (SEQ ID NO: 61)

FIG. 17 cont'd

Clathrin heavy chain 2 isoform 1 [Homo sapiens], NP_009029.3:
MAQILPVRFQEHFQLQNLGINPANIGFSTLTMESDKFICIREKVGEQAQVTIIDMSDPMAPIRRPI
SAESAIMNPASKVIALKAGKTLQIFNIEMKSKMKAHTMAEEVIFWKWVSVNTVALVTETAVYHW
SMEGDSQPMKMFDRHTSLVGCQVIHYRTDEYQKWLLLVGISAQQNRVVGAMQLYSVDRKVS
QPIEGHAAAFAEFKMEGNAKPATLFCFAVRNPTGGKLHIIEVGQPAAGNQPFVKKAVDVFFPPE
AQNDFPVAMQIGAKHGVIYLITKYGYLHLYDLESGVCICMNRISADTIFVTAPHKPTSGIIGVNKK
GQVLSVCVEEDNIVNYATNVLQNPDLGLRLAVRSNLAGAEKLFVRKFNTLFAQGSYAEAAKVA
ASAPKGILRTRETVQKFQSIPAQSGQASPLLQYFGILLDQGQLNKLESLELCHLVLQQGRKQLL
EKWLKEDKLECSEELGDLVKTTDPMLALSVYLRANVPSKVIQCFAETGQFQKIVLYAKKVGYTP
DWIFLLRGVMKISPEQGLQFSRMLVQDEEPLANISQIVDIFMENSLIQQCTSFLLDALKNNRPAE
GLLQTWLLEMNLVHAPQVADAILGNKMFTHYDRAHIAQLCEKAGLLQQALEHYTDLYDIKRAVV
HTHLLNPEWLVNFFGSLSVEDSVECLHAMLSANIRQNLQLCVQVASKYHEQLGTQALVELFES
FKSYKGLFYFLGSIVNFSQDPDVHLKYIQAACKTGQIKEVERICRESSCYNPERVKNFLKEAKLT
DQLPLIIVCDRFGFVHDLVLYLYRNNLQRYIEIYVQKVNPSRTPAVIGGLLDVDCSEEVIKHLIMAV
RGQFSTDELVAEVEKRNRLKLLLPWLESQIQEGCEEPATHNALAKIYIDSNNSPECFLRENAYY
DSSVVGRYCEKRDPHLACVAYERGQCDLELIKVCNENSLFKSEARYLVCRKDPELWAHVLEET
NPSRRQLIDQVVQTALSETRDPEEISVTVKAFMTADLPNELIELLEKIVLDNSVFSEHRNLQNLLI
LTAIKADRTRVMEYISRLDNYDALDIASIAVSSALYEEAFTVFHKFDMNASAIQVLIEHIGNLDRAY
EFAERCNEPAVWSQLAQAQLQKDLVKEAINSYIRGDDPSSYLEVVQSASRSNNWEDLVKFLQ
MARKKGRESYIETELIFALAKTSRVSELEDFINGPNNAHIQQVGDRCYEEGMYEAAKLLYSNVS
NFARLASTLVHLGEYQAAVDNSRKASSTRTWKEVCFACMDGQEFRFAQLCGLHIVIHADELEE
LMCYYQDRGYFEELILLLEAALGLERAHMGMFTELAILYSKFKPQKMLEHLELFWSRVNIPKVLR
AAEQAHLWAELVFLYDKYEEYDNAVLTMMSHPTEAWKEGQFKDIITKVANVELCYRALQFYLD
YKPLLINDLLLVLSPRLDHTWTVSFFSKAGQLPLVKPYLRSVQSHNNKSVNEALNHLLTEEEDY
QGLRASIDAYDNFDNISLAQQLEKHQLMEFRCIAAYLYKGNNWWAQSVELCKKDHLYKDAMQ
HAAESRDAELAQKLLQWFLEEGKRECFAACLFTCYDLLRPDMVLELAWRHNLVDLAMPYFIQV
MREYLSKVDKLDALESLRKQEEHVTEPAPLVFDFDGHE (SEQ ID NO: 62)

Clathrin light chain A isoform a [Homo sapiens], NP_001824.1:
MAELDPFGAPAGAPGGPALGNGVAGAGEEDPAAAFLAQQESEIAGIENDEAFAILDGGAPGPQ
PHGEPPGGPDAVDGVMNGEYYQESNGPTDSYAAISQVDRLQSEPESIRKWREEQMERLEAL
DANSRKQEAEWKEKAIKELEEWYARQDEQLQKTKANNRAAEEAFVNDIDESSPGTEWERVAR
LCDFNPKSSKQAKDVSRMRSVLISLKQAPLVH (SEQ ID NO: 63)

Clathrin light chain B isoform a [Homo sapiens], NP_001825.1:
MADDFGFFSSSESGAPEAAEEDPAAAFLAQQESEIAGIENDEGFGAPAGSHAAPAQPGPTSGA
GSEDMGTTVNGDVFQEANGPADGYAAIAQADRLTQEPESIRKWREEQRKRLQELDAASKVTE
QEWREKAKKDLEEWNQRQSEQVEKNKINNRASEEAFVKESKEETPGTEWEKVAQLCDFNPK
SSKQCKDVSRLRSVLMSLKQTPLSR (SEQ ID NO: 64)

Ras-related protein Rab-4A isoform 1 [Homo sapiens], NP_004569.2:
MSQTAMSETYDFLFKFLVIGNAGTGKSCLLHQFIEKKFKDDSNHTIGVEFGSKIINVGGKYVKLQI
WDTAGQERFRSVTRSYYRGAAGALLVYDITSRETYNALTNWLTDARMLASQNIVIILCGNKKDL
DADREVTFLEASRFAQENELMFLETSALTGENVEEAFVQCARKILNKIESGELDPERMGSGIQY
GDAALRQLRSPRRAQAPNAQECGC (SEQ ID NO: 65)

Ras-related protein Rab-11A, UniProtKB/Swiss-Prot: P62491.3:
MGTRDDEYDYLFKVVLIGDSGVGKSNLLSRFTRNEFNLESKSTIGVEFATRSIQVDGKTIKAQIW
DTAGQERYRAITSAYYRGAVGALLVYDIAKHLTYENVERWLKELRDHADSNIVIMLVGNKSDLR

FIG. 17 cont'd

HLRAVPTDEARAFAEKNGLSFIETSALDSTNVEAAFQTILTEIYRIVSQKQMSDRRENDMSPSNN
VVPIHVPPTTENKPKVQCCQNI (SEQ ID NO: 66)

Platelet-derived growth factor [Homo sapiens], GenBank: AAA60552.1:
MNRCWALFLSLCCYLRLVSAEGDPIPEELYEMLSDHSIRSFDDLQRLLHGDPGEEDGAELDLN
MTRSHSGGELESLARGRRSLGSLTIAEPAMIAECKTRTEVFEISRRLIDRTNANFLVWPPCVEV
QRCSGCCNNRNVQCRPTQVQLRPVQVRKIEIVRKKPIFKKATVTLEDHLACKCETVAAARPVT
RSPGGSQEQRAKTPQTRVTIRTVRVRRPPKGKHRKFKHTHDKTALKETLGA (SEQ ID NO: 67)

Transforming growth factor-beta3 [Homo sapiens], GenBank: AAA61161.1:
MKMHLQRALVVLALLNFATVSLSLSTCTTLDFGHIKKKRVEAIRGQILSKLRLTSPPEPTVMTHV
PYQVLALYNSTRELLEEMHGEREEGCTQENTESEYYAKEIHKFDMIQGLAEHNELAVCPKGITS
KVFRFNVSSVEKNRTNLFRAEFRVLRVPNPSSKRNEQRIELFQILRPDEHIAKQRYIGGKNLPTR
GTAEWLSFDVTDTVREWLLRRESNLGLEISIHCPCHTFQPNGDILENIHEVMEIKFKGVDNEDD
HGRGDLGRLKKQKDHHNPHLILMMIPPHRLDNPGQGGQRKKRALDTNYCFRNLEENCCVRPL
YIDFRQDLGWKWVHEPKGYYANFCSGPCPYLRSADTTHSTVLGLYNTLNPEASASPCCVPQD
LEPLTILYYVGRTPKVEQLSNMVVKSCKCS (SEQ ID NO: 68)

Nerve growth factor [Homo sapiens], GenBank: CAA37703.1:
MSILFYVIFLAYLRGIQGNNMDQRSLPEDSLNSLIIKLIQADILKNKLSKQMVDVKENYQSTLPKA
EAPREPERGGPAKSAFQPVIAMDTELLRQQRRYNSPRVLLSDSTPLEPPPLYLMEDYVGSPVV
ANRTSRRKRYAEHKSHRGEYSVCDSESLWVTDKSSAIDIRGHQVTVLGEIKTGNSPVKQYFYE
TRCKEARPVKNGCRGIDDKHWNSQCKTSQTYVRALTSENNKLVGWRWIRIDTSCVCALSRKIG
RT (SEQ ID NO: 69)

Epidermal growth factor (EGF) [Homo sapiens], GenBank: CAA34902.2:
MRPSGTAGAALLALLAALCPASRALEEKKGKGVSRRLPRRPRIAPRTPQPAQPRTGAPARARA
PARPFLFP (SEQ ID NO: 70)

GTPase HRas [Homo sapiens]:
MTEYKLVVVGAGGVGKSALTIQLIQNHFVDEYDPTIEDSYRKQVVIDGETCLLDILDTAGQEEYS
AMRDQYMRTGEGFLCVFAINNTKSFEDIHQYREQIKRVKDSDDVPMVLVGNKCDLAARTVESR
QAQDLARSYGIPYIETSAKTRQGVEDAFYTLVREIRQHKLRKLNPPDESGPGCMSCKCVLS
(SEQ ID NO: 71)

Cocaine And Amphetamine Regulated Transcript (Chain A) [Homo sapiens], PDB: 1HY9_A:
YGQVPMCDAGEQCAVRKGARIGKLCDCPRGTSCNSFLLKCL (SEQ ID NO: 72)

Protachykinin-1 [Homo sapiens], UniProtKB - P20366:
MKILVALAVFFLVSTQLFAEEIGANDDLNYWSDWYDSDQIKEELPEPFEHLLQRIARRPKPQQFF
GLMGKRDADSSIEKQVALLKALYGHGQISHKRHKTDSFVGLMGKRALNSVAYERSAMQNYER
RR (SEQ ID NO: 73)

Substance P is position 58-68 of Protachykinin-1 [Homo sapiens]:
RPKPQQFFGLM (SEQ ID NO: 74)

Oxytocin-neurophysin 1 [Homo sapiens], UniProtKB - P01178:

FIG. 17 cont'd

MAGPSLACCLLGLLALTSACYIQNCPLGGKRAAPDLDVRKCLPCGPGGKGRCFGPNICCAEEL GCFVGTAEALRCQEENYLPSPCQSGQKACGSGGRCAVLGLCCSPDGCHADPACDAEATFSQ R (SEQ ID NO: 75)

Oxytocin is position 20-28 of Oxytocin-neurophysin 1 [Homo sapiens]:
CYIQNCPLG (SEQ ID NO: 76)

Somatostatin [Homo sapiens], GenBank: AAH32625.1:
MLSCRLQCALAALSIVLALGCVTGAPSDPRLRQFLQKSLAAAAGKQELAKYFLAELLSEPNQTE NDALEPEDLSQAAEQDEMRLELQRSANSNPAMAPRERKAGCKNFFWKTFTSC (SEQ ID NO: 77)

Myosin light chain kinase, Green fluorescent protein, Calmodulin chimera (Chain A) [synthetic construct], PDB: 3EKJ_A:
MRGSHHHHHHGMASMTGGQQMGRDLYDDDDKDLATMVDSSRRKWNKTGHAVRAIGRLSSL ENVYIMADKQKNGIKANFKIRHNIEDGGVQLAYHYQQNTPIGDGPVLLPDNHYLSTQSKLSKDP NEKRDHMVLLEFVTAAGITLGMDELYKGGTGGSMVSKGEELFTGVVPILVELDGDVNGHKFSV SGEGEGDATYGKLTLKFICTTGKLPVPWPTLVTTLXVQCFSRYPDHMKQHDFFKSAMPEGYIQ ERTIFFKDDGNYKTRAEVKFEGDTLVNRIELKGIDFKEDGNILGHKLEYNTRDQLTEEQIAEFKE AFSLFDKDGDGGITTKQLGTVMRSLGQNPTEAELQDMINEVGADGNGTIDFPQFLTMMARKMK DTDSEEEIREAFRVFGKDGNGYISAAQLRHVMTNLGEKLTDEEVDEMIREAGIDGDGQVNYEQ FVQMMTAK (SEQ ID NO: 78)

Genetically-encoded green calcium indicator NTnC (chain A) [synthetic construct], PDB: 5MWC_A:
MVSKGEEDNMASLPATHELHIFGSINGVDFDMVGQGSGNPNVGYEELNLKSTKGDLQFSPWIL VPHIXFHQYLPYPDGMSPFQAAMVDGSGYQVHRTVQFEDGASLTVNYRYTYEGSHIKGEAQV KGTGFPADGPVMANSLTAMVPSEEELSECFRTFDKDGDGFIDREEFGGIIRLTGEQLTDEDPD EIFGDSDTDKNGRIDFDEFLKMVENVQLSMADWCRSKMACPNDKTLISTLKWSYTTGNGKRYR STARTTYTFAKPMAANYLKNQPMYVFRKTELKHSKTELNFKEWQKAFTDVMGMDELYK (SEQ ID NO: 79)

Calcium indicator TN-XXL [synthetic construct], GenBank: ACF93133.1:
MVSKGEELFTGVVPILVELDGDVNGHKFSVRGEGEGDATNGKLTLKFICTTGKLPVPWPTLVTT LTWGVQCFSRYPDHMKQHDFFKSAMPEGYVQERTIFFKDDGNYKTRAEVKFEGDTLVNRIELK GIDFKEDGNILGHKLEYNYISHNVYITADKQKNGIKAHFKIRHNIEDGSVQLADHYQQNTPIGDG PVLLPDNHYLSTQSKLSKDPNEKRDHMVLLEFVTAARMLSEEELANCFRIFDKDANGFIDIEELG EILRATGEHVTEEDIEDLMKDSDKNNDGRIDFDEFLKMMEGVQGTSEEELANCFRIFDKDANGF IDIEELGEILRATGEHVTEEDIEDLMKDSDKNNDGRIDFDEFLKMMEGVQELMGGVQLADHYQQ NTPIGDGPVLLPDNHYLSYQSKLSKDPNEKRDHMVLLEFVTAAGITLGMDELYKGGTGGSMVS KGEELFTGVVPILVELDGDVNGHKFSVRGEGEGDATNGKLTLKFICTTGKLPVPWPTLVTTLGY GLMCFARYPDHMKQHDFFKSAMPEGYVQERTIFFKDDGNYKTRAEVKFEGDTLVNRIELKGID FKEDGNILGHKLEYNYNSHNVYIMADKQKNGIKANFKIRHNIED (SEQ ID NO: 80)

BRET-based auto-luminescent calcium indicator [synthetic construct], GenBank: ADF42668.1:
MVSKGEELFTGVVPILVELDGDVNGHKFSVSGEGEGDATYGKLTLKLICTTGKLPVPWPTLVTT LGYGLQCFARYPDHMKQHDFFKSAMPEGYVQERTIFFKDDGNYKTRAEVKFEGDTLVNRIELK GIDFKEDGNILGHKLEYNYNSHNVYITADKQKNGIKANFKIRHNIEDGGVQLADHYQQNTPIGDG

FIG. 17 cont'd

PVLLPDNHYLSYQSKLSKDPNEKRDHMVLLEFVTAAGITLGMDELYKRMHDQLTEEQIAEFKEA
FSLFDKDGDGTITTKELGTVMRSLGQNPTEAELQDMINEVDADGNGTIYFPEFLTMMARKMKD
TDSEEEIREAFRVFDKDGNGYISAAQLRHVMTNLGEKLTDEEVDEMIREADIDGDGQVNYEEFV
QMMTAKGGKRRWKKNFIAVSAANRFKKISSSGALELMTSKVYDPEQRKRMITGPQWWARCK
QMNVLDSFINYYDSEKHAENAVIFLHGNATSSYLWRHVVPHIEPVARCIIPDLIGMGKSGKSGN
GSYRLLDHYKYLTAWFELLNLPKKIIFVGHDWGAALAFHYAYEHQDRIKAIVHMESVVDVIESW
DEWPDIEEDIALIKSEEGEKMVLENNFFVETVLPSKIMRKLEPEEFAAYLEPFKEKGEVRRPTLS
WPREIPLVKGGKPDVVQIVRNYNAYLRASDDLPKLFIESDPGFFSNAIVEGAKKFPNTEFVKVK
GLHFLQEDAPDEMGKYIKSFVERVLKNEQ (SEQ ID NO: 81)

Calcium indicator protein OeNL(Ca2+)-18u [synthetic construct], GenBank: BBB18812.1:
MVSVIKPEMKMRYYMDGSVNGHEFTIEGEGTGRPYEGHQEMTLRVTMAEGGPMPFAFDLVS
HVFCYGHRVFTKYPEEIPDYFKQAFPEGLSWERSLEFEDGGSASVSAHISLRGNTFYHKSKFT
GVNFPADGPIMQNQSVDWEPSTEKITASDGVLKGDVTMYLKLEGGGNHKCQFKTTYKAAKEIL
EMPGDHYIGHRLVRKTEGNITEQVEDAVAHSGTLEDFVGDWRQTAGYNLDQVLEQGGVSSLF
QNLGVSVTPIQRIVLSGENGLKIDIHVIIPYEGPWMHDQLTEEQIAEFKEAFSLFDKDGDGTITTK
ELGTVMRSLGQNPTEAELQDMINEVDADGNGTIYFPDFLTMMARKMKDTDSEEEIREAFRVFD
KDGNGYISAADLRHVMTNLGEKLTDEEVDEMIREADIDGEGQVNYEEFVQMMTAKGGKRRWK
KNFIAVSAANRFKKISSSGALELLSGDQMGQIEKIFKVVYPVDDHHFKVILHYGTLVIDGVTPNMI
DYFGRPYEGIAVFDGKKITVTGTLWNGNKIIDERLINPDGSLLFRVTINGVTGWRLCERILA (SEQ
ID NO: 82)

GCaMP6m
ATGGGTTCTCATCATCATCATCATCATGGTATGGCTAGCATGACTGGTGGACAGCAAATGG
GTCGGGATCTGTACGACGATGACGATAAGGATCTCGCCACCATGGTCGACTCATCACGTC
GTAAGTGGAATAAGACAGGTCACGCAGTCAGAGCTATAGGTCGGCTGAGCTCACTCGAGA
ACGTCTATATCAAGGCCGACAAGCAGAAGAACGGCATCAAGGCGAACTTCAAGATCCGCC
ACAACATCGAGGACGGCGGCGTGCAGCTCGCCTACCACTACCAGCAGAACACCCCCATC
GGCGACGGCCCCGTGCTGCTGCCCGACAACCACTACCTGAGCGTGCAGTCCAAACTTTCG
AAAGACCCCAACGAGAAGCGCGATCACATGGTCCTGCTGGAGTTCGTGACCGCCGCCGG
GATCACTCTCGGCATGGACGAGCTGTACAAGGGCGGTACCGGAGGGAGCATGGTGAGCA
AGGGCGAGGAGCTGTTCACCGGGGTGGTGCCCATCCTGGTCGAGCTGGACGGCGACGTA
AACGGCCACAAGTTCAGCGTGTCCGGCGAGGGTGAGGGCGATGCCACCTACGGCAAGCT
GACCCTGAAGTTCATCTGCACCACCGGCAAGCTGCCCGTGCCCTGGCCCACCCTCGTGAC
CACCCTGACCTACGGCGTGCAGTGCTTCAGCCGCTACCCCGACCACATGAAGCAGCACGA
CTTCTTCAAGTCCGCCATGCCCGAAGGCTACATCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACCTGCCGGACCAACTGACTGAAGAGCAGATCGCAGAATTTAAAGAGGCTTTCTC
CCTATTTGACAAGGACGGGGATGGGACAATAACAACCAAGGAGCTGGGGACGGTGATGC
GGTCTCTGGGGCAGAACCCCACAGAAGCAGAGCTGCAGGACATGATCAATGAAGTAGATG
CCGACGGTGACGGCACAATCGACTTCCCTGAGTTCCTGACAATGATGGCAAGAAAAGGGA
GCTACAGGGACACGGAAGAAGAAATTAGAGAAGCGTTCGGTGTGTTTGATAAGGATGGCA
ATGGCTACATCAGTGCAGCAGAGCTTCGCCACGTGATGACAAACCTTGGAGAGAAGTTAA
CAGATGAAGAGGTTGATGAAATGATCAGGGAAGCAGACATCGATGGGGATGGTCAGGTAA
ACTACGAAGAGTTTGTACAAATGATGACAGCGAAGTGA (SEQ ID NO: 99)

GCaMP6s

FIG. 17 cont'd

ATGGGTTCTCATCATCATCATCATCATGGTATGGCTAGCATGACTGGTGGACAGCAAATGG
GTCGGGATCTGTACGACGATGACGATAAGGATCTCGCCACCATGGTCGACTCATCACGTC
GTAAGTGGAATAAGACAGGTCACGCAGTCAGAGCTATAGGTCGGCTGAGCTCACTCGAGA
ACGTCTATATCAAGGCCGACAAGCAGAAGAACGGCATCAAGGCGAACTTCCACATCCGCC
ACAACATCGAGGACGGCGGCGTGCAGCTCGCCTACCACTACCAGCAGAACACCCCCATC
GGCGACGGCCCCGTGCTGCTGCCCGACAACCACTACCTGAGCGTGCAGTCCAAACTTTCG
AAAGACCCCAACGAGAAGCGCGATCACATGGTCCTGCTGGAGTTCGTGACCGCCGCCGG
GATCACTCTCGGCATGGACGAGCTGTACAAGGGCGGTACCGGAGGGAGCATGGTGAGCA
AGGGCGAGGAGCTGTTCACCGGGGTGGTGCCCATCCTGGTCGAGCTGGACGGCGACGTA
AACGGCCACAAGTTCAGCGTGTCCGGCGAGGGTGAGGGCGATGCCACCTACGGCAAGCT
GACCCTGAAGTTCATCTGCACCACCGGCAAGCTGCCCGTGCCCTGGCCCACCCTCGTGAC
CACCCTGACCTACGGCGTGCAGTGCTTCAGCCGCTACCCCGACCACATGAAGCAGCACGA
CTTCTTCAAGTCCGCCATGCCCGAAGGCTACATCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACCTGCCGGACCAACTGACTGAAGAGCAGATCGCAGAATTTAAAGAGGCTTTCTC
CCTATTTGACAAGGACGGGGATGGGACAATAACAACCAAGGAGCTGGGGACGGTGATGC
GGTCTCTGGGGCAGAACCCCACAGAAGCAGAGCTGCAGGACATGATCAATGAAGTAGATG
CCGACGGTGACGGCACAATCGACTTCCCTGAGTTCCTGACAATGATGGCAAGAAAAATGA
AATACAGGGACACGGAAGAAGAAATTAGAGAAGCGTTCGGTGTGTTTGATAAGGATGGCA
ATGGCTACATCAGTGCAGCAGAGCTTCGCCACGTGATGACAAACCTTGGAGAGAAGTTAA
CAGATGAAGAGGTTGATGAAATGATCAGGGAAGCAGACATCGATGGGGATGGTCAGGTAA
ACTACGAAGAGTTTGTACAAATGATGACAGCGAAGTGA (SEQ ID NO: 100)

GCaMP6f

ATGGGTTCTCATCATCATCATCATCATGGTATGGCTAGCATGACTGGTGGACAGCAAATGG
GTCGGGATCTGTACGACGATGACGATAAGGATCTCGCCACCATGGTCGACTCATCACGTC
GTAAGTGGAATAAGACAGGTCACGCAGTCAGAGCTATAGGTCGGCTGAGCTCACTCGAGA
ACGTCTATATCAAGGCCGACAAGCAGAAGAACGGCATCAAGGCGAACTTCAAGATCCGCC
ACAACATCGAGGACGGCGGCGTGCAGCTCGCCTACCACTACCAGCAGAACACCCCCATC
GGCGACGGCCCCGTGCTGCTGCCCGACAACCACTACCTGAGCGTGCAGTCCAAACTTTCG
AAAGACCCCAACGAGAAGCGCGATCACATGGTCCTGCTGGAGTTCGTGACCGCCGCCGG
GATCACTCTCGGCATGGACGAGCTGTACAAGGGCGGTACCGGAGGGAGCATGGTGAGCA
AGGGCGAGGAGCTGTTCACCGGGGTGGTGCCCATCCTGGTCGAGCTGGACGGCGACGTA
AACGGCCACAAGTTCAGCGTGTCCGGCGAGGGTGAGGGCGATGCCACCTACGGCAAGCT
GACCCTGAAGTTCATCTGCACCACCGGCAAGCTGCCCGTGCCCTGGCCCACCCTCGTGAC
CACCCTGACCTACGGCGTGCAGTGCTTCAGCCGCTACCCCGACCACATGAAGCAGCACGA
CTTCTTCAAGTCCGCCATGCCCGAAGGCTACATCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACCTGCCGGACCAACTGACTGAAGAGCAGATCGCAGAATTTAAAGAGGAATTCTC
CCTATTTGACAAGGACGGGGATGGGACAATAACAACCAAGGAGCTGGGGACGGTGATGC
GGTCTCTGGGGCAGAACCCCACAGAAGCAGAGCTGCAGGACATGATCAATGAAGTAGATG
CCGACGGTGACGGCACAATCGACTTCCCTGAGTTCCTGACAATGATGGCAAGAAAAATGA
AATACAGGGACACGGAAGAAGAAATTAGAGAAGCGTTCGGTGTGTTTGATAAGGATGGCA
ATGGCTACATCAGTGCAGCAGAGCTTCGCCACGTGATGACAAACCTTGGAGAGAAGTTAA
CAGATGAAGAGGTTGATGAAATGATCAGGGAAGCAGACATCGATGGGGATGGTCAGGTAA
ACTACGAAGAGTTTGTACAAATGATGACAGCGAAGTGA (SEQ ID NO: 101)

FIG. 17 cont'd

**Channelopsin *1* [Mesostigma viride], *UniPro*tKB - F8UVI5:**
MSPPTSPTPDTGHDTPDTGHDTGGHGAVEICFAPCEEDCVTIRYFVENDFEGCIPGHFDQYSS
HGSLHDIVKAALYICMVISILQILFYGFQWWRKTCGWEVWFVACIETSIYIIAITSEADSPFTLYLT
NGQISPQLRYMEWLMTCPVILIALSNITGMAEEYNKRTMTLLTSDVCCIVLGMMSAASKPRLKGI
LYAVGWAFGAWTYWTALQVYRDAHKAVPKPLAWYVRAMGYVFFTSWLTFPGWFLLGPEGLE
VVTGTVSTLMHACSDLISKNLWGFMDWHLRVLVARHHRKLFKAEEEHALKKGQTLEPGMPRS
TSFVRGLGDDVEIDPSYELYRLKRQNHPEYFLSPAQTPRRGPSFDKRTSFEMDGGKNGMLQM
MPVTGMGMGMGMGMGGGKTVLFLDYTGGGYVSFFEQQLSNMGVNVTKCWSDDDMYNTAG
VANVKQLFHFAMIPNNALGGQMVMDLRGTGLLVVAYGPEPPMPGMGQDEFVPLQMPGVPYD
ESILHNLVMRHAITQGLGMNGMQGNMGQQQQMMGMQGNMNGMQGNMNGMQGNMNGMQ
GNMSGMQGNMNGMQGNSGMNQGWNNQGFTNTGAFGY (SEQ ID NO: 83)

Channelopsin 1 [Chlamydomonas yellowstonensis], GenBank: AER58217.1
MDTLAWVARELLSSGHGTDTATDSGHGTDTSGGHDSSHDAVAHNVTLLIAPPHAGGHAGPTD
TSQQITGIDGWIAIPAGDCYCAGWYVSHGSSFEATFAHVCQWSIFAVCVLSLLWYAYQYWKAT
CGWEEVYVCCIELVFICFELYHEFDSPCSLYLSTSNVVNWLRYSEWLLCCPVILIHLSNVTGLSD
DYGRRTMGLLVSDIATIVFGVTAAMLVNWPKIIFYLIGFTMCCYTFFLAAKVLIESFHQVPKGICR
HLVKAMAITYFVGWSFFPLIFLFGQSGFKKISPYADVIASSFGDLISKNAFGMLGHFLRVKIHEHIL
KHGDIRKTTHLRIAGEEKEVETFVEEEDEDTAKHSTKELANRGSFIVMRDKMKEQGIDVRASLD
MDEDEEARTGKGKGAGATSLVPGRVILAVPDISMVDFFHDHFAHLGASIELVPALGVENTLLLV
QQAMQLGGLDFVLVHPEFLRDRSQNGLVSRLKMTGHGVCAFGWVPSGPMREIIESAGVDGW
LDGPSFGTGIDQEQLIELIGYMQAKRKFGMRFGGGGASKAGYSSDGGFGGKGMLEMQPSMS
QGSGVPLLQQNNSMMRAPPSPMGNMANNGMMNPMMSMNNPMMGGGAVMMTSMGSMQQ
AANPLYGAPPSPLSSQPGAGMYGAPAQPQMGSQGSMHGSMYGGSQQQHQQPQQAAAAPA
AADGGSEAEMLKQLMSEINRLKAELGES (SEQ ID NO: 102)

Channelrhodopsin-2 [Volvox carteri f. nagariensis], UniProtKB - B4Y105:
MDHPVARSLIGSSYTNLNNGSIVIPSDACFCMKWLKSKGSPVALKMANALQWAAFALSVIILIYY
AYATWRTTCGWEEVYVCCVELTKVVIEFFHEFDEPGMLYLANGNRVLWLRYGEWLLTCPVILI
HLSNLTGLKDDYNKRTMRLLVSDVGTIVWGATAAMSTGYIKVIFFLLGCMYGANTFFHAAKVYIE
SYHTVPKGLCRQLVRAMAWLFFVSWGMFPVLFLLGPEGFGHLSVYGSTIGHTIIDLLSKNCWG
LLGHFLRLKIHEHILLYGDIRKVQKIRVAGEELEVETLMTEEAPDTVKKSTAQYANRESFLTMRD
KLKEKGFEVRASLDNSGIDAVINHNNNYNNALANAAAAVGKPGMELSKLDHVAANAAGMGGIA
DHVATTSGAISPGRVILAVPDISMVDYFREQFAQLPVQYEVVPALGADNAVQLVVQAAGLGGC
DFVLLHPEFLRDKSSTSLPARLRSIGQRVAAFGWSPVGPVRDLIESAGLDGWLEGPSFGLGISL
PNLASLVLRMQHARKMAAMLGGMGGMLGSNLMSGSGGVGLMGAGSPGGGGGAMGVGMTG
MGMVGTNAMGRGAVGNSVANASMGGGSAGMGMGMMGMVGAGVGGQQQMGANGMGPTS
FQLGSNPLYNTAPSPLSSQPGGDASAAAAAAAAAATGAASNSMNAMQAGGSVRNSGILAGG
LGSMMGPPGAPAAPTAAATAAPAVTMGAPGGGGAAASEAEMLQQLMAEINRLKSELGE (SEQ
ID NO: 84)

Channel rhodopsin 2 [synthetic construct], GenBank: ABO64386.1
MDYGGALSAVGRELLFVTNPVVVNGSVLVPEDQCYCAGWIESRGTNGAQTASNVLQWLAAGF
SILLLMFYAYQTWKSTCGWEEIYVCAIEMVKVILEFFFEFKNPSMLYLATGHRVQWLRYAEWLL
TCPVILIHLSNLTGLSNDYSRRTMGLLVSDIGTIVWGATSAMATGYVKVIFFCLGLCYGANTFFH
AAKAYIEGYHTVPKGRCRQVVTGMAWLFFVSWGMFPILFILGPEGFGVLSVYGSTVGHTIIDLM
SKNCWGLLGHYLRVLIHEHILIHGDIRKTTKLNIGGTEIEVETLVEDEAEAGAVP (SEQ ID NO:
103)

FIG. 17 cont'd

CRISPR-associated protein (Cas) [Streptococcus pyogenes], GenBank: AKG27598.1:
MLEHKIDFMVTLEVKEANANGDPLNGNMPRTDAKGYGVMSDVSIKRKIRNRLQDMGKSIFVQA
NERIEDDFRSLEKRFSQHFTAKTPDKEIEEKANALWFDVRAFGQVFTYLKKSIGVRGPVSISMA
KSLEPIVISSLQITRSTNGMEAKNNSGRSSDTMGTKHFVDYGVYVLKGSINAYFAEKTGFSQED
AEAIKEVLVSLFENDASSARPEGSMRVCEVFWFTHSSKLGNVSSARVFDLLEYHQSIEEKSTYD
AYQIHLNQEKLAKYEAKGLTLEILEGL (SEQ ID NO: 85)

Cas9 [synthetic construct], GenBank: AST09977.1:
MDKKYSIGLDIGTNSVGWAVITDEYKVPSKKFKVLGNTDRHSIKKNLIGALLFDSGETAEATRLK
RTARRRYTRRKNRICYLQEIFSNEMAKVDDSFFHRLEESFLVEEDKKHERHPIFGNIVDEVAYH
EKYPTIYHLRKKLVDSTDKADLRLIYLALAHMIKFRGHFLIEGDLNPDNSDVDKLFIQLVQTYNQL
FEENPINASGVDAKAILSARLSKSRRLENLIAQLPGEKKNGLFGNLIALSLGLTPNFKSNFDLAED
AKLQLSKDTYDDDLDNLLAQIGDQYADLFLAAKNLSDAILLSDILRVNTEITKAPLSASMIKRYDE
HHQDLTLLKALVRQQLPEKYKEIFFDQSKNGYAGYIDGGASQEEFYKFIKPILEKMDGTEELLVK
LNREDLLRKQRTFDNGSIPHQIHLGELHAILRRQEDFYPFLKDNREKIEKILTFRIPYYVGPLARG
NSRFAWMTRKSEETITPWNFEEVVDKGASAQSFIERMTNFDKNLPNEKVLPKHSLLYEYFTVY
NELTKVKYVTEGMRKPAFLSGEQKKAIVDLLFKTNRKVTVKQLKEDYFKKIECFDSVEISGVEDR
FNASLGTYHDLLKIIKDKDFLDNEENEDILEDIVLTLTLFEDREMIEERLKTYAHLFDDKVMKQLK
RRRYTGWGRLSRKLINGIRDKQSGKTILDFLKSDGFANRNFMQLIHDDSLTFKEDIQKAQVSGQ
GDSLHEHIANLAGSPAIKKGILQTVKVVDELVKVMGRHKPENIVIEMARENQTTQKGQKNSRER
MKRIEEGIKELGSQILKEHPVENTQLQNEKLYLYYLQNGRDMYVDQELDINRLSDYDVDHIVPQ
SFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFY
KVREINNYHHAHDAYLNAVVGTALIKKYPKLESEFVYGDYKVYDVRKMIAKSEQEIGKATAKYFF
YSNIMNFFKTEITLANGEIRKRPLIETNGETGEIVWDKGRDFATVRKVLSMPQVNIVKKTEVQTG
GFSKESILPKRNSDKLIARKKDWDPKKYGGFDSPTVAYSVLVVAKVEKGKSKKLKSVKELLGITI
MERSSFEKNPIDFLEAKGYKEVKKDLIIKLPKYSLFELENGRKRMLASAGELQKGNELALPSKYV
NFLYLASHYEKLKGSPEDNEQKQLFVEQHKHYLDEIIEQISEFSKRVILADANLDKVLSAYNKHR
DKPIREQAENIIHLFTLTNLGAPAAFKYFDTTIDRKRYTSTKEVLDATLIHQSITGLYETRIDLSQLG
GD (SEQ ID NO: 86)

CRISPR-associated endonuclease Cpf1 [Acidaminococcus sp. BV3L6], UniProtKB/Swiss-Prot: U2UMQ6.1:
MTQFEGFTNLYQVSKTLRFELIPQGKTLKHIQEQGFIEEDKARNDHYKELKPIIDRIYKTYADQCL
QLVQLDWENLSAAIDSYRKEKTEETRNALIEEQATYRNAIHDYFIGRTDNLTDAINKRHAEIYKGL
FKAELFNGKVLKQLGTVTTTEHENALLRSFDKFTTYFSGFYENRKNVFSAEDISTAIPHRIVQDN
FPKFKENCHIFTRLITAVPSLREHFENVKKAIGIFVSTSIEEVFSFPFYNQLLTQTQIDLYNQLLGGI
SREAGTEKIKGLNEVLNLAIQKNDETAHIIASLPHRFIPLFKQILSDRNTLSFILEEFKSDEEVIQSF
CKYKTLLRNENVLETAEALFNELNSIDLTHIFISHKKLETISSALCDHWDTLRNALYERRISELTGK
ITKSAKEKVQRSLKHEDINLQEIISAAGKELSEAFKQKTSEILSHAHAALDQPLPTTLKKQEEKEIL
KSQLDSLLGLYHLLDWFAVDESNEVDPEFSARLTGIKLEMEPSLSFYNKARNYATKKPYSVEKF
KLNFQMPTLASGWDVNKEKNNGAILFVKNGLYYLGIMPKQKGRYKALSFEPTEKTSEGFDKMY
YDYFPDAAKMIPKCSTQLKAVTAHFQTHTTPILLSNNFIEPLEITKEIYDLNNPEKEPKKFQTAYA
KKTGDQKGYREALCKWIDFTRDFLSKYTKTTSIDLSSLRPSSQYKDLGEYYAELNPLLYHISFQR
IAEKEIMDAVETGKLYLFQIYNKDFAKGHHGKPNLHTLYWTGLFSPENLAKTSIKLNGQAELFYR
PKSRMKRMAHRLGEKMLNKKLKDQKTPIPDTLYQELYDYVNHRLSHDLSDEARALLPNVITKEV
SHEIIKDRRFTSDKFFFHVPITLNYQAANSPSKFNQRVNAYLKEHPETPIIGIDRGERNLIYITVIDS
TGKILEQRSLNTIQQFDYQKKLDNREKERVAARQAWSVVGTIKDLKQGYLSQVIHEIVDLMIHYQ
AVVVLENLNFGFKSKRTGIAEKAVYQQFEKMLIDKLNCLVLKDYPAEKVGGVLNPYQLTDQFTS

FIG. 17 cont'd

FAKMGTQSGFLFYVPAPYTSKIDPLTGFVDPFVWKTIKNHESRKHFLEGFDFLHYDVKTGDFIL
HFKMNRNLSFQRGLPGFMPAWDIVFEKNETQFDAKGTPFIAGKRIVPVIENHRFTGRYRDLYPA
NELIALLEEKGIVFRDGSNILPKLLENDDSHAIDTMVALIRSVLQMRNSNAATGEDYINSPVRDLN
GVCFDSRFQNPEWPMDADANGAYHIALKGQLLLNHLKESKDLKLQNGISNQDWLAYIQELRN
(SEQ ID NO: 87)

Ribonuclease 4 or Ribonuclease L [Homo sapiens], UniProtKB/Swiss-Prot: Q05823.2:
MESRDHNNPQEGPTSSSGRRAAVEDNHLLIKAVQNEDVDLVQQLLEGGANVNFQEEEGGWT
PLHNAVQMSREDIVELLLRHGADPVLRKKNGATPFILAAIAGSVKLLKLFLSKGADVNECDFYGF
TAFMEAAVYGKVKALKFLYKRGANVNLRRKTKEDQERLRKGGATALMDAAEKGHVEVLKILLD
EMGADVNACDNMGRNALIHALLSSDDSDVEAITHLLLDHGADVNVRGERGKTPLILAVEKKHLG
LVQRLLEQEHIEINDTDSDGKTALLLAVELKLKKIAELLCKRGASTDCGDLVMTARRNYDHSLVK
VLLSHGAKEDFHPPAEDWKPQSSHWGAALKDLHRIYRPMIGKLKFFIDEKYKIADTSEGGIYLG
FYEKQEVAVKTFCEGSPRAQREVSCLQSSRENSHLVTFYGSESHRGHLFVCVTLCEQTLEACL
DVHRGEDVENEEDEFARNVLSSIFKAVQELHLSCGYTHQDLQPQNILIDSKKAAHLADFDKSIK
WAGDPQEVKRDLEDLGRLVLYVVKKGSISFEDLKAQSNEEVVQLSPDEETKDLIHRLFHPGEH
VRDCLSDLLGHPFFWTWESRYRTLRNVGNESDIKTRKSESEILRLLQPGPSEHSKSFDKWTTKI
NECVMKKMNKFYEKRGNFYQNTVGDLLKFIRNLGEHIDEEKHKKMKLKIGDPSLYFQKTFPDLV
IYVYTKLQNTEYRKHFPQTHSPNKPQCDGAGGASGLASPGC (SEQ ID NO: 88)

Deoxyribonuclease II beta [Homo sapiens], GenBank: AAF76893.1:
MMARLLRTSFALLFLGLFGVLGAATISCRNEEGKAVDWFTFYKLPKRQNKESGETGLEYLYLDS
TTRSWRKSEQLMNDTKSVLGRTLQQLYEAYASKSNNTAYLIYNDGVPKPVNYSRKYGHTKGLL
LWNRVQGFWLIHSIPQFPPIPEEGYDYPPTGRRNGQSGICITFKYNQYEAIDSQLLVCNPNVYS
CSIPATFHQELIHMPQLCTRASSSEIPGRLLTTLQSAQGQKFLHFAKSDSFLDDIFAAWMAQRLK
THLLTETWQRKRQELPSNCSLPYHVYNIKAIKLSRHSYFSSYQDHAKWCISQKGTKNRWTCIG
DLNRSPHQAFRSGGFICTQNWQIYQAFQGLVLYYESCK (SEQ ID NO: 89)

Sodium channel protein type 1 subunit alpha [Homo sapiens], UniProtKB - P35498
MEQTVLVPPGPDSFNFFTRESLAAIERRIAEEKAKNPKPDKKDDDENGPKPNSDLEAGKNLPFI
YGDIPPEMVSEPLEDLDPYYINKKTFIVLNKGKAIFRFSATSALYILTPFNPLRKIAIKILVHSLFSML
IMCTILTNCVFMTMSNPPDWTKNVEYTFTGIYTFESLIKIIARGFCLEDFTFLRDPWNWLDFTVIT
FAYVTEFVDLGNVSALRTFRVLRALKTISVIPGLKTIVGALIQSVKKLSDVMILTVFCLSVFALIGLQ
LFMGNLRNKCIQWPPTNASLEEHSIEKNITVNYNGTLINETVFEFDWKSYIQDSRYHYFLEGFLD
ALLCGNSSDAGQCPEGYMCVKAGRNPNYGYTSFDTFSWAFLSLFRLMTQDFWENLYQLTLRA
AGKTYMIFFVLVIFLGSFYLINLILAVVAMAYEEQNQATLEEAEQKEAEFQQMIEQLKKQQEAAQ
QAATATASEHSREPSAAGRLSDSSSEASKLSSKSAKERRNRRKKRKQKEQSGGEEKDEDEFQ
KSESEDSIRRKGFRFSIEGNRLTYEKRYSSPHQSLLSIRGSLFSPRRNSRTSLFSFRGRAKDVG
SENDFADDEHSTFEDNESRRDSLFVPRRHGERRNSNLSQTSRSSRMLAVFPANGKMHSTVD
CNGVVSLVGGPSVPTSPVGQLLPEVIIDKPATDDNGTTTETEMRKRRSSSFHVSMDFLEDPSQ
RQRAMSIASILTNTVEELEESRQKCPPCWYKFSNIFLIWDCSPYWLKVKHVVNLVVMDPFVDLA
ITICIVLNTLFMAMEHYPMTDHFNNVLTVGNLVFTGIFTAEMFLKIIAMDPYYYFQEGWNIFDGFIV
TLSLVELGLANVEGLSVLRSFRLLRVFKLAKSWPTLNMLIKIIGNSVGALGNLTLVLAIIVFIFAVVG
MQLFGKSYKDCVCKIASDCQLPRWHMNDFFHSFLIVFRVLCGEWIETMWDCMEVAGQAMCLT
VFMMVMVIGNLVVLNLFLALLLSSFSADNLAATDDDNEMNNLQIAVDRMHKGVAYVKRKIYEFI
QQSFIRKQKILDEIKPLDDLNNKKDSCMSNHTAEIGKDLDYLKDVNGTTSGIGTGSSVEKYIIDES
DYMSFINNPSLTVTVPIAVGESDFENLNTEDFSSESDLEESKEKLNESSSSSEGSTVDIGAPVEE
QPVVEPEETLEPEACFTEGCVQRFKCCQINVEEGRGKQWWNLRRTCFRIVEHNWFETFIVFMI
LLSSGALAFEDIYIDQRKTIKTMLEYADKVFTYIFILEMLLKWVAYGYQTYFTNAWCWLDFLIVDV

FIG. 17 cont'd

SLVSLTANALGYSELGAIKSLRTLRALRPLRALSRFEGMRVVVNALLGAIPSIMNVLLVCLIFWLIF
SIMGVNLFAGKFYHCINTTTGDRFDIEDVNNHTDCLKLIERNETARWKNVKVNFDNVGFGYLSL
LQVATFKGWMDIMYAAVDSRNVELQPKYEESLYMYLYFVIFIIFGSFFTLNLFIGVIIDNFNQQKK
KFGGQDIFMTEEQKKYYNAMKKLGSKKPQKPIPRPGNKFQGMVFDFVTRQVFDISIMILICLNM
VTMMVETDDQSEYVTTILSRINLVFIVLFTGECVLKLISLRHYYFTIGWNIFDFVVVILSIVGMFLAE
LIEKYFVSPTLFRVIRLARIGRILRLIKGAKGIRTLLFALMMSLPALFNIGLLLFLVMFIYAIFGMSNF
AYVKREVGIDDMFNFETFGNSMICLFQITTSAGWDGLLAPILNSKPPDCDPNKVNPGSSVKGDC
GNPSVGIFFFVSYIIISFLVVVNMYIAVILENFSVATEESAEPLSEDDFEMFYEVWEKFDPDATQF
MEFEKLSQFAAALEPPLNLPQPNKLQLIAMDLPMVSGDRIHCLDILFAFTKRVLGESGEMDALRI
QMEERFMASNPSKVSYQPITTTLKRKQEEVSAVIIQRAYRRHLLKRTVKQASFTYNKNKIKGGA
NLLIKEDMIIDRINENSITEKTDLTMSTAACPPSYDRVTKPIVEKHEQEGKDEKAKGK (SEQ ID NO: 104)

Potassium voltage-gated channel subfamily KQT member 2 [Homo sapiens], UniProtKB - O43526

MVQKSRNGGVYPGPSGEKKLKVGFVGLDPGAPDSTRDGALLIAGSEAPKRGSILSKPRAGGA
GAGKPPKRNAFYRKLQNFLYNVLERPRGWAFIYHAYVFLLVFSCLVLSVFSTIKEYEKSSEGAL
YILEIVTIVVFGVEYFVRIWAAGCCCRYRGWRGRLKFARKPFCVIDIMVLIASIAVLAAGSQGNVF
ATSALRSLRFLQILRMIRMDRRGGTWKLLGSVVYAHSKELVTAWYIGFLCLILASFLVYLAEKGE
NDHFDTYADALWWGLITLTTIGYGDKYPQTWNGRLLAATFTLIGVSFFALPAGILGSGFALKVQE
QHRQKHFEKRRNPAAGLIQSAWRFYATNLSRTDLHSTWQYYERTVTVPMYSSQTQTYGASRL
IPPLNQLELLRNLKSKSGLAFRKDPPPEPSPSKGSPCRGPLCGCCPGRSSQKVSLKDRVFSSP
RGVAAKGKGSPQAQTVRRSPSADQSLEDSPSKVPKSWSFGDRSRARQAFRIKGAASRQNSE
EASLPGEDIVDDKSCPCEFVTEDLTPGLKVSIRAVCVMRFLVSKRKFKESLRPYDVMDVIEQYS
AGHLDMLSRIKSLQSRVDQIVGRGPAITDKDRTKGPAEAELPEDPSMMGRLGKVEKQVLSMEK
KLDFLVNIYMQRMGIPPTETEAYFGAKEPEPAPPYHSPEDSREHVDRHGCIVKIVRSSSSTGQK
NFSAPPAAPPVQCPPSTSWQPQSHPRQGHGTSPVGDHGSLVRIPPPPAHERSLSAYGGGNR
ASMEFLRQEDTPGCRPPEGNLRDSDTSISIPSVDHEELERSFSGFSISQSKENLDALNSCYAAV
APCAKVRPYIAEGESDTDSDLCTPCGPPPRSATGEGPFGDVGWAGPRK (SEQ ID NO: 105)

Voltage-dependent L-type calcium channel subunit alpha-1C [Homo sapiens], UniProtKB - Q13936

MVNENTRMYIPEENHQGSNYGSPRPAHANMNANAAAGLAPEHIPTPGAALSWQAAIDAARQA
KLMGSAGNATISTVSSTQRKRQQYGKPKKQGSTTATRPPRALLCLTLKNPIRRACISIVEWKPF
EIIILLTIFANCVALAIYIPFPEDDSNATNSNLERVEYLFLIIFTVEAFLKVIAYGLLFHPNAYLRNGW
NLLDFIIVVVGLFSAILEQATKADGANALGGKGAGFDVKALRAFRVLRPLRLVSGVPSLQVVLNSI
IKAMVPLLHIALLVLFVIIIYAIIGLELFMGKMHKTCYNQEGIADVPAEDDPSPCALETGHGRQCQN
GTVCKPGWDGPKHGITNFDNFAFAMLTVFQCITMEGWTDVLYWVNDAVGRDWPWIYFVTLIII
GSFFVLNLVLGVLSGEFSKEREKAKARGDFQKLREKQQLEEDLKGYLDWITQAEDIDPENEDE
GMDEEKPRNMSMPTSETESVNTENVAGGDIEGENCGARLAHRISKSKFSRYWRRWNRFCRR
KCRAAVKSNVFYWLVIFLVFLNTLTIASEHYNQPNWLTEVQDTANKALLALFTAEMLLKMYSLGL
QAYFVSLFNRFDCFVVCGGILETILVETKIMSPLGISVLRCVRLLRIFKITRYWNSLSNLVASLLNS
VRSIASLLLLLFLFIIIFSLLGMQLFGGKFNFDEMQTRRSTFDNFPQSLLTVFQILTGEDWNSVMY
DGIMAYGGPSFPGMLVCIYFIILFICGNYILLNVFLAIAVDNLADAESLTSAQKEEEEEKERKKLAR
TASPEKKQELVEKPAVGESKEEKIELKSITADGESPPATKINMDDLQPNENEDKSPYPNPETTG
EEDEEEPEMPVGPRPRPLSELHLKEKAVPMPEASAFFIFSSNNRFRLQCHRIVNDTIFTNLILFFI
LLSSISLAAEDPVQHTSFRNHILFYFDIVFTTIFTIEIALKILGNADYVFTSIFTLEIILKMTAYGAFLH
KGSFCRNYFNILDLLVVSVSLISFGIQSSAINVVKILRVLRVLRPLRAINRAKGLKHVVQCVFVAIR
TIGNIVIVTTLLQFMFACIGVQLFKGKLYTCSDSSKQTEAECKGNYITYKDGEVDHPIIQPRSWEN

FIG. 17 cont'd

SKFDFDNVLAAMMALFTVSTFEGWPELLYRSIDSHTEDKGPIYNYRVEISIFFIIYIIIIAFFMMNIFV
GFVIVTFQEQGEQEYKNCELDKNQRQCVEYALKARPLRRYIPKNQHQYKVWYVVNSTYFEYL
MFVLILLNTICLAMQHYGQSCLFKIAMNILNMLFTGLFTVEMILKLIAFKPKGYFSDPWNVFDFLIV
IGSIIDVILSETNHYFCDAWNTFDALIVVGSIVDIAITEVNPAEHTQCSPSMNAEENSRISITFFRLF
RVMRLVKLLSRGEGIRTLLWTFIKSFQALPYVALLIVMLFFIYAVIGMQVFGKIALNDTTEINRNNN
FQTFPQAVLLLFRCATGEAWQDIMLACMPGKKCAPESEPSNSTEGETPCGSSFAVFYFISFYM
LCAFLIINLFVAVIMDNFDYLTRDWSILGPHHLDEFKRIWAEYDPEAKGRIKHLDVVTLLRRIQPPL
GFGKLCPHRVACKRLVSMNMPLNSDGTVMFNATLFALVRTALRIKTEGNLEQANEELRAIIKKI
WKRTSMKLLDQVVPPAGDDEVTVGKFYATFLIQEYFRKFKKRKEQGLVGKPSQRNALSLQAGL
RTLHDIGPEIRRAISGDLTAEEELDKAMKEAVSAASEDDIFRRAGGLFGNHVSYYQSDGRSAFP
QTFTTQRPLHINKAGSSQGDTESPSHEKLVDSTFTPSSYSSTGSNANINNANNTALGRLPRPA
GYPSTVSTVEGHGPPLSPAIRVQEVAWKLSSNRERHVPMCEDLELRRDSGSAGTQAHCLLLR
KANPSRCHSRESQAAMAGQEETSQDETYEVKMNHDTEACSEPSLLSTEMLSYQDDENRQLTL
PEEDKRDIRQSPKRGFLRSASLGRRASFHLECLKRQKDRGGDISQKTVLPLHLVHHQALAVAG
LSPLLQRSHSPASFPRPFATPPATPGSRGWPPQPVPTLRLEGVESSEKLNSSFPSIHCGSWAE
TTPGGGGSSAARRVRPVSLMVPSQAGAPGRQFHGSASSLVEAVLISEGLGQFAQDPKFIEVTT
QELADACDMTIEEMESAADNILSGGAPQSPNGALLPFVNCRDAGQDRAGGEEDAGCVRARGR
PSEEELQDSRVYVSSL (SEQ ID NO: 106)

ARTIFICIAL EXPRESSION CONSTRUCTS FOR SELECTIVELY MODULATING GENE EXPRESSION IN INTERNEURONS

CROSS-REFERENCE TO RELATED APPLICATIONS

This application is a U.S. National Phase Application based on International Patent Application No. PCT/US2019/054539, filed on Oct. 3, 2019, which claims priority to U.S. Provisional Patent Application Nos. 62/742,835 filed Oct. 8, 2018; 62/749,012 filed Oct. 22, 2018; and 62/810,281 filed Feb. 25, 2019, each of which is incorporated herein by reference in its entirety as if fully set forth herein.

STATEMENT REGARDING FEDERALLY SPONSORED RESEARCH OR DEVELOPMENT

This invention was made with government support under grant RF1MH114126 awarded by the National Institutes of Health. The government has certain rights in the invention.

REFERENCE TO SEQUENCE LISTING

The Sequence Listing associated with this application is provided in text format in lieu of a paper copy and is hereby incorporated by reference into the specification. The name of the text file containing the Sequence Listing is 2G84652_ST25.txt. The text file is 379 KB, was created on Mar. 2, 2021, and is being submitted electronically via EFS-Web.

FIELD OF THE DISCLOSURE

The current disclosure provides artificial expression constructs for selectively modulating gene expression in selected central nervous system cell types. The artificial expression constructs can be used to selectively express synthetic genes or modify gene expression in GABAergic forebrain interneurons.

BACKGROUND OF THE DISCLOSURE

GABAergic interneurons play critical roles in central nervous system processing as well as development. Dysfunction of these cells can also contribute to numerous neuropsychiatric disorders, such as schizophrenia and autism. GABAergic interneurons also play a role in epilepsy.

Cell-type or cell-class specific gene delivery using non-pathogenic recombinant adeno-associated virus (rAAV) is showing increasing promise for the treatment of diverse diseases. Inclusion within rAAVs of one or more cis-acting DNA-control elements, such as specific promoters or enhancers, has been beneficial to provide specificity of expression within particular target cells, including specific cell types or cell classes in the brain.

Dimidschstein and colleagues (*Nat Neurosci* 19(12): 1743-1749, 2016) developed a rAAV that permits largely selective gene expression in GABAergic interneurons within the telencephalon. This rAAV includes a 527 bp enhancer sequence (referred to as mI56i or mDlx) from the intergenic interval between the distal-less homeobox 5 and 6 genes (Dlx5/6), which are naturally expressed by forebrain GABAergic interneurons during embryonic development. The construct of Dimidschstein et al. is available on Addgene as ID #83900 (in which the enhancer drives eGFP expression). Additional constructs which employ the murine or human I56i enhancer to drive various transgenes are available through Addgene, such as Plasmid ID #s 83899 (driving GCaMP6f expression), 83898 (driving ChR2 expression), 83895 (driving synthetic eGFP expression), 89897 (driving hM3DREADD expression), 83896 (driving hM4Di expression), and 83894 (driving synthetic tdTomato expression). See also U.S. Patent Publication No. US2018/0078658.

Additionally, the mI56i enhancer has previously been used to reliably target reporter genes in a pattern very similar to the normal patterns of Dlx5/6 expression during embryonic development (Zerucha et al., *J Neuroscience* 20:709-721, 2000; Stühmer et al., *Cerebral Cortex* 12:75-85, 2002; Stenman et al., *J Neuroscience* 23:167-174, 2003; Monory et al., *Neuron.* 51:455-455, 2006; Miyoshi et al., *J Neuroscience* 30:1532-1594, 2010).

One significant drawback to using rAAVs as a gene-delivery system is the restricted packaging limit of AAVs; this is particularly limiting to the inclusion of lengthy genetic control and expression elements. In addition, many existing interneuron-specific rAAV expression constructs can provide weak gene expression reducing their usefulness in research and therapeutic uses.

SUMMARY OF THE DISCLOSURE

The current disclosure overcomes drawbacks of the prior art by providing engineered enhancer elements that provide rapid and strong cell-specific expression of heterologous encoding sequences in forebrain GABAergic interneurons.

In particular embodiments, the artificial enhancer elements include a concatemerized core of a I56i enhancer. These artificial enhancer elements provide more rapid onset of transgene expression compared to a single full length original (native) enhancer.

In particular embodiments, the I56i enhancer core can be derived from, for example the human, murine, or zebrafish I56i enhancer (SEQ ID NOs. 1, 4, and 5 respectively). The selected cores of the I56i enhancer can include SEQ ID NO: 2 (core shared by human and mouse) or SEQ ID NO: 6 (zebrafish core). In particular embodiments, the cores are concatemerized. For example, SEQ ID NO: 3 provides a three-copy concatemer of the selected human/murine I56i core while SEQ ID NO: 7 provides a three-copy concatemer of the selected zebrafish I56i core.

Of particular interest, the synthetic 3× human/murine core (referred to herein as the 3xhI56iCore; SEQ ID NO: 3) is shorter than the original full length enhancer sequence reported in Dimidschstein et al. (*Nat Neurosci* 19(12):1743-1749, 2016), despite being a 3× concatemer. Thus, this concatemerized core provides more room for cargo genes linked to the enhancer, which is highly desirable. Moreover, the peak level of transgene expression driven by the 3xhI56iCore enhancer is much greater than simply three times the level of the original single full-length original enhancer.

The engineered concatemerized I56i cores disclosed herein enable new and improved gene delivery vectors that are particularly useful for achieving selective transgene expression in forebrain GABAergic interneurons in diverse animal species, including humans.

BRIEF DESCRIPTION OF THE FIGURES

Many of the drawings submitted herein are better understood in color. Applicants consider the color versions of the drawings as part of the original submission and reserve the right to present color images of the drawings in later proceedings.

(FIG. 2A) Schematic representations of three vector constructs, CN1390, CN1389, and CN1244 (CN1203 scAAV). Key: hI56i—full length human enhancer (black box; SEQ ID NO: 1); selected hI56i core (grey box; SEQ ID NO: 2) and 3× concatemer of core (grey boxes; SEQ ID NO: 3); minBG—minimal beta globin promoter; SYFP2—super yellow fluorescent protein 2; WPRE3—woodchuck hepatitis virus post-transcriptional regulatory element 3; BGHpA—bovine growth hormone polyA sequence; L-ITR and R-ITR—Adeno-associated virus-2 (AAV2) inverted terminal repeats (ITRs). (FIG. 2B) Fluorograph images showing relative expression of SYFP2 from AAV vector constructs CN1244, CN1389, and CN1390. Adult wild type mice were retro-orbitally injected with 1E+11 genome copies of the indicated viruses. Animals were maintained for 3-4 weeks, then euthanized, with brains extracted and sliced, followed by live tissue epifluorescence imaging of native fluorescence. Exposure times were matched to allow direct comparison of transgene expression levels. The first three panels are a 500 msec exposure for each of the indicated constructs; the fourth panel is a shorter (50 msec) exposure image of CN1390. CN1390 with the engineered concatemerized core demonstrated strong and more rapid transgene expression.

(FIG. 4A) Fluorograph images showing relative expression of SYFP2 from AAV vector constructs CN1244 and CN1390. Neocortical slices were cultured from adult macaque brain and infected with nominally-matched titers of the indicated viruses. Brain slice cultures were maintained in the incubator for 4 days in vitro, 4 days post infection (4 DIV/4 DPI), then used for live tissue epifluorescence imaging of native fluorescence. Exposure times were matched to allow direct comparison of transgene expression levels. CN1390 with the engineered concatemerized core demonstrated strong and more rapid transgene expression. (FIG. 4B) Fluorograph images showing relative expression of SYFP2 from AAV vector constructs CN1244 and CN1390. Hippocampal slices were cultured from adult macaque brain and infected with nominally-matched titers of the indicated viruses. Brain slice cultures were maintained in the incubator for 6 days in vitro, 6 days post infection (6 DIV/6 DPI), then used for live tissue epifluorescence imaging of native fluorescence. Exposure times were matched to allow direct comparison of transgene expression levels. CN1390 with the engineered concatemerized core demonstrated strong and more rapid transgene expression.

FIGS. 5A-5D illustrate rapid viral-genetic labeling of human neocortical interneurons for targeted patch clamp recording and analysis. (FIG. 5A) Time course of virus-mediated YFP expression following human brain slice transduction with CN1390 eB. (FIG. 5B) Expanded view of the boxed region in (FIG. 5A). (FIG. 5C) High magnification view of a virus labeled interneuron with bipolar morphology. (FIG. 5D) Example whole cell recordings from four different virus-labeled YFP+ human interneurons demonstrating diverse firing patterns to supra-threshold current injection. (FIG. 5E) At various times in culture, slices were taken for terminal patch clamp recording analysis to establish the firing properties of labeled neurons. Functional analysis of human neocortical interneuron firing patterns and electrical properties by patch clamp recording was feasible as early as 40 hours post-infection with CN1390 AAV-PHP.eB virus.

LAMP5 LTK, 83 Exc L2-4 LINC00507 GLP2R, 84 Exc L2-3 LINC00507 FREM3, 85 Exc L5-6 THEMIS C1QL3, 87 Exc L3-4 RORB CARM1P1, 89 Exc L3-5 RORB ESR1, 90 Exc L3-5 RORB COL22A1, 92 Exc L3-5 RORB FILIP1L, 93 Exc L3-5 RORB TWIST2, 96 Exc L4-5 RORB FOLH1B, 98 Exc L4-6 RORB SEMA3E, 99 Exc L4-5 RORB DAPK2, 100 Exc L5-6 RORB TTC12, 101 Exc L4-6 RORB C1R, Exc L4-5 FEZF2 SCN4B (PT), 102 Exc L5-6 THEMIS DCSTAMP, 103 Exc L5-6 THEMIS CRABP1, 104 Exc L5-6 THEMIS FGF10, 105 Exc L4-6 FEZF2 IL26 (NP), 106 Exc L5-6 FEZF2 ABO, 107 Exc L6 FEZF2 SCUBE1, 108 Exc L5-6 SLC17A7 IL15, 109 Exc L6 FEZF2 OR2T8, 110 Exc L5-6 FEZF2 EFTUD1P1, Glial types; OPC L1-6 PDGFRA, Astro L1-6 FGFR3 SLC14A1, Astro L1-2 FGFR3 GFAP, Oligo L1-6 OPALIN, Endo L2-6 NOSTRIN, AND Micro L1-3 TYROBP.

Figure 7:
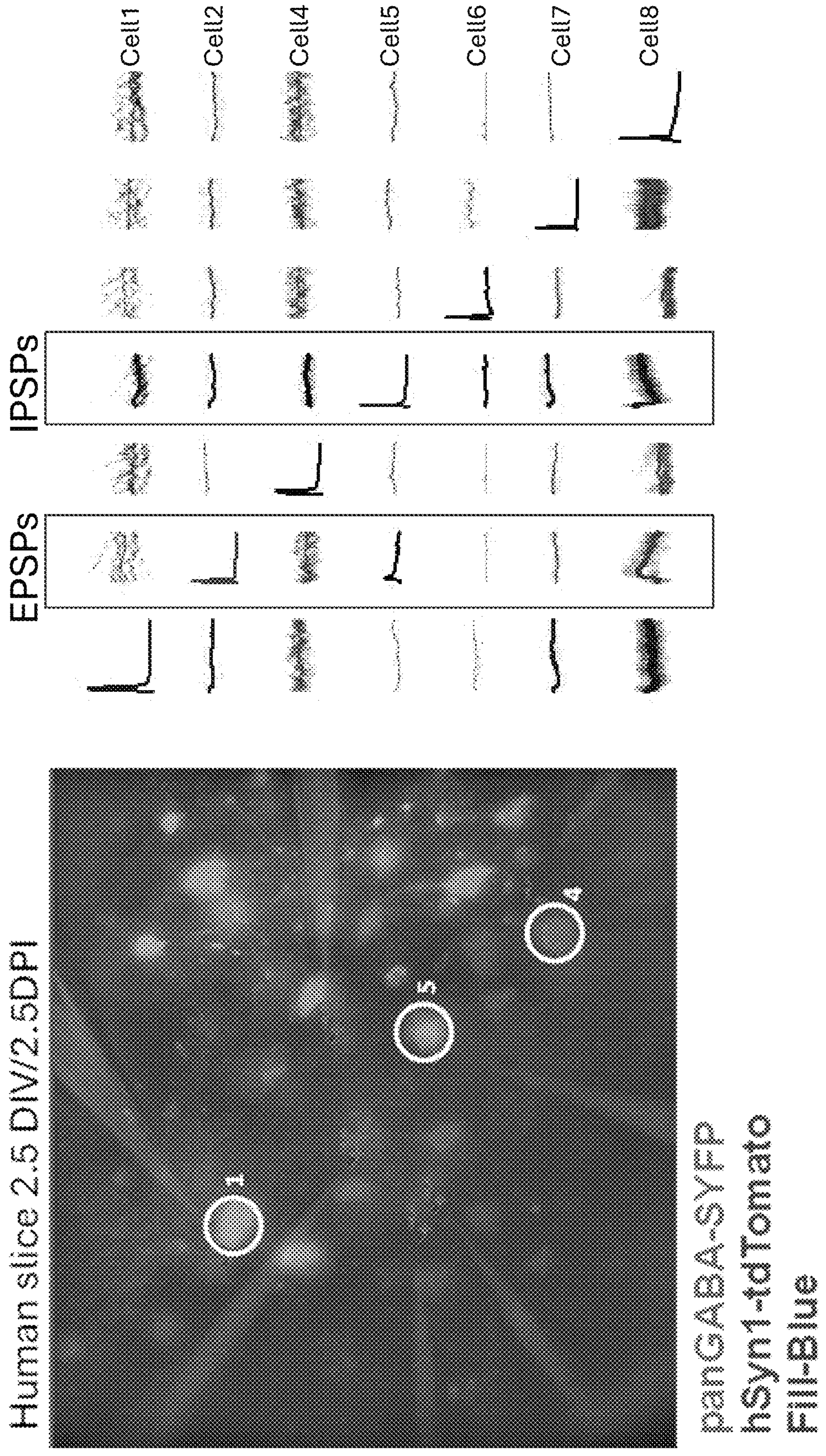

FIG. 7: Fast expression from CN1390 allows assessment of human circuit connectivity. Human neocortical organotypic slice was transduced with CN1390 and AAV-hSyn1-dTomato for 2.5 days. After only two and half days in culture, GABAergic and all neuronal cells can be labeled in culture using CN1390 and AAV-hSyn1-dTomato, respectively. Human synapsin 1 (hSyn1) is a well-known pan-neuronal promoter. This allows the assessment of connectivity between prospectively virally marked patched cells (labeled by cascade blue). The fluorescent dyes listed in the bottom left corner of the fluorescent image are (from top to bottom): panGABA-SYFP, hSyn1-tdTomato, and Fill-Blue.

Figure 8A:
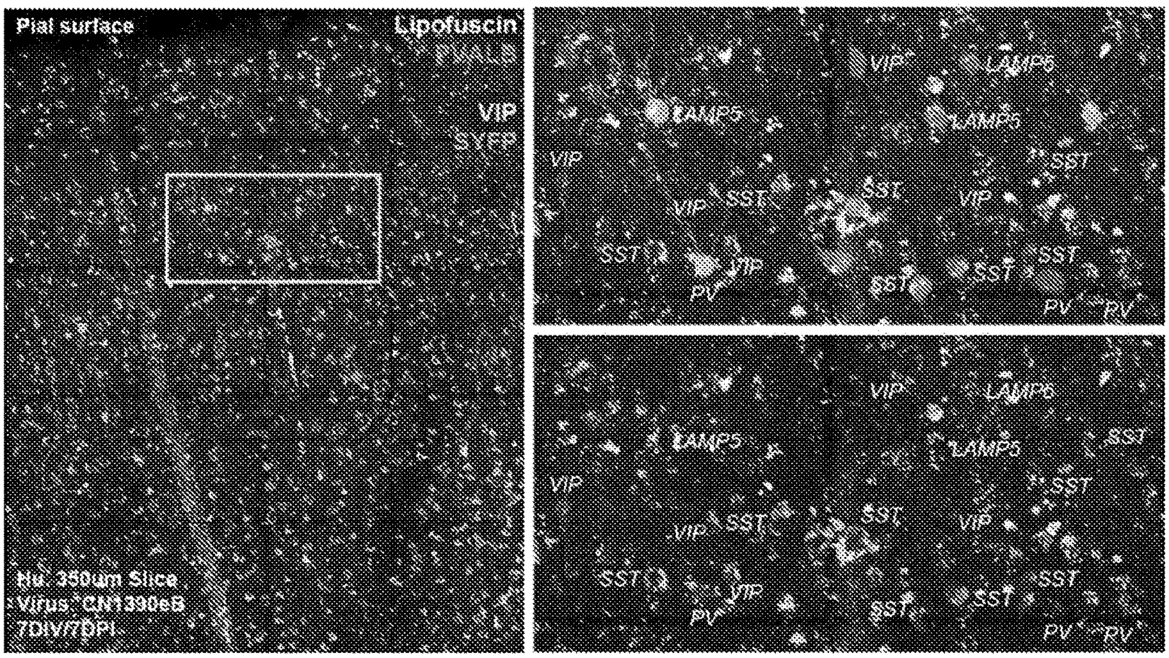
Figure 8B:
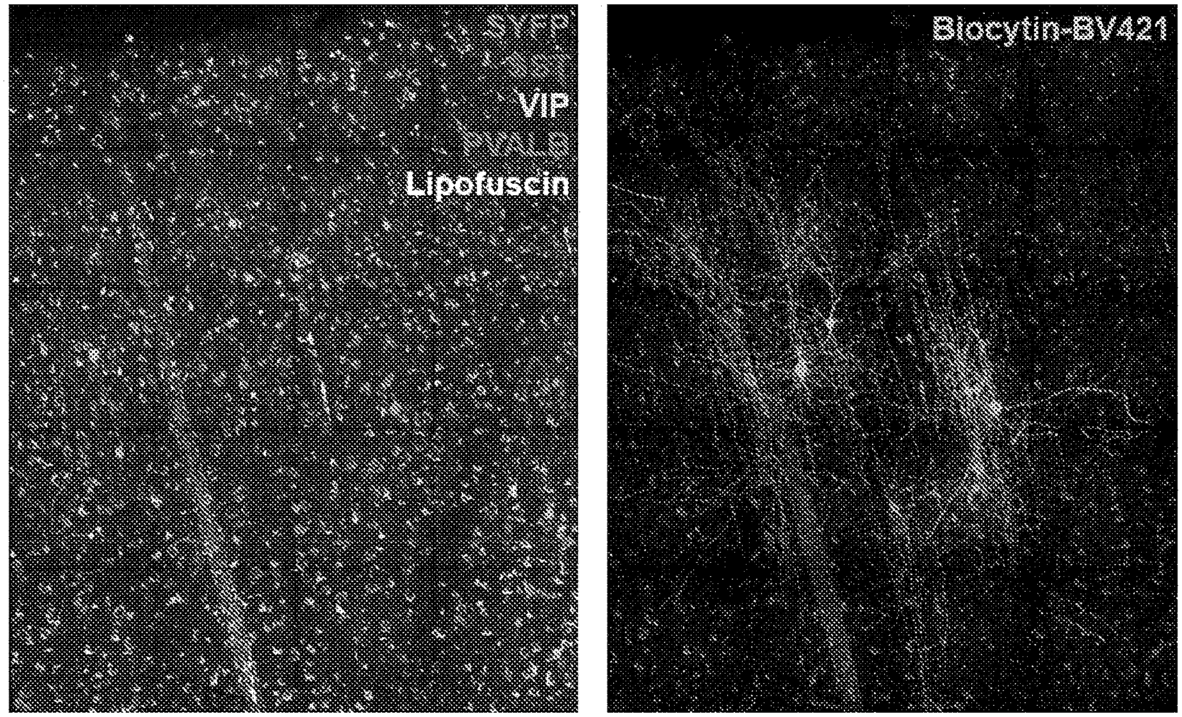
Figure 9A:
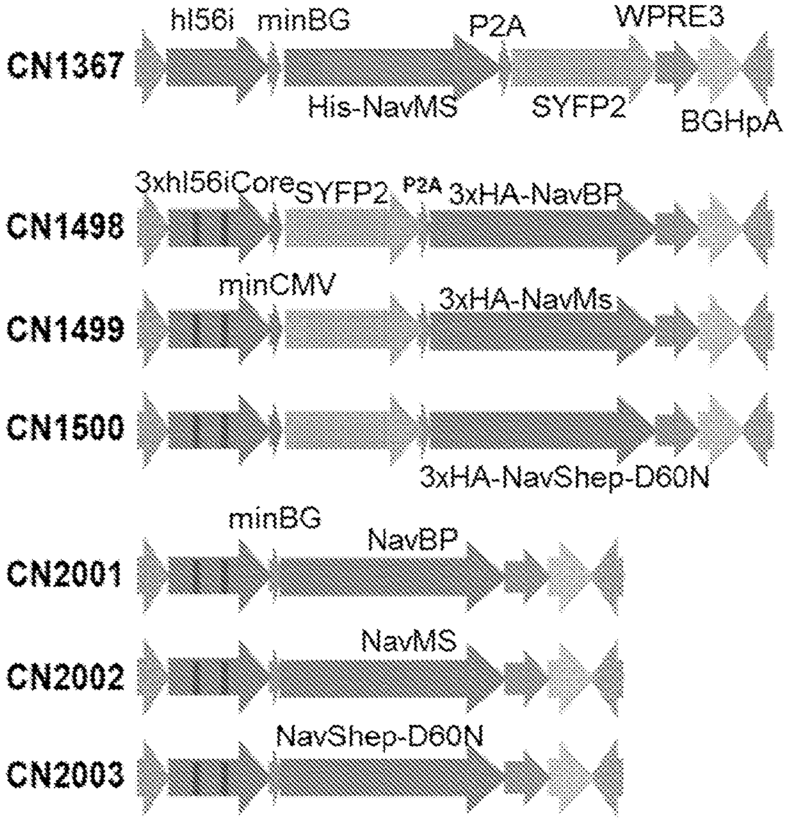
Figure 9B:
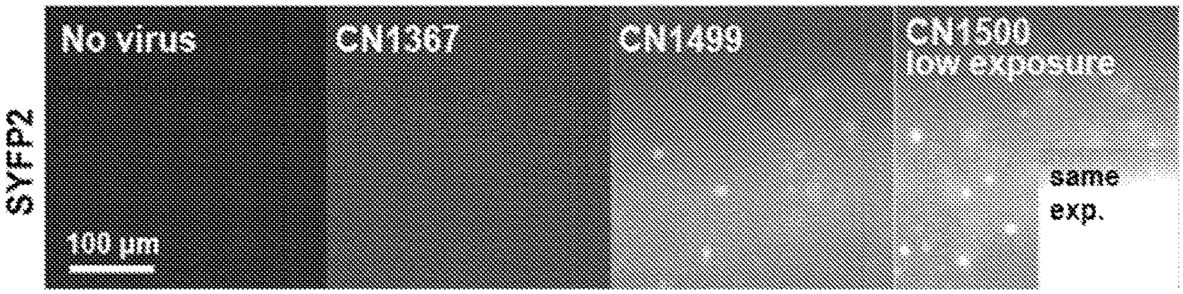
Figure 9C:
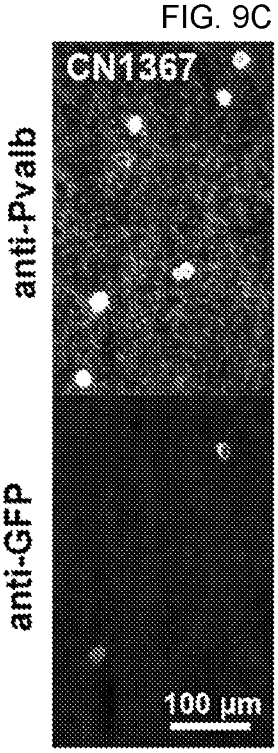
Figure 9D:
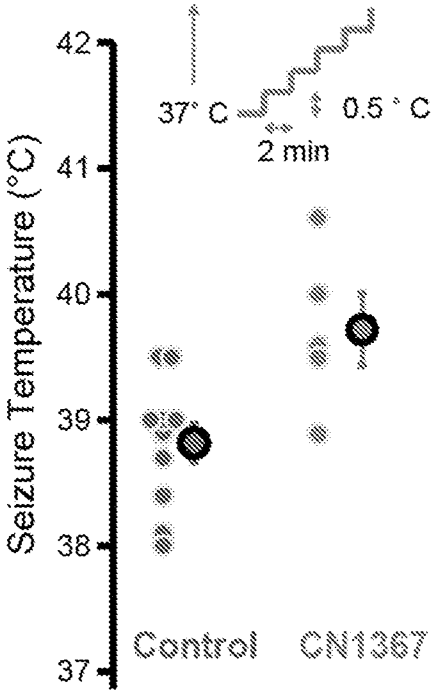
Figure 9E:
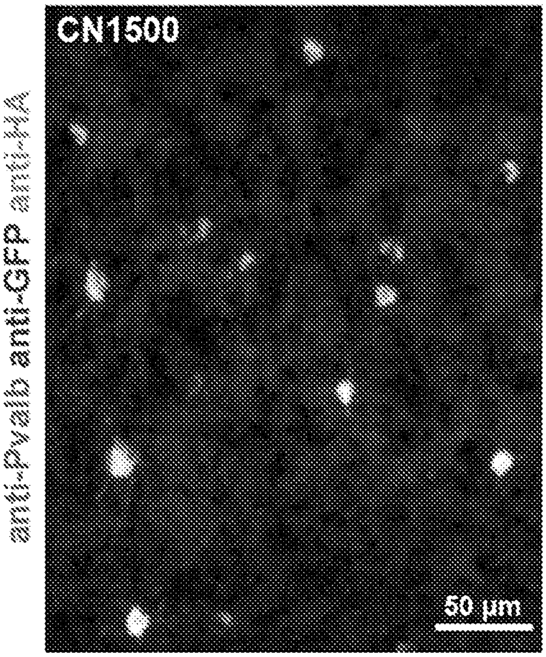
Figure 9F:
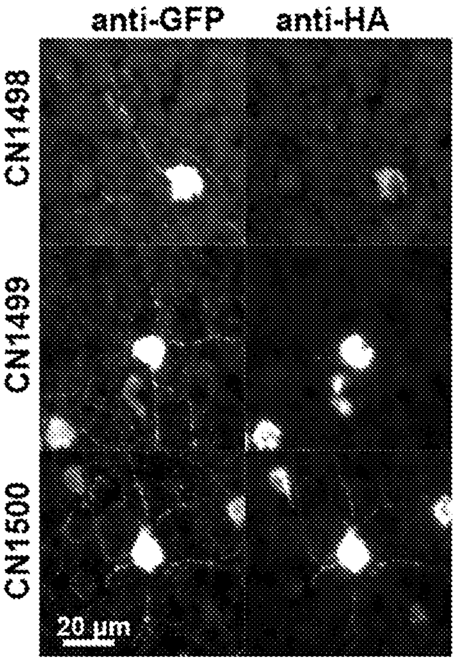

FIGS. 8A, 8B: All major classes of human neocortical GABAergic neurons are marked by CN1390. (FIG. 8A) Multiplexed FISH using HCR v3.0 reveals major classes of GABAergic neurons labeled by somatostatin (SST), parvalbumin (PVALB), or vasoactive intestinal peptide (VIP) genes. Labeling by CN1390 in 350 μm thick neocortical brain slice culture is shown. Text on the left image of FIG. 8A are as follows: (top left) Pial surface; (top right) Lipofuscin, PVALB, SST, VIP, and SYFP; and (bottom left) Hu, 350 μm Slice, Virus CN1390eB, 7 DIV/DPI. (FIG. 8B) Prospective cell class marking for physiology, connectivity and morphology. Multiplexed FISH reveals molecular identities of the CN1390-labeled cell classes and some of the patched cells that were back-filled with neurobiotin and visualized by Streptavidin-BV421. The left image of FIG. 8B is labeled with SYFP, SST, VIP, PVALB, and Lipofuscin. The right image of FIG. 8B is labeled Biocytin-BV421. All these cells show GABAergic cell morphology and most were marked by expression of SYFP2 from CN1390.

FIGS. 9A-9F. AAV vector reagents to reverse Dravet Syndrome (DS) symptoms in Scn1a$^{+/-}$ mice. (9A) Vectors to deliver epitope-tagged Nav genes of bacterial origin (NavBacs). The Nav genes shown here are NavMs (from *Magnetococcus marinus*), NavBp (from *Bacillus pseudofirmus*), and NavSheP-D60N (from *Shewanella putrifaciens* with an engineered D60N mutation). These examples all have N-terminal epitope tags (hexahistidine in the case of CN1367, or 3×HA for CN1498, CN1499, and CN1500). hI56i refers to the full-length I56i enhancer of SEQ ID NO: 1; 3×hI56iCore refers to the concatemerized core of the I56i enhancer (SEQ ID NO: 3); (9B) Graded expression levels from NavBac vectors. (9C) Weak but detectable expression in Pvalb interneurons from vector CN1367. (9D) Trend towards seizure protection with vector CN1367. (9E) Vector 1500 drives high-level expression in Pvalb$^{+}$ and Pvalb$^{-}$ interneurons throughout cortex. (9F) Abundant production of HA-tagged NavBacs in cell bodies and proximal processes with vectors 1498 and 1500, but not 1499.

Figure 10:
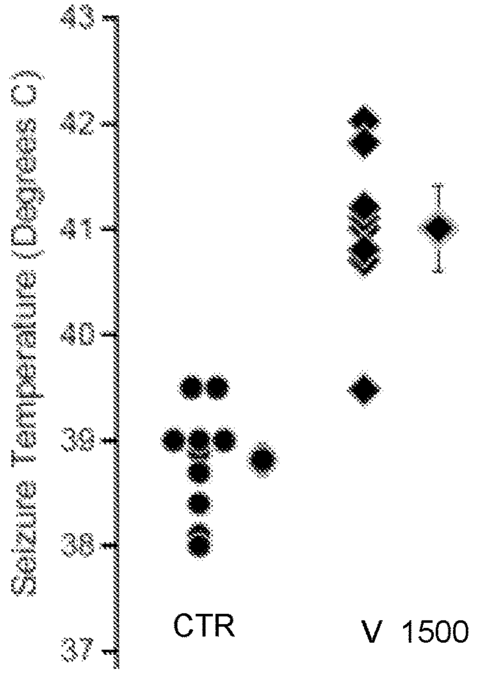
Figure 10:
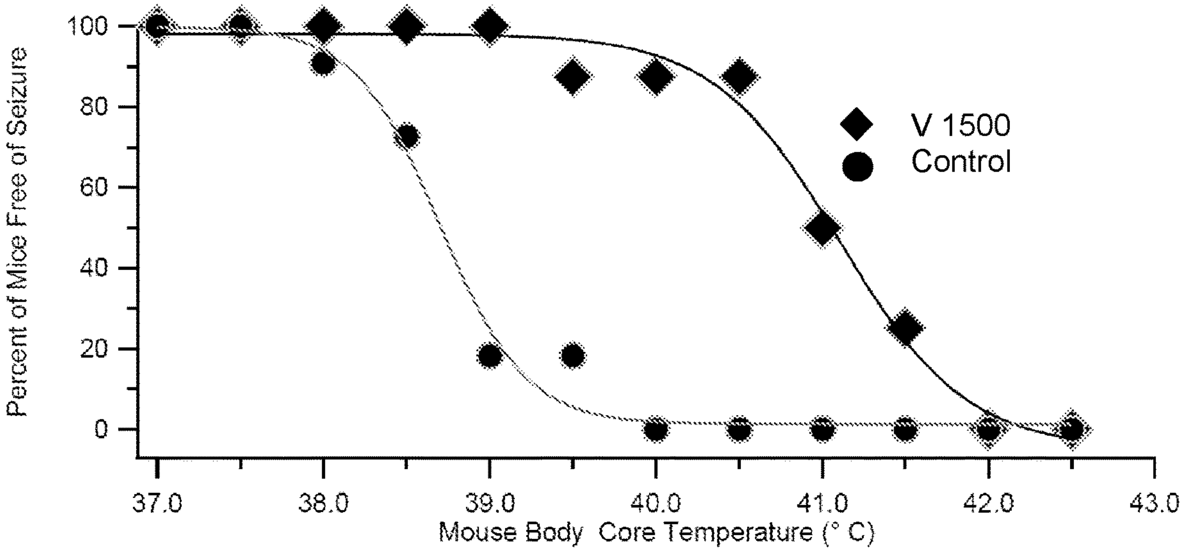

FIG. 10. CN1500 rAAV vector substantially reverses febrile seizures in Scn1a$^{+/-}$ mice. Febrile seizure assay shown as internal temperature where a seizure is first detected. (Top) Circles show Scn1a$^{+/-}$ mice untransduced with AAVs, while the diamonds represent animal that were transduced with CN1500. The large dot and error bars represent the average+/− SEM for each group of animals. (Bottom) Trends of the same data are shown as the percentage of mice in each group that remain seizure free at different temperatures using a Kaplan-Meier curve.

Figure 11A:
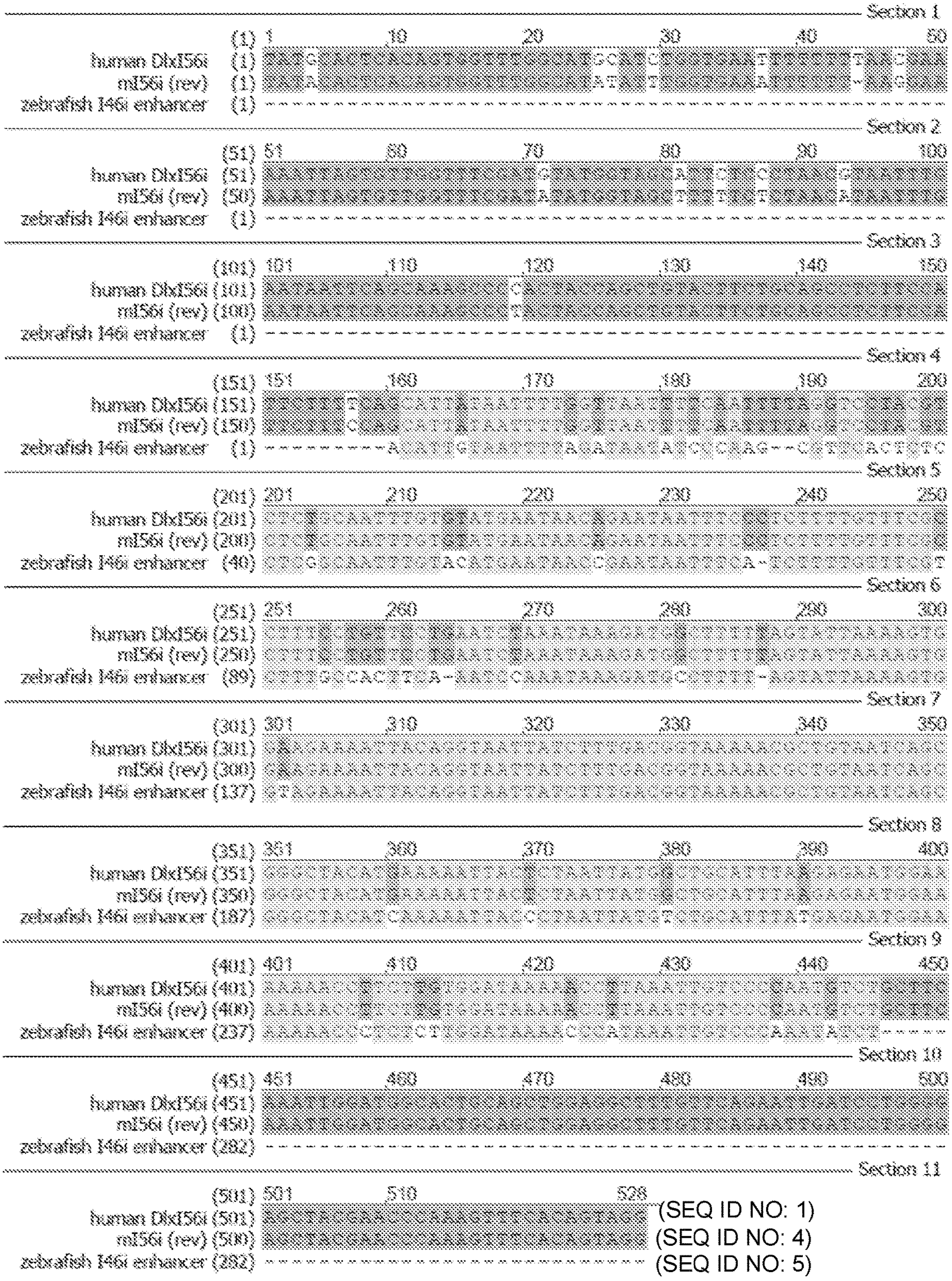
Figure 11B:
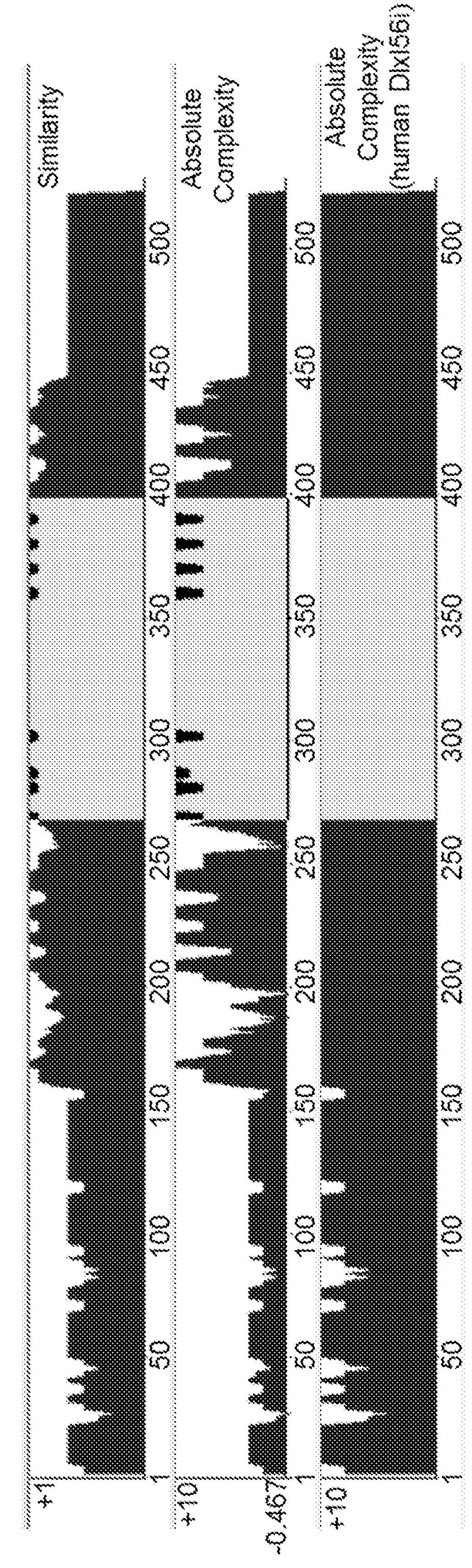

FIGS. 11A, 11B: Conservation of I56i enhancer sequences. (FIG. 11A) alignment of the human (SEQ ID NO: 1) I56i, murine (SEQ ID NO: 4) I56i, and zebrafish (SEQ ID NO: 5) I46i enhancer sequences. Residues shared by all three sequences are highlighted in light gray; those shared by the murine and human sequences are highlighted in dark gray. The core sequence (SEQ ID NO: 2) corresponds to positions 268-398 of the illustrated human sequence. The mouse and human I56i enhancer core sequences are exactly identical (100% sequence identity), as this is an ultraconserved enhancer sequence. It is also highly similar with the zebrafish genomic sequence, and the orthologous zebrafish enhancer (called I46i) has been used in many contexts over the years to drive transgene expression in neocortical interneurons, including for mouse neocortical interneurons. (FIG. 11B) graph illustrating the similarity between the human, murine, and zebrafish enhancer sequences. Graph shows (from right to left, and as labeled) Similarity, Absolute Complexity, and Absolute Complexity (human I56i).

Figure 12:
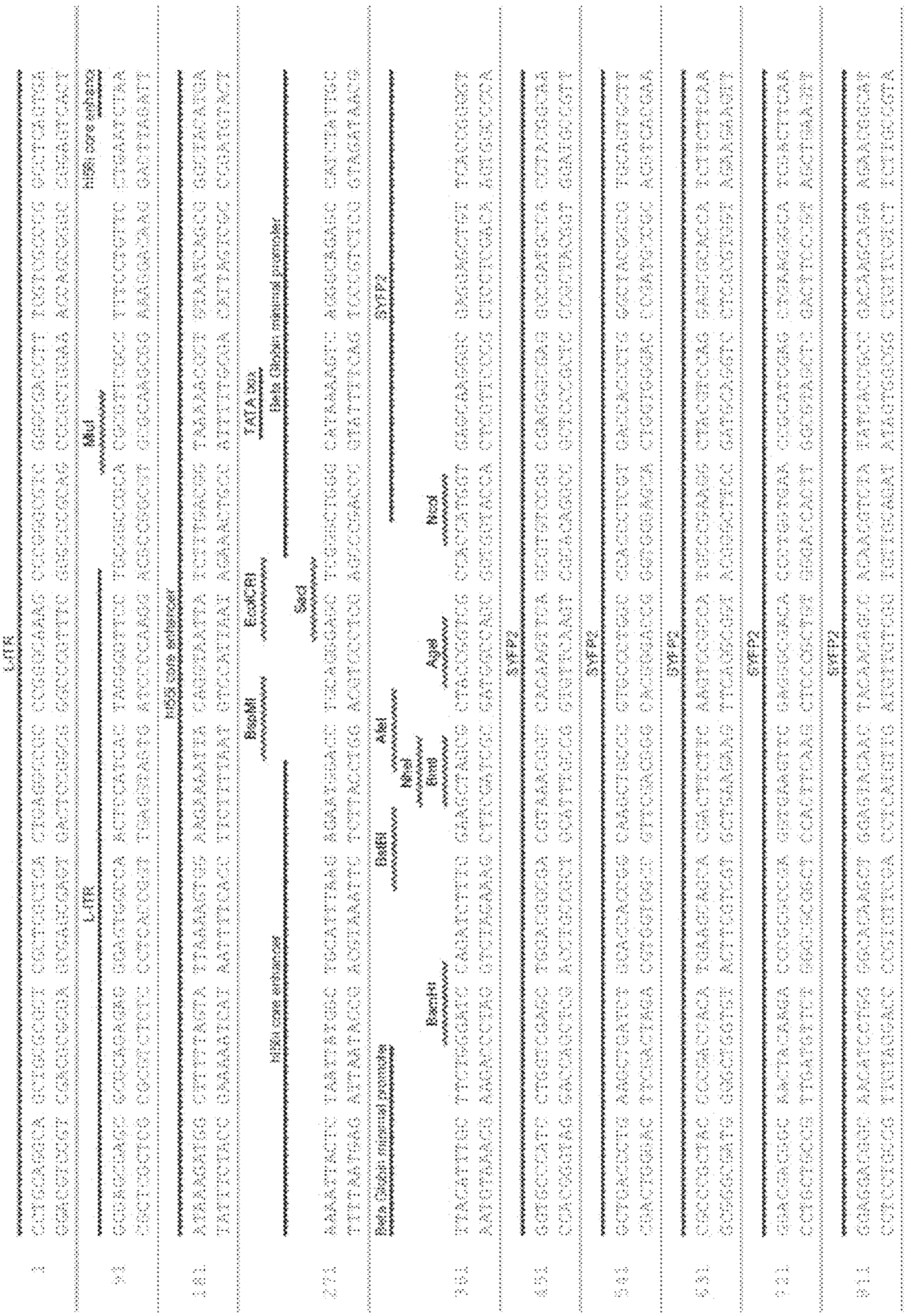

FIG. 12: the sequence and indicated features of construct CN1389 pAAV-hI56i(core)-minBG-SYFP2-WPRE3-BGHpA (SEQ ID NO: 41). Select restriction endonuclease sites are indicated, as are the regions corresponding to different parts of the construct.

Figure 13:
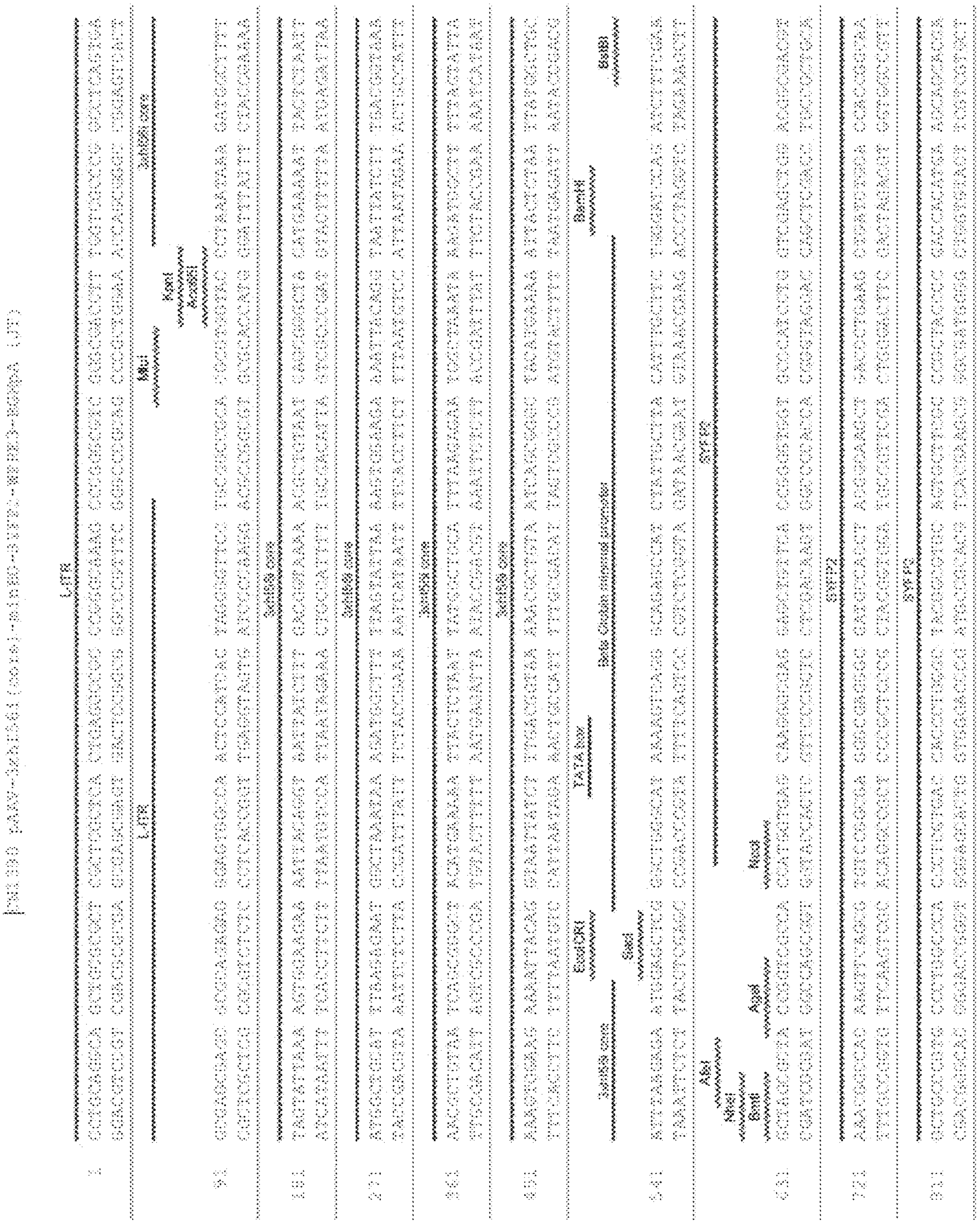

FIG. 13: the sequence and indicated features of construct CN1390 pAAV-3×hI56i(core)-minBG-SYFP2-WPRE3-BGHpA (SEQ ID NO: 42). Select restriction endonuclease sites are indicated, as are the regions corresponding to different parts of the construct.

Figure 14:
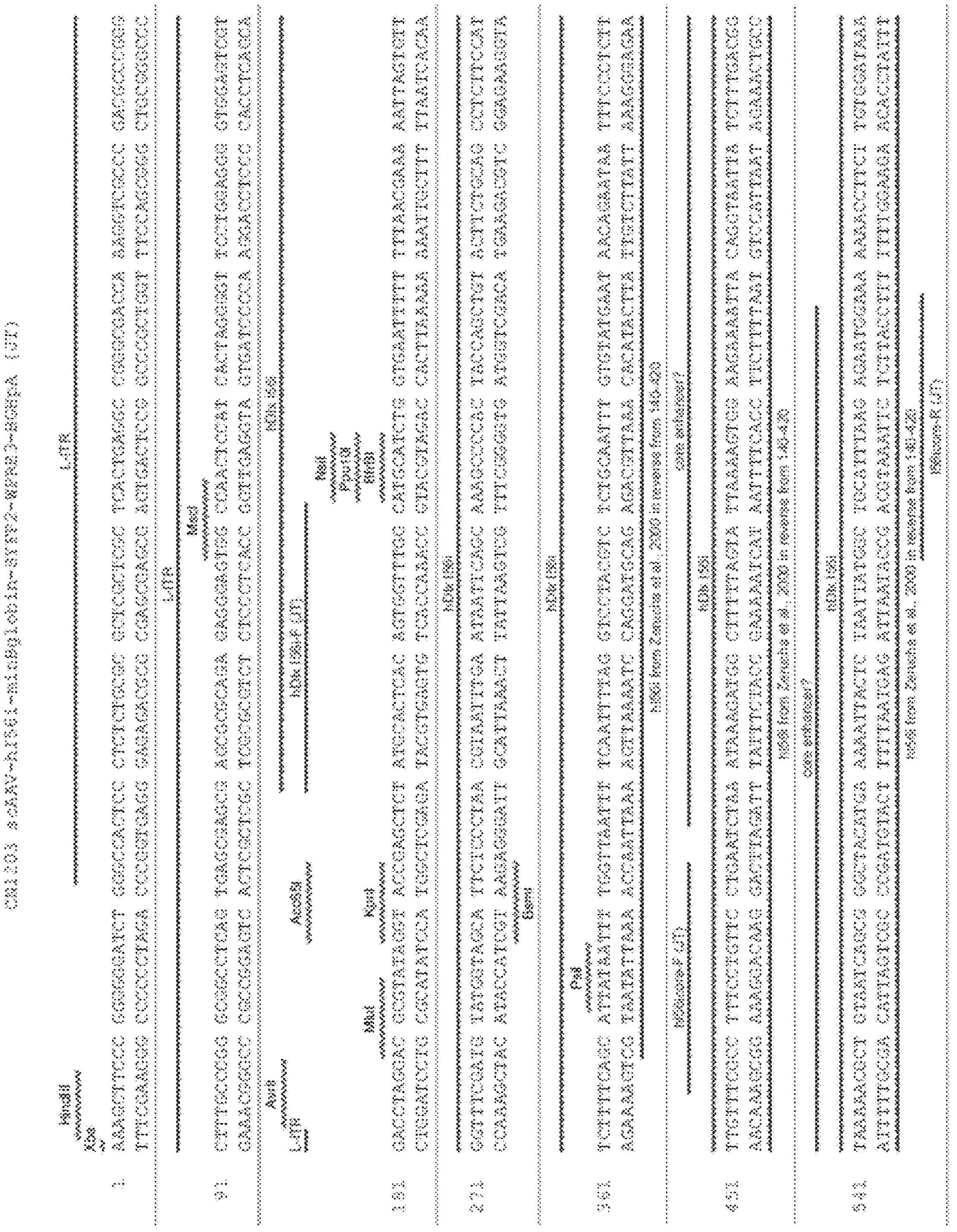

FIG. 14: the sequence and indicated features of construct CN1203 scAAV-hI56i-minbGlobin-SYFP2-WPRE3-BGHpA (SEQ ID NO: 43). Select restriction endonuclease sites are indicated, as are the regions corresponding to different parts of the construct.

FIG. 15. Features of exemplary vectors disclosed herein.

FIG. 16. Artificial expression constructs within the teaching of the current disclosure. Each construct begins with a concatemerized core of the hI56i core (e.g., SEQ ID NO: 3 or 7) designated as *. The following abbreviations are also used: Beta-Globin minimal promoter (minB, referred to as minBglobin elsewhere herein), Minimal cytomegalovirus promoter (minC, referred to as minCMV elsewhere herein), Mutated minimal cytomegalovirus promoter (mut), Minimal rhodopsin promoter (minR, referred to as minRho elsewhere herein), Cytomegalovirus promoter (CMV), Simian vacuolating virus 40 promoter (SV40), Hsp68 minimal promoter (H68, referred to as proHSP68 elsewhere herein), Rous Sarcoma Virus long-terminal repeat promoter (RSV), Fluorescent protein (FP), Blue fluorescent protein (BFP), Cyan fluorescent protein (CFP), Green fluorescent protein (GFP), Orange fluorescent protein (OFP), Red fluorescent protein (RFP), Far red fluorescent protein (fRFP), Yellow fluorescent protein (YFP), Luciferase (Luc), Enzyme (enz), Transcription factor (TF), Receptor (rec), Cellular trafficking protein (CTP), Signaling molecule (SM), Neurotransmitter (NT), Calcium reporter (CR), hannel rhodopsin (ChR), Guide RNA (gRNA), Nuclease (Nuc), Woodchuck hepatitis virus post-transcriptional response element (W, referred to as WPRE3 elsewhere herein), Bovine growth hormone polyadenylation signal (bG, referred to as bGHpA elsewhere herein), Simian vacuolating virus 40 polyadenylation signal (S, referred to as SV40 pA elsewhere herein), Internal ribosome entry site 2 (12, referred to as IRES2 elsewhere herein), and 2A skipping elements (T2A, P2A, E2A, and F2A).

FIG. 17. Additional sequences supporting the disclosure: hI56i enhancer: (SEQ ID NO: 1); Core of the hI56i enhancer: (SEQ ID NO: 2); 3×hI56iCore, Triply Concatamerized Core of the hI56i enhancer: (SEQ ID NO: 3); Murine I56i Enhancer (core is the same as human): (SEQ ID NO: 4); Zebrafish I46i Enhancer: (SEQ ID NO: 5); Core of the Zebrafish I46i Enhancer: (SEQ ID NO: 6); 3× Concatamerized Core of the Zebrafish I46i Enhancer: (SEQ ID NO: 7); Beta-Globin Minimal Promoter pBGmin/minBGlobin/minBGprom): (SEQ ID NO: 8); minCMV Promoter: (SEQ ID NO: 9); Mutated minCMV Promoter (SacI RE site removed): (SEQ ID NO: 10); minRho Promoter: (SEQ ID NO: 11); Hsp68 minimal Promoter (proHsp68): (SEQ ID NO: 12); SYFP2: (SEQ ID NO: 13); EGFP: (SEQ ID NO: 14); Optimized FIp recombinase (FIpO): (SEQ ID NO: 15); Improved Cre recombinase (iCre): (SEQ ID NO: 16); NavMs, endogenous sequence: (SEQ ID NO: 17); NavMs, codon optimized, with N-terminal 3× HA tag and linker: (SEQ ID NO: 18); NavMs, codon optimized, with N-terminal His tag and linker: (SEQ ID NO: 19); NavBp, endogenous sequence: (SEQ ID NO: 20); NavBp, codon optimized, with N-terminal 3× HA tag: (SEQ ID NO: 21); NavSheP-D60N, codon optimized, with N-terminal 3× HA tag: (SEQ ID NO: 22); NavSheP endogenous sequence: (SEQ ID NO: 23); WPRE3: (SEQ ID NO: 24); BGHpA: (SEQ ID NO: 25); P2A Encoding Sequence: (SEQ ID NO: 26); P2A: (SEQ ID NO: 27); T2A: (SEQ ID NO: 28); E2A: (SEQ ID NO: 29); F2A: (SEQ ID NO: 30); N-terminal 3×HA tag: (SEQ ID NO: 31); N-terminal 3×HA tag: (SEQ ID NO: 32); PHP.eB capsid: (SEQ ID NO: 90); AAV9 VP1 capsid protein: (SEQ ID NO: 34); tet-Transactivator version 2 (tTA2): (SEQ ID NO: 35); CN1367—The portion between L-ITR and R-ITR: positions 142-2984: (SEQ ID NO: 36); CN1500—The portion between L-ITR and R-ITR: positions 142-2976: (SEQ ID NO: 37); CN1498—The portion between L-ITR and R-ITR: positions 142-2943: (SEQ ID NO: 38); CN1499—The portion between L-ITR and R-ITR: positions 142-2946: (SEQ ID NO: 39); CN1244—The portion between L-ITR and R-ITR: positions 142-2042: (SEQ ID NO: 40); CN1389—The portion between L-ITR and R-ITR corresponds to positions 142-1660: (SEQ ID NO: 41); CN1390—The portion between L-ITR and R-ITR corresponds to positions 142-1897: (SEQ ID NO: 42); CN1203—The portion between L-ITR and R-ITR corresponds to positions 183-2052: (SEQ ID NO: 43); Lactase (SEQ ID NO: 44); Lipase (SEQ ID NO:45); Helicase (SEQ ID NO: 46); Amylase (SEQ ID NO: 47); α-glucosidase (SEQ ID NO: 48); Transcription factor SP1 (SEQ ID NO: 49); Transcription factor AP-1 (SEQ ID NO: 50); Heat shock factor protein 1 (SEQ ID NO: 51); CCAAT/enhancer-binding protein (C/EBP) β isoform a (SEQ ID NO: 52); Octamer-binding protein 1 (SEQ ID NO: 53); Transforming growth factor receptor β1 (SEQ ID NO: 54); Platelet-derived growth factor receptor (SEQ ID NO: 55); Epidermal growth factor receptor (SEQ ID NO: 56); Vascular endothelial growth factor receptor (SEQ ID NO: 57); Interleukin 8 receptor a (SEQ ID NO: 58); Caveolin (SEQ ID NO: 59); Dynamin (SEQ ID NO: 60); Clathrin heavy chain 1 isoform 1 (SEQ ID NO: 61); Clathrin heavy chain 2 isoform 1 (SEQ ID NO: 62); Clathrin light chain A isoform a (SEQ ID NO: 63); Clathrin light chain B isoform a (SEQ ID NO: 64); Ras-related protein Rab-4A isoform 1 (SEQ ID NO: 65); Ras-related protein Rab-11A (SEQ ID NO: 66); Platelet-derived growth factor (SEQ ID NO: 67); Transforming growth factor-β3 (SEQ ID NO: 68); Nerve growth factor (SEQ ID NO: 69); Epidermal growth factor (SEQ ID NO: 70); GTPase HRas (SEQ ID NO: 71); Cocaine And Amphetamine Regulated Transcript (Chain A) (SEQ ID NO: 72); Protachykinin-1 (SEQ ID NO: 73); Substance P (SEQ ID NO: 74); Oxytocin-neurophysin 1 (SEQ ID NO: 75); Oxytocin (SEQ ID NO: 76); Somatostatin (SEQ ID NO: 77); Myosin light chain kinase, Green fluorescent protein, Calmodulin chimera (Chain A) (SEQ ID NO: 78); Genetically-encoded green calcium indicator NTnC (chain A) (SEQ ID NO: 79); Calcium indicator TN-XXL (SEQ ID NO: 80); BRET-based auto-luminescent calcium indicator (SEQ ID NO: 81); Calcium indicator protein OeNL(Ca2+)-18u (SEQ ID NO: 82); GCaMP6m (SEQ ID NO: 99); GCaMP6s (SEQ ID NO: 100); GCaMP6f (SEQ ID NO: 101); Channelopsin 1 (SEQ ID NOs: 83 and 102); Channelrhodopsin-2 (SEQ ID NOs: 84 and 103); CRISPR-associated protein (Cas) (SEQ ID NO: 85); Cas9 (SEQ ID NO: 86); CRISPR-associated endonuclease Cpf1 (SEQ ID NO: 87); Ribonuclease 4 or Ribonuclease L (SEQ ID NO: 88); Deoxyribonuclease II β (SEQ ID NO: 89); Sodium channel protein type 1 subunit alpha (SEQ ID NO: 104); Potassium voltage-gated channel subfamily KQT member 2 (SEQ ID NO: 105); and Voltage-dependent L-type calcium channel subunit alpha-1C (SEQ ID NO: 106).

DETAILED DESCRIPTION

To fully understand the biology of the brain, different cell types need to be distinguished and defined. To identify and/or study these different cell types, vectors that can selectively label and perturb them need to be identified. In mouse, recombinase driver lines have been used to great effect to label cell populations that share marker gene expression. However, the creation, maintenance, and use of such lines that label cell types with high specificity can be costly, frequently requiring triple transgenic crosses, which yield a low frequency of experimental animals. Furthermore, those tools require germline transgenic animals and thus are not applicable to humans, and recent advances in single-cell profiling, such as single-cell RNA-seq (Tasic et al., Nature 563, 72-78 (2018); Tasic 2016, Nat Neurosci 19, 335-346) and surveys of neural electrophysiology and morphology (Gouwens 2019, Nat Neurosci 22, 1182-1195), have revealed that many recombinant driver lines label heterogeneous mixtures of cell types, and often include cells from multiple subclasses. For example, the Rbp4-Cre mouse driver line, which is commonly used to label layer 5 (L5) neurons, also labels cells with drastically different connectivity patterns: L5 intratelencephalic (IT, also called cortico-cortical) and pyramidal tract (PT, also called cortico-subcortical) neurons.

Dimidschstein and colleagues (*Nat Neurosci* 19(12): 1743-1749, 2016) developed a rAAV that permits largely selective gene expression in GABAergic interneurons within the telencephalon. This rAAV includes a 527 bp enhancer sequence (referred to as mI56i or mDlx) from the intergenic interval between the distal-less homeobox 5 and 6 genes (Dlx5/6), which are naturally expressed by forebrain GABAergic interneurons during embryonic development. The construct of Dimidschstein et al. is available on Addgene as ID #83900 (in which the enhancer drives eGFP expression). Additional constructs which employ the murine or human I56i enhancer to drive various transgenes are available through Addgene, such as Plasmid ID #s 83899 (driving GCaMP6f expression), 83898 (driving ChR2 expression), 83895 (driving synthetic eGFP expression), 89897 (driving hM3DREADD expression), 83896 (driving hM4Di expression), and 83894 (driving synthetic tdTomato expression). See also U.S. Patent Publication No. US2018/0078658.

Additionally, the mI56i enhancer has previously been used to reliably target reporter genes in a pattern very similar to the normal patterns of Dlx5/6 expression during embryonic development (Zerucha et al., *J Neuroscience* 20:709-721, 2000; Stühmer et al., *Cerebral Cortex* 12:75-85, 2002; Stenman et al., *J Neuroscience* 23:167-174, 2003; Monory et al., *Neuron.* 51:455-455, 2006; Miyoshi et al., *J Neuroscience* 30:1532-1594, 2010).

One significant drawback to using rAAVs as a gene-delivery system is the restricted packaging limit of AAVs; this is particularly limiting to the inclusion of lengthy genetic control and expression elements. In addition, many existing interneuron-specific rAAV expression constructs can provide weak gene expression reducing their usefulness in research and therapeutic uses.

Figure 1:
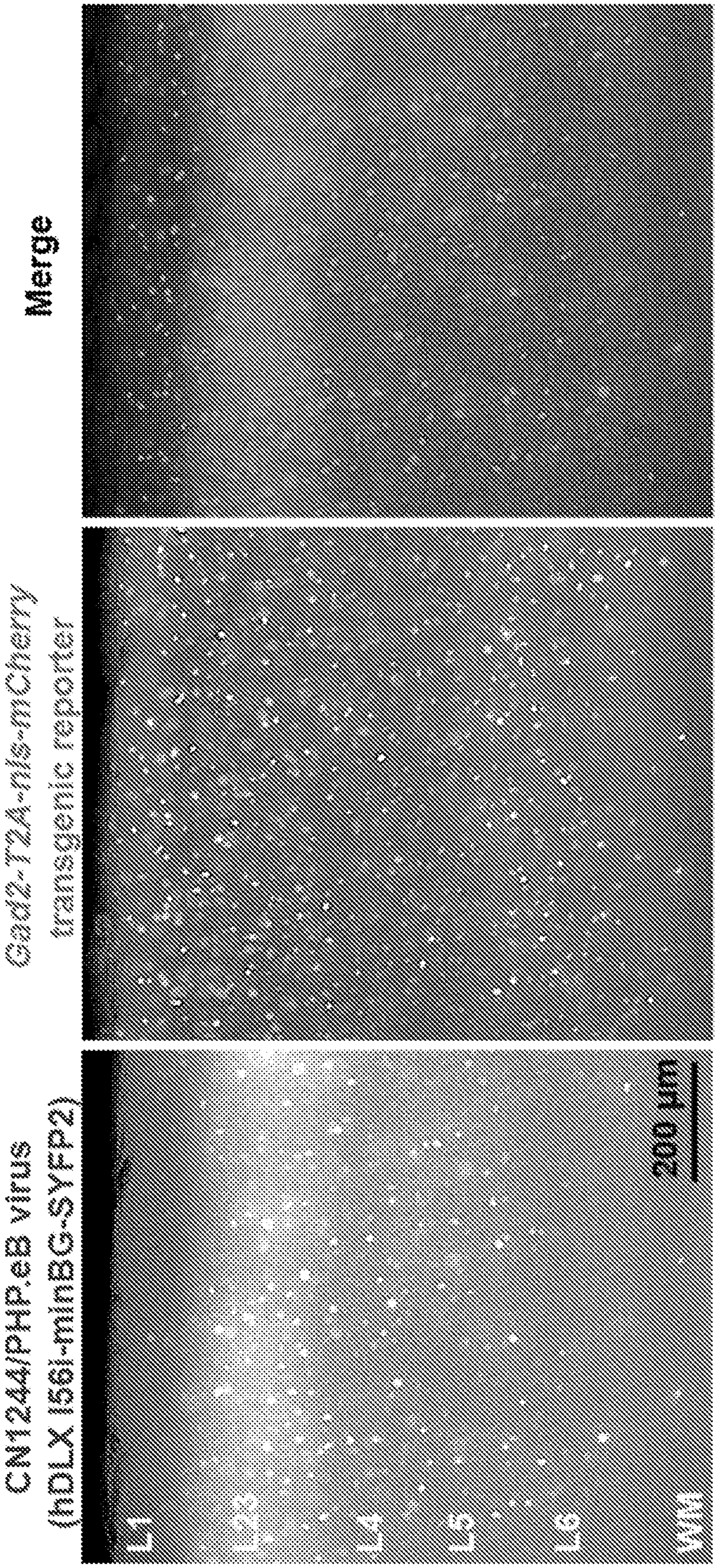
FIG. 1: Virus CN1244/PHP.eB. $10^{11}$ genome copies delivered intravenously (IV) in adult mouse. PHP.eB encodes for a capsid originating from AAV9 that allows efficient AAV transit across the mouse blood brain barrier, which enables delivery of AAV vectors in a brain-wide fashion. This capsid differs from AAV9 such that amino acids starting at residue 586: SAQA (SEQ ID NO: 98) are changed to SDGTLAVPFKA (SEQ ID NO: 33). The Gad2-T2A-nls-mCherry reporter marks nearly all inhibitory neurons in the mouse brain (here shown V1 visual cortex), and the delivered CN1244/PHP.eB virus drives specific SYFP2 reporter activity in forebrain GABAergic neurons.
Figure 2A:
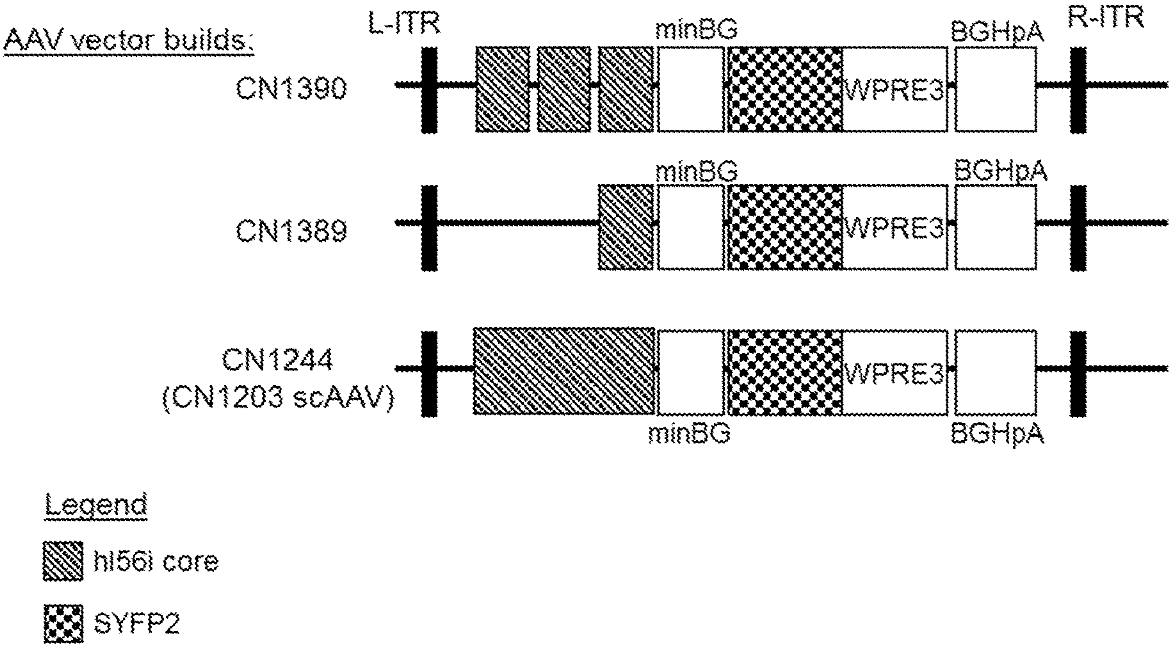
FIGS. 2A,2B: Comparison of CN1244 vs CN1389 vs CN1390.
Figure 2B:
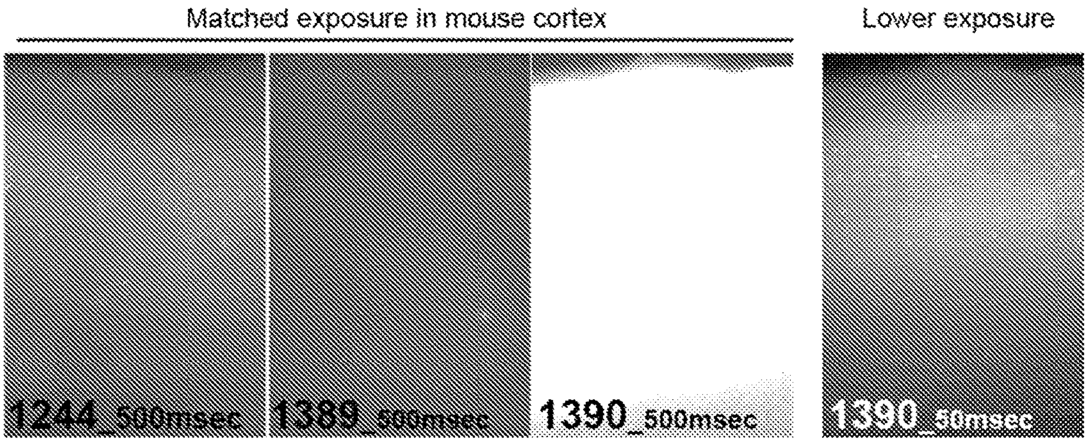
Figure 3:
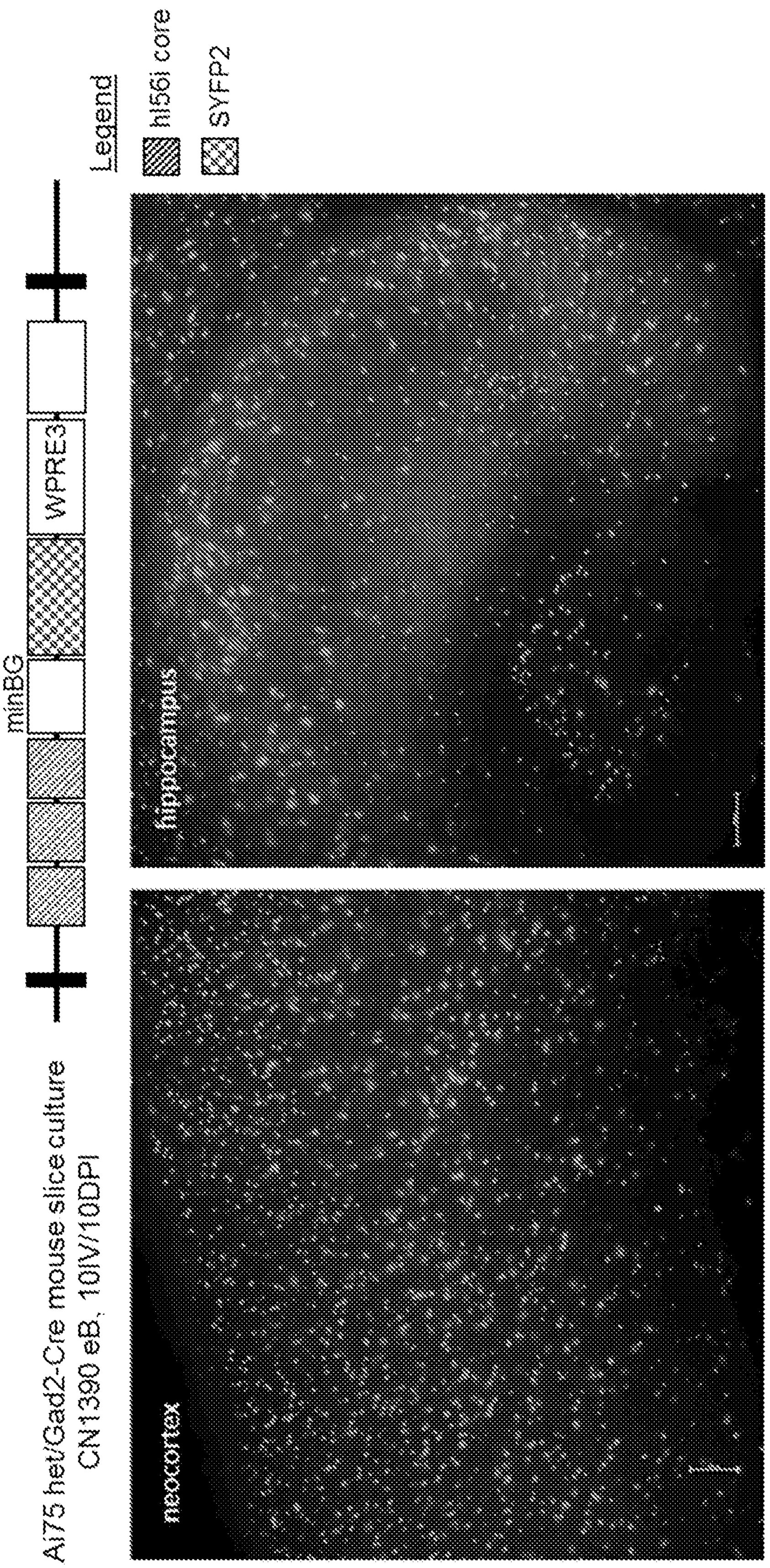
FIG. 3: CN1390 retains cell type specificity for the pan-GABAergic neuron population. Cortical/hippocampal brain slice cultures were prepared from P5-10 Gad2-IRES-Cre het/Ai75 het animals. One hour after culturing, CN1390 viral suspension was pipetted onto the slice surface to transduce brain cell types. At 10 DIV/10 DPI, native fluorescence was imaged in green and red channels on a Nikon inverted microscope. 10 DIV/10 DPI. DIV: days in vitro, DPI: days post infection.
Figure 4A:
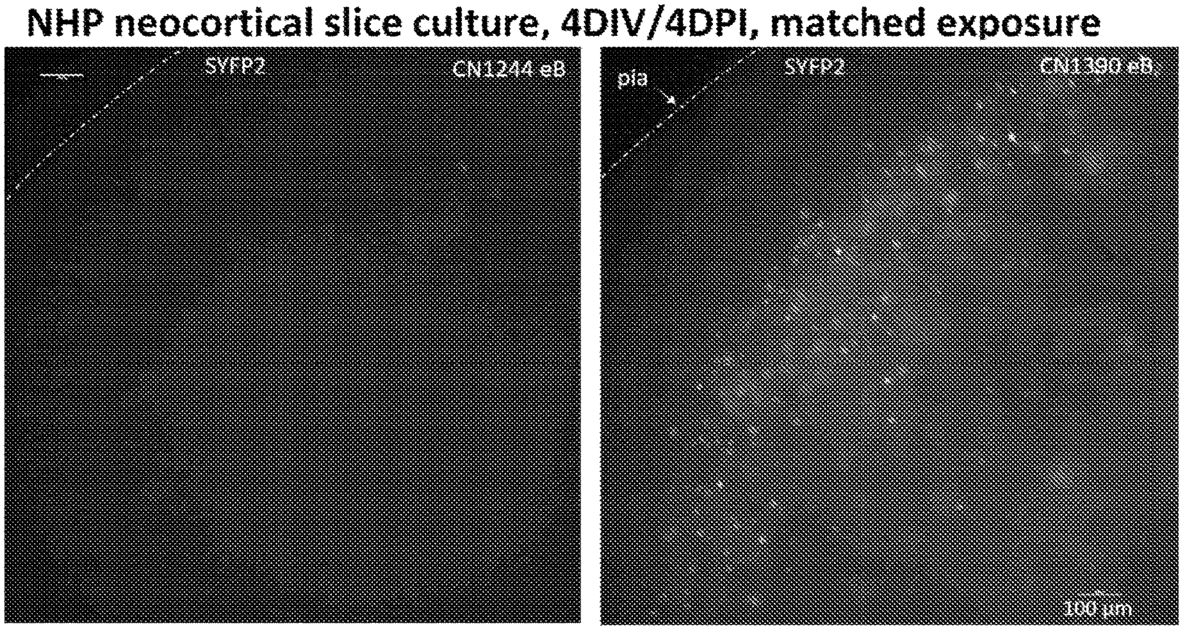
FIGS. 4A, 4B: Comparison of CN1244 vs CN1390 in non-human primate ex vivo brain slice culture.
Figure 4B:
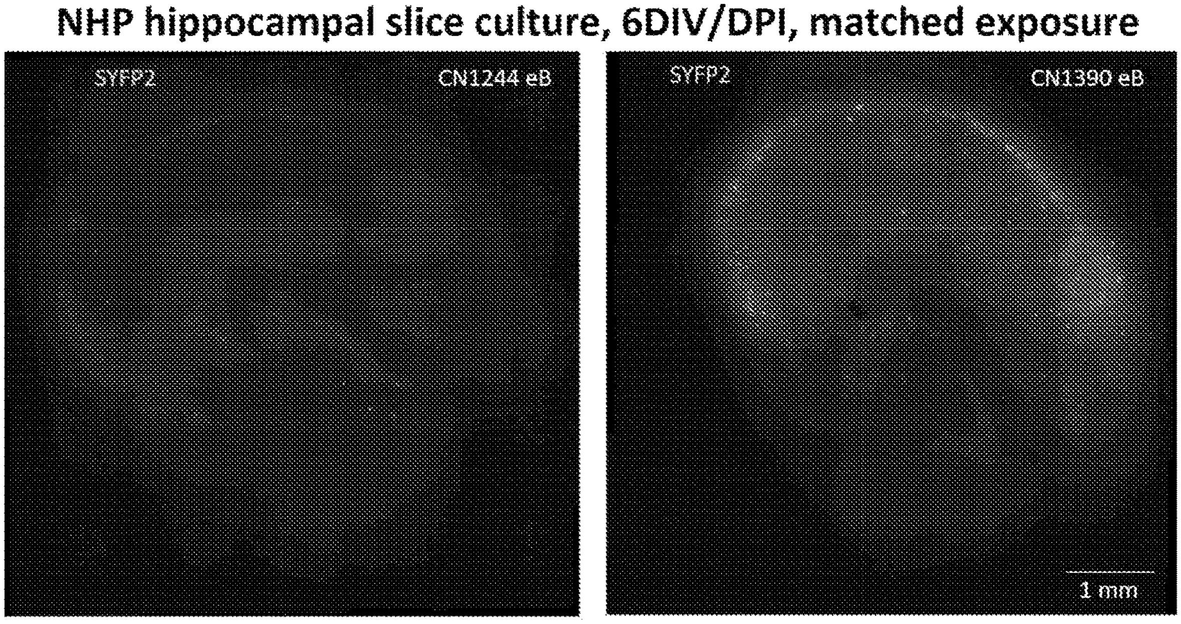
Figure 5A:
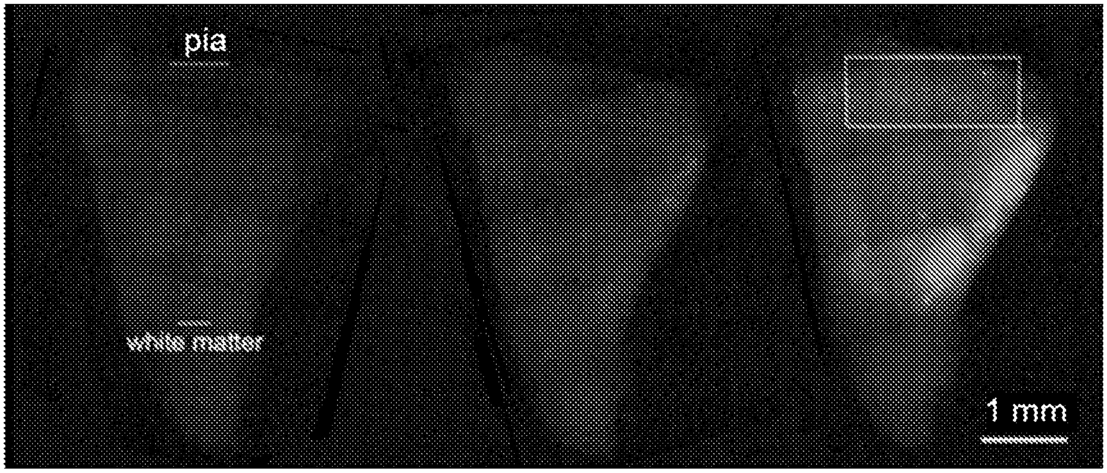
FIGS. 5A-5E: CN1390 exhibits rapid onset of transgene expression in human ex vivo brain slices. Human ex vivo neocortical brain slice cultures were prepared from live neurosurgical specimens as described in Ting et al., Scientific Reports 8(1):8407, 2018. One hour after culturing, CN1390 viral suspension was pipetted onto the slice surface to transduce brain cell types. At 1, 3, and 6 DIV/DPI, native SYFP2 fluorescence was imaged using matched exposure times on a Nikon microscope.
Figure 5B:
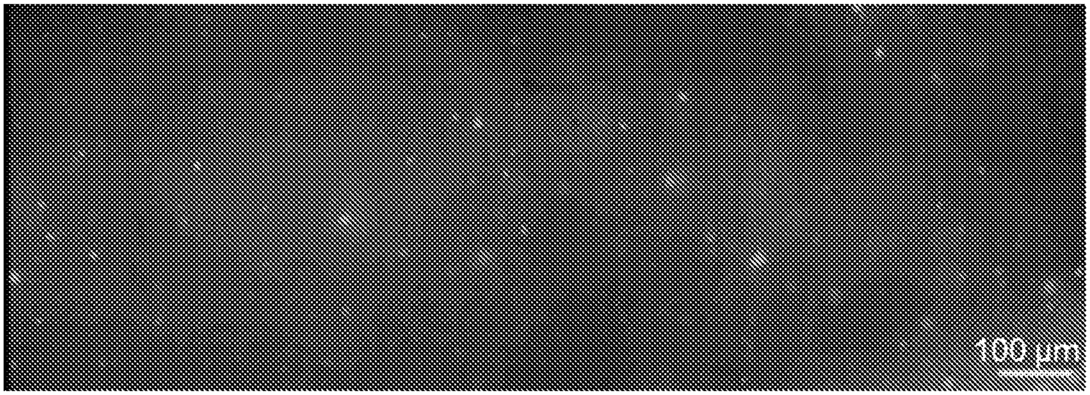
Figure 5C:
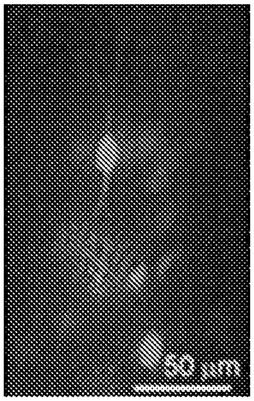
Figure 5D:
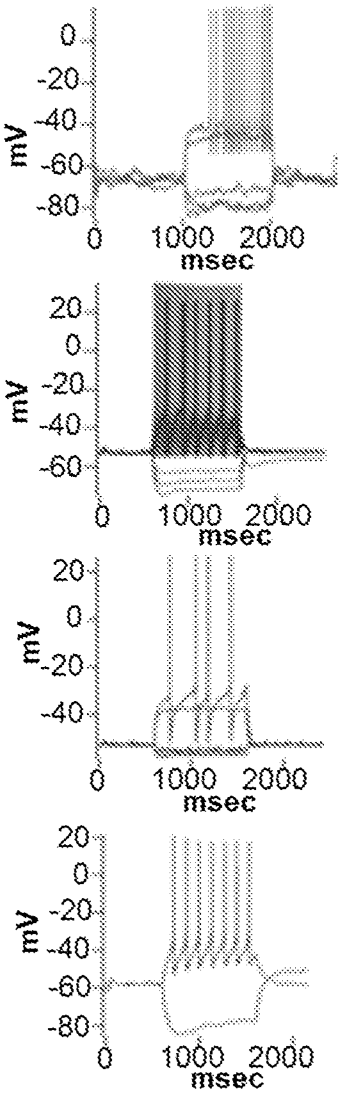
Figure 5E:
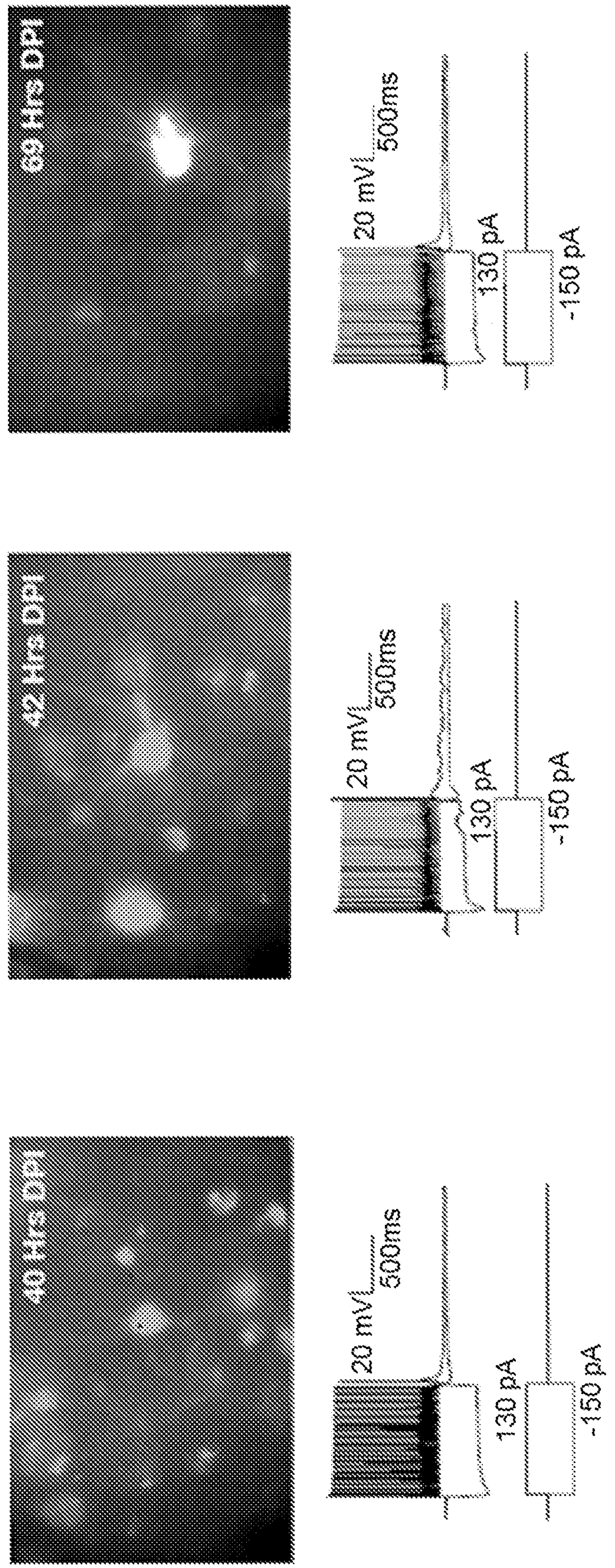
Figure 6:
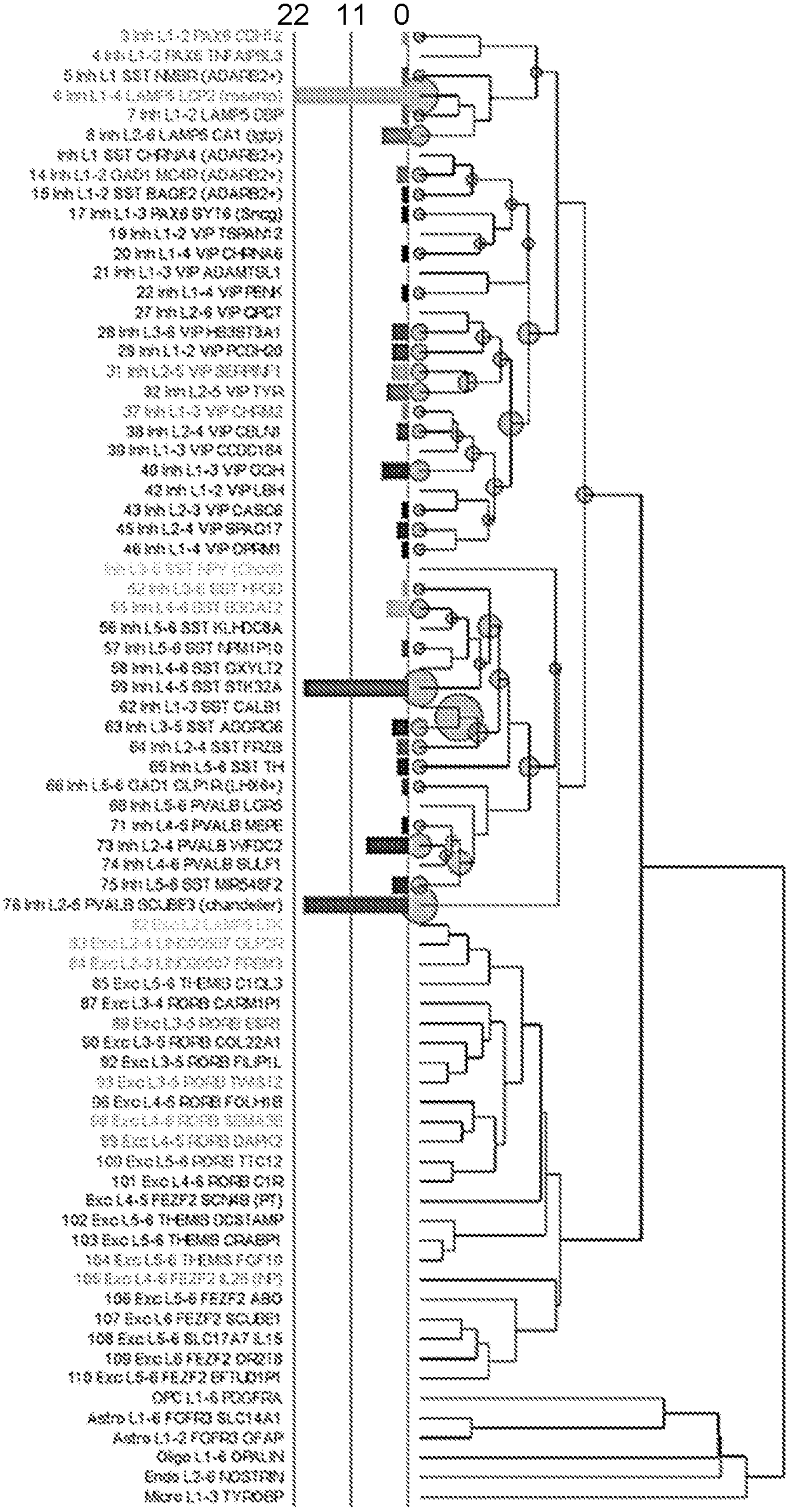
FIG. 6: CN1390 maintains GABAergic cell class selectivity. At 7 to 34 DIV/DPI, virally transduced human organotypic slices from 4 unique human donors were transduced, dissociated, and 234 single SYFP2+ cells were FACS sorted from glia and debris-depleted cell suspensions, and profiled by single cell RNA-seq (SMARTer V.4). These cells were mapped to the existing MTG cell type taxonomy. Bars at the bottom of the taxonomy indicate the number of SYFP+ cells that mapped to the final leaf. Circles farther up the taxonomy indicate the number of cells that could only be mapped to that branch point. Note that cells from all major GABAergic classes were labeled, and no glutamatergic or glial cells were recovered. The listed cell types from top to bottom are: GABAergic types; 3 Inh L1-2 PAX-6 CDH12, 4 Inh L1-2 PAX6 TNF AIP8L3, 5 Inh L1 SST NMBR (ADARB2+), 6 Inh L1-4 LAMP5 LCP2 (rosehip), 7 Inh L1-2 LAMP5 DBP, 8 Inh L2-6 LAMP5 CA1 (Igtp), Inh L1 SST CHRNA4 (ADARB2+), 14 Inh L1-2 GAD1 MC4R (ADARB2+), 15 Inh L1-2 SST BAGE2 (ADARB2+), 17 Inh L1-3 PAX6 SYT6 (Sncg), 19 Inh L1-2 VIP TSPAN12, 20 Inh L1-4 VIP CHRNA6, 21 Inh L1-3 VIP ADAMTSL1, 22 Inh L1-4 VIP PENK, 27 Inh L2-6 VIP QPCT, 28 Inh L3-6 VIP HS3ST3A1, 29 Inh L1-2 VIP PCDH20, 31 Inh L2-5 VIP SERPINF1, 32 Inh L2-5 VIP TYR, 37 Inh L1-3 VIP CHRM2, 38 Inh L2-4 VIP CBLN1, 39 Inh L1-3 VIP CCDC184, 40 Inh L1-3 VIP GGH, 42 Inh L1-2 VIP LBH, 43 Inh L2-3 VIP CASC6, 45 Inh L2-4 VIP SPAG17, 46 Inh L1-4 VIP OPRM1, Inh L3-6 SST NPY (Chodl), 52 Inh L3-6 SST HPGD, 55 Inh L4-6 SST B3GAT2, 56 Inh L5-6 SST KLHDC8A, 57 Inh L5-6 SST NPM1P10, 58 Inh L4-6 SST GXYLT2, 59 Inh L4-5 SST STK32A, 62 Inh L1-3 SST CALB1, 63 Inh L3-5 SST ADGRG6, 64 Inh L2-4 SST FRZB, 65 Inh L5-6 SST TH, 66 Inh L5-6 GAD1 GLP1R (LHX6+), 68 Inh L5-6 PVALB LGRS, 71 Inh L4-5 PVALB MEPE, 73 Inh L2-4 PVALB WFDC2, 74 Inh L4-6 PVALB SULF1, 75 Inh L5-6 SST MIR548F2, 76 Inh L2-5 PVALB SCUBE3 (chandelier), Excitatory types; 82 Exc L2-5

The current disclosure overcomes drawbacks of the prior art by providing artificial enhancer elements that include a concatemerized core of a I56i enhancer. These artificial enhancer elements provide unexpectedly strong peak transgene expression in forebrain GABAergic interneurons following viral transduction of mouse, monkey, and human brain tissue (see FIGS. 2A, 2B, 3, 4, 5A, 5E, 7, 8A, and 8B). The onset is also surprisingly rapid (see FIGS. 5A-5E), leading to faster and higher expression in direct comparison to virus packaged with, for instance, Addgene plasmid #83900. The increase in expression appears to be synergistically supra-linear and not simply three times the level driven by the original enhancer (FIG. 2B).

In particular embodiments, the I56i enhancer core can be derived from, for example the human and murine I56i enhancer, or zebrafish I46i enhancer (SEQ ID NOs. 1, 4, and 5 respectively). The selected cores of the I56i enhancer can include SEQ ID NO: 2 (core shared by human and mouse) or SEQ ID NO: 6 (zebrafish I46icore). In particular embodiments, the cores are concatemerized. For example, SEQ ID NO: 3 provides a three-copy concatemer of the selected human/murine I56i core while SEQ ID NO: 7 provides a three-copy concatemer of the selected zebrafish I46i core.

Of particular interest, the synthetic 3× human/murine core (referred to herein as the 3×hI56iCore; SEQ ID NO: 3) is shorter than the original full-length enhancer sequence reported in Dimidschstein et al. (*Nat Neurosci* 19(12):1743-1749, 2016), despite being a 3× concatemer. When used to construct a heterologous expression cassette, such as a recombinant adeno-associated virus (rAAV), this artificial enhancer element provides more room for cargo genes (heterologous encoding sequences) linked to the enhancer. This is highly desirable in many gene expression vectors. For instance, many functioning protein cargo genes (more generally, effector elements) are too long to fit in an AAV vector design, so space (length of sequence) is at a premium in the overall vector.

The engineered concatemerized I56i cores disclosed herein enable new and improved gene delivery vectors that are particularly useful for achieving selective transgene expression in neocortical GABAergic interneurons in diverse animal species, including humans and non-human primates. Importantly, GABAergic interneurons are highly involved in central processing and development and their dysfunction is implicated in a variety of brain disorders. As such, the herein-described enhancers and expression constructs have many immediate applications in research and clinical treatment development. The artificial enhancers can be used in experimental contexts where the original enhancer hI56i proved insufficient (e.g. retroorbital delivery of virus encoding transgenes for functional perturbation experiments).

Aspects of the disclosure are now described with the following additional options and detail: (i) Artificial Expression Constructs & Vectors for Selective Expression of Genes in Selected Cell Types; (ii) Compositions for Administration (iii) Cell Lines Including Artificial Expression Constructs; (iv) Transgenic Animals; (v) Methods of Use; (vi) Kits and Commercial Packages; (vii) Exemplary Embodiments; (viii) Experimental Examples; and (ix) Closing Paragraphs.

(i) Artificial Expression Constructs & Vectors for Selective Expression of Genes in Selected Cell Types. Artificial expression constructs disclosed herein include (i) an enhancer sequence that leads to selective expression of a coding sequence within a targeted central nervous system cell type, (ii) a coding sequence that is expressed, and (iii) a promoter. The expression construct can also include other regulatory elements if necessary or beneficial.

In particular embodiments, an "enhancer" or an "enhancer element" is a cis-acting sequence that increases the level of transcription associated with a promoter and can function in either orientation relative to the promoter and the coding sequence that is to be transcribed and can be located upstream or downstream relative to the promoter or the coding sequence to be transcribed. There are art-recognized methods and techniques for measuring function(s) of enhancer element sequences. Particular examples of enhancer sequences utilized within artificial expression constructs disclosed herein include concatemerized cores of I56i enhancers, such as concatamerizations of SEQ ID NO: 2 and/or 6 including, as examples, SEQ ID NO: 3 and 7. Additional particular examples of concatemerized cores of I56i enhancers can include SEQ ID NO: 2 and SEQ ID NO: 6 within one sequence such as SEQ ID NO: 2—SEQ ID NO: 2—SEQ ID NO: 6; SEQ ID NO: 2—SEQ ID NO: 6—SEQ ID NO: 6; SEQ ID NO: 2—SEQ ID NO: 6—SEQ ID NO: 2; SEQ ID NO: 6—SEQ ID NO: 6—SEQ ID NO: 2; SEQ ID NO: 6—SEQ ID NO: 2—SEQ ID NO: 2; and SEQ ID NO: 6—SEQ ID NO: 2—SEQ ID NO: 6.

In particular embodiments, a targeted central nervous system cell type enhancer is an enhancer that is uniquely or predominantly utilized by the targeted central nervous system cell type. A targeted central nervous system cell type enhancer enhances expression of a gene in the targeted central nervous system cell type but does not substantially direct expression of genes in other non-targeted cell types, thus having neural specific transcriptional activity.

When a coding sequence is selectively expressed in selected neural cells and is not substantially expressed in other neural cell types, the product of the coding sequence is preferentially expressed in the selected cell type. In particular embodiments, preferential expression is greater than 50% expression as compared to a reference cell type; greater than 60% expression as compared to a reference cell type; greater than 70% expression as compared to a reference cell type; greater than 80% expression as compared to a reference cell type; or greater than 90% expression as compared to a reference cell type. In particular embodiments, a reference cell type refers to non-targeted neural cells. The non-targeted neural cells can be within the same anatomical structure as the targeted cells and/or can project to a common anatomical area. In particular embodiments, a reference cell type is within an anatomical structure that is adjacent to an anatomical structure that includes the targeted cell type. In particular embodiments, a reference cell type is a non-targeted neural cell with a different gene expression profile than the targeted cells.

In particular embodiments, the product of the coding sequence may be expressed at low levels in non-selected cell types, for example at less than 1% or 1%, 2%, 3%, 5%, 10%, 15% or 20% of the levels at which the product is expressed in selected neural cells. In particular embodiments, the targeted central nervous system cell type is the only cell type that expresses the right combination of transcription factors that bind an enhancer disclosed herein to drive gene expression. Thus, in particular embodiments, expression occurs exclusively within the targeted cell type.

In particular embodiments, targeted cell types (e.g. neural, neuronal, and/or non-neuronal) can be identified based on transcriptional profiles, such as those described in Tasic et al., 2018 Nature. For reference, the following description of neural cell types and distinguishing features is also provided:

GABAergic Interneurons: express GABA synthesis genes Gad1/GAD1 and/or Gad2/GAD2.

GABAergic Subclasses:

Lamp5: Found in many cortical layers, especially upper (L1-L2/3), and have mainly neurogliaform and single bouquet morphology.

Sncg: Found in many cortical layers, and have molecular overlaps with Lamp5 and Vip cells, but inconsistent expression of Lamp5 or Vip, with more consistent expression of Sncg. These neurons express the neurotransmitter Cck and have primarily multipolar or basket cell morphology.

Serpinf1: Found in many cortical layers, and have molecular overlaps with Sncg and Vip cells, but inconsistent expression of Sncg or Vip, with more consistent expression of Serpinf1.

Vip: Found in many cortical layers, but especially frequent in upper layers (L1-L4), and highly express the neurotransmitter vasoactive intestinal peptide (Vip).

Sst: Found in many cortical layers, but especially frequent in lower layers (L5-L6). They highly express the neurotransmitter somatostatin (Sst), and frequently block dendritic inputs to postsynaptic neurons. Included in this subclass are sleep-active horizontal-projecting Sst Chodl (or Sst Nos1) neurons that are highly distinct from other Sst neurons, but express shared marker genes including Sst.

Pvalb: Found in many cortical layers, but especially frequent in lower layers (L5-L6). They highly express the neurotransmitter parvalbumin (Pvalb), express Tact, and frequently dampen the output of postsynaptic neurons. Included in this subclass are chandelier cells, which have distinct, chandelier-like morphology and express the markers Cpne5 and Vipr2 in mouse, and NOG and UNC5B in human.

Meis2: A distinct subclass defined by a single type, found in L6b and subcortical white matter. Lamp5, Sncg, Serpinf1, and VIP: Developmentally derived from precursor neurons in the caudal ganglionic eminence (CGE).

Sst and Pvalb: Developmentally derived from precursor neurons in the medial ganglionic eminence (MGE).

Glutamatergic Subclasses:

All: Express glutamate transmitters Slc17a6 and/or Slc17a7.

L2/3 IT: Primarily reside in Layer 2/3 and have mainly intratelencephalic (cortico-cortical) projections.

L4 IT: Primarily reside in Layer 4 and have mainly intratelencephalic (cortico-cortical) projections.

L5 IT: Primarily reside in Layer 5 and have mainly intratelencephalic (cortico-cortical) projections. Also called L5a.

L5 PT: Primarily reside in Layer 5 and have mainly cortico-subcortical (pyramidal tract or corticofugal) projections. Also called L5b or L5 CF. These cells are located in primary motor cortex and neighboring areas and are corticospinal projection neurons. They are associated with motor neuron/movement disorders, such as ALS.

Neocortical L5 extratelencephalic (ET)-projecting pyramidal neurons (L5 ET): thick-tufted pyramidal neurons, including distinctive subtypes found only in specialized regions, e.g. Betz cells, Meynert cells, and von Economo cells.

L5 NP: Primarily reside in Layer 5 and have mainly nearby projections.

L6 CT: Primarily reside in Layer 6 and have mainly cortico-thalamic projections.

L6 IT: Primarily reside in Layer 6 and have mainly intratelencephalic (cortico-cortical) projections. Included in this subclass are L6 IT Car3 cells, which are highly similar to intracortical-projecting cells in the claustrum.

L6b: Primarily reside in the cortical subplate (L6b), with observed projections to local regions (near the cell body), cortico-cortical projections from VISp to anterior cingulate, and cortico-subcortical projections to the thalamus.

CR: A distinct subclass defined by a single type in L1, Cajal-Retzius cells express distinct molecular markers Lhx5 and Trp73.

Non-Neuronal Subclasses:

Astrocytes: Neuroectoderm-derived glial cells which express the marker Aqp4. They have a distinct star-shaped morphology and are involved in metabolic support of other cells in the brain. Oligodendrocytes: Neuroectoderm-derived glial cells, which express the marker Sox10. This category includes oligodendrocyte precursor cells (OPCs). Oligodendrocytes are the subclass that is primarily responsible for myelination of neurons.

VLMCs: Vascular leptomeningeal cells (VLMCs) are part of the meninges that surround the outer layer of the cortex and express the marker genes Lum and Col1a1.

Pericytes: Blood vessel-associated cells, also called mural cells, that express the marker genes Kcnj8 and Abcc9. Pericytes wrap around endothelial cells and are important for regulation of capillary blood flow and are involved in blood-brain barrier permeability.

SMCs: Blood vessel-associated cells, also called mural cells, that express the marker gene Acta2. SMCs cover arterioles in the brain and are involved in blood-brain barrier permeability.

Endothelial: Cells that line blood vessels of the brain. Endothelial cells express the markers Tek and PDGF-β.

Macrophages: Immune cells, including macrophages, which are brain-resident macrophages, and perivascular macrophages (PVMs) that may be transitionally associated with brain tissue, or included as a biproduct of brain dissection methods.

In particular embodiments, a coding sequence is a heterologous coding sequence that encodes an effector element. An effector element is a sequence that is expressed to achieve, and that in fact achieves, an intended effect. Examples of effector elements include reporter genes/proteins and functional genes/proteins.

Exemplary reporter genes/proteins include those expressed by Addgene ID #s 83894 (pAAV-hDlx-Flex-dTomato-Fishell_7), 83895 (pAAV-hDlx-Flex-GFP-Fishell_6), 83896 (pAAV-hDlx-GiDREADD-dTomato-Fishell-5), 83898 (pAAV-mDlx-ChR2-mCherry-Fishell-3), 83899 (pAAV-mDlx-GCaMP6f-Fishell-2), 83900 (pAAV-mDlx-GFP-Fishell-1), and 89897 (pcDNA3-FLAG-mTET2 (N500)). Exemplary reporter genes particularly can include those which encode an expressible fluorescent protein, or expressible biotin; blue fluorescent proteins (e.g. eBFP, eBFP2, Azurite, mKalama1, GFPuv, Sapphire, T-sapphire); cyan fluorescent proteins (e.g. eCFP, Cerulean, CyPet, AmCyanl, Midoriishi-Cyan, mTurquoise); green fluorescent proteins (e.g. GFP, GFP-2, tagGFP, turboGFP, EGFP, Emerald, Azami Green, Monomeric Azami Green (mAzami-green), CopGFP, AceGFP, avGFP, ZsGreenl, Oregon Green™ (Thermo Fisher Scientific)); Luciferase; orange fluorescent proteins (mOrange, mKO, Kusabira-Orange, Monomeric Kusabira-Orange, mTangerine, tdTomato, dTomato); red fluorescent proteins (mKate, mKate2, mPlum, DsRed monomer, mCherry, mRuby, mRFP1, DsRed-Express, DsRed2, DsRed-Monomer, HcRed-Tandem, HcRedl, AsRed2, eqFP611, mRaspberry, mStrawberry, Jred, Texas Red™ (Thermo Fisher Scientific)); far red fluorescent proteins (e.g., mPlum and mNeptune); yellow fluorescent proteins (e.g., YFP, eYFP, Citrine, SYFP2, Venus, YPet, PhiYFP, ZsYellowl); and tandem conjugates.

GFP is composed of 238 amino acids (26.9 kDa), originally isolated from the jellyfish *Aequorea victoria/Aequorea aequorea/Aequorea forskalea* that fluoresces green when exposed to blue light. The GFP from *A. victoria* has a major excitation peak at a wavelength of 395 nm and a minor one at 475 nm. Its emission peak is at 509 nm which is in the lower green portion of the visible spectrum. The GFP from the sea pansy (*Renilla reniformis*) has a single major excitation peak at 498 nm. Due to the potential for widespread usage and the evolving needs of researchers, many different mutants of GFP have been engineered. The first major improvement was a single point mutation (S65T) reported in 1995 in Nature by Roger Tsien. This mutation dramatically improved the spectral characteristics of GFP, resulting in increased fluorescence, photostability and a shift of the major excitation peak to 488 nm with the peak emission kept at 509 nm. The addition of the 37° C. folding efficiency (F64L) point mutant to this scaffold yielded enhanced GFP (EGFP). EGFP has an extinction coefficient (denoted 0, also known as its optical cross section of 9.13×10-21 $m^2$/molecule, also quoted as 55,000 L/(mol·cm). Superfolder GFP, a series of mutations that allow GFP to rapidly fold and mature even when fused to poorly folding peptides, was reported in 2006.

The "yellow fluorescent protein" (YFP) is a genetic mutant of green fluorescent protein, derived from *Aequorea victoria*. Its excitation peak is 514 nm and its emission peak is 527 nm.

Exemplary functional molecules include functioning ion transporters, cellular trafficking proteins, enzymes, transcription factors, neurotransmitters, calcium reporters, channel rhodopsins, guide RNA, nucleases, or designer receptors exclusively activated by designer drugs (DREADDs).

Ion transporters are transmembrane proteins that mediate transport of ions across cell membranes. These transporters are pervasive throughout most cell types and important for regulating cellular excitability and homeostasis. Ion transporters participate in numerous cellular processes such as action potentials, synaptic transmission, hormone secretion, and muscle contraction. Many important biological processes in living cells involve the translocation of cations, such as calcium (Ca2+), potassium (K+), and sodium (Na+) ions, through such ion channels. In particular embodiments, ion transporters include voltage gated sodium channels (e.g., SCN1A), potassium channels (e.g., KCNQ2), and calcium channels (e.g. CACNA1C)).

Exemplary enzymes, transcription factors, receptors, membrane proteins, cellular trafficking proteins, signaling molecules, and neurotransmitters include enzymes such as lactase, lipase, helicase, alpha-glucosidase, amylase; transcription factors such as SP1, AP-1, Heat shock factor protein 1, C/EBP (CCAA-T/enhancer binding protein), and Oct-1; receptors such as transforming growth factor receptor beta 1, platelet-derived growth factor receptor, epidermal growth factor receptor, vascular endothelial growth factor receptor, and interleukin 8 receptor alpha; membrane proteins, cellular trafficking proteins such as clathrin, dynamin, caveolin, Rab-4A, and Rab-11A; signaling molecules such as nerve growth factor (NGF), platelet-derived growth factor (PDGF), transforming growth factor β (TGFβ), epidermal growth factor (EGF), GTPase and HRas; and neurotransmitters such as cocaine and amphetamine regulated transcript, substance P, oxytocin, and somatostatin.

In particular embodiments, functional molecules include reporters of neural function and states such as calcium reporters. Intracellular calcium concentration is an important predictor of numerous cellular activities, which include neuronal activation, muscle cell contraction and second messenger signaling. A sensitive and convenient technique to monitor the intracellular calcium levels is through the genetically encoded calcium indicator (GECI). Among the GECIs, green fluorescent protein (GFP) based calcium sensors named GCaMPs are efficient and widely used tools. The GCaMPs are formed by fusion of M13 and calmodulin protein to N- and C-termini of circularly permutated GFP. Some GCaMPs yield distinct fluorescence emission spectra (Zhao et al., Science, 2011, 333(6051): 1888-1891). Exemplary GECIs with green fluorescence include GCaMP3, GCaMP5G, GCaMP6s, GCaMP6m, GCaMP6f, jGCaMP7s, jGCaMP7c, jGCaMP7b, and jGCaMP7f. Furthermore, GECIs with red fluorescence include jRGECO1a and jRGECO1b. AAV products containing GECIs are commercially available. For example, Vigene Biosciences provides AAV products including AAV8-CAG-GCaMP3 (Cat. No:BS4-CX3AAV8), AAV8-Syn-FLEX-GCaMP6s-WPRE (Cat. No:BS1-NXSAAV8), AAV8-Syn-FLEX-GCaMP6s-WPRE (Cat. No:BS1-NXSAAV8), AAV9-CAG-FLEX-GCaMP6m-WPRE (Cat. No:BS2-CXMAAV9), AAV9-Syn-FLEX-jGCaMP7s-WPRE (Cat. No: BS12-NXSAAV9), AAV9-CAG-FLEX-jGCaMP7f-WPRE (Cat. No:BS12-CXFAAV9), AAV9-Syn-FLEX-jGCaMP7b-WPRE (Cat. No:BS12-NXBAAV9), AAV9-Syn-FLEX-jGCaMP7c-WPRE (Cat. No:BS12-NXCAAV9), AAV9-Syn-FLEX-NES-jRGECO1a-WPRE (Cat. No:BS8-NXAAAV9), and AAV8-Syn-FLEX-NES-jRCaMP1b-WPRE (Cat. No:BS7-NXBAAV8).

In particular embodiments calcium reporters include the genetically encoded calcium indicators GECI, NTnC; Myosin light chain kinase, GFP, Calmodulin chimera; Calcium indicator TN-XXL; BRET-based auto-luminescent calcium indicator; and/or Calcium indicator protein OeNL(Ca2+)-18u).

In particular embodiments, functional molecules include modulators of neuronal activity like channel rhodopsins (e.g., channelopsin-1, channelrhodopsin-2, and variants thereof). Channelrhodopsins are a subfamily of retinylidene proteins (rhodopsins) that function as light-gated ion channels. In addition to channelrhodopsin 1 (ChR1) and channelrhodopsin 2 (ChR2), several variants of channelrhodopsins have been developed. For example, Lin et al. (*Biophys J,* 2009, 96(5): 1803-14) describe making chimeras of the transmembrane domains of ChR1 and ChR2, combined with site-directed mutagenesis. Zhang et al. (*Nat Neurosci,* 2008, 11(6): 631-3) describe VChR1, which is a red-shifted channelrhodopsin variant. VChR1 has lower light sensitivity and poor membrane trafficking and expression. Other known channelrhodopsin variants include the ChR2 variant described in Nagel, et al., *Proc Natl Acad Sci USA,* 2003, 100(24): 13940-5), ChR2/H134R (Nagel, G., et al., *Curr Biol,* 2005, 15(24): 2279-84), and ChD/ChEF/ChIEF (Lin, J. Y., et al., *Biophys J,* 2009, 96(5): 1803-14), which are activated by blue light (470 nm) but show no sensitivity to orange/red light. Additional variants are described in Lin, *Experimental Physiology,* 2010, 96.1: 19-25 and Knopfel et al., *The Journal of Neuroscience,* 2010, 30(45): 14998-15004).

In particular embodiments, functional molecules include DNA and RNA editing tools such CRISPR/CAS (e.g., guide RNA and a nuclease, such as Cas, Cas9 or cpf1). Functional molecules can also include engineered Cpf1s such as those described in US 2018/0030425, US 2016/0208243, WO/2017/184768 and Zetsche et al. (2015) *Cell* 163: 759-771; single gRNA (see e.g., Jinek et al. (2012) *Science* 337:816-821; Jinek et al. (2013) eLife 2:e00471; Segal (2013) eLife 2:e00563) or editase, guide RNA molecules or homologous recombination donor cassettes.

Additional information regarding CRISPR-Cas systems and components thereof are described in, U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641 and applications related thereto; and WO2014/018423, WO2014/093595, WO2014/093622, WO2014/093635, WO2014/093655, WO2014/093661, WO2014/093694, WO2014/093701, WO2014/093709, WO2014/093712, WO2014/093718, WO2014/145599, WO2014/204723, WO2014/204724, WO2014/204725, WO2014/204726, WO2014/204727, WO2014/204728, WO2014/204729, WO2015/065964, WO2015/089351, WO2015/089354, WO2015/089364, WO2015/089419, WO2015/089427, WO2015/089462, WO2015/089465, WO2015/089473 and WO2015/089486, WO2016205711, WO2017/106657, WO2017/127807 and applications related thereto.

In particular embodiments, functional molecules include designer receptor exclusively activated by designer drug (DREADD). Designer receptors exclusively activated by designer drugs (DREADDs) can be used to modulate cellular functions (Rogan and Roth, Pharmacol. Rev. 2011, 63(2): 291-315). This family of evolved muscarinic receptors has been shown to increase (Gs-DREADD; Gq-DREADD) or decrease (Gi/o-DREADD) cellular activity following administration of an otherwise inert synthetic ligand, clozapine-n-oxide (Armbruster et al., PNAS, 2007, 104(12): 5163-5168). When packaged into viral vectors or expressed in transgenic mouse models, these tools allow cellular activity to be controlled in a defined spatial and temporal manner. For example, activation of hippocampal neurons by Gq-DREADD receptors amplifies y-rhythms and increases locomotor activity and stereotypy in mice (Alexander et al., Neuron, 2009, 63(1): 27-39). DREADDs are formed by point mutations in the third and fifth transmembrane regions of muscarinic receptors (Y149C and A239G in hM3). In addition, the Gs-coupled DREADD contains the second and third intracellular loops of the $\beta$1-AR in place of those of the M3 muscarinic receptor. Some exemplary DREADDs include hM3DREADD (hM3D) and hM4DREADD (hM4D). Various plasmids containing DREADDs are commercially available. For example, on addgene, AAV plasmids containing DREADDs include: pAAV-hSyn-DIO-hM3D(Gq)-mCherry (Plasmid #44361), pAAV-hSyn-DIO-hM4d(Gi)-mCherry) (Plasmid #44362), pAAV-EF1a-DIO-hM4d(Gi)-mCherry) (Plasmid #50461), pAAV-GFAP-HA-hM3D(Gq)-IRES)-mCitrine (Plasmid #50470), and pAAV-CaMKIIa-hM4D(GO-mCherry (Plasmid #50477).

Additional effector elements include Cre, iCre, dgCre, FIpO, and tTA2. iCre refers to a codon-improved Cre. dgCre refers to an enhanced GFP/Cre recombinase fusion gene with an N terminal fusion of the first 159 amino acids of the *Escherichia coli* K-12 strain chromosomal dihydrofolate reductase gene (DHFR or foIA) harboring a G67S mutation and modified to also include the R12Y/Y100I destabilizing domain mutation. FIpO refers to a codon-optimized form of FLPe that greatly increases protein expression and FRT recombination efficiency in mouse cells. Like the Cre/LoxP system, the FLP/FRT system has been widely used for gene expression (and generating conditional knockout mice, mediated by the FLP/FRT system). tTA2 refers to tetracycline transactivator.

Exemplary expressible elements are expression products that do not include effector elements, for example, a non-functioning or defective protein. In particular embodiments, expressible elements can provide methods to study the effects of their functioning counterparts. In particular embodiments, expressible elements are non-functioning or defective based on an engineered mutation that renders them non-functioning. In these aspects, non-expressible elements are as similar in structure as possible to their functioning counterparts.

Exemplary self-cleaving peptides include the 2A peptides which lead to the production of two proteins from one mRNA. The 2A sequences are short (e.g., 20 amino acids), allowing more use in size-limited constructs. Particular examples include P2A, T2A, E2A, and F2A. In particular embodiments, the expression constructs include an internal ribosome entry site (IRES) sequence. IRES allow ribosomes to initiate translation at a second internal site on a mRNA molecule, leading to production of two proteins from one mRNA.

Coding sequences encoding molecules (e.g., RNA, proteins) described herein can be readily obtained from publicly available databases and publications. Coding sequences can further include various sequence polymorphisms, mutations, and/or sequence variants wherein such alterations do not affect the function of the encoded molecule. The term "encode" or "encoding" refers to a property of sequences of nucleic acids, such as a vector, a plasmid, a gene, cDNA, mRNA, to serve as templates for synthesis of other molecules such as proteins.

The term "gene" may include not only coding sequences but also regulatory regions such as promoters, enhancers, and termination regions. The term further can include all introns and other DNA sequences spliced from the mRNA transcript, along with variants resulting from alternative splice sites. The sequences can also include degenerate codons of a reference sequence or sequences that may be introduced to provide codon preference in a specific organism or cell type.

Promoters can include general promoters, tissue-specific promoters, cell-specific promoters, and/or promoters specific for the cytoplasm. Promoters may include strong promoters, weak promoters, constitutive expression promoters, and/or inducible promoters. Inducible promoters direct expression in response to certain conditions, signals or cellular events. For example, the promoter may be an inducible promoter that requires a particular ligand, small molecule, transcription factor or hormone protein in order to effect transcription from the promoter. Particular examples of promoters include minBglobin, CMV, minCMV, a mutated minCMV, SV40 immediately early promoter, the Hsp68 minimal promoter (proHSP68), and the Rous Sarcoma Virus (RSV) long-terminal repeat (LTR) promoter. Minimal promoters have no activity to drive gene expression on their own, but can be activated to drive gene expression when linked to a proximal enhancer element.

In particular embodiments, expression constructs are provided within vectors. The term vector refers to a nucleic acid molecule capable of transferring or transporting another nucleic acid molecule, such as an expression construct. The transferred nucleic acid is generally linked to, e.g., inserted into, the vector nucleic acid molecule. A vector may include sequences that direct autonomous replication in a cell or may include sequences that permit integration into host cell DNA. Useful vectors include, for example, plasmids (e.g., DNA plasmids or RNA plasmids), transposons, cosmids, bacterial artificial chromosomes, and viral vectors.

Viral vector is widely used to refer to a nucleic acid molecule that includes virus-derived nucleic acid elements that facilitate transfer and expression of non-native nucleic acid molecules within a cell. The term adeno-associated viral vector refers to a viral vector or plasmid containing structural and functional genetic elements, or portions thereof, that are primarily derived from AAV. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, that are primarily derived from a lentivirus, and so on. The term "hybrid vector" refers to a vector including structural and/or functional genetic elements from more than one virus type.

Adenovirus. "Adenovirus vectors" refer to those constructs containing adenovirus sequences sufficient to (a) support packaging of an expression construct and (b) to express a coding sequence that has been cloned therein in a sense or antisense orientation. A recombinant Adenovirus vector includes a genetically engineered form of an adenovirus. Knowledge of the genetic organization of adenovirus, a 36 kb, linear, double-stranded DNA virus, allows substitution of large pieces of adenoviral DNA with foreign sequences up to 7 kb. In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range, and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut-off. The products of the late genes, including the majority of the viral capsid proteins, are expressed only after significant processing of a single primary transcript issued by the major late promoter (MLP). The MLP is particularly efficient during the late phase of infection, and all the mRNAs issued from this promoter possess a 5'-tripartite leader (TPL) sequence which makes them preferred mRNAs for translation.

Other than the requirement that an adenovirus vector be replication defective, or at least conditionally defective, the nature of the adenovirus vector is not believed to be crucial to the successful practice of particular embodiments disclosed herein. The adenovirus may be of any of the 42 different known serotypes or subgroups A-F. In particular embodiments, adenovirus type 5 of subgroup C is the preferred starting material in order to obtain a conditional replication-defective adenovirus vector for use in particular embodiments, since Adenovirus type 5 is a human adenovirus about which a great deal of biochemical and genetic information is known, and it has historically been used for most constructions employing adenovirus as a vector.

As indicated, the typical vector is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical. The polynucleotide encoding the gene of interest may also be inserted in lieu of a deleted E3 region in E3 replacement vectors or in the E4 region where a helper cell line or helper virus complements the E4 defect.

Adeno-Associated Virus (AAV) is a parvovirus, discovered as a contamination of adenoviral stocks. It is a ubiquitous virus (antibodies are present in 85% of the US human population) that has not been linked to any disease. It is also classified as a dependovirus, because its replication is dependent on the presence of a helper virus, such as adenovirus. Various serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter.

The AAV DNA is 4.7 kilobases long. It contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three AAV viral promoters have been identified and named p5, p19, and p40, according to their map position. Transcription from p5 and p19 results in production of rep proteins, and transcription from p40 produces the capsid proteins.

AAVs stand out for use within the current disclosure because of their superb safety profile and because their capsids and genomes can be tailored to allow expression in selected cell populations. scAAV refers to a self-complementary AAV. pAAV refers to a plasmid adeno-associated virus. rAAV refers to a recombinant adeno-associated virus.

Other viral vectors may also be employed. For example, vectors derived from viruses such as vaccinia virus, polioviruses and herpes viruses may be employed. They offer several attractive features for various mammalian cells.

Retrovirus. Retroviruses are a common tool for gene delivery. "Retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV) and lentivirus.

"Lentivirus" refers to a group (or genus) of complex retroviruses. Illustrative lentiviruses include: HIV (human immunodeficiency virus; including HIV type 1, and HIV type 2); visna-maedi virus (VMV); the caprine arthritis-encephalitis virus (CAEV); equine infectious anemia virus (EIAV); feline immunodeficiency virus (FIV); bovine immune deficiency virus (BIV); and simian immunodeficiency virus (SIV). In particular embodiments, HIV based vector backbones (i.e., HIV cis-acting sequence elements) can be used.

A safety enhancement for the use of some vectors can be provided by replacing the U3 region of the 5' LTR with a heterologous promoter to drive transcription of the viral genome during production of viral particles. Examples of heterologous promoters which can be used for this purpose include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system. In particular embodiments, the heterologous promoter has additional advantages in controlling the manner in which the viral genome is transcribed. For example, the heterologous promoter can be inducible, such that transcription of all or part of the viral genome will occur only when the induction factors are present. Induction factors include one or more chemical compounds or the physiological conditions such as temperature or pH, in which the host cells are cultured.

In particular embodiments, viral vectors include a TAR element. The term "TAR" refers to the "trans-activation response" genetic element located in the R region of lentiviral LTRs. This element interacts with the lentiviral trans-activator (tat) genetic element to enhance viral replication. However, this element is not required in embodiments wherein the U3 region of the 5' LTR is replaced by a heterologous promoter.

The "R region" refers to the region within retroviral LTRs beginning at the start of the capping group (i.e., the start of transcription) and ending immediately prior to the start of the poly(A) tract. The R region is also defined as being flanked by the U3 and U5 regions. The R region plays a role during reverse transcription in permitting the transfer of nascent DNA from one end of the genome to the other.

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid. Examples include the woodchuck hepatitis virus posttranscriptional regulatory element (WPRE; Zufferey et al., 1999, J. Virol., 73:2886); the posttranscriptional regulatory element present in hepatitis B virus (HPRE) (Smith et al., Nucleic Acids Res. 26(21):4818-4827, 1998); and the like (Liu et al., 1995, Genes Dev., 9:1766). In particular embodiments, vectors include a posttranscriptional regulatory element such as a WPRE or HPRE. In particular embodiments, vectors lack or do not include a posttranscriptional regulatory element such as a WPRE or HPRE.

Elements directing the efficient termination and polyadenylation of a heterologous nucleic acid transcript can increase heterologous gene expression. Transcription termination signals are generally found downstream of the polyadenylation signal. In particular embodiments, vectors include a polyadenylation sequence 3' of a polynucleotide encoding a molecule (e.g., protein) to be expressed. The term "poly(A) site" or "poly(A) sequence" denotes a DNA sequence which directs both the termination and polyadenylation of the nascent RNA transcript by RNA polymerase II. Polyadenylation sequences can promote mRNA stability by addition of a poly(A) tail to the 3' end of the coding sequence and thus, contribute to increased translational efficiency. Particular embodiments may utilize BGHpA or SV40pA. In particular embodiments, a preferred embodiment of an expression construct includes a terminator element. These elements can serve to enhance transcript levels and to minimize read through from the construct into other plasmid sequences.

In particular embodiments, a viral vector further includes one or more insulator elements. Insulators elements may contribute to protecting viral vector-expressed sequences, e.g., effector elements or expressible elements, from integration site effects, which may be mediated by cis-acting elements present in genomic DNA and lead to deregulated expression of transferred sequences (i.e., position effect; see, e.g., Burgess-Beusse et al., *PNAS., USA,* 99:16433, 2002; and Zhan et al., *Hum. Genet.,* 109:471, 2001). In particular embodiments, viral transfer vectors include one or more insulator elements at the 3' LTR and upon integration of the provirus into the host genome, the provirus includes the one or more insulators at both the 5' LTR and 3' LTR, by virtue of duplicating the 3' LTR. Suitable insulators for use in particular embodiments include the chicken β-globin insulator (see Chung et al., *Cell* 74:505, 1993; Chung et al., *PNAS USA* 94:575, 1997; and Bell et al., *Cell* 98:387, 1999), SP10 insulator (Abhyankar et al., *JBC* 282:36143, 2007), or other small CTCF recognition sequences that function as enhancer blocking insulators (Liu et al., *Nature Biotechnology,* 33:198, 2015).

Beyond the foregoing description, a wide range of suitable expression vector types will be known to a person of ordinary skill in the art. These can include commercially available expression vectors designed for general recombinant procedures, for example plasmids that contain one or more reporter genes and regulatory elements required for expression of the reporter gene in cells. Numerous vectors are commercially available, e.g., from Invitrogen, Stratagene, Clontech, etc., and are described in numerous associated guides. In particular embodiments, suitable expression vectors include any plasmid, cosmid or phage construct that is capable of supporting expression of encoded genes in mammalian cell, such as pUC or Bluescript plasmid series.

Particular embodiments of vectors disclosed herein include:

| Expression Construct Name | Features |
|---|---|
| CN1390 | rAAV: 3xhl56Core-minBglobin-SYFP2-WPRE3-BGHpA |
| CN1244 | rAAV: hl56i-minBglobin-SYFP2-WPRE3-BGHpA |
| CN1389 | rAAV: hl56Core-minBglobin-SYFP2-WPRE3-BGHpA |
| CN1203 | scAAV: hl56i-minBglobin-SYFP2-WPRE3-BGHpA |
| CN1367 | rAAV: hl56i-minBglobin-His-NavMs-P2A-SYFP2-WPRE3-BGHpA |
| CN1498 | rAAV: 3xhl56iCore-minCMV-SYFP2-P2A-3xHA-NavBp-WPRE3-BGHpA |
| CN1499 | rAAV: 3xhl56iCore-minCMV-SYFP2-P2A-3xHA-NavMs-WPRE3-BGHpA |
| CN1500 | rAAV: 3xhl56iCore-minCMV-SYFP2-P2A-3xHA-NavSheP-D60N-WPRE3-BGHpA |
| CN1838 | scAAV-3Xzl46i-minBG-SYFP2-WPRE3-SPA |

In particular embodiments, SYFP2 within CN1390, CN1244, CN1389, CN1203, CN1367, CN1498, CN1499, CN1500, and CN1838 can be replaced with a channel rhodopsin or calcium reporter, such as ChR2 or GCaMP. In particular embodiments, SYFP2 within CN1390 is replaced with ChR2 or GCaMP. 3Xzl46i within CN1838 refers to the 3× concatemer of the zebrafish I46iCore. See also FIG. 16 which provides additional exemplary vector components and combinations of the disclosure.

In particular embodiments vectors (e.g., AAV) with capsids that cross the blood-brain barrier (BBB) are selected. In particular embodiments, vectors are modified to include capsids that cross the BBB. Examples of AAV with viral capsids that cross the blood brain barrier include AAV9 (Gombash et al., Front Mol Neurosci. 2014; 7:81), AAVrh.10 (Yang, et al., Mol Ther. 2014; 22(7): 1299-1309), AAV1R6, AAV1R7 (Albright et al., Mol Ther. 2018; 26(2): 510), rAAVrh.8 (Yang, et al., supra), AAV-BR1 (Marchio et al., EMBO Mol Med. 2016; 8(6): 592), AAV-PHP.S (Chan et al., Nat Neurosci. 2017; 20(8): 1172), AAV-PHP.B (Deverman et al., Nat Biotechnol. 2016; 34(2): 204), and AAV-PPS (Chen et al., Nat Med. 2009; 15: 1215). The PHP.eB capsid differs from AAV9 such that, using AAV9 as a reference, amino acids starting at residue 586: S-AQ-A (SEQ ID NO: 98) are changed to S-DGTLAVPFK-A (SEQ ID NO: 33).

AAV9 is a naturally occurring AAV serotype that, unlike many other naturally occurring serotypes, can cross the BBB following intravenous injection. It transduces large sections of the central nervous system (CNS), thus permitting minimally invasive treatments (Naso et al., BioDrugs. 2017; 31(4): 317), for example, as described in relation to clinical trials for the treatment of superior mesenteric artery (SMA) syndrome by AveXis (AVXS-101, NCT03505099) and the treatment of CLN3 gene-Related Neuronal Ceroid-Lipofuscinosis (NCT03770572).

AAVrh.10, was originally isolated from rhesus macaques and shows low seropositivity in humans when compared with other common serotypes used for gene delivery applications (Selot et al., Front Pharmacol. 2017; 8: 441) and has been evaluated in clinical trials LYS-SAF302, LYSOGENE, and NCT03612869.

AAV1R6 and AAV1R7, two variants isolated from a library of chimeric AAV vectors (AAV1 capsid domains swapped into AAVrh.10), retain the ability to cross the BBB and transduce the CNS while showing significantly reduced hepatic and vascular endothelial transduction.

rAAVrh.8, also isolated from rhesus macaques, shows a global transduction of glial and neuronal cell types in regions of clinical importance following peripheral administration and also displays reduced peripheral tissue tropism compared to other vectors.

AAV-BR1 is an AAV2 variant displaying the NRGTEWD (SEQ ID NO: 91) epitope that was isolated during in vivo screening of a random AAV display peptide library. It shows high specificity accompanied by high transgene expression in the brain with minimal off-target affinity (including for the liver) (Körbelin et al., EMBO Mol Med. 2016; 8(6): 609).

AAV-PHP.S (Addgene, Watertown, MA) is a variant of AAV9 generated with the CREATE method that encodes the 7-mer sequence QAVRTSL (SEQ ID NO: 92), transduces neurons in the enteric nervous system, and strongly transduces peripheral sensory afferents entering the spinal cord and brain stem.

AAV-PHP.B (Addgene, Watertown, MA) is a variant of AAV9 generated with the CREATE method that encodes the 7-mer sequence TLAVPFK (SEQ ID NO: 93). It transfers genes throughout the CNS with higher efficiency than AAV9 and transduces the majority of astrocytes and neurons across multiple CNS regions.

AAV-PPS, an AAV2 variant crated by insertion of the DSPAHPS (SEQ ID NO: 94) epitope into the capsid of AAV2, shows a dramatically improved brain tropism relative to AAV2.

For additional information regarding capsids that cross the blood brain barrier, see Chan et al., Nat. Neurosci. 2017 August: 20(8): 1172-1179.

(ii) Compositions for Administration. Artificial expression constructs and vectors of the present disclosure (referred to herein as physiologically active components) can be formulated with a carrier that is suitable for administration to a cell, tissue slice, animal (e.g., mouse, non-human primate), or human. Physiologically active components within compositions described herein can be prepared in neutral forms, as freebases, or as pharmacologically acceptable salts.

Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Carriers of physiologically active components can include solvents, dispersion media, vehicles, coatings, diluents, isotonic and absorption delaying agents, buffers, solutions, suspensions, colloids, and the like. The use of such carriers for physiologically active components is well known in the art. Except insofar as any conventional media or agent is incompatible with the physiologically active components, it can be used with compositions as described herein.

The phrase "pharmaceutically-acceptable carriers" refer to carriers that do not produce an allergic or similar untoward reaction when administered to a human, and in particular embodiments, when administered intravenously (e.g. at the retro-orbital plexus).

In particular embodiments, compositions can be formulated for intravenous, intraocular, intravitreal, parenteral, subcutaneous, intracerebro-ventricular, intramuscular, intrathecal, intraspinal, oral, intraperitoneal, oral or nasal inhalation, or by direct injection in or application to one or more cells, tissues, or organs.

Compositions may include liposomes, lipids, lipid complexes, microspheres, microparticles, nanospheres, and/or nanoparticles.

The formation and use of liposomes is generally known to those of skill in the art. Liposomes have been developed with improved serum stability and circulation half-times (see, for instance, U.S. Pat. No. 5,741,516). Further, various methods of liposome and liposome like preparations as potential drug carriers have been described (see, for instance U.S. Pat. Nos. 5,567,434; 5,552,157; 5,565,213; 5,738,868; and 5,795,587).

The disclosure also provides for pharmaceutically acceptable nanocapsule formulations of the physiologically active components. Nanocapsules can generally entrap compounds in a stable and reproducible way (Quintanar-Guerrero et al., *Drug Dev Ind Pharm* 24(12):1113-1128, 1998; Quintanar-Guerrero et al., *Pharm Res.* 15(7):1056-1062, 1998; Quintanar-Guerrero et al., *J. Microencapsul.* 15(1):107-119, 1998; Douglas et al., *Crit Rev Ther Drug Carrier Syst* 3(3):233-261, 1987). To avoid side effects due to intracellular polymeric overloading, such ultrafine particles can be designed using polymers able to be degraded in vivo. Biodegradable polyalkyl-cyanoacrylate nanoparticles that meet these requirements are contemplated for use in the present disclosure. Such particles can be easily made, as described in Couvreur et al., *J Pharm Sci* 69(2):199-202, 1980; Couvreur et al., *Crit Rev Ther Drug Carrier Syst.* 5(1)1-20, 1988; zur Muhlen et al., *Eur J Pharm Biopharm,* 45(2):149-155, 1998; Zambaux et al., *J Control Release* 50(1-3):31-40, 1998; and U.S. Pat. No. 5,145,684.

Injectable compositions can include sterile aqueous solutions or dispersions and sterile powders for the extemporaneous preparation of sterile injectable solutions or dispersions (U.S. Pat. No. 5,466,468). For delivery via injection, the form is sterile and fluid to the extent that it can be delivered by syringe. In particular embodiments, it is stable under the conditions of manufacture and storage, and optionally contains one or more preservative compounds against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and/or antifungal agents, for example, parabens, chlorobutanol, phenol, sorbic acid, thimerosal, and the like. In various embodiments, the preparation will include an isotonic agent(s), for example, sugar(s) or sodium chloride. Prolonged absorption of the injectable compositions can be accomplished by including in the compositions of agents that delay absorption, for example, aluminum monostearate and gelatin. Injectable compositions can be suitably buffered, if necessary, and the liquid diluent first rendered isotonic with sufficient saline or glucose.

Dispersions may also be prepared in glycerol, liquid polyethylene glycols, and mixtures thereof and in oils. As indicated, under ordinary conditions of storage and use, these preparations can contain a preservative to prevent the growth of microorganisms.

Sterile compositions can be prepared by incorporating the physiologically active component in an appropriate amount of a solvent with other optional ingredients (e.g., as enumerated above), followed by filtered sterilization. Generally, dispersions are prepared by incorporating the various sterilized physiologically active components into a sterile vehicle that contains the basic dispersion medium and the required other ingredients (e.g., from those enumerated above). In the case of sterile powders for the preparation of sterile injectable solutions, preferred methods of preparation can be vacuum-drying and freeze-drying techniques which yield a powder of the physiologically active components plus any additional desired ingredient from a previously sterile-filtered solution thereof.

Oral compositions may be in liquid form, for example, as solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). Tablets may be coated by methods well-known in the art.

Inhalable compositions can be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Compositions can also include microchip devices (U.S. Pat. No. 5,797,898), ophthalmic formulations (Bourlais et al., *Prog Retin Eye Res,* 17(1):33-58, 1998), transdermal matrices (U.S. Pat. Nos. 5,770,219 and 5,783,208) and feedback-controlled delivery (U.S. Pat. No. 5,697,899).

Supplementary active ingredients can also be incorporated into the compositions.

Typically, compositions can include at least 0.1% of the physiologically active components or more, although the percentage of the physiologically active components may, of course, be varied and may conveniently be between 1 or 2% and 70% or 80% or more or 0.5-99% of the weight or volume of the total composition. Naturally, the amount of physiologically active components in each physiologically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of compositions and dosages may be desirable.

In particular embodiments, for administration to humans, compositions should meet sterility, pyrogenicity, and the general safety and purity standards as required by United States Food and Drug Administration (FDA) or other applicable regulatory agencies in other countries.

(iii) Cell Lines Including Artificial Expression Constructs. The present disclosure includes cells including an artificial expression construct described herein. A cell that has been transformed with an artificial expression construct can be used for many purposes, including in neuroanatomical studies, assessments of functioning and/or non-functioning proteins, and drug screens that assess the regulatory properties of enhancers.

A variety of host cell lines can be used, but in particular embodiments, the cell is a mammalian neural cell. In particular embodiments, the enhancer sequence of the artificial expression construct is SEQ ID NO: 3 and/or 7 and/or a CN1390, CN1244, CN1389, CN1203, CN1367, CN1498, CN1499, CN1500, CN1838 or a combination of components depicted in FIG. 16, and the cell line is a human, primate, or murine neural cell. Cell lines which can be utilized for transgenesis in the present disclosure also include primary cell lines derived from living tissue such as rat or mouse brains and organotypic cell cultures, including brain slices from animals such as rats or mice. The PC12 cell line (available from the American Type Culture Collection, ATCC, Manassas, VA) has been shown to express a number of neuronal marker proteins in response to Neuronal Growth Factor (NGF). The PC12 cell line is considered to be a neuronal cell line and is applicable for use with this disclosure. JAR cells (available from ATCC) are a platelet derived cell-line that express some neuronal genes, such as the serotonin transporter gene, and may be used with embodiments described herein.

WO 91/13150 describes a variety of cell lines, including neuronal cell lines, and methods of producing them. Similarly, WO 97/39117 describes a neuronal cell line and methods of producing such cell lines. The neuronal cell lines disclosed in these patent applications are applicable for use in the present disclosure.

In particular embodiments, a "neural cell" refers to a cell or cells located within the central nervous system, and includes neurons and glia, and cells derived from neurons and glia, including neoplastic and tumor cells derived from neurons or glia. A "cell derived from a neural cell" refers to a cell which is derived from or originates or is differentiated from a neural cell.

In particular embodiments, "neuronal" describes something that is of, related to, or includes, neuronal cells. Neuronal cells are defined by the presence of an axon and dendrites. The term "neuronal-specific" refers to something that is found, or an activity that occurs, in neuronal cells or cells derived from neuronal cells, but is not found in or occur in, or is not found substantially in or occur substantially in, non-neuronal cells or cells not derived from neuronal cells, for example glial cells such as astrocytes or oligodendrocytes.

In particular embodiments, non-neuronal cell lines may be used, including mouse embryonic stem cells. Cultured mouse embryonic stem cells can be used to analyze expression of genetic constructs using transient transfection with plasmid constructs. Mouse embryonic stem cells are pluripotent and undifferentiated. These cells can be maintained in this undifferentiated state by Leukemia Inhibitory Factor (LIF). Withdrawal of LIF induces differentiation of the embryonic stem cells. In culture, the stem cells form a variety of differentiated cell types. Differentiation is caused by the expression of tissue specific transcription factors, allowing the function of an enhancer sequence to be evaluated. (See for example Fiskerstrand et al., *FEBS Lett* 458: 171-174, 1999.)

Methods to differentiate stem cells into neuronal cells include replacing a stem cell culture media with a media including basic fibroblast growth factor (bFGF) heparin, an N2 supplement (e.g., transferrin, insulin, progesterone, putrescine, and selenite), laminin and polyornithine. A process to produce myelinating oligodendrocytes from stem cells is described in Hu, et al., 2009, *Nat. Protoc.* 4:1614-22. Bibel, et al., 2007, *Nat. Protoc.* 2:1034-43 describes a protocol to produce glutamatergic neurons from stem cells while Chatzi, et al., 2009, *Exp Neurol.* 217:407-16 describes a procedure to produce GABAergic neurons. This procedure includes exposing stem cells to all-trans-RA for three days. After subsequent culture in serum-free neuronal induction medium including Neurobasal medium supplemented with B27, bFGF and EGF, 95% GABA neurons develop U.S. Publication No. 2012/0329714 describes use of prolactin to increase neural stem cell numbers while U.S. Publication No. 2012/0308530 describes a culture surface with amino groups that promotes neuronal differentiation into neurons, astrocytes and oligodendrocytes. Thus, the fate of neural stem cells can be controlled by a variety of extracellular factors. Commonly used factors include brain derived growth factor (BDNF; Shetty and Turner, 1998, *J. Neurobiol.* 35:395-425); fibroblast growth factor (bFGF; U.S. Pat. No. 5,766,948; FGF-1, FGF-2); Neurotrophin-3 (NT-3) and Neurotrophin-4 (NT-4); Caldwell, et al., 2001, *Nat. Biotechnol.* 1; 19:475-9); ciliary neurotrophic factor (CNTF); BMP-2 (U.S. Pat. Nos. 5,948,428 and 6,001,654); isobutyl 3-methylxanthine; leukemia inhibitory growth factor (LIF; U.S. Pat. No. 6,103,530); somatostatin; amphiregulin; neurotrophins (e.g., cyclic adenosine monophosphate; epidermal growth factor (EGF); dexamethasone (glucocorticoid hormone); forskolin; GDNF family receptor ligands; potassium; retinoic acid (U.S. Pat. No. 6,395,546); tetanus toxin; and transforming growth factor-α and TGF-β (U.S. Pat. Nos. 5,851,832 and 5,753,506).

In particular embodiments, yeast one-hybrid systems may also be used to identify compounds that inhibit specific protein/DNA interactions, such as transcription factors for I56i enhancers, cores thereof and/or the SEQ ID NO: 3 and/or 7

Transgenic animals are described below. Cell lines may also be derived from such transgenic animals. For example, primary tissue culture from transgenic mice (e.g., also as described below) can provide cell lines with the expression construct already integrated into the genome. (for an example see MacKenzie & Quinn, *Proc Natl Acad Sci USA* 96: 15251-15255, 1999).

(iv) Transgenic Animals. Another aspect of the disclosure includes transgenic animals, the genome of which contains an artificial expression construct including concatamerizations of I56i enhancer cores such as SEQ ID NO: 2 and/or 6 (e.g., SEQ ID NO: 3 and/or 7) operatively linked to a heterologous coding sequence. In particular embodiments, the genome of a transgenic animal includes the CN1390, CN1244, CN1389, CN1203, CN1367, CN1498, CN1499, CN1500, CN1838 or a combination of components depicted in FIG. 16. In particular embodiments, when a non-integrating vector is utilized, a transgenic animal includes an artificial expression construct including concatemerizations of I56i enhancer cores such as SEQ ID NO: 2 and/or 6 (e.g., SEQ ID NO: 3 and/or 7) and/or CN1390, CN1244, CN1389, CN1203, CN1367, CN1498, CN1499, CN1500, CN1838 or a combination of components depicted in FIG. 16 within one or more of its cells.

Detailed methods for producing transgenic animals are described in U.S. Pat. No. 4,736,866. Transgenic animals may be of any nonhuman species, but preferably include nonhuman primates (NHPs), sheep, horses, cattle, pigs, goats, dogs, cats, rabbits, chickens, and rodents such as guinea pigs, hamsters, gerbils, rats, mice, and ferrets.

In particular embodiments, construction of a transgenic animal results in an organism that has an engineered construct present in all cells in the same genomic integration site. Thus, cell lines derived from such transgenic animals will be consistent in as much as the engineered construct will be in the same genomic integration site in all cells and hence will suffer the same position effect variegation. In contrast, introducing genes into cell lines or primary cell cultures can give rise to heterologous expression of the construct. A disadvantage of this approach is that the expression of the introduced DNA may be affected by the specific genetic background of the host animal.

As indicated above in relation to cell lines, the artificial expression constructs of this disclosure can be used to genetically modify mouse embryonic stem cells using techniques known in the art. Typically, the artificial expression construct is introduced into cultured murine embryonic stem cells. Transformed ES cells are then injected into a blastocyst from a host mother and the host embryo re-implanted into the mother. This results in a chimeric mouse whose tissues are composed of cells derived from both the embryonic stem cells present in the cultured cell line and the embryonic stem cells present in the host embryo. Usually the mice from which the cultured ES cells used for transgenesis are derived are chosen to have a different coat color from the host mouse into whose embryos the transformed cells are to be injected. Chimeric mice will then have a variegated coat color. As long as the germ-line tissue is derived, at least in part, from the genetically modified cells, then the chimeric mice be crossed with an appropriate strain to produce offspring that will carry the transgene.

In addition to the methods of delivery described above, the following techniques are also contemplated as alternative methods of delivering artificial expression constructs to target cells or selected tissues and organs of an animal, and in particular, to cells, organs, or tissues of a vertebrate mammal: sonophoresis (e.g., ultrasound, as described in U.S. Pat. No. 5,656,016); intraosseous injection (U.S. Pat. No. 5,779,708); microchip devices (U.S. Pat. No. 5,797,898); ophthalmic formulations (Bourlais et al., *Prog Retin Eye Res,* 17(1):33-58, 1998); transdermal matrices (U.S. Pat. Nos. 5,770,219 and 5,783,208); and feedback-controlled delivery (U.S. Pat. No. 5,697,899).

(v) Methods of Use. In particular embodiments, a composition including a physiologically active component described herein is administered to a subject to result in a physiological effect.

In particular embodiments, the disclosure includes the use of the artificial expression constructs described herein to modulate expression of a heterologous gene which is either partially or wholly encoded in a location downstream to that enhancer in an engineered sequence. Thus, there are provided herein methods of use of the disclosed artificial expression constructs in the research, study, and potential development of medicaments for preventing, treating or ameliorating the symptoms of a disease, dysfunction, or disorder.

Particular embodiments include methods of administering to a subject an artificial expression construct that includes SEQ ID NO: 2, SEQ ID NO: 6, SEQ ID NO: 3 and/or SEQ ID NO: 7 as described herein to drive selective expression of a gene in a selected neural cell type.

Particular embodiments include methods of administering to a subject an artificial expression construct that includes CN1390, CN1244, CN1389, CN1203, CN1367, CN1498, CN1499, CN1500, CN1838 or a combination of components depicted in FIG. 16 as described herein to drive selective expression of a gene in a selected neural cell type wherein the subject can be an isolated cell, a network of cells, a tissue slice, an experimental animal, a veterinary animal, or a human.

As is well known in the medical arts, dosages for any one subject depends upon many factors, including the subject's size, surface area, age, the particular compound to be administered, sex, time and route of administration, general health, and other drugs being administered concurrently. Dosages for the compounds of the disclosure will vary, but, in particular embodiments, a dose could be from $10^5$ to $10^{100}$ copies of an artificial expression construct of the disclosure. In particular embodiments, a patient receiving intravenous, intraspinal, retro-orbital, or intrathecal administration can be infused with from $10^6$ to $10^{22}$ copies of the artificial expression construct.

An "effective amount" is the amount of a composition necessary to result in a desired physiological change in the subject. Effective amounts are often administered for research purposes. Effective amounts disclosed herein can cause a statistically-significant effect in an animal model or in vitro assay.

In particular embodiments, constructs disclosed herein can be utilized to treat Dravet Syndrome. In particular embodiments, the methods reduce or prevent seizures, or symptoms thereof in a patient in need thereof. In particular embodiments, the methods provided may reduce or prevent one or more different types of seizures. Ideally, the methods of the disclosure result in a total prevention of seizures. However, the disclosure also encompasses methods in which the instances of seizures are decreased by at least 10%, at least 20%, at least 30%, at least 40%, at least 50%, at least 60%, at least 70%, at least 80% or at least 90%.

Generally, a seizure can include convulsions, repetitive movements, unusual sensations, and combinations thereof. Seizures can be categorized as focal seizures (also referred to as partial seizures) and generalized seizures. Focal seizures affect only one side of the brain, while generalized seizures affect both sides of the brain. Specific types of focal seizures include simple focal seizures, complex focal seizures, and secondarily generalized seizures. Simple focal seizures can be restricted or focused on a particular lobe (e.g., temporal lobe, frontal lobe, parietal lobe, or occipital lobe). Complex focal seizures generally affect a larger part of one hemisphere than simple focal seizures, but commonly originate in the temporal lobe or the frontal lobe. When a focal seizure spreads from one side (hemisphere) to both sides of the brain, the seizure is referred to as a secondarily generalized seizure. Specific types of generalized seizures include absences (also referred to as petit mal seizures), tonic seizures, atonic seizures, myoclonic seizures, tonic clonic seizures (also referred to as grand mal seizures), and clonic seizures.

In particular embodiments, methods described herein may reduce the frequency of seizures, reduce the severity of seizures, change the type of seizures (e.g., from a more severe type to a less severe type), or a combination thereof in a patient after treatment compared to the absence of treatment (e.g., before treatment), or compared to treatment with an alternative conventional treatment.

The amount of expression constructs and time of administration of such compositions will be within the purview of the skilled artisan having benefit of the present teachings. It is likely, however, that the administration of effective amounts of the disclosed compositions may be achieved by a single administration, such as for example, a single injection of sufficient numbers of infectious particles to provide an effect in the subject. Alternatively, in some circumstances, it may be desirable to provide multiple, or successive administrations of the artificial expression construct compositions or other genetic constructs, either over a relatively short, or a relatively prolonged period of time, as may be determined by the individual overseeing the administration of such compositions. For example, the number of infectious particles administered to a mammal may be $10^7$, $10^8$, $10^9$, $10^{10}$, $10^{11}$, $10^{12}$, $10^{13}$, or even higher, infectious particles/ml given either as a single dose or divided into two or more administrations as may be required to achieve an intended effect. In fact, in certain embodiments, it may be desirable to administer two or more different expression constructs in combination to achieve a desired effect.

In certain circumstances it will be desirable to deliver the artificial expression construct in suitably formulated compositions disclosed herein either by pipette, retro-orbital injection, subcutaneously, intraocularly, intravitreally, parenterally, subcutaneously, intravenously, intracerebro-ventricularly, intramuscularly, intrathecally, intraspinally, orally, intraperitoneally, by oral or nasal inhalation, or by direct application or injection to one or more cells, tissues, or organs. The methods of administration may also include those modalities as described in U.S. Pat. Nos. 5,543,158; 5,641,515 and 5,399,363.

(vi) Kits and Commercial Packages. Kits and commercial packages contain an artificial expression construct described herein. The expression construct can be isolated. In particular embodiments, the components of an expression product can be isolated from each other. In particular embodiments, the expression product can be within a vector, within a viral vector, within a cell, within a tissue slice or sample, and/or within a transgenic animal. Such kits may further include one or more reagents, restriction enzymes, peptides, therapeutics, pharmaceutical compounds, or means for delivery of the compositions such as syringes, injectables, and the like.

Embodiments of a kit or commercial package will also contain instructions regarding use of the included components, for example, in basic research, electrophysiological research, neuroanatomical research, and/or the research and/or treatment of a disorder, disease or condition.

The Exemplary Embodiments and Experimental Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

(vii) Exemplary Embodiments

1. A core of a I56i enhancer, a concatemerized core of a I56i enhancer, or a concatemerized I56i enhancer.

2. The I56i enhancer core, concatemerized I56i enhancer core, or concatemerized I56i enhancer of embodiment 1, wherein the I56i enhancer is human, murine, or zebrafish (I46i).

3. The I56i enhancer core, concatemerized I56i enhancer core, or concatemerized I56i enhancer of embodiment 1 or 2, wherein the concatemerized core includes SEQ ID NO: 2 or 6.

4. The I56i enhancer core, concatemerized I56i enhancer core, or concatemerized I56i enhancer of any of embodiments 1-3, wherein the concatemerized core includes 2, 3, 4, 5, 6, 7, 8, 9, or 10 copies of the I56i core.

5. The I56i enhancer core, concatemerized I56i enhancer core, or concatemerized I56i enhancer of embodiment 4, including 2, 3, 4, 5, 6, 7, 8, 9, or 10 copies of SEQ ID NO: 2 and/or 6 (e.g., SEQ ID NO: 2 and SEQ ID NO: 6 within one sequence such as SEQ ID NO: 2—SEQ ID NO: 2—SEQ ID NO: 6; SEQ ID NO: 2—SEQ ID NO: 6—SEQ ID NO: 6; SEQ ID NO: 2—SEQ ID NO: 6—SEQ ID NO: 2; SEQ ID NO: 6—SEQ ID NO: 6—SEQ ID NO: 2; SEQ ID NO: 6—SEQ ID NO: 2—SEQ ID NO: 2; and SEQ ID NO: 6—SEQ ID NO: 2—SEQ ID NO: 6).

6. The I56i enhancer core, concatemerized I56i enhancer core, or concatemerized I56i enhancer of embodiment 4 or 5, including 2, 3, 4, 5, 6, 7, 8, 9, or 10 copies of SEQ ID NO: 2.

7. The I56i enhancer core, concatemerized I56i enhancer core, or concatemerized I56i enhancer of embodiment 4 or 5, including 2, 3, 4, 5, 6, 7, 8, 9, or 10 copies of SEQ ID NO: 6.

8. The I56i enhancer core, concatemerized I56i enhancer core, or concatemerized I56i enhancer of embodiment 4 or 5, including 3 copies of SEQ ID NO: 2.

9. The I56i enhancer core, concatemerized I56i enhancer core, or concatemerized I56i enhancer of embodiment 4 or 5, including 3 copies of SEQ ID NO: 6.

10. The I56i enhancer core, concatemerized I56i enhancer core, or concatemerized I56i enhancer of embodiment 8, wherein the concatemerized core includes SEQ ID NO: 3.

11. The I56i enhancer core, concatemerized I56i enhancer core, or concatemerized I56i enhancer of embodiment 9, wherein the concatemerized core includes SEQ ID NO: 7.

12. An artificial expression construct including (i) an I56i enhancer core, concatemerized I56i enhancer core, or concatemerized I56i enhancer of any of embodiments 1-11, (ii) a promoter; and (iii) a heterologous encoding sequence.

13. The artificial expression construct of embodiment 12, wherein the heterologous encoding sequence encodes an effector element or an expressible element.

14. The artificial expression construct of embodiment 12 or 13, wherein the effector element includes a reporter protein or a functional molecule.

15. The artificial expression construct of embodiment 14, wherein the reporter protein is a fluorescent protein.

16. The artificial expression construct of embodiment 14 or 15, wherein the effector element is Cre, iCre, dgCre, FIpE, FIpO, or tTA2 or a functional molecule selected from a functional ion transporter, enzyme, a transcription factor, a receptor, a membrane protein, a cellular trafficking protein, a signaling molecule, a neurotransmitter, a calcium reporter, a channel rhodopsin, a CRISPR/CAS molecule, an editase, a guide RNA molecule, a homologous recombination donor cassette, or a designer receptor exclusively activated by designer drug (DREADD).

17. The artificial expression construct of any of embodiments 13, wherein the expressible element is a non-functional molecule.

18. The artificial expression construct of embodiment 17, wherein the non-functional molecule is a non-functional ion transporter, enzyme, transcription factor, receptor, membrane protein, cellular trafficking protein, signaling molecule, neurotransmitter, calcium reporter, channel rhodopsin, CRISPR/CAS molecule, editase, guide RNA molecule, homologous recombination donor cassette, or a DREADD.

19. The artificial expression construct of any of embodiments 12-18, wherein the expression construct is associated with a capsid that crosses the blood brain barrier.

20. The artificial expression construct of embodiment 19, wherein the capsid includes PHP.eB, AAV-BR1, AAV-PHP.S, AAV-PHP.B, or AAV-PPS.

21. The artificial expression construct of any of embodiments 12-20, wherein the expression construct includes or encodes a skipping element.

22. The artificial expression construct of embodiment 21, wherein the skipping element includes a 2A peptide and/or an internal ribosome entry site (IRES).

23. The artificial expression construct of embodiment 22, wherein the 2A peptide is selected from T2A, P2A, E2A, or F2A.

24. The artificial expression construct of any of embodiments 12-23, wherein the expression construct includes a set of features selected from: 3×hI56Core, minBglobin, minCMV, SYFP2, His, 3×HA, NavMs, NavBp, NavSheP-D60N, WPRE3, BGHpA or a combination of features selected from a construct depicted in FIG. 16.

25. A vector including an artificial expression construct of any of embodiments 12-24.

26. A vector including a combination of components depicted in FIG. 16.

27. The vector of embodiment 26, wherein the vector is a viral vector.

28. The vector of embodiment 26 or 27, wherein the viral vector is a recombinant adeno-associated viral (AAV) vector.

29. An adeno-associated viral (AAV) vector including at least one heterologous encoding sequence, wherein the heterologous encoding sequence is under control of a promoter and an enhancer selected from SEQ ID NO: 3 and/or 7.

30. The AAV vector of embodiment 29, wherein the AAV vector is replication-competent.

31. A transgenic cell including an expression construct or vector of any of the preceding embodiments.

32. The transgenic cell of embodiment 31, wherein the transgenic cell is a GABAergic interneuron.

33. A non-human transgenic animal including an expression construct, vector, or transgenic cell of any of the preceding embodiments.

34. The non-human transgenic animal of embodiment 33 wherein the non-human transgenic animal is a mouse or a non-human primate.

35. An administrable composition including an expression construct, vector, or transgenic cell of any of the preceding embodiments.

36. A kit including an expression construct, vector, transgenic cell, transgenic animal, and/or administrable compositions of any of the preceding embodiments.

37. A method for selectively expressing a heterologous gene within a population of neural cells in vivo or in vitro, the method including providing the administrable composition of embodiment 35 in a sufficient dosage and for a sufficient time to a sample or subject including the population of neural cells thereby selectively expressing the gene within the population of neural cells.

38. The method of embodiment 37, wherein the heterologous gene encodes an effector element or an expressible element.

39. The method of embodiment 38, wherein the effector element includes a reporter protein or a functional molecule.

40. The method of embodiment 39, wherein the reporter protein is a fluorescent protein.

41. The method of embodiment 39 or 40, wherein the effector element is Cre, iCre, dgCre, FIpE, FIpO, or tTA2 or a functional molecule selected from a functional ion transporter, enzyme, a transcription factor, a receptor, a membrane protein, a cellular trafficking protein, a signaling molecule, a neurotransmitter, a calcium reporter, a channel rhodopsin, a CRISPR/CAS molecule, an editase, a guide RNA molecule, a homologous recombination donor cassette, or a DREADD.

42. The method of embodiment 38, wherein the expressible element is a non-functional molecule.

43. The method of embodiment 42, wherein the non-functional molecule is a non-functional ion transporter, enzyme, transcription factor, receptor, membrane protein, cellular trafficking protein, signaling molecule, neurotransmitter, calcium reporter, channel rhodopsin, CRISPR/CAS molecule, editase, guide RNA molecule, homologous recombination donor cassette, or DREADD.

44. The method of any of embodiments 37-43, wherein the providing includes pipetting.

45. The method of embodiment 44, wherein the pipetting is to a brain slice.

46. The method of embodiment 45, wherein the brain slice includes a GABAergic interneuron.

47. The method of any of embodiments 45 or 46, wherein the brain slice is murine, human, or non-human primate.

48. The method of any of embodiments 37-43, wherein the providing includes administering to a living subject.

49. The method of embodiment 48, wherein the living subject is a human, non-human primate, or a mouse.

50. The method of any of embodiments 48 or 49, wherein the administering to a living subject is through injection.

51. The method of embodiment 50, wherein the injection includes intravenous injection, intraparenchymal injection into brain tissue, intracerebroventricular (ICV) injection, intra-cisterna magna (ICM) injection, or intrathecal injection.

52. An artificial expression construct consisting of or consisting essentially of a combination of features depicted in FIG. 16.

53. Any of the embodiments above including an effector element or expressible element wherein the effector element or expressible element is an ion transporter selected from a voltage gated sodium channel (e.g., SCN1A), a potassium channel (e.g., KCNQ2), or a calcium channel (e.g., CACNA1C); a cellular trafficking protein selected from clathrin, dynamin, caveolin, Rab-4A, or Rab-11A; an enzyme selected from lactase, lipase, helicase, alpha-glucosidase, and amylase); a transcription factor selected from SP1, AP-1, Heat shock factor protein 1, C/EBP (CCAA-T/enhancer binding protein), and Oct-1; a receptor selected from transforming growth factor receptor beta 1, platelet-derived growth factor receptor, epidermal growth factor receptor, vascular endothelial growth factor receptor, and interleukin 8 receptor alpha; a signaling molecule selected from nerve growth factor (NGF), platelet-derived growth factor (PDGF), transforming growth factor β (TGFβ), epidermal growth factor (EGF), and GTPase HRas; a neurotransmitter selected from cocaine and amphetamine regulated transcript, substance P, oxytocin, and somatostatin; a calcium reporter selected from genetically encoded calcium indicators (GECI, NTnC, GCaMP6s, GCaMP6f, GCaMP6m, jGCaMP7s, jGCaMP7f, jGCaMP7b, jGCaMP7c, jRGECO1a, jRGECO1b), Myosin light chain kinase, Green fluorescent protein, Calmodulin chimera, Calcium indicator TN-XXL, BRET-based auto-luminescent calcium indicator, and Calcium indicator protein OeNL(Ca2+)-18u); a channel rhodopsin selected from channelrhodopsin-1 and channelrhodopsin-2 or a variant thereof; guide RNA; a nuclease selected from Cas, Cas9, Cpf1, ribonuclease 4, and deoxyribonuclease II beta; and/or a DREADD (e.g., hM3DREADD, hM4DREADD).

Within this disclosure I56i should be interpreted to be I46i when the context demonstrates reference to or use of the zebrafish form of the enhancers described herein (viii) Experimental Example. Dravet syndrome (DS) is a drug-resistant and life-threatening form of epilepsy. It typically begins in the first year of life, with fever- or temperature-induced seizures that evolve into generalized clonic, tonic-clonic, and unilateral seizures. These seizures are often resistant to current anti-epileptic drugs, the first-line therapies for this syndrome; complete seizure control is typically not achieved. As the disease progresses, most affected children also suffer from comorbid conditions including developmental delays, intellectual disabilities, impaired motor control and coordination, autistic behaviors, sleep disturbances, and many die prematurely.

Heterozygous loss-of-function mutations in SCN1A, the gene that encodes the pore-forming subunit of the voltage-gated sodium channel Nav1.1 are the most common cause of DS and occur in nearly 1/16,000 newborns.

A mouse model, generated by knock-out of Scn1a, replicates the several key phenotypic features of this epilepsy including infantile (P21)-epilepsy onset, high susceptibility to thermal seizures, ataxia, spontaneous seizures, sleep impairments, autistic behaviors, and premature death. Seizures and several comorbidities arise from impaired interneuron function in these mice.

This mouse model was used to investigate the efficacy of a new viral vector for DS. The virus was delivered by retro-orbital injection using an insulin syringe and its ability to suppress seizure was evaluated using the thermal seizure test. In this test, the mouse body core temperature is elevated slowly, using a temperature controller and a heat lamp, until a seizure occurs, or 42.5° C. is attained. The temperature of seizure onset in treated and control mice are compared to determine the efficacy of the intervention. In additional tests, the efficacy of treatment on spontaneous seizure and premature mortality are assessed using video and electroencephalographic monitoring.

The viral vector is a new AAV viral vector named CN1500. This viral vector is a recombinant AAV that expresses the transgene SYFP2-P2A-NavSheP-D60N to rescue the loss of the voltage-gated sodium channel Nav1.1. NavSheP-D60N is a modified voltage-gated sodium channel of bacterial origin that has been modified to improve the kinetics and expression in mammalian cells. The transgene expression level is elevated by the addition of a WPRE3 element, and transcription is terminated with the bovine growth hormone poly adenylation sequence. Expression of the transgene is high and limited to inhibitory cells in forebrain structures including the cortex and the hippocampus, via the 3×hI56iCore synthetic enhancer (SEQ ID NO: 3) directly 5' of a CMV minimal promoter. Furthermore, the therapeutic transgene NavSheP-D60N is labeled by an HA epitope tag to verify correct protein localization.

To test the efficacy of the therapeutic AAV viral vector, CN1500 package using the PHP.eB serotype was used. A cohort of postnatal day 35 Scn1a$^{+/-}$ mice were either injected with $2\times10^{11}$ vg per animal or were left un-injected. The AAV was introduced intravenously using the retro-orbital delivery route. Two weeks after viral administration, animals from the treatment and control groups were assessed for their susceptibility to febrile seizures. As indicated previously, febrile seizures were measured by steadily raising the mouse's temperature under a heat lamp 0.5 Celsius every two minutes and measuring the internal temperature of the mouse with a rectal probe. The temperature where the mouse experienced a seizure is recorded.

The new therapeutic vector CN1500 was both highly expressed in mouse cortical and hippocampal GABAergic cells, but also raised the average temperature where Scn1a$^{+/-}$ mice experienced febrile seizures from 38.7° C. to 41° C. These data show that CN1500 can substantially rescue the loss of Scn1a.

Example 1 references include: Catterall et al. (2010) The Journal of physiology 588:1849-1859; Cheah et al. (2012) Proceedings of the National Academy of Sciences of the United States of America 109:14646-14651; Kalume (2013) *Respir Physiol Neurobiol.* 189(2):324-8; Kalume et al., (2007) J Neurosci 27:11065-11074; Kalume et al., (2013) The Journal of clinical investigation 123:1798-1808; Oakley et al., (2009) Proceedings of the National Academy of Sciences of the United States of America 106:3994-3999.

(ix) Closing Paragraphs. Nucleic acid sequences described herein are shown using standard letter abbreviations for nucleotide bases, as defined in 37 C.F.R. § 1.822. Only one strand of each nucleic acid sequence is shown, but the complementary strand is understood as included in embodiments where it would be appropriate.

Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wisconsin) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gin), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (Ile), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (non-polar): Proline (Pro), Ala, Val, Leu, Ile, Phe, Met, and Trp; Group 11 (aliphatic): Gly, Ala, Val, Leu, and Ile; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157(1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridizes under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M $NaH_2PO_4$; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in selective expression in the targeted cell population as determined by scRNA-Seq and the following enhancer/targeted cell population pairing: concatemerized core of the I56i enhancer (e.g., SEQ ID NO: 3)/GABAergic interneurons.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. An artificial expression construct comprising (i) a concatemer comprising 2, 3, 4, 5, 6, 7, 8, 9, or 10 copies of a sequence consisting of SEQ ID NO: 2 or SEQ ID NO: 6; (ii) a promoter; and (iii) a coding sequence.

2. The artificial expression construct of claim 1, wherein the coding sequence encodes a fluorescent protein or an ion transporter selected from a potassium channel, or a calcium channel.

3. The artificial expression construct of claim 1, within a vector for delivery into a cell.

4. The artificial expression construct of claim 3, wherein the vector is a viral vector.

5. The artificial expression construct of claim 4, wherein the viral vector is a recombinant adeno-associated viral (AAV) vector.

6. The artificial expression construct of claim 1, wherein the concatemer comprises 2, 3, 4, 5, or 6 copies of the sequence consisting of SEQ ID NO: 2 or 2, 3, 4, 5, or 6 copies of the sequence consisting of SEQ ID NO: 6.

7. The artificial expression construct of claim 1, wherein the concatemer has 3 copies of the sequence consisting of SEQ ID NO: 2 or 3 copies of the sequence consisting of SEQ ID NO: 6.

8. The artificial expression construct of claim 1, wherein the concatemer consists of the sequence of SEQ ID NO: 3 or SEQ ID NO: 7.

9. The artificial expression construct of claim 1, wherein the artificial expression construct is associated with a capsid that crosses the blood brain barrier.

10. The artificial expression construct of claim 9, wherein the capsid is PHP.eB, AAV-BR1, AAV-PHP.S, AAV-PHP.B, or AAV-PPS.

11. The artificial expression construct of claim 1, wherein the artificial expression construct encodes a skipping element.

12. The artificial expression construct of claim 11, wherein the skipping element comprises a 2A peptide or an internal ribosome entry site (IRES).

13. The artificial expression construct of claim 12, wherein the 2A peptide is selected from T2A, P2A, E2A, or F2A.

14. The artificial expression construct of claim 1, wherein the artificial expression construct encodes a set of features selected from: 3Xhl56Core, minBglobin, minCMV, SYFP2, His, 3×HA, NavMs, NavBp, NavSheP-D60N, WPRE3, or BGHpA.

15. The artificial expression construct of claim 1, comprising a sequence having at least 95% sequence identity to the sequence of SEQ ID NO: 37, SEQ ID NO: 38, SEQ ID NO: 39, or SEQ ID NO: 42.

16. The artificial expression construct of claim 1, having the sequence of SEQ ID NO: 37, SEQ ID NO: 38, SEQ ID NO: 39, or SEQ ID NO: 42.

17. The artificial expression construct of claim 5, wherein the AAV vector is replication-competent.

18. The artificial expression construct of claim 1, wherein the coding sequence encodes an ion transporter, an enzyme, a transcription factor, a receptor, a membrane protein, a cellular trafficking protein, a signaling molecule, a neurotransmitter, a calcium reporter, a channel rhodopsin, a CRISPR/CAS molecule, an editase, a guide RNA molecule, a homologous recombination donor cassette, or a designer receptor exclusively activated by designer drug (DREADD).

* * * * *

SEQUENCE LISTING

```
<160> NUMBER OF SEQ ID NOS: 106

<210> SEQ ID NO 1
<211> LENGTH: 528
<212> TYPE: DNA
<213> ORGANISM: Homo sapiens

<400> SEQUENCE: 1

tatgcactca cagtggtttg gcatgcatct ggtgaatttt ttttaacgaa aaattagtgt      60

tggtttcgat gtatggtagc attctcccta acgtaatttg aataattcag caaagcccca     120

ctaccagctg tacttctgca gcctcttcca ttcttttcag cattataatt ttggttaatt     180

ttcaatttta ggtcctacgt ctctgcaatt tgtgtatgaa taacagaata atttccctct     240

tttgtttcgc ctttcctgtt cctgaatcta aataaagatg gctttttagt attaaaagtg     300

gaagaaaatt acaggtaatt atctttgacg gtaaaaacgc tgtaatcagc gggctacatg     360

aaaaattact ctaattatgg ctgcatttaa gagaatggaa aaaaaccttc ttgtggataa     420

aaaccttaaa ttgtccccaa tgtctgcttc aaattggatg gcactgcagc tggaggcttt     480

gttcagaatt gatcctgggg agctacgaac ccaaagtttc acagtagg                  528


<210> SEQ ID NO 2
<211> LENGTH: 131
<212> TYPE: DNA
<213> ORGANISM: Homo sapiens

<400> SEQUENCE: 2

ctaaataaag atggcttttt agtattaaaa gtggaagaaa attacaggta attatctttg      60

acggtaaaaa cgctgtaatc agcgggctac atgaaaaatt actctaatta tggctgcatt     120

taagagaatg g                                                          131


<210> SEQ ID NO 3
<211> LENGTH: 393
<212> TYPE: DNA
<213> ORGANISM: Artificial Sequence
<220> FEATURE:
<223> OTHER INFORMATION: Triply concatamerized core of Homo spaiens I56i
      Core

<400> SEQUENCE: 3

ctaaataaag atggcttttt agtattaaaa gtggaagaaa attacaggta attatctttg      60

acggtaaaaa cgctgtaatc agcgggctac atgaaaaatt actctaatta tggctgcatt     120

taagagaatg gctaaataaa gatggctttt tagtattaaa agtggaagaa aattacaggt     180

aattatcttt gacggtaaaa acgctgtaat cagcgggcta catgaaaaat tactctaatt     240

atggctgcat ttaagagaat ggctaaataa agatggcttt ttagtattaa aagtggaaga     300

aaattacagg taattatctt tgacggtaaa aacgctgtaa tcagcgggct acatgaaaaa     360

ttactctaat tatggctgca tttaagagaa tgg                                  393
```

<210> SEQ ID NO 4
<211> LENGTH: 527
<212> TYPE: DNA
<213> ORGANISM: Mus musculus

<400> SEQUENCE: 4
tatacactca cagtggtttg gcatatattt ggtgaaattt tttaaggaaa aattagtgtt 60
ggtttcgata tatggtagct ttttctctaa cataatttga ataattcagc aaagccctac 120
taccagctgt acttctgcag cctcttccat tctttccagc attataattt tggttaattt 180
tcaattttag gtcctacgtc tctgcaattt gtgtatgaat aacagaataa tttccctctt 240
ttgtttcgcc tttcctgttc ctgaatctaa ataaagatgg ctttttagta ttaaaagtgg 300
aagaaaatta caggtaatta tctttgacgg taaaaacgct gtaatcagcg ggctacatga 360
aaaattactc taattatggc tgcatttaag agaatggaaa aaaaccttct tgtggataaa 420
aaccttaaat tgtccccaat gtctgcttca aattggatgg cactgcagct ggaggctttg 480
ttcagaattg atcctgggga gctacgaacc caaagtttca cagtagg 527

<210> SEQ ID NO 5
<211> LENGTH: 281
<212> TYPE: DNA
<213> ORGANISM: Danio rerio

<400> SEQUENCE: 5
acattgtaat tttagataat atcccaagcg ttcactctcc tcggcaattt gtacatgaat 60
aaccgaataa tttcatcttt tgtttcgtct ttgccacttc aaatccaaat aaagatgcct 120
tttagtatta aaagtggtag aaaattacag gtaattatct ttgacggtaa aaacgctgta 180
atcagcgggc tacatcaaaa attaccctaa ttatgtctgc atttatgaga atggaaaaaa 240
accctctctt ggataaaacc cataaattgt cccaaatatc t 281

<210> SEQ ID NO 6
<211> LENGTH: 130
<212> TYPE: DNA
<213> ORGANISM: Danio rerio

<400> SEQUENCE: 6
ccaaataaag atgcctttta gtattaaaag tggtagaaaa ttacaggtaa ttatctttga 60
cggtaaaaac gctgtaatca gcgggctaca tcaaaaatta ccctaattat gtctgcattt 120
atgagaatgg 130

<210> SEQ ID NO 7
<211> LENGTH: 390
<212> TYPE: DNA
<213> ORGANISM: Artificial Sequence
<220> FEATURE:
<223> OTHER INFORMATION: Triply concatamerized core of I56i enhancer from Danio rerio

<400> SEQUENCE: 7
ccaaataaag atgcctttta gtattaaaag tggtagaaaa ttacaggtaa ttatctttga 60
cggtaaaaac gctgtaatca gcgggctaca tcaaaaatta ccctaattat gtctgcattt 120
atgagaatgg ccaaataaag atgcctttta gtattaaaag tggtagaaaa ttacaggtaa 180
ttatctttga cggtaaaaac gctgtaatca gcgggctaca tcaaaaatta ccctaattat 240
gtctgcattt atgagaatgg ccaaataaag atgcctttta gtattaaaag tggtagaaaa 300
ttacaggtaa ttatctttga cggtaaaaac gctgtaatca gcgggctaca tcaaaaatta 360
ccctaattat gtctgcattt atgagaatgg 390

<210> SEQ ID NO 8
<211> LENGTH: 53
<212> TYPE: DNA
<213> ORGANISM: Artificial Sequence
<220> FEATURE:
<223> OTHER INFORMATION: Beta-Globin Minimal Promoter

<400> SEQUENCE: 8
gggctgggca taaaagtcag ggcagagcca tctattgctt acatttgctt ctg 53

<210> SEQ ID NO 9
<211> LENGTH: 68
<212> TYPE: DNA
<213> ORGANISM: Artificial Sequence
<220> FEATURE:
<223> OTHER INFORMATION: minCMV Promoter

<400> SEQUENCE: 9
gaggtaggcg tgtacggtgg gaggcctata taagcagagc tcgtttagtg aaccgtcaga 60
tcgcctgg 68

<210> SEQ ID NO 10
<211> LENGTH: 68
<212> TYPE: DNA
<213> ORGANISM: Artificial Sequence
<220> FEATURE:
<223> OTHER INFORMATION: Mutated minCMV Promoter

<400> SEQUENCE: 10
gaggtaggcg tgtacggtgg gaggcctata taagcagagc tggtttagtg aaccgtcaga 60
tcgcctgg 68

<210> SEQ ID NO 11
<211> LENGTH: 120
<212> TYPE: DNA
<213> ORGANISM: Artificial Sequence
<220> FEATURE:
<223> OTHER INFORMATION: minRho Promoter

<400> SEQUENCE: 11
gattcagccg ggagcttagg gaggggaggt cacttcataa gggcctgggg ggggagttgg 60
agccacgagt cgtccagccg gagccccgtg tggctgagct ccggcctcag aagcatcccc 120

<210> SEQ ID NO 12
<211> LENGTH: 867
<212> TYPE: DNA
<213> ORGANISM: Artificial Sequence
<220> FEATURE:
<223> OTHER INFORMATION: Hsp68 minimal Promoter

<400> SEQUENCE: 12
caggaacatc caaactgagc agccggggtc cccccaccc cccaccccgc cccacgcggc 60
aactttgagc ctgtgctggg acagagcctc tagttcctaa attagtccat gaggtcagag 120
gcagcactgc cattgtaacg cgattggaga ggatcacgtc accggacacg cccccaggca 180
tctccctggg tctcctaaac ttggcgggga gaagttttag cccttaagtt ttagccttta 240
acccccatat tcagaactgt gcgagttggc gaaaccccac aaatcacaac aaactgtaca 300
caacaccgag ctagaggtga tctttcttgt ccattccaca caggccttag taatgcgtcg 360
ccatagcaac agtgtcacta gtagcaccag cacttcccca caccctcccc ctcaggaatc 420
cgtactctcc agtgaacccc agaaacctct ggagagttct ggacaagggc ggaacccaca 480
actccgatta ctcaagggag gcggggaagc tccaccagac gcgaaactgc tggaagattc 540
ctggccccaa ggcctcctcc ggctcgctga ttggcccagc ggagagtggg cggggccggt 600
gaagactcct taaaggcgca gggcggcgag caggtcacca gacgctgaca gctactcaga 660
accaaatctg gttccatcca gagacaagcg aagacaagag aagcagagcg agcggcgcgt 720
tcccgatcct cggccaggac cagccttccc cagagcatcc ctgccgcgga gcgcaacctt 780
cccaggagca tccctgccgc ggagcgcaac tttccccgga gcatccacgc cgcggagcgc 840
agccttccag aagcagagcg cggcgcc 867

<210> SEQ ID NO 13
<211> LENGTH: 720
<212> TYPE: DNA
<213> ORGANISM: Artificial Sequence
<220> FEATURE:
<223> OTHER INFORMATION: SYFP2

<400> SEQUENCE: 13
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagct gatctgcacc accggcaagc tgcccgtgcc ctggcccacc 180
ctcgtgacca ccctgggcta cggcgtgcag tgcttcgccc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca ccgccgacaa gcagaagaac 480
ggcatcaagg ccaacttcaa gatccgccac aacatcgagg acggcggcgt gcagctcgcc 540
gaccactacc agcagaacac ccccatcggc gacggccccg tgctgctgcc cgacaaccac 600
tacctgagct accagtccaa gctgagcaaa gaccccaacg agaagcgcga tcacatggtc 660
ctgctggagt tcgtgaccgc cgccgggatc actctcggca tggacgagct gtacaagtaa 720

<210> SEQ ID NO 14
<211> LENGTH: 720
<212> TYPE: DNA
<213> ORGANISM: Artificial Sequence
<220> FEATURE:
<223> OTHER INFORMATION: enhanced green fluorescent protein (EGFP)

<400> SEQUENCE: 14
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtaa 720

<210> SEQ ID NO 15
<211> LENGTH: 1299
<212> TYPE: DNA
<213> ORGANISM: Artificial Sequence
<220> FEATURE:
<223> OTHER INFORMATION: Optimized Flp recombinase

<400> SEQUENCE: 15
atggctccta agaagaagag gaaggtgatg agccagttcg acatcctgtg caagaccccc 60
cccaaggtgc tggtgcggca gttcgtggag agattcgaga ggcccagcgg cgagaagatc 120
gccagctgtg ccgccgagct gacctacctg tgctggatga tcacccacaa cggcaccgcc 180
atcaagaggg ccaccttcat gagctacaac accatcatca gcaacagcct gagcttcgac 240
atcgtgaaca agagcctgca gttcaagtac aagacccaga aggccaccat cctggaggcc 300
agcctgaaga agctgatccc cgcctgggag ttcaccatca tcccttacaa cggccagaag 360
caccagagcg acatcaccga catcgtgtcc agcctgcagc tgcagttcga gagcagcgag 420
gaggccgaca agggcaacag ccacagcaag aagatgctga aggccctgct gtccgagggc 480
gagagcatct gggagatcac cgagaagatc ctgaacagct tcgagtacac cagcaggttc 540
accaagacca agaccctgta ccagttcctg ttcctggcca cattcatcaa ctgcggcagg 600
ttcagcgaca tcaagaacgt ggaccccaag agcttcaagc tggtgcagaa caagtacctg 660
ggcgtgatca ttcagtgcct ggtgaccgag accaagacaa gcgtgtccag gcacatctac 720
tttttcagcg ccagaggcag gatcgacccc ctggtgtacc tggacgagtt cctgaggaac 780
agcgagcccg tgctgaagag agtgaacagg accggcaaca gcagcagcaa caagcaggag 840
taccagctgc tgaaggacaa cctggtgcgc agctacaaca aggccctgaa gaagaacgcc 900
ccctacccca tcttcgctat caagaacggc cctaagagcc acatcggcag gcacctgatg 960
accagctttc tgagcatgaa gggcctgacc gagctgacaa acgtggtggg caactggagc 1020
gacaagaggg cctccgccgt ggccaggacc acctacaccc accagatcac cgccatcccc 1080
gaccactact tcgccctggt gtccaggtac tacgcctacg accccatcag caaggagatg 1140
atcgccctga aggacgagac caaccccatc gaggagtggc agcacatcga gcagctgaag 1200
ggcagcgccg agggcagcat cagatacccc gcctggaacg gcatcatcag ccaggaggtg 1260
ctggactacc tgagcagcta catcaacagg cggatctga 1299

<210> SEQ ID NO 16
<211> LENGTH: 1056
<212> TYPE: DNA
<213> ORGANISM: Artificial Sequence
<220> FEATURE:
<223> OTHER INFORMATION: Improved Cre recombinase (iCre)

<400> SEQUENCE: 16
atggtgccca agaagaagag gaaagtctcc aacctgctga ctgtgcacca aaacctgcct 60
gccctccctg tggatgccac ctctgatgaa gtcaggaaga acctgatgga catgttcagg 120
gacaggcagg ccttctctga acacacctgg aagatgctcc tgtctgtgtg cagatcctgg 180
gctgcctggt gcaagctgaa caacaggaaa tggttccctg ctgaacctga ggatgtgagg 240

```
gactacctcc tgtacctgca agccagaggc ctggctgtga agaccatcca acagcacctg    300

ggccagctca acatgctgca caggagatct ggcctgcctc gcccttctga ctccaatgct    360

gtgtccctgg tgatgaggag aatcagaaag gagaatgtgg atgctgggga gagagccaag    420

caggccctgg cctttgaacg cactgacttt gaccaagtca gatccctgat ggagaactct    480

gacagatgcc aggacatcag gaacctggcc ttcctgggca ttgcctacaa caccctgctg    540

cgcattgccg aaattgccag aatcagagtg aaggacatct cccgcaccga tggtgggaga    600

atgctgatcc acattggcag gaccaagacc ctggtgtcca cagctggtgt ggagaaggcc    660

ctgtccctgg gggttaccaa gctggtggag agatggatct ctgtgtctgg tgtggctgat    720

gaccccaaca actacctgtt ctgccgggtc agaaagaatg gtgtggctgc cccttctgcc    780

acctcccaac tgtccacccg ggccctggaa gggatctttg aggccaccca ccgcctgatc    840

tatggtgcca aggatgactc tgggcagaga tacctggcct ggtctggcca ctctgccaga    900

gtgggtgctg ccagggacat ggccagggct ggtgtgtcca tccctgaaat catgcaggct    960

ggtggctgga ccaatgtgaa cattgtgatg aactacatca gaaacctgga ctctgagact   1020

ggggccatgg tgaggctgct cgaggatggg gactaa                             1056
```

<210> SEQ ID NO 17
<211> LENGTH: 825
<212> TYPE: DNA
<213> ORGANISM: Magnetococcus marinus

<400> SEQUENCE: 17

```
atgtcacgca aaataagaga tttaatcgaa tccaaacgct ttcaaaacgt catcaccgcc     60

attattgtgc tcaatggcgc tgtgctgggt ctgctgaccg atacaaccct atcggcctcc    120

agccaaaacc tgctggagcg tgtggatcaa ctttgtctga ctatctttat tgttgaaata    180

tccctgaaaa tatacgccta tggcgtgcga ggctttttcc gcagcggctg gaatctgttt    240

gattttgtga ttgtggccat cgcgcttatg cccgcccagg gtagcctatc ggtgctgcga    300

accttccgta tattccgcgt catgcggctc gtatcggtca taccaaccat gcgaagagtg    360

gtgcaaggca tgctcttggc actgcccggc gtgggatcgg tagcggcact gttgacggtg    420

gtcttctata ttgcggctgt catggccacc aatctctacg gggcaacctt ccctgaatgg    480

tttggtgatc ttagcaagag cctgtacaca ctatttcagg tgatgacctt agagtcatgg    540

tctatgggca ttgtgcgtcc agtgatgaac gttcatccca acgcatgggt ttttttcatc    600

cccttcatca tgctcaccac ctttaccgtg ctcaacctgt ttattggcat tattgtagat    660

gccatggcca tcaccaagga acaggaggaa gaggccaaaa ccggccacca ccaagagcct    720

attagccaaa cattgctcca tctgggagat cgcctagata ggatcgaaaa gcagcttgcg    780

caaaacaacg agctcttaca acgacaacag ccgcaaaaaa aatag                    825
```

<210> SEQ ID NO 18
<211> LENGTH: 954
<212> TYPE: DNA
<213> ORGANISM: Artificial Sequence
<220> FEATURE:
<223> OTHER INFORMATION: Magnetococcus marinus, codon optimized, with N-terminal 3x HA tag and linker:

<400> SEQUENCE: 18

```
atggtttatc cgtatgatgt tcctgactat gcaggatcct atccttatga tgttcccgat     60

tacgctggtt cttaccctta cgatgttccc gattatgcca gttctggatt ggtgccacga    120
```

```
ggcagccaca tgagccggaa gatcagagat cttatcgaat ctaagagatt tcagaatgtt    180

attaccgcga taatcgtact caacggggcg gtgctcggtc tcctcaccga taccacattg    240

agcgcttcta gccagaacct gctcgaaagg gttgaccaac tgtgcctgac aatttttatc    300

gtggaaatta gcttgaaaat ttacgcctac ggcgttcgcg gtttttttccg gagcggttgg    360

aatcttttttg acttcgttat cgttgccatc gcgctcatgc ccgcacaggg ttctttgtct    420

gtgttgagga cattccgaat atttcgcgtg atgcgcttgg tatccgtgat ccctacgatg    480

cgccgcgtcg tacaaggaat gttgctggct ctccccggcg tcgggagcgt tgctgccctc    540

cttaccgtgg tattttacat agcggcggtt atggctacta atctttacgg agctaccttc    600

ccggagtggt tcggggattt gtccaagagc ctctatacat tgtttcaagt tatgaccctg    660

gagtcctggt ctatgggcat tgtccggccc gtaatgaacg tacacccaaa tgcgtgggtg    720

tttttcattc cattcatcat gctgactacc tttaccgtgc tgaacttgtt cattgggatt    780

atcgtggatg cgatggccat cactaaggag caagaagaag aggctaaaac tggccaccac    840

caagagccaa tttctcaaac cctcttgcat ctcggggacc gactggaccg cattgagaag    900

caactcgcgc agaacaatga gctgttgcag cgacagcaac ctcaaaaaaa ataa          954
```

<210> SEQ ID NO 19
<211> LENGTH: 885
<212> TYPE: DNA
<213> ORGANISM: Artificial Sequence
<220> FEATURE:
<223> OTHER INFORMATION: Magnetococcus marinus

<400> SEQUENCE: 19

```
atgggcagca gccatcatca tcatcatcac agcagcggcc tggtgccgcg cggcagccat     60

atgtcacgca aaatccgcga tttaatcgaa tccaaacgct ttcaaaacgt catcaccgcc    120

attattgtgc tcaatggcgc tgtgctgggt ctgctgaccg atacaaccct gtcggcctcc    180

agccaaaacc tgctggagcg tgtggatcaa ctttgtctga ctatctttat tgttgaaatc    240

tccctgaaaa tctacgccta tggcgtgcgc ggctttttcc gcagcggctg gaatctgttt    300

gattttgtga ttgtggccat cgcgcttatg ccggcccagg gtagcctgtc ggtgctgcgt    360

accttccgta tcttccgcgt catgcgcctc gtatcggtca tcccaaccat gcgccgtgtg    420

gtgcaaggca tgctcttggc actgccgggc gtgggctcgg tagcggcact gttgacggtg    480

gtcttctata ttgcggctgt catggccacc aatctctacg ggcaaccttt ccctgaatgg    540

tttggtgatc ttagcaagag cctgtacaca ctgtttcagg tgatgacctt agagtcatgg    600

tctatgggca ttgtgcgtcc agtgatgaac gttcatccga acgcatgggt tttttttcatc    660

ccgttcatca tgctcaccac ctttaccgtg ctcaacctgt ttattggcat tattgtagat    720

gcaatggcaa tcaccaagga acaggaggaa gaggccaaaa ccggtcacca tcaagaacct    780

atttctcaaa ctcttcttca tcttggtgat cgtcttgatc gtattgaaaa acaacttgct    840

caaaataatg aacttcttca acgtcaacaa cctcaaaaaa aataa                    885
```

<210> SEQ ID NO 20
<211> LENGTH: 855
<212> TYPE: DNA
<213> ORGANISM: Bacillus pseudofirmus

<400> SEQUENCE: 20

```
atggaaaaca atccagccga acaacaagtt ccaccattag tagccttagc tcagcgtatc     60

gtctttcata aggcctttac cccaactatt attaccttga ttatcattaa tgccattatt    120
```

gtaggccttg aaacatatcc tactgtttat caaggttata atgattggtt ctacgcagca 180
gatttagcct tactttggat ttttacaatt gagattacac tgcgttttat cgcagcgaga 240
ccgactaaat cttttttaa aagcagctgg aactggtttg atttattaat cgttcttgcc 300
ggtcatgtct ttgccggtgc tcattttgta acggttcttc gtatcctgcg cgttcttcgc 360
gtattacgtg ccatttctgt cattccttct ctgcgtcgtt tagtcgatgc tttgctgatg 420
accatcccgg ctttaggaaa cattatgatc ctgatgggaa ttattttcta tattttcgct 480
gtgattggaa cgatgttatt tgcttctgta gcacctgagt actttggtaa cttacagctt 540
tctttattaa cattattcca agttgttaca cttgaatctt gggcaagcgg tgtcatgagg 600
ccgatttttg cagaggtttg gtggtcttgg atttattttg tcatctttat tttagtaggg 660
acatttattg tctttaactt atttatcggt gttatcgtta ataacgttga aaaagcaaac 720
gaagaagaac tcaaatcaga attagatgat aaagaggcag atacaaaaga agagcttgct 780
tctctgcgta atgaagtagc agagatgaaa gacctcatta aacaaatgca taaacagcaa 840
acaaaaaaag ggtaa 855

<210> SEQ ID NO 21
<211> LENGTH: 951
<212> TYPE: DNA
<213> ORGANISM: Artificial Sequence
<220> FEATURE:
<223> OTHER INFORMATION: Bacillus pseudofirmus, codon optimized, with N-terminal 3x HA tag

<400> SEQUENCE: 21
atggtttacc cgtatgatgt cccggattac gctggcagct acccatacga tgtacccgac 60
tatgccggca gttatcccta cgacgtccct gactacgcag aaaacaaccc agccgaacag 120
caagtcccac ccctcgtggc gctcgcccaa cgcatagtat ttcacaaggc gtttacgccg 180
acgataatca ccctcatcat tattaatgcg atcattgtgg gactcgagac atacccaacg 240
gtttaccagg gttacaatga ttggttctat gctgccgacc ttgctttgtt gtggatattc 300
actattgaaa tcacgctccg attcatcgcc gcccgaccga cgaagagttt cttcaagtct 360
agctggaact ggtttgatct gcttatcgta ttggcgggcc acgtcttcgc tggcgcccat 420
tttgttacgg tgcttaggat cctccgcgtc ctgagggtcc tcagagctat ctcagtcata 480
cccagtctcc ggcggctggt tgacgcactt ttgatgacaa tcccagcact cggtaacatc 540
atgatactga tggggattat tttttacata ttcgcggtta tcgggacgat gctctttgca 600
tcagtagcgc cagaatactt tggcaatttg cagctgtctc tgcttacact gttccaagtg 660
gttacgctgg aaagttgggc tagtggggtt atgcgaccta tttttgccga agtctggtgg 720
tcttggatct attttgtaat ctttattctc gtgggaactt tcatagtatt taaccttttc 780
attggcgtca tcgtgaacaa tgtggaaaaa gctaacgaag aggaactgaa aagcgaactg 840
gatgataaag aggctgatac aaaagaagaa ctggcatcat tgcgaaacga ggtggcagaa 900
atgaaggatc tcataaaaca gatgcataaa cagcaaacaa aaaagggtta a 951

<210> SEQ ID NO 22
<211> LENGTH: 984
<212> TYPE: DNA
<213> ORGANISM: Artificial Sequence
<220> FEATURE:
<223> OTHER INFORMATION: Shewanella putrifaciens-D60N, codon optimized, with N-terminal 3x HA tag

<400> SEQUENCE: 22
atggtttacc cgtatgatgt cccggattac gctggcagct acccatacga tgtacccgac 60
tatgccggca gttatcccta cgacgtccct gactacgcat ctacgtccct tttgaatgcg 120
cctaccggcc ttcaagctag agtcattaat ctcgtcgaac aaaactggtt tggacacttt 180
atactgactc tcatactcat taatgctgtg cagcttggaa tggaaactag cgccagcctc 240
atggcacaat atggcgcgct gcttatgtcc ttgaataagg tccttctctc tgtgttcgtg 300
gtcgaactgc tgctccggat ttatgcgtat cggggcaagt tttttaagga cccgtggaat 360
gtgtttgact tcactgttat tgttattgct ctgattcctg catctggccc attggctgtc 420
ctccgctccc tccgagttct ccgcgtcttg agggttctga cgattgtccc cagcatgaaa 480
agagtagtgt cagcactgct tgggagcttg cccgggttgg cctccattgc aaccgtgctt 540
ctgttgatct attacgtttt cgctgtgatc gccactaaaa ttttcgggga tgcttttccg 600
gaatggttcg ggacgatagc ggactccttc tataccttt ttcaaattat gaccttggaa 660
agttggtcta tggggatctc taggccagtg atggaggtgt acccttacgc ttgggtattc 720
tttgtgccct ttattcttgt tgctactttt accatgctta accttttcat cgccatcata 780
gtgaatacta tgcagacatt ctctgacgag gaacatgctc tggagcgaga gcaagataaa 840
cagatcttgg aacaggagca gagacaaatg cacgaggaac tgaaggccat tcgactcgag 900
cttcagcaac tccaaaccct tttgcgaaat gcggctgggg actcctccaa tgtctccaca 960
aagggcaata tcggctcaga ctaa 984

<210> SEQ ID NO 23
<211> LENGTH: 888
<212> TYPE: DNA
<213> ORGANISM: Shewanella putrifaciens

<400> SEQUENCE: 23
atgagtacat ctttacttaa cgcgccaacg ggtttgcagg cacgagtgat taacttggtt 60
gagcaaaact ggtttggtca ttttattttg acattgattt taatcaacgc ggtgcagtta 120
ggtatggaga cctcagccag cctgatggcg caatacggtg ctttgttgat gagtcttgat 180
aaggtgctgc tgagtgtatt tgtggtggag ttattgctgc ggatttatgc ctacaggggg 240
aaattttta aagacccttg gaacgtgttc gattttaccg tgatagtgat agcactgatc 300
cctgcatctg ggccattggc tgtcctgcgt tcgctcaggg tattgcgggt gctgagagtg 360
ttaacaattg tgccatcaat gaaacgggtg gtgtctgcgc tgttgggatc acttcctgga 420
ttggcatcga tcgccacagt attactgctg atttattatg tgtttgcggt gatcgctacc 480
aaaattttg gcgatgcatt ccctgaatgg tttggcacta ttgctgactc attttatacc 540
ctatttcaaa taatgacgct tgaaagctgg tctatgggaa tttcgcggcc agtgatggaa 600
gtctaccctt atgcttgggt atttttcgta ccatttattc tggtagcgac tttcacaatg 660
ctaaatttgt ttattgcgat tatcgtcaat accatgcaaa ccttcagcga cgaagagcat 720
gcattagagc gtgagcaaga caaacaaatc ttagagcagg aacaaagaca aatgcacgag 780
gagttgaaag ccatcagact cgagctacaa caattacaaa ccttgctgcg caatgctgct 840
ggtgattctt ctaatgtgtc gacaaaggga aacattggtt ctgactaa 888

<210> SEQ ID NO 24
<211> LENGTH: 246
<212> TYPE: DNA
<213> ORGANISM: Artificial Sequence

<220> FEATURE:
<223> OTHER INFORMATION: WPRE3

<400> SEQUENCE: 24
ataatcaacc tctggattac aaaatttgtg aaagattgac tggtattctt aactatgttg 60
ctccttttac gctatgtgga tacgctgctt taatgccttt gtatcatgct attgcttccc 120
gtatggcttt cattttctcc tccttgtata aatcctggtt agttcttgcc acggcggaac 180
tcatcgccgc ctgccttgcc cgctgctgga caggggctcg gctgttgggc actgacaatt 240
ccgtgg 246

<210> SEQ ID NO 25
<211> LENGTH: 204
<212> TYPE: DNA
<213> ORGANISM: Artificial Sequence
<220> FEATURE:
<223> OTHER INFORMATION: BGHpA

<400> SEQUENCE: 25
cgactgtgcc ttctagttgc cagccatctg ttgtttgccc ctcccccgtg ccttccttga 60
ccctggaagg tgccactccc actgtccttt cctaataaaa tgaggaaatt gcatcgcatt 120
gtctgagtag gtgtcattct attctggggg gtggggtggg gcaggacagc aagggggagg 180
attgggaaga caatagcagg catg 204

<210> SEQ ID NO 26
<211> LENGTH: 78
<212> TYPE: DNA
<213> ORGANISM: Artificial Sequence
<220> FEATURE:
<223> OTHER INFORMATION: P2A

<400> SEQUENCE: 26
ggcagcggcg ccaccaactt cagcctgctg aagcaggccg gcgacgtgga ggagaacccc 60
ggccccggag ctagcgga 78

<210> SEQ ID NO 27
<211> LENGTH: 26
<212> TYPE: PRT
<213> ORGANISM: Artificial Sequence
<220> FEATURE:
<223> OTHER INFORMATION: P2A
<220> FEATURE:
<221> NAME/KEY: MISC_FEATURE
<222> LOCATION: (1)..(3)
<223> OTHER INFORMATION: (GSG) residues can be added to the 5' end of the peptide to improve cleavage efficiency

<400> SEQUENCE: 27

Gly Ser Gly Ala Thr Asn Phe Ser Leu Leu Lys Gln Ala Gly Asp Val
1 5 10 15

Glu Glu Asn Pro Gly Pro Gly Ala Ser Gly
20 25

<210> SEQ ID NO 28
<211> LENGTH: 21
<212> TYPE: PRT
<213> ORGANISM: Artificial Sequence
<220> FEATURE:
<223> OTHER INFORMATION: T2A
<220> FEATURE:
<221> NAME/KEY: MISC_FEATURE
<222> LOCATION: (1)..(3)
<223> OTHER INFORMATION: (GSG) residues can be added to the 5' end of the peptide to improve cleavage efficiency

<400> SEQUENCE: 28

Gly Ser Gly Glu Gly Arg Gly Ser Leu Leu Thr Cys Gly Asp Val Glu
1 5 10 15

Glu Asn Pro Gly Pro
20

<210> SEQ ID NO 29
<211> LENGTH: 24
<212> TYPE: PRT
<213> ORGANISM: Artificial Sequence
<220> FEATURE:
<223> OTHER INFORMATION: E2A
<220> FEATURE:
<221> NAME/KEY: MISC_FEATURE
<222> LOCATION: (1)..(3)
<223> OTHER INFORMATION: (GSG) residues can be added to the 5' end of the peptide to improve cleavage efficiency

<400> SEQUENCE: 29

Gly Ser Gly Gln Cys Thr Asn Tyr Ala Leu Leu Lys Leu Ala Gly Asp
1 5 10 15

Val Glu Ser Asn Pro Gly Pro Pro
20

<210> SEQ ID NO 30
<211> LENGTH: 25
<212> TYPE: PRT
<213> ORGANISM: Artificial Sequence
<220> FEATURE:
<223> OTHER INFORMATION: F2A
<220> FEATURE:
<221> NAME/KEY: MISC_FEATURE
<222> LOCATION: (1)..(3)
<223> OTHER INFORMATION: (GSG) residues can be added to the 5' end of the peptide to improve cleavage efficiency

<400> SEQUENCE: 30

Gly Ser Gly Val Lys Gln Thr Leu Asn Phe Asp Leu Leu Lys Leu Ala
1 5 10 15

Gly Asp Val Glu Ser Asn Pro Gly Pro
20 25

<210> SEQ ID NO 31
<211> LENGTH: 99
<212> TYPE: DNA
<213> ORGANISM: Artificial Sequence
<220> FEATURE:
<223> OTHER INFORMATION: N-terminal 3XHA tag

<400> SEQUENCE: 31
atggtttacc cgtatgatgt cccggattac gctggcagct acccatacga tgtacccgac 60
tatgccggca gttatcccta cgacgtccct gactacgca 99

<210> SEQ ID NO 32
<211> LENGTH: 33
<212> TYPE: PRT
<213> ORGANISM: Artificial Sequence
<220> FEATURE:
<223> OTHER INFORMATION: N-terminal 3XHA tag

<400> SEQUENCE: 32

Met Val Tyr Pro Tyr Asp Val Pro Asp Tyr Ala Gly Ser Tyr Pro Tyr
1 5 10 15

```
Asp Val Pro Asp Tyr Ala Gly Ser Tyr Pro Tyr Asp Val Pro Asp Tyr
            20                  25                  30

Ala


<210> SEQ ID NO 33
<211> LENGTH: 11
<212> TYPE: PRT
<213> ORGANISM: Artificial Sequence
<220> FEATURE:
<223> OTHER INFORMATION: change from AAV9 to PHP.eB capsid

<400> SEQUENCE: 33

Ser Asp Gly Thr Leu Ala Val Pro Phe Lys Ala
1               5                   10


<210> SEQ ID NO 34
<211> LENGTH: 736
<212> TYPE: PRT
<213> ORGANISM: Adeno-associated virus

<400> SEQUENCE: 34

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

-continued

```
Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700
```

```
Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 35
<211> LENGTH: 747
<212> TYPE: DNA
<213> ORGANISM: Artificial Sequence
<220> FEATURE:
<223> OTHER INFORMATION: tet-Transactivator version 2 (tTA2)

<400> SEQUENCE: 35

atgtctagac tggacaagag caaagtcata aactctgctc tggaattact caatgaagtc      60

ggtatcgaag gcctgacgac aaggaaactc gctcaaaagc tgggagttga gcagcctacc     120

ctgtactggc acgtgaagaa caagcgggcc ctgctcgatg ccctggcaat cgagatgctg     180

gacaggcatc atacccactt ctgccccctg gaaggcgagt catggcaaga ctttctgcgg     240

aacaacgcca agtcattccg ctgtgctctc ctctcacatc gcgacggggc taaagtgcat     300

ctcggcaccc gcccaacaga gaaacagtac gaaaccctgg aaaatcagct cgcgttcctg     360

tgtcagcaag gcttctccct ggagaacgca ctgtacgctc tgtccgccgt gggccacttt     420

acactgggct gcgtattgga ggatcaggag catcaagtag caaaagagga aagagagaca     480

cctaccaccg attctatgcc cccacttctg agacaagcaa ttgagctgtt cgaccatcag     540

ggagccgaac ctgccttcct tttcggcctg gaactaatca tatgtggcct ggagaaacag     600

ctaaagtgcg aaagcggcgg gccggccgac gcccttgacg attttgactt agacatgctc     660

ccagccgatg cccttgacga ctttgacctt gatatgctgc ctgctgacgc tcttgacgat     720

tttgaccttg acatgctccc cgggtaa                                         747


<210> SEQ ID NO 36
<211> LENGTH: 2843
<212> TYPE: DNA
<213> ORGANISM: Artificial Sequence
<220> FEATURE:
<223> OTHER INFORMATION: rAAV: hI56i-minBglobin-His-NavMs-P2A-SYFP2-
      WPRE3-BGHpA

<400> SEQUENCE: 36

gcggccgcac gcgtataggt accgagctct atgcactcac agtggtttgg catgcatctg      60

gtgaattttt tttaacgaaa aattagtgtt ggtttcgatg tatggtagca ttctccctaa     120

cgtaatttga ataattcagc aaagccccac taccagctgt acttctgcag cctcttccat     180

tcttttcagc attataattt tggttaattt tcaattttag gtcctacgtc tctgcaattt     240

gtgtatgaat aacagaataa tttccctctt ttgtttcgcc tttcctgttc ctgaatctaa     300

ataaagatgg ctttttagta ttaaaagtgg aagaaaatta caggtaatta tctttgacgg     360

taaaaacgct gtaatcagcg ggctacatga aaaattactc taattatggc tgcatttaag     420

agaatggaaa aaaaccttct tgtggataaa aaccttaaat tgtccccaat gtctgcttca     480

aattggatgg cactgcagct ggaggctttg ttcagaattg atcctgggga gctacgaacc     540

caaagtttca cagtagggag ctcgggctgg gcataaaagt cagggcagag ccatctattg     600

cttacatttg cttctgggat ccagatcttt cgaagctagc gctaccggtc gccaccatgg     660

gcagcagcca tcatcatcat catcacagca gcggcctggt gccgcgcggc agccatatgt     720

cacgcaaaat ccgcgattta atcgaatcca aacgctttca aaacgtcatc accgccatta     780
```

-continued

```
ttgtgctcaa tggcgctgtg ctgggtctgc tgaccgatac aaccctgtcg gcctccagcc    840
aaaacctgct ggagcgtgtg gatcaacttt gtctgactat ctttattgtt gaaatctccc    900
tgaaaatcta cgcctatggc gtgcgcggct ttttccgcag cggctggaat ctgtttgatt    960
ttgtgattgt ggccatcgcg cttatgccgg cccagggtag cctgtcggtg ctgcgtacct   1020
tccgtatctt ccgcgtcatg cgcctcgtat cggtcatccc aaccatgcgc cgtgtggtgc   1080
aaggcatgct cttggcactg ccgggcgtgg gctcggtagc ggcactgttg acggtggtct   1140
tctatattgc ggctgtcatg gccaccaatc tctacggggc aaccttccct gaatggtttg   1200
gtgatcttag caagagcctg tacacactgt ttcaggtgat gaccttagag tcatggtcta   1260
tgggcattgt gcgtccagtg atgaacgttc atccgaacgc atgggttttt ttcatcccgt   1320
tcatcatgct caccaccttt accgtgctca acctgtttat tggcattatt gtagatgcaa   1380
tggcaatcac caaggaacag gaggaagagg ccaaaaccgg tcaccatcaa gaacctattt   1440
ctcaaactct tcttcatctt ggtgatcgtc ttgatcgtat tgaaaaacaa cttgctcaaa   1500
ataatgaact tcttcaacgt caacaacctc aaaaaaaagg cagcggcgcc accaacttca   1560
gcctgctgaa gcaggccggc gacgtggagg agaaccccgg ccccatggtg agcaagggcg   1620
aggagctgtt caccggggtg gtgcccatcc tggtcgagct ggacggcgac gtaaacggcc   1680
acaagttcag cgtgtccggc gagggcgagg gcgatgccac ctacggcaag ctgaccctga   1740
agctgatctg caccaccggc aagctgcccg tgccctggcc caccctcgtg accaccctgg   1800
gctacggcgt gcagtgcttc gcccgctacc ccgaccacat gaagcagcac gacttcttca   1860
agtccgccat gcccgaaggc tacgtccagg agcgcaccat cttcttcaag gacgacggca   1920
actacaagac ccgcgccgag gtgaagttcg agggcgacac cctggtgaac cgcatcgagc   1980
tgaagggcat cgacttcaag gaggacggca acatcctggg gcacaagctg gagtacaact   2040
acaacagcca caacgtctat atcaccgccg acaagcagaa gaacggcatc aaggccaact   2100
tcaagatccg ccacaacatc gaggacggcg gcgtgcagct cgccgaccac taccagcaga   2160
acacccccat cggcgacggc cccgtgctgc tgcccgacaa ccactacctg agctaccagt   2220
ccaagctgag caaagacccc aacgagaagc gcgatcacat ggtcctgctg gagttcgtga   2280
ccgccgccgg gatcactctc ggcatggacg agctgtacaa gtaagtcgac ggcgcgccgc   2340
ggccgcgaat tcgatatcat aatcaacctc tggattacaa aatttgtgaa agattgactg   2400
gtattcttaa ctatgttgct ccttttacgc tatgtggata cgctgcttta atgcctttgt   2460
atcatgctat tgcttcccgt atggctttca ttttctcctc cttgtataaa tcctggttag   2520
ttcttgccac ggcggaactc atcgccgcct gccttgcccg ctgctggaca ggggctcggc   2580
tgttgggcac tgacaattcc gtggctcgag agatcttcga ctgtgccttc tagttgccag   2640
ccatctgttg tttgcccctc ccccgtgcct tccttgaccc tggaaggtgc cactcccact   2700
gtcctttcct aataaaatga ggaaattgca tcgcattgtc tgagtaggtg tcattctatt   2760
ctggggggtg gggtggggca ggacagcaag ggggaggatt gggaagacaa tagcaggcat   2820
gcacgtgcgg accgagcggc cgc                                           2843
```

<210> SEQ ID NO 37
<211> LENGTH: 2835
<212> TYPE: DNA
<213> ORGANISM: Artificial Sequence
<220> FEATURE:
<223> OTHER INFORMATION: rAAV:3xhI56iCore-minCMV-SYFP2-P2A-3xHA-NavSheP-
D60N-WPRE3-BGHpA

<400> SEQUENCE: 37
gcggccgcac gcgtggtacc ctaaataaag atggcttttt agtattaaaa gtggaagaaa 60
attacaggta attatctttg acggtaaaaa cgctgtaatc agcgggctac atgaaaaatt 120
actctaatta tggctgcatt taagagaatg gctaaataaa gatggctttt tagtattaaa 180
agtggaagaa aattacaggt aattatcttt gacggtaaaa acgctgtaat cagcgggcta 240
catgaaaaat tactctaatt atggctgcat ttaagagaat ggctaaataa agatggcttt 300
ttagtattaa aagtggaaga aaattacagg taattatctt tgacggtaaa aacgctgtaa 360
tcagcgggct acatgaaaaa ttactctaat tatggctgca tttaagagaa tggagctcgg 420
gctggtcgac acaattggag gtaggcgtgt acggtgggag gcctatataa gcagagctcg 480
tttagtgaac cgtcagatcg cctggaggat ccttcgaaaa gcttgctacc ggtcgccacc 540
atggtcagca agggcgagga gctgttcacc ggggtggtgc ccatcctggt cgagctggac 600
ggcgacgtca atggccacaa gttcagcgtg tccggcgagg gcgagggcga tgccacctac 660
ggcaagctga ccctgaagct gatctgcacc accggcaagc tgcccgtgcc ctggcccacc 720
ctcgtgacca ccctgggcta cggcgtgcag tgcttcgccc gctaccccga ccacatgaag 780
cagcacgact tcttcaagtc cgccatgccc gaaggctacg tccaggagcg caccatcttc 840
ttcaaagacg acggcaacta caagacccgc gccgaggtga agttcgaggg cgacaccctg 900
gtgaaccgca tcgagctgaa gggcatcgac ttcaaggagg acggcaacat cctggggcac 960
aagctggagt acaactacaa cagccacaac gtctatatca ccgccgacaa gcagaagaac 1020
ggcatcaagg ccaacttcaa gatccgccac aacatcgagg acggcggcgt gcagctcgcc 1080
gaccactacc agcagaacac ccccatcggc gacggccccg tgctgctgcc cgacaaccac 1140
tacctgagct accagtccaa gctgagcaaa gaccccaacg agaagcgcga tcacatggtc 1200
ctgctggagt tcgtgaccgc cgccgggatc actctcggca tggacgagct gtacaaaggc 1260
agcggcgcca ccaacttcag cctgctgaag caggccggcg acgtggagga gaaccccggc 1320
cccggagcta gcggaatggt ttacccgtat gatgtcccgg attacgctgg cagctaccca 1380
tacgatgtac ccgactatgc cggcagttat ccctacgacg tccctgacta cgcatctacg 1440
tcccttttga atgcgcctac cggccttcaa gctagagtca ttaatctcgt cgaacaaaac 1500
tggtttggac actttatact gactctcata ctcattaatg ctgtgcagct tggaatggaa 1560
actagcgcca gcctcatggc acaatatggc gcgctgctta tgtccttgaa taaggtcctt 1620
ctctctgtgt tcgtggtcga actgctgctc cggatttatg cgtatcgggg caagtttttt 1680
aaggacccgt ggaatgtgtt tgacttcact gttattgtta ttgctctgat tcctgcatct 1740
ggcccattgg ctgtcctccg ctccctccga gttctccgcg tcttgagggt tctgacgatt 1800
gtccccagca tgaaaagagt agtgtcagca ctgcttggga gcttgcccgg gttggcctcc 1860
attgcaaccg tgcttctgtt gatctattac gttttcgctg tgatcgccac taaaattttc 1920
ggggatgctt ttccggaatg gttcgggacg atagcggact ccttctatac cctttttcaa 1980
attatgacct tggaaagttg gtctatgggg atctctaggc cagtgatgga ggtgtaccct 2040
tacgcttggg tattctttgt gccctttatt cttgttgcta cttttaccat gcttaacctt 2100
ttcatcgcca tcatagtgaa tactatgcag acattctctg acgaggaaca tgctctggag 2160
cgagagcaag ataaacagat cttggaacag gagcagagac aaatgcacga ggaactgaag 2220
gccattcgac tcgagcttca gcaactccaa accctttttgc gaaatgcggc tggggactcc 2280
tccaatgtct ccacaaaggg caatatcggc tcagactaat gaccgcggcc gcgaattcga 2340

```
tatcataatc aacctctgga ttacaaaatt tgtgaaagat tgactggtat tcttaactat   2400

gttgctcctt ttacgctatg tggatacgct gctttaatgc ctttgtatca tgctattgct   2460

tcccgtatgg ctttcatttt ctcctccttg tataaatcct ggttagttct tgccacggcg   2520

gaactcatcg ccgcctgcct tgcccgctgc tggacagggg ctcggctgtt gggcactgac   2580

aattccgtgg ctcgagagat cttcgactgt gccttctagt tgccagccat ctgttgtttg   2640

cccctccccc gtgccttcct tgaccctgga aggtgccact cccactgtcc tttcctaata   2700

aaatgaggaa attgcatcgc attgtctgag taggtgtcat tctattctgg ggggtggggt   2760

ggggcaggac agcaaggggg aggattggga agacaatagc aggcatgaga tctcacgtgc   2820

ggaccgagcg gccgc                                                     2835
```

<210> SEQ ID NO 38
<211> LENGTH: 2802
<212> TYPE: DNA
<213> ORGANISM: Artificial Sequence
<220> FEATURE:
<223> OTHER INFORMATION: rAAV: 3xhI56iCore-minCMV-SYFP2-P2A-3xHA-NavBp-WPRE3-BGHpA

<400> SEQUENCE: 38

```
gcggccgcac gcgtggtacc ctaaataaag atggcttttt agtattaaaa gtggaagaaa     60

attacaggta attatctttg acggtaaaaa cgctgtaatc agcgggctac atgaaaaatt    120

actctaatta tggctgcatt taagagaatg gctaaataaa gatggctttt tagtattaaa    180

agtggaagaa aattacaggt aattatcttt gacggtaaaa acgctgtaat cagcgggcta    240

catgaaaaat tactctaatt atggctgcat ttaagagaat ggctaaataa agatggcttt    300

ttagtattaa aagtggaaga aaattacagg taattatctt tgacggtaaa aacgctgtaa    360

tcagcgggct acatgaaaaa ttactctaat tatggctgca tttaagagaa tggagctcgg    420

gctggtcgac acaattggag gtaggcgtgt acggtgggag gcctatataa gcagagctcg    480

tttagtgaac cgtcagatcg cctggaggat ccttcgaaaa gcttgctacc ggtcgccacc    540

atggtcagca agggcgagga gctgttcacc ggggtggtgc ccatcctggt cgagctggac    600

ggcgacgtca atggccacaa gttcagcgtg tccggcgagg gcgagggcga tgccacctac    660

ggcaagctga ccctgaagct gatctgcacc accggcaagc tgcccgtgcc ctggcccacc    720

ctcgtgacca ccctgggcta cggcgtgcag tgcttcgccc gctaccccga ccacatgaag    780

cagcacgact tcttcaagtc cgccatgccc gaaggctacg tccaggagcg caccatcttc    840

ttcaaagacg acggcaacta caagacccgc gccgaggtga agttcgaggg cgacaccctg    900

gtgaaccgca tcgagctgaa gggcatcgac ttcaaggagg acggcaacat cctggggcac    960

aagctggagt acaactacaa cagccacaac gtctatatca ccgccgacaa gcagaagaac   1020

ggcatcaagg ccaacttcaa gatccgccac aacatcgagg acggcggcgt gcagctcgcc   1080

gaccactacc agcagaacac ccccatcggc gacggccccg tgctgctgcc cgacaaccac   1140

tacctgagct accagtccaa gctgagcaaa gaccccaacg agaagcgcga tcacatggtc   1200

ctgctggagt tcgtgaccgc cgccgggatc actctcggca tggacgagct gtacaaaggc   1260

agcggcgcca ccaacttcag cctgctgaag caggccggcg acgtggagga gaacccccggc   1320

cccggagcta gcggaatggt ttacccgtat gatgtcccgg attacgctgg cagctaccca   1380

tacgatgtac ccgactatgc cggcagttat ccctacgacg tccctgacta cgcagaaaac   1440

aacccagccg aacagcaagt cccacccctc gtggcgctcg cccaacgcat agtatttcac   1500
```

aaggcgttta cgccgacgat aatcaccctc atcattatta atgcgatcat tgtgggactc 1560
gagacatacc caacggttta ccagggttac aatgattggt tctatgctgc cgaccttgct 1620
ttgttgtgga tattcactat tgaaatcacg ctccgattca tcgccgcccg accgacgaag 1680
agtttcttca agtctagctg gaactggttt gatctgctta tcgtattggc gggccacgtc 1740
ttcgctggcg cccattttgt tacggtgctt aggatcctcc gcgtcctgag ggtcctcaga 1800
gctatctcag tcatacccag tctccggcgg ctggttgacg cacttttgat gacaatccca 1860
gcactcggta acatcatgat actgatgggg attatttttt acatattcgc ggttatcggg 1920
acgatgctct ttgcatcagt agcgccagaa tactttggca atttgcagct gtctctgctt 1980
acactgttcc aagtggttac gctggaaagt tgggctagtg ggttatgcg acctattttt 2040 gccgaagtct ggtggtcttg gatctatttt gtaatcttta ttctcgtggg aactttcata 2100
gtatttaacc ttttcattgg cgtcatcgtg aacaatgtgg aaaaagctaa cgaagaggaa 2160
ctgaaaagcg aactggatga taaagaggct gatacaaaag aagaactggc atcattgcga 2220
aacgaggtgg cagaaatgaa ggatctcata aaacagatgc ataaacagca aacaaaaaag 2280
ggttaatgac cgcggccgcg aattcgatat cataatcaac ctctggatta caaaatttgt 2340
gaaagattga ctggtattct taactatgtt gctcctttta cgctatgtgg atacgctgct 2400
ttaatgcctt tgtatcatgc tattgcttcc cgtatggctt tcattttctc ctccttgtat 2460
aaatcctggt tagttcttgc cacggcggaa ctcatcgccg cctgccttgc ccgctgctgg 2520
acaggggctc ggctgttggg cactgacaat tccgtggctc gagagatctt cgactgtgcc 2580
ttctagttgc cagccatctg ttgtttgccc ctcccccgtg ccttccttga ccctggaagg 2640
tgccactccc actgtccttt cctaataaaa tgaggaaatt gcatcgcatt gtctgagtag 2700
gtgtcattct attctggggg gtggggtggg gcaggacagc aagggggagg attgggaaga 2760
caatagcagg catgagatct cacgtgcgga ccgagcggcc gc 2802

<210> SEQ ID NO 39
<211> LENGTH: 2805
<212> TYPE: DNA
<213> ORGANISM: Artificial Sequence
<220> FEATURE:
<223> OTHER INFORMATION: rAAV: 3xhI56iCore-minCMV-SYFP2-P2A-3xHA-NavMs-WPRE3-BGHpA

<400> SEQUENCE: 39
gcggccgcac gcgtggtacc ctaaataaag atggcttttt agtattaaaa gtggaagaaa 60
attacaggta attatctttg acggtaaaaa cgctgtaatc agcgggctac atgaaaaatt 120
actctaatta tggctgcatt taagagaatg gctaaataaa gatggctttt tagtattaaa 180
agtggaagaa aattacaggt aattatcttt gacggtaaaa acgctgtaat cagcgggcta 240
catgaaaaat tactctaatt atggctgcat ttaagagaat ggctaaataa agatggcttt 300
ttagtattaa aagtggaaga aaattacagg taattatctt tgacggtaaa aacgctgtaa 360
tcagcgggct acatgaaaaa ttactctaat tatggctgca tttaagagaa tggagctcgg 420
gctggtcgac acaattggag gtaggcgtgt acggtgggag gcctatataa gcagagctcg 480
tttagtgaac cgtcagatcg cctggaggat ccttcgaaaa gcttgctacc ggtcgccacc 540
atggtcagca agggcgagga gctgttcacc ggggtggtgc ccatcctggt cgagctggac 600
ggcgacgtca atggccacaa gttcagcgtg tccggcgagg gcgagggcga tgccacctac 660
ggcaagctga ccctgaagct gatctgcacc accggcaagc tgcccgtgcc ctggcccacc 720

```
ctcgtgacca ccctgggcta cggcgtgcag tgcttcgccc gctaccccga ccacatgaag    780
cagcacgact tcttcaagtc cgccatgccc gaaggctacg tccaggagcg caccatcttc    840
ttcaaagacg acggcaacta caagacccgc gccgaggtga agttcgaggg cgacaccctg    900
gtgaaccgca tcgagctgaa gggcatcgac ttcaaggagg acggcaacat cctggggcac    960
aagctggagt acaactacaa cagccacaac gtctatatca ccgccgacaa gcagaagaac   1020
ggcatcaagg ccaacttcaa gatccgccac aacatcgagg acggcggcgt gcagctcgcc   1080
gaccactacc agcagaacac ccccatcggc gacggccccg tgctgctgcc cgacaaccac   1140
tacctgagct accagtccaa gctgagcaaa gaccccaacg agaagcgcga tcacatggtc   1200
ctgctggagt tcgtgaccgc cgccgggatc actctcggca tggacgagct gtacaaaggc   1260
agcggcgcca ccaacttcag cctgctgaag caggccggcg acgtggagga gaaccccggc   1320
cccggagcta gcggaatggt ttatccgtat gatgttcctg actatgcagg atcctatcct   1380
tatgatgttc ccgattacgc tggttcttac ccttacgatg ttcccgatta tgccagttct   1440
ggattggtgc cacgaggcag ccacatgagc cggaagatca gagatcttat cgaatctaag   1500
agatttcaga atgttattac cgcgataatc gtactcaacg gggcggtgct cggtctcctc   1560
accgatacca cattgagcgc ttctagccag aacctgctcg aaagggttga ccaactgtgc   1620
ctgacaattt ttatcgtgga aattagcttg aaaatttacg cctacggcgt tcgcggtttt   1680
ttccggagcg gttggaatct ttttgacttc gttatcgttg ccatcgcgct catgcccgca   1740
cagggttctt tgtctgtgtt gaggacattc cgaatatttc gcgtgatgcg cttggtatcc   1800
gtgatcccta cgatgcgccg cgtcgtacaa ggaatgttgc tggctctccc cggcgtcggg   1860
agcgttgctg ccctccttac cgtggtattt tacatagcgg cggttatggc tactaatctt   1920
tacggagcta ccttcccgga gtggttcggg gatttgtcca agagcctcta tacattgttt   1980
caagttatga ccctggagtc ctggtctatg ggcattgtcc ggcccgtaat gaacgtacac   2040
ccaaatgcgt gggtgttttt cattccattc atcatgctga ctacctttac cgtgctgaac   2100
ttgttcattg ggattatcgt ggatgcgatg gccatcacta aggagcaaga agaagaggct   2160
aaaactggcc accaccaaga gccaatttct caaaccctct tgcatctcgg ggaccgactg   2220
gaccgcattg agaagcaact cgcgcagaac aatgagctgt tgcagcgaca gcaacctcaa   2280
aaaaaataat gaccgcggcc gcgaattcga tatcataatc aacctctgga ttacaaaatt   2340
tgtgaaagat tgactggtat tcttaactat gttgctcctt ttacgctatg tggatacgct   2400
gctttaatgc ctttgtatca tgctattgct tcccgtatgg ctttcatttt ctcctccttg   2460
tataaatcct ggttagttct tgccacggcg gaactcatcg ccgcctgcct tgcccgctgc   2520
tggacagggg ctcggctgtt gggcactgac aattccgtgg ctcgagagat cttcgactgt   2580
gccttctagt tgccagccat ctgttgtttg cccctccccc gtgccttcct tgaccctgga   2640
aggtgccact cccactgtcc tttcctaata aaatgaggaa attgcatcgc attgtctgag   2700
taggtgtcat tctattctgg ggggtggggt ggggcaggac agcaaggggg aggattggga   2760
agacaatagc aggcatgaga tctcacgtgc ggaccgagcg gccgc                   2805
```

<210> SEQ ID NO 40
<211> LENGTH: 1901
<212> TYPE: DNA
<213> ORGANISM: Artificial Sequence
<220> FEATURE:
<223> OTHER INFORMATION: rAAV: hI56i-minBglobin-SYFP2-WPRE3-BGHpA

<400> SEQUENCE: 40
gcggccgcac gcgtataggt accgagctct atgcactcac agtggtttgg catgcatctg 60
gtgaattttt tttaacgaaa aattagtgtt ggtttcgatg tatggtagca ttctccctaa 120
cgtaatttga ataattcagc aaagccccac taccagctgt acttctgcag cctcttccat 180
tcttttcagc attataattt tggttaattt tcaattttag gtcctacgtc tctgcaattt 240
gtgtatgaat aacagaataa tttccctctt ttgtttcgcc tttcctgttc ctgaatctaa 300
ataaagatgg ctttttagta ttaaaagtgg aagaaaatta caggtaatta tctttgacgg 360
taaaaacgct gtaatcagcg ggctacatga aaaattactc taattatggc tgcatttaag 420
agaatggaaa aaaaccttct tgtggataaa aaccttaaat tgtccccaat gtctgcttca 480
aattggatgg cactgcagct ggaggctttg ttcagaattg atcctgggga gctacgaacc 540
caaagtttca cagtagggag ctcgggctgg gcataaaagt cagggcagag ccatctattg 600
cttacatttg cttctgggat ccagatcttt cgaagctagc gctaccggtc gccaccatgg 660
tgagcaaggg cgaggagctg ttcaccgggg tggtgcccat cctggtcgag ctggacggcg 720
acgtaaacgg ccacaagttc agcgtgtccg gcgagggcga gggcgatgcc acctacggca 780
agctgaccct gaagctgatc tgcaccaccg gcaagctgcc cgtgccctgg cccaccctcg 840
tgaccaccct gggctacggc gtgcagtgct tcgcccgcta ccccgaccac atgaagcagc 900
acgacttctt caagtccgcc atgcccgaag gctacgtcca ggagcgcacc atcttcttca 960
aggacgacgg caactacaag acccgcgccg aggtgaagtt cgagggcgac accctggtga 1020
accgcatcga gctgaagggc atcgacttca aggaggacgg caacatcctg gggcacaagc 1080
tggagtacaa ctacaacagc cacaacgtct atatcaccgc cgacaagcag aagaacggca 1140
tcaaggccaa cttcaagatc cgccacaaca tcgaggacgg cggcgtgcag ctcgccgacc 1200
actaccagca gaacaccccc atcggcgacg gccccgtgct gctgcccgac aaccactacc 1260
tgagctacca gtccaagctg agcaaagacc ccaacgagaa gcgcgatcac atggtcctgc 1320
tggagttcgt gaccgccgcc gggatcactc tcggcatgga cgagctgtac aagtaagtcg 1380
acggcgcgcc gcggccgcga attcgatatc ataatcaacc tctggattac aaaatttgtg 1440
aaagattgac tggtattctt aactatgttg ctccttttac gctatgtgga tacgctgctt 1500
taatgccttt gtatcatgct attgcttccc gtatggcttt cattttctcc tccttgtata 1560
aatcctggtt agttcttgcc acggcggaac tcatcgccgc ctgccttgcc cgctgctgga 1620
caggggctcg gctgttgggc actgacaatt ccgtggctcg agagatcttc gactgtgcct 1680
tctagttgcc agccatctgt tgtttgcccc tcccccgtgc cttccttgac cctggaaggt 1740
gccactccca ctgtcctttc ctaataaaat gaggaaattg catcgcattg tctgagtagg 1800
tgtcattcta ttctgggggg tggggtgggg caggacagca agggggagga ttgggaagac 1860
aatagcaggc atgagatctc acgtgcggac cgagcggccg c 1901

<210> SEQ ID NO 41
<211> LENGTH: 4398
<212> TYPE: DNA
<213> ORGANISM: Artificial Sequence
<220> FEATURE:
<223> OTHER INFORMATION: rAAV: hI56core-minBglobin-SYFP2-WPRE3-BGHpA

<400> SEQUENCE: 41
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120

```
actccatcac taggggttcc tgcggccgca cgcgttcgcc tttcctgttc ctgaatctaa    180
ataaagatgg ctttttagta ttaaaagtgg aagaaaatta caggtaatta tctttgacgg    240
taaaaacgct gtaatcagcg ggctacatga aaaattactc taattatggc tgcatttaag    300
agaatggacc tgcagggagc tcgggctggg cataaaagtc agggcagagc catctattgc    360
ttacatttgc ttctgggatc cagatctttc gaagctagcg ctaccggtcg ccaccatggt    420
gagcaagggc gaggagctgt tcaccggggt ggtgcccatc ctggtcgagc tggacggcga    480
cgtaaacggc cacaagttca gcgtgtccgg cgagggcgag ggcgatgcca cctacggcaa    540
gctgaccctg aagctgatct gcaccaccgg caagctgccc gtgccctggc ccaccctcgt    600
gaccaccctg ggctacggcg tgcagtgctt cgcccgctac cccgaccaca tgaagcagca    660
cgacttcttc aagtccgcca tgcccgaagg ctacgtccag gagcgcacca tcttcttcaa    720
ggacgacggc aactacaaga cccgcgccga ggtgaagttc gagggcgaca ccctggtgaa    780
ccgcatcgag ctgaagggca tcgacttcaa ggaggacggc aacatcctgg ggcacaagct    840
ggagtacaac tacaacagcc acaacgtcta tatcaccgcc gacaagcaga agaacggcat    900
caaggccaac ttcaagatcc gccacaacat cgaggacggc ggcgtgcagc tcgccgacca    960
ctaccagcag aacaccccca tcggcgacgg ccccgtgctg ctgcccgaca accactacct   1020
gagctaccag tccaagctga gcaaagaccc caacgagaag cgcgatcaca tggtcctgct   1080
ggagttcgtg accgccgccg ggatcactct cggcatggac gagctgtaca agtaagtcga   1140
cggcgcgccg cggccgcgaa ttcgatatca taatcaacct ctggattaca aaatttgtga   1200
aagattgact ggtattctta actatgttgc tccttttacg ctatgtggat acgctgcttt   1260
aatgcctttg tatcatgcta ttgcttcccg tatggctttc attttctcct ccttgtataa   1320
atcctggtta gttcttgcca cggcggaact catcgccgcc tgccttgccc gctgctggac   1380
aggggctcgg ctgttgggca ctgacaattc cgtggctcga gagatcttcg actgtgcctt   1440
ctagttgcca gccatctgtt gtttgcccct cccccgtgcc ttccttgacc ctggaaggtg   1500
ccactcccac tgtcctttcc taataaaatg aggaaattgc atcgcattgt ctgagtaggt   1560
gtcattctat tctggggggt ggggtggggc aggacagcaa gggggaggat tgggaagaca   1620
atagcaggca tgagatctca cgtgcggacc gagcggccgc aggaacccct agtgatggag   1680
ttggccactc cctctctgcg cgctcgctcg ctcactgagg ccgggcgacc aaaggtcgcc   1740
cgacgcccgg gctttgcccg ggcggcctca gtgagcgagc gagcgcgcag ctgcctgcag   1800
gggcgcctga tgcggtattt tctccttacg catctgtgcg gtatttcaca ccgcatacgt   1860
caaagcaacc atagtacgcg ccctgtagcg gcgcattaag cgcggcgggt gtggtggtta   1920
cgcgcagcgt gaccgctaca cttgccagcg ccctagcgcc cgctcctttc gctttcttcc   1980
cttcctttct cgccacgttc gccggctttc cccgtcaagc tctaaatcgg gggctccctt   2040
tagggttccg atttagtgct ttacggcacc tcgaccccaa aaaacttgat ttgggtgatg   2100
gttcacgtag tgggccatcg ccctgataga cggtttttcg ccctttgacg ttggagtcca   2160
cgttctttaa tagtggactc ttgttccaaa ctggaacaac actcaaccct atctcgggct   2220
attcttttga tttataaggg attttgccga tttcggccta ttggttaaaa aatgagctga   2280
tttaacaaaa atttaacgcg aattttaaca aaatattaac gtttacaatt ttatggtgca   2340
ctctcagtac aatctgctct gatgccgcat agttaagcca gccccgacac ccgccaacac   2400
ccgctgacgc gccctgacgg gcttgtctgc tcccggcatc cgcttacaga caagctgtga   2460
```

```
ccgtctccgg gagctgcatg tgtcagaggt tttcaccgtc atcaccgaaa cgcgcgagac   2520

gaaagggcct cgtgatacgc ctatttttat aggttaatgt catgataata atggtttctt   2580

agacgtcagg tggcactttt cggggaaatg tgcgcggaac ccctatttgt ttatttttct   2640

aaatacattc aaatatgtat ccgctcatga gacaataacc ctgataaatg cttcaataat   2700

attgaaaaag gaagagtatg agtattcaac atttccgtgt cgcccttatt cccttttttg   2760

cggcattttg ccttcctgtt tttgctcacc cagaaacgct ggtgaaagta aaagatgctg   2820

aagatcagtt gggtgcacga gtgggttaca tcgaactgga tctcaacagc ggtaagatcc   2880

ttgagagttt tcgccccgaa gaacgttttc caatgatgag cacttttaaa gttctgctat   2940

gtggcgcggt attatcccgt attgacgccg ggcaagagca actcggtcgc cgcatacact   3000

attctcagaa tgacttggtt gagtactcac cagtcacaga aaagcatctt acggatggca   3060

tgacagtaag agaattatgc agtgctgcca taaccatgag tgataacact gcggccaact   3120

tacttctgac aacgatcgga ggaccgaagg agctaaccgc ttttttgcac aacatggggg   3180

atcatgtaac tcgccttgat cgttgggaac cggagctgaa tgaagccata ccaaacgacg   3240

agcgtgacac cacgatgcct gtagcaatgg caacaacgtt gcgcaaacta ttaactggcg   3300

aactacttac tctagcttcc cggcaacaat taatagactg gatggaggcg gataaagttg   3360

caggaccact tctgcgctcg gcccttccgg ctggctggtt tattgctgat aaatctggag   3420

ccggtgagcg tgggtctcgc ggtatcattg cagcactggg gccagatggt aagccctccc   3480

gtatcgtagt tatctacacg acggggagtc aggcaactat ggatgaacga aatagacaga   3540

tcgctgagat aggtgcctca ctgattaagc attggtaact gtcagaccaa gtttactcat   3600

atatacttta gattgattta aaacttcatt tttaatttaa aaggatctag gtgaagatcc   3660

tttttgataa tctcatgacc aaaatccctt aacgtgagtt ttcgttccac tgagcgtcag   3720

accccgtaga aaagatcaaa ggatcttctt gagatccttt ttttctgcgc gtaatctgct   3780

gcttgcaaac aaaaaaacca ccgctaccag cggtggtttg tttgccggat caagagctac   3840

caactctttt tccgaaggta actggcttca gcagagcgca gataccaaat actgtccttc   3900

tagtgtagcc gtagttaggc caccacttca agaactctgt agcaccgcct acatacctcg   3960

ctctgctaat cctgttacca gtggctgctg ccagtggcga taagtcgtgt cttaccgggt   4020

tggactcaag acgatagtta ccggataagg cgcagcggtc gggctgaacg gggggttcgt   4080

gcacacagcc cagcttggag cgaacgacct acaccgaact gagataccta cagcgtgagc   4140

tatgagaaag cgccacgctt cccgaaggga gaaaggcgga caggtatccg gtaagcggca   4200

gggtcggaac aggagagcgc acgagggagc ttccaggggg aaacgcctgg tatctttata   4260

gtcctgtcgg gtttcgccac ctctgacttg agcgtcgatt tttgtgatgc tcgtcagggg   4320

ggcggagcct atggaaaaac gccagcaacg cggccttttt acggttcctg gccttttgct   4380

ggccttttgc tcacatgt                                                 4398
```

<210> SEQ ID NO 42
<211> LENGTH: 4635
<212> TYPE: DNA
<213> ORGANISM: Artificial Sequence
<220> FEATURE:
<223> OTHER INFORMATION: rAAV: 3XhI56core-minBglobin-SYFP2-WPRE3-BGHpA

<400> SEQUENCE: 42

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120
```

```
actccatcac taggggttcc tgcggccgca cgcgtggtac cctaaataaa gatggctttt    180
tagtattaaa agtggaagaa aattacaggt aattatcttt gacggtaaaa acgctgtaat    240
cagcgggcta catgaaaaat tactctaatt atggctgcat ttaagagaat ggctaaataa    300
agatggcttt ttagtattaa aagtggaaga aaattacagg taattatctt tgacggtaaa    360
aacgctgtaa tcagcgggct acatgaaaaa ttactctaat tatggctgca tttaagagaa    420
tggctaaata aagatggctt tttagtatta aaagtggaag aaaattacag gtaattatct    480
ttgacggtaa aaacgctgta atcagcgggc tacatgaaaa attactctaa ttatggctgc    540
atttaagaga atggagctcg ggctgggcat aaaagtcagg gcagagccat ctattgctta    600
catttgcttc tgggatccag atctttcgaa gctagcgcta ccggtcgcca ccatggtgag    660
caagggcgag gagctgttca ccggggtggt gcccatcctg gtcgagctgg acggcgacgt    720
aaacggccac aagttcagcg tgtccggcga gggcgagggc gatgccacct acggcaagct    780
gaccctgaag ctgatctgca ccaccggcaa gctgcccgtg ccctggccca ccctcgtgac    840
caccctgggc tacggcgtgc agtgcttcgc ccgctacccc gaccacatga agcagcacga    900
cttcttcaag tccgccatgc ccgaaggcta cgtccaggag cgcaccatct tcttcaagga    960
cgacggcaac tacaagaccc gcgccgaggt gaagttcgag ggcgacaccc tggtgaaccg   1020
catcgagctg aagggcatcg acttcaagga ggacggcaac atcctggggc acaagctgga   1080
gtacaactac aacagccaca acgtctatat caccgccgac aagcagaaga acggcatcaa   1140
ggccaacttc aagatccgcc acaacatcga ggacggcggc gtgcagctcg ccgaccacta   1200
ccagcagaac acccccatcg gcgacggccc cgtgctgctg cccgacaacc actacctgag   1260
ctaccagtcc aagctgagca aagaccccaa cgagaagcgc gatcacatgg tcctgctgga   1320
gttcgtgacc gccgccggga tcactctcgg catggacgag ctgtacaagt aagtcgacgg   1380
cgcgccgcgg ccgcgaattc gatatcataa tcaacctctg gattacaaaa tttgtgaaag   1440
attgactggt attcttaact atgttgctcc ttttacgcta tgtggatacg ctgctttaat   1500
gcctttgtat catgctattg cttcccgtat ggctttcatt ttctcctcct tgtataaatc   1560
ctggttagtt cttgccacgg cggaactcat cgccgcctgc cttgcccgct gctggacagg   1620
ggctcggctg ttgggcactg acaattccgt ggctcgagag atcttcgact gtgccttcta   1680
gttgccagcc atctgttgtt tgcccctccc ccgtgccttc cttgaccctg gaaggtgcca   1740
ctcccactgt cctttcctaa taaaatgagg aaattgcatc gcattgtctg agtaggtgtc   1800
attctattct ggggggtggg gtggggcagg acagcaaggg ggaggattgg gaagacaata   1860
gcaggcatga gatctcacgt gcggaccgag cggccgcagg aacccctagt gatggagttg   1920
gccactccct ctctgcgcgc tcgctcgctc actgaggccg ggcgaccaaa ggtcgcccga   1980
cgcccgggct ttgcccgggc ggcctcagtg agcgagcgag cgcgcagctg cctgcagggg   2040
cgcctgatgc ggtattttct ccttacgcat ctgtgcggta tttcacaccg catacgtcaa   2100
agcaaccata gtacgcgccc tgtagcggcg cattaagcgc ggcgggtgtg gtggttacgc   2160
gcagcgtgac cgctacactt gccagcgccc tagcgcccgc tcctttcgct ttcttccctt   2220
cctttctcgc cacgttcgcc ggctttcccc gtcaagctct aaatcggggg ctccctttag   2280
ggttccgatt tagtgcttta cggcacctcg accccaaaaa acttgatttg ggtgatggtt   2340
cacgtagtgg gccatcgccc tgatagacgg tttttcgccc tttgacgttg gagtccacgt   2400
tctttaatag tggactcttg ttccaaactg gaacaacact caaccctatc tcgggctatt   2460
```

```
cttttgattt ataagggatt ttgccgattt cggcctattg gttaaaaaat gagctgattt   2520
aacaaaaatt taacgcgaat tttaacaaaa tattaacgtt tacaatttta tggtgcactc   2580
tcagtacaat ctgctctgat gccgcatagt taagccagcc ccgacacccg ccaacacccg   2640
ctgacgcgcc ctgacgggct tgtctgctcc cggcatccgc ttacagacaa gctgtgaccg   2700
tctccgggag ctgcatgtgt cagaggtttt caccgtcatc accgaaacgc gcgagacgaa   2760
agggcctcgt gatacgccta tttttatagg ttaatgtcat gataataatg gtttcttaga   2820
cgtcaggtgg cacttttcgg ggaaatgtgc gcggaacccc tatttgttta tttttctaaa   2880
tacattcaaa tatgtatccg ctcatgagac aataaccctg ataaatgctt caataatatt   2940
gaaaaaggaa gagtatgagt attcaacatt tccgtgtcgc ccttattccc ttttttgcgg   3000
cattttgcct tcctgttttt gctcacccag aaacgctggt gaaagtaaaa gatgctgaag   3060
atcagttggg tgcacgagtg ggttacatcg aactggatct caacagcggt aagatccttg   3120
agagttttcg ccccgaagaa cgttttccaa tgatgagcac ttttaaagtt ctgctatgtg   3180
gcgcggtatt atcccgtatt gacgccgggc aagagcaact cggtcgccgc atacactatt   3240
ctcagaatga cttggttgag tactcaccag tcacagaaaa gcatcttacg gatggcatga   3300
cagtaagaga attatgcagt gctgccataa ccatgagtga taacactgcg gccaacttac   3360
ttctgacaac gatcggagga ccgaaggagc taaccgcttt tttgcacaac atgggggatc   3420
atgtaactcg ccttgatcgt tgggaaccgg agctgaatga agccatacca aacgacgagc   3480
gtgacaccac gatgcctgta gcaatggcaa caacgttgcg caaactatta actggcgaac   3540
tacttactct agcttcccgg caacaattaa tagactggat ggaggcggat aaagttgcag   3600
gaccacttct gcgctcggcc cttccggctg gctggtttat tgctgataaa tctggagccg   3660
gtgagcgtgg gtctcgcggt atcattgcag cactggggcc agatggtaag ccctcccgta   3720
tcgtagttat ctacacgacg gggagtcagg caactatgga tgaacgaaat agacagatcg   3780
ctgagatagg tgcctcactg attaagcatt ggtaactgtc agaccaagtt tactcatata   3840
tactttagat tgatttaaaa cttcattttt aatttaaaag gatctaggtg aagatccttt   3900
ttgataatct catgaccaaa atcccttaac gtgagttttc gttccactga gcgtcagacc   3960
ccgtagaaaa gatcaaagga tcttcttgag atcctttttt tctgcgcgta atctgctgct   4020
tgcaaacaaa aaaaccaccg ctaccagcgg tggtttgttt gccggatcaa gagctaccaa   4080
ctctttttcc gaaggtaact ggcttcagca gagcgcagat accaaatact gtccttctag   4140
tgtagccgta gttaggccac cacttcaaga actctgtagc accgcctaca tacctcgctc   4200
tgctaatcct gttaccagtg gctgctgcca gtggcgataa gtcgtgtctt accgggttgg   4260
actcaagacg atagttaccg gataaggcgc agcggtcggg ctgaacgggg ggttcgtgca   4320
cacagcccag cttggagcga acgacctaca ccgaactgag atacctacag cgtgagctat   4380
gagaaagcgc cacgcttccc gaagggagaa aggcggacag gtatccggta agcggcaggg   4440
tcggaacagg agagcgcacg agggagcttc caggggggaaa cgcctggtat ctttatagtc   4500
ctgtcgggtt tcgccacctc tgacttgagc gtcgattttt gtgatgctcg tcaggggggc   4560
ggagcctatg gaaaaacgcc agcaacgcgg cctttttacg gttcctggcc ttttgctggc   4620
cttttgctca catgt                                                     4635
```

<210> SEQ ID NO 43
<211> LENGTH: 4841
<212> TYPE: DNA
<213> ORGANISM: Artificial Sequence
<220> FEATURE:
<223> OTHER INFORMATION: rAAV: hI56i-minBglobin-SYFP2-WPRE3-BGHpA

<400> SEQUENCE: 43

```
aaagcttccc ggggggatct gggccactcc ctctctgcgc gctcgctcgc tcactgaggc      60
cgggcgacca aaggtcgccc gacgcccggg ctttgcccgg gcggcctcag tgagcgagcg     120
agcgcgcaga gagggagtgg ccaactccat cactaggggt tcctggaggg gtggagtcgt     180
gacctaggac gcgtataggt accgagctct atgcactcac agtggtttgg catgcatctg     240
gtgaattttt tttaacgaaa aattagtgtt ggtttcgatg tatggtagca ttctccctaa     300
cgtaatttga ataattcagc aaagccccac taccagctgt acttctgcag cctcttccat     360
tcttttcagc attataattt tggttaattt tcaattttag gtcctacgtc tctgcaattt     420
gtgtatgaat aacagaataa tttccctctt ttgtttcgcc tttcctgttc ctgaatctaa     480
ataaagatgg ctttttagta ttaaaagtgg aagaaaatta caggtaatta tctttgacgg     540
taaaaacgct gtaatcagcg ggctacatga aaaattactc taattatggc tgcatttaag     600
agaatggaaa aaaaccttct tgtggataaa aaccttaaat tgtccccaat gtctgcttca     660
aattggatgg cactgcagct ggaggctttg ttcagaattg atcctgggga gctacgaacc     720
caaagtttca cagtagggag ctcgggctgg gcataaaagt cagggcagag ccatctattg     780
cttacatttg cttctgggat ccagatcttt cgaagctagc gctaccggtc gccaccatgg     840
tgagcaaggg cgaggagctg ttcaccgggg tggtgcccat cctggtcgag ctggacggcg     900
acgtaaacgg ccacaagttc agcgtgtccg gcgagggcga gggcgatgcc acctacggca     960
agctgaccct gaagctgatc tgcaccaccg gcaagctgcc cgtgccctgg cccaccctcg    1020
tgaccaccct gggctacggc gtgcagtgct tcgcccgcta ccccgaccac atgaagcagc    1080
acgacttctt caagtccgcc atgcccgaag gctacgtcca ggagcgcacc atcttcttca    1140
aggacgacgg caactacaag acccgcgccg aggtgaagtt cgagggcgac accctggtga    1200
accgcatcga gctgaagggc atcgacttca aggaggacgg caacatcctg gggcacaagc    1260
tggagtacaa ctacaacagc cacaacgtct atatcaccgc cgacaagcag aagaacggca    1320
tcaaggccaa cttcaagatc cgccacaaca tcgaggacgg cggcgtgcag ctcgccgacc    1380
actaccagca gaacaccccc atcggcgacg gccccgtgct gctgcccgac aaccactacc    1440
tgagctacca gtccaagctg agcaaagacc ccaacgagaa gcgcgatcac atggtcctgc    1500
tggagttcgt gaccgccgcc gggatcactc tcggcatgga cgagctgtac aagtaagtcg    1560
acggcgcgcc gcggccgcga attcgatatc ataatcaacc tctggattac aaaatttgtg    1620
aaagattgac tggtattctt aactatgttg ctccttttac gctatgtgga tacgctgctt    1680
taatgccttt gtatcatgct attgcttccc gtatggcttt cattttctcc tccttgtata    1740
aatcctggtt agttcttgcc acggcggaac tcatcgccgc ctgccttgcc cgctgctgga    1800
caggggctcg gctgttgggc actgacaatt ccgtggctcg agcgactgtg ccttctagtt    1860
gccagccatc tgttgtttgc ccctcccccg tgccttcctt gaccctggaa ggtgccactc    1920
ccactgtcct ttcctaataa aatgaggaaa ttgcatcgca ttgtctgagt aggtgtcatt    1980
ctattctggg gggtggggtg gggcaggaca gcaaggggga ggattgggaa gacaatagca    2040
ggcatgacta gtccactccc tctctgcgcg ctcgctcgct cactgaggcc gggcgaccaa    2100
aggtcgcccg acgcccgggc tttgcccggg cggcctcagt gagcgagcga gcgcgcagag    2160
agggacagat ccgggcccgc atgcgtcgac aattcactgg ccgtcgtttt acaacgtcgt    2220
```

-continued

```
gactgggaaa accctggcgt tacccaactt aatcgccttg cagcacatcc ccctttcgcc   2280
agctggcgta atagcgaaga ggcccgcacc gatcgccctt cccaacagtt gcgcagcctg   2340
aatggcgaat ggcgcctgat gcggtatttt ctccttacgc atctgtgcgg tatttcacac   2400
cgcatatggt gcactctcag tacaatctgc tctgatgccg catagttaag ccagccccga   2460
cacccgccaa cacccgctga cgcgccctga cgggcttgtc tgctcccggc atccgcttac   2520
agacaagctg tgaccgtctc cgggagctgc atgtgtcaga ggttttcacc gtcatcaccg   2580
aaacgcgcga gacgaaaggg cctcgtgata cgcctatttt tataggttaa tgtcatgata   2640
ataatggttt cttagacgtc aggtggcact tttcggggaa atgtgcgcgg aacccctatt   2700
tgtttatttt tctaaataca ttcaaatatg tatccgctca tgagacaata accctgataa   2760
atgcttcaat aatattgaaa aaggaagagt atgagtattc aacatttccg tgtcgccctt   2820
attccctttt ttgcggcatt ttgccttcct gtttttgctc acccagaaac gctggtgaaa   2880
gtaaaagatg ctgaagatca gttgggtgca cgagtgggtt acatcgaact ggatctcaac   2940
agcggtaaga tccttgagag ttttcgcccc gaagaacgtt ttccaatgat gagcactttt   3000
aaagttctgc tatgtggcgc ggtattatcc cgtattgacg ccgggcaaga gcaactcggt   3060
cgccgcatac actattctca gaatgacttg gttgagtact caccagtcac agaaaagcat   3120
cttacggatg gcatgacagt aagagaatta tgcagtgctg ccataaccat gagtgataac   3180
actgcggcca acttacttct gacaacgatc ggaggaccga aggagctaac cgcttttttg   3240
cacaacatgg gggatcatgt aactcgcctt gatcgttggg aaccggagct gaatgaagcc   3300
ataccaaacg acgagcgtga caccacgatg cctgtagcaa tggcaacaac gttgcgcaaa   3360
ctattaactg gcgaactact tactctagct tcccggcaac aattaataga ctggatggag   3420
gcggataaag ttgcaggacc acttctgcgc tcggcccttc cggctggctg gtttattgct   3480
gataaatctg gagccggtga gcgtgggtct cgcggtatca ttgcagcact ggggccagat   3540
ggtaagccct cccgtatcgt agttatctac acgacgggga gtcaggcaac tatggatgaa   3600
cgaaatagac agatcgctga gataggtgcc tcactgatta agcattggta actgtcagac   3660
caagtttact catatatact ttagattgat ttaaaacttc atttttaatt taaaaggatc   3720
taggtgaaga tcctttttga taatctcatg accaaaatcc cttaacgtga gttttcgttc   3780
cactgagcgt cagaccccgt agaaaagatc aaaggatctt cttgagatcc tttttttctg   3840
cgcgtaatct gctgcttgca aacaaaaaaa ccaccgctac cagcggtggt ttgtttgccg   3900
gatcaagagc taccaactct ttttccgaag gtaactggct tcagcagagc gcagatacca   3960
aatactgttc ttctagtgta gccgtagtta ggccaccact tcaagaactc tgtagcaccg   4020
cctacatacc tcgctctgct aatcctgtta ccagtggctg ctgccagtgg cgataagtcg   4080
tgtcttaccg ggttggactc aagacgatag ttaccggata aggcgcagcg gtcgggctga   4140
acggggggtt cgtgcacaca gcccagcttg gagcgaacga cctacaccga actgagatac   4200
ctacagcgtg agctatgaga aagcgccacg cttcccgaag ggagaaaggc ggacaggtat   4260
ccggtaagcg gcagggtcgg aacaggagag cgcacgaggg agcttccagg gggaaacgcc   4320
tggtatcttt atagtcctgt cgggtttcgc cacctctgac ttgagcgtcg atttttgtga   4380
tgctcgtcag gggggcggag cctatggaaa aacgccagca acgcggcctt tttacggttc   4440
ctggcctttt gctggccttt tgctcacatg ttctttcctg cgttatcccc tgattctgtg   4500
gataaccgta ttaccgcctt tgagtgagct gataccgctc gccgcagccg aacgaccgag   4560
cgcagcgagt cagtgagcga ggaagcggaa gagcgcccaa tacgcaaacc gcctctcccc   4620
```

```
gcgcgttggc cgattcatta atgcagctgg cacgacaggt ttcccgactg gaaagcgggc   4680

agtgagcgca acgcaattaa tgtgagttag ctcactcatt aggcacccca ggctttacac   4740

tttatgcttc cggctcgtat gttgtgtgga attgtgagcg gataacaatt tcacacagga   4800

aacagctatg accatgatta cgccaagctc tcgagatcta g                       4841


<210> SEQ ID NO 44
<211> LENGTH: 1927
<212> TYPE: PRT
<213> ORGANISM: Homo sapiens

<400> SEQUENCE: 44

Met Glu Leu Ser Trp His Val Val Phe Ile Ala Leu Leu Ser Phe Ser
1               5                   10                  15

Cys Trp Gly Ser Asp Trp Glu Ser Asp Arg Asn Phe Ile Ser Thr Ala
            20                  25                  30

Gly Pro Leu Thr Asn Asp Leu Leu His Asn Leu Ser Gly Leu Leu Gly
        35                  40                  45

Asp Gln Ser Ser Asn Phe Val Ala Gly Asp Lys Asp Met Tyr Val Cys
    50                  55                  60

His Gln Pro Leu Pro Thr Phe Leu Pro Glu Tyr Phe Ser Ser Leu His
65                  70                  75                  80

Ala Ser Gln Ile Thr His Tyr Lys Val Phe Leu Ser Trp Ala Gln Leu
                85                  90                  95

Leu Pro Ala Gly Ser Thr Gln Asn Pro Asp Glu Lys Thr Val Gln Cys
            100                 105                 110

Tyr Arg Arg Leu Leu Lys Ala Leu Lys Thr Ala Arg Leu Gln Pro Met
        115                 120                 125

Val Ile Leu His His Gln Thr Leu Pro Ala Ser Thr Leu Arg Arg Thr
    130                 135                 140

Glu Ala Phe Ala Asp Leu Phe Ala Asp Tyr Ala Thr Phe Ala Phe His
145                 150                 155                 160

Ser Phe Gly Asp Leu Val Gly Ile Trp Phe Thr Phe Ser Asp Leu Glu
                165                 170                 175

Glu Val Ile Lys Glu Leu Pro His Gln Glu Ser Arg Ala Ser Gln Leu
            180                 185                 190

Gln Thr Leu Ser Asp Ala His Arg Lys Ala Tyr Glu Ile Tyr His Glu
        195                 200                 205

Ser Tyr Ala Phe Gln Gly Gly Lys Leu Ser Val Val Leu Arg Ala Glu
    210                 215                 220

Asp Ile Pro Glu Leu Leu Leu Glu Pro Pro Ile Ser Ala Leu Ala Gln
225                 230                 235                 240

Asp Thr Val Asp Phe Leu Ser Leu Asp Leu Ser Tyr Glu Cys Gln Asn
                245                 250                 255

Glu Ala Ser Leu Arg Gln Lys Leu Ser Lys Leu Gln Thr Ile Glu Pro
            260                 265                 270

Lys Val Lys Val Phe Ile Phe Asn Leu Lys Leu Pro Asp Cys Pro Ser
        275                 280                 285

Thr Met Lys Asn Pro Ala Ser Leu Leu Phe Ser Leu Phe Glu Ala Ile
    290                 295                 300

Asn Lys Asp Gln Val Leu Thr Ile Gly Phe Asp Ile Asn Glu Phe Leu
305                 310                 315                 320

Ser Cys Ser Ser Ser Ser Lys Lys Ser Met Ser Cys Ser Leu Thr Gly
                325                 330                 335
```

```
Ser Leu Ala Leu Gln Pro Asp Gln Gln Gln Asp His Glu Thr Thr Asp
            340                 345                 350

Ser Ser Pro Ala Ser Ala Tyr Gln Arg Val Trp Glu Ala Phe Ala Asn
        355                 360                 365

Gln Ser Arg Ala Glu Arg Asp Ala Phe Leu Gln Asp Thr Phe Pro Glu
    370                 375                 380

Gly Phe Leu Trp Gly Ala Ser Thr Gly Ala Phe Asn Val Glu Gly Gly
385                 390                 395                 400

Trp Ala Glu Gly Gly Arg Gly Val Ser Ile Trp Asp Pro Arg Arg Pro
                405                 410                 415

Leu Asn Thr Thr Glu Gly Gln Ala Thr Leu Glu Val Ala Ser Asp Ser
            420                 425                 430

Tyr His Lys Val Ala Ser Asp Val Ala Leu Leu Cys Gly Leu Arg Ala
        435                 440                 445

Gln Val Tyr Lys Phe Ser Ile Ser Trp Ser Arg Ile Phe Pro Met Gly
    450                 455                 460

His Gly Ser Ser Pro Ser Leu Pro Gly Val Ala Tyr Tyr Asn Lys Leu
465                 470                 475                 480

Ile Asp Arg Leu Gln Asp Ala Gly Ile Glu Pro Met Ala Thr Leu Phe
                485                 490                 495

His Trp Asp Leu Pro Gln Ala Leu Gln Asp His Gly Gly Trp Gln Asn
            500                 505                 510

Glu Ser Val Val Asp Ala Phe Leu Asp Tyr Ala Ala Phe Cys Phe Ser
        515                 520                 525

Thr Phe Gly Asp Arg Val Lys Leu Trp Val Thr Phe His Glu Pro Trp
    530                 535                 540

Val Met Ser Tyr Ala Gly Tyr Gly Thr Gly Gln His Pro Pro Gly Ile
545                 550                 555                 560

Ser Asp Pro Gly Val Ala Ser Phe Lys Val Ala His Leu Val Leu Lys
                565                 570                 575

Ala His Ala Arg Thr Trp His His Tyr Asn Ser His His Arg Pro Gln
            580                 585                 590

Gln Gln Gly His Val Gly Ile Val Leu Asn Ser Asp Trp Ala Glu Pro
        595                 600                 605

Leu Ser Pro Glu Arg Pro Glu Asp Leu Arg Ala Ser Glu Arg Phe Leu
    610                 615                 620

His Phe Met Leu Gly Trp Phe Ala His Pro Val Phe Val Asp Gly Asp
625                 630                 635                 640

Tyr Pro Ala Thr Leu Arg Thr Gln Ile Gln Gln Met Asn Arg Gln Cys
                645                 650                 655

Ser His Pro Val Ala Gln Leu Pro Glu Phe Thr Glu Ala Glu Lys Gln
            660                 665                 670

Leu Leu Lys Gly Ser Ala Asp Phe Leu Gly Leu Ser His Tyr Thr Ser
        675                 680                 685

Arg Leu Ile Ser Asn Ala Pro Gln Asn Thr Cys Ile Pro Ser Tyr Asp
    690                 695                 700

Thr Ile Gly Gly Phe Ser Gln His Val Asn His Val Trp Pro Gln Thr
705                 710                 715                 720

Ser Ser Ser Trp Ile Arg Val Val Pro Trp Gly Ile Arg Arg Leu Leu
                725                 730                 735

Gln Phe Val Ser Leu Glu Tyr Thr Arg Gly Lys Val Pro Ile Tyr Leu
            740                 745                 750
```

```
Ala Gly Asn Gly Met Pro Ile Gly Glu Ser Glu Asn Leu Phe Asp Asp
        755                 760                 765

Ser Leu Arg Val Asp Tyr Phe Asn Gln Tyr Ile Asn Glu Val Leu Lys
    770                 775                 780

Ala Ile Lys Glu Asp Ser Val Asp Val Arg Ser Tyr Ile Ala Arg Ser
785                 790                 795                 800

Leu Ile Asp Gly Phe Glu Gly Pro Ser Gly Tyr Ser Gln Arg Phe Gly
                805                 810                 815

Leu His His Val Asn Phe Ser Asp Ser Ser Lys Ser Arg Thr Pro Arg
            820                 825                 830

Lys Ser Ala Tyr Phe Phe Thr Ser Ile Ile Glu Lys Asn Gly Phe Leu
        835                 840                 845

Thr Lys Gly Ala Lys Arg Leu Leu Pro Pro Asn Thr Val Asn Leu Pro
    850                 855                 860

Ser Lys Val Arg Ala Phe Thr Phe Pro Ser Glu Val Pro Ser Lys Ala
865                 870                 875                 880

Lys Val Val Trp Glu Lys Phe Ser Ser Gln Pro Lys Phe Glu Arg Asp
                885                 890                 895

Leu Phe Tyr His Gly Thr Phe Arg Asp Asp Phe Leu Trp Gly Val Ser
            900                 905                 910

Ser Ser Ala Tyr Gln Ile Glu Gly Ala Trp Asp Ala Asp Gly Lys Gly
        915                 920                 925

Pro Ser Ile Trp Asp Asn Phe Thr His Thr Pro Gly Ser Asn Val Lys
    930                 935                 940

Asp Asn Ala Thr Gly Asp Ile Ala Cys Asp Ser Tyr His Gln Leu Asp
945                 950                 955                 960

Ala Asp Leu Asn Met Leu Arg Ala Leu Lys Val Lys Ala Tyr Arg Phe
                965                 970                 975

Ser Ile Ser Trp Ser Arg Ile Phe Pro Thr Gly Arg Asn Ser Ser Ile
            980                 985                 990

Asn Ser His Gly Val Asp Tyr Tyr  Asn Arg Leu Ile Asn  Gly Leu Val
        995                 1000                1005

Ala Ser  Asn Ile Phe Pro Met  Val Thr Leu Phe His  Trp Asp Leu
    1010                1015                1020

Pro Gln  Ala Leu Gln Asp Ile  Gly Gly Trp Glu Asn  Pro Ala Leu
    1025                1030                1035

Ile Asp  Leu Phe Asp Ser Tyr  Ala Asp Phe Cys Phe  Gln Thr Phe
    1040                1045                1050

Gly Asp  Arg Val Lys Phe Trp  Met Thr Phe Asn Glu  Pro Met Tyr
    1055                1060                1065

Leu Ala  Trp Leu Gly Tyr Gly  Ser Gly Glu Phe Pro  Pro Gly Val
    1070                1075                1080

Lys Asp  Pro Gly Trp Ala Pro  Tyr Arg Ile Ala His  Ala Val Ile
    1085                1090                1095

Lys Ala  His Ala Arg Val Tyr  His Thr Tyr Asp Glu  Lys Tyr Arg
    1100                1105                1110

Gln Glu  Gln Lys Gly Val Ile  Ser Leu Ser Leu Ser  Thr His Trp
    1115                1120                1125

Ala Glu  Pro Lys Ser Pro Gly  Val Pro Arg Asp Val  Glu Ala Ala
    1130                1135                1140

Asp Arg  Met Leu Gln Phe Ser  Leu Gly Trp Phe Ala  His Pro Ile
    1145                1150                1155

Phe Arg  Asn Gly Asp Tyr Pro  Asp Thr Met Lys Trp  Lys Val Gly
```

```
    1160                1165                1170

Asn Arg  Ser Glu Leu Gln His  Leu Ala Thr Ser Arg  Leu Pro Ser
    1175                1180                1185

Phe Thr  Glu Glu Glu Lys Arg  Phe Ile Arg Ala Thr  Ala Asp Val
    1190                1195                1200

Phe Cys  Leu Asn Thr Tyr Tyr  Ser Arg Ile Val Gln  His Lys Thr
    1205                1210                1215

Pro Arg  Leu Asn Pro Pro Ser  Tyr Glu Asp Asp Gln  Glu Met Ala
    1220                1225                1230

Glu Glu  Glu Asp Pro Ser Trp  Pro Ser Thr Ala Met  Asn Arg Ala
    1235                1240                1245

Ala Pro  Trp Gly Thr Arg Arg  Leu Leu Asn Trp Ile  Lys Glu Glu
    1250                1255                1260

Tyr Gly  Asp Ile Pro Ile Tyr  Ile Thr Glu Asn Gly  Val Gly Leu
    1265                1270                1275

Thr Asn  Pro Asn Thr Glu Asp  Thr Asp Arg Ile Phe  Tyr His Lys
    1280                1285                1290

Thr Tyr  Ile Asn Glu Ala Leu  Lys Ala Tyr Arg Leu  Asp Gly Ile
    1295                1300                1305

Asp Leu  Arg Gly Tyr Val Ala  Trp Ser Leu Met Asp  Asn Phe Glu
    1310                1315                1320

Trp Leu  Asn Gly Tyr Thr Val  Lys Phe Gly Leu Tyr  His Val Asp
    1325                1330                1335

Phe Asn  Asn Thr Asn Arg Pro  Arg Thr Ala Arg Ala  Ser Ala Arg
    1340                1345                1350

Tyr Tyr  Thr Glu Val Ile Thr  Asn Asn Gly Met Pro  Leu Ala Arg
    1355                1360                1365

Glu Asp  Glu Phe Leu Tyr Gly  Arg Phe Pro Glu Gly  Phe Ile Trp
    1370                1375                1380

Ser Ala  Ala Ser Ala Ala Tyr  Gln Ile Glu Gly Ala  Trp Arg Ala
    1385                1390                1395

Asp Gly  Lys Gly Leu Ser Ile  Trp Asp Thr Phe Ser  His Thr Pro
    1400                1405                1410

Leu Arg  Val Glu Asn Asp Ala  Ile Gly Asp Val Ala  Cys Asp Ser
    1415                1420                1425

Tyr His  Lys Ile Ala Glu Asp  Leu Val Thr Leu Gln  Asn Leu Gly
    1430                1435                1440

Val Ser  His Tyr Arg Phe Ser  Ile Ser Trp Ser Arg  Ile Leu Pro
    1445                1450                1455

Asp Gly  Thr Thr Arg Tyr Ile  Asn Glu Ala Gly Leu  Asn Tyr Tyr
    1460                1465                1470

Val Arg  Leu Ile Asp Thr Leu  Leu Ala Ala Ser Ile  Gln Pro Gln
    1475                1480                1485

Val Thr  Ile Tyr His Trp Asp  Leu Pro Gln Thr Leu  Gln Asp Val
    1490                1495                1500

Gly Gly  Trp Glu Asn Glu Thr  Ile Val Gln Arg Phe  Lys Glu Tyr
    1505                1510                1515

Ala Asp  Val Leu Phe Gln Arg  Leu Gly Asp Lys Val  Lys Phe Trp
    1520                1525                1530

Ile Thr  Leu Asn Glu Pro Phe  Val Ile Ala Tyr Gln  Gly Tyr Gly
    1535                1540                1545

Tyr Gly  Thr Ala Ala Pro Gly  Val Ser Asn Arg Pro  Gly Thr Ala
    1550                1555                1560
```

```
Pro Tyr  Ile Val Gly His Asn  Leu Ile Lys Ala His  Ala Glu Ala
    1565                 1570                 1575

Trp His  Leu Tyr Asn Asp Val  Tyr Arg Ala Ser Gln  Gly Gly Val
    1580                 1585                 1590

Ile Ser  Ile Thr Ile Ser Ser  Asp Trp Ala Glu Pro  Arg Asp Pro
    1595                 1600                 1605

Ser Asn  Gln Glu Asp Val Glu  Ala Ala Arg Arg Tyr  Val Gln Phe
    1610                 1615                 1620

Met Gly  Gly Trp Phe Ala His  Pro Ile Phe Lys Asn  Gly Asp Tyr
    1625                 1630                 1635

Asn Glu  Val Met Lys Thr Arg  Ile Arg Asp Arg Ser  Leu Ala Ala
    1640                 1645                 1650

Gly Leu  Asn Lys Ser Arg Leu  Pro Glu Phe Thr Glu  Ser Glu Lys
    1655                 1660                 1665

Arg Arg  Ile Asn Gly Thr Tyr  Asp Phe Phe Gly Phe  Asn His Tyr
    1670                 1675                 1680

Thr Thr  Val Leu Ala Tyr Asn  Leu Asn Tyr Ala Thr  Ala Ile Ser
    1685                 1690                 1695

Ser Phe  Asp Ala Asp Arg Gly  Val Ala Ser Ile Ala  Asp Arg Ser
    1700                 1705                 1710

Trp Pro  Asp Ser Gly Ser Phe  Trp Leu Lys Met Thr  Pro Phe Gly
    1715                 1720                 1725

Phe Arg  Arg Ile Leu Asn Trp  Leu Lys Glu Glu Tyr  Asn Asp Pro
    1730                 1735                 1740

Pro Ile  Tyr Val Thr Glu Asn  Gly Val Ser Gln Arg  Glu Glu Thr
    1745                 1750                 1755

Asp Leu  Asn Asp Thr Ala Arg  Ile Tyr Tyr Leu Arg  Thr Tyr Ile
    1760                 1765                 1770

Asn Glu  Ala Leu Lys Ala Val  Gln Asp Lys Val Asp  Leu Arg Gly
    1775                 1780                 1785

Tyr Thr  Val Trp Ser Ala Met  Asp Asn Phe Glu Trp  Ala Thr Gly
    1790                 1795                 1800

Phe Ser  Glu Arg Phe Gly Leu  His Phe Val Asn Tyr  Ser Asp Pro
    1805                 1810                 1815

Ser Leu  Pro Arg Ile Pro Lys  Ala Ser Ala Lys Phe  Tyr Ala Ser
    1820                 1825                 1830

Val Val  Arg Cys Asn Gly Phe  Pro Asp Pro Ala Thr  Gly Pro His
    1835                 1840                 1845

Ala Cys  Leu His Gln Pro Asp  Ala Gly Pro Thr Ile  Ser Pro Val
    1850                 1855                 1860

Arg Gln  Glu Glu Val Gln Phe  Leu Gly Leu Met Leu  Gly Thr Thr
    1865                 1870                 1875

Glu Ala  Gln Thr Ala Leu Tyr  Val Leu Phe Ser Leu  Val Leu Leu
    1880                 1885                 1890

Gly Val  Cys Gly Leu Ala Phe  Leu Ser Tyr Lys Tyr  Cys Lys Arg
    1895                 1900                 1905

Ser Lys  Gln Gly Lys Thr Gln  Arg Ser Gln Gln Glu  Leu Ser Pro
    1910                 1915                 1920

Val Ser  Ser Phe
    1925
```

<210> SEQ ID NO 45
<211> LENGTH: 465

<212> TYPE: PRT
<213> ORGANISM: Homo sapiens

<400> SEQUENCE: 45

```
Met Leu Pro Leu Trp Thr Leu Ser Leu Leu Leu Gly Ala Val Ala Gly
1               5                   10                  15

Lys Glu Val Cys Tyr Glu Arg Leu Gly Cys Phe Ser Asp Asp Ser Pro
            20                  25                  30

Trp Ser Gly Ile Thr Glu Arg Pro Leu His Ile Leu Pro Trp Ser Pro
        35                  40                  45

Lys Asp Val Asn Thr Arg Phe Leu Leu Tyr Thr Asn Glu Asn Pro Asn
    50                  55                  60

Asn Phe Gln Glu Val Ala Ala Asp Ser Ser Ser Ile Ser Gly Ser Asn
65                  70                  75                  80

Phe Lys Thr Asn Arg Lys Thr Arg Phe Ile Ile His Gly Phe Ile Asp
                85                  90                  95

Lys Gly Glu Glu Asn Trp Leu Ala Asn Val Cys Lys Asn Leu Phe Lys
            100                 105                 110

Val Glu Ser Val Asn Cys Ile Cys Val Asp Trp Lys Gly Gly Ser Arg
        115                 120                 125

Thr Gly Tyr Thr Gln Ala Ser Gln Asn Ile Arg Ile Val Gly Ala Glu
    130                 135                 140

Val Ala Tyr Phe Val Glu Phe Leu Gln Ser Ala Phe Gly Tyr Ser Pro
145                 150                 155                 160

Ser Asn Val His Val Ile Gly His Ser Leu Gly Ala His Ala Ala Gly
                165                 170                 175

Glu Ala Gly Arg Arg Thr Asn Gly Thr Ile Gly Arg Ile Thr Gly Leu
            180                 185                 190

Asp Pro Ala Glu Pro Cys Phe Gln Gly Thr Pro Glu Leu Val Arg Leu
        195                 200                 205

Asp Pro Ser Asp Ala Lys Phe Val Asp Val Ile His Thr Asp Gly Ala
    210                 215                 220

Pro Ile Val Pro Asn Leu Gly Phe Gly Met Ser Gln Val Val Gly His
225                 230                 235                 240

Leu Asp Phe Phe Pro Asn Gly Gly Val Glu Met Pro Gly Cys Lys Lys
                245                 250                 255

Asn Ile Leu Ser Gln Ile Val Asp Ile Asp Gly Ile Trp Glu Gly Thr
            260                 265                 270

Arg Asp Phe Ala Ala Cys Asn His Leu Arg Ser Tyr Lys Tyr Tyr Thr
        275                 280                 285

Asp Ser Ile Val Asn Pro Asp Gly Phe Ala Gly Phe Pro Cys Ala Ser
    290                 295                 300

Tyr Asn Val Phe Thr Ala Asn Lys Cys Phe Pro Cys Pro Ser Gly Gly
305                 310                 315                 320

Cys Pro Gln Met Gly His Tyr Ala Asp Arg Tyr Pro Gly Lys Thr Asn
                325                 330                 335

Asp Val Gly Gln Lys Phe Tyr Leu Asp Thr Gly Asp Ala Ser Asn Phe
            340                 345                 350

Ala Arg Trp Arg Tyr Lys Val Ser Val Thr Leu Ser Gly Lys Lys Val
        355                 360                 365

Thr Gly His Ile Leu Val Ser Leu Phe Gly Asn Lys Gly Asn Ser Lys
    370                 375                 380

Gln Tyr Glu Ile Phe Lys Gly Thr Leu Lys Pro Asp Ser Thr His Ser
385                 390                 395                 400
```

```
Asn Glu Phe Asp Ser Asp Val Asp Val Gly Asp Leu Gln Met Val Lys
                405                 410                 415

Phe Ile Trp Tyr Asn Asn Val Ile Asn Pro Thr Leu Pro Arg Val Gly
            420                 425                 430

Ala Ser Lys Ile Ile Val Glu Thr Asn Val Gly Lys Gln Phe Asn Phe
        435                 440                 445

Cys Ser Pro Glu Thr Val Arg Glu Glu Val Leu Leu Thr Leu Thr Pro
    450                 455                 460

Cys
465


<210> SEQ ID NO 46
<211> LENGTH: 824
<212> TYPE: PRT
<213> ORGANISM: Homo sapiens

<400> SEQUENCE: 46

Met Ser Ile Ser Ser Leu Phe Gly Gly Arg Tyr Asp Asn Lys Phe Leu
1               5                   10                  15

Leu Asn Met Ser Ser Ala Pro Lys Ile Glu Leu Ile Val Asp Lys Val
            20                  25                  30

Ala Ser Leu Ser Glu Gly Arg Leu Glu Gly Arg Leu Pro Glu Asp Trp
        35                  40                  45

Phe Arg His Ile Met Asp Pro Glu Thr Glu Phe Asn Ser Glu Phe Ala
    50                  55                  60

Asp Ala Leu Cys Ile Gly Ile Asp Glu Phe Ala Gln Pro Leu Pro Phe
65                  70                  75                  80

Leu Pro Phe Lys Ala Leu Leu Val Thr Gly Thr Ala Gly Ala Gly Lys
                85                  90                  95

Thr Asn Ser Ile Gln Thr Leu Ala Ala Asn Leu Asp Cys Ile Val Thr
            100                 105                 110

Ala Thr Thr Ser Ile Ala Ala Gln Asn Leu Ser Val Val Leu Asn Arg
        115                 120                 125

Ser Lys Ser Ala Gln Val Lys Thr Ile Phe Lys Thr Phe Gly Phe Asn
    130                 135                 140

Ser Ser His Val Ser Met Ser Glu Arg Gln Ser Tyr Ile Ala Asn Asp
145                 150                 155                 160

Glu Arg Ser Ile Gln Ile Gln Gln Lys Gln Asp Leu Ser Ile Tyr Trp
                165                 170                 175

Asn Val Ile Ser Asp Ile Ala Asp Arg Ala Leu Gly Ala Val Ala Cys
            180                 185                 190

Lys Thr Lys Glu Leu Pro Asp Leu Cys Glu Ser Ser Val Ile Val Ile
        195                 200                 205

Asp Glu Ala Gly Val Ile Leu Arg His Ile Leu His Thr Val Val Phe
    210                 215                 220

Phe Tyr Trp Phe Tyr Asn Ala Leu Tyr Lys Thr Pro Leu Tyr Glu Asp
225                 230                 235                 240

Gly Ile Val Pro Cys Ile Val Cys Val Gly Ser Pro Thr Gln Ser Asn
                245                 250                 255

Ala Leu Val Thr Ser Phe Asn Pro Leu Thr Gln Asn Lys Asp Val Lys
            260                 265                 270

Arg Gly Ile Asp Val Leu Ser Ala Leu Ile Cys Asp Asp Val Leu Ser
        275                 280                 285

Lys Tyr Cys Glu Val Asp Asn Asn Trp Ile Ile Phe Val Asn Asn Lys
```

```
    290                 295                 300

Arg Cys Ala Asp His Ala Phe Gly Asp Phe Leu Lys His Ile Glu Phe
305                 310                 315                 320

Gly Leu Pro Leu Lys Pro Glu Leu Ile Glu Tyr Val Asp Gln Phe Val
                325                 330                 335

Lys Pro Ala Ser Tyr Ile Arg Asn Pro Met Asn Glu Ile Glu Thr Thr
            340                 345                 350

Arg Leu Phe Leu Ser His Asn Glu Val Lys Asn Tyr Phe Arg Ser Leu
        355                 360                 365

His Glu Gln Val Glu Val Thr Asn Arg Asn Asn Leu Phe Val Phe Pro
    370                 375                 380

Val Tyr Phe Leu Ile Lys Asn Lys Thr Phe Glu Asp Tyr Lys Ser Glu
385                 390                 395                 400

Ile Gly Asn Phe Ser Leu Glu Ile Glu Pro Trp Phe Lys Ser Asn Ile
                405                 410                 415

His Arg Leu Asn Thr Tyr Ser Gln Phe Ala Asp Gln Asp Leu Ser Lys
            420                 425                 430

Thr Val Gln Leu Glu Glu Ile Val Leu Glu Asp Gly Ser Val Glu Glu
        435                 440                 445

Thr Leu Ile Thr Cys His Leu Lys His Ile Arg Asn Ser Ser Ile Gly
    450                 455                 460

Val Thr Ser Lys Ile Lys Ala Ser Thr Val Gly Phe Ser Gly Thr Tyr
465                 470                 475                 480

Glu Lys Phe Val Glu Leu Leu Gln Ser Asp Leu Phe Ile Glu Lys Thr
                485                 490                 495

Ser Cys Asp Gln Thr Ile His Ala Tyr Ser Phe Leu Ser Gly Leu Met
            500                 505                 510

Phe Gly Gly Met Tyr Ser Phe Cys Cys Ser Lys Phe Thr Thr Pro Glu
        515                 520                 525

Val Leu Met Glu Ile Lys Asn Ile Lys Met Pro Ser Ile Glu Phe Leu
    530                 535                 540

Glu Ser Glu Met Ser Arg Met Ser Pro Asp Val Gln Thr Val Glu Thr
545                 550                 555                 560

Asp Glu Arg Tyr Asp Phe Gly Leu Val Asp Asp Gly Leu Ser Asp Val
                565                 570                 575

Asp Leu Leu Glu Ile Asp Pro Cys Gly Asp Pro Phe Phe Thr Arg Tyr
            580                 585                 590

Ser Lys Leu Pro Leu Thr Asn Ser Leu Ser Phe Glu Glu Ile Ser Leu
        595                 600                 605

Leu Tyr Thr Thr Phe Lys Asp Ile Phe Ile Ser Arg Phe Ala Ile Leu
    610                 615                 620

Gln Lys His Thr Lys Gly Lys Phe Gly Lys Thr Leu Leu Val Thr Tyr
625                 630                 635                 640

Asn Arg Asn Asn Val Ser Arg Lys Gln Cys Gly Glu Ile Tyr Ser His
                645                 650                 655

Leu Lys Ser Phe Tyr Gly Met Leu Thr Tyr Ala Ile Pro Ala Asn Asn
            660                 665                 670

Tyr Thr Leu Glu Gly Tyr Thr Asn Asp Asn Val Val His Leu Gly Thr
        675                 680                 685

Asp Lys Gln Leu Pro Gln Ile Leu Tyr Lys Lys Gly Leu Pro Arg Leu
    690                 695                 700

Val Ile Lys Asp Glu Met Gly Phe Ile Ser Val Leu Asp Asn Asn Val
705                 710                 715                 720
```

```
Ser Lys Phe Ile Asp Val Val Asn Gly Gln Ser Phe His Leu Cys Thr
                725                 730                 735

Thr Val Asp Tyr Ala Thr Val Ser Lys Val Ser Met Thr Ile Thr Lys
            740                 745                 750

Ser Gln Gly Leu Ser Ile Gln Lys Val Ala Ile Asp Phe Gly Ser Asp
        755                 760                 765

Pro Lys Asn Leu Lys Leu Ser Ser Ile Tyr Val Gly Met Ser Arg Val
    770                 775                 780

Thr Asp Pro Asn Asn Leu Ile Met Asn Val Asn Pro Leu Arg Leu Asn
785                 790                 795                 800

Tyr Glu Asn Asp Asn Phe Ile Ala Pro His Ile Val Lys Ala Leu Lys
                805                 810                 815

Asn Glu Asn Thr Met Leu Ile Phe
            820


<210> SEQ ID NO 47
<211> LENGTH: 511
<212> TYPE: PRT
<213> ORGANISM: Homo sapiens

<400> SEQUENCE: 47

Met Lys Phe Phe Leu Leu Leu Phe Thr Ile Gly Phe Cys Trp Ala Gln
1               5                   10                  15

Tyr Ser Pro Asn Thr Gln Gln Gly Arg Thr Ser Ile Val His Leu Phe
            20                  25                  30

Glu Trp Arg Trp Val Asp Ile Ala Leu Glu Cys Glu Arg Tyr Leu Ala
        35                  40                  45

Pro Lys Gly Phe Gly Gly Val Gln Val Ser Pro Pro Asn Glu Asn Val
    50                  55                  60

Ala Ile Tyr Asn Pro Phe Arg Pro Trp Trp Glu Arg Tyr Gln Pro Val
65                  70                  75                  80

Ser Tyr Lys Leu Cys Thr Arg Ser Gly Asn Glu Asp Glu Phe Arg Asn
                85                  90                  95

Met Val Thr Arg Cys Asn Asn Val Gly Val Arg Ile Tyr Val Asp Ala
            100                 105                 110

Val Ile Asn His Met Cys Gly Asn Ala Val Ser Ala Gly Thr Ser Ser
        115                 120                 125

Thr Cys Gly Ser Tyr Phe Asn Pro Gly Ser Arg Asp Phe Pro Ala Val
    130                 135                 140

Pro Tyr Ser Gly Trp Asp Phe Asn Asp Gly Lys Cys Lys Thr Gly Ser
145                 150                 155                 160

Gly Asp Ile Glu Asn Tyr Asn Asp Ala Thr Gln Val Arg Asp Cys Arg
                165                 170                 175

Leu Thr Gly Leu Leu Asp Leu Ala Leu Glu Lys Asp Tyr Val Arg Ser
            180                 185                 190

Lys Ile Ala Glu Tyr Met Asn His Leu Ile Asp Ile Gly Val Ala Gly
        195                 200                 205

Phe Arg Leu Asp Ala Ser Lys His Met Trp Pro Gly Asp Ile Lys Ala
    210                 215                 220

Ile Leu Asp Lys Leu His Asn Leu Asn Ser Asn Trp Phe Pro Ala Gly
225                 230                 235                 240

Ser Lys Pro Phe Ile Tyr Gln Glu Val Ile Asp Leu Gly Gly Glu Pro
                245                 250                 255

Ile Lys Ser Ser Asp Tyr Phe Gly Asn Gly Arg Val Thr Glu Phe Lys
```

```
            260                 265                 270

Tyr Gly Ala Lys Leu Gly Thr Val Ile Arg Lys Trp Asn Gly Glu Lys
        275                 280                 285

Met Ser Tyr Leu Lys Asn Trp Gly Glu Gly Trp Gly Phe Val Pro Ser
    290                 295                 300

Asp Arg Ala Leu Val Phe Val Asp Asn His Asp Asn Gln Arg Gly His
305                 310                 315                 320

Gly Ala Gly Gly Ala Ser Ile Leu Thr Phe Trp Asp Ala Arg Leu Tyr
                325                 330                 335

Lys Met Ala Val Gly Phe Met Leu Ala His Pro Tyr Gly Phe Thr Arg
            340                 345                 350

Val Met Ser Ser Tyr Arg Trp Pro Arg Gln Phe Gln Asn Gly Asn Asp
        355                 360                 365

Val Asn Asp Trp Val Gly Pro Pro Asn Asn Asn Gly Val Ile Lys Glu
    370                 375                 380

Val Thr Ile Asn Pro Asp Thr Thr Cys Gly Asn Asp Trp Val Cys Glu
385                 390                 395                 400

His Arg Trp Arg Gln Ile Arg Asn Met Val Ile Phe Arg Asn Val Val
                405                 410                 415

Asp Gly Gln Pro Phe Thr Asn Trp Tyr Asp Asn Gly Ser Asn Gln Val
            420                 425                 430

Ala Phe Gly Arg Gly Asn Arg Gly Phe Ile Val Phe Asn Asn Asp Asp
        435                 440                 445

Trp Ser Phe Ser Leu Thr Leu Gln Thr Gly Leu Pro Ala Gly Thr Tyr
    450                 455                 460

Cys Asp Val Ile Ser Gly Asp Lys Ile Asn Gly Asn Cys Thr Gly Ile
465                 470                 475                 480

Lys Ile Tyr Val Ser Asp Asp Gly Lys Ala His Phe Ser Ile Ser Asn
                485                 490                 495

Ser Ala Glu Asp Pro Phe Ile Ala Ile His Ala Glu Ser Lys Leu
            500                 505                 510


<210> SEQ ID NO 48
<211> LENGTH: 952
<212> TYPE: PRT
<213> ORGANISM: Homo sapiens

<400> SEQUENCE: 48

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125
```

-continued

```
Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
    370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Leu Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
    530                 535                 540

Pro Gly Val Val Gly Gly Thr Leu Gln Ala Ala Thr Ile Cys Ala Ser
```

```
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
        675                 680                 685

Glu Pro Ala Gln Gln Ala Met Arg Lys Ala Leu Thr Leu Arg Tyr Ala
    690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Ile Glu Ala Leu Gly
    770                 775                 780

Ser Leu Pro Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950
```

<210> SEQ ID NO 49

```
<211> LENGTH: 785
<212> TYPE: PRT
<213> ORGANISM: Homo sapiens

<400> SEQUENCE: 49

Met Ser Asp Gln Asp His Ser Met Asp Glu Met Thr Ala Val Val Lys
1               5                   10                  15

Ile Glu Lys Gly Val Gly Gly Asn Asn Gly Gly Asn Gly Asn Gly Gly
            20                  25                  30

Gly Ala Phe Ser Gln Ala Arg Ser Ser Ser Thr Gly Ser Ser Ser Ser
        35                  40                  45

Thr Gly Gly Gly Gly Gln Glu Ser Gln Pro Ser Pro Leu Ala Leu Leu
    50                  55                  60

Ala Ala Thr Cys Ser Arg Ile Glu Ser Pro Asn Glu Asn Ser Asn Asn
65                  70                  75                  80

Ser Gln Gly Pro Ser Gln Ser Gly Gly Thr Gly Glu Leu Asp Leu Thr
                85                  90                  95

Ala Thr Gln Leu Ser Gln Gly Ala Asn Gly Trp Gln Ile Ile Ser Ser
            100                 105                 110

Ser Ser Gly Ala Thr Pro Thr Ser Lys Glu Gln Ser Gly Ser Ser Thr
        115                 120                 125

Asn Gly Ser Asn Gly Ser Glu Ser Ser Lys Asn Arg Thr Val Ser Gly
    130                 135                 140

Gly Gln Tyr Val Val Ala Ala Ala Pro Asn Leu Gln Asn Gln Gln Val
145                 150                 155                 160

Leu Thr Gly Leu Pro Gly Val Met Pro Asn Ile Gln Tyr Gln Val Ile
                165                 170                 175

Pro Gln Phe Gln Thr Val Asp Gly Gln Gln Leu Gln Phe Ala Ala Thr
            180                 185                 190

Gly Ala Gln Val Gln Gln Asp Gly Ser Gly Gln Ile Gln Ile Ile Pro
        195                 200                 205

Gly Ala Asn Gln Gln Ile Ile Thr Asn Arg Gly Ser Gly Gly Asn Ile
    210                 215                 220

Ile Ala Ala Met Pro Asn Leu Leu Gln Gln Ala Val Pro Leu Gln Gly
225                 230                 235                 240

Leu Ala Asn Asn Val Leu Ser Gly Gln Thr Gln Tyr Val Thr Asn Val
                245                 250                 255

Pro Val Ala Leu Asn Gly Asn Ile Thr Leu Leu Pro Val Asn Ser Val
            260                 265                 270

Ser Ala Ala Thr Leu Thr Pro Ser Ser Gln Ala Val Thr Ile Ser Ser
        275                 280                 285

Ser Gly Ser Gln Glu Ser Gly Ser Gln Pro Val Thr Ser Gly Thr Thr
    290                 295                 300

Ile Ser Ser Ala Ser Leu Val Ser Ser Gln Ala Ser Ser Ser Ser Phe
305                 310                 315                 320

Phe Thr Asn Ala Asn Ser Tyr Ser Thr Thr Thr Thr Thr Ser Asn Met
                325                 330                 335

Gly Ile Met Asn Phe Thr Thr Ser Gly Ser Ser Gly Thr Asn Ser Gln
            340                 345                 350

Gly Gln Thr Pro Gln Arg Val Ser Gly Leu Gln Gly Ser Asp Ala Leu
        355                 360                 365

Asn Ile Gln Gln Asn Gln Thr Ser Gly Gly Ser Leu Gln Ala Gly Gln
    370                 375                 380

Gln Lys Glu Gly Glu Gln Asn Gln Gln Thr Gln Gln Gln Gln Ile Leu
```

```
385                 390                 395                 400

Ile Gln Pro Gln Leu Val Gln Gly Gly Gln Ala Leu Gln Ala Leu Gln
                405                 410                 415

Ala Ala Pro Leu Ser Gly Gln Thr Phe Thr Thr Gln Ala Ile Ser Gln
            420                 425                 430

Glu Thr Leu Gln Asn Leu Gln Leu Gln Ala Val Pro Asn Ser Gly Pro
        435                 440                 445

Ile Ile Ile Arg Thr Pro Thr Val Gly Pro Asn Gly Gln Val Ser Trp
    450                 455                 460

Gln Thr Leu Gln Leu Gln Asn Leu Gln Val Gln Asn Pro Gln Ala Gln
465                 470                 475                 480

Thr Ile Thr Leu Ala Pro Met Gln Gly Val Ser Leu Gly Gln Thr Ser
                485                 490                 495

Ser Ser Asn Thr Thr Leu Thr Pro Ile Ala Ser Ala Ala Ser Ile Pro
            500                 505                 510

Ala Gly Thr Val Thr Val Asn Ala Ala Gln Leu Ser Ser Met Pro Gly
        515                 520                 525

Leu Gln Thr Ile Asn Leu Ser Ala Leu Gly Thr Ser Gly Ile Gln Val
    530                 535                 540

His Pro Ile Gln Gly Leu Pro Leu Ala Ile Ala Asn Ala Pro Gly Asp
545                 550                 555                 560

His Gly Ala Gln Leu Gly Leu His Gly Ala Gly Gly Asp Gly Ile His
                565                 570                 575

Asp Asp Thr Ala Gly Gly Glu Glu Gly Glu Asn Ser Pro Asp Ala Gln
            580                 585                 590

Pro Gln Ala Gly Arg Arg Thr Arg Arg Glu Ala Cys Thr Cys Pro Tyr
        595                 600                 605

Cys Lys Asp Ser Glu Gly Arg Gly Ser Gly Asp Pro Gly Lys Lys Lys
    610                 615                 620

Gln His Ile Cys His Ile Gln Gly Cys Gly Lys Val Tyr Gly Lys Thr
625                 630                 635                 640

Ser His Leu Arg Ala His Leu Arg Trp His Thr Gly Glu Arg Pro Phe
                645                 650                 655

Met Cys Thr Trp Ser Tyr Cys Gly Lys Arg Phe Thr Arg Ser Asp Glu
            660                 665                 670

Leu Gln Arg His Lys Arg Thr His Thr Gly Glu Lys Lys Phe Ala Cys
        675                 680                 685

Pro Glu Cys Pro Lys Arg Phe Met Arg Ser Asp His Leu Ser Lys His
    690                 695                 700

Ile Lys Thr His Gln Asn Lys Lys Gly Gly Pro Gly Val Ala Leu Ser
705                 710                 715                 720

Val Gly Thr Leu Pro Leu Asp Ser Gly Ala Gly Ser Glu Gly Ser Gly
                725                 730                 735

Thr Ala Thr Pro Ser Ala Leu Ile Thr Thr Asn Met Val Ala Met Glu
            740                 745                 750

Ala Ile Cys Pro Glu Gly Ile Ala Arg Leu Ala Asn Ser Gly Ile Asn
        755                 760                 765

Val Met Gln Val Ala Asp Leu Gln Ser Ile Asn Ile Ser Gly Asn Gly
    770                 775                 780

Phe
785
```

<210> SEQ ID NO 50

<211> LENGTH: 331
<212> TYPE: PRT
<213> ORGANISM: Homo sapiens

<400> SEQUENCE: 50

Met Thr Ala Lys Met Glu Thr Thr Phe Tyr Asp Asp Ala Leu Asn Ala
1 5 10 15

Ser Phe Leu Pro Ser Glu Ser Gly Pro Tyr Gly Tyr Ser Asn Pro Lys
20 25 30

Ile Leu Lys Gln Ser Met Thr Leu Asn Leu Ala Asp Pro Val Gly Ser
35 40 45

Leu Lys Pro His Leu Arg Ala Lys Asn Ser Asp Leu Leu Thr Ser Pro
50 55 60

Asp Val Gly Leu Leu Lys Leu Ala Ser Pro Glu Leu Glu Arg Leu Ile
65 70 75 80

Ile Gln Ser Ser Asn Gly His Ile Thr Thr Thr Pro Thr Pro Thr Gln
85 90 95

Phe Leu Cys Pro Lys Asn Val Thr Asp Glu Gln Glu Gly Phe Ala Glu
100 105 110

Gly Phe Val Arg Ala Leu Ala Glu Leu His Ser Gln Asn Thr Leu Pro
115 120 125

Ser Val Thr Ser Ala Ala Gln Pro Val Asn Gly Ala Gly Met Val Ala
130 135 140

Pro Ala Val Ala Ser Val Ala Gly Gly Ser Gly Ser Gly Gly Phe Ser
145 150 155 160

Ala Ser Leu His Ser Glu Pro Pro Val Tyr Ala Asn Leu Ser Asn Phe
165 170 175

Asn Pro Gly Ala Leu Ser Ser Gly Gly Gly Ala Pro Ser Tyr Gly Ala
180 185 190

Ala Gly Leu Ala Phe Pro Ala Gln Pro Gln Gln Gln Gln Gln Pro Pro
195 200 205

His His Leu Pro Gln Gln Met Pro Val Gln His Pro Arg Leu Gln Ala
210 215 220

Leu Lys Glu Glu Pro Gln Thr Val Pro Glu Met Pro Gly Glu Thr Pro
225 230 235 240

Pro Leu Ser Pro Ile Asp Met Glu Ser Gln Glu Arg Ile Lys Ala Glu
245 250 255

Arg Lys Arg Met Arg Asn Arg Ile Ala Ala Ser Lys Cys Arg Lys Arg
260 265 270

Lys Leu Glu Arg Ile Ala Arg Leu Glu Glu Lys Val Lys Thr Leu Lys
275 280 285

Ala Gln Asn Ser Glu Leu Ala Ser Thr Ala Asn Met Leu Arg Glu Gln
290 295 300

Val Ala Gln Leu Lys Gln Lys Val Met Asn His Val Asn Ser Gly Cys
305 310 315 320

Gln Leu Met Leu Thr Gln Gln Leu Gln Thr Phe
325 330

<210> SEQ ID NO 51
<211> LENGTH: 529
<212> TYPE: PRT
<213> ORGANISM: Homo sapiens

<400> SEQUENCE: 51

Met Asp Leu Pro Val Gly Pro Gly Ala Ala Gly Pro Ser Asn Val Pro
1 5 10 15

```
Ala Phe Leu Thr Lys Leu Trp Thr Leu Val Ser Asp Pro Asp Thr Asp
            20                  25                  30

Ala Leu Ile Cys Trp Ser Pro Ser Gly Asn Ser Phe His Val Phe Asp
        35                  40                  45

Gln Gly Gln Phe Ala Lys Glu Val Leu Pro Lys Tyr Phe Lys His Asn
    50                  55                  60

Asn Met Ala Ser Phe Val Arg Gln Leu Asn Met Tyr Gly Phe Arg Lys
65                  70                  75                  80

Val Val His Ile Glu Gln Gly Gly Leu Val Lys Pro Glu Arg Asp Asp
                85                  90                  95

Thr Glu Phe Gln His Pro Cys Phe Leu Arg Gly Gln Glu Gln Leu Leu
            100                 105                 110

Glu Asn Ile Lys Arg Lys Val Thr Ser Val Ser Thr Leu Lys Ser Glu
        115                 120                 125

Asp Ile Lys Ile Arg Gln Asp Ser Val Thr Lys Leu Leu Thr Asp Val
    130                 135                 140

Gln Leu Met Lys Gly Lys Gln Glu Cys Met Asp Ser Lys Leu Leu Ala
145                 150                 155                 160

Met Lys His Glu Asn Glu Ala Leu Trp Arg Glu Val Ala Ser Leu Arg
                165                 170                 175

Gln Lys His Ala Gln Gln Gln Lys Val Val Asn Lys Leu Ile Gln Phe
            180                 185                 190

Leu Ile Ser Leu Val Gln Ser Asn Arg Ile Leu Gly Val Lys Arg Lys
        195                 200                 205

Ile Pro Leu Met Leu Asn Asp Ser Gly Ser Ala His Ser Met Pro Lys
    210                 215                 220

Tyr Ser Arg Gln Phe Ser Leu Glu His Val His Gly Ser Gly Pro Tyr
225                 230                 235                 240

Ser Ala Pro Ser Pro Ala Tyr Ser Ser Ser Ser Leu Tyr Ala Pro Asp
                245                 250                 255

Ala Val Ala Ser Ser Gly Pro Ile Ile Ser Asp Ile Thr Glu Leu Ala
            260                 265                 270

Pro Ala Ser Pro Met Ala Ser Pro Gly Gly Ser Ile Asp Glu Arg Pro
        275                 280                 285

Leu Ser Ser Ser Pro Leu Val Arg Val Lys Glu Glu Pro Pro Ser Pro
    290                 295                 300

Pro Gln Ser Pro Arg Val Glu Glu Ala Ser Pro Gly Arg Pro Ser Ser
305                 310                 315                 320

Val Asp Thr Leu Leu Ser Pro Thr Ala Leu Ile Asp Ser Ile Leu Arg
                325                 330                 335

Glu Ser Glu Pro Ala Pro Ala Ser Val Thr Ala Leu Thr Asp Ala Arg
            340                 345                 350

Gly His Thr Asp Thr Glu Gly Arg Pro Pro Ser Pro Pro Pro Thr Ser
        355                 360                 365

Thr Pro Glu Lys Cys Leu Ser Val Ala Cys Leu Asp Lys Asn Glu Leu
    370                 375                 380

Ser Asp His Leu Asp Ala Met Asp Ser Asn Leu Asp Asn Leu Gln Thr
385                 390                 395                 400

Met Leu Ser Ser His Gly Phe Ser Val Asp Thr Ser Ala Leu Leu Asp
                405                 410                 415

Leu Phe Ser Pro Ser Val Thr Val Pro Asp Met Ser Leu Pro Asp Leu
            420                 425                 430
```

```
Asp Ser Ser Leu Ala Ser Ile Gln Glu Leu Leu Ser Pro Gln Glu Pro
        435                 440                 445

Pro Arg Pro Pro Glu Ala Glu Asn Ser Ser Pro Asp Ser Gly Lys Gln
    450                 455                 460

Leu Val His Tyr Thr Ala Gln Pro Leu Phe Leu Leu Asp Pro Gly Ser
465                 470                 475                 480

Val Asp Thr Gly Ser Asn Asp Leu Pro Val Leu Phe Glu Leu Gly Glu
                485                 490                 495

Gly Ser Tyr Phe Ser Glu Gly Asp Gly Phe Ala Glu Asp Pro Thr Ile
            500                 505                 510

Ser Leu Leu Thr Gly Ser Glu Pro Pro Lys Ala Lys Asp Pro Thr Val
        515                 520                 525

Ser


<210> SEQ ID NO 52
<211> LENGTH: 345
<212> TYPE: PRT
<213> ORGANISM: Homo sapiens

<400> SEQUENCE: 52

Met Gln Arg Leu Val Ala Trp Asp Pro Ala Cys Leu Pro Leu Pro Pro
1               5                   10                  15

Pro Pro Pro Ala Phe Lys Ser Met Glu Val Ala Asn Phe Tyr Tyr Glu
            20                  25                  30

Ala Asp Cys Leu Ala Ala Ala Tyr Gly Gly Lys Ala Ala Pro Ala Ala
        35                  40                  45

Pro Pro Ala Ala Arg Pro Gly Pro Arg Pro Pro Ala Gly Glu Leu Gly
    50                  55                  60

Ser Ile Gly Asp His Glu Arg Ala Ile Asp Phe Ser Pro Tyr Leu Glu
65                  70                  75                  80

Pro Leu Gly Ala Pro Gln Ala Pro Ala Pro Ala Thr Ala Thr Asp Thr
                85                  90                  95

Phe Glu Ala Ala Pro Pro Ala Pro Ala Pro Ala Pro Ala Ser Ser Gly
            100                 105                 110

Gln His His Asp Phe Leu Ser Asp Leu Phe Ser Asp Asp Tyr Gly Gly
        115                 120                 125

Lys Asn Cys Lys Lys Pro Ala Glu Tyr Gly Tyr Val Ser Leu Gly Arg
    130                 135                 140

Leu Gly Ala Ala Lys Gly Ala Leu His Pro Gly Cys Phe Ala Pro Leu
145                 150                 155                 160

His Pro Pro Pro Pro Pro Pro Pro Pro Pro Ala Glu Leu Lys Ala Glu
                165                 170                 175

Pro Gly Phe Glu Pro Ala Asp Cys Lys Arg Lys Glu Glu Ala Gly Ala
            180                 185                 190

Pro Gly Gly Gly Ala Gly Met Ala Ala Gly Phe Pro Tyr Ala Leu Arg
        195                 200                 205

Ala Tyr Leu Gly Tyr Gln Ala Val Pro Ser Gly Ser Ser Gly Ser Leu
    210                 215                 220

Ser Thr Ser Ser Ser Ser Ser Pro Pro Gly Thr Pro Ser Pro Ala Asp
225                 230                 235                 240

Ala Lys Ala Pro Pro Thr Ala Cys Tyr Ala Gly Ala Ala Pro Ala Pro
                245                 250                 255

Ser Gln Val Lys Ser Lys Ala Lys Lys Thr Val Asp Lys His Ser Asp
            260                 265                 270
```

```
Glu Tyr Lys Ile Arg Arg Glu Arg Asn Asn Ile Ala Val Arg Lys Ser
        275                 280                 285

Arg Asp Lys Ala Lys Met Arg Asn Leu Glu Thr Gln His Lys Val Leu
    290                 295                 300

Glu Leu Thr Ala Glu Asn Glu Arg Leu Gln Lys Lys Val Glu Gln Leu
305                 310                 315                 320

Ser Arg Glu Leu Ser Thr Leu Arg Asn Leu Phe Lys Gln Leu Pro Glu
                325                 330                 335

Pro Leu Leu Ala Ser Ser Gly His Cys
            340                 345
```

<210> SEQ ID NO 53
<211> LENGTH: 743
<212> TYPE: PRT
<213> ORGANISM: Homo sapiens

<400> SEQUENCE: 53

```
Met Asn Asn Pro Ser Glu Thr Ser Lys Pro Ser Met Glu Ser Gly Asp
1               5                   10                  15

Gly Asn Thr Gly Thr Gln Thr Asn Gly Leu Asp Phe Gln Lys Gln Pro
            20                  25                  30

Val Pro Val Gly Gly Ala Ile Ser Thr Ala Gln Ala Gln Ala Phe Leu
        35                  40                  45

Gly His Leu His Gln Val Gln Leu Ala Gly Thr Ser Leu Gln Ala Ala
    50                  55                  60

Ala Gln Ser Leu Asn Val Gln Ser Lys Ser Asn Glu Glu Ser Gly Asp
65                  70                  75                  80

Ser Gln Gln Pro Ser Gln Pro Ser Gln Gln Pro Ser Val Gln Ala Ala
                85                  90                  95

Ile Pro Gln Thr Gln Leu Met Leu Ala Gly Gly Gln Ile Thr Gly Leu
            100                 105                 110

Thr Leu Thr Pro Ala Gln Gln Gln Leu Leu Leu Gln Gln Ala Gln Ala
        115                 120                 125

Gln Ala Gln Leu Leu Ala Ala Ala Val Gln Gln His Ser Ala Ser Gln
    130                 135                 140

Gln His Ser Ala Ala Gly Ala Thr Ile Ser Ala Ser Ala Ala Thr Pro
145                 150                 155                 160

Met Thr Gln Ile Pro Leu Ser Gln Pro Ile Gln Ile Ala Gln Asp Leu
                165                 170                 175

Gln Gln Leu Gln Gln Leu Gln Gln Gln Asn Leu Asn Leu Gln Gln Phe
            180                 185                 190

Val Leu Val His Pro Thr Thr Asn Leu Gln Pro Ala Gln Phe Ile Ile
        195                 200                 205

Ser Gln Thr Pro Gln Gly Gln Gln Gly Leu Leu Gln Ala Gln Asn Leu
    210                 215                 220

Leu Thr Gln Leu Pro Gln Gln Ser Gln Ala Asn Leu Leu Gln Ser Gln
225                 230                 235                 240

Pro Ser Ile Thr Leu Thr Ser Gln Pro Ala Thr Pro Thr Arg Thr Ile
                245                 250                 255

Ala Ala Thr Pro Ile Gln Thr Leu Pro Gln Ser Gln Ser Thr Pro Lys
            260                 265                 270

Arg Ile Asp Thr Pro Ser Leu Glu Glu Pro Ser Asp Leu Glu Glu Leu
        275                 280                 285

Glu Gln Phe Ala Lys Thr Phe Lys Gln Arg Arg Ile Lys Leu Gly Phe
    290                 295                 300
```

```
Thr Gln Gly Asp Val Gly Leu Ala Met Gly Lys Leu Tyr Gly Asn Asp
305                 310                 315                 320

Phe Ser Gln Thr Thr Ile Ser Arg Phe Glu Ala Leu Asn Leu Ser Phe
                325                 330                 335

Lys Asn Met Cys Lys Leu Lys Pro Leu Leu Glu Lys Trp Leu Asn Asp
            340                 345                 350

Ala Glu Asn Leu Ser Ser Asp Ser Ser Leu Ser Ser Pro Ser Ala Leu
        355                 360                 365

Asn Ser Pro Gly Ile Glu Gly Leu Ser Arg Arg Arg Lys Lys Arg Thr
    370                 375                 380

Ser Ile Glu Thr Asn Ile Arg Val Ala Leu Glu Lys Ser Phe Leu Glu
385                 390                 395                 400

Asn Gln Lys Pro Thr Ser Glu Glu Ile Thr Met Ile Ala Asp Gln Leu
                405                 410                 415

Asn Met Glu Lys Glu Val Ile Arg Val Trp Phe Cys Asn Arg Arg Gln
            420                 425                 430

Lys Glu Lys Arg Ile Asn Pro Pro Ser Ser Gly Gly Thr Ser Ser Ser
        435                 440                 445

Pro Ile Lys Ala Ile Phe Pro Ser Pro Thr Ser Leu Val Ala Thr Thr
    450                 455                 460

Pro Ser Leu Val Thr Ser Ser Ala Ala Thr Thr Leu Thr Val Ser Pro
465                 470                 475                 480

Val Leu Pro Leu Thr Ser Ala Ala Val Thr Asn Leu Ser Val Thr Gly
                485                 490                 495

Thr Ser Asp Thr Thr Ser Asn Asn Thr Ala Thr Val Ile Ser Thr Ala
            500                 505                 510

Pro Pro Ala Ser Ser Ala Val Thr Ser Pro Ser Leu Ser Pro Ser Pro
        515                 520                 525

Ser Ala Ser Ala Ser Thr Ser Glu Ala Ser Ser Ala Ser Glu Thr Ser
    530                 535                 540

Thr Thr Gln Thr Thr Ser Thr Pro Leu Ser Ser Pro Leu Gly Thr Ser
545                 550                 555                 560

Gln Val Met Val Thr Ala Ser Gly Leu Gln Thr Ala Ala Ala Ala Ala
                565                 570                 575

Leu Gln Gly Ala Ala Gln Leu Pro Ala Asn Ala Ser Leu Ala Ala Met
            580                 585                 590

Ala Ala Ala Ala Gly Leu Asn Pro Ser Leu Met Ala Pro Ser Gln Phe
        595                 600                 605

Ala Ala Gly Gly Ala Leu Leu Ser Leu Asn Pro Gly Thr Leu Ser Gly
    610                 615                 620

Ala Leu Ser Pro Ala Leu Met Ser Asn Ser Thr Leu Ala Thr Ile Gln
625                 630                 635                 640

Ala Leu Ala Ser Gly Gly Ser Leu Pro Ile Thr Ser Leu Asp Ala Thr
                645                 650                 655

Gly Asn Leu Val Phe Ala Asn Ala Gly Gly Ala Pro Asn Ile Val Thr
            660                 665                 670

Ala Pro Leu Phe Leu Asn Pro Gln Asn Leu Ser Leu Leu Thr Ser Asn
        675                 680                 685

Pro Val Ser Leu Val Ser Ala Ala Ala Ala Ser Ala Gly Asn Ser Ala
    690                 695                 700

Pro Val Ala Ser Leu His Ala Thr Ser Thr Ser Ala Glu Ser Ile Gln
705                 710                 715                 720
```

```
Asn Ser Leu Phe Thr Val Ala Ser Ala Ser Gly Ala Ala Ser Thr Thr
                725                 730                 735

Thr Thr Ala Ser Lys Ala Gln
            740


<210> SEQ ID NO 54
<211> LENGTH: 507
<212> TYPE: PRT
<213> ORGANISM: Homo sapiens

<400> SEQUENCE: 54

Met Glu Ala Ala Val Ala Ala Pro Arg Pro Arg Leu Leu Leu Leu Val
1               5                   10                  15

Leu Ala Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Gly Pro Phe Ser Val Lys Ser Ser Pro Gly Leu Gly Pro Val
        115                 120                 125

Glu Leu Ala Ala Val Ile Ala Gly Pro Val Cys Phe Val Cys Ile Ser
    130                 135                 140

Leu Met Leu Met Val Tyr Ile Cys His Asn Arg Thr Val Ile His His
145                 150                 155                 160

Arg Val Pro Asn Glu Glu Asp Pro Ser Leu Asp Arg Pro Phe Ile Ser
                165                 170                 175

Glu Gly Thr Thr Leu Lys Asp Leu Ile Tyr Asp Met Thr Thr Ser Gly
            180                 185                 190

Ser Gly Ser Gly Leu Pro Leu Leu Val Gln Arg Thr Ile Ala Arg Thr
        195                 200                 205

Ile Val Leu Gln Glu Ser Ile Gly Lys Gly Arg Phe Gly Glu Val Trp
    210                 215                 220

Arg Gly Lys Trp Arg Gly Glu Glu Val Ala Val Lys Ile Phe Ser Ser
225                 230                 235                 240

Arg Glu Glu Arg Ser Trp Phe Arg Glu Ala Glu Ile Tyr Gln Thr Val
                245                 250                 255

Met Leu Arg His Glu Asn Ile Leu Gly Phe Ile Ala Ala Asp Asn Lys
            260                 265                 270

Asp Asn Gly Thr Trp Thr Gln Leu Trp Leu Val Ser Asp Tyr His Glu
        275                 280                 285

His Gly Ser Leu Phe Asp Tyr Leu Asn Arg Tyr Thr Val Thr Val Glu
    290                 295                 300

Gly Met Ile Lys Leu Ala Leu Ser Thr Ala Ser Gly Leu Ala His Leu
305                 310                 315                 320

His Met Glu Ile Val Gly Thr Gln Gly Lys Pro Ala Ile Ala His Arg
                325                 330                 335

Asp Leu Lys Ser Lys Asn Ile Leu Val Lys Lys Asn Gly Thr Cys Cys
            340                 345                 350
```

Ile Ala Asp Leu Gly Leu Ala Val Arg His Asp Ser Ala Thr Asp Thr
355 360 365

Ile Asp Ile Ala Pro Asn His Arg Val Gly Thr Lys Arg Tyr Met Ala
370 375 380

Pro Glu Val Leu Asp Asp Ser Ile Asn Met Lys His Phe Glu Ser Phe
385 390 395 400

Lys Arg Ala Asp Ile Tyr Ala Met Gly Leu Val Phe Trp Glu Ile Ala
405 410 415

Arg Arg Cys Ser Ile Gly Gly Ile His Glu Asp Tyr Gln Leu Pro Tyr
420 425 430

Tyr Asp Leu Val Pro Ser Asp Pro Ser Val Glu Glu Met Arg Lys Val
435 440 445

Val Cys Glu Gln Lys Leu Arg Pro Asn Ile Pro Asn Arg Trp Gln Ser
450 455 460

Cys Glu Ala Leu Arg Val Met Ala Lys Ile Met Arg Glu Cys Trp Tyr
465 470 475 480

Ala Asn Gly Ala Ala Arg Leu Thr Ala Leu Arg Ile Lys Lys Thr Leu
485 490 495

Ser Gln Leu Ser Gln Gln Glu Gly Ile Lys Met
500 505

<210> SEQ ID NO 55
<211> LENGTH: 1106
<212> TYPE: PRT
<213> ORGANISM: Homo sapiens

<400> SEQUENCE: 55

Met Arg Leu Pro Gly Ala Met Pro Ala Leu Ala Leu Lys Gly Glu Leu
1 5 10 15

Leu Leu Leu Ser Leu Leu Leu Leu Leu Glu Pro Gln Ile Ser Gln Gly
20 25 30

Leu Val Val Thr Pro Pro Gly Pro Glu Leu Val Leu Asn Val Ser Ser
35 40 45

Thr Phe Val Leu Thr Cys Ser Gly Ser Ala Pro Val Val Trp Glu Arg
50 55 60

Met Ser Gln Glu Pro Pro Gln Glu Met Ala Lys Ala Gln Asp Gly Thr
65 70 75 80

Phe Ser Ser Val Leu Thr Leu Thr Asn Leu Thr Gly Leu Asp Thr Gly
85 90 95

Glu Tyr Phe Cys Thr His Asn Asp Ser Arg Gly Leu Glu Thr Asp Glu
100 105 110

Arg Lys Arg Leu Tyr Ile Phe Val Pro Asp Pro Thr Val Gly Phe Leu
115 120 125

Pro Asn Asp Ala Glu Glu Leu Phe Ile Phe Leu Thr Glu Ile Thr Glu
130 135 140

Ile Thr Ile Pro Cys Arg Val Thr Asp Pro Gln Leu Val Val Thr Leu
145 150 155 160

His Glu Lys Lys Gly Asp Val Ala Leu Pro Val Pro Tyr Asp His Gln
165 170 175

Arg Gly Phe Ser Gly Ile Phe Glu Asp Arg Ser Tyr Ile Cys Lys Thr
180 185 190

Thr Ile Gly Asp Arg Glu Val Asp Ser Asp Ala Tyr Tyr Val Tyr Arg
195 200 205

Leu Gln Val Ser Ser Ile Asn Val Ser Val Asn Ala Val Gln Thr Val

```
    210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
        355                 360                 365

Thr Arg Asn Val Ser Glu Thr Arg Tyr Val Ser Glu Leu Thr Leu Val
    370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
        435                 440                 445

Ser Ala Cys Arg Asp Leu Lys Arg Cys Pro Arg Glu Leu Pro Pro Thr
    450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
        515                 520                 525

Pro Phe Lys Val Val Val Ile Ser Ala Ile Leu Ala Leu Val Val Leu
    530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
                565                 570                 575

His Glu Tyr Ile Tyr Val Asp Pro Met Gln Leu Pro Tyr Asp Ser Thr
            580                 585                 590

Trp Glu Leu Pro Arg Asp Gln Leu Val Leu Gly Arg Thr Leu Gly Ser
        595                 600                 605

Gly Ala Phe Gly Gln Val Val Glu Ala Thr Ala His Gly Leu Ser His
    610                 615                 620

Ser Gln Ala Thr Met Lys Val Ala Val Lys Met Leu Lys Ser Thr Ala
625                 630                 635                 640
```

```
Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
        675                 680                 685

Leu Val Asp Tyr Leu His Arg Asn Lys His Thr Phe Leu Gln His His
    690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
        755                 760                 765

Ser Asn Tyr Met Ala Pro Tyr Asp Asn Tyr Val Pro Ser Ala Pro Glu
    770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
                805                 810                 815

Leu Ala Ser Lys Asn Cys Val His Arg Asp Leu Ala Ala Arg Asn Val
            820                 825                 830

Leu Ile Cys Glu Gly Lys Leu Val Lys Ile Cys Asp Phe Gly Leu Ala
        835                 840                 845

Arg Asp Ile Met Arg Asp Ser Asn Tyr Ile Ser Lys Gly Ser Thr Phe
    850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
                885                 890                 895

Phe Thr Leu Gly Gly Thr Pro Tyr Pro Glu Leu Pro Met Asn Glu Gln
            900                 905                 910

Phe Tyr Asn Ala Ile Lys Arg Gly Tyr Arg Met Ala Gln Pro Ala His
        915                 920                 925

Ala Ser Asp Glu Ile Tyr Glu Ile Met Gln Lys Cys Trp Glu Glu Lys
    930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Lys Tyr Gln Gln Val Asp Glu Glu
                965                 970                 975

Phe Leu Arg Ser Asp His Pro Ala Ile Leu Arg Ser Gln Ala Arg Leu
            980                 985                 990

Pro Gly Phe His Gly Leu Arg Ser  Pro Leu Asp Thr Ser  Ser Val Leu
        995                 1000                1005

Tyr Thr  Ala Val Gln Pro Asn  Glu Gly Asp Asn Asp  Tyr Ile Ile
    1010                1015                1020

Pro Leu  Pro Asp Pro Lys Pro  Glu Val Ala Asp Glu  Gly Pro Leu
    1025                1030                1035

Glu Gly  Ser Pro Ser Leu Ala  Ser Ser Thr Leu Asn  Glu Val Asn
    1040                1045                1050
```

```
Thr Ser  Ser Thr Ile Ser Cys  Asp Ser Pro Leu Glu  Pro Gln Asp
    1055                1060                1065

Glu Pro  Glu Pro Glu Pro Gln  Leu Glu Leu Gln Val  Glu Pro Glu
    1070                1075                1080

Pro Glu  Leu Glu Gln Leu Pro  Asp Ser Gly Cys Pro  Ala Pro Arg
    1085                1090                1095

Ala Glu  Ala Glu Asp Ser Phe  Leu
    1100                1105


<210> SEQ ID NO 56
<211> LENGTH: 1210
<212> TYPE: PRT
<213> ORGANISM: Homo sapiens

<400> SEQUENCE: 56

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320
```

```
Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735
```

-continued

```
Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                 1005

Asp Val  Val Asp Ala Asp Glu  Tyr Leu Ile Pro Gln  Gln Gly Phe
    1010                 1015                 1020

Phe Ser  Ser Pro Ser Thr Ser  Arg Thr Pro Leu Leu  Ser Ser Leu
    1025                 1030                 1035

Ser Ala  Thr Ser Asn Asn Ser  Thr Val Ala Cys Ile  Asp Arg Asn
    1040                 1045                 1050

Gly Leu  Gln Ser Cys Pro Ile  Lys Glu Asp Ser Phe  Leu Gln Arg
    1055                 1060                 1065

Tyr Ser  Ser Asp Pro Thr Gly  Ala Leu Thr Glu Asp  Ser Ile Asp
    1070                 1075                 1080

Asp Thr  Phe Leu Pro Val Pro  Glu Tyr Ile Asn Gln  Ser Val Pro
    1085                 1090                 1095

Lys Arg  Pro Ala Gly Ser Val  Gln Asn Pro Val Tyr  His Asn Gln
    1100                 1105                 1110

Pro Leu  Asn Pro Ala Pro Ser  Arg Asp Pro His Tyr  Gln Asp Pro
    1115                 1120                 1125

His Ser  Thr Ala Val Gly Asn  Pro Glu Tyr Leu Asn  Thr Val Gln
    1130                 1135                 1140

Pro Thr  Cys Val Asn Ser Thr  Phe Asp Ser Pro Ala  His Trp Ala
```

```
    1145                1150                1155

Gln Lys  Gly Ser His Gln Ile  Ser Leu Asp Asn Pro  Asp Tyr Gln
    1160                1165                1170

Gln Asp  Phe Phe Pro Lys Glu  Ala Lys Pro Asn Gly  Ile Phe Lys
    1175                1180                1185

Gly Ser  Thr Ala Glu Asn Ala  Glu Tyr Leu Arg Val  Ala Pro Gln
    1190                1195                1200

Ser Ser  Glu Phe Ile Gly Ala
    1205                1210


<210> SEQ ID NO 57
<211> LENGTH: 1338
<212> TYPE: PRT
<213> ORGANISM: Homo sapiens

<400> SEQUENCE: 57

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300
```

-continued

```
Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Ser Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
    690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
```

```
                725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
        755                 760                 765

Ala Thr Leu Phe Trp Leu Leu Leu Thr Leu Phe Ile Arg Lys Met Lys
    770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
        835                 840                 845

Ile Lys Lys Ser Pro Thr Cys Arg Thr Val Ala Val Lys Met Leu Lys
    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
        915                 920                 925

Phe Leu Asn Lys Asp Ala Ala Leu His Met Glu Pro Lys Lys Glu Lys
    930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Glu Asp Ser Asp Gly Phe Tyr Lys Glu
            980                 985                 990

Pro Ile Thr Met Glu Asp Leu Ile  Ser Tyr Ser Phe Gln  Val Ala Arg
        995                 1000                1005

Gly Met  Glu Phe Leu Ser Ser  Arg Lys Cys Ile His  Arg Asp Leu
    1010                 1015                 1020

Ala Ala  Arg Asn Ile Leu Leu  Ser Glu Asn Asn Val  Val Lys Ile
    1025                 1030                 1035

Cys Asp  Phe Gly Leu Ala Arg  Asp Ile Tyr Lys Asn  Pro Asp Tyr
    1040                 1045                 1050

Val Arg  Lys Gly Asp Thr Arg  Leu Pro Leu Lys Trp  Met Ala Pro
    1055                 1060                 1065

Glu Ser  Ile Phe Asp Lys Ile  Tyr Ser Thr Lys Ser  Asp Val Trp
    1070                 1075                 1080

Ser Tyr  Gly Val Leu Leu Trp  Glu Ile Phe Ser Leu  Gly Gly Ser
    1085                 1090                 1095

Pro Tyr  Pro Gly Val Gln Met  Asp Glu Asp Phe Cys  Ser Arg Leu
    1100                 1105                 1110

Arg Glu  Gly Met Arg Met Arg  Ala Pro Glu Tyr Ser  Thr Pro Glu
    1115                 1120                 1125

Ile Tyr  Gln Ile Met Leu Asp  Cys Trp His Arg Asp  Pro Lys Glu
    1130                 1135                 1140
```

```
Arg Pro  Arg Phe Ala Glu Leu  Val Glu Lys Leu Gly  Asp Leu Leu
    1145                 1150                 1155

Gln Ala  Asn Val Gln Gln Asp  Gly Lys Asp Tyr Ile  Pro Ile Asn
    1160                 1165                 1170

Ala Ile  Leu Thr Gly Asn Ser  Gly Phe Thr Tyr Ser  Thr Pro Ala
    1175                 1180                 1185

Phe Ser  Glu Asp Phe Phe Lys  Glu Ser Ile Ser Ala  Pro Lys Phe
    1190                 1195                 1200

Asn Ser  Gly Ser Ser Asp Asp  Val Arg Tyr Val Asn  Ala Phe Lys
    1205                 1210                 1215

Phe Met  Ser Leu Glu Arg Ile  Lys Thr Phe Glu Glu  Leu Leu Pro
    1220                 1225                 1230

Asn Ala  Thr Ser Met Phe Asp  Asp Tyr Gln Gly Asp  Ser Ser Thr
    1235                 1240                 1245

Leu Leu  Ala Ser Pro Met Leu  Lys Arg Phe Thr Trp  Thr Asp Ser
    1250                 1255                 1260

Lys Pro  Lys Ala Ser Leu Lys  Ile Asp Leu Arg Val  Thr Ser Lys
    1265                 1270                 1275

Ser Lys  Glu Ser Gly Leu Ser  Asp Val Ser Arg Pro  Ser Phe Cys
    1280                 1285                 1290

His Ser  Ser Cys Gly His Val  Ser Glu Gly Lys Arg  Arg Phe Thr
    1295                 1300                 1305

Tyr Asp  His Ala Glu Leu Glu  Arg Lys Ile Ala Cys  Cys Ser Pro
    1310                 1315                 1320

Pro Pro  Asp Tyr Asn Ser Val  Val Leu Tyr Ser Thr  Pro Pro Ile
    1325                 1330                 1335


<210> SEQ ID NO 58
<211> LENGTH: 350
<212> TYPE: PRT
<213> ORGANISM: Homo sapiens

<400> SEQUENCE: 58

Met Ser Asn Ile Thr Asp Pro Gln Met Trp Asp Phe Asp Asp Leu Asn
1               5                   10                  15

Phe Thr Gly Met Pro Pro Ala Asp Glu Asp Tyr Ser Pro Cys Met Leu
            20                  25                  30

Glu Thr Glu Thr Leu Asn Lys Tyr Val Val Ile Ile Ala Tyr Ala Leu
        35                  40                  45

Val Phe Leu Leu Ser Leu Leu Gly Asn Ser Leu Val Met Leu Val Ile
    50                  55                  60

Leu Tyr Ser Arg Val Gly Arg Ser Val Thr Asp Val Tyr Leu Leu Asn
65                  70                  75                  80

Leu Ala Leu Ala Asp Leu Leu Phe Ala Leu Thr Leu Pro Ile Trp Ala
                85                  90                  95

Ala Ser Lys Val Asn Gly Trp Ile Phe Gly Thr Phe Leu Cys Lys Val
            100                 105                 110

Val Ser Leu Leu Lys Glu Val Asn Phe Tyr Ser Gly Ile Leu Leu Leu
        115                 120                 125

Ala Cys Ile Ser Val Asp Arg Tyr Leu Ala Ile Val His Ala Thr Arg
    130                 135                 140

Thr Leu Thr Gln Lys Arg His Leu Val Lys Phe Val Cys Leu Gly Cys
145                 150                 155                 160

Trp Gly Leu Ser Met Asn Leu Ser Leu Pro Phe Phe Leu Phe Arg Gln
```

```
                165                 170                 175

Ala Tyr His Pro Asn Asn Ser Ser Pro Val Cys Tyr Glu Val Leu Gly
            180                 185                 190

Asn Asp Thr Ala Lys Trp Arg Met Val Leu Arg Ile Leu Pro His Thr
        195                 200                 205

Phe Gly Phe Ile Val Pro Leu Phe Val Met Leu Phe Cys Tyr Gly Phe
    210                 215                 220

Thr Leu Arg Thr Leu Phe Lys Ala His Met Gly Gln Lys His Arg Ala
225                 230                 235                 240

Met Arg Val Ile Phe Ala Val Val Leu Ile Phe Leu Leu Cys Trp Leu
                245                 250                 255

Pro Tyr Asn Leu Val Leu Leu Ala Asp Thr Leu Met Arg Thr Gln Val
            260                 265                 270

Ile Gln Glu Ser Cys Glu Arg Arg Asn Asn Ile Gly Arg Ala Leu Asp
        275                 280                 285

Ala Thr Glu Ile Leu Gly Phe Leu His Ser Cys Leu Asn Pro Ile Ile
    290                 295                 300

Tyr Ala Phe Ile Gly Gln Asn Phe Arg His Gly Phe Leu Lys Ile Leu
305                 310                 315                 320

Ala Met His Gly Leu Val Ser Lys Glu Phe Leu Ala Arg His Arg Val
                325                 330                 335

Thr Ser Tyr Thr Ser Ser Ser Val Asn Val Ser Ser Asn Leu
            340                 345                 350


<210> SEQ ID NO 59
<211> LENGTH: 178
<212> TYPE: PRT
<213> ORGANISM: Homo sapiens

<400> SEQUENCE: 59

Met Ser Gly Gly Lys Tyr Val Asp Ser Glu Gly His Leu Tyr Thr Val
1               5                   10                  15

Pro Ile Arg Glu Gln Gly Asn Ile Tyr Lys Pro Asn Asn Lys Ala Met
            20                  25                  30

Ala Asp Glu Leu Ser Glu Lys Gln Val Tyr Asp Ala His Thr Lys Glu
        35                  40                  45

Ile Asp Leu Val Asn Arg Asp Pro Lys His Leu Asn Asp Asp Val Val
    50                  55                  60

Lys Ile Asp Phe Glu Asp Val Ile Ala Glu Pro Glu Gly Thr His Ser
65                  70                  75                  80

Phe His Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
            100                 105                 110

Leu Ile Trp Gly Ile Tyr Phe Ala Ile Leu Ser Phe Leu His Ile Trp
        115                 120                 125

Ala Val Val Pro Cys Ile Lys Ser Phe Leu Ile Glu Ile Gln Cys Thr
    130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175

Glu Ile
```

<210> SEQ ID NO 60
<211> LENGTH: 866
<212> TYPE: PRT
<213> ORGANISM: Homo sapiens

<400> SEQUENCE: 60

```
Met Gly Asn Arg Gly Met Glu Glu Leu Ile Pro Leu Val Asn Lys Leu
1               5                   10                  15

Gln Asp Ala Phe Ser Ser Ile Gly Gln Ser Cys His Leu Asp Leu Pro
            20                  25                  30

Gln Ile Ala Val Val Gly Gly Gln Ser Ala Gly Lys Ser Ser Val Leu
        35                  40                  45

Glu Asn Phe Val Gly Arg Asp Phe Leu Pro Arg Gly Ser Gly Ile Val
    50                  55                  60

Thr Arg Arg Pro Leu Ile Leu Gln Leu Ile Phe Ser Lys Thr Glu His
65                  70                  75                  80

Ala Glu Phe Leu His Cys Lys Ser Lys Lys Phe Thr Asp Phe Asp Glu
                85                  90                  95

Val Arg Gln Glu Ile Glu Ala Glu Thr Asp Arg Val Thr Gly Thr Asn
            100                 105                 110

Lys Gly Ile Ser Pro Val Pro Ile Asn Leu Arg Val Tyr Ser Pro His
        115                 120                 125

Val Leu Asn Leu Thr Leu Ile Asp Leu Pro Gly Ile Thr Lys Val Pro
    130                 135                 140

Val Gly Asp Gln Pro Pro Asp Ile Glu Tyr Arg Val Lys Asp Met Ile
145                 150                 155                 160

Leu Gln Phe Ile Ser Arg Glu Ser Ser Leu Ile Leu Ala Val Thr Pro
                165                 170                 175

Ala Asn Met Asp Leu Ala Asn Ser Asp Ala Leu Lys Leu Ala Lys Glu
            180                 185                 190

Val Asp Pro Gln Gly Leu Arg Thr Ile Gly Val Ile Thr Lys Leu Asp
        195                 200                 205

Leu Met Asp Glu Gly Thr Asp Ala Arg Asp Val Leu Glu Asn Lys Leu
    210                 215                 220

Leu Pro Leu Arg Arg Gly Tyr Ile Gly Val Val Asn Arg Ser Gln Lys
225                 230                 235                 240

Asp Ile Glu Gly Lys Lys Asp Ile Arg Ala Ala Leu Ala Ala Glu Arg
                245                 250                 255

Lys Phe Phe Leu Ser His Pro Ala Tyr Arg His Met Ala Asp Arg Met
            260                 265                 270

Gly Thr Pro His Leu Gln Lys Thr Leu Asn Gln Gln Leu Thr Asn His
        275                 280                 285

Ile Arg Glu Ser Leu Pro Ala Leu Arg Ser Lys Leu Gln Ser Gln Leu
    290                 295                 300

Leu Ser Leu Glu Lys Glu Val Glu Glu Tyr Lys Ile Phe Arg Pro Asp
305                 310                 315                 320

Asp Pro Thr Pro Lys Thr Lys Ala Leu Leu Gln Met Val Gln Gln Phe
                325                 330                 335

Gly Val Asp Phe Glu Lys Arg Ile Glu Gly Ser Gly Asp Gln Val Asp
            340                 345                 350

Thr Leu Glu Leu Ser Gly Gly Ala Arg Ile Asn Arg Ile Phe His Glu
        355                 360                 365

Arg Phe Pro Phe Glu Leu Val Lys Met Glu Phe Asp Glu Lys Asp Leu
    370                 375                 380
```

```
Arg Arg Glu Ile Ser Tyr Ala Ile Lys Asn Ile His Gly Val Arg Thr
385                 390                 395                 400

Gly Leu Phe Thr Pro Asp Leu Ala Phe Glu Ala Ile Val Lys Lys Gln
                405                 410                 415

Val Val Lys Leu Lys Glu Pro Cys Leu Lys Cys Val Asp Leu Val Ile
            420                 425                 430

Gln Glu Leu Ile Asn Thr Val Arg Gln Cys Thr Ser Lys Leu Ser Ser
        435                 440                 445

Tyr Pro Arg Leu Arg Glu Glu Thr Glu Arg Ile Val Thr Thr Tyr Ile
    450                 455                 460

Arg Glu Arg Glu Gly Arg Thr Lys Asp Gln Ile Leu Leu Leu Ile Asp
465                 470                 475                 480

Ile Glu Gln Ser Tyr Ile Asn Thr Asn His Glu Asp Phe Ile Gly Phe
                485                 490                 495

Ala Asn Ala Gln Gln Arg Ser Thr Gln Leu Asn Lys Lys Arg Ala Ile
            500                 505                 510

Pro Asn Gln Val Ile Arg Arg Gly Trp Leu Thr Ile Asn Asn Ile Ser
        515                 520                 525

Leu Met Lys Gly Gly Ser Lys Glu Tyr Trp Phe Val Leu Thr Ala Glu
    530                 535                 540

Ser Leu Ser Trp Tyr Lys Asp Glu Glu Glu Lys Glu Lys Lys Tyr Met
545                 550                 555                 560

Leu Pro Leu Asp Asn Leu Lys Ile Arg Asp Val Glu Lys Gly Phe Met
                565                 570                 575

Ser Asn Lys His Val Phe Ala Ile Phe Asn Thr Glu Gln Arg Asn Val
            580                 585                 590

Tyr Lys Asp Leu Arg Gln Ile Glu Leu Ala Cys Asp Ser Gln Glu Asp
        595                 600                 605

Val Asp Ser Trp Lys Ala Ser Phe Leu Arg Ala Gly Val Tyr Pro Glu
    610                 615                 620

Lys Asp Gln Ala Glu Asn Glu Asp Gly Ala Gln Glu Asn Thr Phe Ser
625                 630                 635                 640

Met Asp Pro Gln Leu Glu Arg Gln Val Glu Thr Ile Arg Asn Leu Val
                645                 650                 655

Asp Ser Tyr Val Ala Ile Ile Asn Lys Ser Ile Arg Asp Leu Met Pro
            660                 665                 670

Lys Thr Ile Met His Leu Met Ile Asn Asn Thr Lys Ala Phe Ile His
        675                 680                 685

His Glu Leu Leu Ala Tyr Leu Tyr Ser Ser Ala Asp Gln Ser Ser Leu
    690                 695                 700

Met Glu Glu Ser Ala Asp Gln Ala Gln Arg Arg Asp Asp Met Leu Arg
705                 710                 715                 720

Met Tyr His Ala Leu Lys Glu Ala Leu Asn Ile Ile Gly Asp Ile Ser
                725                 730                 735

Thr Ser Thr Val Ser Thr Pro Val Pro Pro Pro Val Asp Asp Thr Trp
            740                 745                 750

Leu Gln Ser Ala Ser Ser His Ser Pro Thr Pro Gln Arg Arg Pro Val
        755                 760                 765

Ser Ser Ile His Pro Pro Gly Arg Pro Pro Ala Val Arg Gly Pro Thr
    770                 775                 780

Pro Gly Pro Pro Leu Ile Pro Val Pro Val Gly Ala Ala Ala Ser Phe
785                 790                 795                 800

Ser Ala Pro Pro Ile Pro Ser Arg Pro Gly Pro Gln Ser Val Phe Ala
```

805 810 815

Asn Ser Asp Leu Phe Pro Ala Pro Pro Gln Ile Pro Ser Arg Pro Val
820 825 830

Arg Ile Pro Pro Gly Ile Pro Pro Gly Val Pro Ser Arg Arg Pro Pro
835 840 845

Ala Ala Pro Ser Arg Pro Thr Ile Ile Arg Pro Ala Glu Pro Ser Leu
850 855 860

Leu Asp
865

<210> SEQ ID NO 61
<211> LENGTH: 1675
<212> TYPE: PRT
<213> ORGANISM: Homo sapiens

<400> SEQUENCE: 61

Met Ala Gln Ile Leu Pro Ile Arg Phe Gln Glu His Leu Gln Leu Gln
1 5 10 15

Asn Leu Gly Ile Asn Pro Ala Asn Ile Gly Phe Ser Thr Leu Thr Met
20 25 30

Glu Ser Asp Lys Phe Ile Cys Ile Arg Glu Lys Val Gly Glu Gln Ala
35 40 45

Gln Val Val Ile Ile Asp Met Asn Asp Pro Ser Asn Pro Ile Arg Arg
50 55 60

Pro Ile Ser Ala Asp Ser Ala Ile Met Asn Pro Ala Ser Lys Val Ile
65 70 75 80

Ala Leu Lys Ala Gly Lys Thr Leu Gln Ile Phe Asn Ile Glu Met Lys
85 90 95

Ser Lys Met Lys Ala His Thr Met Thr Asp Asp Val Thr Phe Trp Lys
100 105 110

Trp Ile Ser Leu Asn Thr Val Ala Leu Val Thr Asp Asn Ala Val Tyr
115 120 125

His Trp Ser Met Glu Gly Glu Ser Gln Pro Val Lys Met Phe Asp Arg
130 135 140

His Ser Ser Leu Ala Gly Cys Gln Ile Ile Asn Tyr Arg Thr Asp Ala
145 150 155 160

Lys Gln Lys Trp Leu Leu Leu Thr Gly Ile Ser Ala Gln Gln Asn Arg
165 170 175

Val Val Gly Ala Met Gln Leu Tyr Ser Val Asp Arg Lys Val Ser Gln
180 185 190

Pro Ile Glu Gly His Ala Ala Ser Phe Ala Gln Phe Lys Met Glu Gly
195 200 205

Asn Ala Glu Glu Ser Thr Leu Phe Cys Phe Ala Val Arg Gly Gln Ala
210 215 220

Gly Gly Lys Leu His Ile Ile Glu Val Gly Thr Pro Pro Thr Gly Asn
225 230 235 240

Gln Pro Phe Pro Lys Lys Ala Val Asp Val Phe Phe Pro Pro Glu Ala
245 250 255

Gln Asn Asp Phe Pro Val Ala Met Gln Ile Ser Glu Lys His Asp Val
260 265 270

Val Phe Leu Ile Thr Lys Tyr Gly Tyr Ile His Leu Tyr Asp Leu Glu
275 280 285

Thr Gly Thr Cys Ile Tyr Met Asn Arg Ile Ser Gly Glu Thr Ile Phe
290 295 300

```
Val Thr Ala Pro His Glu Ala Thr Ala Gly Ile Ile Gly Val Asn Arg
305                 310                 315                 320

Lys Gly Gln Val Leu Ser Val Cys Val Glu Glu Glu Asn Ile Ile Pro
                325                 330                 335

Tyr Ile Thr Asn Val Leu Gln Asn Pro Asp Leu Ala Leu Arg Met Ala
            340                 345                 350

Val Arg Asn Asn Leu Ala Gly Ala Glu Glu Leu Phe Ala Arg Lys Phe
        355                 360                 365

Asn Ala Leu Phe Ala Gln Gly Asn Tyr Ser Glu Ala Ala Lys Val Ala
    370                 375                 380

Ala Asn Ala Pro Lys Gly Ile Leu Arg Thr Pro Asp Thr Ile Arg Arg
385                 390                 395                 400

Phe Gln Ser Val Pro Ala Gln Pro Gly Gln Thr Ser Pro Leu Leu Gln
                405                 410                 415

Tyr Phe Gly Ile Leu Leu Asp Gln Gly Gln Leu Asn Lys Tyr Glu Ser
            420                 425                 430

Leu Glu Leu Cys Arg Pro Val Leu Gln Gln Gly Arg Lys Gln Leu Leu
        435                 440                 445

Glu Lys Trp Leu Lys Glu Asp Lys Leu Glu Cys Ser Glu Glu Leu Gly
    450                 455                 460

Asp Leu Val Lys Ser Val Asp Pro Thr Leu Ala Leu Ser Val Tyr Leu
465                 470                 475                 480

Arg Ala Asn Val Pro Asn Lys Val Ile Gln Cys Phe Ala Glu Thr Gly
                485                 490                 495

Gln Val Gln Lys Ile Val Leu Tyr Ala Lys Lys Val Gly Tyr Thr Pro
            500                 505                 510

Asp Trp Ile Phe Leu Leu Arg Asn Val Met Arg Ile Ser Pro Asp Gln
        515                 520                 525

Gly Gln Gln Phe Ala Gln Met Leu Val Gln Asp Glu Glu Pro Leu Ala
    530                 535                 540

Asp Ile Thr Gln Ile Val Asp Val Phe Met Glu Tyr Asn Leu Ile Gln
545                 550                 555                 560

Gln Cys Thr Ala Phe Leu Leu Asp Ala Leu Lys Asn Asn Arg Pro Ser
                565                 570                 575

Glu Gly Pro Leu Gln Thr Arg Leu Leu Glu Met Asn Leu Met His Ala
            580                 585                 590

Pro Gln Val Ala Asp Ala Ile Leu Gly Asn Gln Met Phe Thr His Tyr
        595                 600                 605

Asp Arg Ala His Ile Ala Gln Leu Cys Glu Lys Ala Gly Leu Leu Gln
    610                 615                 620

Arg Ala Leu Glu His Phe Thr Asp Leu Tyr Asp Ile Lys Arg Ala Val
625                 630                 635                 640

Val His Thr His Leu Leu Asn Pro Glu Trp Leu Val Asn Tyr Phe Gly
                645                 650                 655

Ser Leu Ser Val Glu Asp Ser Leu Glu Cys Leu Arg Ala Met Leu Ser
            660                 665                 670

Ala Asn Ile Arg Gln Asn Leu Gln Ile Cys Val Gln Val Ala Ser Lys
        675                 680                 685

Tyr His Glu Gln Leu Ser Thr Gln Ser Leu Ile Glu Leu Phe Glu Ser
    690                 695                 700

Phe Lys Ser Phe Glu Gly Leu Phe Tyr Phe Leu Gly Ser Ile Val Asn
705                 710                 715                 720

Phe Ser Gln Asp Pro Asp Val His Phe Lys Tyr Ile Gln Ala Ala Cys
```

```
                725                 730                 735

Lys Thr Gly Gln Ile Lys Glu Val Glu Arg Ile Cys Arg Glu Ser Asn
            740                 745                 750

Cys Tyr Asp Pro Glu Arg Val Lys Asn Phe Leu Lys Glu Ala Lys Leu
        755                 760                 765

Thr Asp Gln Leu Pro Leu Ile Ile Val Cys Asp Arg Phe Asp Phe Val
    770                 775                 780

His Asp Leu Val Leu Tyr Leu Tyr Arg Asn Asn Leu Gln Lys Tyr Ile
785                 790                 795                 800

Glu Ile Tyr Val Gln Lys Val Asn Pro Ser Arg Leu Pro Val Val Ile
                805                 810                 815

Gly Gly Leu Leu Asp Val Asp Cys Ser Glu Asp Val Ile Lys Asn Leu
            820                 825                 830

Ile Leu Val Val Arg Gly Gln Phe Ser Thr Asp Glu Leu Val Ala Glu
        835                 840                 845

Val Glu Lys Arg Asn Arg Leu Lys Leu Leu Leu Pro Trp Leu Glu Ala
    850                 855                 860

Arg Ile His Glu Gly Cys Glu Glu Pro Ala Thr His Asn Ala Leu Ala
865                 870                 875                 880

Lys Ile Tyr Ile Asp Ser Asn Asn Asn Pro Glu Arg Phe Leu Arg Glu
                885                 890                 895

Asn Pro Tyr Tyr Asp Ser Arg Val Val Gly Lys Tyr Cys Glu Lys Arg
            900                 905                 910

Asp Pro His Leu Ala Cys Val Ala Tyr Glu Arg Gly Gln Cys Asp Leu
        915                 920                 925

Glu Leu Ile Asn Val Cys Asn Glu Asn Ser Leu Phe Lys Ser Leu Ser
    930                 935                 940

Arg Tyr Leu Val Arg Arg Lys Asp Pro Glu Leu Trp Gly Ser Val Leu
945                 950                 955                 960

Leu Glu Ser Asn Pro Tyr Arg Arg Pro Leu Ile Asp Gln Val Val Gln
                965                 970                 975

Thr Ala Leu Ser Glu Thr Gln Asp Pro Glu Glu Val Ser Val Thr Val
            980                 985                 990

Lys Ala Phe Met Thr Ala Asp Leu  Pro Asn Glu Leu Ile  Glu Leu Leu
        995                 1000                1005

Glu Lys  Ile Val Leu Asp Asn  Ser Val Phe Ser Glu  His Arg Asn
    1010                1015                1020

Leu Gln  Asn Leu Leu Ile Leu  Thr Ala Ile Lys Ala  Asp Arg Thr
    1025                1030                1035

Arg Val  Met Glu Tyr Ile Asn  Arg Leu Asp Asn Tyr  Asp Ala Pro
    1040                1045                1050

Asp Ile  Ala Asn Ile Ala Ile  Ser Asn Glu Leu Phe  Glu Glu Ala
    1055                1060                1065

Phe Ala  Ile Phe Arg Lys Phe  Asp Val Asn Thr Ser  Ala Val Gln
    1070                1075                1080

Val Leu  Ile Glu His Ile Gly  Asn Leu Asp Arg Ala  Tyr Glu Phe
    1085                1090                1095

Ala Glu  Arg Cys Asn Glu Pro  Ala Val Trp Ser Gln  Leu Ala Lys
    1100                1105                1110

Ala Gln  Leu Gln Lys Gly Met  Val Lys Glu Ala Ile  Asp Ser Tyr
    1115                1120                1125

Ile Lys  Ala Asp Asp Pro Ser  Ser Tyr Met Glu Val  Val Gln Ala
    1130                1135                1140
```

```
Ala Asn Thr Ser Gly Asn Trp Glu Glu Leu Val Lys Tyr Leu Gln
    1145                1150                1155

Met Ala Arg Lys Lys Ala Arg Glu Ser Tyr Val Glu Thr Glu Leu
    1160                1165                1170

Ile Phe Ala Leu Ala Lys Thr Asn Arg Leu Ala Glu Leu Glu Glu
    1175                1180                1185

Phe Ile Asn Gly Pro Asn Asn Ala His Ile Gln Gln Val Gly Asp
    1190                1195                1200

Arg Cys Tyr Asp Glu Lys Met Tyr Asp Ala Ala Lys Leu Leu Tyr
    1205                1210                1215

Asn Asn Val Ser Asn Phe Gly Arg Leu Ala Ser Thr Leu Val His
    1220                1225                1230

Leu Gly Glu Tyr Gln Ala Ala Val Asp Gly Ala Arg Lys Ala Asn
    1235                1240                1245

Ser Thr Arg Thr Trp Lys Glu Val Cys Phe Ala Cys Val Asp Gly
    1250                1255                1260

Lys Glu Phe Arg Leu Ala Gln Met Cys Gly Leu His Ile Val Val
    1265                1270                1275

His Ala Asp Glu Leu Glu Glu Leu Ile Asn Tyr Tyr Gln Asp Arg
    1280                1285                1290

Gly Tyr Phe Glu Glu Leu Ile Thr Met Leu Glu Ala Ala Leu Gly
    1295                1300                1305

Leu Glu Arg Ala His Met Gly Met Phe Thr Glu Leu Ala Ile Leu
    1310                1315                1320

Tyr Ser Lys Phe Lys Pro Gln Lys Met Arg Glu His Leu Glu Leu
    1325                1330                1335

Phe Trp Ser Arg Val Asn Ile Pro Lys Val Leu Arg Ala Ala Glu
    1340                1345                1350

Gln Ala His Leu Trp Ala Glu Leu Val Phe Leu Tyr Asp Lys Tyr
    1355                1360                1365

Glu Glu Tyr Asp Asn Ala Ile Ile Thr Met Met Asn His Pro Thr
    1370                1375                1380

Asp Ala Trp Lys Glu Gly Gln Phe Lys Asp Ile Ile Thr Lys Val
    1385                1390                1395

Ala Asn Val Glu Leu Tyr Tyr Arg Ala Ile Gln Phe Tyr Leu Glu
    1400                1405                1410

Phe Lys Pro Leu Leu Leu Asn Asp Leu Leu Met Val Leu Ser Pro
    1415                1420                1425

Arg Leu Asp His Thr Arg Ala Val Asn Tyr Phe Ser Lys Val Lys
    1430                1435                1440

Gln Leu Pro Leu Val Lys Pro Tyr Leu Arg Ser Val Gln Asn His
    1445                1450                1455

Asn Asn Lys Ser Val Asn Glu Ser Leu Asn Asn Leu Phe Ile Thr
    1460                1465                1470

Glu Glu Asp Tyr Gln Ala Leu Arg Thr Ser Ile Asp Ala Tyr Asp
    1475                1480                1485

Asn Phe Asp Asn Ile Ser Leu Ala Gln Arg Leu Glu Lys His Glu
    1490                1495                1500

Leu Ile Glu Phe Arg Arg Ile Ala Ala Tyr Leu Phe Lys Gly Asn
    1505                1510                1515

Asn Arg Trp Lys Gln Ser Val Glu Leu Cys Lys Lys Asp Ser Leu
    1520                1525                1530
```

Tyr Lys Asp Ala Met Gln Tyr Ala Ser Glu Ser Lys Asp Thr Glu
1535 1540 1545

Leu Ala Glu Glu Leu Leu Gln Trp Phe Leu Gln Glu Glu Lys Arg
1550 1555 1560

Glu Cys Phe Gly Ala Cys Leu Phe Thr Cys Tyr Asp Leu Leu Arg
1565 1570 1575

Pro Asp Val Val Leu Glu Thr Ala Trp Arg His Asn Ile Met Asp
1580 1585 1590

Phe Ala Met Pro Tyr Phe Ile Gln Val Met Lys Glu Tyr Leu Thr
1595 1600 1605

Lys Val Asp Lys Leu Asp Ala Ser Glu Ser Leu Arg Lys Glu Glu
1610 1615 1620

Glu Gln Ala Thr Glu Thr Gln Pro Ile Val Tyr Gly Gln Pro Gln
1625 1630 1635

Leu Met Leu Thr Ala Gly Pro Ser Val Ala Val Pro Pro Gln Ala
1640 1645 1650

Pro Phe Gly Tyr Gly Tyr Thr Ala Pro Pro Tyr Gly Gln Pro Gln
1655 1660 1665

Pro Gly Phe Gly Tyr Ser Met
1670 1675

<210> SEQ ID NO 62
<211> LENGTH: 1640
<212> TYPE: PRT
<213> ORGANISM: Homo sapiens

<400> SEQUENCE: 62

Met Ala Gln Ile Leu Pro Val Arg Phe Gln Glu His Phe Gln Leu Gln
1 5 10 15

Asn Leu Gly Ile Asn Pro Ala Asn Ile Gly Phe Ser Thr Leu Thr Met
20 25 30

Glu Ser Asp Lys Phe Ile Cys Ile Arg Glu Lys Val Gly Glu Gln Ala
35 40 45

Gln Val Thr Ile Ile Asp Met Ser Asp Pro Met Ala Pro Ile Arg Arg
50 55 60

Pro Ile Ser Ala Glu Ser Ala Ile Met Asn Pro Ala Ser Lys Val Ile
65 70 75 80

Ala Leu Lys Ala Gly Lys Thr Leu Gln Ile Phe Asn Ile Glu Met Lys
85 90 95

Ser Lys Met Lys Ala His Thr Met Ala Glu Glu Val Ile Phe Trp Lys
100 105 110

Trp Val Ser Val Asn Thr Val Ala Leu Val Thr Glu Thr Ala Val Tyr
115 120 125

His Trp Ser Met Glu Gly Asp Ser Gln Pro Met Lys Met Phe Asp Arg
130 135 140

His Thr Ser Leu Val Gly Cys Gln Val Ile His Tyr Arg Thr Asp Glu
145 150 155 160

Tyr Gln Lys Trp Leu Leu Leu Val Gly Ile Ser Ala Gln Gln Asn Arg
165 170 175

Val Val Gly Ala Met Gln Leu Tyr Ser Val Asp Arg Lys Val Ser Gln
180 185 190

Pro Ile Glu Gly His Ala Ala Ala Phe Ala Glu Phe Lys Met Glu Gly
195 200 205

Asn Ala Lys Pro Ala Thr Leu Phe Cys Phe Ala Val Arg Asn Pro Thr
210 215 220

```
Gly Gly Lys Leu His Ile Ile Glu Val Gly Gln Pro Ala Ala Gly Asn
225                 230                 235                 240

Gln Pro Phe Val Lys Lys Ala Val Asp Val Phe Phe Pro Pro Glu Ala
                245                 250                 255

Gln Asn Asp Phe Pro Val Ala Met Gln Ile Gly Ala Lys His Gly Val
            260                 265                 270

Ile Tyr Leu Ile Thr Lys Tyr Gly Tyr Leu His Leu Tyr Asp Leu Glu
        275                 280                 285

Ser Gly Val Cys Ile Cys Met Asn Arg Ile Ser Ala Asp Thr Ile Phe
    290                 295                 300

Val Thr Ala Pro His Lys Pro Thr Ser Gly Ile Ile Gly Val Asn Lys
305                 310                 315                 320

Lys Gly Gln Val Leu Ser Val Cys Val Glu Glu Asp Asn Ile Val Asn
                325                 330                 335

Tyr Ala Thr Asn Val Leu Gln Asn Pro Asp Leu Gly Leu Arg Leu Ala
            340                 345                 350

Val Arg Ser Asn Leu Ala Gly Ala Glu Lys Leu Phe Val Arg Lys Phe
        355                 360                 365

Asn Thr Leu Phe Ala Gln Gly Ser Tyr Ala Glu Ala Ala Lys Val Ala
    370                 375                 380

Ala Ser Ala Pro Lys Gly Ile Leu Arg Thr Arg Glu Thr Val Gln Lys
385                 390                 395                 400

Phe Gln Ser Ile Pro Ala Gln Ser Gly Gln Ala Ser Pro Leu Leu Gln
                405                 410                 415

Tyr Phe Gly Ile Leu Leu Asp Gln Gly Gln Leu Asn Lys Leu Glu Ser
            420                 425                 430

Leu Glu Leu Cys His Leu Val Leu Gln Gln Gly Arg Lys Gln Leu Leu
        435                 440                 445

Glu Lys Trp Leu Lys Glu Asp Lys Leu Glu Cys Ser Glu Glu Leu Gly
    450                 455                 460

Asp Leu Val Lys Thr Thr Asp Pro Met Leu Ala Leu Ser Val Tyr Leu
465                 470                 475                 480

Arg Ala Asn Val Pro Ser Lys Val Ile Gln Cys Phe Ala Glu Thr Gly
                485                 490                 495

Gln Phe Gln Lys Ile Val Leu Tyr Ala Lys Lys Val Gly Tyr Thr Pro
            500                 505                 510

Asp Trp Ile Phe Leu Leu Arg Gly Val Met Lys Ile Ser Pro Glu Gln
        515                 520                 525

Gly Leu Gln Phe Ser Arg Met Leu Val Gln Asp Glu Glu Pro Leu Ala
    530                 535                 540

Asn Ile Ser Gln Ile Val Asp Ile Phe Met Glu Asn Ser Leu Ile Gln
545                 550                 555                 560

Gln Cys Thr Ser Phe Leu Leu Asp Ala Leu Lys Asn Asn Arg Pro Ala
                565                 570                 575

Glu Gly Leu Leu Gln Thr Trp Leu Leu Glu Met Asn Leu Val His Ala
            580                 585                 590

Pro Gln Val Ala Asp Ala Ile Leu Gly Asn Lys Met Phe Thr His Tyr
        595                 600                 605

Asp Arg Ala His Ile Ala Gln Leu Cys Glu Lys Ala Gly Leu Leu Gln
    610                 615                 620

Gln Ala Leu Glu His Tyr Thr Asp Leu Tyr Asp Ile Lys Arg Ala Val
625                 630                 635                 640
```

```
Val His Thr His Leu Leu Asn Pro Glu Trp Leu Val Asn Phe Phe Gly
                645                 650                 655

Ser Leu Ser Val Glu Asp Ser Val Glu Cys Leu His Ala Met Leu Ser
            660                 665                 670

Ala Asn Ile Arg Gln Asn Leu Gln Leu Cys Val Gln Val Ala Ser Lys
        675                 680                 685

Tyr His Glu Gln Leu Gly Thr Gln Ala Leu Val Glu Leu Phe Glu Ser
    690                 695                 700

Phe Lys Ser Tyr Lys Gly Leu Phe Tyr Phe Leu Gly Ser Ile Val Asn
705                 710                 715                 720

Phe Ser Gln Asp Pro Asp Val His Leu Lys Tyr Ile Gln Ala Ala Cys
                725                 730                 735

Lys Thr Gly Gln Ile Lys Glu Val Glu Arg Ile Cys Arg Glu Ser Ser
            740                 745                 750

Cys Tyr Asn Pro Glu Arg Val Lys Asn Phe Leu Lys Glu Ala Lys Leu
        755                 760                 765

Thr Asp Gln Leu Pro Leu Ile Ile Val Cys Asp Arg Phe Gly Phe Val
    770                 775                 780

His Asp Leu Val Leu Tyr Leu Tyr Arg Asn Asn Leu Gln Arg Tyr Ile
785                 790                 795                 800

Glu Ile Tyr Val Gln Lys Val Asn Pro Ser Arg Thr Pro Ala Val Ile
                805                 810                 815

Gly Gly Leu Leu Asp Val Asp Cys Ser Glu Glu Val Ile Lys His Leu
            820                 825                 830

Ile Met Ala Val Arg Gly Gln Phe Ser Thr Asp Glu Leu Val Ala Glu
        835                 840                 845

Val Glu Lys Arg Asn Arg Leu Lys Leu Leu Leu Pro Trp Leu Glu Ser
    850                 855                 860

Gln Ile Gln Glu Gly Cys Glu Glu Pro Ala Thr His Asn Ala Leu Ala
865                 870                 875                 880

Lys Ile Tyr Ile Asp Ser Asn Asn Ser Pro Glu Cys Phe Leu Arg Glu
                885                 890                 895

Asn Ala Tyr Tyr Asp Ser Ser Val Val Gly Arg Tyr Cys Glu Lys Arg
            900                 905                 910

Asp Pro His Leu Ala Cys Val Ala Tyr Glu Arg Gly Gln Cys Asp Leu
        915                 920                 925

Glu Leu Ile Lys Val Cys Asn Glu Asn Ser Leu Phe Lys Ser Glu Ala
    930                 935                 940

Arg Tyr Leu Val Cys Arg Lys Asp Pro Glu Leu Trp Ala His Val Leu
945                 950                 955                 960

Glu Glu Thr Asn Pro Ser Arg Arg Gln Leu Ile Asp Gln Val Val Gln
                965                 970                 975

Thr Ala Leu Ser Glu Thr Arg Asp Pro Glu Glu Ile Ser Val Thr Val
            980                 985                 990

Lys Ala Phe Met Thr Ala Asp Leu  Pro Asn Glu Leu Ile  Glu Leu Leu
        995                 1000                1005

Glu Lys  Ile Val Leu Asp Asn  Ser Val Phe Ser Glu  His Arg Asn
    1010                1015                1020

Leu Gln  Asn Leu Leu Ile Leu  Thr Ala Ile Lys Ala  Asp Arg Thr
    1025                1030                1035

Arg Val  Met Glu Tyr Ile Ser  Arg Leu Asp Asn Tyr  Asp Ala Leu
    1040                1045                1050

Asp Ile  Ala Ser Ile Ala Val  Ser Ser Ala Leu Tyr  Glu Glu Ala
```

```
    1055                1060                1065

Phe Thr  Val Phe His Lys Phe  Asp Met Asn Ala Ser  Ala Ile Gln
    1070                1075                1080

Val Leu  Ile Glu His Ile Gly  Asn Leu Asp Arg Ala  Tyr Glu Phe
    1085                1090                1095

Ala Glu  Arg Cys Asn Glu Pro  Ala Val Trp Ser Gln  Leu Ala Gln
    1100                1105                1110

Ala Gln  Leu Gln Lys Asp Leu  Val Lys Glu Ala Ile  Asn Ser Tyr
    1115                1120                1125

Ile Arg  Gly Asp Asp Pro Ser  Ser Tyr Leu Glu Val  Val Gln Ser
    1130                1135                1140

Ala Ser  Arg Ser Asn Asn Trp  Glu Asp Leu Val Lys  Phe Leu Gln
    1145                1150                1155

Met Ala  Arg Lys Lys Gly Arg  Glu Ser Tyr Ile Glu  Thr Glu Leu
    1160                1165                1170

Ile Phe  Ala Leu Ala Lys Thr  Ser Arg Val Ser Glu  Leu Glu Asp
    1175                1180                1185

Phe Ile  Asn Gly Pro Asn Asn  Ala His Ile Gln Gln  Val Gly Asp
    1190                1195                1200

Arg Cys  Tyr Glu Glu Gly Met  Tyr Glu Ala Ala Lys  Leu Leu Tyr
    1205                1210                1215

Ser Asn  Val Ser Asn Phe Ala  Arg Leu Ala Ser Thr  Leu Val His
    1220                1225                1230

Leu Gly  Glu Tyr Gln Ala Ala  Val Asp Asn Ser Arg  Lys Ala Ser
    1235                1240                1245

Ser Thr  Arg Thr Trp Lys Glu  Val Cys Phe Ala Cys  Met Asp Gly
    1250                1255                1260

Gln Glu  Phe Arg Phe Ala Gln  Leu Cys Gly Leu His  Ile Val Ile
    1265                1270                1275

His Ala  Asp Glu Leu Glu Glu  Leu Met Cys Tyr Tyr  Gln Asp Arg
    1280                1285                1290

Gly Tyr  Phe Glu Glu Leu Ile  Leu Leu Leu Glu Ala  Ala Leu Gly
    1295                1300                1305

Leu Glu  Arg Ala His Met Gly  Met Phe Thr Glu Leu  Ala Ile Leu
    1310                1315                1320

Tyr Ser  Lys Phe Lys Pro Gln  Lys Met Leu Glu His  Leu Glu Leu
    1325                1330                1335

Phe Trp  Ser Arg Val Asn Ile  Pro Lys Val Leu Arg  Ala Ala Glu
    1340                1345                1350

Gln Ala  His Leu Trp Ala Glu  Leu Val Phe Leu Tyr  Asp Lys Tyr
    1355                1360                1365

Glu Glu  Tyr Asp Asn Ala Val  Leu Thr Met Met Ser  His Pro Thr
    1370                1375                1380

Glu Ala  Trp Lys Glu Gly Gln  Phe Lys Asp Ile Ile  Thr Lys Val
    1385                1390                1395

Ala Asn  Val Glu Leu Cys Tyr  Arg Ala Leu Gln Phe  Tyr Leu Asp
    1400                1405                1410

Tyr Lys  Pro Leu Leu Ile Asn  Asp Leu Leu Leu Val  Leu Ser Pro
    1415                1420                1425

Arg Leu  Asp His Thr Trp Thr  Val Ser Phe Phe Ser  Lys Ala Gly
    1430                1435                1440

Gln Leu  Pro Leu Val Lys Pro  Tyr Leu Arg Ser Val  Gln Ser His
    1445                1450                1455
```

Asn Asn Lys Ser Val Asn Glu Ala Leu Asn His Leu Leu Thr Glu
1460 1465 1470

Glu Glu Asp Tyr Gln Gly Leu Arg Ala Ser Ile Asp Ala Tyr Asp
1475 1480 1485

Asn Phe Asp Asn Ile Ser Leu Ala Gln Gln Leu Glu Lys His Gln
1490 1495 1500

Leu Met Glu Phe Arg Cys Ile Ala Ala Tyr Leu Tyr Lys Gly Asn
1505 1510 1515

Asn Trp Trp Ala Gln Ser Val Glu Leu Cys Lys Lys Asp His Leu
1520 1525 1530

Tyr Lys Asp Ala Met Gln His Ala Ala Glu Ser Arg Asp Ala Glu
1535 1540 1545

Leu Ala Gln Lys Leu Leu Gln Trp Phe Leu Glu Glu Gly Lys Arg
1550 1555 1560

Glu Cys Phe Ala Ala Cys Leu Phe Thr Cys Tyr Asp Leu Leu Arg
1565 1570 1575

Pro Asp Met Val Leu Glu Leu Ala Trp Arg His Asn Leu Val Asp
1580 1585 1590

Leu Ala Met Pro Tyr Phe Ile Gln Val Met Arg Glu Tyr Leu Ser
1595 1600 1605

Lys Val Asp Lys Leu Asp Ala Leu Glu Ser Leu Arg Lys Gln Glu
1610 1615 1620

Glu His Val Thr Glu Pro Ala Pro Leu Val Phe Asp Phe Asp Gly
1625 1630 1635

His Glu
1640

<210> SEQ ID NO 63
<211> LENGTH: 218
<212> TYPE: PRT
<213> ORGANISM: Homo sapiens

<400> SEQUENCE: 63

Met Ala Glu Leu Asp Pro Phe Gly Ala Pro Ala Gly Ala Pro Gly Gly
1 5 10 15

Pro Ala Leu Gly Asn Gly Val Ala Gly Ala Gly Glu Glu Asp Pro Ala
20 25 30

Ala Ala Phe Leu Ala Gln Gln Glu Ser Glu Ile Ala Gly Ile Glu Asn
35 40 45

Asp Glu Ala Phe Ala Ile Leu Asp Gly Gly Ala Pro Gly Pro Gln Pro
50 55 60

His Gly Glu Pro Pro Gly Gly Pro Asp Ala Val Asp Gly Val Met Asn
65 70 75 80

Gly Glu Tyr Tyr Gln Glu Ser Asn Gly Pro Thr Asp Ser Tyr Ala Ala
85 90 95

Ile Ser Gln Val Asp Arg Leu Gln Ser Glu Pro Glu Ser Ile Arg Lys
100 105 110

Trp Arg Glu Glu Gln Met Glu Arg Leu Glu Ala Leu Asp Ala Asn Ser
115 120 125

Arg Lys Gln Glu Ala Glu Trp Lys Glu Lys Ala Ile Lys Glu Leu Glu
130 135 140

Glu Trp Tyr Ala Arg Gln Asp Glu Gln Leu Gln Lys Thr Lys Ala Asn
145 150 155 160

Asn Arg Ala Ala Glu Glu Ala Phe Val Asn Asp Ile Asp Glu Ser Ser

```
                165                 170                 175

Pro Gly Thr Glu Trp Glu Arg Val Ala Arg Leu Cys Asp Phe Asn Pro
            180                 185                 190

Lys Ser Ser Lys Gln Ala Lys Asp Val Ser Arg Met Arg Ser Val Leu
        195                 200                 205

Ile Ser Leu Lys Gln Ala Pro Leu Val His
    210                 215


<210> SEQ ID NO 64
<211> LENGTH: 211
<212> TYPE: PRT
<213> ORGANISM: Homo sapiens

<400> SEQUENCE: 64

Met Ala Asp Asp Phe Gly Phe Phe Ser Ser Ser Glu Ser Gly Ala Pro
1               5                   10                  15

Glu Ala Ala Glu Glu Asp Pro Ala Ala Ala Phe Leu Ala Gln Gln Glu
            20                  25                  30

Ser Glu Ile Ala Gly Ile Glu Asn Asp Glu Gly Phe Gly Ala Pro Ala
        35                  40                  45

Gly Ser His Ala Ala Pro Ala Gln Pro Gly Pro Thr Ser Gly Ala Gly
    50                  55                  60

Ser Glu Asp Met Gly Thr Thr Val Asn Gly Asp Val Phe Gln Glu Ala
65                  70                  75                  80

Asn Gly Pro Ala Asp Gly Tyr Ala Ala Ile Ala Gln Ala Asp Arg Leu
                85                  90                  95

Thr Gln Glu Pro Glu Ser Ile Arg Lys Trp Arg Glu Glu Gln Arg Lys
            100                 105                 110

Arg Leu Gln Glu Leu Asp Ala Ala Ser Lys Val Thr Glu Gln Glu Trp
        115                 120                 125

Arg Glu Lys Ala Lys Lys Asp Leu Glu Glu Trp Asn Gln Arg Gln Ser
    130                 135                 140

Glu Gln Val Glu Lys Asn Lys Ile Asn Asn Arg Ala Ser Glu Glu Ala
145                 150                 155                 160

Phe Val Lys Glu Ser Lys Glu Glu Thr Pro Gly Thr Glu Trp Glu Lys
                165                 170                 175

Val Ala Gln Leu Cys Asp Phe Asn Pro Lys Ser Ser Lys Gln Cys Lys
            180                 185                 190

Asp Val Ser Arg Leu Arg Ser Val Leu Met Ser Leu Lys Gln Thr Pro
        195                 200                 205

Leu Ser Arg
    210


<210> SEQ ID NO 65
<211> LENGTH: 218
<212> TYPE: PRT
<213> ORGANISM: Homo sapiens

<400> SEQUENCE: 65

Met Ser Gln Thr Ala Met Ser Glu Thr Tyr Asp Phe Leu Phe Lys Phe
1               5                   10                  15

Leu Val Ile Gly Asn Ala Gly Thr Gly Lys Ser Cys Leu Leu His Gln
            20                  25                  30

Phe Ile Glu Lys Lys Phe Lys Asp Asp Ser Asn His Thr Ile Gly Val
        35                  40                  45

Glu Phe Gly Ser Lys Ile Ile Asn Val Gly Gly Lys Tyr Val Lys Leu
```

```
    50                  55                  60

Gln Ile Trp Asp Thr Ala Gly Gln Glu Arg Phe Arg Ser Val Thr Arg
65                  70                  75                  80

Ser Tyr Tyr Arg Gly Ala Ala Gly Ala Leu Leu Val Tyr Asp Ile Thr
                85                  90                  95

Ser Arg Glu Thr Tyr Asn Ala Leu Thr Asn Trp Leu Thr Asp Ala Arg
            100                 105                 110

Met Leu Ala Ser Gln Asn Ile Val Ile Ile Leu Cys Gly Asn Lys Lys
        115                 120                 125

Asp Leu Asp Ala Asp Arg Glu Val Thr Phe Leu Glu Ala Ser Arg Phe
    130                 135                 140

Ala Gln Glu Asn Glu Leu Met Phe Leu Glu Thr Ser Ala Leu Thr Gly
145                 150                 155                 160

Glu Asn Val Glu Glu Ala Phe Val Gln Cys Ala Arg Lys Ile Leu Asn
                165                 170                 175

Lys Ile Glu Ser Gly Glu Leu Asp Pro Glu Arg Met Gly Ser Gly Ile
            180                 185                 190

Gln Tyr Gly Asp Ala Ala Leu Arg Gln Leu Arg Ser Pro Arg Arg Ala
        195                 200                 205

Gln Ala Pro Asn Ala Gln Glu Cys Gly Cys
    210                 215


<210> SEQ ID NO 66
<211> LENGTH: 216
<212> TYPE: PRT
<213> ORGANISM: Homo sapiens

<400> SEQUENCE: 66

Met Gly Thr Arg Asp Asp Glu Tyr Asp Tyr Leu Phe Lys Val Val Leu
1               5                   10                  15

Ile Gly Asp Ser Gly Val Gly Lys Ser Asn Leu Leu Ser Arg Phe Thr
            20                  25                  30

Arg Asn Glu Phe Asn Leu Glu Ser Lys Ser Thr Ile Gly Val Glu Phe
        35                  40                  45

Ala Thr Arg Ser Ile Gln Val Asp Gly Lys Thr Ile Lys Ala Gln Ile
    50                  55                  60

Trp Asp Thr Ala Gly Gln Glu Arg Tyr Arg Ala Ile Thr Ser Ala Tyr
65                  70                  75                  80

Tyr Arg Gly Ala Val Gly Ala Leu Leu Val Tyr Asp Ile Ala Lys His
                85                  90                  95

Leu Thr Tyr Glu Asn Val Glu Arg Trp Leu Lys Glu Leu Arg Asp His
            100                 105                 110

Ala Asp Ser Asn Ile Val Ile Met Leu Val Gly Asn Lys Ser Asp Leu
        115                 120                 125

Arg His Leu Arg Ala Val Pro Thr Asp Glu Ala Arg Ala Phe Ala Glu
    130                 135                 140

Lys Asn Gly Leu Ser Phe Ile Glu Thr Ser Ala Leu Asp Ser Thr Asn
145                 150                 155                 160

Val Glu Ala Ala Phe Gln Thr Ile Leu Thr Glu Ile Tyr Arg Ile Val
                165                 170                 175

Ser Gln Lys Gln Met Ser Asp Arg Arg Glu Asn Asp Met Ser Pro Ser
            180                 185                 190

Asn Asn Val Val Pro Ile His Val Pro Pro Thr Thr Glu Asn Lys Pro
        195                 200                 205
```

Lys Val Gln Cys Cys Gln Asn Ile
    210                 215

<210> SEQ ID NO 67
<211> LENGTH: 241
<212> TYPE: PRT
<213> ORGANISM: Homo sapiens

<400> SEQUENCE: 67

```
Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala
```

<210> SEQ ID NO 68
<211> LENGTH: 412
<212> TYPE: PRT
<213> ORGANISM: Homo sapiens

<400> SEQUENCE: 68

```
Met Lys Met His Leu Gln Arg Ala Leu Val Val Leu Ala Leu Leu Asn
1               5                   10                  15

Phe Ala Thr Val Ser Leu Ser Leu Ser Thr Cys Thr Thr Leu Asp Phe
            20                  25                  30

Gly His Ile Lys Lys Lys Arg Val Glu Ala Ile Arg Gly Gln Ile Leu
        35                  40                  45

Ser Lys Leu Arg Leu Thr Ser Pro Pro Glu Pro Thr Val Met Thr His
    50                  55                  60

Val Pro Tyr Gln Val Leu Ala Leu Tyr Asn Ser Thr Arg Glu Leu Leu
```

```
65                  70                  75                  80

Glu Glu Met His Gly Glu Arg Glu Glu Gly Cys Thr Gln Glu Asn Thr
                85                  90                  95

Glu Ser Glu Tyr Tyr Ala Lys Glu Ile His Lys Phe Asp Met Ile Gln
            100                 105                 110

Gly Leu Ala Glu His Asn Glu Leu Ala Val Cys Pro Lys Gly Ile Thr
        115                 120                 125

Ser Lys Val Phe Arg Phe Asn Val Ser Ser Val Glu Lys Asn Arg Thr
    130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
        195                 200                 205

Arg Glu Trp Leu Leu Arg Arg Glu Ser Asn Leu Gly Leu Glu Ile Ser
    210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
            260                 265                 270

His His Asn Pro His Leu Ile Leu Met Met Ile Pro Pro His Arg Leu
        275                 280                 285

Asp Asn Pro Gly Gln Gly Gly Gln Arg Lys Lys Arg Ala Leu Asp Thr
    290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
            340                 345                 350

Ser Ala Asp Thr Thr His Ser Thr Val Leu Gly Leu Tyr Asn Thr Leu
        355                 360                 365

Asn Pro Glu Ala Ser Ala Ser Pro Cys Cys Val Pro Gln Asp Leu Glu
    370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410


<210> SEQ ID NO 69
<211> LENGTH: 257
<212> TYPE: PRT
<213> ORGANISM: Homo sapiens

<400> SEQUENCE: 69

Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30
```

Ser Leu Ile Ile Lys Leu Ile Gln Ala Asp Ile Leu Lys Asn Lys Leu
35 40 45

Ser Lys Gln Met Val Asp Val Lys Glu Asn Tyr Gln Ser Thr Leu Pro
50 55 60

Lys Ala Glu Ala Pro Arg Glu Pro Glu Arg Gly Gly Pro Ala Lys Ser
65 70 75 80

Ala Phe Gln Pro Val Ile Ala Met Asp Thr Glu Leu Leu Arg Gln Gln
85 90 95

Arg Arg Tyr Asn Ser Pro Arg Val Leu Leu Ser Asp Ser Thr Pro Leu
100 105 110

Glu Pro Pro Pro Leu Tyr Leu Met Glu Asp Tyr Val Gly Ser Pro Val
115 120 125

Val Ala Asn Arg Thr Ser Arg Arg Lys Arg Tyr Ala Glu His Lys Ser
130 135 140

His Arg Gly Glu Tyr Ser Val Cys Asp Ser Glu Ser Leu Trp Val Thr
145 150 155 160

Asp Lys Ser Ser Ala Ile Asp Ile Arg Gly His Gln Val Thr Val Leu
165 170 175

Gly Glu Ile Lys Thr Gly Asn Ser Pro Val Lys Gln Tyr Phe Tyr Glu
180 185 190

Thr Arg Cys Lys Glu Ala Arg Pro Val Lys Asn Gly Cys Arg Gly Ile
195 200 205

Asp Asp Lys His Trp Asn Ser Gln Cys Lys Thr Ser Gln Thr Tyr Val
210 215 220

Arg Ala Leu Thr Ser Glu Asn Asn Lys Leu Val Gly Trp Arg Trp Ile
225 230 235 240

Arg Ile Asp Thr Ser Cys Val Cys Ala Leu Ser Arg Lys Ile Gly Arg
245 250 255

Thr

<210> SEQ ID NO 70
<211> LENGTH: 71
<212> TYPE: PRT
<213> ORGANISM: Homo sapiens

<400> SEQUENCE: 70

Met Arg Pro Ser Gly Thr Ala Gly Ala Ala Leu Leu Ala Leu Leu Ala
1 5 10 15

Ala Leu Cys Pro Ala Ser Arg Ala Leu Glu Glu Lys Lys Gly Lys Gly
20 25 30

Val Ser Arg Arg Leu Pro Arg Arg Pro Arg Ile Ala Pro Arg Thr Pro
35 40 45

Gln Pro Ala Gln Pro Arg Thr Gly Ala Pro Ala Arg Ala Arg Ala Pro
50 55 60

Ala Arg Pro Phe Leu Phe Pro
65 70

<210> SEQ ID NO 71
<211> LENGTH: 189
<212> TYPE: PRT
<213> ORGANISM: Homo sapiens

<400> SEQUENCE: 71

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr

```
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185


<210> SEQ ID NO 72
<211> LENGTH: 41
<212> TYPE: PRT
<213> ORGANISM: Homo sapiens

<400> SEQUENCE: 72

Tyr Gly Gln Val Pro Met Cys Asp Ala Gly Glu Gln Cys Ala Val Arg
1               5                   10                  15

Lys Gly Ala Arg Ile Gly Lys Leu Cys Asp Cys Pro Arg Gly Thr Ser
            20                  25                  30

Cys Asn Ser Phe Leu Leu Lys Cys Leu
        35                  40


<210> SEQ ID NO 73
<211> LENGTH: 129
<212> TYPE: PRT
<213> ORGANISM: Homo sapiens

<400> SEQUENCE: 73

Met Lys Ile Leu Val Ala Leu Ala Val Phe Phe Leu Val Ser Thr Gln
1               5                   10                  15

Leu Phe Ala Glu Glu Ile Gly Ala Asn Asp Asp Leu Asn Tyr Trp Ser
            20                  25                  30

Asp Trp Tyr Asp Ser Asp Gln Ile Lys Glu Glu Leu Pro Glu Pro Phe
        35                  40                  45

Glu His Leu Leu Gln Arg Ile Ala Arg Arg Pro Lys Pro Gln Gln Phe
    50                  55                  60

Phe Gly Leu Met Gly Lys Arg Asp Ala Asp Ser Ser Ile Glu Lys Gln
65                  70                  75                  80

Val Ala Leu Leu Lys Ala Leu Tyr Gly His Gly Gln Ile Ser His Lys
                85                  90                  95

Arg His Lys Thr Asp Ser Phe Val Gly Leu Met Gly Lys Arg Ala Leu
            100                 105                 110

Asn Ser Val Ala Tyr Glu Arg Ser Ala Met Gln Asn Tyr Glu Arg Arg
```

115 120 125

Arg

<210> SEQ ID NO 74
<211> LENGTH: 11
<212> TYPE: PRT
<213> ORGANISM: Homo sapiens

<400> SEQUENCE: 74

Arg Pro Lys Pro Gln Gln Phe Phe Gly Leu Met
1 5 10

<210> SEQ ID NO 75
<211> LENGTH: 125
<212> TYPE: PRT
<213> ORGANISM: Homo sapiens

<400> SEQUENCE: 75

Met Ala Gly Pro Ser Leu Ala Cys Cys Leu Leu Gly Leu Leu Ala Leu
1 5 10 15

Thr Ser Ala Cys Tyr Ile Gln Asn Cys Pro Leu Gly Gly Lys Arg Ala
20 25 30

Ala Pro Asp Leu Asp Val Arg Lys Cys Leu Pro Cys Gly Pro Gly Gly
35 40 45

Lys Gly Arg Cys Phe Gly Pro Asn Ile Cys Cys Ala Glu Glu Leu Gly
50 55 60

Cys Phe Val Gly Thr Ala Glu Ala Leu Arg Cys Gln Glu Glu Asn Tyr
65 70 75 80

Leu Pro Ser Pro Cys Gln Ser Gly Gln Lys Ala Cys Gly Ser Gly Gly
85 90 95

Arg Cys Ala Val Leu Gly Leu Cys Cys Ser Pro Asp Gly Cys His Ala
100 105 110

Asp Pro Ala Cys Asp Ala Glu Ala Thr Phe Ser Gln Arg
115 120 125

<210> SEQ ID NO 76
<211> LENGTH: 9
<212> TYPE: PRT
<213> ORGANISM: Homo sapiens

<400> SEQUENCE: 76

Cys Tyr Ile Gln Asn Cys Pro Leu Gly
1 5

<210> SEQ ID NO 77
<211> LENGTH: 116
<212> TYPE: PRT
<213> ORGANISM: Homo sapiens

<400> SEQUENCE: 77

Met Leu Ser Cys Arg Leu Gln Cys Ala Leu Ala Ala Leu Ser Ile Val
1 5 10 15

Leu Ala Leu Gly Cys Val Thr Gly Ala Pro Ser Asp Pro Arg Leu Arg
20 25 30

Gln Phe Leu Gln Lys Ser Leu Ala Ala Ala Ala Gly Lys Gln Glu Leu
35 40 45

Ala Lys Tyr Phe Leu Ala Glu Leu Leu Ser Glu Pro Asn Gln Thr Glu
50 55 60

Asn Asp Ala Leu Glu Pro Glu Asp Leu Ser Gln Ala Ala Glu Gln Asp 65 70 75 80

Glu Met Arg Leu Glu Leu Gln Arg Ser Ala Asn Ser Asn Pro Ala Met
85 90 95

Ala Pro Arg Glu Arg Lys Ala Gly Cys Lys Asn Phe Phe Trp Lys Thr
100 105 110

Phe Thr Ser Cys
115

<210> SEQ ID NO 78
<211> LENGTH: 449
<212> TYPE: PRT
<213> ORGANISM: Artificial Sequence
<220> FEATURE:
<223> OTHER INFORMATION: synthetic construct of Myosin light chain kinase, Green fluorescent protein, Calmodulin chimera
<220> FEATURE:
<221> NAME/KEY: misc_feature
<222> LOCATION: (223)..(223)
<223> OTHER INFORMATION: Xaa can be any naturally occurring amino acid

<400> SEQUENCE: 78

Met Arg Gly Ser His His His His His His Gly Met Ala Ser Met Thr
1 5 10 15

Gly Gly Gln Gln Met Gly Arg Asp Leu Tyr Asp Asp Asp Asp Lys Asp
20 25 30

Leu Ala Thr Met Val Asp Ser Ser Arg Arg Lys Trp Asn Lys Thr Gly
35 40 45

His Ala Val Arg Ala Ile Gly Arg Leu Ser Ser Leu Glu Asn Val Tyr
50 55 60

Ile Met Ala Asp Lys Gln Lys Asn Gly Ile Lys Ala Asn Phe Lys Ile
65 70 75 80

Arg His Asn Ile Glu Asp Gly Gly Val Gln Leu Ala Tyr His Tyr Gln
85 90 95

Gln Asn Thr Pro Ile Gly Asp Gly Pro Val Leu Leu Pro Asp Asn His
100 105 110

Tyr Leu Ser Thr Gln Ser Lys Leu Ser Lys Asp Pro Asn Glu Lys Arg
115 120 125

Asp His Met Val Leu Leu Glu Phe Val Thr Ala Ala Gly Ile Thr Leu
130 135 140

Gly Met Asp Glu Leu Tyr Lys Gly Gly Thr Gly Gly Ser Met Val Ser
145 150 155 160

Lys Gly Glu Glu Leu Phe Thr Gly Val Val Pro Ile Leu Val Glu Leu
165 170 175

Asp Gly Asp Val Asn Gly His Lys Phe Ser Val Ser Gly Glu Gly Glu
180 185 190

Gly Asp Ala Thr Tyr Gly Lys Leu Thr Leu Lys Phe Ile Cys Thr Thr
195 200 205

Gly Lys Leu Pro Val Pro Trp Pro Thr Leu Val Thr Thr Leu Xaa Val
210 215 220

Gln Cys Phe Ser Arg Tyr Pro Asp His Met Lys Gln His Asp Phe Phe
225 230 235 240

Lys Ser Ala Met Pro Glu Gly Tyr Ile Gln Glu Arg Thr Ile Phe Phe
245 250 255

Lys Asp Asp Gly Asn Tyr Lys Thr Arg Ala Glu Val Lys Phe Glu Gly
260 265 270

Asp Thr Leu Val Asn Arg Ile Glu Leu Lys Gly Ile Asp Phe Lys Glu
275 280 285

```
Asp Gly Asn Ile Leu Gly His Lys Leu Glu Tyr Asn Thr Arg Asp Gln
    290                 295                 300

Leu Thr Glu Glu Gln Ile Ala Glu Phe Lys Glu Ala Phe Ser Leu Phe
305                 310                 315                 320

Asp Lys Asp Gly Asp Gly Gly Ile Thr Thr Lys Gln Leu Gly Thr Val
                325                 330                 335

Met Arg Ser Leu Gly Gln Asn Pro Thr Glu Ala Glu Leu Gln Asp Met
            340                 345                 350

Ile Asn Glu Val Gly Ala Asp Gly Asn Gly Thr Ile Asp Phe Pro Gln
        355                 360                 365

Phe Leu Thr Met Met Ala Arg Lys Met Lys Asp Thr Asp Ser Glu Glu
    370                 375                 380

Glu Ile Arg Glu Ala Phe Arg Val Phe Gly Lys Asp Gly Asn Gly Tyr
385                 390                 395                 400

Ile Ser Ala Ala Gln Leu Arg His Val Met Thr Asn Leu Gly Glu Lys
                405                 410                 415

Leu Thr Asp Glu Glu Val Asp Glu Met Ile Arg Glu Ala Gly Ile Asp
            420                 425                 430

Gly Asp Gly Gln Val Asn Tyr Glu Gln Phe Val Gln Met Met Thr Ala
        435                 440                 445

Lys
```

<210> SEQ ID NO 79
<211> LENGTH: 309
<212> TYPE: PRT
<213> ORGANISM: Artificial Sequence
<220> FEATURE:
<223> OTHER INFORMATION: synthetic construct of Genetically-encoded green calcium indicator NTnC
<220> FEATURE:
<221> NAME/KEY: misc_feature
<222> LOCATION: (68)..(68)
<223> OTHER INFORMATION: Xaa can be any naturally occurring amino acid

<400> SEQUENCE: 79

```
Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
            20                  25                  30

Val Gly Gln Gly Ser Gly Asn Pro Asn Val Gly Tyr Glu Glu Leu Asn
        35                  40                  45

Leu Lys Ser Thr Lys Gly Asp Leu Gln Phe Ser Pro Trp Ile Leu Val
    50                  55                  60

Pro His Ile Xaa Phe His Gln Tyr Leu Pro Tyr Pro Asp Gly Met Ser
65                  70                  75                  80

Pro Phe Gln Ala Ala Met Val Asp Gly Ser Gly Tyr Gln Val His Arg
                85                  90                  95

Thr Val Gln Phe Glu Asp Gly Ala Ser Leu Thr Val Asn Tyr Arg Tyr
            100                 105                 110

Thr Tyr Glu Gly Ser His Ile Lys Gly Glu Ala Gln Val Lys Gly Thr
        115                 120                 125

Gly Phe Pro Ala Asp Gly Pro Val Met Ala Asn Ser Leu Thr Ala Met
    130                 135                 140

Val Pro Ser Glu Glu Glu Leu Ser Glu Cys Phe Arg Thr Phe Asp Lys
145                 150                 155                 160

Asp Gly Asp Gly Phe Ile Asp Arg Glu Glu Phe Gly Gly Ile Ile Arg
```

```
                165                 170                 175

Leu Thr Gly Glu Gln Leu Thr Asp Glu Asp Pro Asp Glu Ile Phe Gly
            180                 185                 190

Asp Ser Asp Thr Asp Lys Asn Gly Arg Ile Asp Phe Asp Glu Phe Leu
        195                 200                 205

Lys Met Val Glu Asn Val Gln Leu Ser Met Ala Asp Trp Cys Arg Ser
    210                 215                 220

Lys Met Ala Cys Pro Asn Asp Lys Thr Leu Ile Ser Thr Leu Lys Trp
225                 230                 235                 240

Ser Tyr Thr Thr Gly Asn Gly Lys Arg Tyr Arg Ser Thr Ala Arg Thr
                245                 250                 255

Thr Tyr Thr Phe Ala Lys Pro Met Ala Ala Asn Tyr Leu Lys Asn Gln
            260                 265                 270

Pro Met Tyr Val Phe Arg Lys Thr Glu Leu Lys His Ser Lys Thr Glu
        275                 280                 285

Leu Asn Phe Lys Glu Trp Gln Lys Ala Phe Thr Asp Val Met Gly Met
    290                 295                 300

Asp Glu Leu Tyr Lys
305


<210> SEQ ID NO 80
<211> LENGTH: 619
<212> TYPE: PRT
<213> ORGANISM: Artificial Sequence
<220> FEATURE:
<223> OTHER INFORMATION: synthetic construct of Calcium indicator TN-XXL

<400> SEQUENCE: 80

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
            20                  25                  30

Glu Gly Glu Gly Asp Ala Thr Asn Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
```

```
    210                 215                 220

Val Thr Ala Ala Arg Met Leu Ser Glu Glu Glu Leu Ala Asn Cys Phe
225                 230                 235                 240

Arg Ile Phe Asp Lys Asp Ala Asn Gly Phe Ile Asp Ile Glu Glu Leu
                245                 250                 255

Gly Glu Ile Leu Arg Ala Thr Gly Glu His Val Thr Glu Glu Asp Ile
            260                 265                 270

Glu Asp Leu Met Lys Asp Ser Asp Lys Asn Asn Asp Gly Arg Ile Asp
        275                 280                 285

Phe Asp Glu Phe Leu Lys Met Met Glu Gly Val Gln Gly Thr Ser Glu
    290                 295                 300

Glu Glu Leu Ala Asn Cys Phe Arg Ile Phe Asp Lys Asp Ala Asn Gly
305                 310                 315                 320

Phe Ile Asp Ile Glu Glu Leu Gly Glu Ile Leu Arg Ala Thr Gly Glu
                325                 330                 335

His Val Thr Glu Glu Asp Ile Glu Asp Leu Met Lys Asp Ser Asp Lys
            340                 345                 350

Asn Asn Asp Gly Arg Ile Asp Phe Asp Glu Phe Leu Lys Met Met Glu
        355                 360                 365

Gly Val Gln Glu Leu Met Gly Gly Val Gln Leu Ala Asp His Tyr Gln
    370                 375                 380

Gln Asn Thr Pro Ile Gly Asp Gly Pro Val Leu Leu Pro Asp Asn His
385                 390                 395                 400

Tyr Leu Ser Tyr Gln Ser Lys Leu Ser Lys Asp Pro Asn Glu Lys Arg
                405                 410                 415

Asp His Met Val Leu Leu Glu Phe Val Thr Ala Ala Gly Ile Thr Leu
            420                 425                 430

Gly Met Asp Glu Leu Tyr Lys Gly Gly Thr Gly Gly Ser Met Val Ser
        435                 440                 445

Lys Gly Glu Glu Leu Phe Thr Gly Val Val Pro Ile Leu Val Glu Leu
    450                 455                 460

Asp Gly Asp Val Asn Gly His Lys Phe Ser Val Arg Gly Glu Gly Glu
465                 470                 475                 480

Gly Asp Ala Thr Asn Gly Lys Leu Thr Leu Lys Phe Ile Cys Thr Thr
                485                 490                 495

Gly Lys Leu Pro Val Pro Trp Pro Thr Leu Val Thr Thr Leu Gly Tyr
            500                 505                 510

Gly Leu Met Cys Phe Ala Arg Tyr Pro Asp His Met Lys Gln His Asp
        515                 520                 525

Phe Phe Lys Ser Ala Met Pro Glu Gly Tyr Val Gln Glu Arg Thr Ile
    530                 535                 540

Phe Phe Lys Asp Asp Gly Asn Tyr Lys Thr Arg Ala Glu Val Lys Phe
545                 550                 555                 560

Glu Gly Asp Thr Leu Val Asn Arg Ile Glu Leu Lys Gly Ile Asp Phe
                565                 570                 575

Lys Glu Asp Gly Asn Ile Leu Gly His Lys Leu Glu Tyr Asn Tyr Asn
            580                 585                 590

Ser His Asn Val Tyr Ile Met Ala Asp Lys Gln Lys Asn Gly Ile Lys
        595                 600                 605

Ala Asn Phe Lys Ile Arg His Asn Ile Glu Asp
    610                 615
```

<210> SEQ ID NO 81

```
<211> LENGTH: 730
<212> TYPE: PRT
<213> ORGANISM: Artificial Sequence
<220> FEATURE:
<223> OTHER INFORMATION: synthetic construct of BRET-based
      auto-luminescent calcium indicator

<400> SEQUENCE: 81

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Arg
225                 230                 235                 240

Met His Asp Gln Leu Thr Glu Glu Gln Ile Ala Glu Phe Lys Glu Ala
                245                 250                 255

Phe Ser Leu Phe Asp Lys Asp Gly Asp Gly Thr Ile Thr Thr Lys Glu
            260                 265                 270

Leu Gly Thr Val Met Arg Ser Leu Gly Gln Asn Pro Thr Glu Ala Glu
        275                 280                 285

Leu Gln Asp Met Ile Asn Glu Val Asp Ala Asp Gly Asn Gly Thr Ile
    290                 295                 300

Tyr Phe Pro Glu Phe Leu Thr Met Met Ala Arg Lys Met Lys Asp Thr
305                 310                 315                 320

Asp Ser Glu Glu Glu Ile Arg Glu Ala Phe Arg Val Phe Asp Lys Asp
                325                 330                 335

Gly Asn Gly Tyr Ile Ser Ala Ala Gln Leu Arg His Val Met Thr Asn
            340                 345                 350

Leu Gly Glu Lys Leu Thr Asp Glu Glu Val Asp Glu Met Ile Arg Glu
        355                 360                 365

Ala Asp Ile Asp Gly Asp Gly Gln Val Asn Tyr Glu Glu Phe Val Gln
```

```
    370                 375                 380

Met Met Thr Ala Lys Gly Gly Lys Arg Arg Trp Lys Lys Asn Phe Ile
385                 390                 395                 400

Ala Val Ser Ala Ala Asn Arg Phe Lys Lys Ile Ser Ser Ser Gly Ala
                405                 410                 415

Leu Glu Leu Met Thr Ser Lys Val Tyr Asp Pro Glu Gln Arg Lys Arg
            420                 425                 430

Met Ile Thr Gly Pro Gln Trp Trp Ala Arg Cys Lys Gln Met Asn Val
        435                 440                 445

Leu Asp Ser Phe Ile Asn Tyr Tyr Asp Ser Glu Lys His Ala Glu Asn
    450                 455                 460

Ala Val Ile Phe Leu His Gly Asn Ala Thr Ser Ser Tyr Leu Trp Arg
465                 470                 475                 480

His Val Val Pro His Ile Glu Pro Val Ala Arg Cys Ile Ile Pro Asp
                485                 490                 495

Leu Ile Gly Met Gly Lys Ser Gly Lys Ser Gly Asn Gly Ser Tyr Arg
            500                 505                 510

Leu Leu Asp His Tyr Lys Tyr Leu Thr Ala Trp Phe Glu Leu Leu Asn
        515                 520                 525

Leu Pro Lys Lys Ile Ile Phe Val Gly His Asp Trp Gly Ala Ala Leu
    530                 535                 540

Ala Phe His Tyr Ala Tyr Glu His Gln Asp Arg Ile Lys Ala Ile Val
545                 550                 555                 560

His Met Glu Ser Val Val Asp Val Ile Glu Ser Trp Asp Glu Trp Pro
                565                 570                 575

Asp Ile Glu Glu Asp Ile Ala Leu Ile Lys Ser Glu Glu Gly Glu Lys
            580                 585                 590

Met Val Leu Glu Asn Asn Phe Phe Val Glu Thr Val Leu Pro Ser Lys
        595                 600                 605

Ile Met Arg Lys Leu Glu Pro Glu Glu Phe Ala Ala Tyr Leu Glu Pro
    610                 615                 620

Phe Lys Glu Lys Gly Glu Val Arg Arg Pro Thr Leu Ser Trp Pro Arg
625                 630                 635                 640

Glu Ile Pro Leu Val Lys Gly Gly Lys Pro Asp Val Val Gln Ile Val
                645                 650                 655

Arg Asn Tyr Asn Ala Tyr Leu Arg Ala Ser Asp Asp Leu Pro Lys Leu
            660                 665                 670

Phe Ile Glu Ser Asp Pro Gly Phe Phe Ser Asn Ala Ile Val Glu Gly
        675                 680                 685

Ala Lys Lys Phe Pro Asn Thr Glu Phe Val Lys Val Lys Gly Leu His
    690                 695                 700

Phe Leu Gln Glu Asp Ala Pro Asp Glu Met Gly Lys Tyr Ile Lys Ser
705                 710                 715                 720

Phe Val Glu Arg Val Leu Lys Asn Glu Gln
                725                 730


<210> SEQ ID NO 82
<211> LENGTH: 568
<212> TYPE: PRT
<213> ORGANISM: Artificial Sequence
<220> FEATURE:
<223> OTHER INFORMATION: synthetic construct of Calcium indicator
      protein OeNL(Ca2+)-18u

<400> SEQUENCE: 82
```

```
Met Val Ser Val Ile Lys Pro Glu Met Lys Met Arg Tyr Tyr Met Asp
1               5                   10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
    50                  55                  60

Cys Tyr Gly His Arg Val Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Gly Asn His Lys Cys Gln Phe
                165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
        195                 200                 205

Glu Gln Val Glu Asp Ala Val Ala His Ser Gly Thr Leu Glu Asp Phe
    210                 215                 220

Val Gly Asp Trp Arg Gln Thr Ala Gly Tyr Asn Leu Asp Gln Val Leu
225                 230                 235                 240

Glu Gln Gly Gly Val Ser Ser Leu Phe Gln Asn Leu Gly Val Ser Val
                245                 250                 255

Thr Pro Ile Gln Arg Ile Val Leu Ser Gly Glu Asn Gly Leu Lys Ile
            260                 265                 270

Asp Ile His Val Ile Ile Pro Tyr Glu Gly Pro Trp Met His Asp Gln
        275                 280                 285

Leu Thr Glu Glu Gln Ile Ala Glu Phe Lys Glu Ala Phe Ser Leu Phe
    290                 295                 300

Asp Lys Asp Gly Asp Gly Thr Ile Thr Thr Lys Glu Leu Gly Thr Val
305                 310                 315                 320

Met Arg Ser Leu Gly Gln Asn Pro Thr Glu Ala Glu Leu Gln Asp Met
                325                 330                 335

Ile Asn Glu Val Asp Ala Asp Gly Asn Gly Thr Ile Tyr Phe Pro Asp
            340                 345                 350

Phe Leu Thr Met Met Ala Arg Lys Met Lys Asp Thr Asp Ser Glu Glu
        355                 360                 365

Glu Ile Arg Glu Ala Phe Arg Val Phe Asp Lys Asp Gly Asn Gly Tyr
    370                 375                 380

Ile Ser Ala Ala Asp Leu Arg His Val Met Thr Asn Leu Gly Glu Lys
385                 390                 395                 400

Leu Thr Asp Glu Glu Val Asp Glu Met Ile Arg Glu Ala Asp Ile Asp
                405                 410                 415

Gly Glu Gly Gln Val Asn Tyr Glu Glu Phe Val Gln Met Met Thr Ala
```

```
            420                 425                 430

Lys Gly Gly Lys Arg Arg Trp Lys Lys Asn Phe Ile Ala Val Ser Ala
        435                 440                 445

Ala Asn Arg Phe Lys Lys Ile Ser Ser Ser Gly Ala Leu Glu Leu Leu
    450                 455                 460

Ser Gly Asp Gln Met Gly Gln Ile Glu Lys Ile Phe Lys Val Val Tyr
465                 470                 475                 480

Pro Val Asp Asp His His Phe Lys Val Ile Leu His Tyr Gly Thr Leu
                485                 490                 495

Val Ile Asp Gly Val Thr Pro Asn Met Ile Asp Tyr Phe Gly Arg Pro
            500                 505                 510

Tyr Glu Gly Ile Ala Val Phe Asp Gly Lys Lys Ile Thr Val Thr Gly
        515                 520                 525

Thr Leu Trp Asn Gly Asn Lys Ile Ile Asp Glu Arg Leu Ile Asn Pro
    530                 535                 540

Asp Gly Ser Leu Leu Phe Arg Val Thr Ile Asn Gly Val Thr Gly Trp
545                 550                 555                 560

Arg Leu Cys Glu Arg Ile Leu Ala
                565


<210> SEQ ID NO 83
<211> LENGTH: 593
<212> TYPE: PRT
<213> ORGANISM: Mesostigma viride

<400> SEQUENCE: 83

Met Ser Pro Pro Thr Ser Pro Thr Pro Asp Thr Gly His Asp Thr Pro
1               5                   10                  15

Asp Thr Gly His Asp Thr Gly Gly His Gly Ala Val Glu Ile Cys Phe
            20                  25                  30

Ala Pro Cys Glu Glu Asp Cys Val Thr Ile Arg Tyr Phe Val Glu Asn
        35                  40                  45

Asp Phe Glu Gly Cys Ile Pro Gly His Phe Asp Gln Tyr Ser Ser His
    50                  55                  60

Gly Ser Leu His Asp Ile Val Lys Ala Ala Leu Tyr Ile Cys Met Val
65                  70                  75                  80

Ile Ser Ile Leu Gln Ile Leu Phe Tyr Gly Phe Gln Trp Trp Arg Lys
                85                  90                  95

Thr Cys Gly Trp Glu Val Trp Phe Val Ala Cys Ile Glu Thr Ser Ile
            100                 105                 110

Tyr Ile Ile Ala Ile Thr Ser Glu Ala Asp Ser Pro Phe Thr Leu Tyr
        115                 120                 125

Leu Thr Asn Gly Gln Ile Ser Pro Gln Leu Arg Tyr Met Glu Trp Leu
    130                 135                 140

Met Thr Cys Pro Val Ile Leu Ile Ala Leu Ser Asn Ile Thr Gly Met
145                 150                 155                 160

Ala Glu Glu Tyr Asn Lys Arg Thr Met Thr Leu Leu Thr Ser Asp Val
                165                 170                 175

Cys Cys Ile Val Leu Gly Met Met Ser Ala Ala Ser Lys Pro Arg Leu
            180                 185                 190

Lys Gly Ile Leu Tyr Ala Val Gly Trp Ala Phe Gly Ala Trp Thr Tyr
        195                 200                 205

Trp Thr Ala Leu Gln Val Tyr Arg Asp Ala His Lys Ala Val Pro Lys
    210                 215                 220
```

```
Pro Leu Ala Trp Tyr Val Arg Ala Met Gly Tyr Val Phe Phe Thr Ser
225                 230                 235                 240

Trp Leu Thr Phe Pro Gly Trp Phe Leu Leu Gly Pro Glu Gly Leu Glu
                245                 250                 255

Val Val Thr Gly Thr Val Ser Thr Leu Met His Ala Cys Ser Asp Leu
            260                 265                 270

Ile Ser Lys Asn Leu Trp Gly Phe Met Asp Trp His Leu Arg Val Leu
        275                 280                 285

Val Ala Arg His His Arg Lys Leu Phe Lys Ala Glu Glu Glu His Ala
    290                 295                 300

Leu Lys Lys Gly Gln Thr Leu Glu Pro Gly Met Pro Arg Ser Thr Ser
305                 310                 315                 320

Phe Val Arg Gly Leu Gly Asp Asp Val Glu Ile Asp Pro Ser Tyr Glu
                325                 330                 335

Leu Tyr Arg Leu Lys Arg Gln Asn His Pro Glu Tyr Phe Leu Ser Pro
            340                 345                 350

Ala Gln Thr Pro Arg Arg Gly Pro Ser Phe Asp Lys Arg Thr Ser Phe
        355                 360                 365

Glu Met Asp Gly Gly Lys Asn Gly Met Leu Gln Met Met Pro Val Thr
    370                 375                 380

Gly Met Gly Met Gly Met Gly Met Gly Met Gly Gly Gly Lys Thr Val
385                 390                 395                 400

Leu Phe Leu Asp Tyr Thr Gly Gly Gly Tyr Val Ser Phe Phe Glu Gln
                405                 410                 415

Gln Leu Ser Asn Met Gly Val Asn Val Thr Lys Cys Trp Ser Asp Asp
            420                 425                 430

Asp Met Tyr Asn Thr Ala Gly Val Ala Asn Val Lys Gln Leu Phe His
        435                 440                 445

Phe Ala Met Ile Pro Asn Asn Ala Leu Gly Gly Gln Met Val Met Asp
    450                 455                 460

Leu Arg Gly Thr Gly Leu Leu Val Val Ala Tyr Gly Pro Glu Pro Pro
465                 470                 475                 480

Met Pro Gly Met Gly Gln Asp Glu Phe Val Pro Leu Gln Met Pro Gly
                485                 490                 495

Val Pro Tyr Asp Glu Ser Ile Leu His Asn Leu Val Met Arg His Ala
            500                 505                 510

Ile Thr Gln Gly Leu Gly Met Asn Gly Met Gln Gly Asn Met Gly Gln
        515                 520                 525

Gln Gln Gln Met Met Gly Met Gln Gly Asn Met Asn Gly Met Gln Gly
    530                 535                 540

Asn Met Asn Gly Met Gln Gly Asn Met Asn Gly Met Gln Gly Asn Met
545                 550                 555                 560

Ser Gly Met Gln Gly Asn Met Asn Gly Met Gln Gly Asn Ser Gly Met
                565                 570                 575

Asn Gln Gly Trp Asn Asn Gln Gly Phe Thr Asn Thr Gly Ala Phe Gly
            580                 585                 590

Tyr
```

<210> SEQ ID NO 84
<211> LENGTH: 747
<212> TYPE: PRT
<213> ORGANISM: Volvox carteri

<400> SEQUENCE: 84

-continued

```
Met Asp His Pro Val Ala Arg Ser Leu Ile Gly Ser Ser Tyr Thr Asn
1               5                   10                  15

Leu Asn Asn Gly Ser Ile Val Ile Pro Ser Asp Ala Cys Phe Cys Met
            20                  25                  30

Lys Trp Leu Lys Ser Lys Gly Ser Pro Val Ala Leu Lys Met Ala Asn
        35                  40                  45

Ala Leu Gln Trp Ala Ala Phe Ala Leu Ser Val Ile Ile Leu Ile Tyr
    50                  55                  60

Tyr Ala Tyr Ala Thr Trp Arg Thr Thr Cys Gly Trp Glu Glu Val Tyr
65                  70                  75                  80

Val Cys Cys Val Glu Leu Thr Lys Val Val Ile Glu Phe Phe His Glu
                85                  90                  95

Phe Asp Glu Pro Gly Met Leu Tyr Leu Ala Asn Gly Asn Arg Val Leu
            100                 105                 110

Trp Leu Arg Tyr Gly Glu Trp Leu Leu Thr Cys Pro Val Ile Leu Ile
        115                 120                 125

His Leu Ser Asn Leu Thr Gly Leu Lys Asp Asp Tyr Asn Lys Arg Thr
    130                 135                 140

Met Arg Leu Leu Val Ser Asp Val Gly Thr Ile Val Trp Gly Ala Thr
145                 150                 155                 160

Ala Ala Met Ser Thr Gly Tyr Ile Lys Val Ile Phe Phe Leu Leu Gly
                165                 170                 175

Cys Met Tyr Gly Ala Asn Thr Phe Phe His Ala Ala Lys Val Tyr Ile
            180                 185                 190

Glu Ser Tyr His Thr Val Pro Lys Gly Leu Cys Arg Gln Leu Val Arg
        195                 200                 205

Ala Met Ala Trp Leu Phe Phe Val Ser Trp Gly Met Phe Pro Val Leu
    210                 215                 220

Phe Leu Leu Gly Pro Glu Gly Phe Gly His Leu Ser Val Tyr Gly Ser
225                 230                 235                 240

Thr Ile Gly His Thr Ile Ile Asp Leu Leu Ser Lys Asn Cys Trp Gly
                245                 250                 255

Leu Leu Gly His Phe Leu Arg Leu Lys Ile His Glu His Ile Leu Leu
            260                 265                 270

Tyr Gly Asp Ile Arg Lys Val Gln Lys Ile Arg Val Ala Gly Glu Glu
        275                 280                 285

Leu Glu Val Glu Thr Leu Met Thr Glu Glu Ala Pro Asp Thr Val Lys
    290                 295                 300

Lys Ser Thr Ala Gln Tyr Ala Asn Arg Glu Ser Phe Leu Thr Met Arg
305                 310                 315                 320

Asp Lys Leu Lys Glu Lys Gly Phe Glu Val Arg Ala Ser Leu Asp Asn
                325                 330                 335

Ser Gly Ile Asp Ala Val Ile Asn His Asn Asn Asn Tyr Asn Asn Ala
            340                 345                 350

Leu Ala Asn Ala Ala Ala Ala Val Gly Lys Pro Gly Met Glu Leu Ser
        355                 360                 365

Lys Leu Asp His Val Ala Ala Asn Ala Ala Gly Met Gly Gly Ile Ala
    370                 375                 380

Asp His Val Ala Thr Thr Ser Gly Ala Ile Ser Pro Gly Arg Val Ile
385                 390                 395                 400

Leu Ala Val Pro Asp Ile Ser Met Val Asp Tyr Phe Arg Glu Gln Phe
                405                 410                 415

Ala Gln Leu Pro Val Gln Tyr Glu Val Val Pro Ala Leu Gly Ala Asp
```

```
            420                 425                 430

Asn Ala Val Gln Leu Val Val Gln Ala Ala Gly Leu Gly Gly Cys Asp
        435                 440                 445

Phe Val Leu Leu His Pro Glu Phe Leu Arg Asp Lys Ser Ser Thr Ser
    450                 455                 460

Leu Pro Ala Arg Leu Arg Ser Ile Gly Gln Arg Val Ala Ala Phe Gly
465                 470                 475                 480

Trp Ser Pro Val Gly Pro Val Arg Asp Leu Ile Glu Ser Ala Gly Leu
                485                 490                 495

Asp Gly Trp Leu Glu Gly Pro Ser Phe Gly Leu Gly Ile Ser Leu Pro
            500                 505                 510

Asn Leu Ala Ser Leu Val Leu Arg Met Gln His Ala Arg Lys Met Ala
        515                 520                 525

Ala Met Leu Gly Gly Met Gly Gly Met Leu Gly Ser Asn Leu Met Ser
    530                 535                 540

Gly Ser Gly Gly Val Gly Leu Met Gly Ala Gly Ser Pro Gly Gly Gly
545                 550                 555                 560

Gly Gly Ala Met Gly Val Gly Met Thr Gly Met Gly Met Val Gly Thr
                565                 570                 575

Asn Ala Met Gly Arg Gly Ala Val Gly Asn Ser Val Ala Asn Ala Ser
            580                 585                 590

Met Gly Gly Gly Ser Ala Gly Met Gly Met Gly Met Met Gly Met Val
        595                 600                 605

Gly Ala Gly Val Gly Gly Gln Gln Gln Met Gly Ala Asn Gly Met Gly
    610                 615                 620

Pro Thr Ser Phe Gln Leu Gly Ser Asn Pro Leu Tyr Asn Thr Ala Pro
625                 630                 635                 640

Ser Pro Leu Ser Ser Gln Pro Gly Gly Asp Ala Ser Ala Ala Ala Ala
                645                 650                 655

Ala Ala Ala Ala Ala Ala Ala Thr Gly Ala Ala Ser Asn Ser Met Asn
            660                 665                 670

Ala Met Gln Ala Gly Gly Ser Val Arg Asn Ser Gly Ile Leu Ala Gly
        675                 680                 685

Gly Leu Gly Ser Met Met Gly Pro Pro Gly Ala Pro Ala Ala Pro Thr
    690                 695                 700

Ala Ala Ala Thr Ala Ala Pro Ala Val Thr Met Gly Ala Pro Gly Gly
705                 710                 715                 720

Gly Gly Ala Ala Ala Ser Glu Ala Glu Met Leu Gln Gln Leu Met Ala
                725                 730                 735

Glu Ile Asn Arg Leu Lys Ser Glu Leu Gly Glu
            740                 745


<210> SEQ ID NO 85
<211> LENGTH: 282
<212> TYPE: PRT
<213> ORGANISM: Streptococcus pyogenes

<400> SEQUENCE: 85

Met Leu Glu His Lys Ile Asp Phe Met Val Thr Leu Glu Val Lys Glu
1               5                   10                  15

Ala Asn Ala Asn Gly Asp Pro Leu Asn Gly Asn Met Pro Arg Thr Asp
            20                  25                  30

Ala Lys Gly Tyr Gly Val Met Ser Asp Val Ser Ile Lys Arg Lys Ile
        35                  40                  45
```

Arg Asn Arg Leu Gln Asp Met Gly Lys Ser Ile Phe Val Gln Ala Asn
50 55 60

Glu Arg Ile Glu Asp Asp Phe Arg Ser Leu Glu Lys Arg Phe Ser Gln
65 70 75 80

His Phe Thr Ala Lys Thr Pro Asp Lys Glu Ile Glu Glu Lys Ala Asn
85 90 95

Ala Leu Trp Phe Asp Val Arg Ala Phe Gly Gln Val Phe Thr Tyr Leu
100 105 110

Lys Lys Ser Ile Gly Val Arg Gly Pro Val Ser Ile Ser Met Ala Lys
115 120 125

Ser Leu Glu Pro Ile Val Ile Ser Ser Leu Gln Ile Thr Arg Ser Thr
130 135 140

Asn Gly Met Glu Ala Lys Asn Asn Ser Gly Arg Ser Ser Asp Thr Met
145 150 155 160

Gly Thr Lys His Phe Val Asp Tyr Gly Val Tyr Val Leu Lys Gly Ser
165 170 175

Ile Asn Ala Tyr Phe Ala Glu Lys Thr Gly Phe Ser Gln Glu Asp Ala
180 185 190

Glu Ala Ile Lys Glu Val Leu Val Ser Leu Phe Glu Asn Asp Ala Ser
195 200 205

Ser Ala Arg Pro Glu Gly Ser Met Arg Val Cys Glu Val Phe Trp Phe
210 215 220

Thr His Ser Ser Lys Leu Gly Asn Val Ser Ser Ala Arg Val Phe Asp
225 230 235 240

Leu Leu Glu Tyr His Gln Ser Ile Glu Glu Lys Ser Thr Tyr Asp Ala
245 250 255

Tyr Gln Ile His Leu Asn Gln Glu Lys Leu Ala Lys Tyr Glu Ala Lys
260 265 270

Gly Leu Thr Leu Glu Ile Leu Glu Gly Leu
275 280

<210> SEQ ID NO 86
<211> LENGTH: 1368
<212> TYPE: PRT
<213> ORGANISM: Artificial Sequence
<220> FEATURE:
<223> OTHER INFORMATION: Cas9

<400> SEQUENCE: 86

Met Asp Lys Lys Tyr Ser Ile Gly Leu Asp Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

-continued

```
His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
```

```
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975
```

```
Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                 1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 87
<211> LENGTH: 1307
<212> TYPE: PRT
<213> ORGANISM: Acidaminococcus sp. BV3L6

<400> SEQUENCE: 87

Met Thr Gln Phe Glu Gly Phe Thr Asn Leu Tyr Gln Val Ser Lys Thr
1 5 10 15

Leu Arg Phe Glu Leu Ile Pro Gln Gly Lys Thr Leu Lys His Ile Gln
20 25 30

Glu Gln Gly Phe Ile Glu Glu Asp Lys Ala Arg Asn Asp His Tyr Lys
35 40 45

Glu Leu Lys Pro Ile Ile Asp Arg Ile Tyr Lys Thr Tyr Ala Asp Gln
50 55 60

Cys Leu Gln Leu Val Gln Leu Asp Trp Glu Asn Leu Ser Ala Ala Ile
65 70 75 80

Asp Ser Tyr Arg Lys Glu Lys Thr Glu Glu Thr Arg Asn Ala Leu Ile
85 90 95

Glu Glu Gln Ala Thr Tyr Arg Asn Ala Ile His Asp Tyr Phe Ile Gly
100 105 110

Arg Thr Asp Asn Leu Thr Asp Ala Ile Asn Lys Arg His Ala Glu Ile
115 120 125

Tyr Lys Gly Leu Phe Lys Ala Glu Leu Phe Asn Gly Lys Val Leu Lys
130 135 140

Gln Leu Gly Thr Val Thr Thr Thr Glu His Glu Asn Ala Leu Leu Arg
145 150 155 160

Ser Phe Asp Lys Phe Thr Thr Tyr Phe Ser Gly Phe Tyr Glu Asn Arg
165 170 175

Lys Asn Val Phe Ser Ala Glu Asp Ile Ser Thr Ala Ile Pro His Arg
180 185 190

Ile Val Gln Asp Asn Phe Pro Lys Phe Lys Glu Asn Cys His Ile Phe
195 200 205

Thr Arg Leu Ile Thr Ala Val Pro Ser Leu Arg Glu His Phe Glu Asn
210 215 220

Val Lys Lys Ala Ile Gly Ile Phe Val Ser Thr Ser Ile Glu Glu Val
225 230 235 240

Phe Ser Phe Pro Phe Tyr Asn Gln Leu Leu Thr Gln Thr Gln Ile Asp
245 250 255

Leu Tyr Asn Gln Leu Leu Gly Gly Ile Ser Arg Glu Ala Gly Thr Glu
260 265 270

Lys Ile Lys Gly Leu Asn Glu Val Leu Asn Leu Ala Ile Gln Lys Asn
275 280 285

Asp Glu Thr Ala His Ile Ile Ala Ser Leu Pro His Arg Phe Ile Pro
290 295 300

Leu Phe Lys Gln Ile Leu Ser Asp Arg Asn Thr Leu Ser Phe Ile Leu
305 310 315 320

Glu Glu Phe Lys Ser Asp Glu Glu Val Ile Gln Ser Phe Cys Lys Tyr
325 330 335

Lys Thr Leu Leu Arg Asn Glu Asn Val Leu Glu Thr Ala Glu Ala Leu
340 345 350

Phe Asn Glu Leu Asn Ser Ile Asp Leu Thr His Ile Phe Ile Ser His
355 360 365

Lys Lys Leu Glu Thr Ile Ser Ser Ala Leu Cys Asp His Trp Asp Thr
370 375 380

```
Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800
```

```
Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
        995                 1000                1005

Lys Ala  Val Tyr Gln Gln Phe  Glu Lys Met Leu Ile  Asp Lys Leu
    1010                1015                1020

Asn Cys  Leu Val Leu Lys Asp  Tyr Pro Ala Glu Lys  Val Gly Gly
    1025                1030                1035

Val Leu  Asn Pro Tyr Gln Leu  Thr Asp Gln Phe Thr  Ser Phe Ala
    1040                1045                1050

Lys Met  Gly Thr Gln Ser Gly  Phe Leu Phe Tyr Val  Pro Ala Pro
    1055                1060                1065

Tyr Thr  Ser Lys Ile Asp Pro  Leu Thr Gly Phe Val  Asp Pro Phe
    1070                1075                1080

Val Trp  Lys Thr Ile Lys Asn  His Glu Ser Arg Lys  His Phe Leu
    1085                1090                1095

Glu Gly  Phe Asp Phe Leu His  Tyr Asp Val Lys Thr  Gly Asp Phe
    1100                1105                1110

Ile Leu  His Phe Lys Met Asn  Arg Asn Leu Ser Phe  Gln Arg Gly
    1115                1120                1125

Leu Pro  Gly Phe Met Pro Ala  Trp Asp Ile Val Phe  Glu Lys Asn
    1130                1135                1140

Glu Thr  Gln Phe Asp Ala Lys  Gly Thr Pro Phe Ile  Ala Gly Lys
    1145                1150                1155

Arg Ile  Val Pro Val Ile Glu  Asn His Arg Phe Thr  Gly Arg Tyr
    1160                1165                1170

Arg Asp  Leu Tyr Pro Ala Asn  Glu Leu Ile Ala Leu  Leu Glu Glu
    1175                1180                1185

Lys Gly  Ile Val Phe Arg Asp  Gly Ser Asn Ile Leu  Pro Lys Leu
    1190                1195                1200

Leu Glu  Asn Asp Asp Ser His  Ala Ile Asp Thr Met  Val Ala Leu
```

1205 1210 1215

Ile Arg Ser Val Leu Gln Met Arg Asn Ser Asn Ala Ala Thr Gly
1220 1225 1230

Glu Asp Tyr Ile Asn Ser Pro Val Arg Asp Leu Asn Gly Val Cys
1235 1240 1245

Phe Asp Ser Arg Phe Gln Asn Pro Glu Trp Pro Met Asp Ala Asp
1250 1255 1260

Ala Asn Gly Ala Tyr His Ile Ala Leu Lys Gly Gln Leu Leu Leu
1265 1270 1275

Asn His Leu Lys Glu Ser Lys Asp Leu Lys Leu Gln Asn Gly Ile
1280 1285 1290

Ser Asn Gln Asp Trp Leu Ala Tyr Ile Gln Glu Leu Arg Asn
1295 1300 1305

<210> SEQ ID NO 88
<211> LENGTH: 741
<212> TYPE: PRT
<213> ORGANISM: Homo sapiens

<400> SEQUENCE: 88

Met Glu Ser Arg Asp His Asn Asn Pro Gln Glu Gly Pro Thr Ser Ser
1 5 10 15

Ser Gly Arg Arg Ala Ala Val Glu Asp Asn His Leu Leu Ile Lys Ala
20 25 30

Val Gln Asn Glu Asp Val Asp Leu Val Gln Gln Leu Leu Glu Gly Gly
35 40 45

Ala Asn Val Asn Phe Gln Glu Glu Glu Gly Gly Trp Thr Pro Leu His
50 55 60

Asn Ala Val Gln Met Ser Arg Glu Asp Ile Val Glu Leu Leu Leu Arg
65 70 75 80

His Gly Ala Asp Pro Val Leu Arg Lys Lys Asn Gly Ala Thr Pro Phe
85 90 95

Ile Leu Ala Ala Ile Ala Gly Ser Val Lys Leu Leu Lys Leu Phe Leu
100 105 110

Ser Lys Gly Ala Asp Val Asn Glu Cys Asp Phe Tyr Gly Phe Thr Ala
115 120 125

Phe Met Glu Ala Ala Val Tyr Gly Lys Val Lys Ala Leu Lys Phe Leu
130 135 140

Tyr Lys Arg Gly Ala Asn Val Asn Leu Arg Arg Lys Thr Lys Glu Asp
145 150 155 160

Gln Glu Arg Leu Arg Lys Gly Gly Ala Thr Ala Leu Met Asp Ala Ala
165 170 175

Glu Lys Gly His Val Glu Val Leu Lys Ile Leu Leu Asp Glu Met Gly
180 185 190

Ala Asp Val Asn Ala Cys Asp Asn Met Gly Arg Asn Ala Leu Ile His
195 200 205

Ala Leu Leu Ser Ser Asp Asp Ser Asp Val Glu Ala Ile Thr His Leu
210 215 220

Leu Leu Asp His Gly Ala Asp Val Asn Val Arg Gly Glu Arg Gly Lys
225 230 235 240

Thr Pro Leu Ile Leu Ala Val Glu Lys Lys His Leu Gly Leu Val Gln
245 250 255

Arg Leu Leu Glu Gln Glu His Ile Glu Ile Asn Asp Thr Asp Ser Asp
260 265 270

```
Gly Lys Thr Ala Leu Leu Leu Ala Val Glu Leu Lys Leu Lys Lys Ile
        275                 280                 285

Ala Glu Leu Leu Cys Lys Arg Gly Ala Ser Thr Asp Cys Gly Asp Leu
    290                 295                 300

Val Met Thr Ala Arg Arg Asn Tyr Asp His Ser Leu Val Lys Val Leu
305                 310                 315                 320

Leu Ser His Gly Ala Lys Glu Asp Phe His Pro Pro Ala Glu Asp Trp
                325                 330                 335

Lys Pro Gln Ser Ser His Trp Gly Ala Ala Leu Lys Asp Leu His Arg
            340                 345                 350

Ile Tyr Arg Pro Met Ile Gly Lys Leu Lys Phe Phe Ile Asp Glu Lys
        355                 360                 365

Tyr Lys Ile Ala Asp Thr Ser Glu Gly Gly Ile Tyr Leu Gly Phe Tyr
    370                 375                 380

Glu Lys Gln Glu Val Ala Val Lys Thr Phe Cys Glu Gly Ser Pro Arg
385                 390                 395                 400

Ala Gln Arg Glu Val Ser Cys Leu Gln Ser Ser Arg Glu Asn Ser His
                405                 410                 415

Leu Val Thr Phe Tyr Gly Ser Glu Ser His Arg Gly His Leu Phe Val
            420                 425                 430

Cys Val Thr Leu Cys Glu Gln Thr Leu Glu Ala Cys Leu Asp Val His
        435                 440                 445

Arg Gly Glu Asp Val Glu Asn Glu Glu Asp Glu Phe Ala Arg Asn Val
    450                 455                 460

Leu Ser Ser Ile Phe Lys Ala Val Gln Glu Leu His Leu Ser Cys Gly
465                 470                 475                 480

Tyr Thr His Gln Asp Leu Gln Pro Gln Asn Ile Leu Ile Asp Ser Lys
                485                 490                 495

Lys Ala Ala His Leu Ala Asp Phe Asp Lys Ser Ile Lys Trp Ala Gly
            500                 505                 510

Asp Pro Gln Glu Val Lys Arg Asp Leu Glu Asp Leu Gly Arg Leu Val
        515                 520                 525

Leu Tyr Val Val Lys Lys Gly Ser Ile Ser Phe Glu Asp Leu Lys Ala
    530                 535                 540

Gln Ser Asn Glu Glu Val Val Gln Leu Ser Pro Asp Glu Glu Thr Lys
545                 550                 555                 560

Asp Leu Ile His Arg Leu Phe His Pro Gly Glu His Val Arg Asp Cys
                565                 570                 575

Leu Ser Asp Leu Leu Gly His Pro Phe Phe Trp Thr Trp Glu Ser Arg
            580                 585                 590

Tyr Arg Thr Leu Arg Asn Val Gly Asn Glu Ser Asp Ile Lys Thr Arg
        595                 600                 605

Lys Ser Glu Ser Glu Ile Leu Arg Leu Leu Gln Pro Gly Pro Ser Glu
    610                 615                 620

His Ser Lys Ser Phe Asp Lys Trp Thr Thr Lys Ile Asn Glu Cys Val
625                 630                 635                 640

Met Lys Lys Met Asn Lys Phe Tyr Glu Lys Arg Gly Asn Phe Tyr Gln
                645                 650                 655

Asn Thr Val Gly Asp Leu Leu Lys Phe Ile Arg Asn Leu Gly Glu His
            660                 665                 670

Ile Asp Glu Glu Lys His Lys Lys Met Lys Leu Lys Ile Gly Asp Pro
        675                 680                 685

Ser Leu Tyr Phe Gln Lys Thr Phe Pro Asp Leu Val Ile Tyr Val Tyr
```

```
    690                 695                 700

Thr Lys Leu Gln Asn Thr Glu Tyr Arg Lys His Phe Pro Gln Thr His
705                 710                 715                 720

Ser Pro Asn Lys Pro Gln Cys Asp Gly Ala Gly Gly Ala Ser Gly Leu
                725                 730                 735

Ala Ser Pro Gly Cys
            740


<210> SEQ ID NO 89
<211> LENGTH: 357
<212> TYPE: PRT
<213> ORGANISM: Homo sapiens

<400> SEQUENCE: 89

Met Met Ala Arg Leu Leu Arg Thr Ser Phe Ala Leu Leu Phe Leu Gly
1               5                   10                  15

Leu Phe Gly Val Leu Gly Ala Ala Thr Ile Ser Cys Arg Asn Glu Glu
            20                  25                  30

Gly Lys Ala Val Asp Trp Phe Thr Phe Tyr Lys Leu Pro Lys Arg Gln
        35                  40                  45

Asn Lys Glu Ser Gly Glu Thr Gly Leu Glu Tyr Leu Tyr Leu Asp Ser
    50                  55                  60

Thr Thr Arg Ser Trp Arg Lys Ser Glu Gln Leu Met Asn Asp Thr Lys
65                  70                  75                  80

Ser Val Leu Gly Arg Thr Leu Gln Gln Leu Tyr Glu Ala Tyr Ala Ser
                85                  90                  95

Lys Ser Asn Asn Thr Ala Tyr Leu Ile Tyr Asn Asp Gly Val Pro Lys
            100                 105                 110

Pro Val Asn Tyr Ser Arg Lys Tyr Gly His Thr Lys Gly Leu Leu Leu
        115                 120                 125

Trp Asn Arg Val Gln Gly Phe Trp Leu Ile His Ser Ile Pro Gln Phe
    130                 135                 140

Pro Pro Ile Pro Glu Glu Gly Tyr Asp Tyr Pro Pro Thr Gly Arg Arg
145                 150                 155                 160

Asn Gly Gln Ser Gly Ile Cys Ile Thr Phe Lys Tyr Asn Gln Tyr Glu
                165                 170                 175

Ala Ile Asp Ser Gln Leu Leu Val Cys Asn Pro Asn Val Tyr Ser Cys
            180                 185                 190

Ser Ile Pro Ala Thr Phe His Gln Glu Leu Ile His Met Pro Gln Leu
        195                 200                 205

Cys Thr Arg Ala Ser Ser Ser Glu Ile Pro Gly Arg Leu Leu Thr Thr
    210                 215                 220

Leu Gln Ser Ala Gln Gly Gln Lys Phe Leu His Phe Ala Lys Ser Asp
225                 230                 235                 240

Ser Phe Leu Asp Asp Ile Phe Ala Ala Trp Met Ala Gln Arg Leu Lys
                245                 250                 255

Thr His Leu Leu Thr Glu Thr Trp Gln Arg Lys Arg Gln Glu Leu Pro
            260                 265                 270

Ser Asn Cys Ser Leu Pro Tyr His Val Tyr Asn Ile Lys Ala Ile Lys
        275                 280                 285

Leu Ser Arg His Ser Tyr Phe Ser Ser Tyr Gln Asp His Ala Lys Trp
    290                 295                 300

Cys Ile Ser Gln Lys Gly Thr Lys Asn Arg Trp Thr Cys Ile Gly Asp
305                 310                 315                 320
```

Leu Asn Arg Ser Pro His Gln Ala Phe Arg Ser Gly Gly Phe Ile Cys
325 330 335

Thr Gln Asn Trp Gln Ile Tyr Gln Ala Phe Gln Gly Leu Val Leu Tyr
340 345 350

Tyr Glu Ser Cys Lys
355

<210> SEQ ID NO 90
<211> LENGTH: 743
<212> TYPE: PRT
<213> ORGANISM: Artificial Sequence
<220> FEATURE:
<223> OTHER INFORMATION: PHP.eB capsid

<400> SEQUENCE: 90

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Gln Pro
20 25 30

Lys Ala Asn Gln Gln His Gln Asp Asn Ala Arg Gly Leu Val Leu Pro
35 40 45

Gly Tyr Lys Tyr Leu Gly Pro Gly Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Leu Leu Glu Pro
115 120 125

Leu Gly Leu Val Glu Glu Ala Ala Lys Thr Ala Pro Gly Lys Lys Arg
130 135 140

Pro Val Glu Gln Ser Pro Gln Glu Pro Asp Ser Ser Ala Gly Ile Gly
145 150 155 160

Lys Ser Gly Ala Gln Pro Ala Lys Lys Arg Leu Asn Phe Gly Gln Thr
165 170 175

Gly Asp Thr Glu Ser Val Pro Asp Pro Gln Pro Ile Gly Glu Pro Pro
180 185 190

Ala Ala Pro Ser Gly Val Gly Ser Leu Thr Met Ala Ser Gly Gly Gly
195 200 205

Ala Pro Val Ala Asp Asn Asn Glu Gly Ala Asp Gly Val Gly Ser Ser
210 215 220

Ser Gly Asn Trp His Cys Asp Ser Gln Trp Leu Gly Asp Arg Val Ile
225 230 235 240

Thr Thr Ser Thr Arg Thr Trp Ala Leu Pro Thr Tyr Asn Asn His Leu
245 250 255

Tyr Lys Gln Ile Ser Asn Ser Thr Ser Gly Gly Ser Ser Asn Asp Asn
260 265 270

Ala Tyr Phe Gly Tyr Ser Thr Pro Trp Gly Tyr Phe Asp Phe Asn Arg
275 280 285

Phe His Cys His Phe Ser Pro Arg Asp Trp Gln Arg Leu Ile Asn Asn
290 295 300

Asn Trp Gly Phe Arg Pro Lys Arg Leu Asn Phe Lys Leu Phe Asn Ile
305 310 315 320

```
Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Asp Gly Thr Leu Ala Val
            580                 585                 590

Pro Phe Lys Ala Gln Ala Gln Thr Gly Trp Val Gln Asn Gln Gly Ile
        595                 600                 605

Leu Pro Gly Met Val Trp Gln Asp Arg Asp Val Tyr Leu Gln Gly Pro
    610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Pro Gln Ile Leu Ile
                645                 650                 655

Lys Asn Thr Pro Val Pro Ala Asp Pro Pro Thr Ala Phe Asn Lys Asp
            660                 665                 670

Lys Leu Asn Ser Phe Ile Thr Gln Tyr Ser Thr Gly Gln Val Ser Val
        675                 680                 685

Glu Ile Glu Trp Glu Leu Gln Lys Glu Asn Ser Lys Arg Trp Asn Pro
    690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
                725                 730                 735

Arg Tyr Leu Thr Arg Asn Leu
```

740

<210> SEQ ID NO 91
<211> LENGTH: 7
<212> TYPE: PRT
<213> ORGANISM: Artificial Sequence
<220> FEATURE:
<223> OTHER INFORMATION: AAV-BR1

<400> SEQUENCE: 91

Asn Arg Gly Thr Glu Trp Asp
1               5

<210> SEQ ID NO 92
<211> LENGTH: 7
<212> TYPE: PRT
<213> ORGANISM: Artificial Sequence
<220> FEATURE:
<223> OTHER INFORMATION: AAV-PHP.S

<400> SEQUENCE: 92

Gln Ala Val Arg Thr Ser Leu
1               5

<210> SEQ ID NO 93
<211> LENGTH: 7
<212> TYPE: PRT
<213> ORGANISM: Artificial Sequence
<220> FEATURE:
<223> OTHER INFORMATION: AAV-PHP.B

<400> SEQUENCE: 93

Thr Leu Ala Val Pro Phe Lys
1               5

<210> SEQ ID NO 94
<211> LENGTH: 7
<212> TYPE: PRT
<213> ORGANISM: Artificial Sequence
<220> FEATURE:
<223> OTHER INFORMATION: AAV-PPS

<400> SEQUENCE: 94

Asp Ser Pro Ala His Pro Ser
1               5

<210> SEQ ID NO 95
<211> LENGTH: 4398
<212> TYPE: DNA
<213> ORGANISM: Artificial Sequence
<220> FEATURE:
<223> OTHER INFORMATION: rAAV: hI56core-minBglobin-SYFP2-WPRE3-BGHpA
      bottom strand

<400> SEQUENCE: 95
acatgtgagc aaaaggccag caaaaggcca ggaaccgtaa aaaggccgcg ttgctggcgt      60
ttttccatag gctccgcccc cctgacgagc atcacaaaaa tcgacgctca agtcagaggt     120
ggcgaaaccc gacaggacta taaagatacc aggcgtttcc ccctggaagc tccctcgtgc     180
gctctcctgt tccgaccctg ccgcttaccg gatacctgtc cgcctttctc ccttcgggaa     240
gcgtggcgct ttctcatagc tcacgctgta ggtatctcag ttcggtgtag gtcgttcgct     300
ccaagctggg ctgtgtgcac gaaccccccg ttcagcccga ccgctgcgcc ttatccggta     360
actatcgtct tgagtccaac ccggtaagac acgacttatc gccactggca gcagccactg     420

```
gtaacaggat tagcagagcg aggtatgtag gcggtgctac agagttcttg aagtggtggc    480
ctaactacgg ctacactaga aggacagtat ttggtatctg cgctctgctg aagccagtta    540
ccttcggaaa aagagttggt agctcttgat ccggcaaaca aaccaccgct ggtagcggtg    600
gtttttttgt ttgcaagcag cagattacgc gcagaaaaaa aggatctcaa gaagatcctt    660
tgatcttttc tacggggtct gacgctcagt ggaacgaaaa ctcacgttaa gggattttgg    720
tcatgagatt atcaaaaagg atcttcacct agatcctttt aaattaaaaa tgaagtttta    780
aatcaatcta aagtatatat gagtaaactt ggtctgacag ttaccaatgc ttaatcagtg    840
aggcacctat ctcagcgatc tgtctatttc gttcatccat agttgcctga ctccccgtcg    900
tgtagataac tacgatacgg gagggcttac catctggccc cagtgctgca atgataccgc    960
gagacccacg ctcaccggct ccagatttat cagcaataaa ccagccagcc ggaagggccg   1020
agcgcagaag tggtcctgca actttatccg cctccatcca gtctattaat tgttgccggg   1080
aagctagagt aagtagttcg ccagttaata gtttgcgcaa cgttgttgcc attgctacag   1140
gcatcgtggt gtcacgctcg tcgtttggta tggcttcatt cagctccggt tcccaacgat   1200
caaggcgagt tacatgatcc cccatgttgt gcaaaaaagc ggttagctcc ttcggtcctc   1260
cgatcgttgt cagaagtaag ttggccgcag tgttatcact catggttatg gcagcactgc   1320
ataattctct tactgtcatg ccatccgtaa gatgcttttc tgtgactggt gagtactcaa   1380
ccaagtcatt ctgagaatag tgtatgcggc gaccgagttg ctcttgcccg gcgtcaatac   1440
gggataatac cgcgccacat agcagaactt taaaagtgct catcattgga aaacgttctt   1500
cggggcgaaa actctcaagg atcttaccgc tgttgagatc cagttcgatg taacccactc   1560
gtgcacccaa ctgatcttca gcatctttta ctttcaccag cgtttctggg tgagcaaaaa   1620
caggaaggca aaatgccgca aaaaagggaa taagggcgac acggaaatgt tgaatactca   1680
tactcttcct ttttcaatat tattgaagca tttatcaggg ttattgtctc atgagcggat   1740
acatatttga atgtatttag aaaaataaac aaataggggt tccgcgcaca tttccccgaa   1800
aagtgccacc tgacgtctaa gaaaccatta ttatcatgac attaacctat aaaaataggc   1860
gtatcacgag gccctttcgt ctcgcgcgtt tcggtgatga cggtgaaaac ctctgacaca   1920
tgcagctccc ggagacggtc acagcttgtc tgtaagcgga tgccgggagc agacaagccc   1980
gtcagggcgc gtcagcgggt gttggcgggt gtcggggctg gcttaactat gcggcatcag   2040
agcagattgt actgagagtg caccataaaa ttgtaaacgt taatattttg ttaaaattcg   2100
cgttaaattt ttgttaaatc agctcatttt ttaaccaata ggccgaaatc ggcaaaatcc   2160
cttataaatc aaaagaatag cccgagatag ggttgagtgt tgttccagtt tggaacaaga   2220
gtccactatt aaagaacgtg gactccaacg tcaaagggcg aaaaaccgtc tatcagggcg   2280
atggcccact acgtgaacca tcacccaaat caagtttttt ggggtcgagg tgccgtaaag   2340
cactaaatcg gaaccctaaa gggagccccc gatttagagc ttgacgggga aagccggcga   2400
acgtggcgag aaaggaaggg aagaaagcga aaggagcggg cgctagggcg ctggcaagtg   2460
tagcggtcac gctgcgcgta accaccacac ccgccgcgct taatgcgccg ctacagggcg   2520
cgtactatgg ttgctttgac gtatgcggtg tgaaataccg cacagatgcg taaggagaaa   2580
ataccgcatc aggcgcccct gcaggcagct gcgcgctcgc tcgctcactg aggccgcccg   2640
ggcaaagccc gggcgtcggg cgacctttgg tcgcccggcc tcagtgagcg agcgagcgcg   2700
cagagaggga gtggccaact ccatcactag gggttcctgc ggccgctcgg tccgcacgtg   2760
agatctcatg cctgctattg tcttcccaat cctcccctt gctgtcctgc cccaccccac   2820
```

cccccagaat agaatgacac ctactcagac aatgcgatgc aatttcctca ttttattagg 2880
aaaggacagt gggagtggca ccttccaggg tcaaggaagg cacgggggag gggcaaacaa 2940
cagatggctg gcaactagaa ggcacagtcg aagatctctc gagccacgga attgtcagtg 3000
cccaacagcc gagcccctgt ccagcagcgg gcaaggcagg cggcgatgag ttccgccgtg 3060
gcaagaacta accaggattt atacaaggag gagaaaatga aagccatacg ggaagcaata 3120
gcatgataca aaggcattaa agcagcgtat ccacatagcg taaaaggagc aacatagtta 3180
agaataccag tcaatctttc acaaattttg taatccagag gttgattatg atatcgaatt 3240
cgcggccgcg gcgcgccgtc gacttacttg tacagctcgt ccatgccgag agtgatcccg 3300
gcggcggtca cgaactccag caggaccatg tgatcgcgct tctcgttggg gtctttgctc 3360
agcttggact ggtagctcag gtagtggttg tcgggcagca gcacggggcc gtcgccgatg 3420
ggggtgttct gctggtagtg gtcggcgagc tgcacgccgc cgtcctcgat gttgtggcgg 3480
atcttgaagt tggccttgat gccgttcttc tgcttgtcgg cggtgatata gacgttgtgg 3540
ctgttgtagt tgtactccag cttgtgcccc aggatgttgc cgtcctcctt gaagtcgatg 3600
cccttcagct cgatgcggtt caccagggtg tcgccctcga acttcacctc ggcgcgggtc 3660
ttgtagttgc cgtcgtcctt gaagaagatg gtgcgctcct ggacgtagcc ttcgggcatg 3720
gcggacttga agaagtcgtg ctgcttcatg tggtcggggt agcgggcgaa gcactgcacg 3780
ccgtagccca gggtggtcac gagggtgggc cagggcacgg gcagcttgcc ggtggtgcag 3840
atcagcttca gggtcagctt gccgtaggtg gcatcgccct cgccctcgcc ggacacgctg 3900
aacttgtggc cgtttacgtc gccgtccagc tcgaccagga tgggcaccac cccggtgaac 3960
agctcctcgc ccttgctcac catggtggcg accggtagcg ctagcttcga aagatctgga 4020
tcccagaagc aaatgtaagc aatagatggc tctgccctga cttttatgcc cagcccgagc 4080
tccctgcagg tccattctct taaatgcagc cataattaga gtaatttttc atgtagcccg 4140
ctgattacag cgtttttacc gtcaaagata attacctgta attttcttcc acttttaata 4200
ctaaaaagcc atctttattt agattcagga acaggaaagg cgaacgcgtg cggccgcagg 4260
aacccctagt gatggagttg gccactccct ctctgcgcgc tcgctcgctc actgaggccg 4320
ggcgaccaaa ggtcgcccga cgcccgggct ttgcccgggc ggcctcagtg agcgagcgag 4380
cgcgcagctg cctgcagg 4398

<210> SEQ ID NO 96
<211> LENGTH: 4635
<212> TYPE: DNA
<213> ORGANISM: Artificial Sequence
<220> FEATURE:
<223> OTHER INFORMATION: rAAV: 3XhI56core-minBglobin-SYFP2-WPRE3-BGHpA
bottom strand

<400> SEQUENCE: 96
acatgtgagc aaaaggccag caaaaggcca ggaaccgtaa aaaggccgcg ttgctggcgt 60
ttttccatag gctccgcccc cctgacgagc atcacaaaaa tcgacgctca agtcagaggt 120
ggcgaaaccc gacaggacta taaagatacc aggcgtttcc ccctggaagc tccctcgtgc 180
gctctcctgt tccgaccctg ccgcttaccg gatacctgtc cgcctttctc ccttcgggaa 240
gcgtggcgct ttctcatagc tcacgctgta ggtatctcag ttcggtgtag gtcgttcgct 300
ccaagctggg ctgtgtgcac gaaccccccg ttcagcccga ccgctgcgcc ttatccggta 360
actatcgtct tgagtccaac ccggtaagac acgacttatc gccactggca gcagccactg 420

```
gtaacaggat tagcagagcg aggtatgtag gcggtgctac agagttcttg aagtggtggc    480
ctaactacgg ctacactaga aggacagtat ttggtatctg cgctctgctg aagccagtta    540
ccttcggaaa aagagttggt agctcttgat ccggcaaaca aaccaccgct ggtagcggtg    600
gtttttttgt ttgcaagcag cagattacgc gcagaaaaaa aggatctcaa gaagatcctt    660
tgatcttttc tacggggtct gacgctcagt ggaacgaaaa ctcacgttaa gggattttgg    720
tcatgagatt atcaaaaagg atcttcacct agatcctttt aaattaaaaa tgaagtttta    780
aatcaatcta aagtatatat gagtaaactt ggtctgacag ttaccaatgc ttaatcagtg    840
aggcacctat ctcagcgatc tgtctatttc gttcatccat agttgcctga ctccccgtcg    900
tgtagataac tacgatacgg gagggcttac catctggccc cagtgctgca atgataccgc    960
gagacccacg ctcaccggct ccagatttat cagcaataaa ccagccagcc ggaagggccg   1020
agcgcagaag tggtcctgca actttatccg cctccatcca gtctattaat tgttgccggg   1080
aagctagagt aagtagttcg ccagttaata gtttgcgcaa cgttgttgcc attgctacag   1140
gcatcgtggt gtcacgctcg tcgtttggta tggcttcatt cagctccggt tcccaacgat   1200
caaggcgagt tacatgatcc cccatgttgt gcaaaaaagc ggttagctcc ttcggtcctc   1260
cgatcgttgt cagaagtaag ttggccgcag tgttatcact catggttatg gcagcactgc   1320
ataattctct tactgtcatg ccatccgtaa gatgcttttc tgtgactggt gagtactcaa   1380
ccaagtcatt ctgagaatag tgtatgcggc gaccgagttg ctcttgcccg gcgtcaatac   1440
gggataatac cgcgccacat agcagaactt taaaagtgct catcattgga aaacgttctt   1500
cggggcgaaa actctcaagg atcttaccgc tgttgagatc cagttcgatg taacccactc   1560
gtgcacccaa ctgatcttca gcatctttta ctttcaccag cgtttctggg tgagcaaaaa   1620
caggaaggca aaatgccgca aaaaagggaa taagggcgac acggaaatgt tgaatactca   1680
tactcttcct ttttcaatat tattgaagca tttatcaggg ttattgtctc atgagcggat   1740
acatatttga atgtatttag aaaaataaac aaataggggt tccgcgcaca tttccccgaa   1800
aagtgccacc tgacgtctaa gaaaccatta ttatcatgac attaacctat aaaaataggc   1860
gtatcacgag gccctttcgt ctcgcgcgtt tcggtgatga cggtgaaaac ctctgacaca   1920
tgcagctccc ggagacggtc acagcttgtc tgtaagcgga tgccgggagc agacaagccc   1980
gtcagggcgc gtcagcgggt gttggcgggt gtcggggctg gcttaactat gcggcatcag   2040
agcagattgt actgagagtg caccataaaa ttgtaaacgt taatattttg ttaaaattcg   2100
cgttaaattt ttgttaaatc agctcatttt ttaaccaata ggccgaaatc ggcaaaatcc   2160
cttataaatc aaaagaatag cccgagatag ggttgagtgt tgttccagtt tggaacaaga   2220
gtccactatt aaagaacgtg gactccaacg tcaaagggcg aaaaaccgtc tatcagggcg   2280
atggcccact acgtgaacca tcacccaaat caagtttttt ggggtcgagg tgccgtaaag   2340
cactaaatcg gaaccctaaa gggagccccc gatttagagc ttgacgggga aagccggcga   2400
acgtggcgag aaaggaaggg aagaaagcga aaggagcggg cgctagggcg ctggcaagtg   2460
tagcggtcac gctgcgcgta accaccacac ccgccgcgct taatgcgccg ctacagggcg   2520
cgtactatgg ttgctttgac gtatgcggtg tgaaataccg cacagatgcg taaggagaaa   2580
ataccgcatc aggcgcccct gcaggcagct gcgcgctcgc tcgctcactg aggccgcccg   2640
ggcaaagccc gggcgtcggg cgacctttgg tcgcccggcc tcagtgagcg agcgagcgcg   2700
cagagaggga gtggccaact ccatcactag gggttcctgc ggccgctcgg tccgcacgtg   2760
```

```
agatctcatg cctgctattg tcttcccaat cctccccctt gctgtcctgc cccaccccac   2820

cccccagaat agaatgacac ctactcagac aatgcgatgc aatttcctca ttttattagg   2880

aaaggacagt gggagtggca ccttccaggg tcaaggaagg cacgggggag ggcaaacaa    2940

cagatggctg gcaactagaa ggcacagtcg aagatctctc gagccacgga attgtcagtg   3000

cccaacagcc gagcccctgt ccagcagcgg gcaaggcagg cggcgatgag ttccgccgtg   3060

gcaagaacta accaggattt atacaaggag gagaaaatga aagccatacg ggaagcaata   3120

gcatgataca aaggcattaa agcagcgtat ccacatagcg taaaaggagc aacatagtta   3180

agaataccag tcaatctttc acaaattttg taatccagag gttgattatg atatcgaatt   3240

cgcggccgcg gcgcgccgtc gacttacttg tacagctcgt ccatgccgag agtgatcccg   3300

gcggcggtca cgaactccag caggaccatg tgatcgcgct tctcgttggg gtctttgctc   3360

agcttggact ggtagctcag gtagtggttg tcgggcagca gcacggggcc gtcgccgatg   3420

ggggtgttct gctggtagtg gtcggcgagc tgcacgccgc cgtcctcgat gttgtggcgg   3480

atcttgaagt tggccttgat gccgttcttc tgcttgtcgg cggtgatata gacgttgtgg   3540

ctgttgtagt tgtactccag cttgtgcccc aggatgttgc cgtcctcctt gaagtcgatg   3600

cccttcagct cgatgcggtt caccagggtg tcgccctcga acttcacctc ggcgcgggtc   3660

ttgtagttgc cgtcgtcctt gaagaagatg gtgcgctcct ggacgtagcc ttcgggcatg   3720

gcggacttga agaagtcgtg ctgcttcatg tggtcggggt agcgggcgaa gcactgcacg   3780

ccgtagccca gggtggtcac gagggtgggc cagggcacgg gcagcttgcc ggtggtgcag   3840

atcagcttca gggtcagctt gccgtaggtg gcatcgccct cgccctcgcc ggacacgctg   3900

aacttgtggc cgtttacgtc gccgtccagc tcgaccagga tgggcaccac cccggtgaac   3960

agctcctcgc ccttgctcac catggtggcg accggtagcg ctagcttcga aagatctgga   4020

tcccagaagc aaatgtaagc aatagatggc tctgccctga cttttatgcc cagcccgagc   4080

tccattctct taaatgcagc cataattaga gtaatttttc atgtagcccg ctgattacag   4140

cgtttttacc gtcaaagata attacctgta attttcttcc acttttaata ctaaaaagcc   4200

atctttattt agccattctc ttaaatgcag ccataattag agtaattttt catgtagccc   4260

gctgattaca gcgtttttac cgtcaaagat aattacctgt aattttcttc cacttttaat   4320

actaaaaagc catctttatt tagccattct cttaaatgca gccataatta gagtaatttt   4380

tcatgtagcc cgctgattac agcgttttta ccgtcaaaga taattacctg taattttctt   4440

ccacttttaa tactaaaaag ccatctttat ttagggtacc acgcgtgcgg ccgcaggaac   4500

ccctagtgat ggagttggcc actccctctc tgcgcgctcg ctcgctcact gaggccgggc   4560

gaccaaaggt cgcccgacgc ccgggctttg cccgggcggc ctcagtgagc gagcgagcgc   4620

gcagctgcct gcagg                                                    4635
```

<210> SEQ ID NO 97
<211> LENGTH: 4841
<212> TYPE: DNA
<213> ORGANISM: Artificial Sequence
<220> FEATURE:
<223> OTHER INFORMATION: rAAV: hI56i-minBglobin-SYFP2-WPRE3-BGHpA bottom strand

<400> SEQUENCE: 97

```
ctagatctcg agagcttggc gtaatcatgg tcatagctgt ttcctgtgtg aaattgttat     60

ccgctcacaa ttccacacaa catacgagcc ggaagcataa agtgtaaagc ctggggtgcc    120
```

```
taatgagtga gctaactcac attaattgcg ttgcgctcac tgcccgcttt ccagtcggga    180
aacctgtcgt gccagctgca ttaatgaatc ggccaacgcg cggggagagg cggtttgcgt    240
attgggcgct cttccgcttc ctcgctcact gactcgctgc gctcggtcgt tcggctgcgg    300
cgagcggtat cagctcactc aaaggcggta atacggttat ccacagaatc aggggataac    360
gcaggaaaga acatgtgagc aaaaggccag caaaaggcca ggaaccgtaa aaaggccgcg    420
ttgctggcgt ttttccatag gctccgcccc cctgacgagc atcacaaaaa tcgacgctca    480
agtcagaggt ggcgaaaccc gacaggacta taaagatacc aggcgtttcc ccctggaagc    540
tccctcgtgc gctctcctgt tccgaccctg ccgcttaccg gatacctgtc cgcctttctc    600
ccttcgggaa gcgtggcgct ttctcatagc tcacgctgta ggtatctcag ttcggtgtag    660
gtcgttcgct ccaagctggg ctgtgtgcac gaaccccccg ttcagcccga ccgctgcgcc    720
ttatccggta actatcgtct tgagtccaac ccggtaagac acgacttatc gccactggca    780
gcagccactg gtaacaggat tagcagagcg aggtatgtag gcggtgctac agagttcttg    840
aagtggtggc ctaactacgg ctacactaga agaacagtat ttggtatctg cgctctgctg    900
aagccagtta ccttcggaaa aagagttggt agctcttgat ccggcaaaca aaccaccgct    960
ggtagcggtg gtttttttgt ttgcaagcag cagattacgc gcagaaaaaa aggatctcaa   1020
gaagatcctt tgatcttttc tacggggtct gacgctcagt ggaacgaaaa ctcacgttaa   1080
gggattttgg tcatgagatt atcaaaaagg atcttcacct agatcctttt aaattaaaaa   1140
tgaagtttta aatcaatcta aagtatatat gagtaaactt ggtctgacag ttaccaatgc   1200
ttaatcagtg aggcacctat ctcagcgatc tgtctatttc gttcatccat agttgcctga   1260
ctccccgtcg tgtagataac tacgatacgg gagggcttac catctggccc cagtgctgca   1320
atgataccgc gagacccacg ctcaccggct ccagatttat cagcaataaa ccagccagcc   1380
ggaagggccg agcgcagaag tggtcctgca actttatccg cctccatcca gtctattaat   1440
tgttgccggg aagctagagt aagtagttcg ccagttaata gtttgcgcaa cgttgttgcc   1500
attgctacag gcatcgtggt gtcacgctcg tcgtttggta tggcttcatt cagctccggt   1560
tcccaacgat caaggcgagt tacatgatcc cccatgttgt gcaaaaaagc ggttagctcc   1620
ttcggtcctc cgatcgttgt cagaagtaag ttggccgcag tgttatcact catggttatg   1680
gcagcactgc ataattctct tactgtcatg ccatccgtaa gatgcttttc tgtgactggt   1740
gagtactcaa ccaagtcatt ctgagaatag tgtatgcggc gaccgagttg ctcttgcccg   1800
gcgtcaatac gggataatac cgcgccacat agcagaactt taaaagtgct catcattgga   1860
aaacgttctt cggggcgaaa actctcaagg atcttaccgc tgttgagatc cagttcgatg   1920
taacccactc gtgcacccaa ctgatcttca gcatctttta ctttcaccag cgtttctggg   1980
tgagcaaaaa caggaaggca aaatgccgca aaaaagggaa taagggcgac acggaaatgt   2040
tgaatactca tactcttcct ttttcaatat tattgaagca tttatcaggg ttattgtctc   2100
atgagcggat acatatttga atgtatttag aaaaataaac aaataggggt tccgcgcaca   2160
tttccccgaa aagtgccacc tgacgtctaa gaaaccatta ttatcatgac attaacctat   2220
aaaaataggc gtatcacgag gccctttcgt ctcgcgcgtt tcggtgatga cggtgaaaac   2280
ctctgacaca tgcagctccc ggagacggtc acagcttgtc tgtaagcgga tgccgggagc   2340
agacaagccc gtcagggcgc gtcagcgggt gttggcgggt gtcggggctg gcttaactat   2400
gcggcatcag agcagattgt actgagagtg caccatatgc ggtgtgaaat accgcacaga   2460
tgcgtaagga gaaaataccg catcaggcgc cattcgccat tcaggctgcg caactgttgg   2520
```

```
gaagggcgat cggtgcgggc ctcttcgcta ttacgccagc tggcgaaagg gggatgtgct   2580
gcaaggcgat taagttgggt aacgccaggg ttttcccagt cacgacgttg taaaacgacg   2640
gccagtgaat tgtcgacgca tgcgggcccg gatctgtccc tctctgcgcg ctcgctcgct   2700
cactgaggcc gcccgggcaa agcccgggcg tcgggcgacc tttggtcgcc cggcctcagt   2760
gagcgagcga gcgcgcagag agggagtgga ctagtcatgc ctgctattgt cttcccaatc   2820
ctcccccttg ctgtcctgcc ccaccccacc ccccagaata gaatgacacc tactcagaca   2880
atgcgatgca atttcctcat tttattagga aaggacagtg ggagtggcac cttccagggt   2940
caaggaaggc acgggggagg ggcaaacaac agatggctgg caactagaag gcacagtcgc   3000
tcgagccacg gaattgtcag tgcccaacag ccgagcccct gtccagcagc gggcaaggca   3060
ggcggcgatg agttccgccg tggcaagaac taaccaggat ttatacaagg aggagaaaat   3120
gaaagccata cgggaagcaa tagcatgata caaaggcatt aaagcagcgt atccacatag   3180
cgtaaaagga gcaacatagt taagaatacc agtcaatctt tcacaaattt tgtaatccag   3240
aggttgatta tgatatcgaa ttcgcggccg cggcgcgccg tcgacttact tgtacagctc   3300
gtccatgccg agagtgatcc cggcggcggt cacgaactcc agcaggacca tgtgatcgcg   3360
cttctcgttg gggtctttgc tcagcttgga ctggtagctc aggtagtggt tgtcgggcag   3420
cagcacgggg ccgtcgccga tgggggtgtt ctgctggtag tggtcggcga gctgcacgcc   3480
gccgtcctcg atgttgtggc ggatcttgaa gttggccttg atgccgttct tctgcttgtc   3540
ggcggtgata tagacgttgt ggctgttgta gttgtactcc agcttgtgcc ccaggatgtt   3600
gccgtcctcc ttgaagtcga tgcccttcag ctcgatgcgg ttcaccaggg tgtcgccctc   3660
gaacttcacc tcggcgcggg tcttgtagtt gccgtcgtcc ttgaagaaga tggtgcgctc   3720
ctggacgtag ccttcgggca tggcggactt gaagaagtcg tgctgcttca tgtggtcggg   3780
gtagcgggcg aagcactgca cgccgtagcc cagggtggtc acgagggtgg gccagggcac   3840
gggcagcttg ccggtggtgc agatcagctt cagggtcagc ttgccgtagg tggcatcgcc   3900
ctcgccctcg ccggacacgc tgaacttgtg gccgtttacg tcgccgtcca gctcgaccag   3960
gatgggcacc accccggtga acagctcctc gcccttgctc accatggtgg cgaccggtag   4020
cgctagcttc gaaagatctg gatcccagaa gcaaatgtaa gcaatagatg gctctgccct   4080
gacttttatg cccagcccga gctccctact gtgaaacttt gggttcgtag ctccccagga   4140
tcaattctga acaaagcctc cagctgcagt gccatccaat ttgaagcaga cattggggac   4200
aatttaaggt ttttatccac aagaaggttt ttttccattc tcttaaatgc agccataatt   4260
agagtaattt ttcatgtagc ccgctgatta cagcgttttt accgtcaaag ataattacct   4320
gtaattttct tccactttta atactaaaaa gccatcttta tttagattca ggaacaggaa   4380
aggcgaaaca aaagagggaa attattctgt tattcataca caaattgcag agacgtagga   4440
cctaaaattg aaaattaacc aaaattataa tgctgaaaag aatggaagag gctgcagaag   4500
tacagctggt agtggggctt tgctgaatta ttcaaattac gttagggaga atgctaccat   4560
acatcgaaac caacactaat tttcgttaa aaaaaattca ccagatgcat gccaaaccac   4620
tgtgagtgca tagagctcgg tacctatacg cgtcctaggt cacgactcca cccctccagg   4680
aacccctagt gatggagttg gccactccct ctctgcgcgc tcgctcgctc actgaggccg   4740
cccgggcaaa gcccgggcgt cgggcgacct ttggtcgccc ggcctcagtg agcgagcgag   4800
cgcgcagaga gggagtggcc cagatccccc cgggaagctt t                        4841
```

<210> SEQ ID NO 98
<211> LENGTH: 4
<212> TYPE: PRT
<213> ORGANISM: Artificial Sequence
<220> FEATURE:
<223> OTHER INFORMATION: Sequence changed in AAV9

<400> SEQUENCE: 98

Ser Ala Gln Ala
1

<210> SEQ ID NO 99
<211> LENGTH: 1353
<212> TYPE: DNA
<213> ORGANISM: Artificial Sequence
<220> FEATURE:
<223> OTHER INFORMATION: GCaMP6m

<400> SEQUENCE: 99
atgggttctc atcatcatca tcatcatggt atggctagca tgactggtgg acagcaaatg 60
ggtcgggatc tgtacgacga tgacgataag gatctcgcca ccatggtcga ctcatcacgt 120
cgtaagtgga ataagacagg tcacgcagtc agagctatag gtcggctgag ctcactcgag 180
aacgtctata tcaaggccga caagcagaag aacggcatca aggcgaactt caagatccgc 240
cacaacatcg aggacggcgg cgtgcagctc gcctaccact accagcagaa cacccccatc 300
ggcgacggcc ccgtgctgct gcccgacaac cactacctga gcgtgcagtc caaactttcg 360
aaagacccca acgagaagcg cgatcacatg gtcctgctgg agttcgtgac cgccgccggg 420
atcactctcg gcatggacga gctgtacaag ggcggtaccg gagggagcat ggtgagcaag 480
ggcgaggagc tgttcaccgg ggtggtgccc atcctggtcg agctggacgg cgacgtaaac 540
ggccacaagt tcagcgtgtc cggcgagggt gagggcgatg ccacctacgg caagctgacc 600
ctgaagttca tctgcaccac cggcaagctg cccgtgccct ggcccaccct cgtgaccacc 660
ctgacctacg gcgtgcagtg cttcagccgc taccccgacc acatgaagca gcacgacttc 720
ttcaagtccg ccatgcccga aggctacatc caggagcgca ccatcttctt caaggacgac 780
ggcaactaca agacccgcgc cgaggtgaag ttcgagggcg acaccctggt gaaccgcatc 840
gagctgaagg gcatcgactt caaggaggac ggcaacatcc tggggcacaa gctggagtac 900
aacctgccgg accaactgac tgaagagcag atcgcagaat ttaaagaggc tttctcccta 960
tttgacaagg acggggatgg gacaataaca accaaggagc tggggacggt gatgcggtct 1020
ctggggcaga accccacaga agcagagctg caggacatga tcaatgaagt agatgccgac 1080
ggtgacggca caatcgactt ccctgagttc ctgacaatga tggcaagaaa agggagctac 1140
agggacacgg aagaagaaat tagagaagcg ttcggtgtgt ttgataagga tggcaatggc 1200
tacatcagtg cagcagagct tcgccacgtg atgacaaacc ttggagagaa gttaacagat 1260
gaagaggttg atgaaatgat cagggaagca gacatcgatg gggatggtca ggtaaactac 1320
gaagagtttg tacaaatgat gacagcgaag tga 1353

<210> SEQ ID NO 100
<211> LENGTH: 1353
<212> TYPE: DNA
<213> ORGANISM: Artificial Sequence
<220> FEATURE:
<223> OTHER INFORMATION: GCaMP6s

<400> SEQUENCE: 100

```
atgggttctc atcatcatca tcatcatggt atggctagca tgactggtgg acagcaaatg     60

ggtcgggatc tgtacgacga tgacgataag gatctcgcca ccatggtcga ctcatcacgt    120

cgtaagtgga ataagacagg tcacgcagtc agagctatag gtcggctgag ctcactcgag    180

aacgtctata tcaaggccga caagcagaag aacggcatca aggcgaactt ccacatccgc    240

cacaacatcg aggacggcgg cgtgcagctc gcctaccact accagcagaa cacccccatc    300

ggcgacggcc ccgtgctgct gcccgacaac cactacctga gcgtgcagtc caaactttcg    360

aaagacccca acgagaagcg cgatcacatg gtcctgctgg agttcgtgac cgccgccggg    420

atcactctcg gcatggacga gctgtacaag ggcggtaccg gagggagcat ggtgagcaag    480

ggcgaggagc tgttcaccgg ggtggtgccc atcctggtcg agctggacgg cgacgtaaac    540

ggccacaagt tcagcgtgtc cggcgagggt gagggcgatg ccacctacgg caagctgacc    600

ctgaagttca tctgcaccac cggcaagctg cccgtgccct ggcccaccct cgtgaccacc    660

ctgacctacg gcgtgcagtg cttcagccgc taccccgacc acatgaagca gcacgacttc    720

ttcaagtccg ccatgcccga aggctacatc caggagcgca ccatcttctt caaggacgac    780

ggcaactaca agacccgcgc cgaggtgaag ttcgagggcg acaccctggt gaaccgcatc    840

gagctgaagg gcatcgactt caaggaggac ggcaacatcc tggggcacaa gctggagtac    900

aacctgccgg accaactgac tgaagagcag atcgcagaat ttaaagaggc tttctcccta    960

tttgacaagg acggggatgg gacaataaca accaaggagc tggggacggt gatgcggtct   1020

ctggggcaga accccacaga agcagagctg caggacatga tcaatgaagt agatgccgac   1080

ggtgacggca caatcgactt ccctgagttc ctgacaatga tggcaagaaa aatgaaatac   1140

agggacacgg aagaagaaat tagagaagcg ttcggtgtgt ttgataagga tggcaatggc   1200

tacatcagtg cagcagagct tcgccacgtg atgacaaacc ttggagagaa gttaacagat   1260

gaagaggttg atgaaatgat cagggaagca gacatcgatg gggatggtca ggtaaactac   1320

gaagagtttg tacaaatgat gacagcgaag tga                                1353
```

<210> SEQ ID NO 101
<211> LENGTH: 1353
<212> TYPE: DNA
<213> ORGANISM: Artificial Sequence
<220> FEATURE:
<223> OTHER INFORMATION: GCaMP6f

<400> SEQUENCE: 101

```
atgggttctc atcatcatca tcatcatggt atggctagca tgactggtgg acagcaaatg     60

ggtcgggatc tgtacgacga tgacgataag gatctcgcca ccatggtcga ctcatcacgt    120

cgtaagtgga ataagacagg tcacgcagtc agagctatag gtcggctgag ctcactcgag    180

aacgtctata tcaaggccga caagcagaag aacggcatca aggcgaactt caagatccgc    240

cacaacatcg aggacggcgg cgtgcagctc gcctaccact accagcagaa cacccccatc    300

ggcgacggcc ccgtgctgct gcccgacaac cactacctga gcgtgcagtc caaactttcg    360

aaagacccca acgagaagcg cgatcacatg gtcctgctgg agttcgtgac cgccgccggg    420

atcactctcg gcatggacga gctgtacaag ggcggtaccg gagggagcat ggtgagcaag    480

ggcgaggagc tgttcaccgg ggtggtgccc atcctggtcg agctggacgg cgacgtaaac    540

ggccacaagt tcagcgtgtc cggcgagggt gagggcgatg ccacctacgg caagctgacc    600

ctgaagttca tctgcaccac cggcaagctg cccgtgccct ggcccaccct cgtgaccacc    660

ctgacctacg gcgtgcagtg cttcagccgc taccccgacc acatgaagca gcacgacttc    720
```

```
ttcaagtccg ccatgcccga aggctacatc caggagcgca ccatcttctt caaggacgac    780

ggcaactaca agacccgcgc cgaggtgaag ttcgagggcg acaccctggt gaaccgcatc    840

gagctgaagg gcatcgactt caaggaggac ggcaacatcc tggggcacaa gctggagtac    900

aacctgccgg accaactgac tgaagagcag atcgcagaat ttaaagagga attctcccta    960

tttgacaagg acggggatgg gacaataaca accaaggagc tggggacggt gatgcggtct   1020

ctggggcaga accccacaga agcagagctg caggacatga tcaatgaagt agatgccgac   1080

ggtgacggca caatcgactt ccctgagttc ctgacaatga tggcaagaaa aatgaaatac   1140

agggacacgg aagaagaaat tagagaagcg ttcggtgtgt ttgataagga tggcaatggc   1200

tacatcagtg cagcagagct tcgccacgtg atgacaaacc ttggagagaa gttaacagat   1260

gaagaggttg atgaaatgat cagggaagca gacatcgatg ggatggtcaa ggtaaactac   1320

gaagagtttg tacaaatgat gacagcgaag tga                                1353
```

<210> SEQ ID NO 102
<211> LENGTH: 717
<212> TYPE: PRT
<213> ORGANISM: Chlamydomonas yellowstonensis

<400> SEQUENCE: 102

```
Met Asp Thr Leu Ala Trp Val Ala Arg Glu Leu Leu Ser Ser Gly His
1               5                   10                  15

Gly Thr Asp Thr Ala Thr Asp Ser Gly His Gly Thr Asp Thr Ser Gly
            20                  25                  30

Gly His Asp Ser Ser His Asp Ala Val Ala His Asn Val Thr Leu Leu
        35                  40                  45

Ile Ala Pro Pro His Ala Gly Gly His Ala Gly Pro Thr Asp Thr Ser
    50                  55                  60

Gln Gln Ile Thr Gly Ile Asp Gly Trp Ile Ala Ile Pro Ala Gly Asp
65                  70                  75                  80

Cys Tyr Cys Ala Gly Trp Tyr Val Ser His Gly Ser Ser Phe Glu Ala
                85                  90                  95

Thr Phe Ala His Val Cys Gln Trp Ser Ile Phe Ala Val Cys Val Leu
            100                 105                 110

Ser Leu Leu Trp Tyr Ala Tyr Gln Tyr Trp Lys Ala Thr Cys Gly Trp
        115                 120                 125

Glu Glu Val Tyr Val Cys Cys Ile Glu Leu Val Phe Ile Cys Phe Glu
    130                 135                 140

Leu Tyr His Glu Phe Asp Ser Pro Cys Ser Leu Tyr Leu Ser Thr Ser
145                 150                 155                 160

Asn Val Val Asn Trp Leu Arg Tyr Ser Glu Trp Leu Leu Cys Cys Pro
                165                 170                 175

Val Ile Leu Ile His Leu Ser Asn Val Thr Gly Leu Ser Asp Asp Tyr
            180                 185                 190

Gly Arg Arg Thr Met Gly Leu Leu Val Ser Asp Ile Ala Thr Ile Val
        195                 200                 205

Phe Gly Val Thr Ala Ala Met Leu Val Asn Trp Pro Lys Ile Ile Phe
    210                 215                 220

Tyr Leu Ile Gly Phe Thr Met Cys Cys Tyr Thr Phe Phe Leu Ala Ala
225                 230                 235                 240

Lys Val Leu Ile Glu Ser Phe His Gln Val Pro Lys Gly Ile Cys Arg
                245                 250                 255
```

```
His Leu Val Lys Ala Met Ala Ile Thr Tyr Phe Val Gly Trp Ser Phe
            260                 265                 270

Phe Pro Leu Ile Phe Leu Phe Gly Gln Ser Gly Phe Lys Lys Ile Ser
        275                 280                 285

Pro Tyr Ala Asp Val Ile Ala Ser Ser Phe Gly Asp Leu Ile Ser Lys
    290                 295                 300

Asn Ala Phe Gly Met Leu Gly His Phe Leu Arg Val Lys Ile His Glu
305                 310                 315                 320

His Ile Leu Lys His Gly Asp Ile Arg Lys Thr Thr His Leu Arg Ile
                325                 330                 335

Ala Gly Glu Glu Lys Glu Val Glu Thr Phe Val Glu Glu Glu Asp Glu
            340                 345                 350

Asp Thr Ala Lys His Ser Thr Lys Glu Leu Ala Asn Arg Gly Ser Phe
        355                 360                 365

Ile Val Met Arg Asp Lys Met Lys Glu Gln Gly Ile Asp Val Arg Ala
    370                 375                 380

Ser Leu Asp Met Asp Glu Asp Glu Glu Ala Arg Thr Gly Lys Gly Lys
385                 390                 395                 400

Gly Ala Gly Ala Thr Ser Leu Val Pro Gly Arg Val Ile Leu Ala Val
                405                 410                 415

Pro Asp Ile Ser Met Val Asp Phe Phe His Asp His Phe Ala His Leu
            420                 425                 430

Gly Ala Ser Ile Glu Leu Val Pro Ala Leu Gly Val Glu Asn Thr Leu
        435                 440                 445

Leu Leu Val Gln Gln Ala Met Gln Leu Gly Gly Leu Asp Phe Val Leu
    450                 455                 460

Val His Pro Glu Phe Leu Arg Asp Arg Ser Gln Asn Gly Leu Val Ser
465                 470                 475                 480

Arg Leu Lys Met Thr Gly His Gly Val Cys Ala Phe Gly Trp Val Pro
                485                 490                 495

Ser Gly Pro Met Arg Glu Ile Ile Glu Ser Ala Gly Val Asp Gly Trp
            500                 505                 510

Leu Asp Gly Pro Ser Phe Gly Thr Gly Ile Asp Gln Glu Gln Leu Ile
        515                 520                 525

Glu Leu Ile Gly Tyr Met Gln Ala Lys Arg Lys Phe Gly Met Arg Phe
    530                 535                 540

Gly Gly Gly Gly Ala Ser Lys Ala Gly Tyr Ser Ser Asp Gly Gly Phe
545                 550                 555                 560

Gly Gly Lys Gly Met Leu Glu Met Gln Pro Ser Met Ser Gln Gly Ser
                565                 570                 575

Gly Val Pro Leu Leu Gln Gln Asn Asn Ser Met Met Arg Ala Pro Pro
            580                 585                 590

Ser Pro Met Gly Asn Met Ala Asn Asn Gly Met Met Asn Pro Met Met
        595                 600                 605

Ser Met Asn Asn Pro Met Met Gly Gly Gly Ala Val Met Met Thr Ser
    610                 615                 620

Met Gly Ser Met Gln Gln Ala Ala Asn Pro Leu Tyr Gly Ala Pro Pro
625                 630                 635                 640

Ser Pro Leu Ser Ser Gln Pro Gly Ala Gly Met Tyr Gly Ala Pro Ala
                645                 650                 655

Gln Pro Gln Met Gly Ser Gln Gly Ser Met His Gly Ser Met Tyr Gly
            660                 665                 670

Gly Ser Gln Gln Gln His Gln Gln Pro Gln Gln Ala Ala Ala Ala Pro
```

```
        675                 680                 685

Ala Ala Ala Asp Gly Gly Ser Glu Ala Glu Met Leu Lys Gln Leu Met
    690                 695                 700

Ser Glu Ile Asn Arg Leu Lys Ala Glu Leu Gly Glu Ser
705                 710                 715


<210> SEQ ID NO 103
<211> LENGTH: 310
<212> TYPE: PRT
<213> ORGANISM: Artificial Sequence
<220> FEATURE:
<223> OTHER INFORMATION: synthetic construct of Channel rhodopsin 2

<400> SEQUENCE: 103

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310
```

<210> SEQ ID NO 104
<211> LENGTH: 2009
<212> TYPE: PRT
<213> ORGANISM: Homo sapiens

<400> SEQUENCE: 104

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380
```

-continued

```
Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Gln Ala Ala Thr Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
        515                 520                 525

Ile Arg Arg Lys Gly Phe Arg Phe Ser Ile Glu Gly Asn Arg Leu Thr
    530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
    610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
        675                 680                 685

Met Arg Lys Arg Arg Ser Ser Ser Phe His Val Ser Met Asp Phe Leu
    690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro
        755                 760                 765

Phe Val Asp Leu Ala Ile Thr Ile Cys Ile Val Leu Asn Thr Leu Phe
    770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
```

```
                805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
        835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Ser Asp Cys Gln
        915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990

Ser Ser Phe Ser Ala Asp Asn Leu  Ala Ala Thr Asp Asp  Asp Asn Glu
        995                 1000                1005

Met Asn  Asn Leu Gln Ile Ala  Val Asp Arg Met His  Lys Gly Val
    1010                 1015                1020

Ala Tyr  Val Lys Arg Lys Ile  Tyr Glu Phe Ile Gln  Gln Ser Phe
    1025                 1030                1035

Ile Arg  Lys Gln Lys Ile Leu  Asp Glu Ile Lys Pro  Leu Asp Asp
    1040                 1045                1050

Leu Asn  Asn Lys Lys Asp Ser  Cys Met Ser Asn His  Thr Ala Glu
    1055                 1060                1065

Ile Gly  Lys Asp Leu Asp Tyr  Leu Lys Asp Val Asn  Gly Thr Thr
    1070                 1075                1080

Ser Gly  Ile Gly Thr Gly Ser  Ser Val Glu Lys Tyr  Ile Ile Asp
    1085                 1090                1095

Glu Ser  Asp Tyr Met Ser Phe  Ile Asn Asn Pro Ser  Leu Thr Val
    1100                 1105                1110

Thr Val  Pro Ile Ala Val Gly  Glu Ser Asp Phe Glu  Asn Leu Asn
    1115                 1120                1125

Thr Glu  Asp Phe Ser Ser Glu  Ser Asp Leu Glu Glu  Ser Lys Glu
    1130                 1135                1140

Lys Leu  Asn Glu Ser Ser Ser  Ser Ser Glu Gly Ser  Thr Val Asp
    1145                 1150                1155

Ile Gly  Ala Pro Val Glu Glu  Gln Pro Val Val Glu  Pro Glu Glu
    1160                 1165                1170

Thr Leu  Glu Pro Glu Ala Cys  Phe Thr Glu Gly Cys  Val Gln Arg
    1175                 1180                1185

Phe Lys  Cys Cys Gln Ile Asn  Val Glu Glu Gly Arg  Gly Lys Gln
    1190                 1195                1200

Trp Trp  Asn Leu Arg Arg Thr  Cys Phe Arg Ile Val  Glu His Asn
    1205                 1210                1215
```

```
Trp Phe  Glu Thr Phe Ile Val  Phe Met Ile Leu Leu  Ser Ser Gly
    1220                 1225                 1230

Ala Leu  Ala Phe Glu Asp Ile  Tyr Ile Asp Gln Arg  Lys Thr Ile
    1235                 1240                 1245

Lys Thr  Met Leu Glu Tyr Ala  Asp Lys Val Phe Thr  Tyr Ile Phe
    1250                 1255                 1260

Ile Leu  Glu Met Leu Leu Lys  Trp Val Ala Tyr Gly  Tyr Gln Thr
    1265                 1270                 1275

Tyr Phe  Thr Asn Ala Trp Cys  Trp Leu Asp Phe Leu  Ile Val Asp
    1280                 1285                 1290

Val Ser  Leu Val Ser Leu Thr  Ala Asn Ala Leu Gly  Tyr Ser Glu
    1295                 1300                 1305

Leu Gly  Ala Ile Lys Ser Leu  Arg Thr Leu Arg Ala  Leu Arg Pro
    1310                 1315                 1320

Leu Arg  Ala Leu Ser Arg Phe  Glu Gly Met Arg Val  Val Val Asn
    1325                 1330                 1335

Ala Leu  Leu Gly Ala Ile Pro  Ser Ile Met Asn Val  Leu Leu Val
    1340                 1345                 1350

Cys Leu  Ile Phe Trp Leu Ile  Phe Ser Ile Met Gly  Val Asn Leu
    1355                 1360                 1365

Phe Ala  Gly Lys Phe Tyr His  Cys Ile Asn Thr Thr  Thr Gly Asp
    1370                 1375                 1380

Arg Phe  Asp Ile Glu Asp Val  Asn Asn His Thr Asp  Cys Leu Lys
    1385                 1390                 1395

Leu Ile  Glu Arg Asn Glu Thr  Ala Arg Trp Lys Asn  Val Lys Val
    1400                 1405                 1410

Asn Phe  Asp Asn Val Gly Phe  Gly Tyr Leu Ser Leu  Leu Gln Val
    1415                 1420                 1425

Ala Thr  Phe Lys Gly Trp Met  Asp Ile Met Tyr Ala  Ala Val Asp
    1430                 1435                 1440

Ser Arg  Asn Val Glu Leu Gln  Pro Lys Tyr Glu Glu  Ser Leu Tyr
    1445                 1450                 1455

Met Tyr  Leu Tyr Phe Val Ile  Phe Ile Ile Phe Gly  Ser Phe Phe
    1460                 1465                 1470

Thr Leu  Asn Leu Phe Ile Gly  Val Ile Ile Asp Asn  Phe Asn Gln
    1475                 1480                 1485

Gln Lys  Lys Lys Phe Gly Gly  Gln Asp Ile Phe Met  Thr Glu Glu
    1490                 1495                 1500

Gln Lys  Lys Tyr Tyr Asn Ala  Met Lys Lys Leu Gly  Ser Lys Lys
    1505                 1510                 1515

Pro Gln  Lys Pro Ile Pro Arg  Pro Gly Asn Lys Phe  Gln Gly Met
    1520                 1525                 1530

Val Phe  Asp Phe Val Thr Arg  Gln Val Phe Asp Ile  Ser Ile Met
    1535                 1540                 1545

Ile Leu  Ile Cys Leu Asn Met  Val Thr Met Met Val  Glu Thr Asp
    1550                 1555                 1560

Asp Gln  Ser Glu Tyr Val Thr  Thr Ile Leu Ser Arg  Ile Asn Leu
    1565                 1570                 1575

Val Phe  Ile Val Leu Phe Thr  Gly Glu Cys Val Leu  Lys Leu Ile
    1580                 1585                 1590

Ser Leu  Arg His Tyr Tyr Phe  Thr Ile Gly Trp Asn  Ile Phe Asp
    1595                 1600                 1605
```

```
Phe Val  Val Val Ile Leu Ser  Ile Val Gly Met Phe  Leu Ala Glu
    1610                 1615                 1620

Leu Ile  Glu Lys Tyr Phe Val  Ser Pro Thr Leu Phe  Arg Val Ile
    1625                 1630                 1635

Arg Leu  Ala Arg Ile Gly Arg  Ile Leu Arg Leu Ile  Lys Gly Ala
    1640                 1645                 1650

Lys Gly  Ile Arg Thr Leu Leu  Phe Ala Leu Met Met  Ser Leu Pro
    1655                 1660                 1665

Ala Leu  Phe Asn Ile Gly Leu  Leu Leu Phe Leu Val  Met Phe Ile
    1670                 1675                 1680

Tyr Ala  Ile Phe Gly Met Ser  Asn Phe Ala Tyr Val  Lys Arg Glu
    1685                 1690                 1695

Val Gly  Ile Asp Asp Met Phe  Asn Phe Glu Thr Phe  Gly Asn Ser
    1700                 1705                 1710

Met Ile  Cys Leu Phe Gln Ile  Thr Thr Ser Ala Gly  Trp Asp Gly
    1715                 1720                 1725

Leu Leu  Ala Pro Ile Leu Asn  Ser Lys Pro Pro Asp  Cys Asp Pro
    1730                 1735                 1740

Asn Lys  Val Asn Pro Gly Ser  Ser Val Lys Gly Asp  Cys Gly Asn
    1745                 1750                 1755

Pro Ser  Val Gly Ile Phe Phe  Phe Val Ser Tyr Ile  Ile Ile Ser
    1760                 1765                 1770

Phe Leu  Val Val Val Asn Met  Tyr Ile Ala Val Ile  Leu Glu Asn
    1775                 1780                 1785

Phe Ser  Val Ala Thr Glu Glu  Ser Ala Glu Pro Leu  Ser Glu Asp
    1790                 1795                 1800

Asp Phe  Glu Met Phe Tyr Glu  Val Trp Glu Lys Phe  Asp Pro Asp
    1805                 1810                 1815

Ala Thr  Gln Phe Met Glu Phe  Glu Lys Leu Ser Gln  Phe Ala Ala
    1820                 1825                 1830

Ala Leu  Glu Pro Pro Leu Asn  Leu Pro Gln Pro Asn  Lys Leu Gln
    1835                 1840                 1845

Leu Ile  Ala Met Asp Leu Pro  Met Val Ser Gly Asp  Arg Ile His
    1850                 1855                 1860

Cys Leu  Asp Ile Leu Phe Ala  Phe Thr Lys Arg Val  Leu Gly Glu
    1865                 1870                 1875

Ser Gly  Glu Met Asp Ala Leu  Arg Ile Gln Met Glu  Glu Arg Phe
    1880                 1885                 1890

Met Ala  Ser Asn Pro Ser Lys  Val Ser Tyr Gln Pro  Ile Thr Thr
    1895                 1900                 1905

Thr Leu  Lys Arg Lys Gln Glu  Glu Val Ser Ala Val  Ile Ile Gln
    1910                 1915                 1920

Arg Ala  Tyr Arg Arg His Leu  Leu Lys Arg Thr Val  Lys Gln Ala
    1925                 1930                 1935

Ser Phe  Thr Tyr Asn Lys Asn  Lys Ile Lys Gly Gly  Ala Asn Leu
    1940                 1945                 1950

Leu Ile  Lys Glu Asp Met Ile  Ile Asp Arg Ile Asn  Glu Asn Ser
    1955                 1960                 1965

Ile Thr  Glu Lys Thr Asp Leu  Thr Met Ser Thr Ala  Ala Cys Pro
    1970                 1975                 1980

Pro Ser  Tyr Asp Arg Val Thr  Lys Pro Ile Val Glu  Lys His Glu
    1985                 1990                 1995

Gln Glu  Gly Lys Asp Glu Lys  Ala Lys Gly Lys
```

```
    2000                2005


<210> SEQ ID NO 105
<211> LENGTH: 872
<212> TYPE: PRT
<213> ORGANISM: Homo sapiens

<400> SEQUENCE: 105

Met Val Gln Lys Ser Arg Asn Gly Gly Val Tyr Pro Gly Pro Ser Gly
1               5                   10                  15

Glu Lys Lys Leu Lys Val Gly Phe Val Gly Leu Asp Pro Gly Ala Pro
            20                  25                  30

Asp Ser Thr Arg Asp Gly Ala Leu Leu Ile Ala Gly Ser Glu Ala Pro
        35                  40                  45

Lys Arg Gly Ser Ile Leu Ser Lys Pro Arg Ala Gly Gly Ala Gly Ala
    50                  55                  60

Gly Lys Pro Pro Lys Arg Asn Ala Phe Tyr Arg Lys Leu Gln Asn Phe
65                  70                  75                  80

Leu Tyr Asn Val Leu Glu Arg Pro Arg Gly Trp Ala Phe Ile Tyr His
                85                  90                  95

Ala Tyr Val Phe Leu Leu Val Phe Ser Cys Leu Val Leu Ser Val Phe
            100                 105                 110

Ser Thr Ile Lys Glu Tyr Glu Lys Ser Ser Glu Gly Ala Leu Tyr Ile
        115                 120                 125

Leu Glu Ile Val Thr Ile Val Val Phe Gly Val Glu Tyr Phe Val Arg
    130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
            180                 185                 190

Ala Thr Ser Ala Leu Arg Ser Leu Arg Phe Leu Gln Ile Leu Arg Met
        195                 200                 205

Ile Arg Met Asp Arg Arg Gly Gly Thr Trp Lys Leu Leu Gly Ser Val
    210                 215                 220

Val Tyr Ala His Ser Lys Glu Leu Val Thr Ala Trp Tyr Ile Gly Phe
225                 230                 235                 240

Leu Cys Leu Ile Leu Ala Ser Phe Leu Val Tyr Leu Ala Glu Lys Gly
                245                 250                 255

Glu Asn Asp His Phe Asp Thr Tyr Ala Asp Ala Leu Trp Trp Gly Leu
            260                 265                 270

Ile Thr Leu Thr Thr Ile Gly Tyr Gly Asp Lys Tyr Pro Gln Thr Trp
        275                 280                 285

Asn Gly Arg Leu Leu Ala Ala Thr Phe Thr Leu Ile Gly Val Ser Phe
    290                 295                 300

Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
                325                 330                 335

Ala Gly Leu Ile Gln Ser Ala Trp Arg Phe Tyr Ala Thr Asn Leu Ser
            340                 345                 350

Arg Thr Asp Leu His Ser Thr Trp Gln Tyr Tyr Glu Arg Thr Val Thr
        355                 360                 365
```

```
Val Pro Met Tyr Ser Ser Gln Thr Gln Thr Tyr Gly Ala Ser Arg Leu
    370                 375                 380

Ile Pro Pro Leu Asn Gln Leu Glu Leu Leu Arg Asn Leu Lys Ser Lys
385                 390                 395                 400

Ser Gly Leu Ala Phe Arg Lys Asp Pro Pro Pro Glu Pro Ser Pro Ser
                405                 410                 415

Lys Gly Ser Pro Cys Arg Gly Pro Leu Cys Gly Cys Cys Pro Gly Arg
            420                 425                 430

Ser Ser Gln Lys Val Ser Leu Lys Asp Arg Val Phe Ser Ser Pro Arg
        435                 440                 445

Gly Val Ala Ala Lys Gly Lys Gly Ser Pro Gln Ala Gln Thr Val Arg
    450                 455                 460

Arg Ser Pro Ser Ala Asp Gln Ser Leu Glu Asp Ser Pro Ser Lys Val
465                 470                 475                 480

Pro Lys Ser Trp Ser Phe Gly Asp Arg Ser Arg Ala Arg Gln Ala Phe
                485                 490                 495

Arg Ile Lys Gly Ala Ala Ser Arg Gln Asn Ser Glu Glu Ala Ser Leu
            500                 505                 510

Pro Gly Glu Asp Ile Val Asp Asp Lys Ser Cys Pro Cys Glu Phe Val
        515                 520                 525

Thr Glu Asp Leu Thr Pro Gly Leu Lys Val Ser Ile Arg Ala Val Cys
    530                 535                 540

Val Met Arg Phe Leu Val Ser Lys Arg Lys Phe Lys Glu Ser Leu Arg
545                 550                 555                 560

Pro Tyr Asp Val Met Asp Val Ile Glu Gln Tyr Ser Ala Gly His Leu
                565                 570                 575

Asp Met Leu Ser Arg Ile Lys Ser Leu Gln Ser Arg Val Asp Gln Ile
            580                 585                 590

Val Gly Arg Gly Pro Ala Ile Thr Asp Lys Asp Arg Thr Lys Gly Pro
        595                 600                 605

Ala Glu Ala Glu Leu Pro Glu Asp Pro Ser Met Met Gly Arg Leu Gly
    610                 615                 620

Lys Val Glu Lys Gln Val Leu Ser Met Glu Lys Lys Leu Asp Phe Leu
625                 630                 635                 640

Val Asn Ile Tyr Met Gln Arg Met Gly Ile Pro Pro Thr Glu Thr Glu
                645                 650                 655

Ala Tyr Phe Gly Ala Lys Glu Pro Glu Pro Ala Pro Pro Tyr His Ser
            660                 665                 670

Pro Glu Asp Ser Arg Glu His Val Asp Arg His Gly Cys Ile Val Lys
        675                 680                 685

Ile Val Arg Ser Ser Ser Ser Thr Gly Gln Lys Asn Phe Ser Ala Pro
    690                 695                 700

Pro Ala Ala Pro Pro Val Gln Cys Pro Pro Ser Thr Ser Trp Gln Pro
705                 710                 715                 720

Gln Ser His Pro Arg Gln Gly His Gly Thr Ser Pro Val Gly Asp His
                725                 730                 735

Gly Ser Leu Val Arg Ile Pro Pro Pro Pro Ala His Glu Arg Ser Leu
            740                 745                 750

Ser Ala Tyr Gly Gly Gly Asn Arg Ala Ser Met Glu Phe Leu Arg Gln
        755                 760                 765

Glu Asp Thr Pro Gly Cys Arg Pro Pro Glu Gly Asn Leu Arg Asp Ser
    770                 775                 780

Asp Thr Ser Ile Ser Ile Pro Ser Val Asp His Glu Glu Leu Glu Arg
```

```
785                 790                 795                 800

Ser Phe Ser Gly Phe Ser Ile Ser Gln Ser Lys Glu Asn Leu Asp Ala
                805                 810                 815

Leu Asn Ser Cys Tyr Ala Ala Val Ala Pro Cys Ala Lys Val Arg Pro
            820                 825                 830

Tyr Ile Ala Glu Gly Glu Ser Asp Thr Asp Ser Asp Leu Cys Thr Pro
        835                 840                 845

Cys Gly Pro Pro Pro Arg Ser Ala Thr Gly Glu Gly Pro Phe Gly Asp
    850                 855                 860

Val Gly Trp Ala Gly Pro Arg Lys
865                 870


<210> SEQ ID NO 106
<211> LENGTH: 2221
<212> TYPE: PRT
<213> ORGANISM: Homo sapiens

<400> SEQUENCE: 106

Met Val Asn Glu Asn Thr Arg Met Tyr Ile Pro Glu Glu Asn His Gln
1               5                   10                  15

Gly Ser Asn Tyr Gly Ser Pro Arg Pro Ala His Ala Asn Met Asn Ala
            20                  25                  30

Asn Ala Ala Ala Gly Leu Ala Pro Glu His Ile Pro Thr Pro Gly Ala
        35                  40                  45

Ala Leu Ser Trp Gln Ala Ala Ile Asp Ala Ala Arg Gln Ala Lys Leu
    50                  55                  60

Met Gly Ser Ala Gly Asn Ala Thr Ile Ser Thr Val Ser Ser Thr Gln
65                  70                  75                  80

Arg Lys Arg Gln Gln Tyr Gly Lys Pro Lys Lys Gln Gly Ser Thr Thr
                85                  90                  95

Ala Thr Arg Pro Pro Arg Ala Leu Leu Cys Leu Thr Leu Lys Asn Pro
            100                 105                 110

Ile Arg Arg Ala Cys Ile Ser Ile Val Glu Trp Lys Pro Phe Glu Ile
        115                 120                 125

Ile Ile Leu Leu Thr Ile Phe Ala Asn Cys Val Ala Leu Ala Ile Tyr
    130                 135                 140

Ile Pro Phe Pro Glu Asp Asp Ser Asn Ala Thr Asn Ser Asn Leu Glu
145                 150                 155                 160

Arg Val Glu Tyr Leu Phe Leu Ile Ile Phe Thr Val Glu Ala Phe Leu
                165                 170                 175

Lys Val Ile Ala Tyr Gly Leu Leu Phe His Pro Asn Ala Tyr Leu Arg
            180                 185                 190

Asn Gly Trp Asn Leu Leu Asp Phe Ile Ile Val Val Val Gly Leu Phe
        195                 200                 205

Ser Ala Ile Leu Glu Gln Ala Thr Lys Ala Asp Gly Ala Asn Ala Leu
    210                 215                 220

Gly Gly Lys Gly Ala Gly Phe Asp Val Lys Ala Leu Arg Ala Phe Arg
225                 230                 235                 240

Val Leu Arg Pro Leu Arg Leu Val Ser Gly Val Pro Ser Leu Gln Val
                245                 250                 255

Val Leu Asn Ser Ile Ile Lys Ala Met Val Pro Leu Leu His Ile Ala
            260                 265                 270

Leu Leu Val Leu Phe Val Ile Ile Ile Tyr Ala Ile Ile Gly Leu Glu
        275                 280                 285
```

```
Leu Phe Met Gly Lys Met His Lys Thr Cys Tyr Asn Gln Glu Gly Ile
    290                 295                 300

Ala Asp Val Pro Ala Glu Asp Asp Pro Ser Pro Cys Ala Leu Glu Thr
305                 310                 315                 320

Gly His Gly Arg Gln Cys Gln Asn Gly Thr Val Cys Lys Pro Gly Trp
                325                 330                 335

Asp Gly Pro Lys His Gly Ile Thr Asn Phe Asp Asn Phe Ala Phe Ala
            340                 345                 350

Met Leu Thr Val Phe Gln Cys Ile Thr Met Glu Gly Trp Thr Asp Val
        355                 360                 365

Leu Tyr Trp Val Asn Asp Ala Val Gly Arg Asp Trp Pro Trp Ile Tyr
    370                 375                 380

Phe Val Thr Leu Ile Ile Ile Gly Ser Phe Phe Val Leu Asn Leu Val
385                 390                 395                 400

Leu Gly Val Leu Ser Gly Glu Phe Ser Lys Glu Arg Glu Lys Ala Lys
                405                 410                 415

Ala Arg Gly Asp Phe Gln Lys Leu Arg Glu Lys Gln Gln Leu Glu Glu
            420                 425                 430

Asp Leu Lys Gly Tyr Leu Asp Trp Ile Thr Gln Ala Glu Asp Ile Asp
        435                 440                 445

Pro Glu Asn Glu Asp Glu Gly Met Asp Glu Glu Lys Pro Arg Asn Met
    450                 455                 460

Ser Met Pro Thr Ser Glu Thr Glu Ser Val Asn Thr Glu Asn Val Ala
465                 470                 475                 480

Gly Gly Asp Ile Glu Gly Glu Asn Cys Gly Ala Arg Leu Ala His Arg
                485                 490                 495

Ile Ser Lys Ser Lys Phe Ser Arg Tyr Trp Arg Arg Trp Asn Arg Phe
            500                 505                 510

Cys Arg Arg Lys Cys Arg Ala Ala Val Lys Ser Asn Val Phe Tyr Trp
        515                 520                 525

Leu Val Ile Phe Leu Val Phe Leu Asn Thr Leu Thr Ile Ala Ser Glu
    530                 535                 540

His Tyr Asn Gln Pro Asn Trp Leu Thr Glu Val Gln Asp Thr Ala Asn
545                 550                 555                 560

Lys Ala Leu Leu Ala Leu Phe Thr Ala Glu Met Leu Leu Lys Met Tyr
                565                 570                 575

Ser Leu Gly Leu Gln Ala Tyr Phe Val Ser Leu Phe Asn Arg Phe Asp
            580                 585                 590

Cys Phe Val Val Cys Gly Gly Ile Leu Glu Thr Ile Leu Val Glu Thr
        595                 600                 605

Lys Ile Met Ser Pro Leu Gly Ile Ser Val Leu Arg Cys Val Arg Leu
    610                 615                 620

Leu Arg Ile Phe Lys Ile Thr Arg Tyr Trp Asn Ser Leu Ser Asn Leu
625                 630                 635                 640

Val Ala Ser Leu Leu Asn Ser Val Arg Ser Ile Ala Ser Leu Leu Leu
                645                 650                 655

Leu Leu Phe Leu Phe Ile Ile Ile Phe Ser Leu Leu Gly Met Gln Leu
            660                 665                 670

Phe Gly Gly Lys Phe Asn Phe Asp Glu Met Gln Thr Arg Arg Ser Thr
        675                 680                 685

Phe Asp Asn Phe Pro Gln Ser Leu Leu Thr Val Phe Gln Ile Leu Thr
    690                 695                 700

Gly Glu Asp Trp Asn Ser Val Met Tyr Asp Gly Ile Met Ala Tyr Gly
```

```
705                 710                 715                 720

Gly Pro Ser Phe Pro Gly Met Leu Val Cys Ile Tyr Phe Ile Ile Leu
                725                 730                 735

Phe Ile Cys Gly Asn Tyr Ile Leu Leu Asn Val Phe Leu Ala Ile Ala
            740                 745                 750

Val Asp Asn Leu Ala Asp Ala Glu Ser Leu Thr Ser Ala Gln Lys Glu
        755                 760                 765

Glu Glu Glu Glu Lys Glu Arg Lys Lys Leu Ala Arg Thr Ala Ser Pro
    770                 775                 780

Glu Lys Lys Gln Glu Leu Val Glu Lys Pro Ala Val Gly Glu Ser Lys
785                 790                 795                 800

Glu Glu Lys Ile Glu Leu Lys Ser Ile Thr Ala Asp Gly Glu Ser Pro
                805                 810                 815

Pro Ala Thr Lys Ile Asn Met Asp Asp Leu Gln Pro Asn Glu Asn Glu
            820                 825                 830

Asp Lys Ser Pro Tyr Pro Asn Pro Glu Thr Thr Gly Glu Glu Asp Glu
        835                 840                 845

Glu Glu Pro Glu Met Pro Val Gly Pro Arg Pro Arg Pro Leu Ser Glu
    850                 855                 860

Leu His Leu Lys Glu Lys Ala Val Pro Met Pro Glu Ala Ser Ala Phe
865                 870                 875                 880

Phe Ile Phe Ser Ser Asn Asn Arg Phe Arg Leu Gln Cys His Arg Ile
                885                 890                 895

Val Asn Asp Thr Ile Phe Thr Asn Leu Ile Leu Phe Phe Ile Leu Leu
            900                 905                 910

Ser Ser Ile Ser Leu Ala Ala Glu Asp Pro Val Gln His Thr Ser Phe
        915                 920                 925

Arg Asn His Ile Leu Phe Tyr Phe Asp Ile Val Phe Thr Thr Ile Phe
    930                 935                 940

Thr Ile Glu Ile Ala Leu Lys Ile Leu Gly Asn Ala Asp Tyr Val Phe
945                 950                 955                 960

Thr Ser Ile Phe Thr Leu Glu Ile Ile Leu Lys Met Thr Ala Tyr Gly
                965                 970                 975

Ala Phe Leu His Lys Gly Ser Phe Cys Arg Asn Tyr Phe Asn Ile Leu
            980                 985                 990

Asp Leu Leu Val Val Ser Val Ser  Leu Ile Ser Phe Gly  Ile Gln Ser
        995                 1000                1005

Ser Ala  Ile Asn Val Val Lys  Ile Leu Arg Val Leu  Arg Val Leu
    1010                1015                1020

Arg Pro  Leu Arg Ala Ile Asn  Arg Ala Lys Gly Leu  Lys His Val
    1025                1030                1035

Val Gln  Cys Val Phe Val Ala  Ile Arg Thr Ile Gly  Asn Ile Val
    1040                1045                1050

Ile Val  Thr Thr Leu Leu Gln  Phe Met Phe Ala Cys  Ile Gly Val
    1055                1060                1065

Gln Leu  Phe Lys Gly Lys Leu  Tyr Thr Cys Ser Asp  Ser Ser Lys
    1070                1075                1080

Gln Thr  Glu Ala Glu Cys Lys  Gly Asn Tyr Ile Thr  Tyr Lys Asp
    1085                1090                1095

Gly Glu  Val Asp His Pro Ile  Ile Gln Pro Arg Ser  Trp Glu Asn
    1100                1105                1110

Ser Lys  Phe Asp Phe Asp Asn  Val Leu Ala Ala Met  Met Ala Leu
    1115                1120                1125
```

```
Phe Thr  Val Ser Thr Phe Glu  Gly Trp Pro Glu Leu  Leu Tyr Arg
    1130                 1135                 1140

Ser Ile  Asp Ser His Thr Glu  Asp Lys Gly Pro Ile  Tyr Asn Tyr
    1145                 1150                 1155

Arg Val  Glu Ile Ser Ile Phe  Phe Ile Ile Tyr Ile  Ile Ile Ile
    1160                 1165                 1170

Ala Phe  Phe Met Met Asn Ile  Phe Val Gly Phe Val  Ile Val Thr
    1175                 1180                 1185

Phe Gln  Glu Gln Gly Glu Gln  Glu Tyr Lys Asn Cys  Glu Leu Asp
    1190                 1195                 1200

Lys Asn  Gln Arg Gln Cys Val  Glu Tyr Ala Leu Lys  Ala Arg Pro
    1205                 1210                 1215

Leu Arg  Arg Tyr Ile Pro Lys  Asn Gln His Gln Tyr  Lys Val Trp
    1220                 1225                 1230

Tyr Val  Val Asn Ser Thr Tyr  Phe Glu Tyr Leu Met  Phe Val Leu
    1235                 1240                 1245

Ile Leu  Leu Asn Thr Ile Cys  Leu Ala Met Gln His  Tyr Gly Gln
    1250                 1255                 1260

Ser Cys  Leu Phe Lys Ile Ala  Met Asn Ile Leu Asn  Met Leu Phe
    1265                 1270                 1275

Thr Gly  Leu Phe Thr Val Glu  Met Ile Leu Lys Leu  Ile Ala Phe
    1280                 1285                 1290

Lys Pro  Lys Gly Tyr Phe Ser  Asp Pro Trp Asn Val  Phe Asp Phe
    1295                 1300                 1305

Leu Ile  Val Ile Gly Ser Ile  Ile Asp Val Ile Leu  Ser Glu Thr
    1310                 1315                 1320

Asn His  Tyr Phe Cys Asp Ala  Trp Asn Thr Phe Asp  Ala Leu Ile
    1325                 1330                 1335

Val Val  Gly Ser Ile Val Asp  Ile Ala Ile Thr Glu  Val Asn Pro
    1340                 1345                 1350

Ala Glu  His Thr Gln Cys Ser  Pro Ser Met Asn Ala  Glu Glu Asn
    1355                 1360                 1365

Ser Arg  Ile Ser Ile Thr Phe  Phe Arg Leu Phe Arg  Val Met Arg
    1370                 1375                 1380

Leu Val  Lys Leu Leu Ser Arg  Gly Glu Gly Ile Arg  Thr Leu Leu
    1385                 1390                 1395

Trp Thr  Phe Ile Lys Ser Phe  Gln Ala Leu Pro Tyr  Val Ala Leu
    1400                 1405                 1410

Leu Ile  Val Met Leu Phe Phe  Ile Tyr Ala Val Ile  Gly Met Gln
    1415                 1420                 1425

Val Phe  Gly Lys Ile Ala Leu  Asn Asp Thr Thr Glu  Ile Asn Arg
    1430                 1435                 1440

Asn Asn  Asn Phe Gln Thr Phe  Pro Gln Ala Val Leu  Leu Leu Phe
    1445                 1450                 1455

Arg Cys  Ala Thr Gly Glu Ala  Trp Gln Asp Ile Met  Leu Ala Cys
    1460                 1465                 1470

Met Pro  Gly Lys Lys Cys Ala  Pro Glu Ser Glu Pro  Ser Asn Ser
    1475                 1480                 1485

Thr Glu  Gly Glu Thr Pro Cys  Gly Ser Ser Phe Ala  Val Phe Tyr
    1490                 1495                 1500

Phe Ile  Ser Phe Tyr Met Leu  Cys Ala Phe Leu Ile  Ile Asn Leu
    1505                 1510                 1515
```

```
Phe Val  Ala Val Ile Met Asp  Asn Phe Asp Tyr Leu  Thr Arg Asp
    1520                 1525                 1530

Trp Ser  Ile Leu Gly Pro His  His Leu Asp Glu Phe  Lys Arg Ile
    1535                 1540                 1545

Trp Ala  Glu Tyr Asp Pro Glu  Ala Lys Gly Arg Ile  Lys His Leu
    1550                 1555                 1560

Asp Val  Val Thr Leu Leu Arg  Arg Ile Gln Pro Pro  Leu Gly Phe
    1565                 1570                 1575

Gly Lys  Leu Cys Pro His Arg  Val Ala Cys Lys Arg  Leu Val Ser
    1580                 1585                 1590

Met Asn  Met Pro Leu Asn Ser  Asp Gly Thr Val Met  Phe Asn Ala
    1595                 1600                 1605

Thr Leu  Phe Ala Leu Val Arg  Thr Ala Leu Arg Ile  Lys Thr Glu
    1610                 1615                 1620

Gly Asn  Leu Glu Gln Ala Asn  Glu Glu Leu Arg Ala  Ile Ile Lys
    1625                 1630                 1635

Lys Ile  Trp Lys Arg Thr Ser  Met Lys Leu Leu Asp  Gln Val Val
    1640                 1645                 1650

Pro Pro  Ala Gly Asp Asp Glu  Val Thr Val Gly Lys  Phe Tyr Ala
    1655                 1660                 1665

Thr Phe  Leu Ile Gln Glu Tyr  Phe Arg Lys Phe Lys  Lys Arg Lys
    1670                 1675                 1680

Glu Gln  Gly Leu Val Gly Lys  Pro Ser Gln Arg Asn  Ala Leu Ser
    1685                 1690                 1695

Leu Gln  Ala Gly Leu Arg Thr  Leu His Asp Ile Gly  Pro Glu Ile
    1700                 1705                 1710

Arg Arg  Ala Ile Ser Gly Asp  Leu Thr Ala Glu Glu  Glu Leu Asp
    1715                 1720                 1725

Lys Ala  Met Lys Glu Ala Val  Ser Ala Ala Ser Glu  Asp Asp Ile
    1730                 1735                 1740

Phe Arg  Arg Ala Gly Gly Leu  Phe Gly Asn His Val  Ser Tyr Tyr
    1745                 1750                 1755

Gln Ser  Asp Gly Arg Ser Ala  Phe Pro Gln Thr Phe  Thr Thr Gln
    1760                 1765                 1770

Arg Pro  Leu His Ile Asn Lys  Ala Gly Ser Ser Gln  Gly Asp Thr
    1775                 1780                 1785

Glu Ser  Pro Ser His Glu Lys  Leu Val Asp Ser Thr  Phe Thr Pro
    1790                 1795                 1800

Ser Ser  Tyr Ser Ser Thr Gly  Ser Asn Ala Asn Ile  Asn Asn Ala
    1805                 1810                 1815

Asn Asn  Thr Ala Leu Gly Arg  Leu Pro Arg Pro Ala  Gly Tyr Pro
    1820                 1825                 1830

Ser Thr  Val Ser Thr Val Glu  Gly His Gly Pro Pro  Leu Ser Pro
    1835                 1840                 1845

Ala Ile  Arg Val Gln Glu Val  Ala Trp Lys Leu Ser  Ser Asn Arg
    1850                 1855                 1860

Glu Arg  His Val Pro Met Cys  Glu Asp Leu Glu Leu  Arg Arg Asp
    1865                 1870                 1875

Ser Gly  Ser Ala Gly Thr Gln  Ala His Cys Leu Leu  Leu Arg Lys
    1880                 1885                 1890

Ala Asn  Pro Ser Arg Cys His  Ser Arg Glu Ser Gln  Ala Ala Met
    1895                 1900                 1905

Ala Gly  Gln Glu Glu Thr Ser  Gln Asp Glu Thr Tyr  Glu Val Lys
```

-continued

```
    1910                1915                1920

Met Asn  His Asp Thr Glu Ala  Cys Ser Glu Pro Ser  Leu Leu Ser
    1925                1930                1935

Thr Glu  Met Leu Ser Tyr Gln  Asp Asp Glu Asn Arg  Gln Leu Thr
    1940                1945                1950

Leu Pro  Glu Glu Asp Lys Arg  Asp Ile Arg Gln Ser  Pro Lys Arg
    1955                1960                1965

Gly Phe  Leu Arg Ser Ala Ser  Leu Gly Arg Arg Ala  Ser Phe His
    1970                1975                1980

Leu Glu  Cys Leu Lys Arg Gln  Lys Asp Arg Gly Gly  Asp Ile Ser
    1985                1990                1995

Gln Lys  Thr Val Leu Pro Leu  His Leu Val His His  Gln Ala Leu
    2000                2005                2010

Ala Val  Ala Gly Leu Ser Pro  Leu Leu Gln Arg Ser  His Ser Pro
    2015                2020                2025

Ala Ser  Phe Pro Arg Pro Phe  Ala Thr Pro Pro Ala  Thr Pro Gly
    2030                2035                2040

Ser Arg  Gly Trp Pro Pro Gln  Pro Val Pro Thr Leu  Arg Leu Glu
    2045                2050                2055

Gly Val  Glu Ser Ser Glu Lys  Leu Asn Ser Ser Phe  Pro Ser Ile
    2060                2065                2070

His Cys  Gly Ser Trp Ala Glu  Thr Thr Pro Gly Gly  Gly Gly Ser
    2075                2080                2085

Ser Ala  Ala Arg Arg Val Arg  Pro Val Ser Leu Met  Val Pro Ser
    2090                2095                2100

Gln Ala  Gly Ala Pro Gly Arg  Gln Phe His Gly Ser  Ala Ser Ser
    2105                2110                2115

Leu Val  Glu Ala Val Leu Ile  Ser Glu Gly Leu Gly  Gln Phe Ala
    2120                2125                2130

Gln Asp  Pro Lys Phe Ile Glu  Val Thr Thr Gln Glu  Leu Ala Asp
    2135                2140                2145

Ala Cys  Asp Met Thr Ile Glu  Glu Met Glu Ser Ala  Ala Asp Asn
    2150                2155                2160

Ile Leu  Ser Gly Gly Ala Pro  Gln Ser Pro Asn Gly  Ala Leu Leu
    2165                2170                2175

Pro Phe  Val Asn Cys Arg Asp  Ala Gly Gln Asp Arg  Ala Gly Gly
    2180                2185                2190

Glu Glu  Asp Ala Gly Cys Val  Arg Ala Arg Gly Arg  Pro Ser Glu
    2195                2200                2205

Glu Glu  Leu Gln Asp Ser Arg  Val Tyr Val Ser Ser  Leu
    2210                2215                2220
```